United States Patent
Kelley et al.

(10) Patent No.: US 11,370,808 B2
(45) Date of Patent: *Jun. 28, 2022

(54) PYRAZOLE COMPOUNDS AND METHODS FOR MAKING AND USING THE COMPOUNDS

(71) Applicant: Rigel Pharmaceuticals, Inc., South San Francisco, CA (US)

(72) Inventors: Ryan Kelley, Pacifica, CA (US); Hui Li, Santa Clara, CA (US); Thilo Heckrodt, San Francisco, CA (US); Yan Chen, Foster City, CA (US); Darren McMurtrie, Daly City, CA (US); Kin Tso, San Francisco, CA (US); Vanessa Taylor, San Francisco, CA (US); Rajinder Singh, Belmont, CA (US); Rose Yen, San Francisco, CA (US); Jack Maung, Daly City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/259,685

(22) Filed: Jan. 28, 2019

(65) Prior Publication Data

US 2019/0153006 A1 May 23, 2019

Related U.S. Application Data

(60) Division of application No. 15/934,692, filed on Mar. 23, 2018, now Pat. No. 10,208,075, which is a continuation of application No. 15/136,508, filed on Apr. 22, 2016, now Pat. No. 9,982,000.

(60) Provisional application No. 62/151,274, filed on Apr. 22, 2015.

(51) Int. Cl.
| | |
|---|---|
| *C07F 9/6558* | (2006.01) |
| *C07D 405/14* | (2006.01) |
| *C07D 405/04* | (2006.01) |
| *C07D 413/04* | (2006.01) |
| *C07D 417/04* | (2006.01) |
| *C07D 417/14* | (2006.01) |
| *C07D 471/04* | (2006.01) |

(52) U.S. Cl.
CPC ........ *C07F 9/65586* (2013.01); *C07D 405/04* (2013.01); *C07D 405/14* (2013.01); *C07D 413/04* (2013.01); *C07D 417/04* (2013.01); *C07D 417/14* (2013.01); *C07D 471/04* (2013.01)

(58) Field of Classification Search
CPC . C07F 9/65586; C07D 405/04; C07D 405/14; C07D 413/04; C07D 417/04; C07D 471/04; C07D 417/14
See application file for complete search history.

(56) References Cited

U.S. PATENT DOCUMENTS

| | | | |
|---|---|---|---|
| 7,897,626 B2 | 3/2011 | Bothe et al. | |
| 7,977,477 B2 | 7/2011 | Berdini | |
| 8,575,336 B2 | 11/2013 | Coe et al. | |
| 8,895,544 B2 | 11/2014 | Coe et al. | |
| 10,774,076 B2 * | 9/2020 | Yen .......................... | A61P 37/02 |
| 2014/0088117 A1 | 3/2014 | Burch | |

FOREIGN PATENT DOCUMENTS

| | | |
|---|---|---|
| EP | 2231654 | 9/2010 |
| EP | 2 674 423 | 12/2013 |
| WO | WO 2004/037248 | 5/2004 |
| WO | WO 2006/070198 | 7/2006 |
| WO | WO 2006/070202 | 7/2006 |
| WO | WO 2009/054468 | 4/2009 |
| WO | WO 2010/121243 | 10/2010 |
| WO | WO 2010/121834 | 10/2010 |
| WO | WO 2011/043371 | 4/2011 |
| WO | WO 2011/043771 | 4/2011 |
| WO | WO 2011/124580 | 10/2011 |
| WO | WO 2012/068546 | 5/2012 |
| WO | WO 2012/072685 | 6/2012 |
| WO | WO 2012/084704 | 6/2012 |
| WO | WO 2012/097013 | 7/2012 |
| WO | WO 2013/045461 | 4/2013 |
| WO | WO 2013/106535 | 7/2013 |
| WO | WO 2014/058691 | 4/2014 |
| WO | WO 2014/121931 | 8/2014 |
| WO | WO 2014/121942 | 8/2014 |
| WO | WO 2015/106058 | 7/2015 |
| WO | WO 2016/081679 | 5/2016 |

OTHER PUBLICATIONS

WO 2011 043371A1 English Translation (Year: 2011).*
Buckley et al., "IRAK-4 inhibitors. Part 1: A series of amides," *Bioorganic & Medicinal Chemistry Letters* 18:3211-3214, available online Apr. 26, 2008.
Chaudhary et al., "Recent Advances in the Discovery of Small Molecule Inhibitors of Interleukin-1 Receptor-Associated Kinase (IRAK4) as a Therapeutic Target for Inflammation and Oncology Disorders," *Journal of Medical Chemistry* 58(1):96-110, Jan. 8, 2015.
Lim et al., "Discovery of 5-Amino-N-(1H-pyrazol-4-yl)pyrazolo[1,5-α]pyrimidine-3-carboxamide Inhibitors of IRAK4," *ACS Medicinal Chemistry Letters* 6(6):683-688, 2015.
Unbekandt et al., "A novel small-molecule MRCK inhibitor cancer cell invasion," *Cell Communication and Signaling* 12(54):1-15, 2014.
CAS Registry No. 1376284-17-1 dated Jun. 7, 2012.

* cited by examiner

*Primary Examiner* — James D. Anderson
*Assistant Examiner* — William Y Lee
(74) *Attorney, Agent, or Firm* — Klarquist Sparkman, LLP

(57) ABSTRACT

Disclosed embodiments concern novel interleukin receptor associated kinases (IRAK) inhibitors and compositions comprising such inhibitors. Also disclosed are methods of making and using the compounds and compositions. The disclosed compounds and/or compositions may be used to treat or prevent an IRAK-associated disease or condition.

17 Claims, No Drawings

PYRAZOLE COMPOUNDS AND METHODS FOR MAKING AND USING THE COMPOUNDS

CROSS REFERENCE TO RELATED APPLICATIONS

This application is a divisional of U.S. patent application Ser. No. 15/934,692 filed on Mar. 23, 2018, which is a continuation of U.S. patent application Ser. No. 15/136,508, filed on Apr. 22, 2016, which claims the benefit of U.S. Provisional Application No. 62/151,274, filed on Apr. 22, 2015, all of which are incorporated herein in their entireties by reference.

FIELD

This disclosure concerns pyrazole compounds, and embodiments of a method for making and using the compounds, such as for inhibiting interleukin receptor-associated kinase (IRAK), and for treating diseases and conditions related to IRAK.

BACKGROUND

Interleukin-1 receptor-associated kinases (IRAKs) are important mediators of signaling processes, such as toll-like receptors (TLR) and interleukin-1 receptor (IL-1R) signaling processes. IRAKs have been implicated in modulating signaling networks that control inflammation, apoptosis, and cellular differentiation. Four IRAK genes have been identified in the human genome (IRAK1, IRAK2, IRAK3 and IRAK4), and studies have revealed distinct, non-redundant biological roles. IRAK1 and IRAK4 have been shown to exhibit kinase activity.

SUMMARY

Disclosed herein are pyrazole compounds, and compositions comprising such compounds that are useful as, inter alia, kinase inhibitors, such as IRAK inhibitors. Certain disclosed embodiments concern pyrazole compounds having a formula

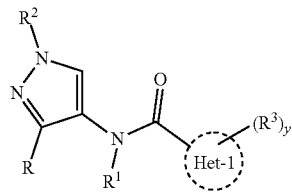

or salt, solvate, N-oxide or prodrug thereof, wherein R is aliphatic, heteroaliphatic, heteroaryl, aryl, halo, amide or CN; $R^1$ is H, aliphatic or heteroaliphatic; or R and $R^1$, together with the atoms to which they are attached, form a heterocyclyl ring; $R^2$ is H, aliphatic, heteroaliphatic, heterocycloaliphatic, aryl, amide, heterocyclyl or araliphatic; each $R^3$ independently is H, aliphatic, halogen, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl, haloalkyl, alkylphosphate, or alkylphosphonate; y is from 1 to the number of possible substituents on the particular system in question; and Het-1 is heteroaryl. In some embodiments, R is alkyl, amide, heteroaryl, or CN.

In certain embodiments, the compound has a formula

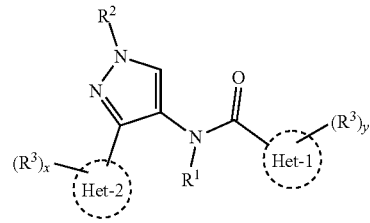

wherein x is from 1 to the number of possible substituents on the particular system in question, and Het-2 is heteroaryl.

In some embodiments, Het-1 and Het-2, if present, independently is a 5- or 6-membered heteroaryl, and maybe selected from furan, thiophene, pyrazole, pyrrole, imidazole, oxazole, thiazole, isoxazole, isothiazole, 1,2,3-triazole, 1,2,4-triazole, 1,3,4-triazole, 1,2,3-oxadiazole, 1,2,4-oxadiazole, 1,3,4-oxadiazole, 1,2,5-oxadiazole, 1,2,3-thiadiazole, 1,2,4-thiadiazole, 1,3,4-thiadiazole, 1,2,5-thiadiazole, tetrazole, pyrimidine, pyridine, 1,2,3-triazine, 1,2,4-triazine, 1,3,5-triazine, pyrazine, or pyridazine. In particular embodiments, Het-1 is furan, thiazole or oxazole. In other embodiments, Het-2 is pyridine, pyrimidine, pyrazine, oxadiazole or thiazole.

In some embodiments, the compound has a formula

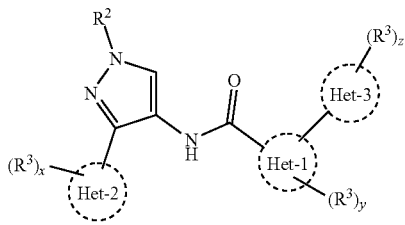

where Het-3 is a heterocycle, and z is from 1 to the number of possible substituents on the particular system in question. Het-3 may be a 5- or 6-membered heteroaryl, and in some embodiments Het-3 is selected from furan, thiophene, pyrazole, pyrrole, imidazole, oxazole, thiazole, isoxazole, isothiazole, 1,2,3-triazole, 1,2,4-triazole, 1,3,4-triazole, 1,2,3-oxadiazole, 1,2,4-oxadiazole, 1,3,4-oxadiazole, 1,2,5-oxadiazole, 1,2,3-thiadiazole, 1,2,4-thiadiazole, 1,3,4-thiadiazole, 1,2,5-thiadiazole or tetrazole. In particular embodiments, Het-3 is pyrazole.

The compound may have a formula selected from

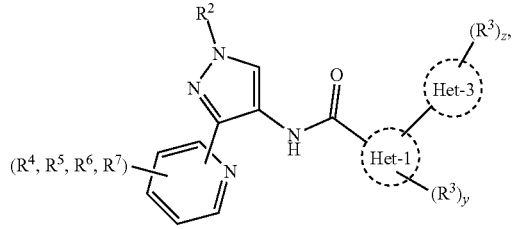

-continued

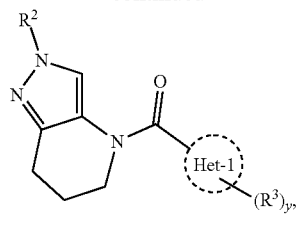

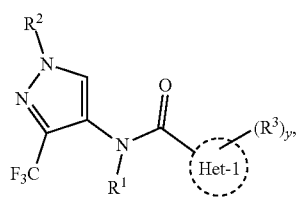

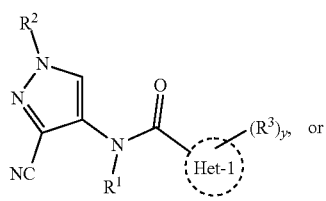

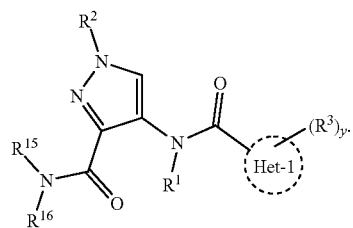

With respect to these formulas, $R^4$, $R^5$, $R^6$ and $R^7$ are each independently H, aliphatic, heteroaliphatic, alkoxy, heterocyclyl, aryl, araliphatic, —O-heterocyclyl, hydroxyl, haloalkyl, halogen, nitro, cyano, carboxyl, carboxyl ester, acyl, amide, amino, sulfonyl, sulfonamide, sulfanyl or sulfinyl. In some examples the compound has a formula

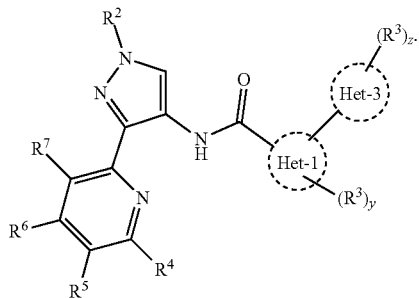

In certain embodiments, the compound has a formula selected from

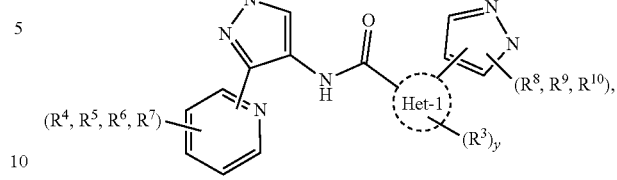

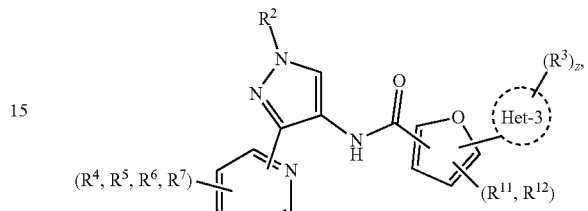

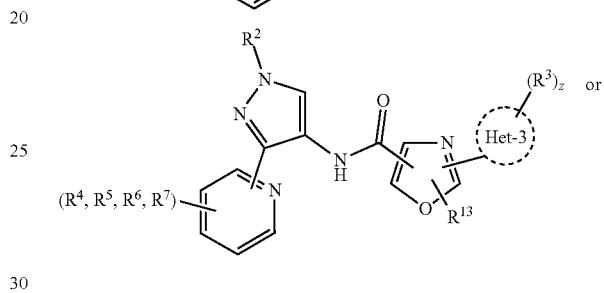

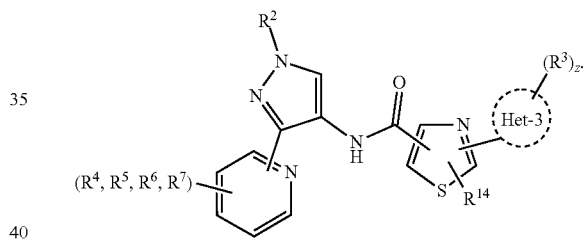

With respect to these formulas, $R^8$, $R^9$ and $R^{10}$ are each independently H, aliphatic, heteroaliphatic, aryl, —O-aliphatic, araliphatic, heterocyclyl, sulfonyl, nitro, OH, halogen, haloalkyl, carboxyl ester, cyano, acyl, amino, alkyl phosphate or alkylphosphonate, and $R^{11}$, $R^{12}$, $R^{13}$ and $R^{14}$ are each independently H, aliphatic, heteroaliphatic, aryl, heterocyclyl, sulfonyl, nitro, carboxyl ester, cyano or amino.

In particular embodiments, the compound has a formula selected from

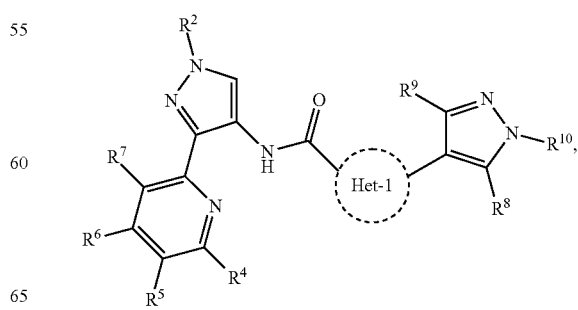

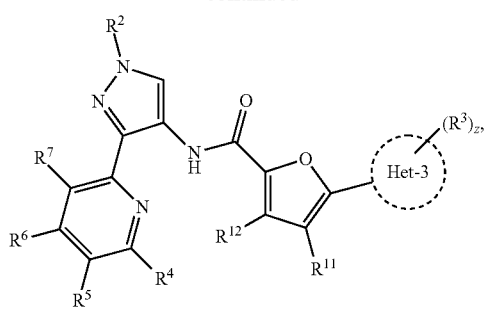
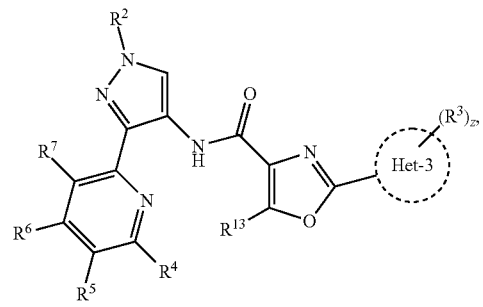
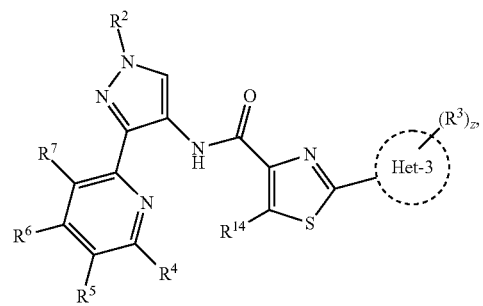
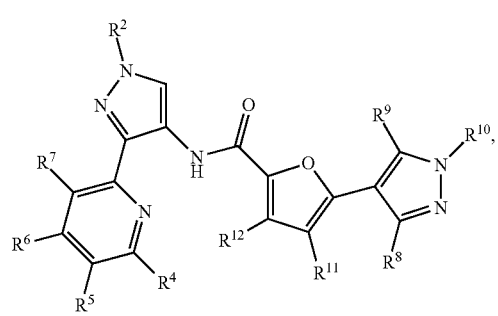
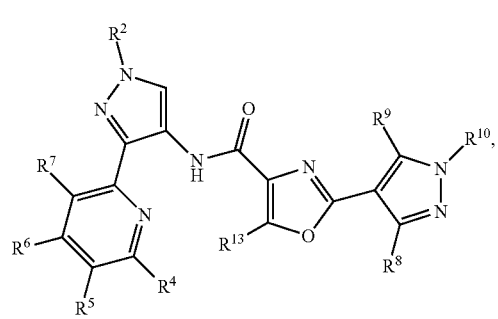
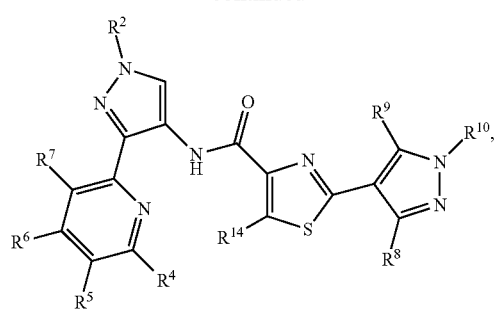
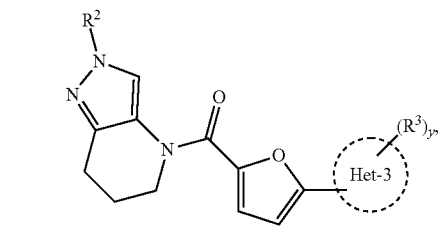
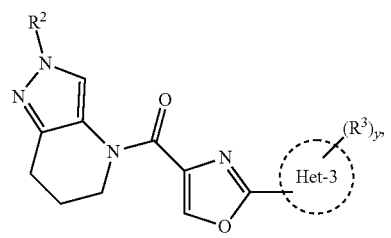
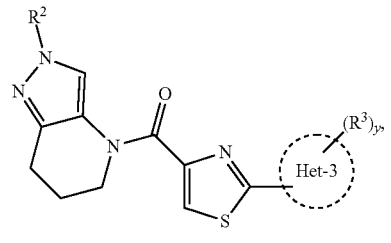
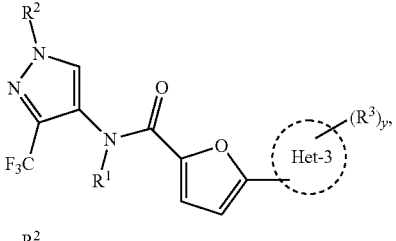
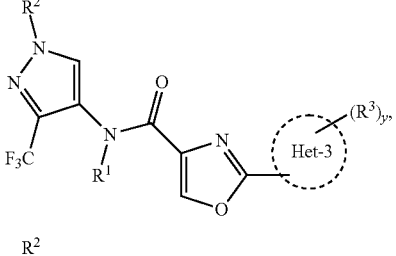
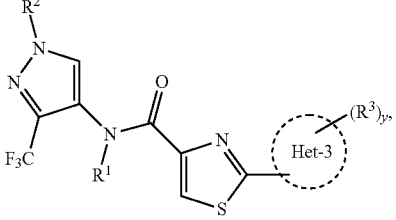

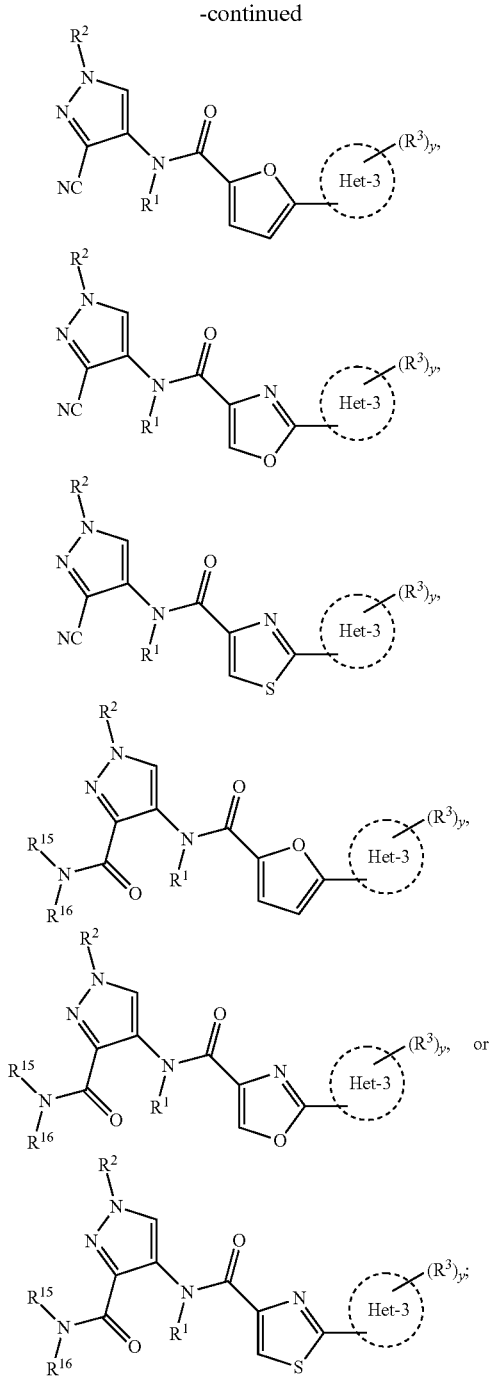

where Het-3 is heteroaryl, and in some embodiments,

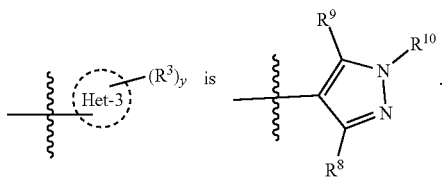

In particular embodiments of the above formulas, $R^8$, $R^9$, $R^{11}$, $R^{12}$, $R^{13}$ and $R^{14}$ are each independently H or alkyl, and $R^{10}$ is H, alkyl, carboxyl ester, acyl, alkyl phosphate, alkyl phosphonate, heterocycloalkyl or aralkyl.

In any of the above formulas, $R^4$, $R^5$, $R^6$ and $R^7$ may be each independently H, halogen, haloalkyl, aliphatic, heteroaliphatic, alkoxy, heterocyclyl or —O-heterocyclyl. In certain examples, $R^5$ is H, halogen, haloaklyl, alkoxy, —O-heterocyclyl or heterocyclyl, and in particular examples, $R^5$ is H, F, $CF_3$, methoxy, morpholin-4-yl, 1-methylpiperidin-4-yl, —O—$CH_2C(CH_3)_2OH$, or —O-(oxetan-3-yl). In certain examples, each of $R^4$, $R^6$ and $R^7$ independently is H, $CF_3$, F.

$R^2$ may be H, amide, alkyl, particularly lower alkyl, cycloalkyl, heteroaliphatic, heteroalicyclyl or haloalkyl, and/or may comprise cyclobutyl, azetidinyl, morpholinyl, 4-methylpiperazinyl, oxetanyl, tetrahydrofuranyl, or tetrahydropyranyl. In certain embodiments, $R^2$ is H, methyl, difluoromethyl, trifluoroethyl, isopropyl, tetrahydropyranyl, tetrahydrofuranyl, oxetanyl, N-tert-butyloxycarbonyl azetidin-3-yl, 3-methyoxy cyclobutyl, 3-benzyloxycyclobutyl, 3-ethyloxy cyclobutyl, 3-isopropyl cyclobutyl, 3-hydroxy cyclobutyl, 4-ethoxy cyclohexyl, 4-hydroxy cyclohexyl, 4-((2,2-difluoroethyl)amino)cyclohexyl, 3-ethyloxy cyclopentyl, or 3-hydroxy cyclopentyl. And in some examples, $R^{10}$ is H, alkyl, carboxyl ester, acyl, alkyl phosphate, alkyl phosphonate or aralkyl. In certain embodiments $R^1$ is $R^a$, —$(CR^aR^a)_m$—O—$R^a$, —$(CH_2)_m$—O—$R^a$, —$(CR^aR^a)_m$—O—$(CR^aR^a)_m$—O—$R^a$ or —$(CH_2)_m$—O—$(CH_2)_m$—O—$R^a$; each m independently is 1, 2 or 3; $R^2$ is $R^a$, $R^b$, $R^a$ substituted with 1, 2 or 3 $R^b$, $R^a$ substituted with $R_b$ and $R^c$, $R^a$ substituted with $R^c$, —$(CR^aR^a)_n$—$R^a$, —$(CH_2)_n$—$R^a$, —$(CR^aR^a)_n$—$R^b$ or —$(CH_2)_n$—$R^b$; each of $R^4$, $R^5$, $R^6$ and $R^7$ independently is $R^a$, $R^b$, $R^a$ substituted with $R^c$, —$OR^a$, —O—$(CR^aR^a)_p$—$R^b$; $R^{10}$ is $R^a$, $R^b$, $R^a$ substituted with —$OP(O)(R^f)_2$, $R^a$ substituted with 1, 2 or 3 $R^b$, $R^a$ substituted with $R^c$, $R^a$ substituted with —$P(O)(R^f)_2$, aralkyl, —$(CR^aR^a)_n$—$R^a$, —$(CH_2)_n$—$R^a$ or —$C(O)C(R^a)_2NR^aR^b$; n is 1, 2 or 3; p is 1, 2, or 3; $R^a$ is independently for each occurrence H, D, $C_{1-6}$alkyl, $C_{3-6}$cycloalkyl, $C_{3-6}$cycloalkenyl, or $C_{3-6}$heteroalicyclyl; $R^b$ is independently for each occurrence —OH, —$CF_3$, —$OR^c$, —$NR^dR^d$, —$C(O)OH$, —$C(O)R^c$, —$C(O)OR^c$, —$C(O)NR^dR^d$ or halogen; $R^c$ is independently for each occurrence $C_{1-6}$alkyl, $C_{3-6}$cycloalkyl, $C_{3-6}$heteroalicyclyl, aralkyl, $C_{1-6}$alkyl substituted with 1, 2 or 3 $R^e$, $C_{3-6}$cycloalkyl substituted with 1, 2 or 3 $R^e$, or $C_{3-6}$heteroalicyclyl substituted with 1, 2 or 3 $R^e$; $R^d$ is independently for each occurrence H, $C_{1-6}$alkyl optionally substituted with 1, 2 or 3 $R^e$, $C_{3-6}$cycloalkyl optionally substituted with 1, 2 or 3 $R^e$, or two $R^d$ groups together with the nitrogen bound thereto form a $C_{3-6}$heteroalicyclyl moiety optionally substituted with $C_{1-6}$alkyl, such as morpholinyl, piperidinyl, N-methylpiperidinyl or pyrrolidinyl; $R^e$ is independently for each occurrence halogen, $C_{1-6}$alkyl, $C_{3-6}$cycloalkyl, $C_{3-6}$heteroalicyclyl, $C_{1-6}$alkyl-OH, —$OR^a$, —$OC(O)R^a$ or —O-aralkyl; $R^f$ is independently for each occurrence —$OR^a$, —$O^-M^+$ or —$O^-[M^{2+}]_{0.5}$; each $M^+$ independently is an alkali metal ion or an ammonium ion; and $M^{2+}$ is an alkaline metal earth ion.

In particular embodiments, $R^2$ is $CH_3OCH_2CH_2$—, $CH_3OCH_2CH_2OCH_2CH_2$—, $CH_3CH_2OCH_2CH_2$—, methyl, 4-pyranyl, F, $CF_3$, or H, $R^3$ is H, and/or $R^4$, $R^5$, $R^6$ and $R^7$ independently are H, F, or $CF_3$.

In any of the above embodiments, the compound may be a salt, such as a pharmaceutically acceptable acid addition salt or a pharmaceutically acceptable base addition salt. In certain examples, the compound is a hydrochloride, formic acid or trifluoroacetic acid salt. In other examples, the compound is a sodium, calcium, ammonium, trimethylamine, tris(hydroxymethyl)aminomethane, lysine, arginine, or potassium salt.

Also disclosed herein are embodiments of a composition comprising a disclosed compound and a pharmaceutically acceptable excipient. The composition may also comprise an additional therapeutic agent. Alternatively, the pyrazole compounds, or compositions comprising the pyrazole compounds, may be administered as a combination with a second therapeutic(s).

Embodiments of a method for administering a pyrazole compound or composition comprising a pyrazole compound(s) are also disclosed. For example, disclosed herein are embodiments of a method for treating different classes of diseases, such as by inhibiting an enzyme, such as a kinase, for example an IRAK protein comprising contacting the IRAK protein with an effective amount of a pyrazole compound. In some embodiments the method comprises contacting the protein in vitro. In other embodiments, the IRAK protein may be in a subject. Exemplary compounds may have an $EC_{50}$ of from greater than 0 to 5 μM, such as from greater than 0 to 1 μM. In certain embodiments, the method comprises administering to a subject in need thereof a therapeutically effective amount of a pyrazole compound or composition comprising the pyrazole compound. The method may be a method of treating a disease or condition for which an IRAK modulator or inhibitor is indicated.

The foregoing and other objects, features, and advantages of the invention will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

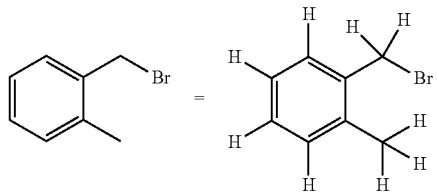

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

A person of ordinary skill in the art will appreciate that the definitions may be combined to further describe a particular compound. For example, hydroxyaliphatic refers to an aliphatic group substituted with an hydroxy (—OH) group, and haloalkylaryl refers to an aryl group substituted with an alkyl group, where the alkyl group too is substituted with a halogen, and where the point of attachment to the parent structure is via the aryl moiety since aryl is the base name of the substituent.

As used herein, the term "substituted" refers to all subsequent modifiers in a term, for example in the term "substituted aryl$C_{1-8}$alkyl," substitution may occur on the "$C_{1-8}$alkyl" portion, the "aryl" portion or both portions of the aryl$C_{1-8}$alkyl group. Also by way of example, alkyl includes substituted cycloalkyl groups.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" substituent may be unsubstituted or substituted, but an "unsubstituted alkyl" may not be substituted.

"Substituents" or "substituent groups" for substituting for one or more hydrogen atoms on saturated carbon atoms in the specified group or moiety are, unless otherwise specified, —$R^{60}$, halo, =O, —$OR^{70}$, —$SR^{70}$, —$N(R^{80})_2$, haloalkyl, perhaloalkyl, —CN, —$NO_2$, =$N_2$, —$N_3$, —$SO_2R^{70}$, —$SO_3^-$ $M^+$, —$SO_3R^{70}$, —$OSO_2R^{70}$, —$OSO_3^-M^+$, —$OSO_3R^{70}$, —$P(O)(O^-)_2(M^+)_2$, —$P(O)(O^-)_2M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)N(R^{80})_2$, —$C(NR^{70})(R^{80})_2$, —$OC(O)R^{70}$, —$OC(S)R^{70}$, —$OCO_2^-M^+$, —$O CO_2R^{70}$, —$OC(S)OR^{70}$, —$NR^{70}C$ (O)$R^{70}$, —$NR^{70}C(S)R^{70}$, —$NR^{70}CO_2M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$ is $C_{1-6}$alkyl optionally substituted with 1, 2, or 3 OH; each $R^{70}$ is independently for each occurrence hydrogen or $R^{60}$; each $R^{80}$ is independently for each occurrence $R^{70}$ or alternatively, two $R^{80}$ groups, taken together with the nitrogen atom to which they are bonded, form a 3- to 7-membered heteroalicyclyl which optionally includes from 1 to 4 of the same or different additional heteroatoms selected from O, N and S, of which N optionally has H or $C_1$-$C_3$alkyl substitution; and each $M^+$ is a counter ion with a net single positive charge. Each $M^+$ is independently for each occurrence, for example, an alkali metal ion, such as $K^+$, $Na^+$, $Li^+$; an ammonium ion, such as $^+N(R^{60})_4$; a protonated amino acid ion, such as a lysine ion, or an arginine ion; or an alkaline metal earth ion, such as $[Ca^{2+}]_{0.5}$, $[Mg^{2+}]_{0.5}$, or $[Ba^{2+}]_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —$N(R^{80})_2$ includes —$NH_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon can be replaced with =O, =$NR^{70}$, =N—$OR^{70}$, =$N_2$ or =S.

Substituent groups for replacing hydrogen atoms on unsaturated carbon atoms in groups containing unsaturated carbons are, unless otherwise specified, —$R^{60}$, halo, —$O^-M^+$, —$SR^{70}$, —$S^-M^+$, —$N(R^{80})_2$, perhaloalkyl, —CN, —OCN, —SCN, —NO, —$NO_2$, —$N_3$, —$SO_2R^{70}$, —$SO_3^-R^{70}$, —$SO_3R^{70}$, —$OSO_2R^{70}$, —$OSO_3^-M^+$, —$OSO_3R^{70}$, —$PO_3^{-2}(M^+)_2$, —$PO_3^{-2}M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})N(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

Substituent groups for replacing hydrogen atoms on nitrogen atoms in groups containing such nitrogen atoms are, unless otherwise
specified, —$R^{60}$, —$O^-M^+$, —$OR^{70}$, —$SR^{70}$, —$S^-M^+$, —$N(R^{80})_2$,
perhaloalkyl, —CN, —NO, —$NO_2$, —$S(O)_2R^{70}$, —$SO_3^-M^+$, —$SO_3R^{70}$, —$OS(O)_2R^{70}$, —$OSO_3^-M^+$, —$OSO_3R^{70}$, —$PO_3^{2-}(M^+)_2$, —$PO_3^{2-}M^{2+}$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2R^{70}$, —$OC(S)OR^{70}$, —$NR^{70}C(O)R^{70}$, —$NR^{70}C(S)R^{70}$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined.

In one embodiment, a group that is substituted has 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

"Acyl" refers to the group —C(O)R, where R is H, aliphatic, heteroaliphatic, heterocyclic or aryl. Exemplary acyl moieties include, but are not limited to, —C(O)H, —C(O)alkyl, —C(O)$C_1$-$C_6$alkyl, —C(O)$C_1$-$C_6$haloalkyl-C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety, including alkyl, alkenyl, alkynyl groups, cyclic versions thereof, such as cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms.

"Lower aliphatic" refers to an aliphatic group containing from one to ten carbon atoms. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, phosphate, or other functionality.

"Alkoxy" refers to the group —OR, where R is a substituted or unsubstituted alkyl group. In certain examples R is a $C_{1-6}$ alkyl group. Methoxy (—$OCH_3$) and ethoxy (—$OCH_2CH_3$) are exemplary alkoxy groups. In a substituted alkoxy, R is substituted alkyl, examples of which useful in the presently disclosed compounds include haloalkoxy groups, such as —$OCF_2H$.

"Alkoxyalkyl" refers to the group -alkyl-OR, where R is a substituted or unsubstituted alkyl group. —$CH_2CH_2$—O—$CH_2CH_3$ is an exemplary alkoxyalkyl group.

"Alkyl" refers to a saturated aliphatic hydrocarbyl group having from 1 to 25 carbon atoms, typically 1 to 10 carbon atoms such as 1 to 6 carbon atoms ($C_1$-$C_6$alkyl). An alkyl moiety may be substituted or unsubstituted. This term includes, by way of example, linear and branched hydrocarbyl groups such as methyl ($CH_3$), ethyl (—$CH_2CH_3$), n-propyl (—$CH_2CH_2CH_3$), isopropyl (—$CH(CH_3)_2$), n-butyl (—$CH_2CH_2CH_2CH_3$), isobutyl (—$CH_2CH(CH_3)_2$), sec-butyl (—$CH(CH_3)(CH_2CH_3)$), t-butyl (—$C(CH_3)_3$), n-pentyl (—$CH_2CH_2CH_2CH_2CH_3$), and neopentyl (—$CH_2C(CH_3)_3$).

"Amino" refers to the group —$NH_2$, —NHR, or —NRR, where each R independently is selected from H, aliphatic, heteroaliphatic, aryl or heterocyclic, or two R groups together with the nitrogen attached thereto form a heterocyclic ring. Examples of such heterocyclic rings include those wherein two R groups together with the nitrogen to which they are attached form a —(CH$_2$)$_{2-5}$— ring optionally interrupted by one or two heteratom groups, such as —O— or —N(R$^g$) such as in the groups

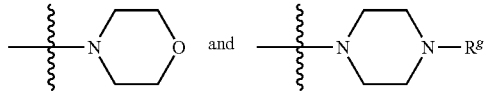

wherein R$^g$ is R$^{70}$, —C(O)R$^{70}$, —C(O)OR$^{60}$ or —C(O)N(R$^{80}$)$_2$.

"Amide" refers to the group —N(H)acyl, or —C(O)amino.

"Aryl" or "aromatic" refers to an aromatic group of, unless specified otherwise, from 5 to 15 ring atoms having a single ring (e.g., phenyl) or multiple fused rings in which at least one ring is aromatic (e.g., naphthyl). For groups having multiple rings, at least one of which is aromatic and one is not, such groups are nevertheless referred to as "aryl" provided that the point of attachment to the remainder of the compound is through an atom of an aromatic portion of the aryl group. Aryl groups may be monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxyl," "carboxy" or "carboxylate" refers to —CO$_2$H, —C(O)O$^-$ or salts thereof.

"Carboxyl ester" or "carboxy ester" refers to the group —C(O)OR, where R is aliphatic, heteroaliphatic, cyclic, and heterocyclic, including aryl and heteroaryl.

"Cyano" refers to the group —CN.

"Cycloaliphatic" refers to a cyclic aliphatic group having a single ring (e.g., cyclohexyl), or multiple rings, such as in a fused, bridged or spirocyclic system, at least one of which is aliphatic, provided that the point of attachment is through an atom of an aliphatic region of the cycloaliphatic group. Cycloaliphatic includes saturated and unsaturated systems, including cycloalkyl, cycloalkenyl and cycloalkynyl. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. An exemplary haloalkyl moiety is CF$_3$.

"Heteroaliphatic" refers to an aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, acyclic or cyclic, such as a heteroalicyclyl group, chiral or achiral, and may include heterocycle, heterocyclyl, heterocycloaliphatic, or heterocyclic groups.

"Heteroaryl" refers to an aryl group where one or more carbon atoms, such as methine (—CH=) or vinylene (—CH=CH—) groups, have been replaced by trivalent or divalent heteroatoms, respectively, in such a way as to maintain aromaticity, such as determined by the continuous, delocalized π-electron system characteristic of the aromatic group, and the number of out of plane π-electrons corresponding to the Hückel rule (4n+2).

"Heterocycloalkyl" and "heterocyclylalkyl" refer to a heterocyclyl moiety attached to the parent structure via an alkyl moiety, for example, (tetrahydropyran-4-yl)methyl, (pyridine-4-yl)methyl, morpholinoethyl or piperazin-1-yl-ethyl.

"Heterocyclyl," "heterocyclo" and "heterocycle" refer to aromatic and non-aromatic ring systems, and more specifically refer to a stable three- to fifteen-membered ring moiety comprising carbon atoms and at least one, such as from one to five heteroatoms. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and the nitrogen, phosphorus, carbon, silicon or sulfur atoms in the heterocyclyl moiety can be optionally oxidized to various oxidation states. For convenience, nitrogens, particularly but not exclusively, those defined as annular aromatic nitrogens, are meant to include their corresponding N-oxide form, although not explicitly defined as such in a particular example. Thus, for a compound having, for example, a pyridyl ring; the corresponding pyridyl-N-oxide is included as another compound of the invention, unless expressly excluded by context. In addition, annular nitrogen atoms can be optionally quaternized. Heterocycle includes heteroaryl moieties, and heteroalicyclyl or heterocycloaliphatic moieties, which are heterocyclyl rings which are partially or fully saturated. Thus a term such as "heterocyclylalkyl" includes heteroalicyclylalkyls and heteroarylalkyls. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO$_2$.

"Phosphate" refers to the group —O—P(O)(OR')$_2$, where each —OR' independently is —OH, —O-aliphatic, such as —O-alkyl, —O-aryl, or —O-aralkyl, or —OR' is —O$^-$M$^+$, where M$^+$ is a counter ion with a single positive charge. Each M$^+$ may be an alkali ion, such as K$^+$, Na$^+$, Li$^+$; an ammonium ion, such as $^+$N(R")$_4$ where R" is H, aliphatic, heterocyclyl or aryl; or an alkaline earth ion, such as [Ca$^{2+}$]$_{0.5}$, [Mg$^{2+}$]$_{0.5}$, or [Ba$^{2+}$]$_{0.5}$. Alkyl phosphate refers to the group -alkylphosphate, such as, for example, —CH$_2$OP(O)(OH)$_2$, or a salt thereof, such as —CH$_2$OP(O)(O$^-$Na$^+$)$_2$.

"Phosphonate" refers to the group —P(O)(OR')$_2$, where each —OR' independently is —OH, —O-aliphatic such as —O-alkyl, —O-aryl, or —O-aralkyl, or where —OR' is —O$^-$M$^+$, and M$^+$ is a counter ion with a single positive charge. Each M⁺ may be an alkali metal ion, such as K⁺, Na⁺, Li⁺; an ammonium ion, such as ⁺N(R")₄ where R" is H, aliphatic, heterocyclyl or aryl; or an alkaline earth metal ion, such as $[Ca^{2+}]_{0.5}$, $[Mg^{2+}]_{0.5}$, or $[Ba^{2+}]_{0.5}$. Alkyl phosphonate refers to the group -alkyl-phosphonate, such as, for example, —CH₂P(O)(OH)₂, or —CH₂P(O)(O⁻Na⁺)₂.

"Patient" or "Subject" refers to mammals and other animals, particularly humans. Thus disclosed methods are applicable to both human therapy and veterinary applications.

"Pharmaceutically acceptable excipient" refers to a substance, other than the active ingredient, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as freund's complete adjuvant or freund's incomplete adjuvant.

"Pharmaceutically acceptable carrier" refers to an excipient that is a carrier or vehicle, such as a suspension aid, solubilizing aid, or aerosolization aid. Pharmaceutically acceptable carriers are conventional. *Remington: The Science and Practice of Pharmacy*, The University of the Sciences in Philadelphia, Editor, Lippincott, Williams, & Wilkins, Philadelphia, Pa., 21ˢᵗ Edition (2005), describes compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the pyrazole compound may be a formate or sodium salt.

"Pharmaceutically effective amount" and "therapeutically effective amount" refer to an amount of a compound sufficient to treat a specified disorder or disease, or to ameliorate or eradicate one or more of its symptoms and/or to prevent the occurrence of the disease or disorder. The amount of a compound which constitutes a "therapeutically effective amount" will vary depending on the compound, the disease state and its severity, the age of the patient to be treated, and the like. The therapeutically effective amount can be determined by a person of ordinary skill in the art.

"Prodrug" refers to compounds that are transformed in vivo to yield a biologically active compound, particularly the parent compound, for example, by hydrolysis in the gut or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—P(O)(OR')$_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —$SO_2$amino, or —$N(R^c)$sulfonyl, where $R^c$ is H, aliphatic, heteroaliphatic, cyclic, and heterocyclic, including aryl and heteroaryl.

"Sulfanyl" refers to the group or —SH, —S-aliphatic, —S-heteroaliphatic, —S-cyclic, —S-heterocyclyl, including —S-aryl and —S-heteroaryl.

"Sulfinyl" refers to the group or moiety —S(O)H, —S(O)aliphatic, —S(O)heteroaliphatic, —S(O)cyclic, —S(O)heterocyclyl, including —S(O)aryl and —S(O)heteroaryl.

"Sulfonyl" refers to the group: —$SO_2$H, —$SO_2$aliphatic, —$SO_2$heteroaliphatic, —$SO_2$cyclic, —$SO_2$heterocyclyl, including —$SO_2$aryl and —$SO_2$heteroaryl.

"Treating" or "treatment" as used herein concerns treatment of a disease or condition of interest in a patient or subject, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substitutents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as the pyrazole and pryidyl rings, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium.

II. IRAK-Active Compounds and Compositions Comprising IRAK-Active Compounds

A. Pyrazoles

Disclosed herein are pyrazole compounds, methods of making the compounds, and methods of using the compounds. In one embodiment the disclosed compounds are tyrosine kinase inhibitors. In a particular embodiment the compounds useful in blocking one or more cytokine signaling pathways, such as the IL-17 signaling pathway. For certain embodiments, the pyrazole compounds are useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3 or IRAK4.

Exemplary pyrazole compounds within the scope of the present invention have a general formula 1

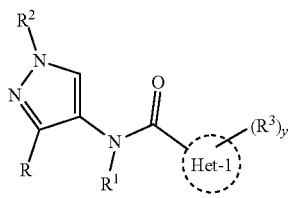

1 or salts, prodrugs, N-oxides or solvates thereof, wherein the compounds are not a compound disclosed in WO 2011/043371. With reference to formula 1, R is aliphatic, including alkyl; heteroaliphatic; heteroaryl; aryl; CN; halo; or amide. In some embodiments, R is alkyl, particularly $CF_3$, heteroaryl, amide or CN. $R^1$ is H, aliphatic or heteroaliphatic. Alternatively, R and $R^1$, together with the atoms to which they are attached, form a ring, such as a heterocyclyl ring, having 3, 4, 5, 6, 7, 8 or more ring atoms, particularly 5, 6, or 7 ring atoms. Het-1 is heteroaryl, and may comprise a single ring or multiple rings, such as in a fused ring system. $R^2$ is H; aliphatic, including alkyl, alkenyl, alkynyl, cycloalkyl, and cycloalkenyl; heteroaliphatic; heterocyclyl, including heteroaryl and heterocycloaliphatic; amide; aryl; or araliphatic. y is from 1 to the number of possible substituents on the particular system in question, such as from 1 to 2, 3, 4, 5, or at least 6. Each $R^3$ independently is H; aliphatic, including alkyl, alkenyl, alkynyl, cycloalkyl, cycloalkenyl and cycloalkynyl; halogen; heteroaliphatic; —O-aliphatic, such as alkoxy; heterocyclyl, including heteroaryl and heterocycloaliphatic; aryl; araliphatic; —O-heterocyclyl; hydroxyl; nitro; cyano; carboxyl; carboxyl ester; acyl; amide; amino; sulfonyl; sulfonamide; sulfanyl; sulfinyl; haloalkyl; alkylphosphate; or alkylphosphonate. Het-1 can be unsubstituted (if $R^3$ is H for all occurrences on that particular moiety) or substituted. In some embodiments of formula I, $R^3$ is not pyridinyl. In other embodiments, $R^3$ is not pyridinyl, thiophenyl, furyl, pyrazinyl, quinolinyl, or pyrrolopyridinyl.

For certain embodiments of formula 1, Het-1 may be a 5- or 6-membered heteroaryl. In some embodiments, Het-1 is a 5-membered heteroaryl ring. In particular examples, Het-1 is furan; thiophene; pyrazole; pyrrole; imidazole; oxazole; thiazole; isoxazole; isothiazole; triazole, such as 1,2,3-triazole, 1,2,4-triazole, or 1,3,4-triazole; oxadiazole, such as 1,2,3-oxadiazole, 1,2,4-oxadiazole, 1,3,4-oxadiazole, or 1,2,5-oxadiazole; thiadiazole, such as 1,2,3-thiadiazole, 1,2,4-thiadiazole, 1,3,4-thiadiazole, or 1,2,5-thiadiazole; or tetrazole. In particular examples, Het-1 is furan, thiazole or oxazole, such as furan-2-yl, furan-3-yl, thiazol-2-yl, thiazol-4-yl, thiazol-5-yl, oxazol-2-yl, oxazol-4-yl or oxazol-5-yl.

In some embodiments of formula 1, $R^2$ is H, alkyl, cycloaliphatic, typically cycloalkyl, such as cyclopropyl, cyclobutyl, cyclopentyl or cyclohexyl, heteroaliphatic, or heterocycloaliphatic. In some examples, $R^2$ may be substituted with a hydroxyl group.

In some embodiments, $R^1$ is $R^a$, —$(CR^aR^a)_m$—O—$R^a$, —$(CH_2)_m$—O—$R^a$, —$(CR^aR^a)_m$—O—$(CR^aR^a)_m$—O—$R^a$, —$[(CH_2)_m$—O—$]_n$—$R^a$ or —$(CH_2)_m$—O—$(CH_2)_m$—O—$R^a$ wherein each m and n independently are 1, 2 or 3;

$R^2$ is $R^a$, $R^b$, $R^a$ substituted with 1, 2, or 3 $R^b$, $R^a$ substituted with $R^b$ and $R^c$, $R^a$ substituted with $R^c$, $(CR^aR^a)_n$—$R^a$, —$(CH_2)_n$—$R^a$, —$(CR^aR^a)_n$—$R^b$, —$(CH_2)_n$—$R^b$, —$[(CH_2)_m$—O—$]_n$—$R^a$, —$[(CH_2)_m$—O—$]_n$—$[R^a$ substituted with 1, 2 or 3 $R^b$], or —$(CH_2)_m$—O—$(CH_2)_m$—O—$R^a$ wherein each m and n independently are 1, 2 or 3;

$R^a$ is independently for each occurrence H, D, $C_{1-6}$alkyl, $C_{3-6}$cycloalkyl, $C_{3-6}$cycloalkenyl or $C_{3-6}$heteroalicyclyl;

$R^b$ is independently for each occurrence —OH, —$CF_3$, —$OR^c$, —$NR^dR^d$, —C(O)OH, —C(O)$R^c$, —C(O)$OR^c$, —C(O)$NR^dR^d$ or halogen;

$R^c$ is independently for each occurrence $C_{1-6}$alkyl, $C_{3-6}$cycloalkyl, $C_{3-6}$heteroalicyclyl, aralkyl, $C_{1-6}$alkyl substituted with 1, 2 or 3 $R^e$, $C_{3-6}$cycloalkyl substituted with 1, 2 or 3 $R^e$, or $C_{3-6}$heteroalicyclyl substituted with 1, 2 or 3 $R^e$;

$R^d$ is independently for each occurrence H, $C_{1-6}$alkyl optionally substituted with 1, 2 or 3 $R^e$, $C_{3-6}$cycloalkyl optionally substituted with 1, 2 or 3 $R^e$, or two $R^d$ groups together with the nitrogen bound thereto form a $C_{3-6}$heteroalicyclyl moiety optionally substituted with $C_{1-6}$alkyl and optionally interrupted with one or two —O— or N($R^g$) wherein $R^g$ is $R^{70}$, —C(O)$R^{70}$, —C(O)O$R^{60}$ or —C(O)N($R^{80}$)$_2$; and $R^e$ is independently for each occurrence halogen, $C_{1-6}$alkyl, $C_{3-6}$cycloalkyl, $C_{3-6}$heteroalicyclyl, $C_{1-6}$alkyl-OH, —$OR^a$, —OC(O)$R^a$ or —O-aralkyl.

With respect to formula 1, Het-1 may be: 1A) a 5-membered heteroaryl; 1B) a 6-membered heteroaryl; 1C) selected from furan, thiazole, or oxazole; 1D) furan; 1E) oxazole; 1F) thiazole; 1G) furan-2-yl; 1H) furan-2-yl substituted at least at the 5-position; 1I) furan-2-yl substituted at least at the 5-position with a heteroaryl moiety; 1J) oxazol-4-yl; 1K) oxazol-4-yl substituted at least at the 2-position; 1L) oxazol-4-yl substituted at least at the 2-position with a heteroaryl moiety; 1M) 2-(pyrazol-4-yl)oxazol-4-yl; 1N) 2-((1-cyclopropylmethyl)pyrazol-4-yl)oxazol-4-yl; 1O) thiazol-4-yl; 1P) thiazol-4-yl substituted at least at the 2-position; or 1Q) thiazol-4-yl substituted at least at the 2-position with a heteroaryl moiety.

With respect to Het-1 embodiments 1A to 1Q, R may be, in combination with 1A to 1Q: 2A) heteroaryl; 2B) aliphatic; 2C) a 5-membered heteroaryl; 2D) a 6-membered heteroaryl; 2E) an alkyl; 2F) amide; 2G) —$CF_3$; 2G) —CN; 2H) —C(O)$NH_2$; 2I) selected from pyridine, thiazole, oxadiazole, pyrazine, or pyrimidine; 2J) thiazol-2-yl; 2K) pyrimidin-2-yl; 2L) pyridin-2-yl; 2M) pyrazine-2-yl; 2N) oxadiazol-2-yl; 2O) 5-morpholinylpyridin-2-yl; 2P) 5-(N-methylpiperidin-1-yl)pyridine-2-yl; 2Q) 5-(2-hydroxy-2-methylpropoxy)pyridin-2-yl; 2R) 5-(oxetan-3-yloxy)pyridin-2-yl; 2S) 5-methoxypyridin-2-yl; 2T) 3-fluoropyrid-2-yl; 2U) 1,3,4-oxadiazol-2-yl; 2V) 5-trifluoromethylpyridin-2-yl; 2W) 3-trifluoromethylpyridin-2-yl; 2X) 6-trifluoromethylpyridin-2-yl; 2Y) 5-fluoropyrid-2-yl; 2Z) 4-fluoropyrid-2-yl; or 2AA) 6-fluoropyrid-2-yl; 3,6-difluoropyridin-2-yl.

A person of ordinary skill in the art will understand that any of 2A to 2AA may be combined with any of 1A to 1Q, to form any and all combinations between such substituents.

With respect to the Het-1 embodiments 1A to 1Q and the R embodiments 2A to 2AB, $R^1$ is, in combination with 1A to 1Q and 2A to 2AA: 3A) aliphatic; 3B) heteroaliphatic; 3C) H; or 3D) —$CH_2CH_2OCH_2CH_2OCH_3$.

Alternatively, with respect to the Het-1 embodiments 1A to 1Q, R and $R^1$ together form combined embodiment 3E) a 6-membered heterocyclyl ring that comprises the atoms to which R and $R^1$ are attached.

A person of ordinary skill in the art will understand that any of 3A to 3E may be combined with any of 1A to 1Q, and any of 2A to 2AA, where appropriate, to form any and all combinations between such substituents.

With respect to the Het-1 embodiments 1A to 1Q, the R embodiments 2A to 2AA and the $R^1$ embodiments 3A to 3D, or the combined R and $R^1$ embodiment 3E, $R^2$ may be, in any combination with 1A to 1Q, and 2A to 2AA and 3A to 3D, or 3E: 4A) H, aliphatic, heteroaliphatic, heterocyclyl, aryl, amide or araliphatic; 4B) H, alkyl, cycloalkyl, cycloalkenyl or heterocycloaliphatic; 4C) heterocycloaliphatic; 4D) alkyl; 4E) cycloalkyl substituted with O-alkyl, N(alkyl)$_2$, OH, halogen, heterocyclyl, or a combination thereof; 4F) tetrahydropyran, oxetane, tetrahydrofuran or azetidine; 4G) cyclobutyl, cyclopentyl, cyclohexyl, or cyclobutenyl; 4H) —C$_{1-6}$alkyl-O—C$_{1-6}$alkyl or —C$_{1-6}$alkyl-O—C$_{1-6}$alkyl-O—C$_{1-6}$alkyl; 4I) —CH$_2$CH$_2$OCH$_2$CH$_2$OCH$_3$; 4J) —CH$_2$CH$_2$OCH$_2$CH$_3$; 4K) —CH$_2$CH$_2$OCH$_2$CH$_2$F; 4L) —CH$_2$CH$_2$OCH$_2$CHF$_2$; 4M) —CH$_2$CH$_2$OCH$_2$CF$_3$; 4N) H; 4O) CH$_2$C(CH$_3$)$_2$OH; 4P) CH$_2$CH$_2$OCH$_3$; 4Q) CH$_2$CH$_2$OH; 4R) —CH$_2$CF$_3$; 4S) —CHF$_2$; 4T) —CH$_2$CH(OH)CF$_3$; 4U) —CH$_2$(OH)(CF$_3$)$_2$; 4V) —C(O)N(CH$_3$)$_2$; 4W) —C(O)N(Et)$_2$; 4X) —C(O)-morpholine; 4Y) benzyl; 4Z) 3-fluorocyclobut-2-en-1-yl; 4AA) 3,3-difluorocyclobut-1-yl; 4AB) tetrahydropyran-4-yl; 4AC) oxetan-3-yl; 4AD) (1r, 3r)-3-ethoxycyclobutyl; 4AE) (1s, 3s)-3-ethoxycyclobutyl; 4AF) (1s, 3s)-3-hydroxycyclobutyl; 4AG) (1r, 3r)-3-hydroxycyclobutyl; 4AH) (1s, 3s)-3-dimethylaminocyclobutyl; 4AI) (1r, 3r)-3-dimethylaminocyclobutyl; 4AJ) (3-methyloxetan-3-yl)methyl; 4AK) methyl; 4AL) 1-(tert-butoxycarbonyl)azetidin-3-yl; 4AM) 3-methoxycyclobutyl; 4AN) (1r, 3r)-3-methoxycyclobutyl; 4AO) (1s, 3s)-3-methoxycyclobutyl; 4AP) 3-benzyloxycyclobutyl; 4AQ) azetidin-3-yl; 4AR) 1-acetoxyazetidin-3-yl; 4AS) 1-(tert-butylcarbamoyl)azetidin-3-yl; 4AT) 1-(propylcarbamoyl)azetidin-3-yl; 4AU) 1-(cyclopropylcarbamoyl)azetidin-3-yl; 4AV) 1-(cyclopropanecarbonyl)azetidin-3-yl; 4AW) 1-(tert-butylcarbonyl)azetidin-3-yl; 4AX) 1-(pyrrolidine-1-carbonyl)azetidin-3-yl; 4AY) 1-(isopropanecarbonyl)azetidin-3-yl; 4AZ) 1-(2,2,2-trifluoroethyl)azetidin-3-yl; 4BA) 1-methylazetidin-3-yl; 4BB) 1-(2,2-difluorocyclopropane-1-carbonyl)azetidin-3-yl; 4BC) isopropyl; 4BD) 2-morpholinoethyl; 4BE) (4-methylpiperazin-1-yl)ethyl; 4BF) tetrahydropyran-3-yl; 4BG) (tetrahydropyran-4-yl)methyl; 4BH) (3-(hydroxymethyl)oxetan-3-yl)methyl; 4BI) 2-(diethylamino)ethyl; 4BJ) 2-fluoroethyl; 4BK) (1R, 3R)-3-hydroxycyclopentyl; 4BL) (1R, 3S)-3-hydroxycyclopentyl; 4BM) (1S, 3R)-3-hydroxycyclopentyl; 4BN) (1S, 3S)-3-hydroxycyclopentyl; 4BO) 1,4-dioxaspiro[4,5]decan-8-yl; 4BP) (1s, 3s)-3-(2-fluoroethoxy)cyclobutyl; 4BQ) (1r, 3r)-3-(2-fluoroethoxy)cyclobutyl; 4BR) (1s, 3s)-3-(2-trifloroethoxy)cyclobutyl; 4BS) (1r, 3r)-3-(2-trifloroethoxy)cyclobutyl; 4BT) (1s, 3s)-3-isopropoxycyclobutyl; 4BU) (1r, 3r)-3-isopropoxycyclobutyl; 4BV) (1r, 3r)-3-hydroxy-3-methylcyclobutyl; 4BW) (1s, 3s)-3-hydroxy-3-methylcyclobutyl; 4BX) (1s, 3s)-3-ethoxy-d$_5$)cyclobutyl; 4BY) (1r, 3r)-3-ethoxy-d$_5$)cyclobutyl; 4BZ) (1R, 3R)-3-ethoxycyclopentyl; 4CA) (1R, 3S)-3-ethoxycyclopentyl; 4CB) (1S, 3R)-3-ethoxycyclopentyl; 4CC) (1S, 3S)-3-ethoxycyclopentyl; 4CD) (1R, 3R)-3-hydroxycyclohexyl; 4CE) (1S, 3S)-3-hydroxycyclohexyl; 4CF) (1R, 3R)-3-ethoxycyclohexyl; 4CG) (1S, 3S)-3-ethoxycyclohexyl; 4CH) (1R, 3S)-3-ethoxy-2-fluorocyclobutyl; 4CI) (1S, 3S)-3-ethoxy-2-fluorocyclobutyl; 4CJ) (1R, 3R)-3-ethoxy-2-fluorocyclobutyl; 4CK) (1S, 3R)-3-ethoxy-2-fluorocyclobutyl; or 4CL) tetrahydrofuran-3-yl.

A person of ordinary skill in the art will understand that any of 4A to 4CL may be combined in Formula 1 with any of 1A to 1Q, any of 2A to 2K and any of 3A to 3D, or 3E, to form any and all combinations between such substituents.

In some embodiments, R is heteroaryl, leading to compounds having formula 2

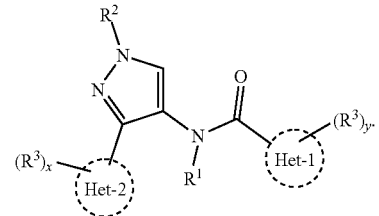

2

With respect to formula 2, Het-2 is a heteroaryl, and may comprise a single ring or multiple rings, such as in a fused ring system. x is from 1 to the number of possible substituents on the particular system in question, such as from 1 to 2, 3, 4, 5, or at least 6, and each $R^3$ independently is as previously defined for formula 1. Het-2 can be unsubstituted (if $R^3$ is H for all occurrences on that particular moiety) or substituted. In particular embodiments of formula 2, Het-2 is not tetrazolyl or oxadiazolyl.

Het-2 may be a 5- or 6-membered heteroaryl. In some examples, Het-2 is furan; thiophene; pyrazole; pyrrole; imidazole; oxazole; thiazole; isoxazole; isothiazole; triazole, such as 1,2,3-triazole, 1,2,4-triazole, or 1,3,4-triazole; oxadiazole, such as 1,2,3-oxadiazole, 1,2,4-oxadiazole, 1,3,4-oxadiazole or 1,2,5-oxadiazole; thiadiazole, such as 1,2,3-thiadiazole, 1,2,4-thiadiazole, 1,3,4-thiadiazole or 1,2,5-thiadiazole; tetrazole; pyrimidine; pyridine; triazine, such as 1,2,3-triazine, 1,2,4-triazine or 1,3,5-triazine; pyrazine; or pyridazine. In particular examples, Het-2 is: pyridine, such as pyrid-2-yl, pyrid-3-yl or pyrid-4-yl; pyrimidine, such as pyramidin-2-yl; pyramidin-4-yl or pyramidin-5-yl; pyrazine, such as pyrazine-2-yl; or thiazole, such as thiazol-2-yl, thiazol-4-yl or thiazol-5-yl.

In some embodiments of formula 2, Het-1 is a substituted heteroaryl. In some embodiments, Het-1 is substituted with at least a heterocycle moiety, leading to compounds having formula 3

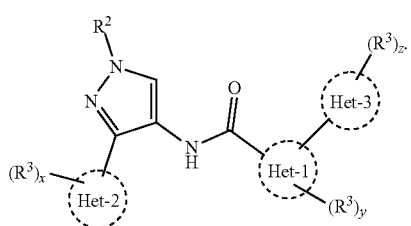

3

With reference to formula 3, Het-1, R, Het-2, $R^2$, $R^3$, x and y are as defined above for formulas 1 and 2. Het-3 is a heterocycle, and may be unsubstituted (if $R^3$ is H for all occurrences on Het-3) or substituted. z is from 1 to the number of possible substituents on the particular system in question, such as from 1 to 2, 3, 4, 5, or at least 6.

In some embodiments of formula 3, Het-3 is a 5- or 6-membered heterocycle, such as a 5- or 6-membered heteroaryl or heteroalicyclyl moiety. In some embodiments, Het-3 is furan; thiophene; pyrazole, such as pyrazol-3-yl, or pyrazol-4-yl; pyrrole; imidazole; oxazole; thiazole; isoxazole; isothiazole; triazole, such as 1,2,3-triazole, 1,2,4-triazole, or 1,3,4-triazole; oxadiazole, such as 1,2,3-oxadiazole, 1,2,4-oxadiazole, 1,3,4-oxadiazole or 1,2,5-oxadiazole; thiadiazole, such as 1,2,3-thiadiazole, 1,2,4-thiadiazole, 1,3,4-thiadiazole or 1,2,5-thiadiazole; tetrazole; pyrimidine; pyridine; triazine, such as 1,2,3-triazine, 1,2,4-triazine or 1,3,5-triazine; pyrazine; or pyridazine. In some embodiments, Het-3 is not pyridinyl. In certain embodiments, Het-3 is not pyridinyl, thiophenyl, furyl, pyrazinyl, quinolinyl, or pyrrolopyridinyl. In particular embodiments, Het-3 is pyrazole, and may be pyrazol-4-yl. Each of $R^3$ independently may be H, aliphatic, alkoxy, heteroaliphatic, carboxyl ester, araliphatic, such as aralkyl, $NO_2$, CN, OH, haloalkyl, such as $CF_3$, alkyl phosphate or alkylphosphonate.

With respect to formula 3 and any of the Het-1 embodiments 1A to 1Q, any of the R embodiments 2A to 2AB, any of the $R^1$ embodiments 3A to 3D, or the combined R and $R^1$ embodiment 3E, and any of the $R^2$ embodiments 4A to 4CL, Het-3 may be, in any combination with 1A to 1Q, 2A to 2AB, 3A to 3D, or 3E, and 4A to 4CL: 5A) a 5-membered heteroaryl; 5B) a 6-membered heteroaryl; 5C) pyrazole; 5D) pyrrole; 5E) pyrazol-4-yl; 5F) pyrrol-3-yl; 5G) 5-nitropyrrol-3-yl; 5H) 1-methylpyrazol-4-yl; 5I) 1-(tert-butoxycarbonyl)pyrazol-4-yl; 5J) 3-methylpyrazol-4-yl; 5K) 1-(((di-tert-butoxyphosphoryl)oxy)methyl)pyrazol-4-yl; 5L) 1-(((tert-butoxy(hydroxy)phosphoryl)oxy)methyl)pyrazol-4-yl; 5M) 1-((phosphonooxy)methyl)pyrazol-4-yl; 5N) 3-trifluoromethylpyrazol-4-yl; 5O) 1-((1-(isobutyryloxy)ethoxy)carbonyl)pyrazol-4-yl; 5P) 1-((tert-butoxycarbonyl)-D-valyl)pyrazol-4-yl; 5Q) 1-((1-methylcyclopropoxy)carbonyl)pyrazol-4-yl; 5R) 1-(((1-((4-methoxybenzyl)oxy)-2-methylpropan-2-yl)oxy)carbonyl)pyrazol-4-yl; 5S) 1-((phosphonooxy)methyl)pyrazol-4-yl sodium salt; 5T) 1-ethylpyrazol-4-yl; 5U) 1-isopentylpyrazol-4-yl; 5V) 1-((3-methyloxetan-3-yl)methyl)pyrazol-4-yl; 5W) 1-(2-(2-methoxyethoxy)ethyl)pyrazol-4-yl; 5X) 3,5-dimethylpyrazol-4-yl; 5Y) 1-((5-methyl-2-oxo-1,3-dioxol-4-yl)methyl)pyrazol-4-yl; 5Z) 1-((diethoxyphosphoryl)methyl)pyrazol-4-yl; 5AA) 1-(phosphonomethyl)pyrazol-4-yl; 5AB) 1-(phosphonomethyl)pyrazol-4-yl sodium salt; 5AC) 1-((phosphonooxy)methyl)pyrazol-4-yl potassium salt; 5AD) 1-(4-methoxybenzyl)pyrazol-4-yl; 5AE) pyrazol-3-yl; 5AF) 1-(cyclobutyl)pyrazol-4-yl; 5AG) 5-fluoro-1-((2-(trimethyl-$\lambda^4$-sulfanyl)ethoxy)methyl)-pyrazol-4-yl; 5AH) 5-fluoropyrazol-4-yl; 5AI) 1-((phosphonooxy)methyl)pyrazol-4-yl calcium salt; 5AJ) 1-((phosphonooxy)methyl)pyrazol-4-yl ammonium salt; 5AK) 1-((phosphonooxy)methyl)pyrazol-4-yl lysine salt; 5AL) 1-((phosphonooxy)methyl)pyrazol-4-yl arginine salt; 5AM) 1-((phosphonooxy)methyl)pyrazol-4-yl tris(hydroxymethyl)aminomethane salt; 5AN) 1-((phosphonooxy)methyl)pyrazol-4-yl triethylamine salt; 5AO) 1-(2,2,2-trifluoroethyl)pyrazol-4-yl; or 5AP) 1-difluoromethylpyrazol-4-yl.

A person of ordinary skill in the art will understand that any of 5A to 5AP may be combined with any of 1A to 1Q, any of 2A to 2AB and any of 3A to 3D, or 3E, and any of 4A to 4CL, to form any and all combinations between such substituents.

In some embodiments of formula 3, Het-2 is pyridine, leading to compounds having formula 4

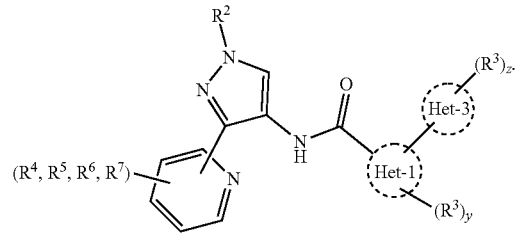

In certain embodiments of formula 4, the pyridine ring is 2-pyridyl, leading to compounds having formula 5

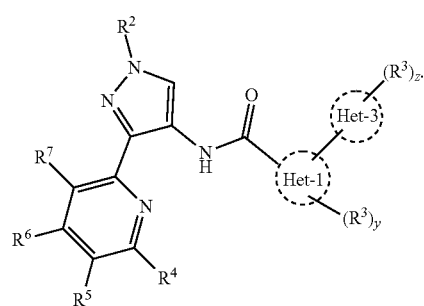

With reference to formula 4 and formula 5, $R^4$-$R^7$ are each independently H, aliphatic, heteroaliphatic, alkoxy, heterocyclyl, aryl, araliphatic, —O-heterocyclyl, hydroxyl, haloalkyl, halogen, nitro, cyano, carboxyl, carboxyl ester, acyl, amide, amino, sulfonyl, sulfonamide, sulfanyl or sulfinyl. In some embodiments, $R^4$-$R^7$ are each independently H, aliphatic, halogen, haloalkyl, heteroaliphatic, alkoxy, heterocyclyl, or —O-heterocyclyl. In particular embodiments, $R^4$-$R^7$ may be independently H, halogen, haloalkyl, alkyl, heterocyclyl, alkoxy, or —O-heterocyclyl. In one embodiment of the compounds according to formulas 4 and 5, at least one of $R^4$-$R^7$ is not H, for example, in one embodiment $R^4$ is not H.

In certain embodiments, each of $R^4$, $R^5$, $R^6$, and $R^7$ independently is $R^a$, $R^b$, $R^a$ substituted with $R^c$, —$OR^a$, —O—$(CR^aR^a)_p$—$R^b$ wherein p is 1, 2 or 3, and $R^a$, $R^b$ and $R^c$ are as previously defined. In specific examples, $R^5$ is H, F, $CF_3$, methoxy, morpholin-4-yl, 1-methylpiperidin-4-yl, —O—$CH_2C(CH_3)_2OH$, or —O-(oxetan-3-yl), and/or $R^4$, $R^6$ and $R^7$ are H, F or $CF_3$.

In some embodiments of formula 4, Het-3 is a pyrazole, leading to compounds having a general formula 6

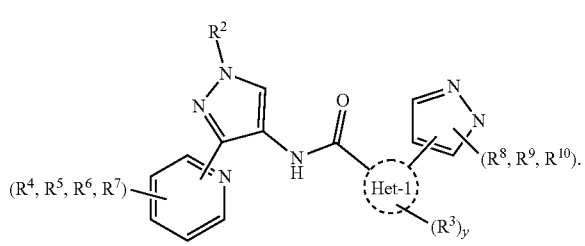

Certain embodiments of formula 6 further satisfy formula 7

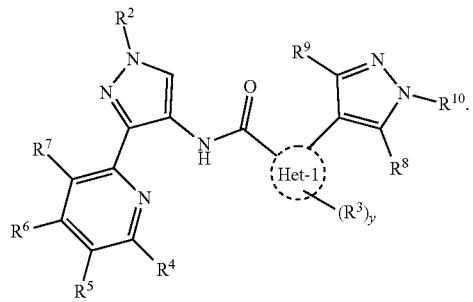

7

With reference to formula 6 and formula 7, $R^2$-$R^7$ and Het-1 are as previously defined for formula 5; $R^8$, $R^9$ and $R^{10}$ are each independently H, aliphatic, heteroaliphatic, aryl, —O-aliphatic, such as alkoxy, araliphatic, such as aralkyl, heterocyclyl, sulfonyl, nitro, OH, haloalkyl, carboxyl ester, cyano, acyl, amino, alkyl phosphate or alkylphosphonate. $R^{10}$ may be H, aliphatic, —O-aliphatic, such as alkoxy, heteroaliphatic, carboxyl ester, acyl, araliphatic, such as aralkyl, $NO_2$, CN, OH, haloalkyl, such as $CF_3$, alkyl phosphate or alkylphosphonate. In particular examples, $R^{10}$ is H, alkyl, carboxyl ester, acyl, alkyl phosphate, alkyl phosphonate, heterocycloalkyl or aralkyl. In certain examples, $R^8$ and $R^9$ are each independently, H, alkyl or haloalkyl, such as trifluoromethyl. In certain embodiments, Het-1 is furan, thiazole or oxazole, and in particular embodiments, $R^8$ and $R^9$ are both H, one of $R^8$ and $R^9$ is H and the other is lower alkyl, such as methyl, or trifluoromethyl, or both of $R^8$ and $R^9$ are lower alkyl.

In some embodiments of formulas 6-7, $R^{10}$ is $R^a$, $R^b$, $R^a$ substituted with —OP(O)($R^f$)$_2$, $R^a$ substituted with 1, 2 or 3 $R^b$, $R^a$ substituted with $R^c$, $R^a$ substituted with —P(O)($R^f$)$_2$, aralkyl, —(CR$^a$R$^a$)$_n$—R$^a$, —(CH$_2$)$_n$—R$^a$ or —C(O)C(R$^a$)$_2$NR$^a$R$^b$, wherein n, $R^a$, $R^b$ and $R^c$ are as previously defined, and $R^f$ is independently for each occurrence —OR$^a$, —O$^-$M$^+$ where each M$^+$ independently is an alkali metal ion, such as K$^+$, Na$^+$, Li$^+$ or an ammonium ion, such as $^+$NH$_4$ or $^+$N(R$^a$)$_4$, or —O$^-$[M$^{2+}$]$_{0.5}$ where M$^{2+}$ is an alkaline metal earth ion, such as Mg$^{2+}$, Ca$^{2+}$ or Ba$^{2+}$. In certain examples of the compounds of formulas 6-7, $R^{10}$ is —CH$_2$OP(O)(OH)$_2$, or a salt thereof.

In other embodiments of formula 5, Het-1 is furan, thiazole or oxazole, such as furan-2-yl, furan-3-yl, thiazol-2-yl, thiazol-4-yl, thiazol-5-yl, oxazol-2-yl, oxazol-4-yl or oxazol-5-yl. In certain embodiments, the compound has a general formula selected from

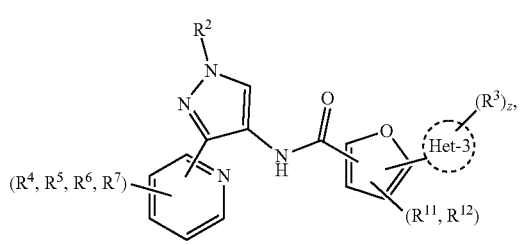

8

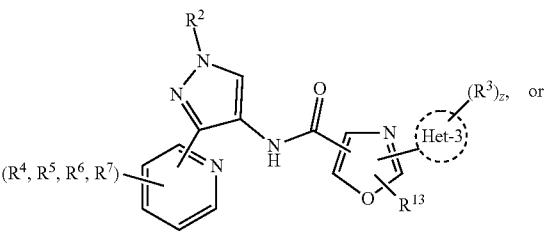

9

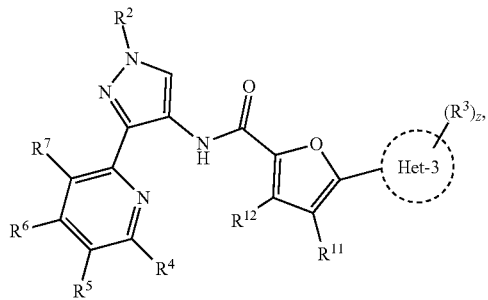

10

With reference to formulas 8, 9 and 10, $R^2$-$R^7$, Het-3 and z are as previously defined for formula 5; and $R^{11}$-$R^{14}$ are each independently H, aliphatic, heteroaliphatic, aryl, heterocyclyl, sulfonyl, nitro, carboxyl ester, cyano or amino. In certain embodiments, the compound has a formula selected from

11

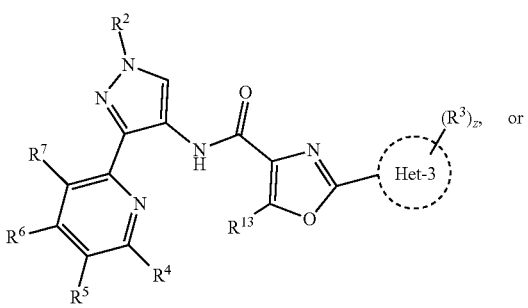

12

-continued

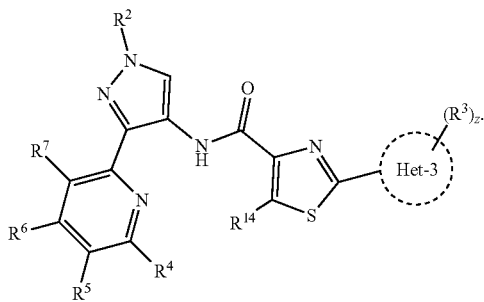

13

With reference to formulas 11, 12 and 13, $R^2$-$R^7$, z and Het-3 are as previously defined for formula 5; $R^{11}$-$R^{14}$ may be each independently H, $C_{1-6}$alkyl, $CF_3$, acyl, CN, or OH. In certain examples, $R^{11}$, $R^{12}$, $R^{13}$ and $R^{14}$ are each independently H or alkyl, and in particular examples, $R^{11}$, $R^{12}$, $R^{13}$ and $R^{14}$ are H.

In some embodiments of formulas 8-13, Het-3 is a pyrazole, such as a pyrazol-1-yl, pyrazol-3-yl, pyrazol-4-yl or pyrazol-5-yl. In particular embodiments, the compound has a formula selected from

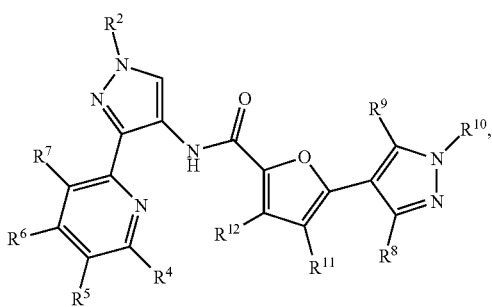

14

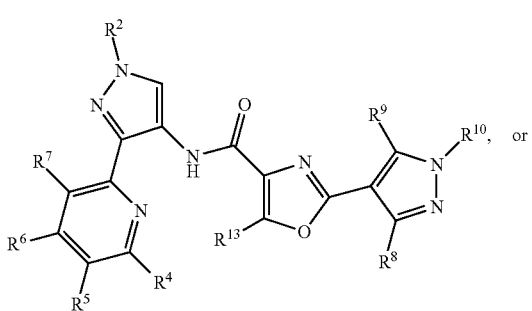

15

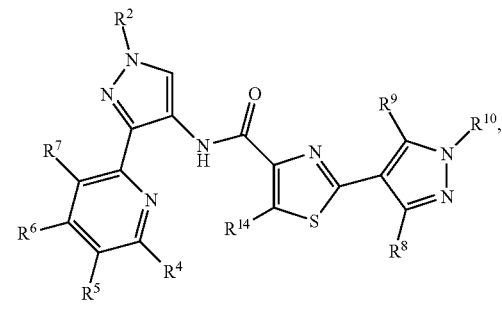

16 where $R^2$-$R^{10}$ are as defined with respect to formula 7.

In certain embodiments of formula 1, R and $R^1$ together with the atoms to which they are attached, form a heterocylyl ring. In certain embodiment of formula 1, compounds have a formula selected from

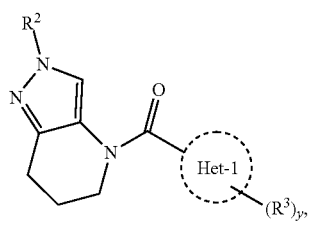

17

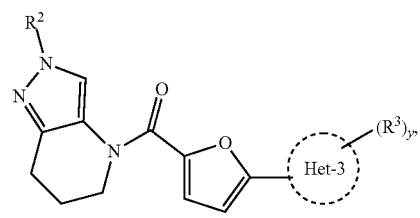

18

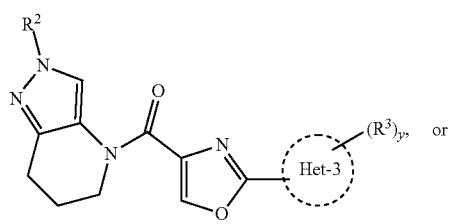

19

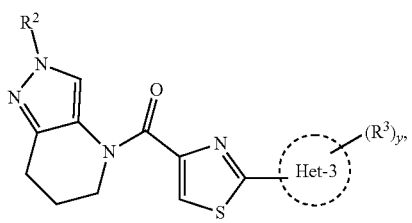

20 wherein Het-3 is heteroaryl.

In other embodiments of formula 1, R is aliphatic, such as alkyl, particularly $CF_3$; CN; or amide. In certain embodiments of formula 1, compound may have a formula selected from

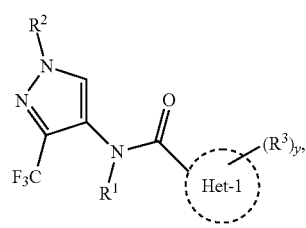

21

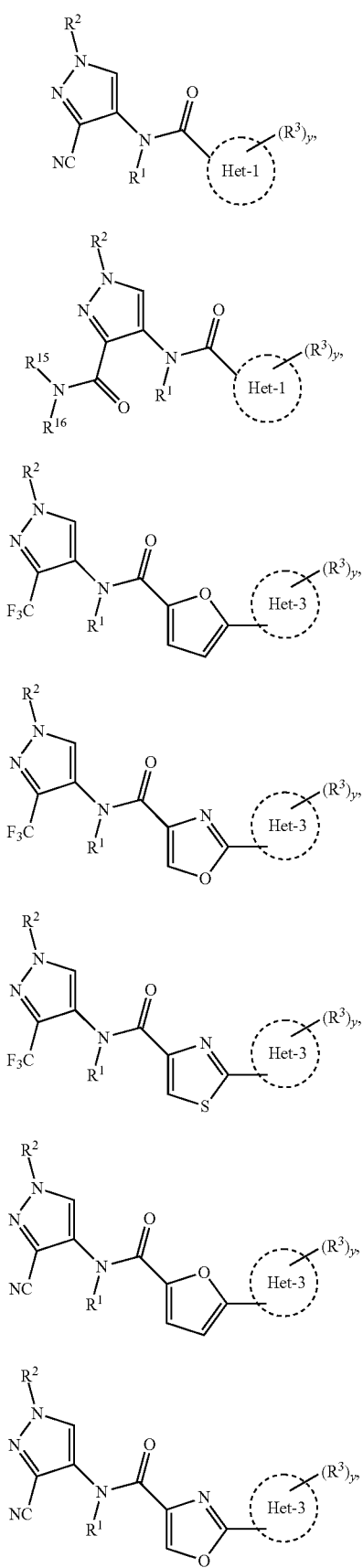
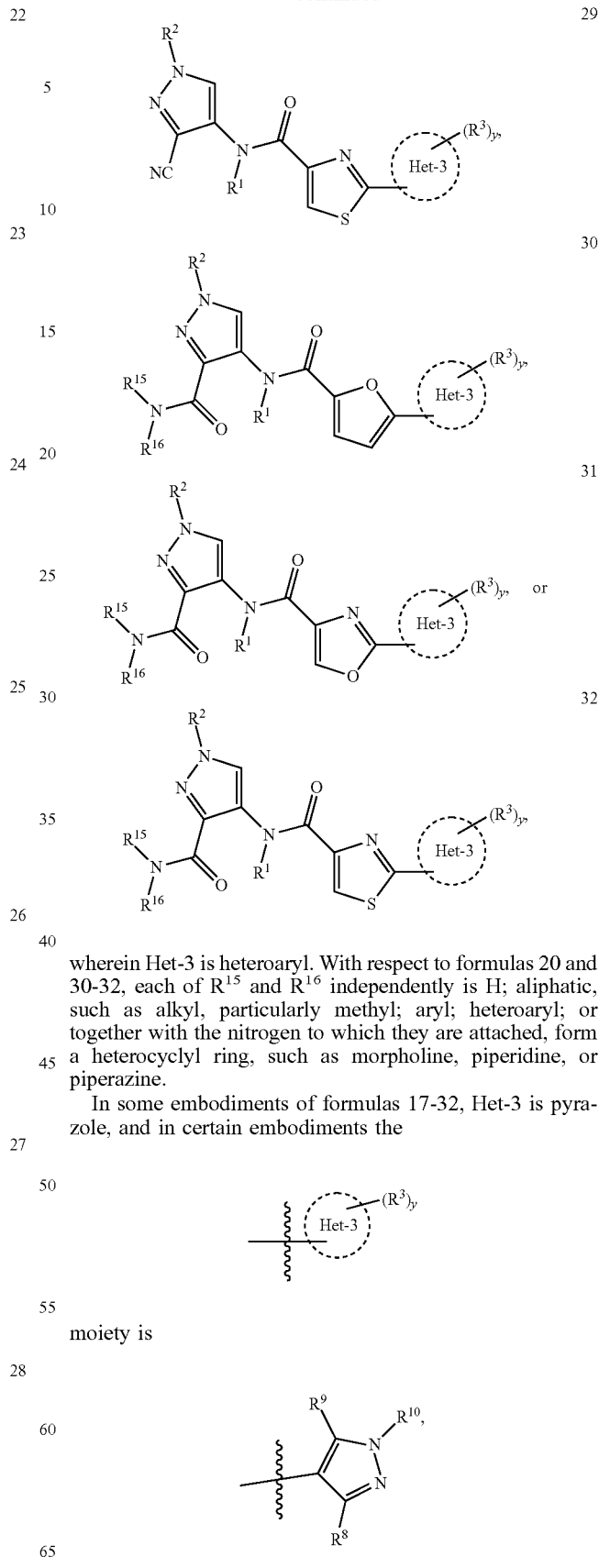

wherein Het-3 is heteroaryl. With respect to formulas 20 and 30-32, each of $R^{15}$ and $R^{16}$ independently is H; aliphatic, such as alkyl, particularly methyl; aryl; heteroaryl; or together with the nitrogen to which they are attached, form a heterocyclyl ring, such as morpholine, piperidine, or piperazine.

In some embodiments of formulas 17-32, Het-3 is pyrazole, and in certain embodiments the

moiety is

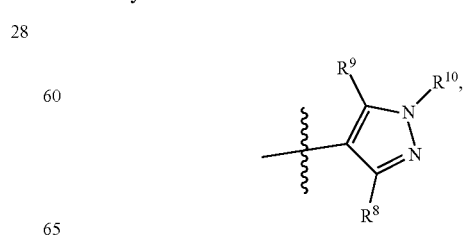

where $R^8$, $R^9$ and $R^{10}$ are as previously defined.

In certain embodiments of any of the above formulas, $R^4$, $R^6$, $R^7$ are H, halogen, or haloalkyl; $R^5$ is H, halogen, haloalkyl, alkoxy or $N(R^dR^d)$ where each $R^d$ independently is as previously defined; $R^{11}$, $R^{12}$, $R^{13}$ and $R^{14}$ are H; and $R^8$ and $R^9$ are both H, or one of $R^8$ and $R^9$ is H and the other is methyl or trifluoromethyl, or both of $R^8$ and $R^9$ are methyl. In some embodiment, each of $R^4$, $R^5$, $R^6$, and $R^7$ independently is H, F or $CF_3$.

Some exemplary compounds according to formula 1 include:

I-1

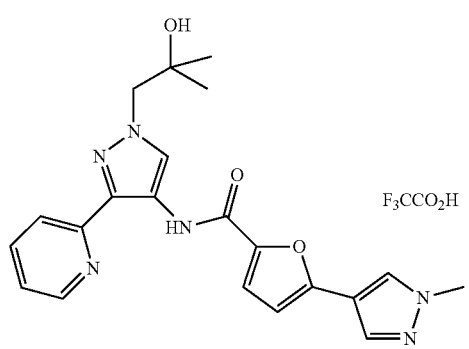

I-2

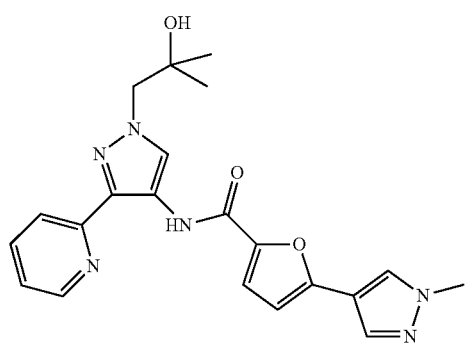

I-3

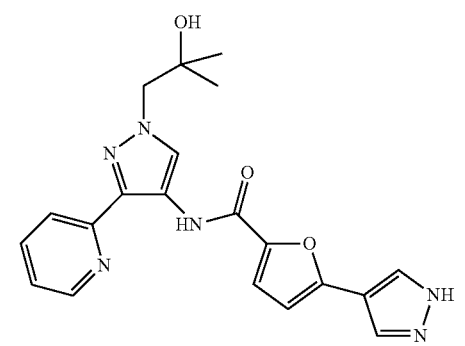

I-4

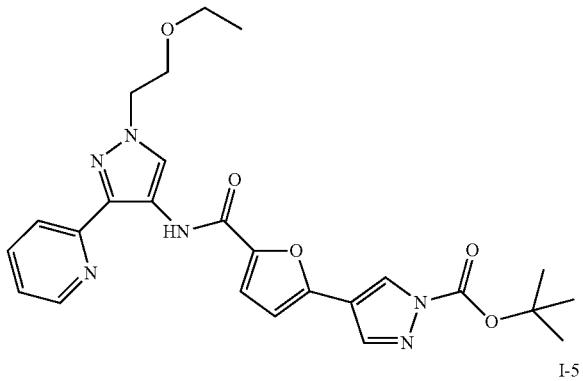

I-5

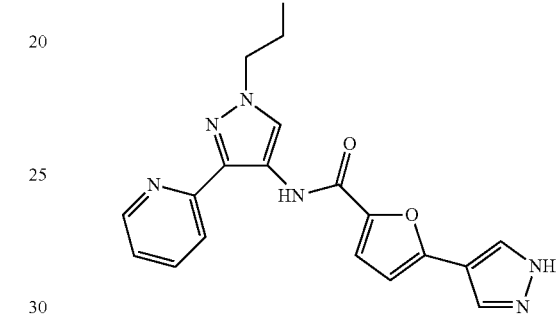

I-6

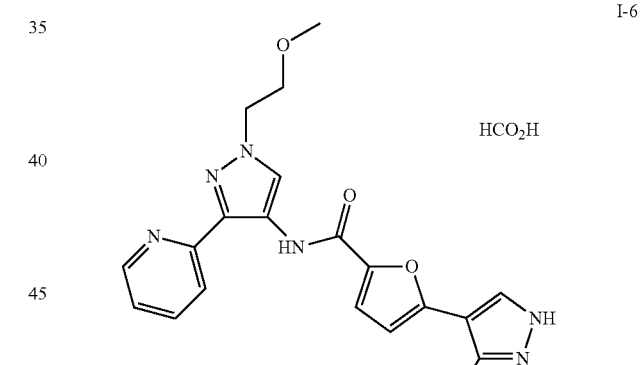

I-7

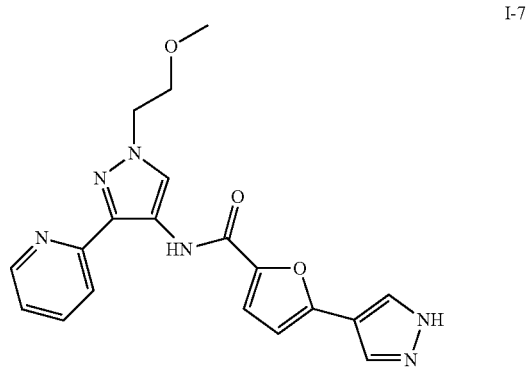

I-8
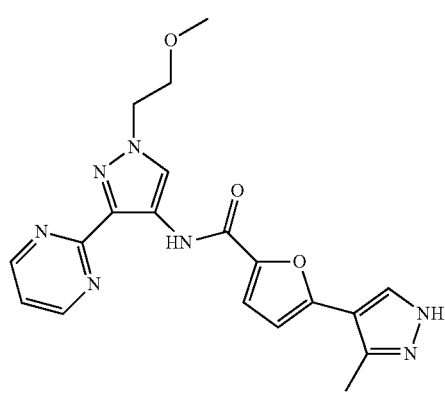
I-9
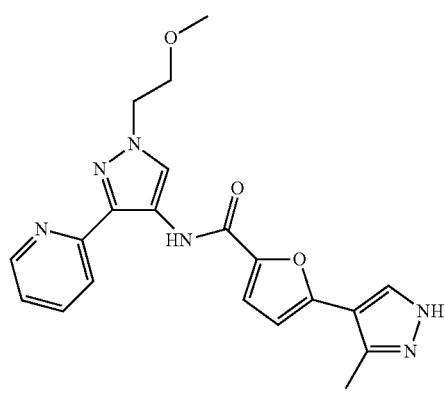
I-10
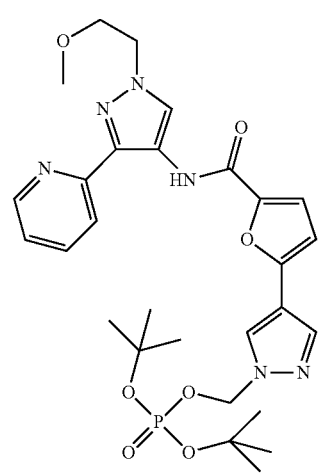
I-11
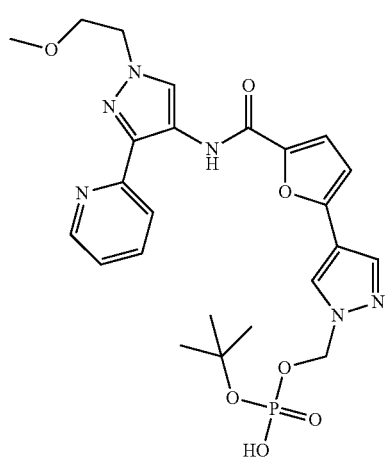
I-12
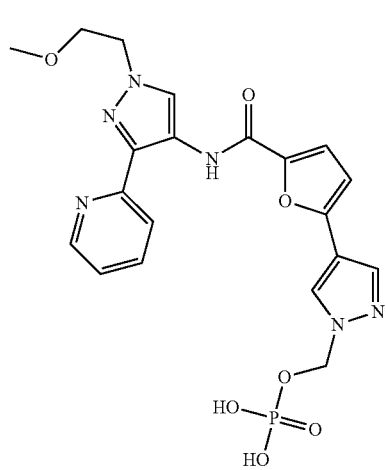
I-13
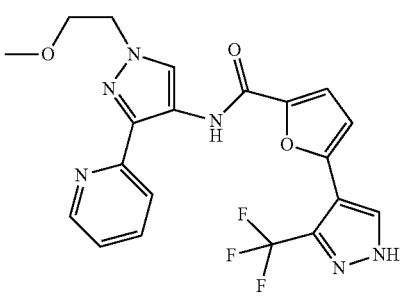

-continued
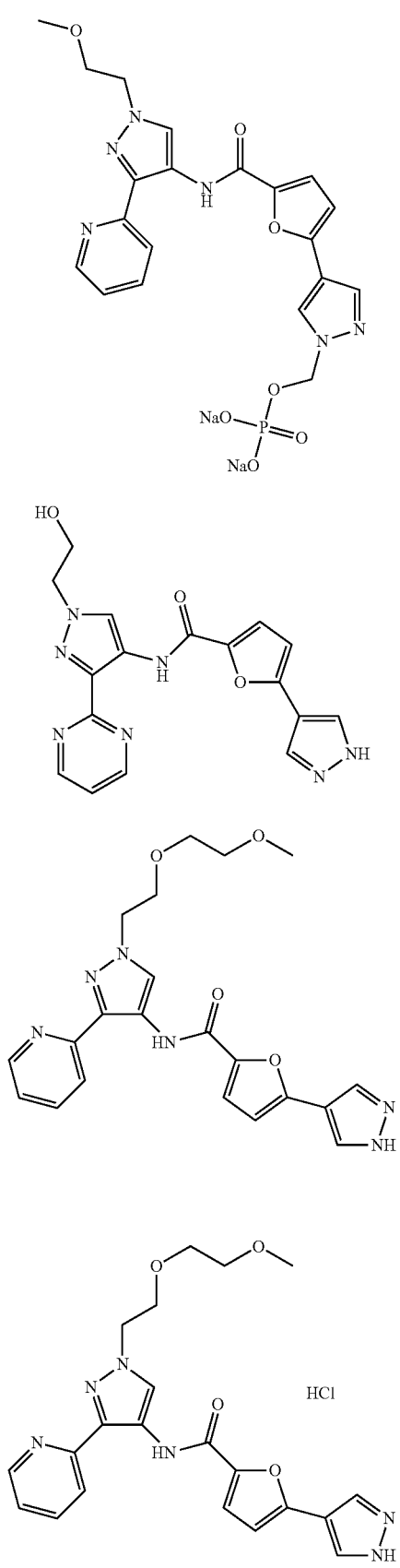
I-14
I-15
I-16
I-17
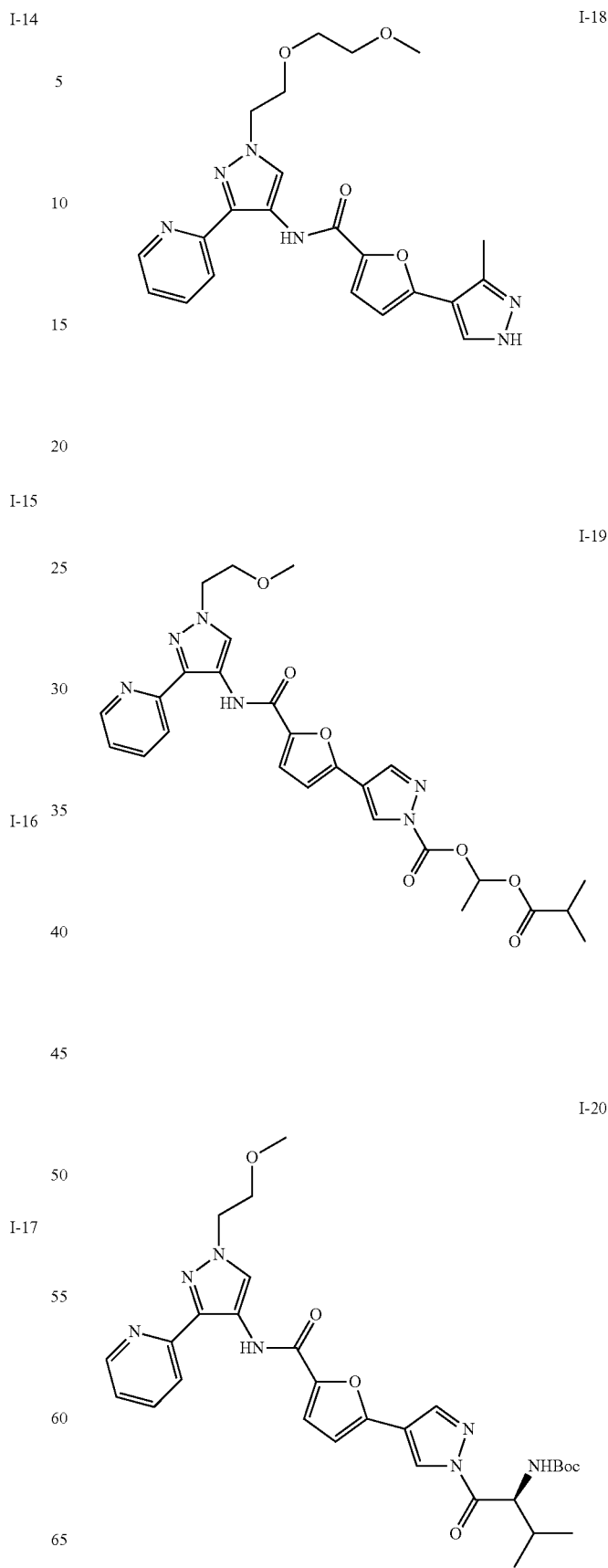
I-18
I-19
I-20

I-21
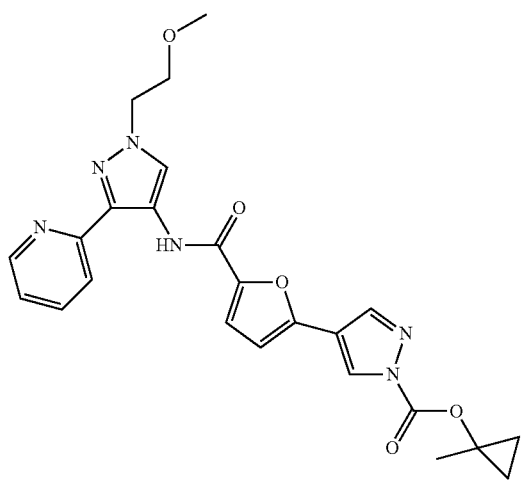
I-22
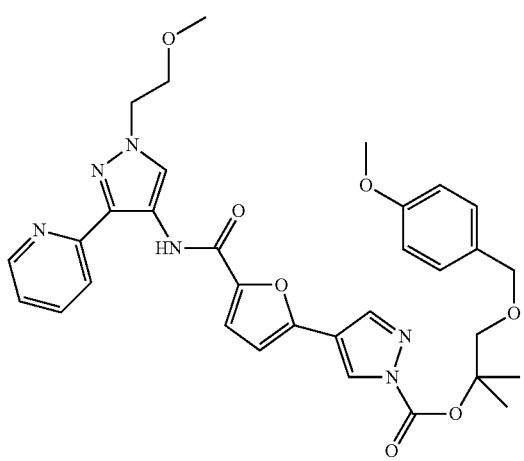
I-23
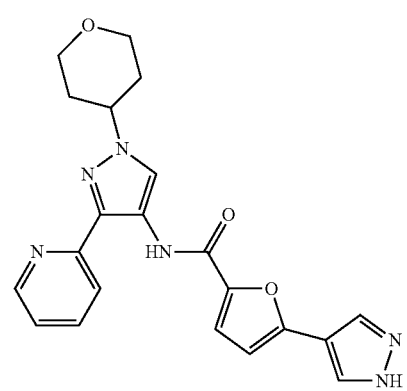
I-24
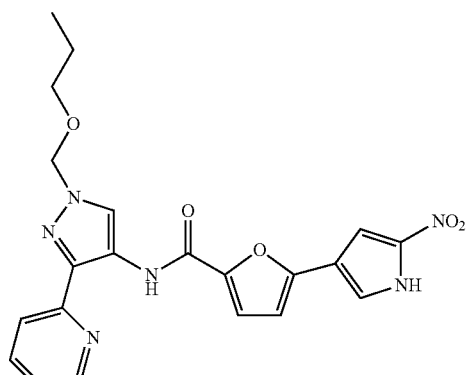
I-25
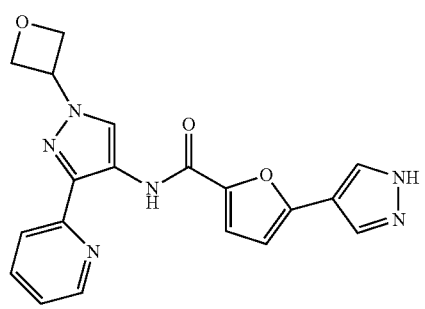
I-26
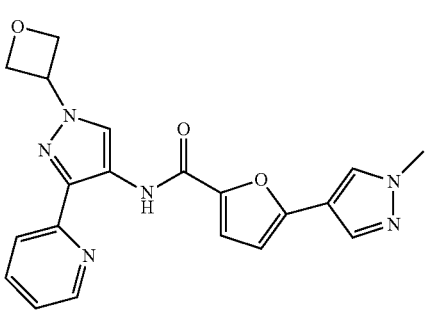
I-27
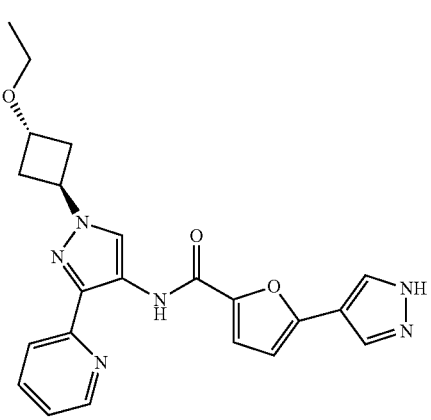

I-28
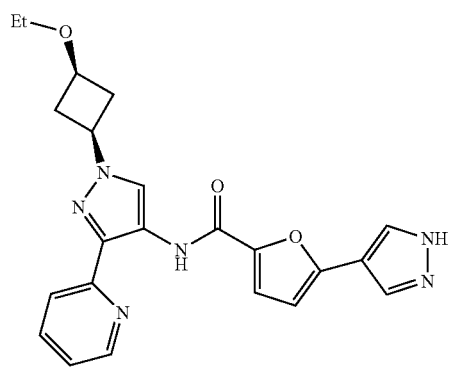
I-29
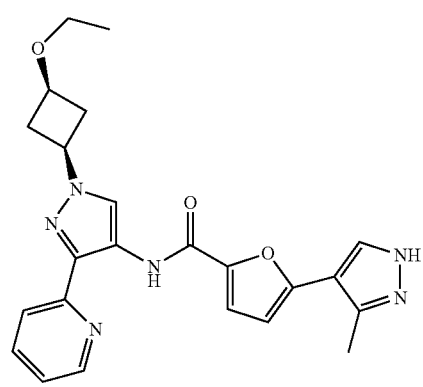
I-30
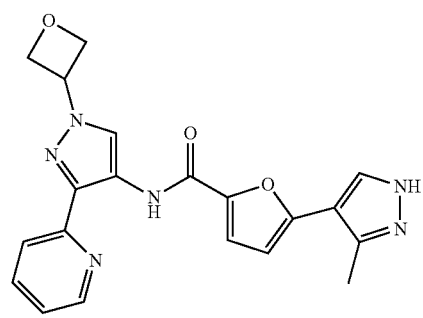
I-31
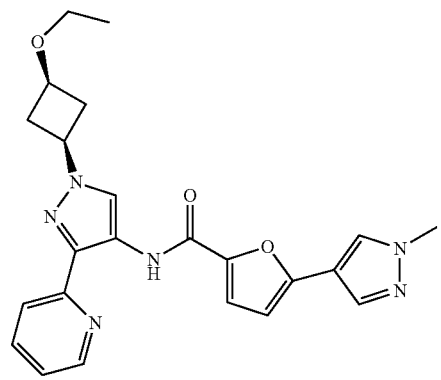
I-32
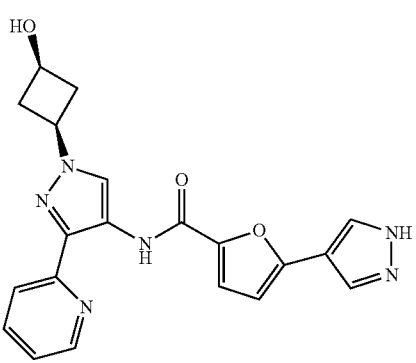
I-33
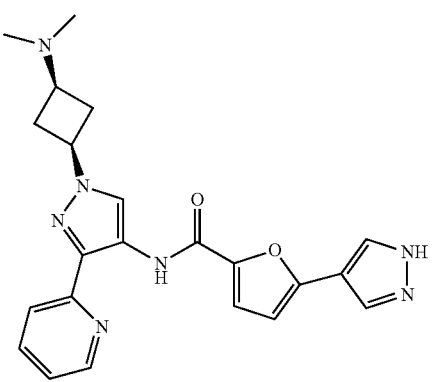
I-34
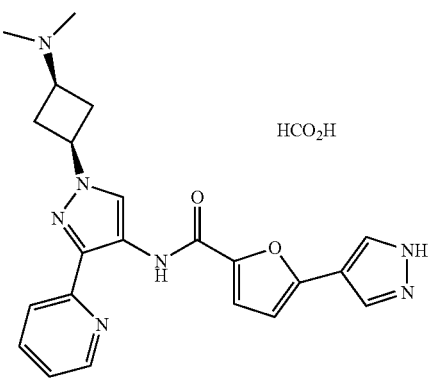 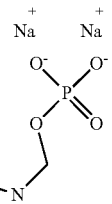
I-35

I-36
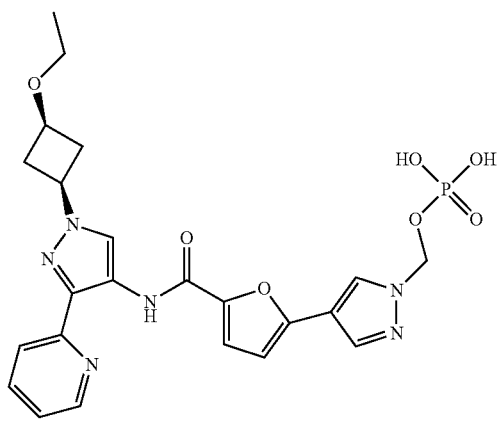
I-37
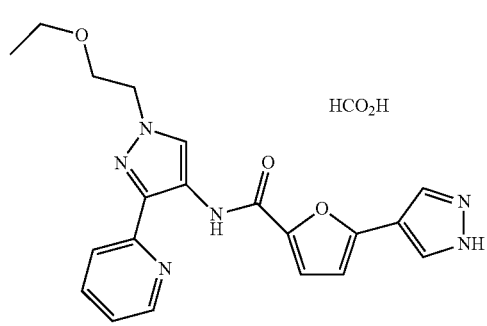
HCO₂H
I-38
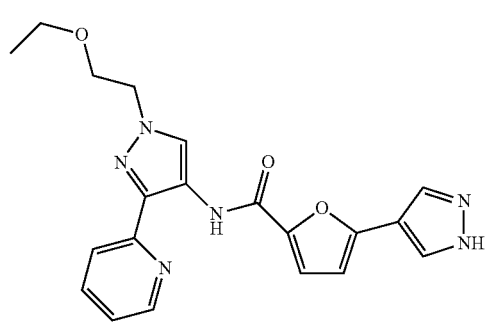
I-39
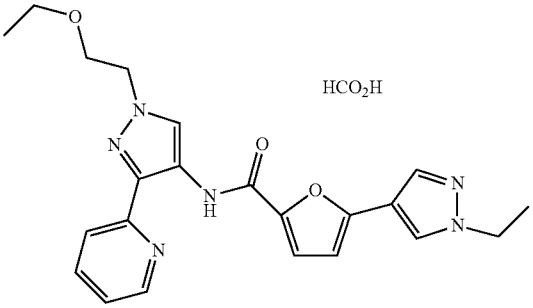
HCO₂H
I-40

I-41
HCO₂H
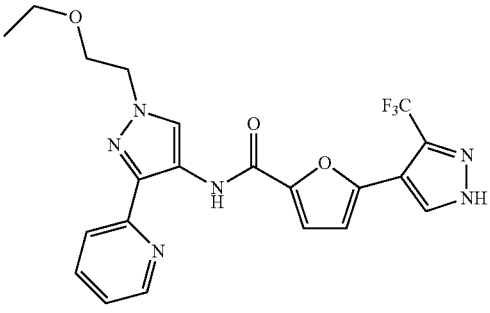
I-42
(structure continues)
I-43
HCO₂H
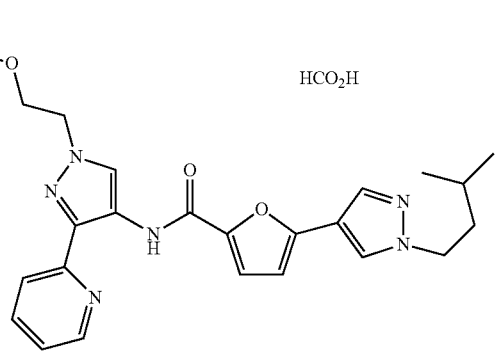

I-44
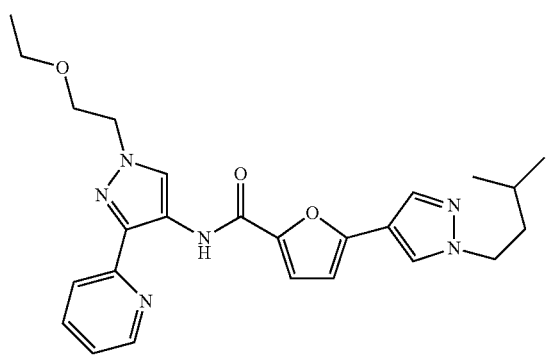
I-45
HCO₂H
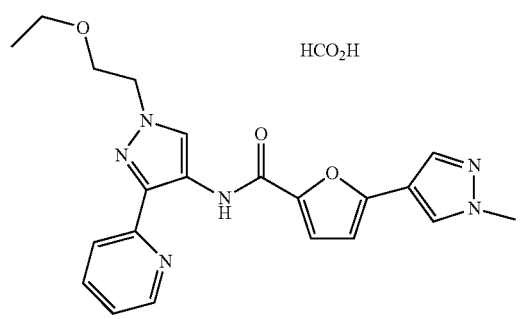
I-46
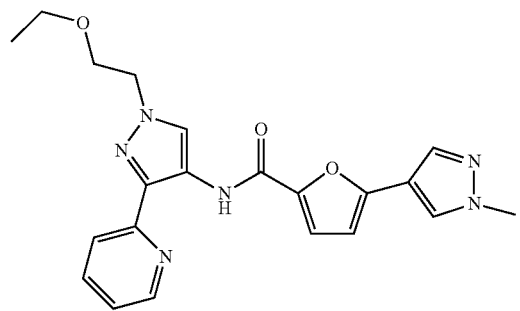
I-47
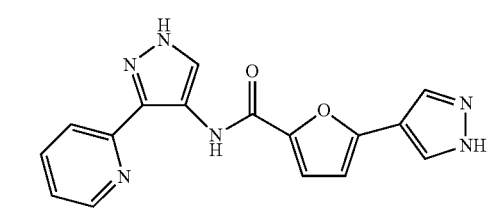
I-48
HCO₂H
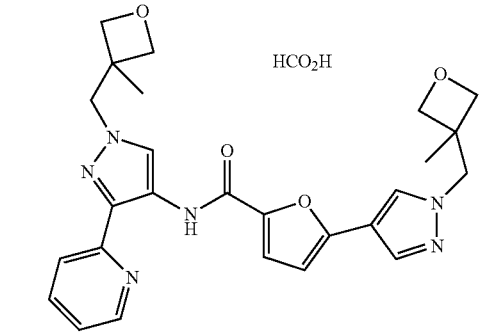
I-49
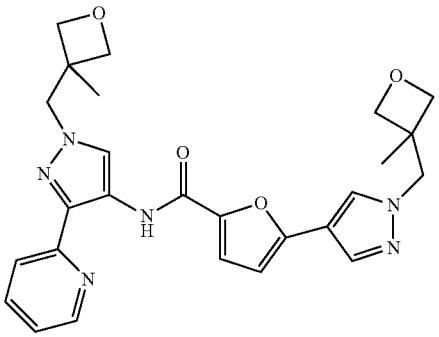
I-50
HCO₂H
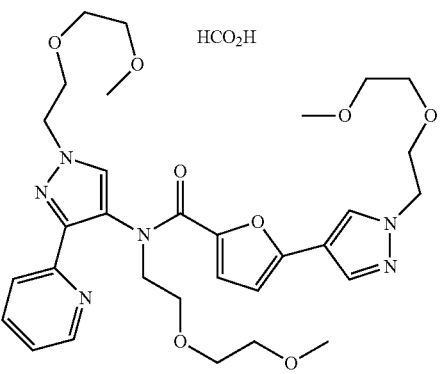
I-51
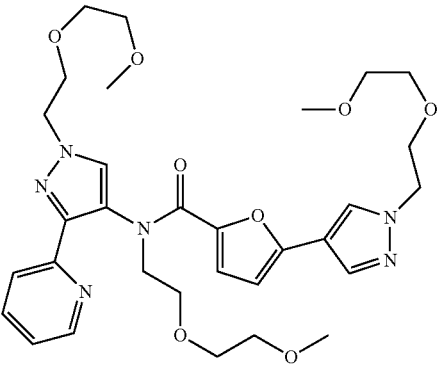
I-52
HCO₂H
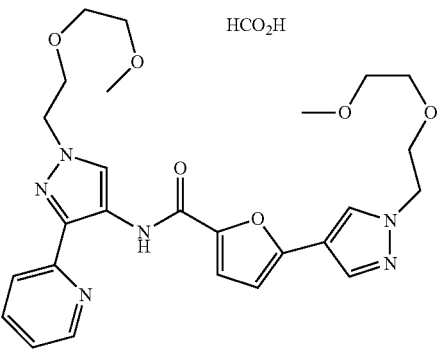

-continued
I-53
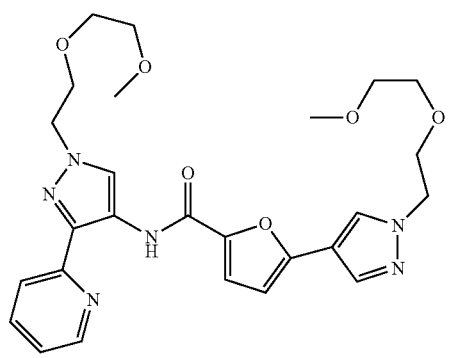
I-54
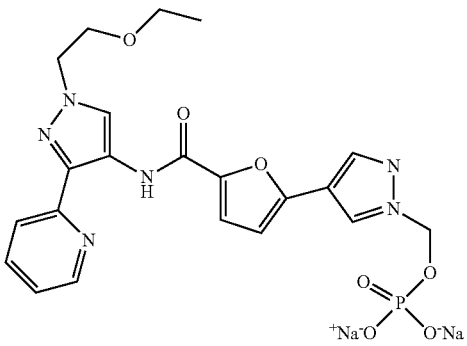
I-55
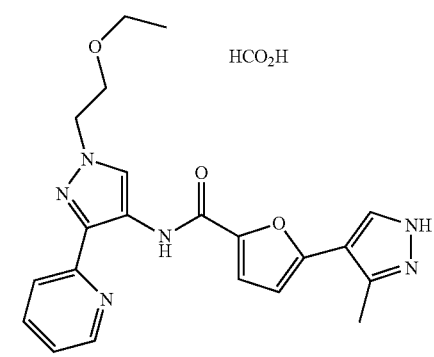
-continued
I-57
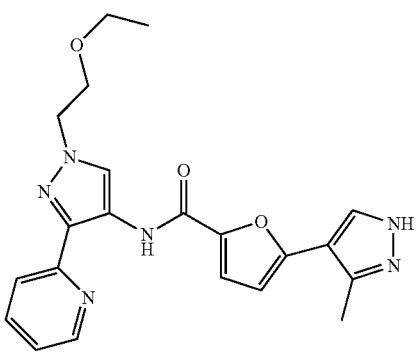
I-58
HCO₂H
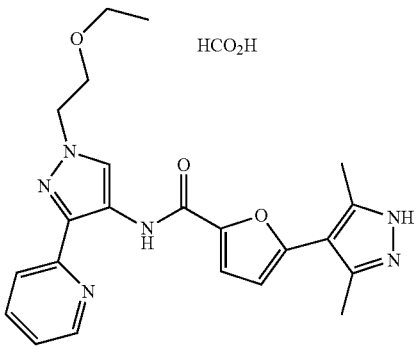
I-59
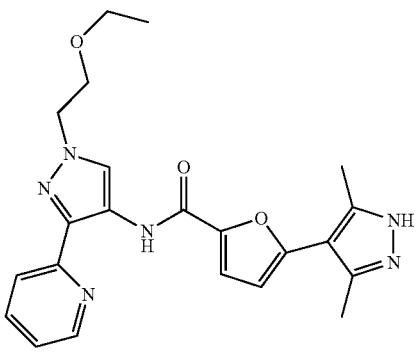
I-56
HCO₂H
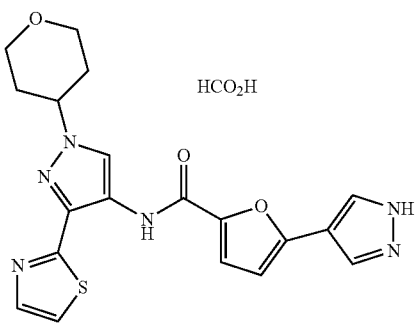
I-60
HCO₂H -continued
I-61
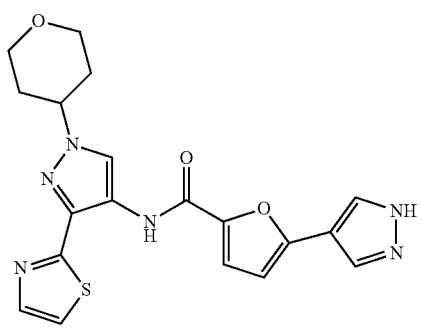
I-62
HCO₂H
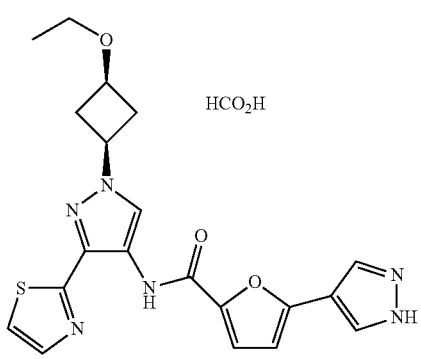
I-63
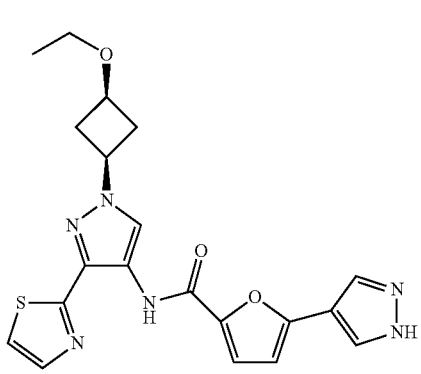
I-64
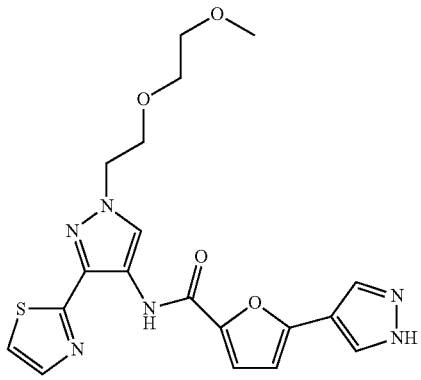
I-65
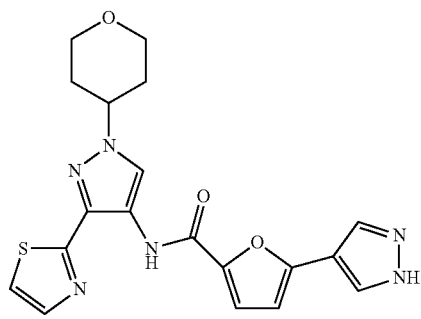
I-66
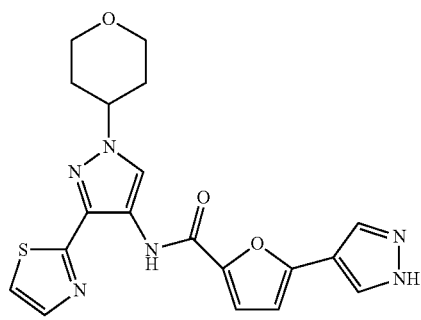
I-67
HCO₂H
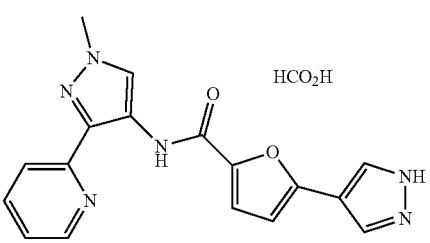
I-68
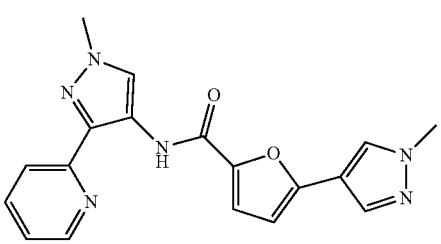
I-69
HCO₂H
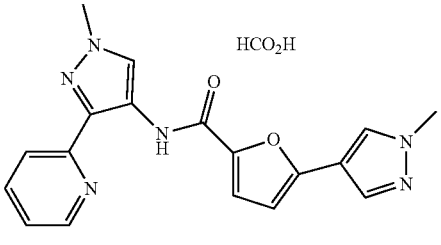

| | |
|---|---|
| I-70 | I-74 |
| I-71 | I-75 |
| I-72 | I-76 |
| I-73 | I-77 |

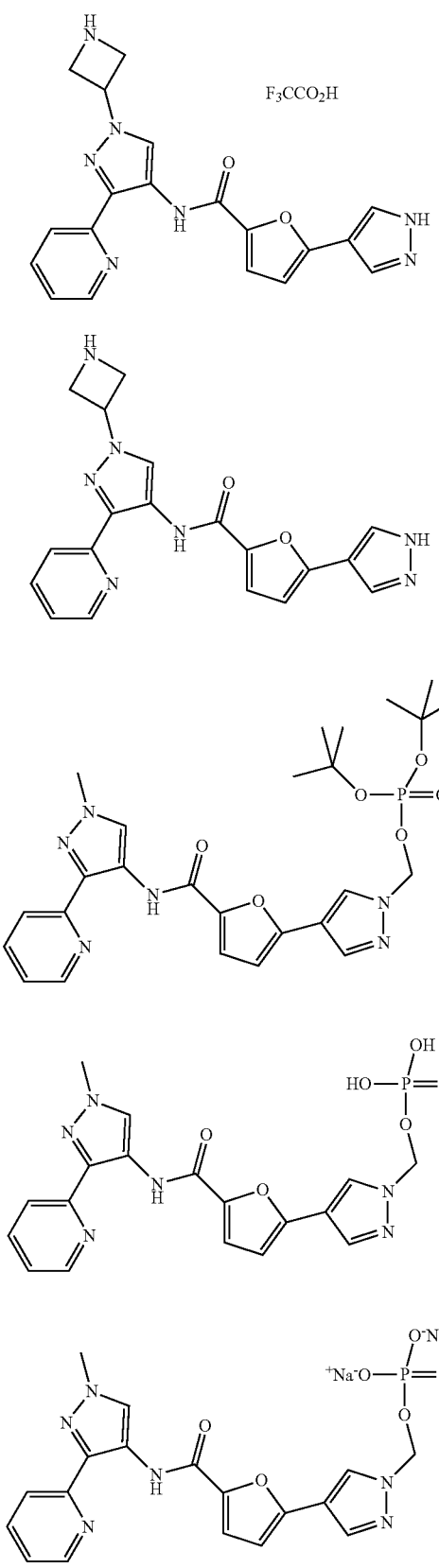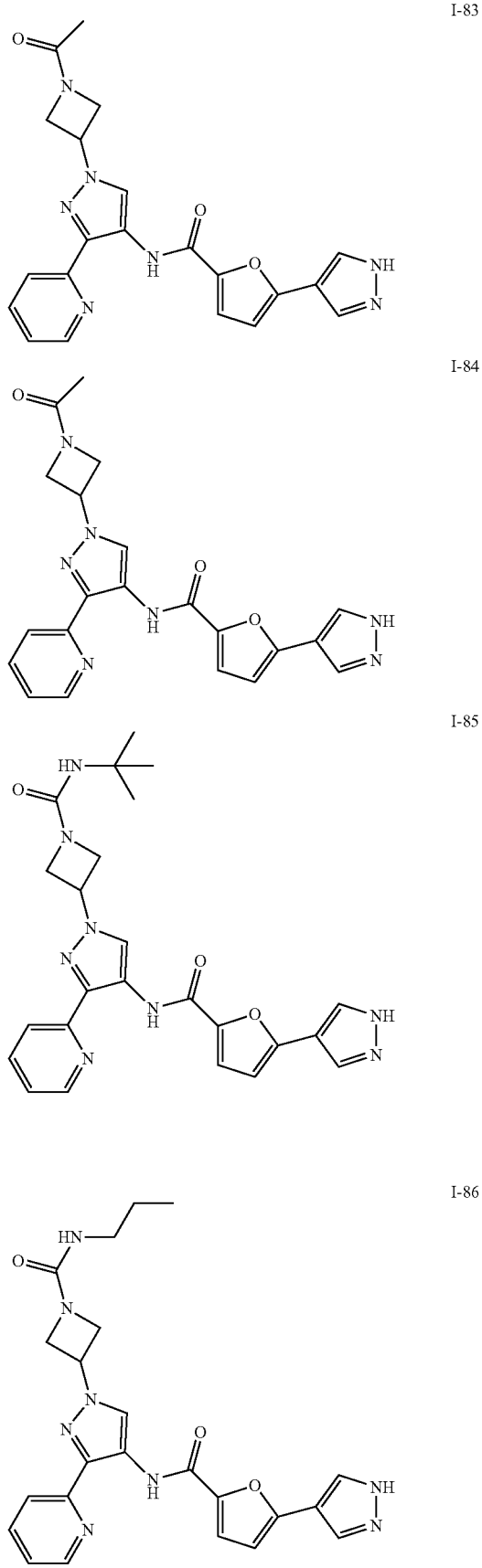

I-87
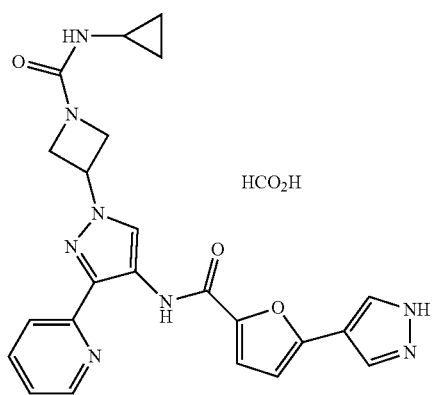
HCO₂H
I-88
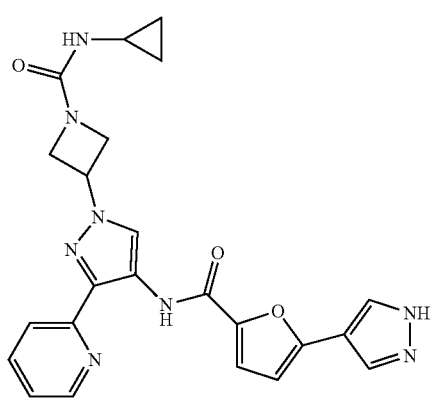
I-89
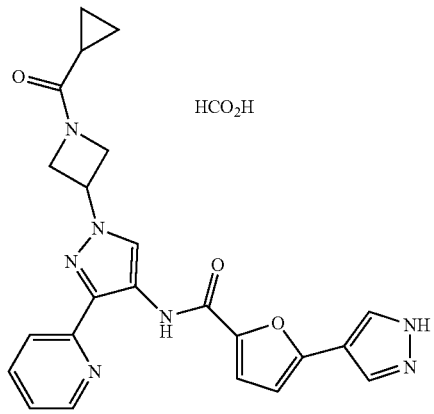
HCO₂H
I-90
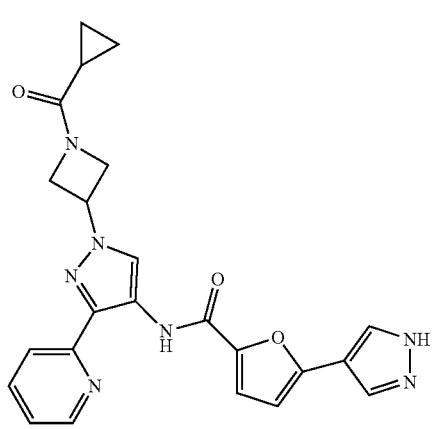
I-91
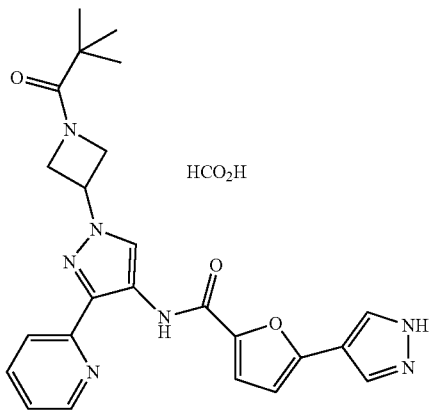
HCO₂H
I-92
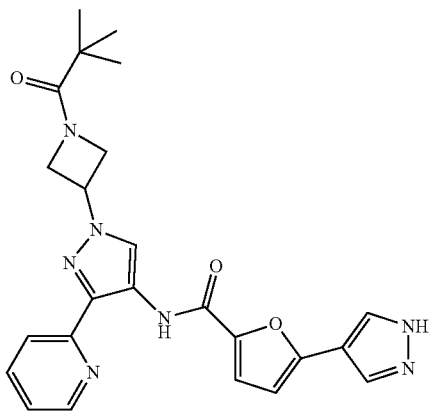
I-93
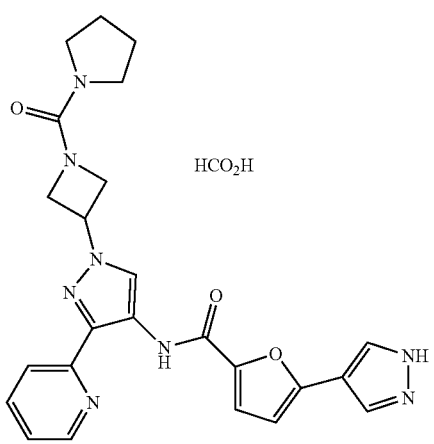
HCO₂H I-94
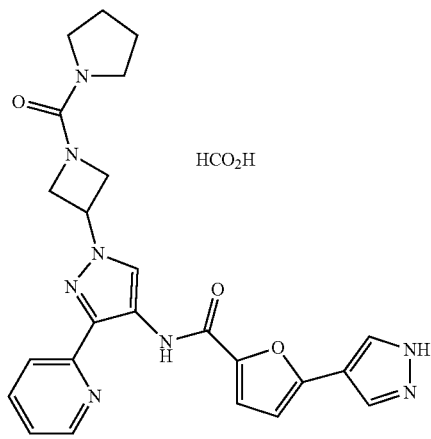
I-95
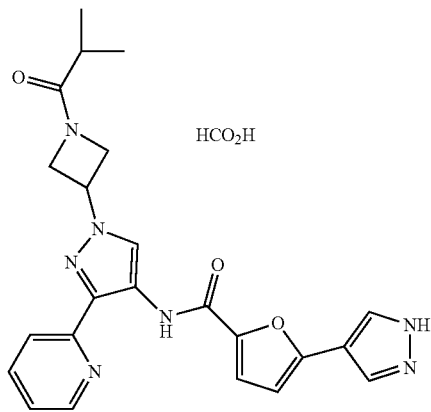
I-96
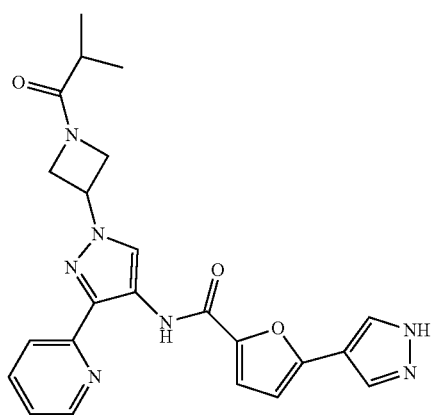
I-97
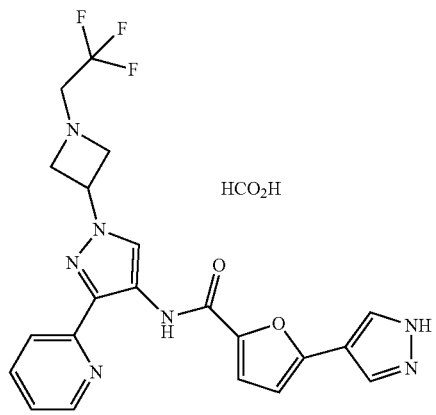
I-98
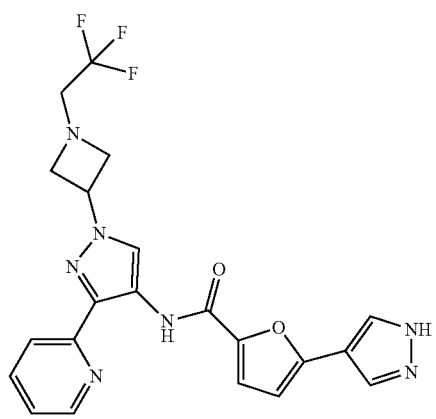
I-99
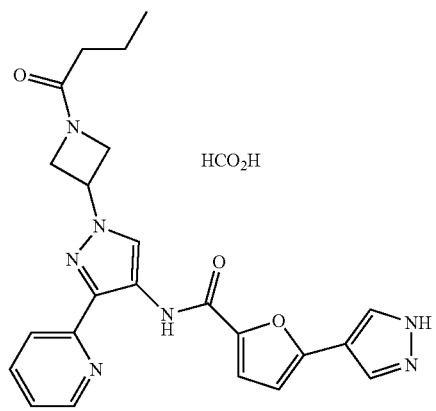
I-100
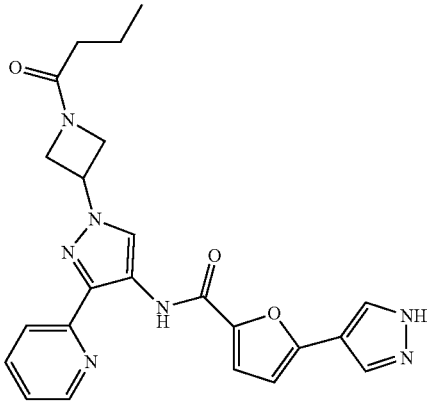

I-101
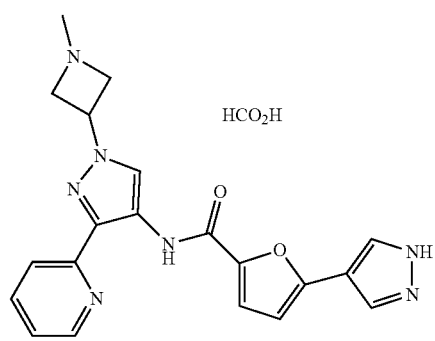
HCO2H
I-102
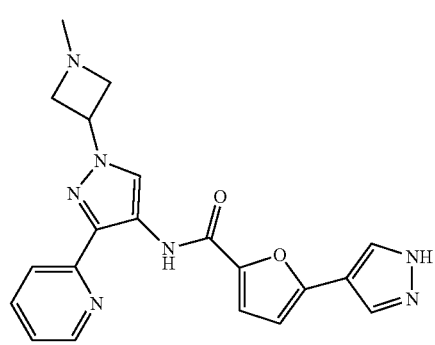
I-103
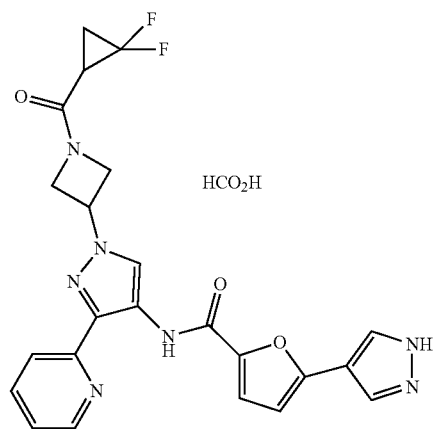
HCO2H
I-104
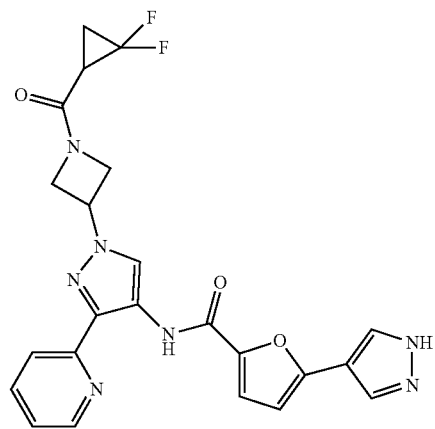
I-105
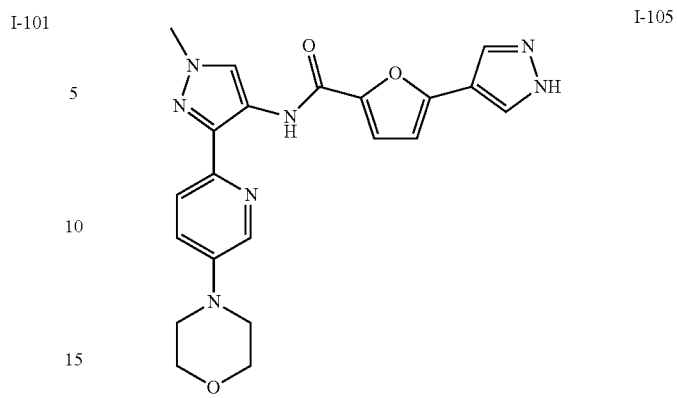
I-106
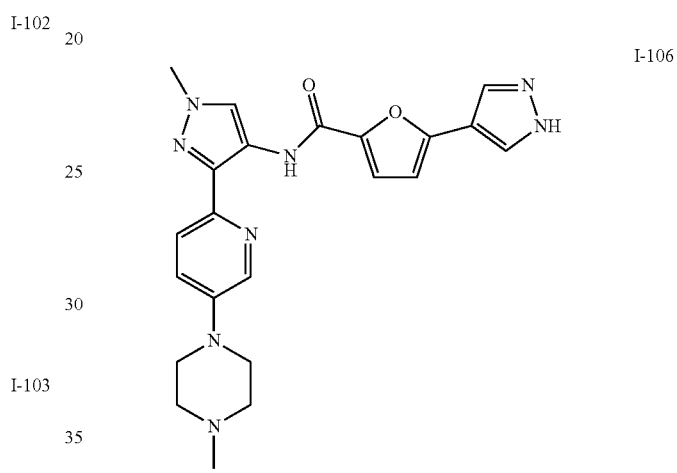
I-107
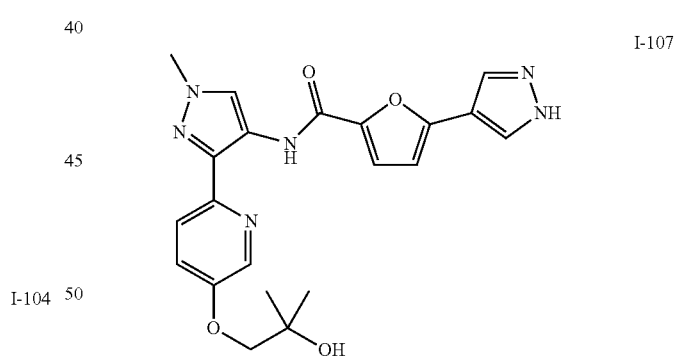
I-108
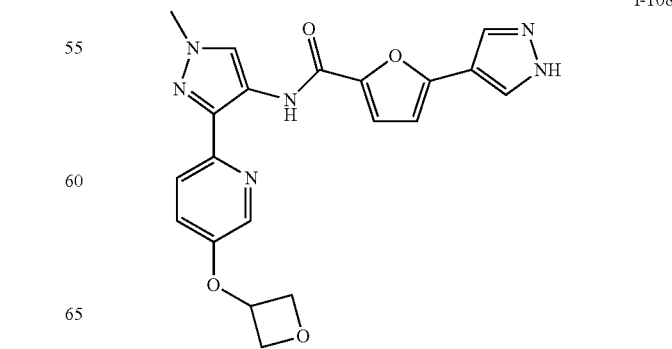

I-109
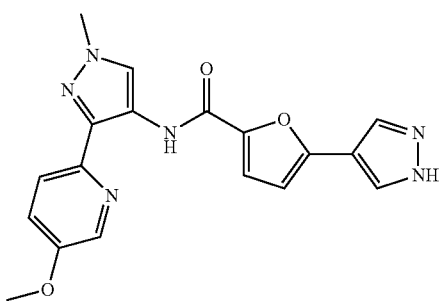
I-113
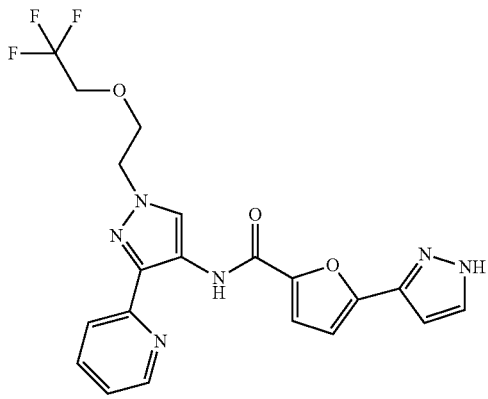
I-110
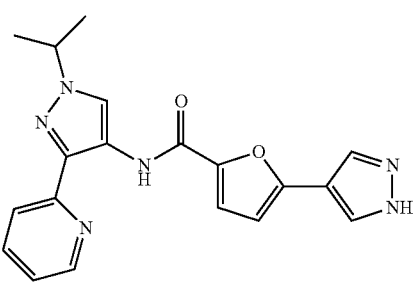
I-114
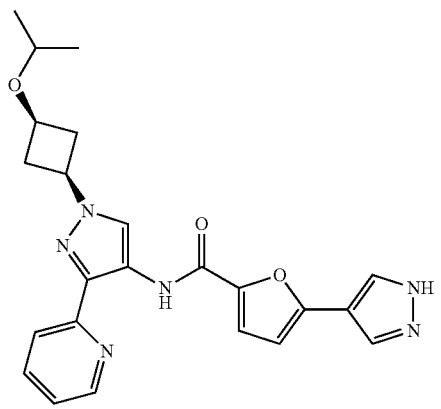
I-111
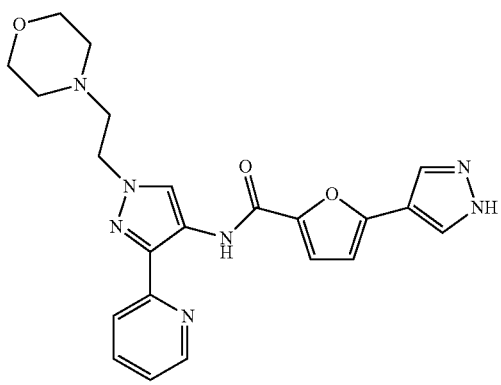
I-115
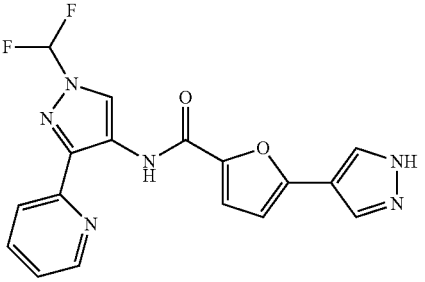
I-112
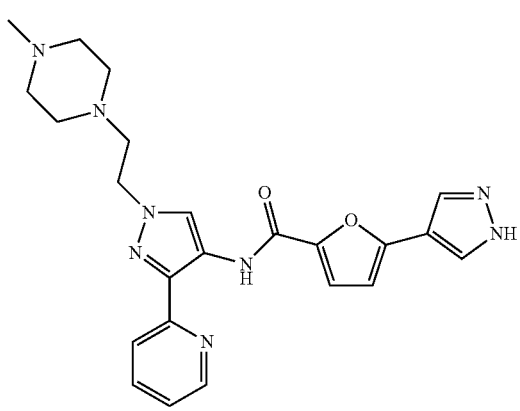
I-116
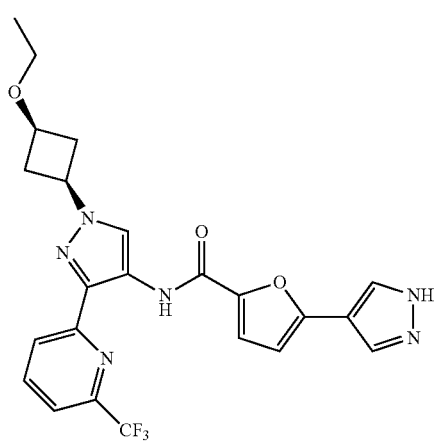

I-117 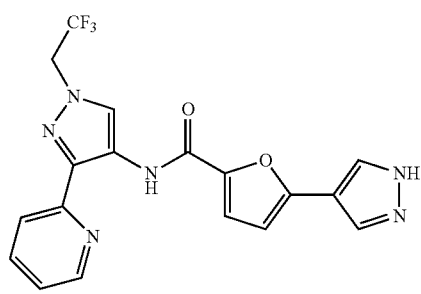
I-118 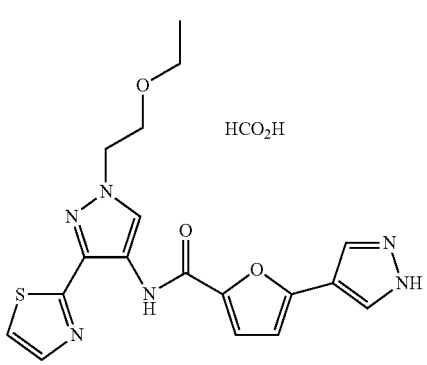
HCO2H
I-119 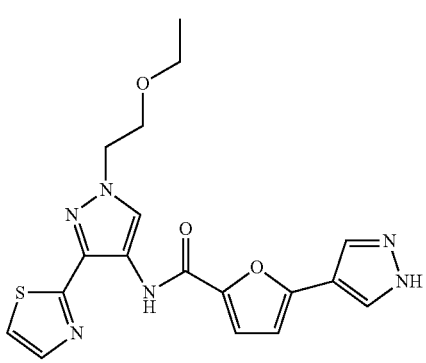
HCO2H
I-120 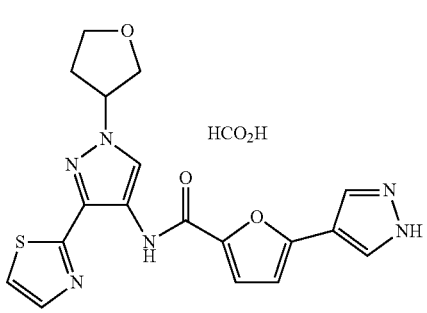
HCO2H
I-121 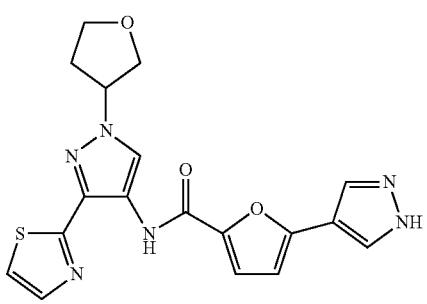
I-122 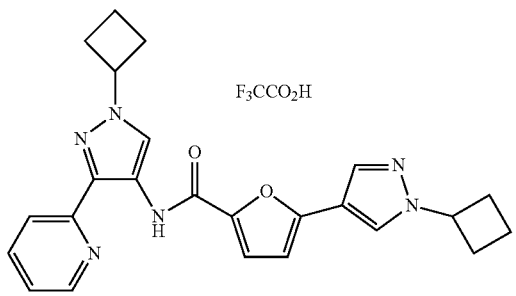
F3CCO2H
I-123 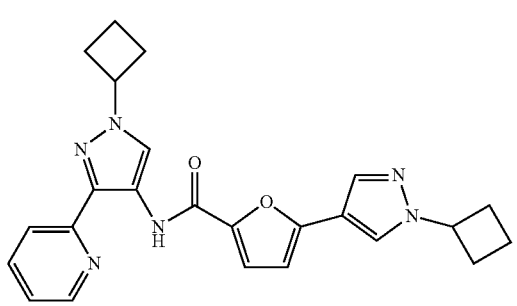
I-124 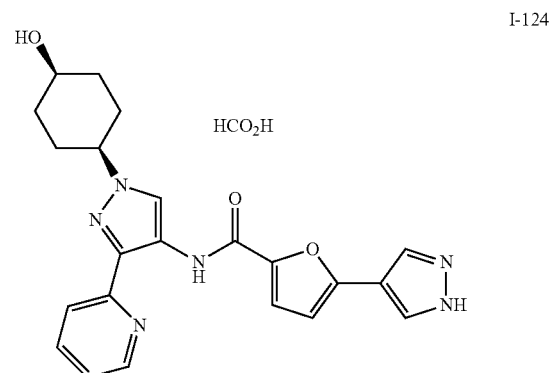
HCO2H
I-125 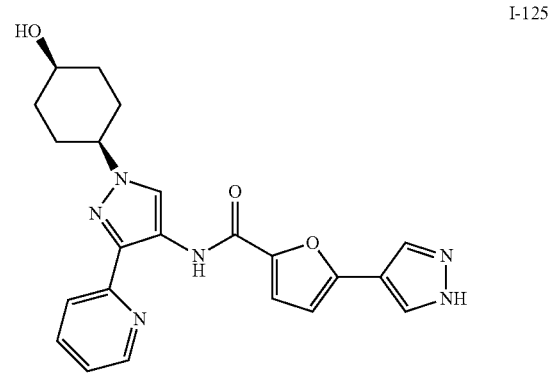

-continued
I-126
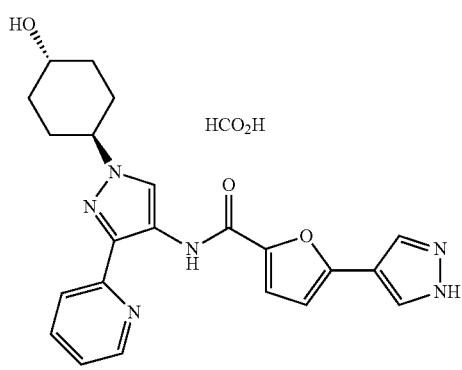
HCO2H
I-130
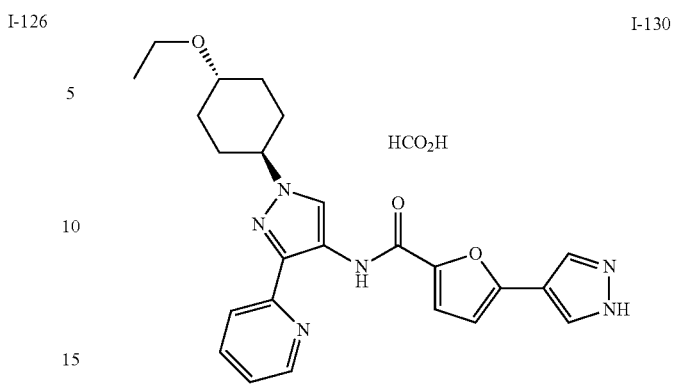
HCO2H
I-127
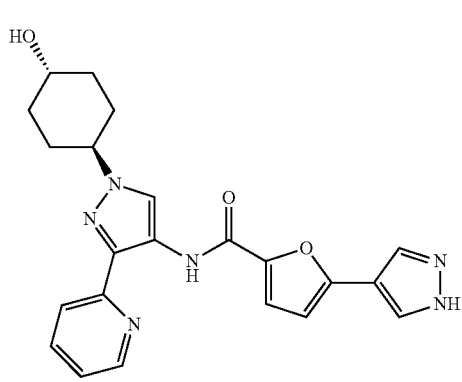
I-131
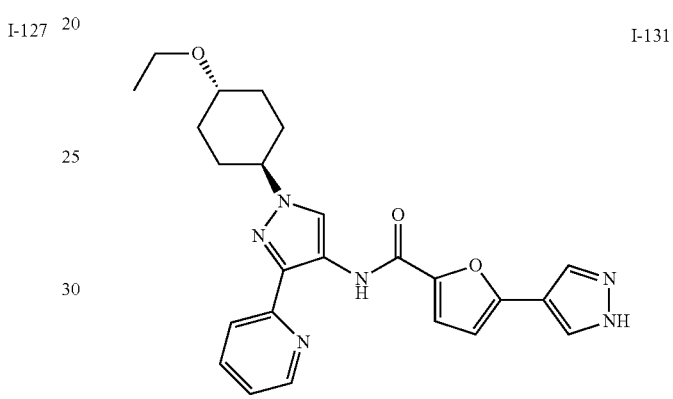
I-128
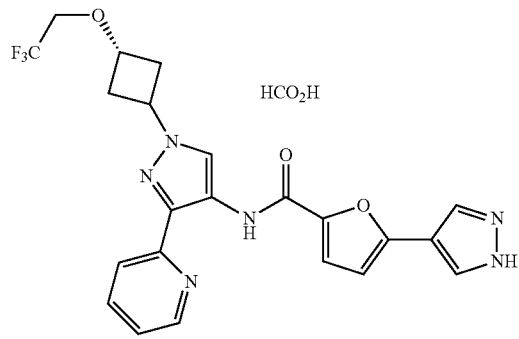
HCO2H
I-132
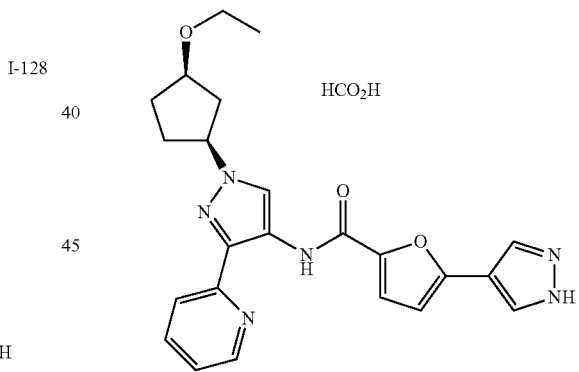
HCO2H
I-129
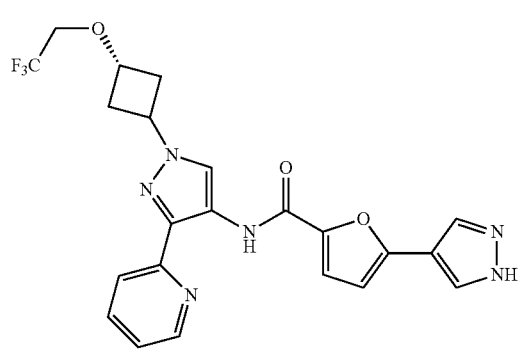
I-133
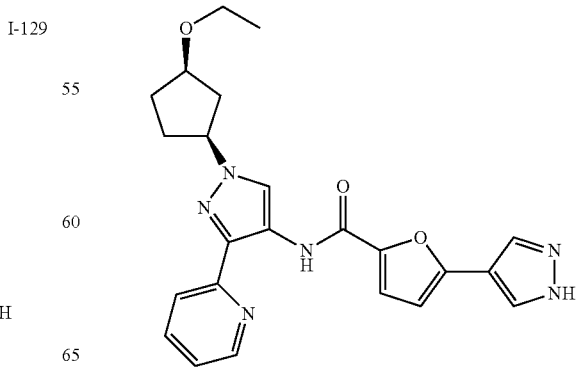

-continued
I-134
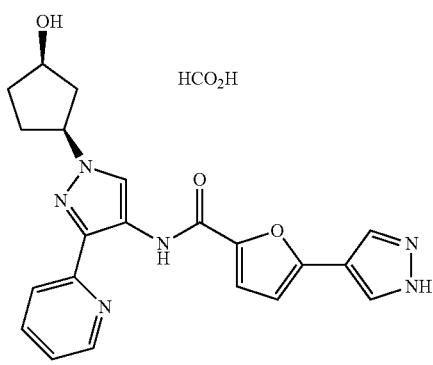
I-135
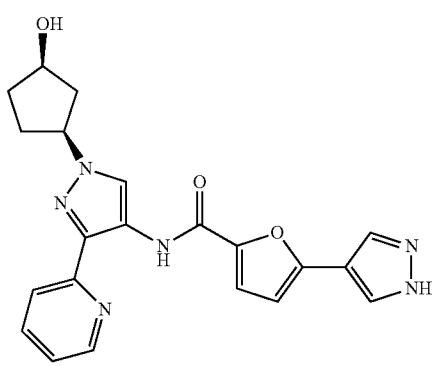
I-136
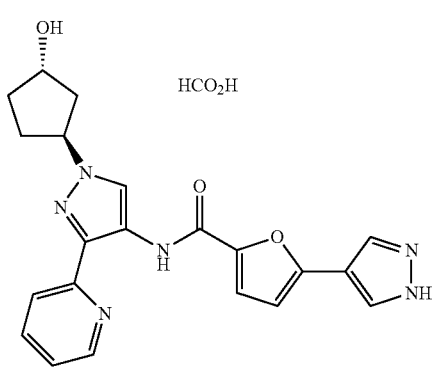
I-137
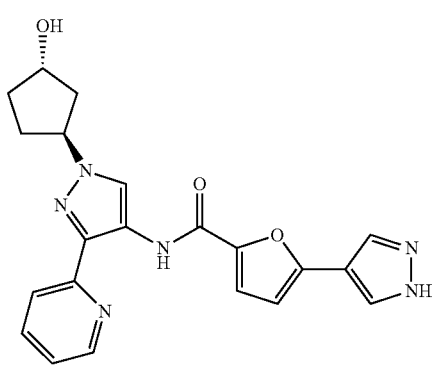
-continued
I-138
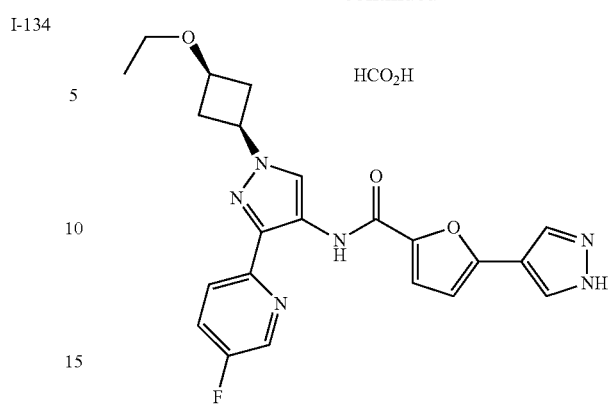
I-139
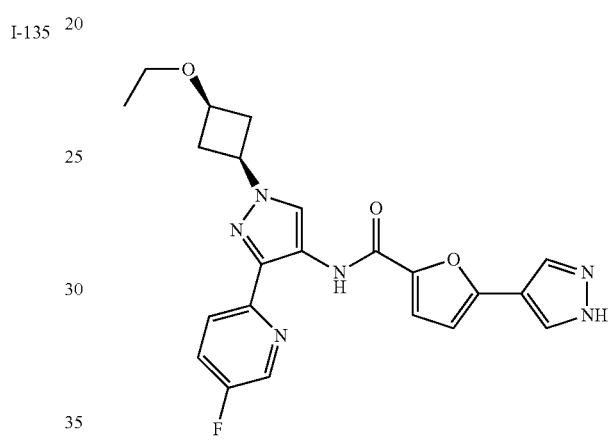
I-140
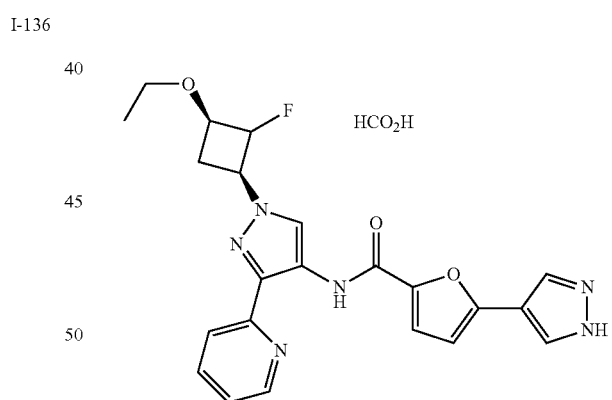
I-141
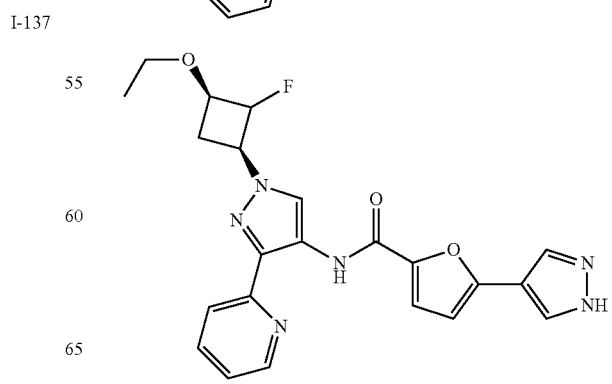

I-142 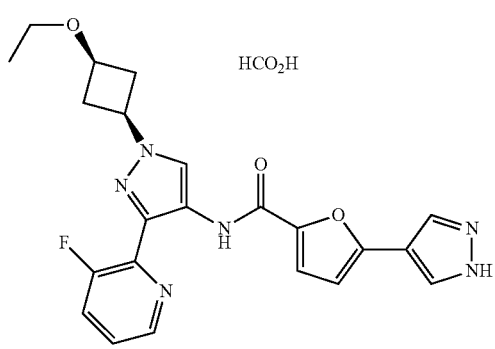
I-146 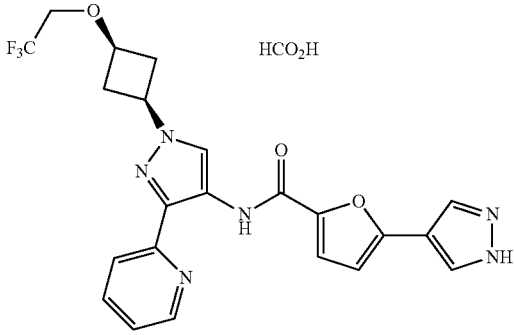
I-143 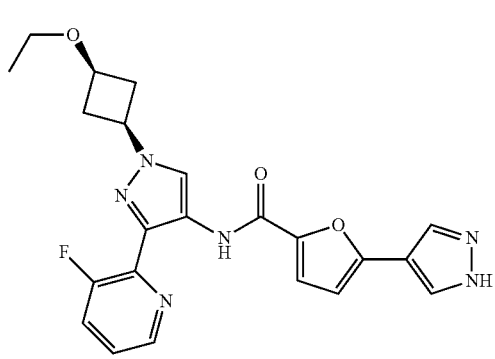
I-147 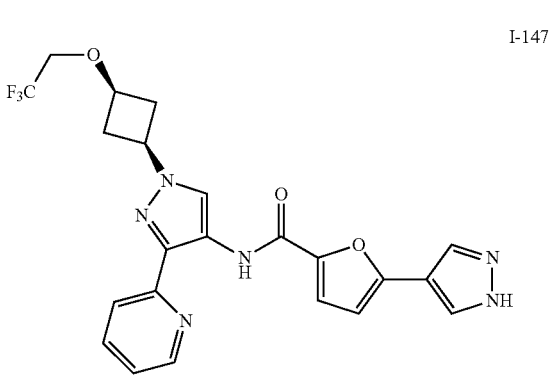
I-144 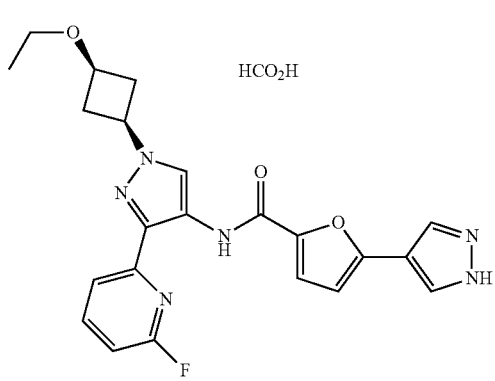
I-148 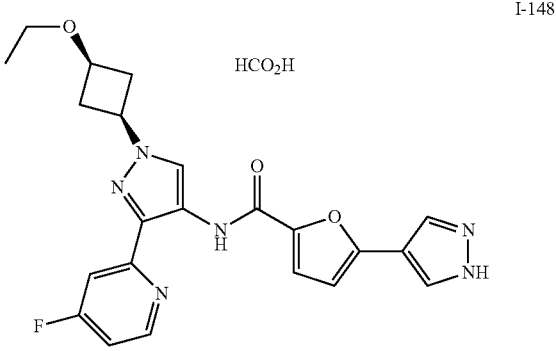
I-145 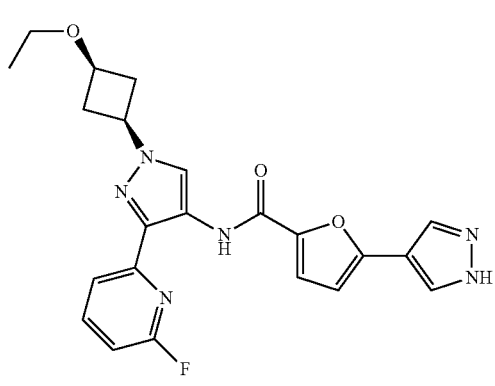
I-149 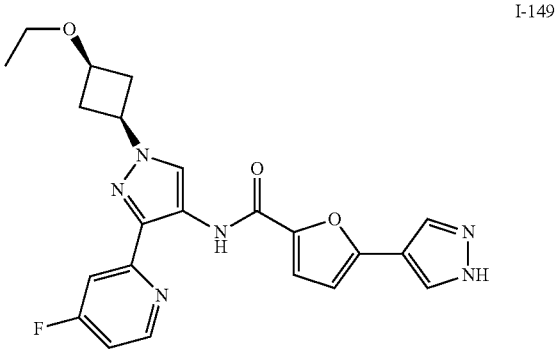

I-150
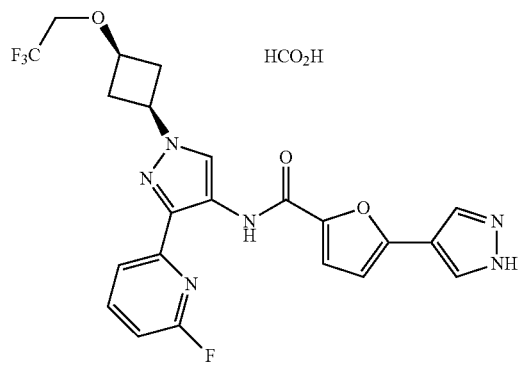
I-151
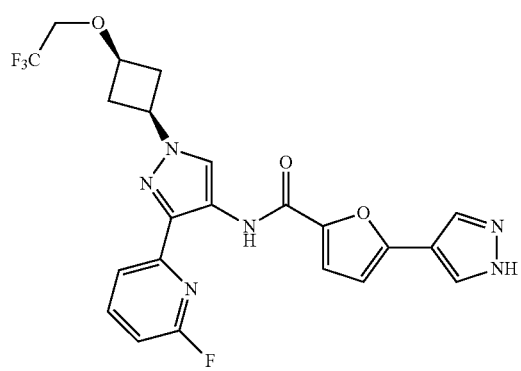
I-152
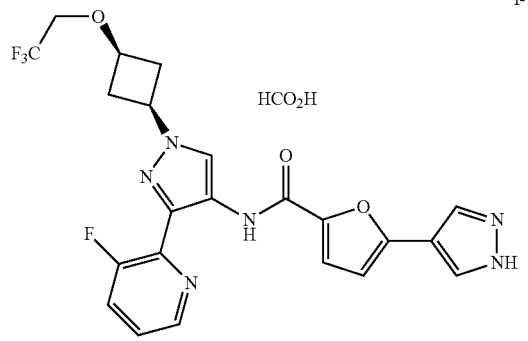
I-153
I-154
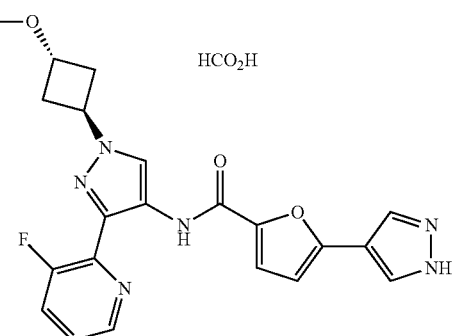
I-155
I-156
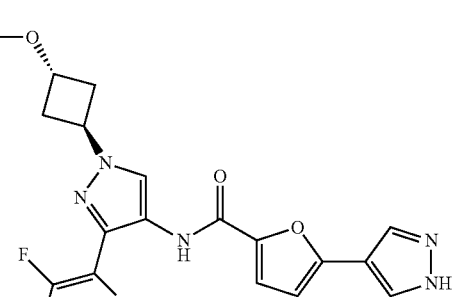
In other embodiments, the compound according to formula 1 is selected from
II-1
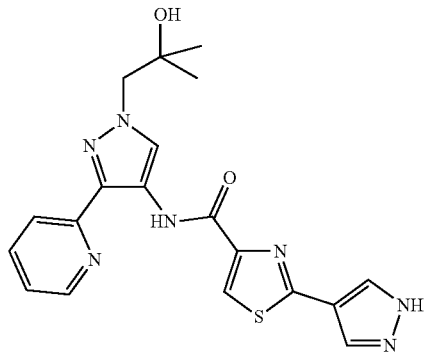

II-2
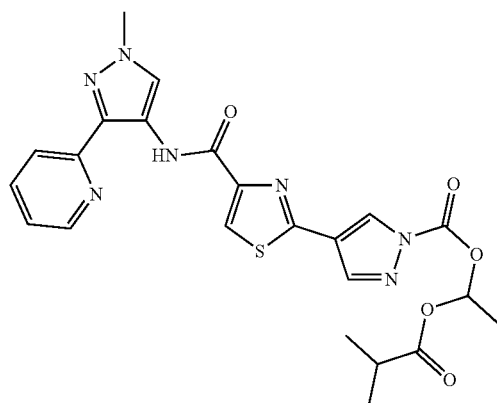
II-3
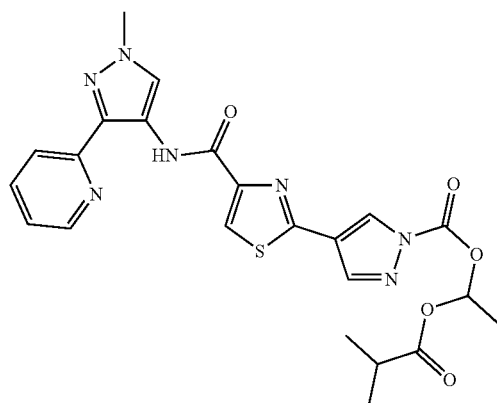
II-4
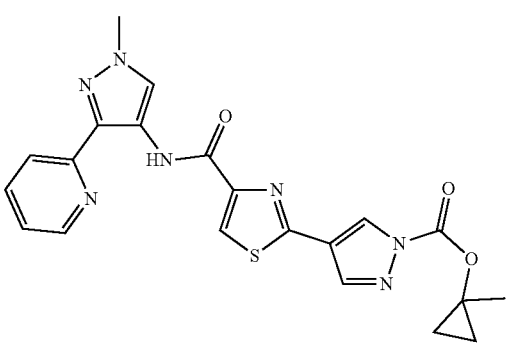
II-5
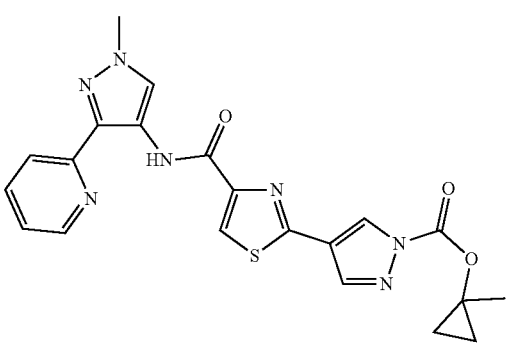
II-6
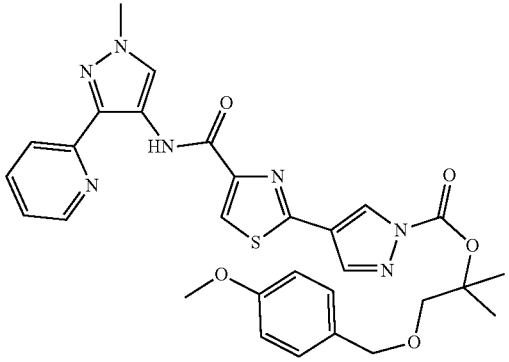
II-7
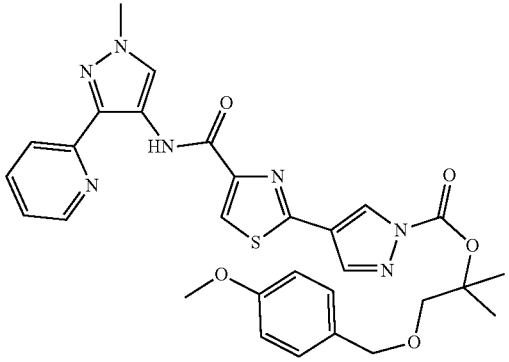
II-8
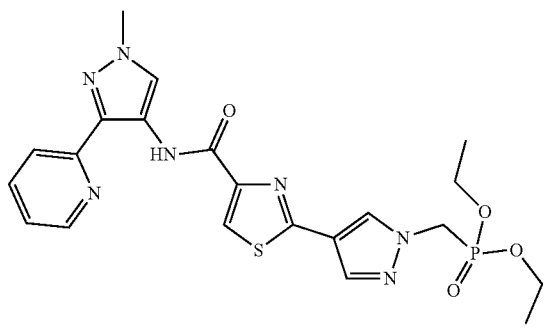
II-9
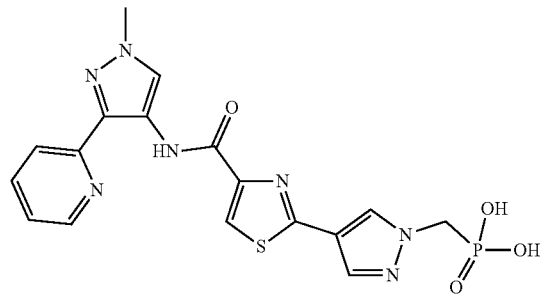

-continued
II-10
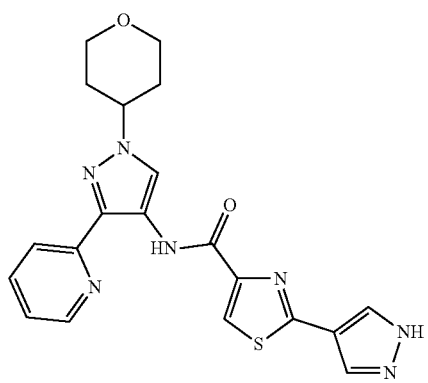
II-11
II-12
II-13
-continued
II-14
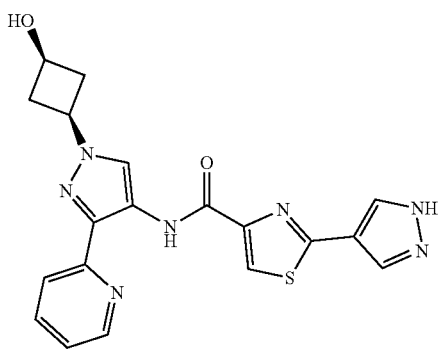
II-15
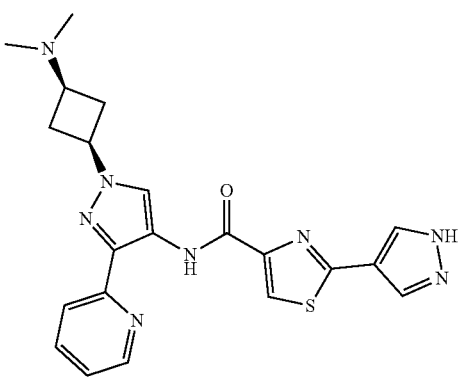
II-16
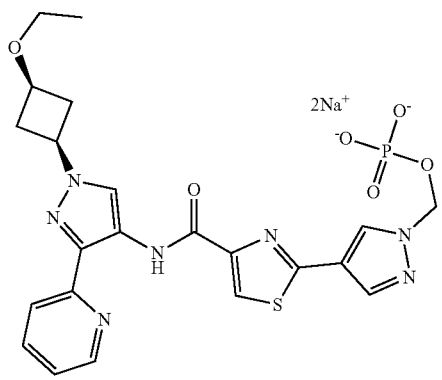
II-17
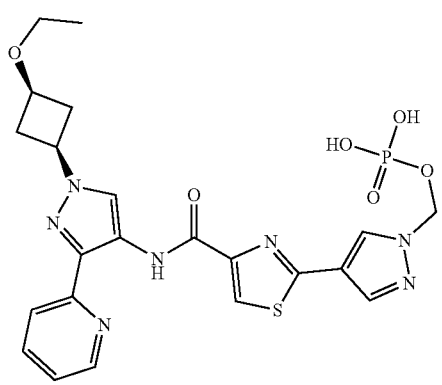

II-18
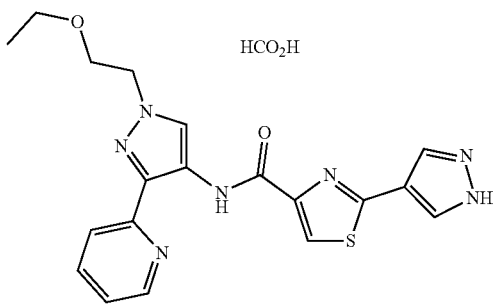
II-19
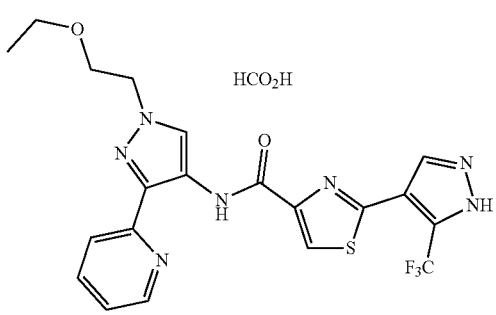
II-20
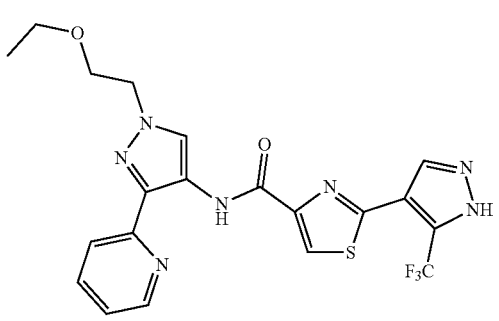
II-21
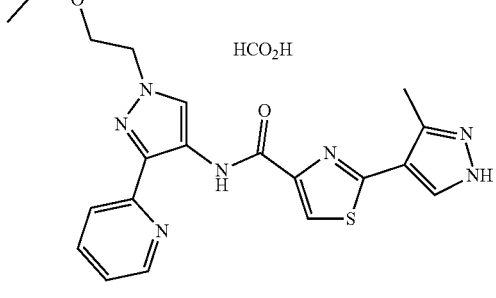
II-22
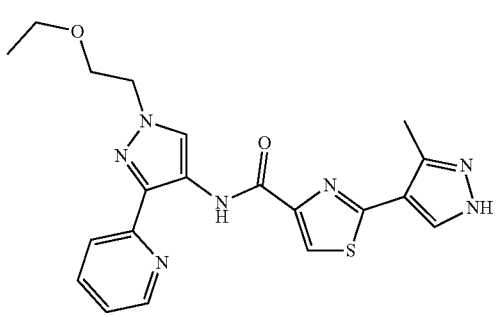
II-23
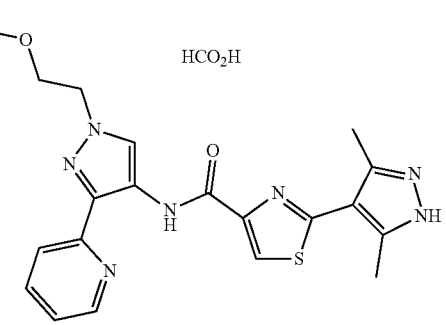
II-24
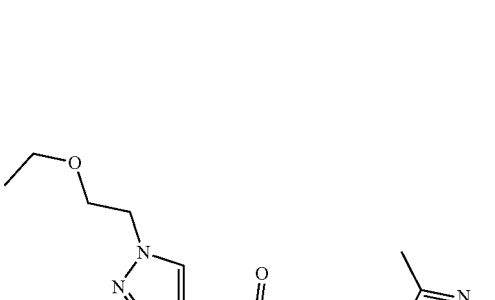
II-25
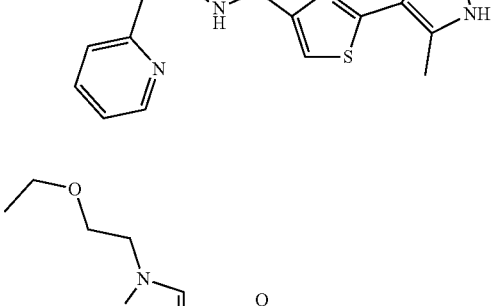
II-26
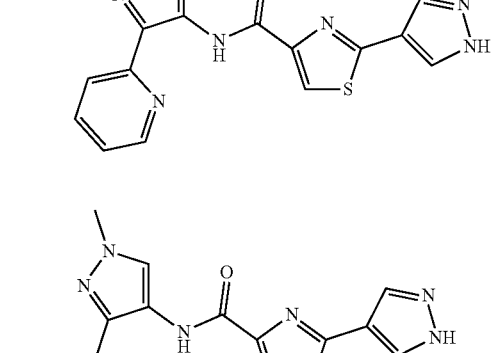
II-27
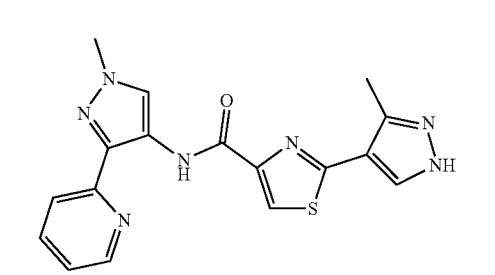

II-28
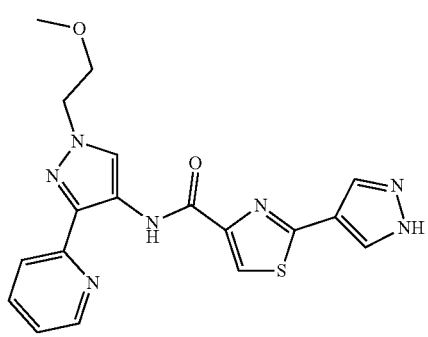
II-29
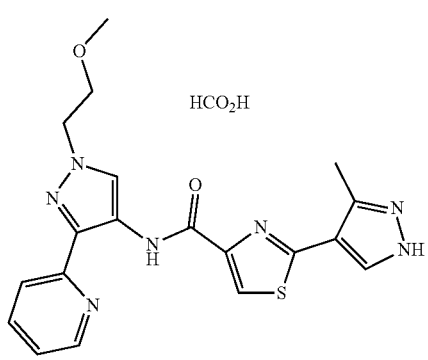
HCO₂H
II-30
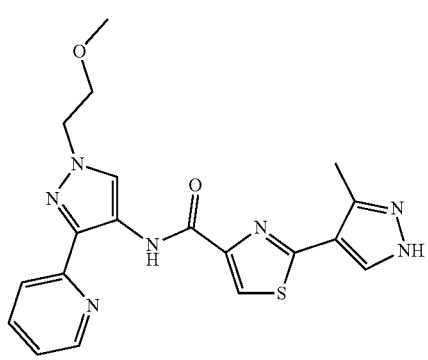
II-31
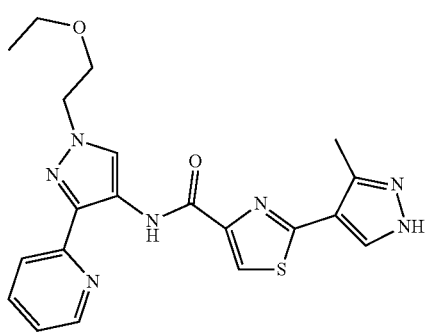
II-32
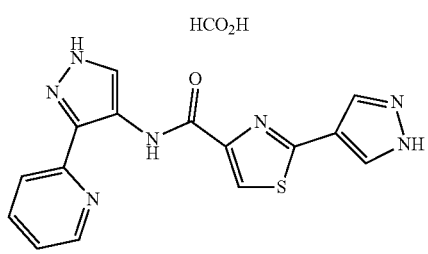
HCO₂H
II-33
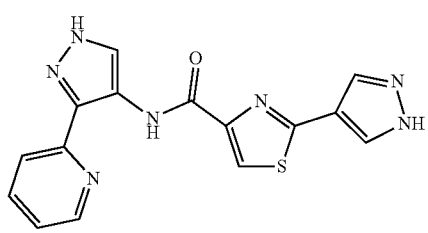
II-34
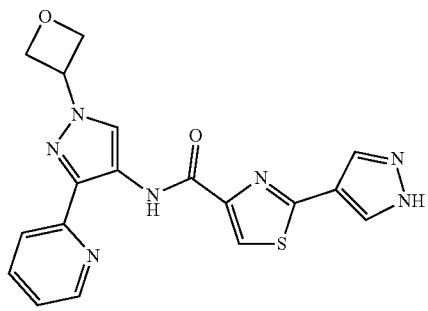
II-35
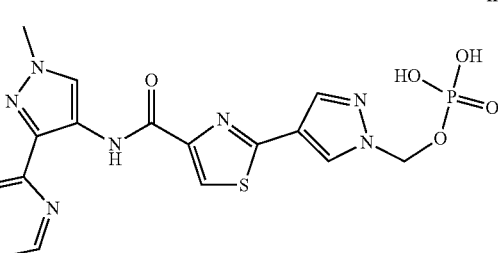
II-36
2Na⁺
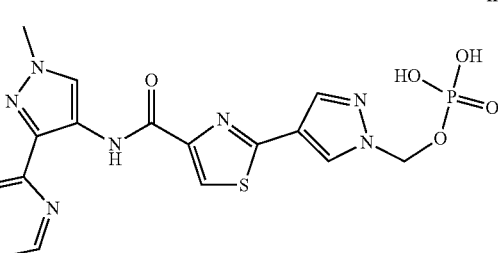
II-37
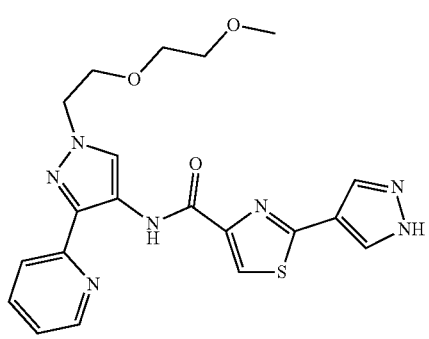

II-38
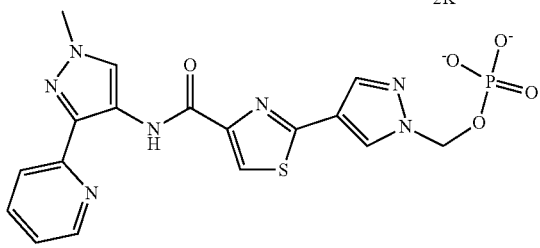
2K⁺
II-39
HCO₂H
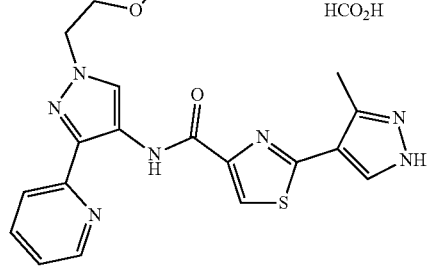
II-40
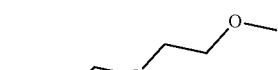
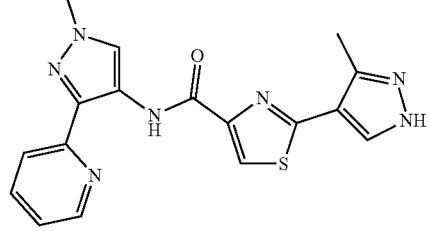
II-41
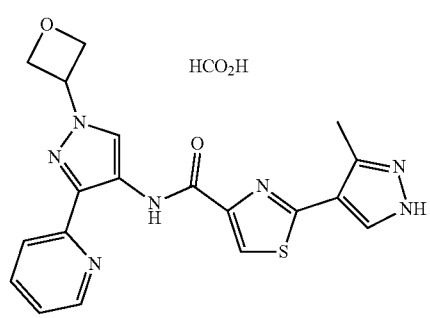
HCO₂H
II-42
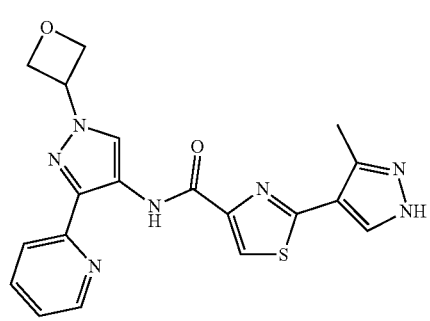
II-43
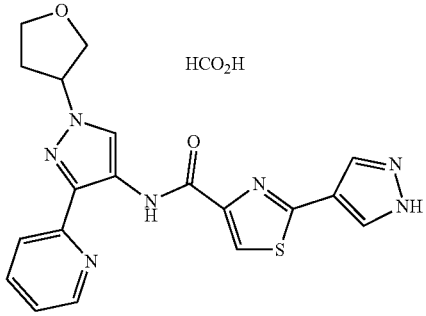
HCO₂H
II-44
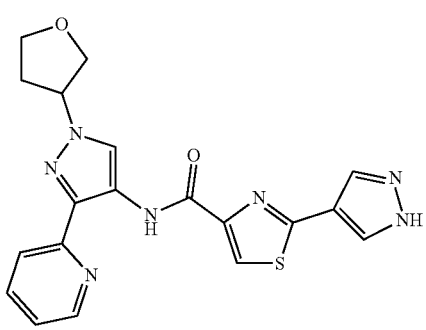
II-45
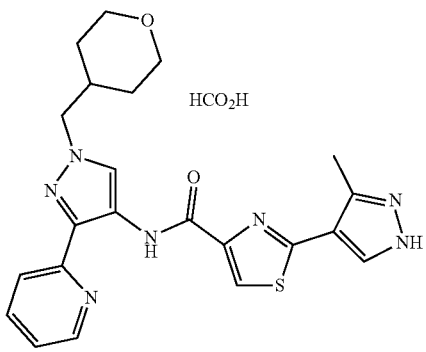
HCO₂H
II-46
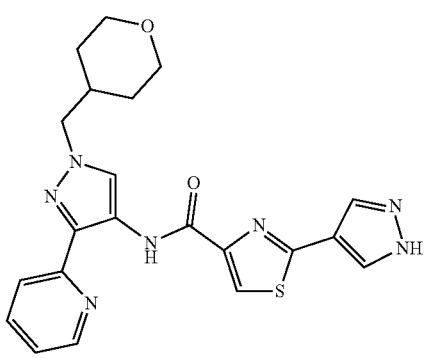

II-47
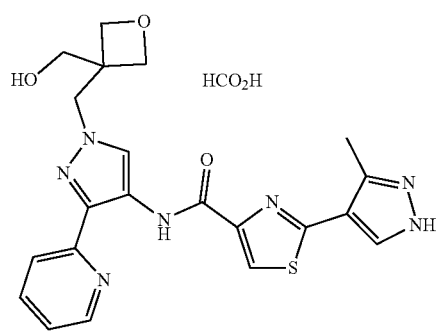
II-51
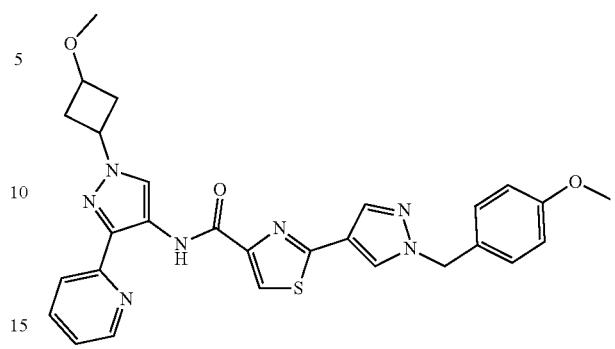
II-48
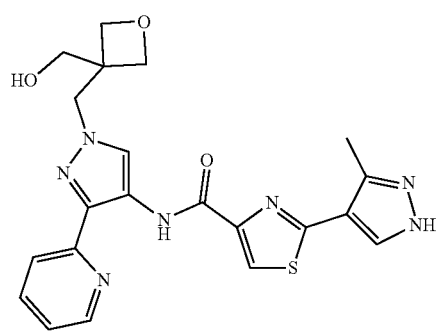
II-52
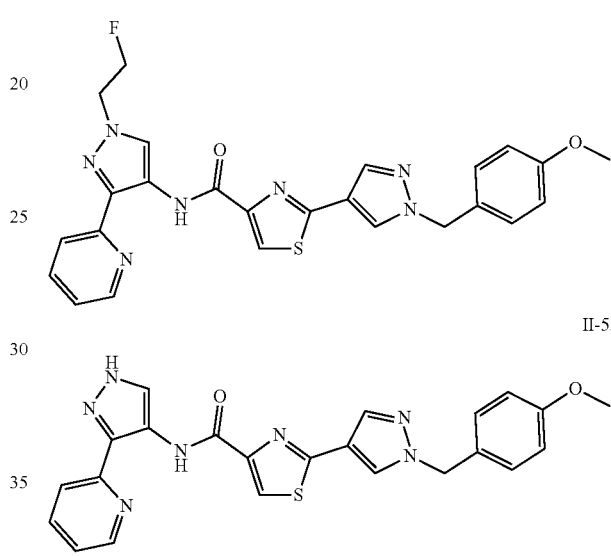
II-49
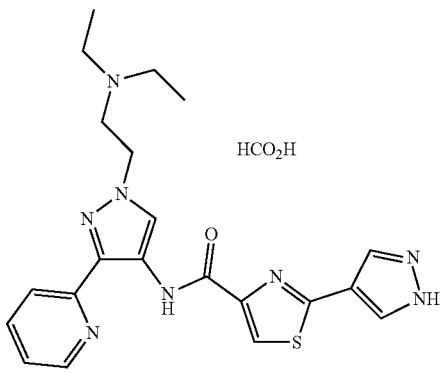
II-53
II-54
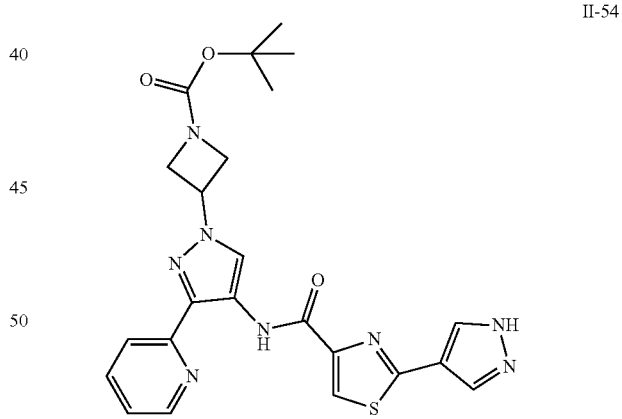
II-50
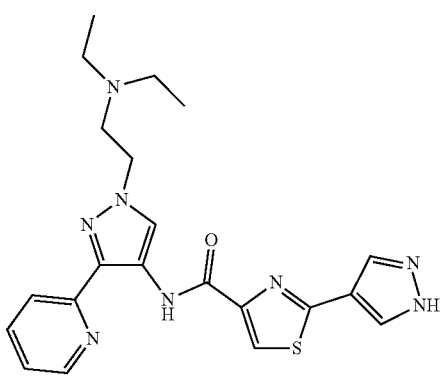
II-55
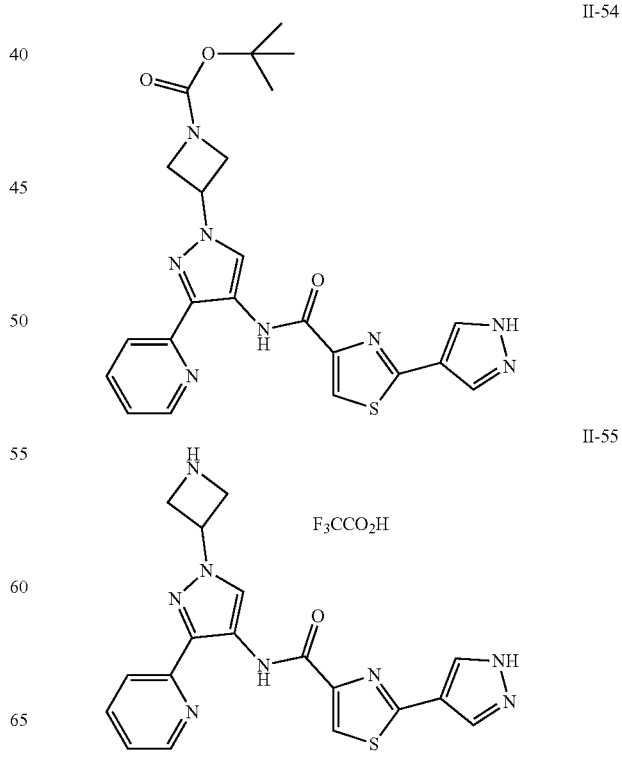

II-56
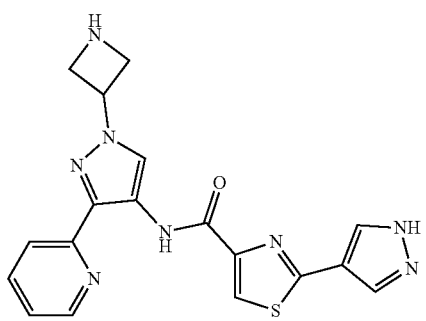
II-57
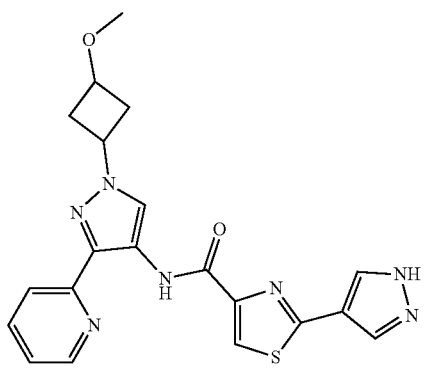
II-58
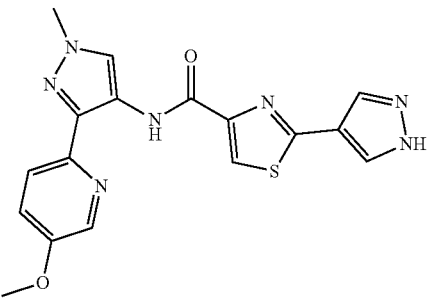
II-59
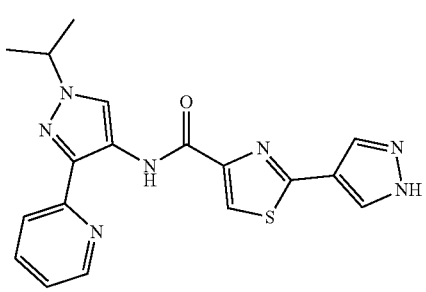
II-60
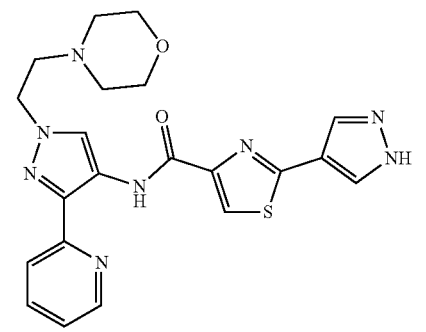
II-61
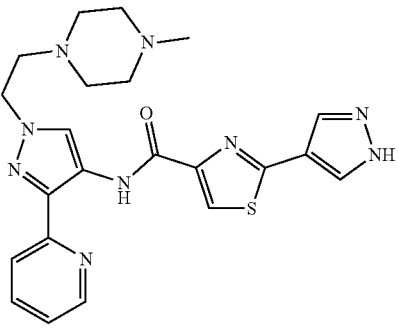
II-62
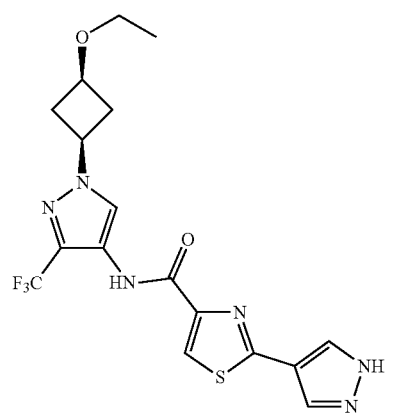
II-63
F₃CCO₂H
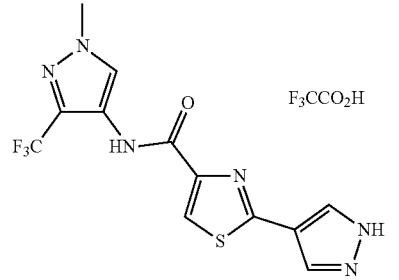
II-64
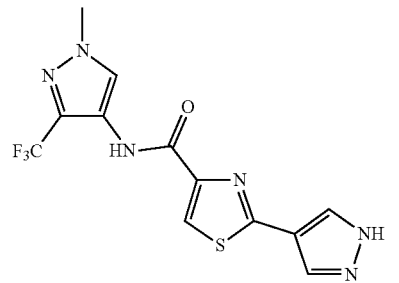

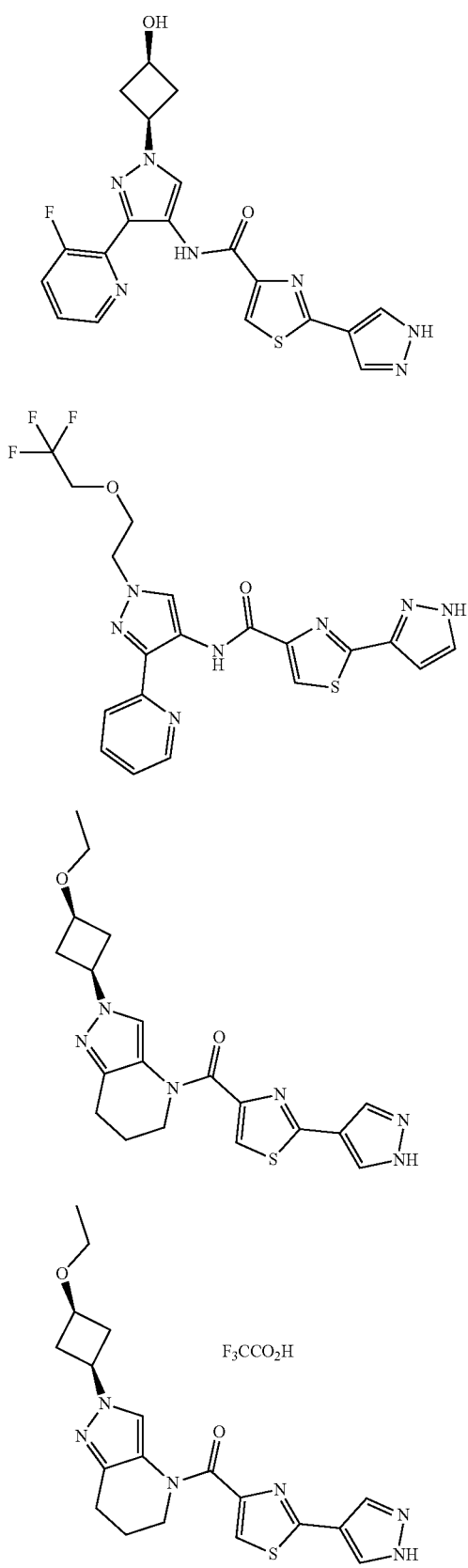
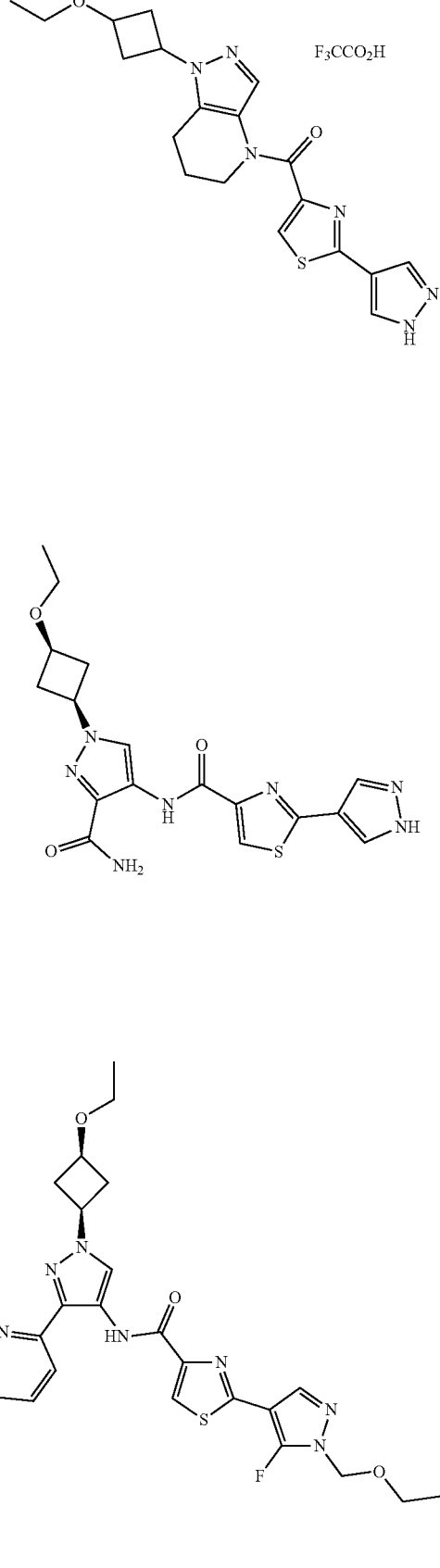

II-72
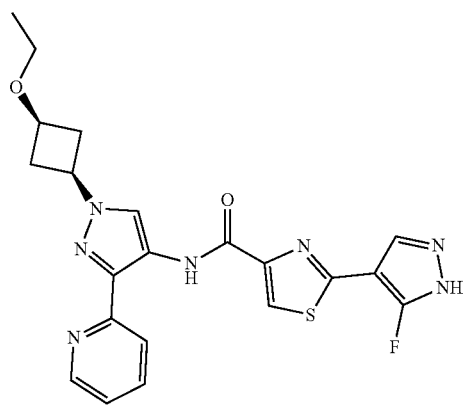
II-73
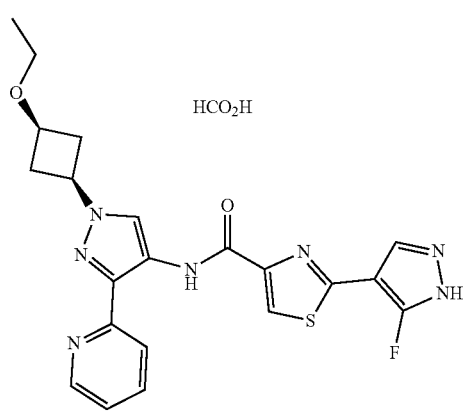
HCO2H
II-74
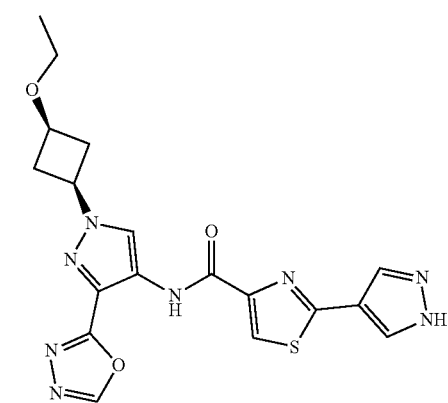
II-75
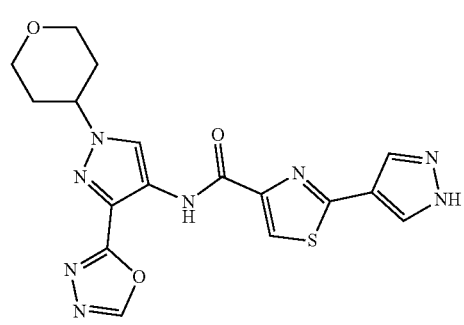
II-76
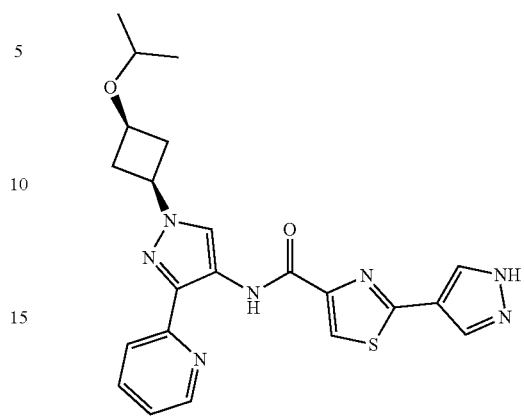
II-77
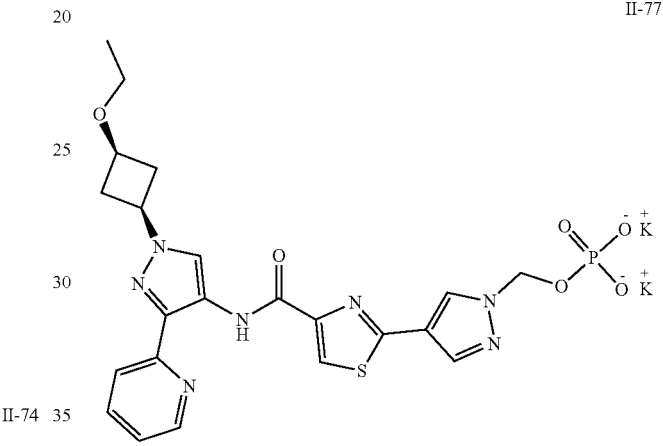
II-78
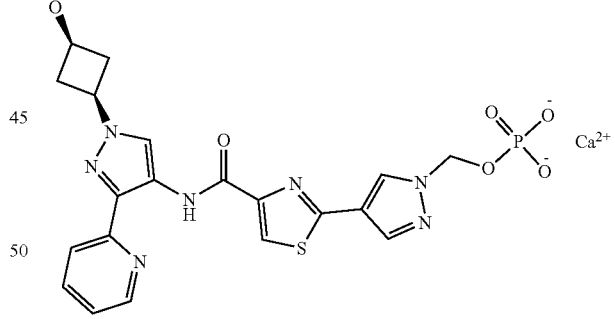
II-79
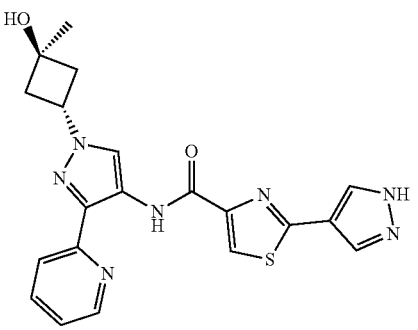

II-80
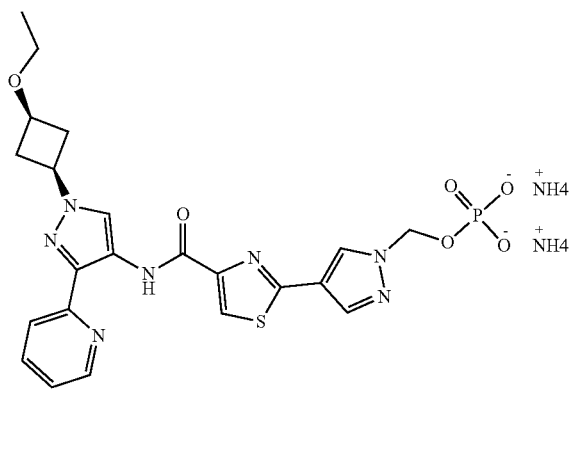
II-83
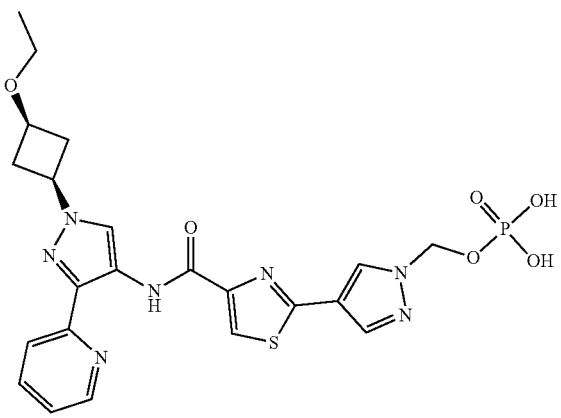
II-81
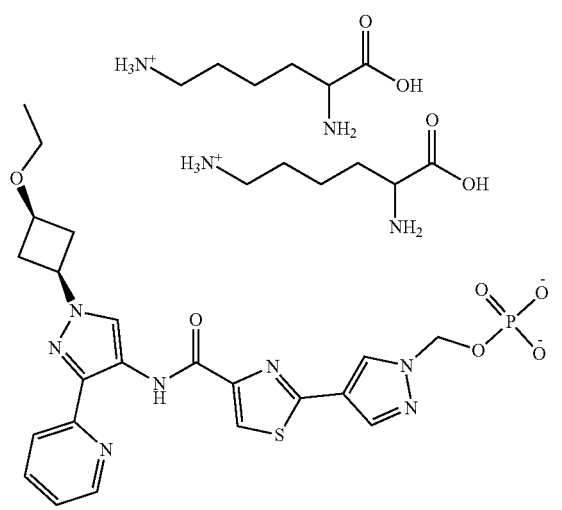
II-84
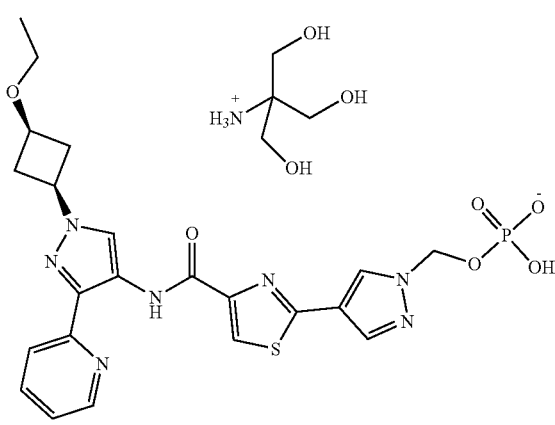
II-82
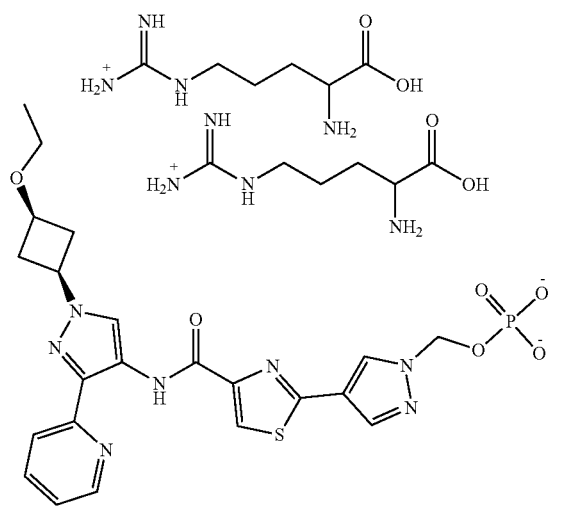
II-85
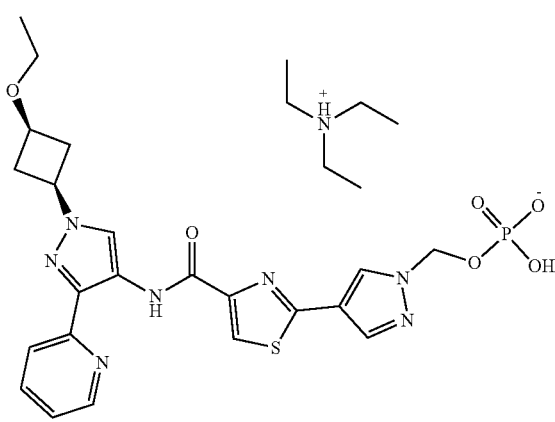

II-86
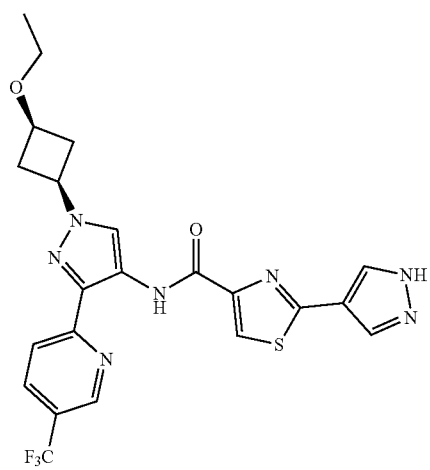
II-87
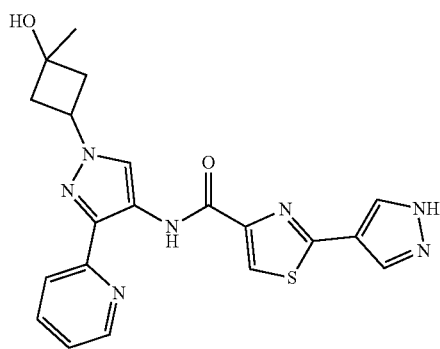
II-88
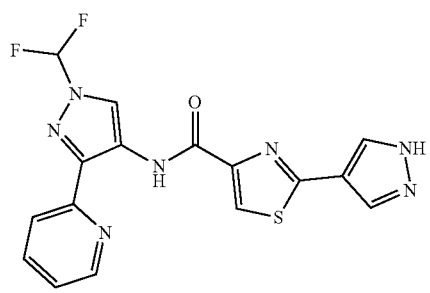
II-89
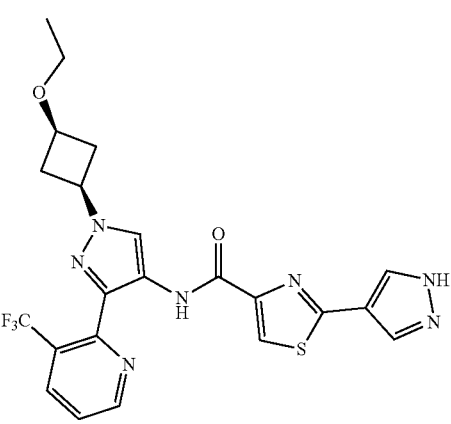
II-90
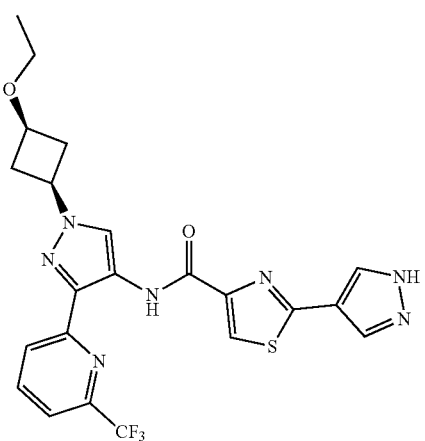
II-91
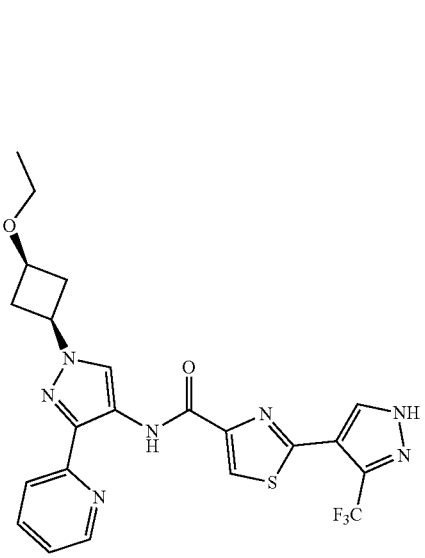
II-92
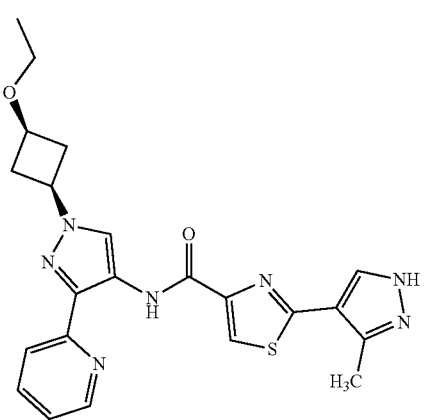

II-93
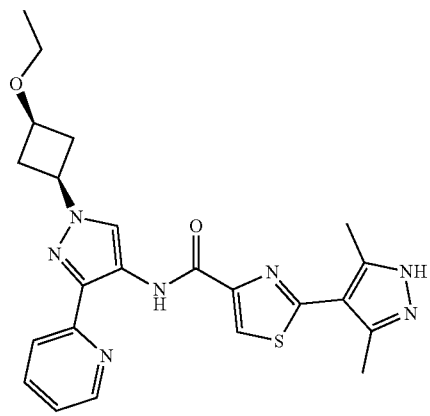
II-94
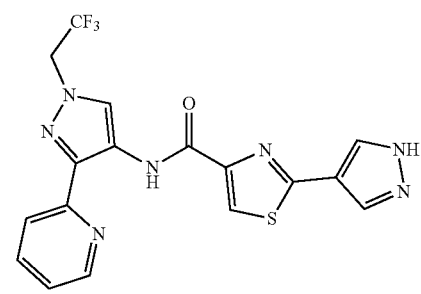
II-95
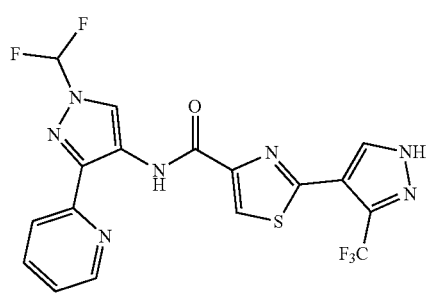
II-96
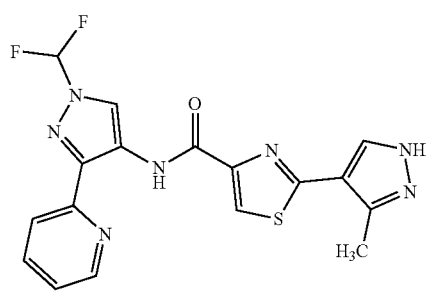
II-97
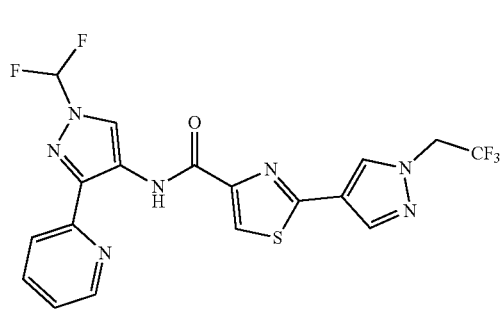
II-98
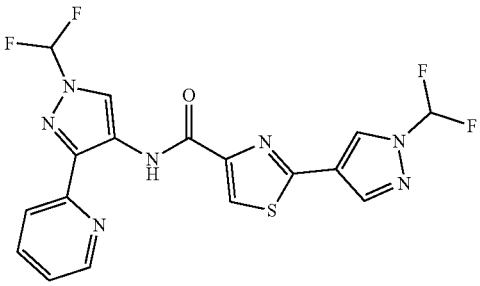
II-99
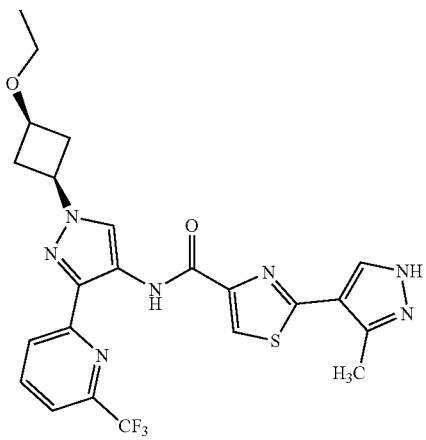
II-100
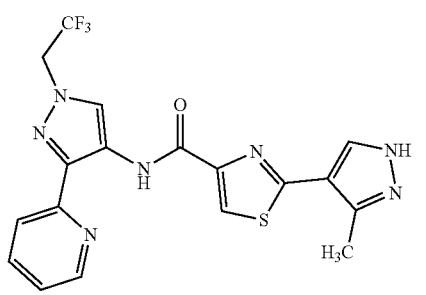
II-101
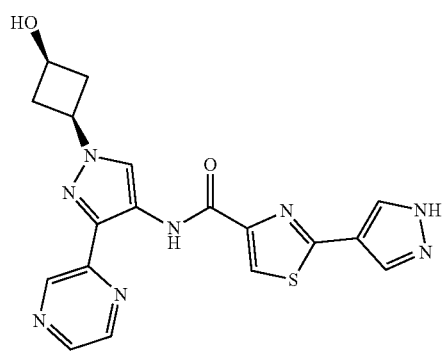

II-102
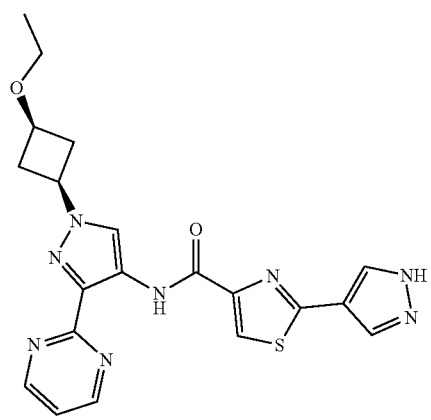
II-103
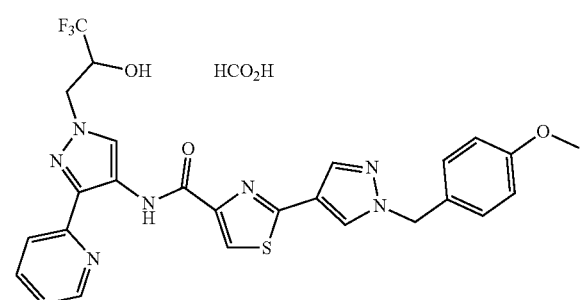
HCO₂H
II-104
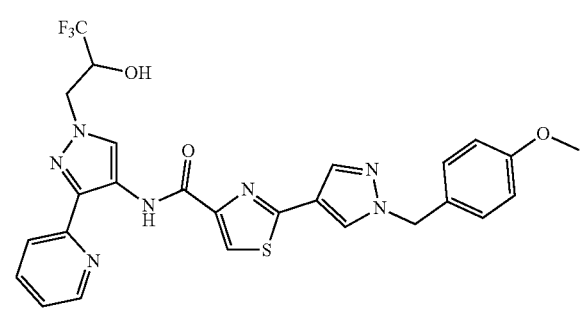
II-105
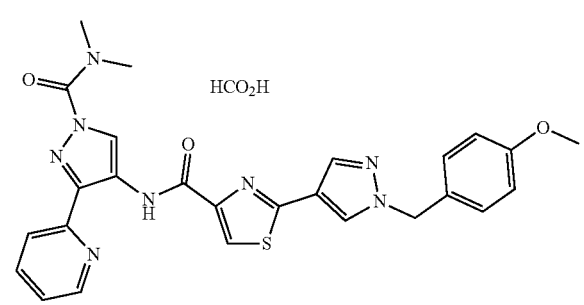
HCO₂H
II-106
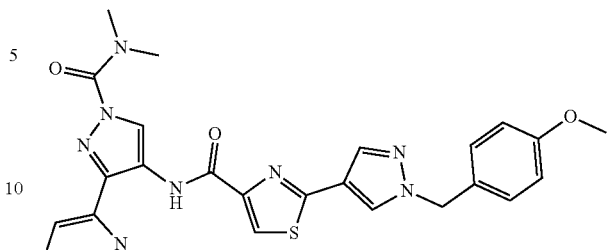
II-107
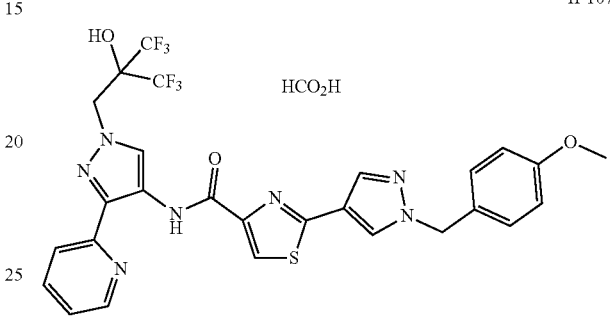
HCO₂H
II-108
II-109
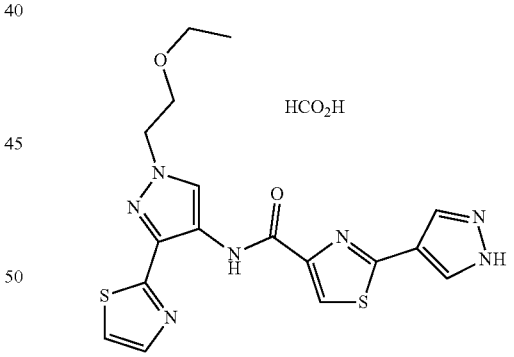
HCO₂H
II-110
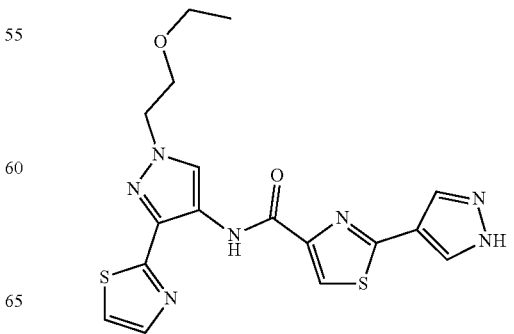

II-111
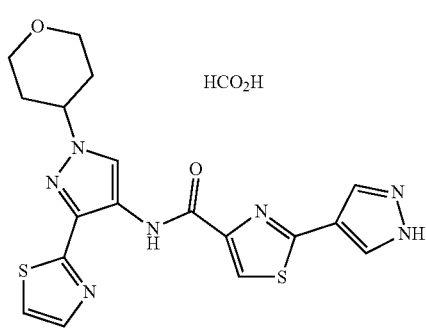
II-112
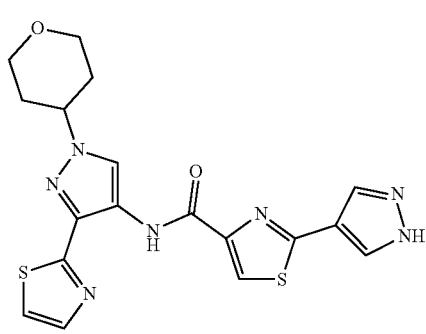
II-113
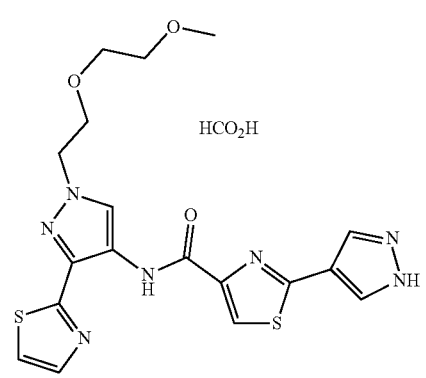
II-114
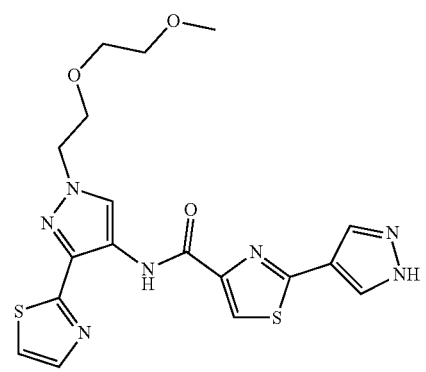
II-115
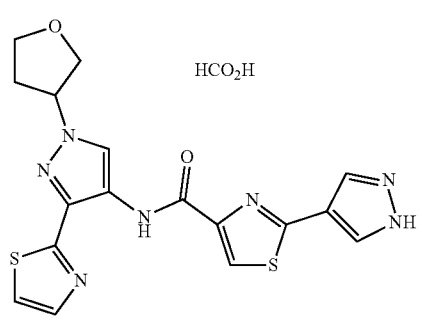
II-116
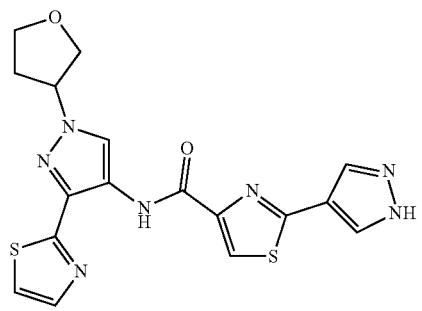
II-117
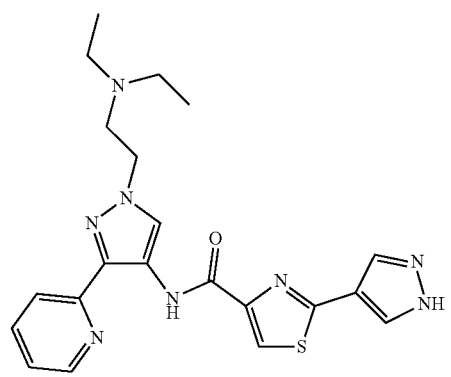
II-118
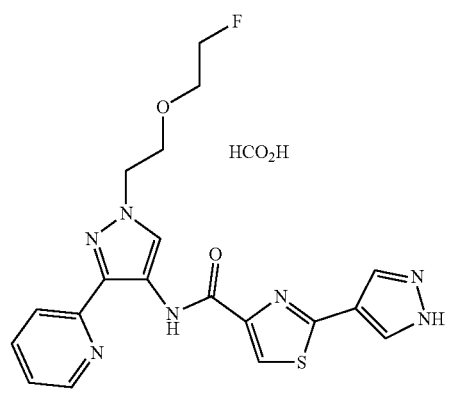

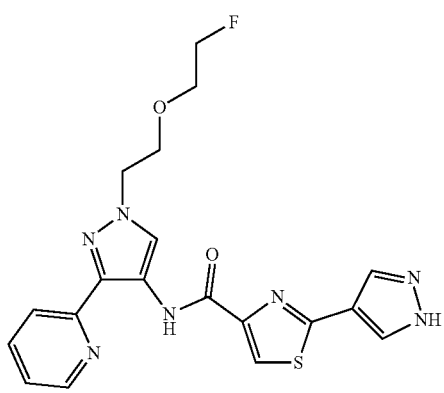
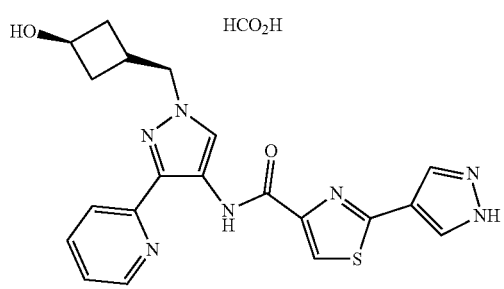

II-127
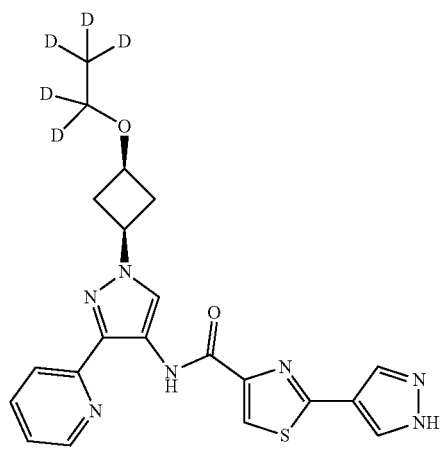
II-128
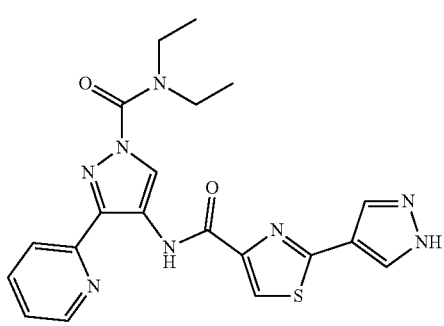
II-129
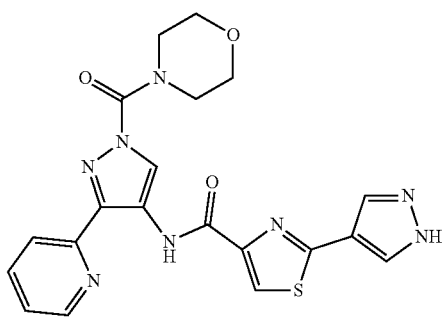
II-130
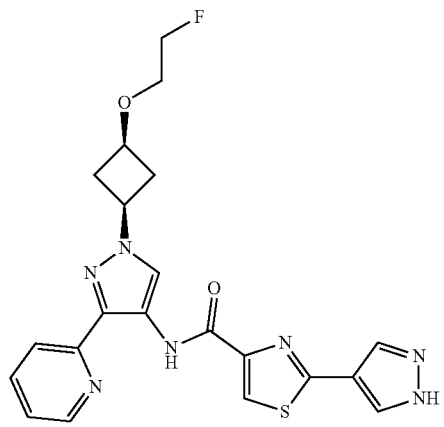
II-131 HCO₂H
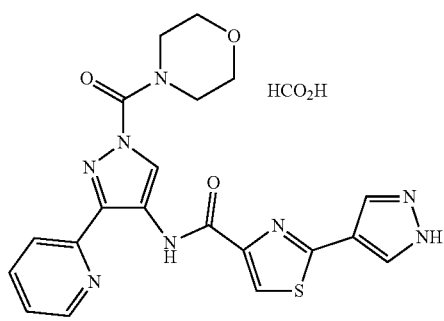
II-132
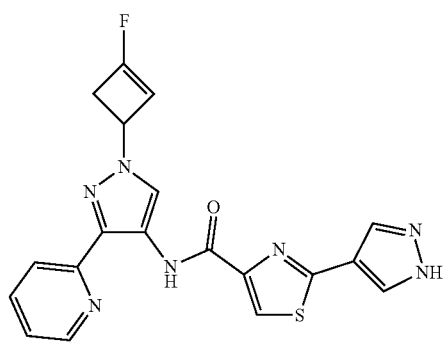
II-133 HCO₂H
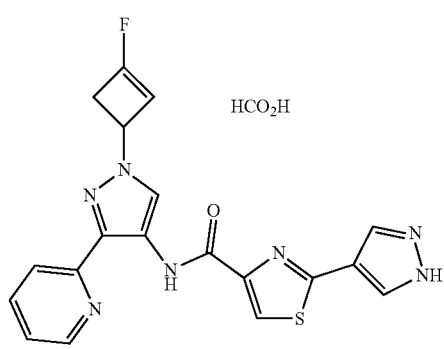
II-134 HCO₂H
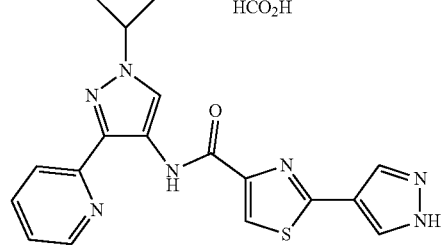

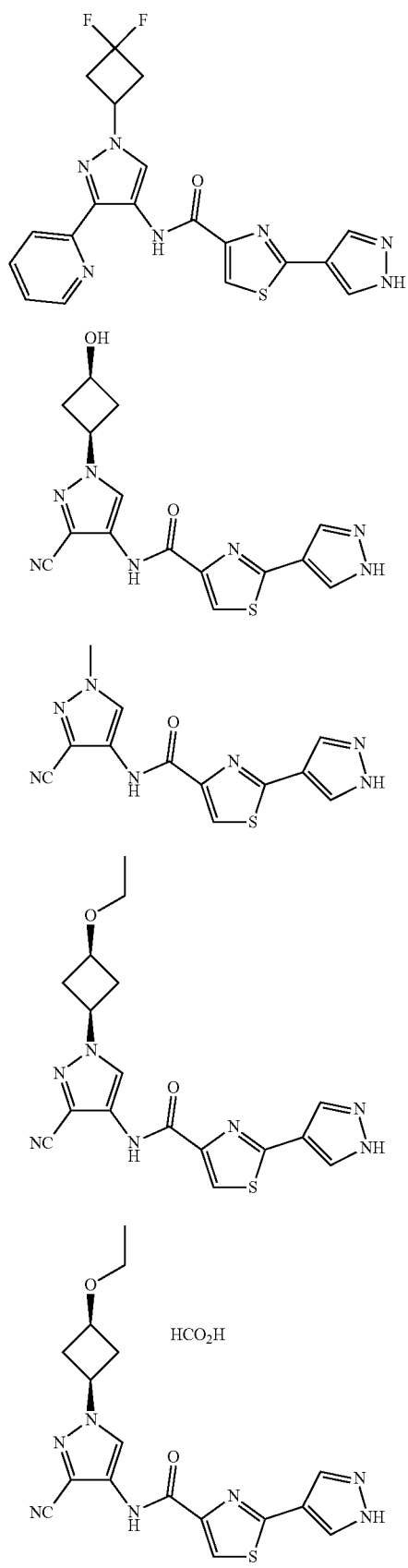
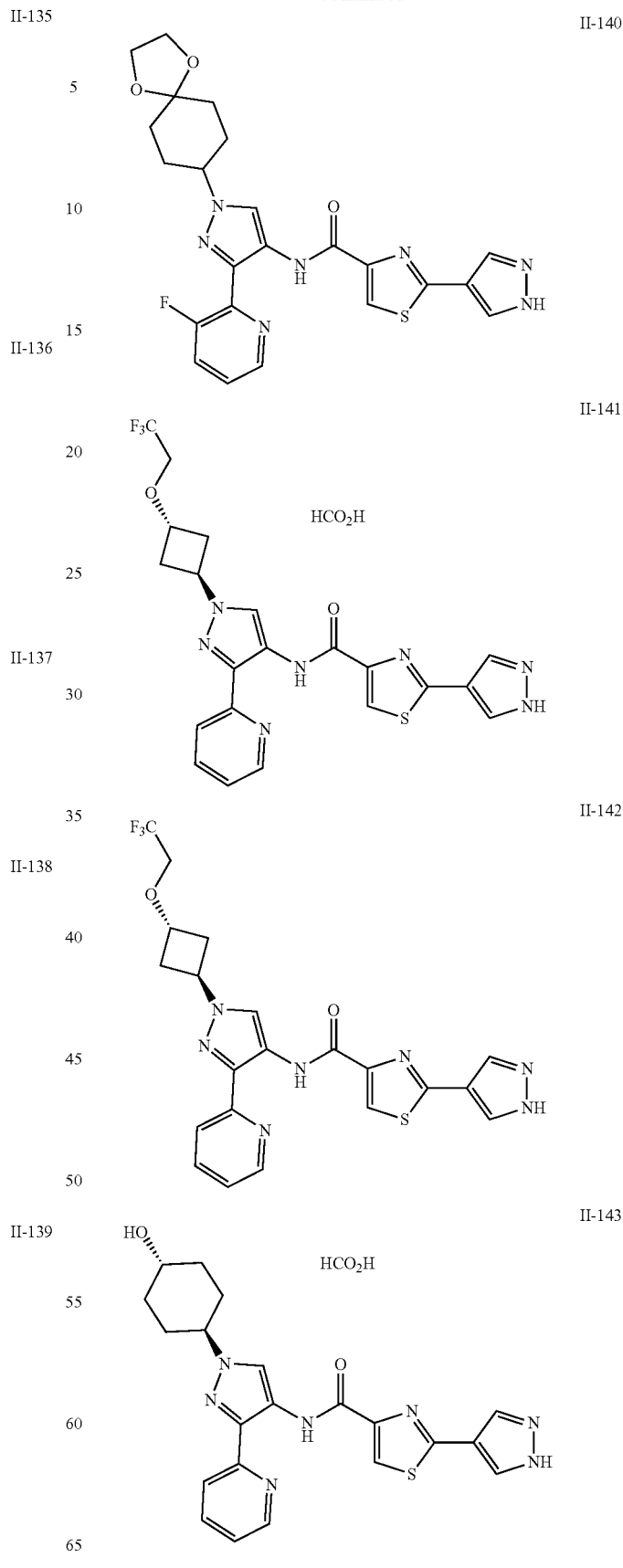

II-144
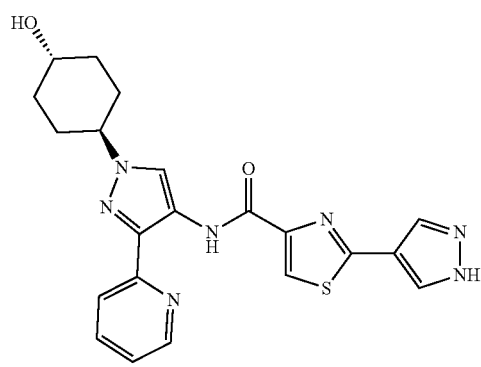
II-145
HCO₂H
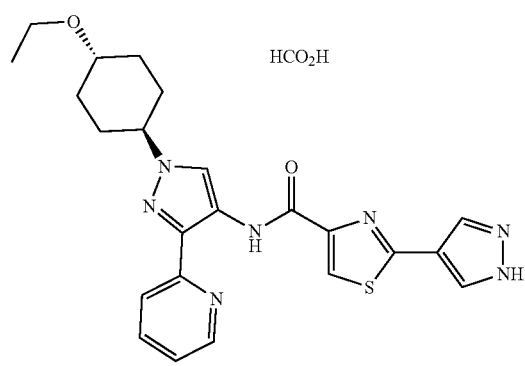
II-146
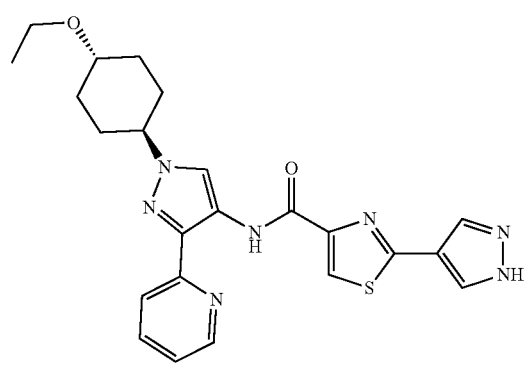
II-147
HCO₂H
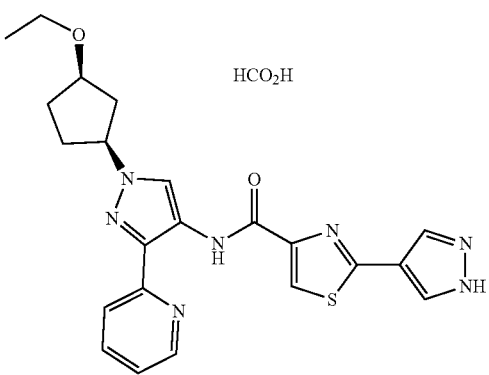
II-148
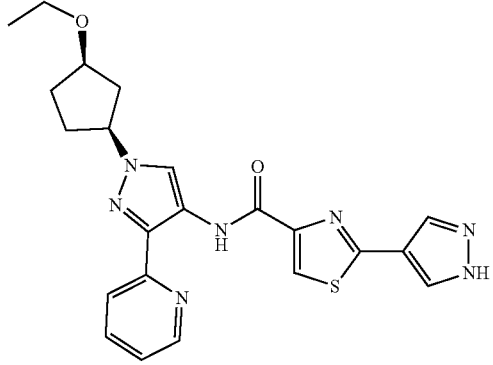
II-149
HCO₂H
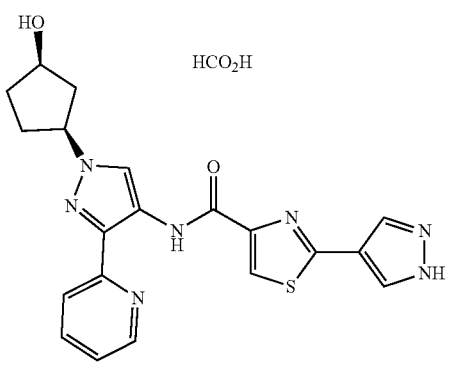
II-150
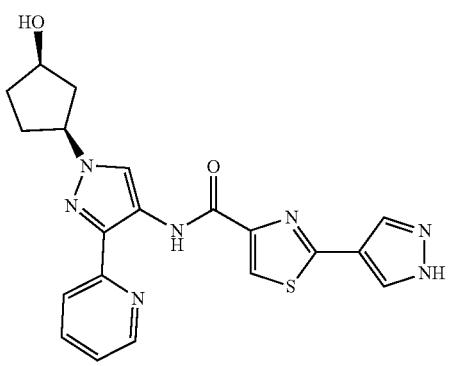
II-151
HCO₂H
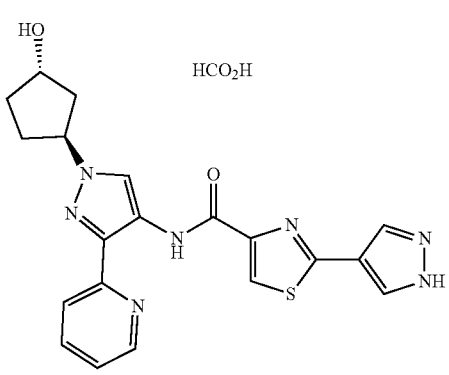

II-152
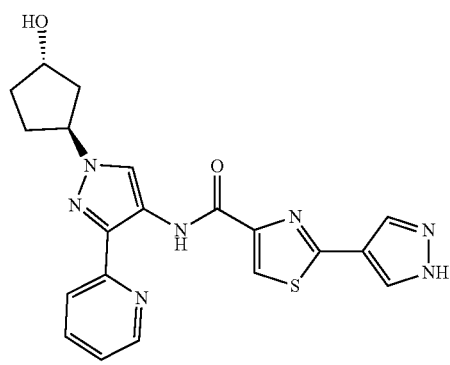
II-156
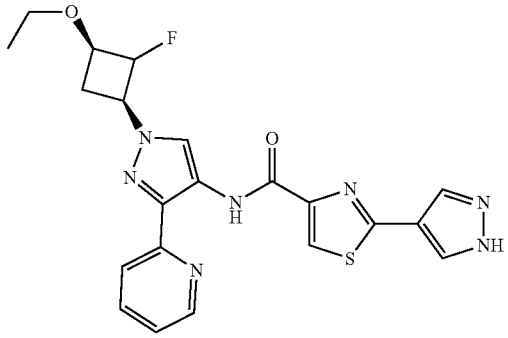
II-153 HCO2H
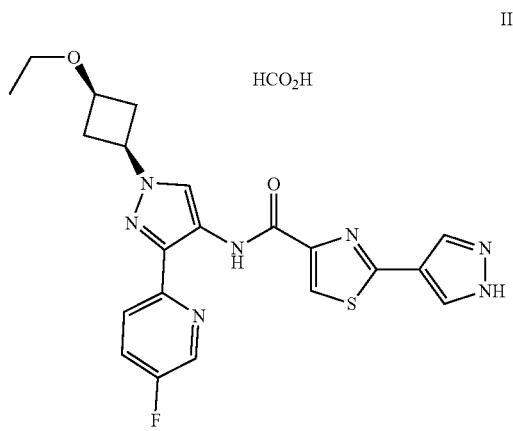
II-157
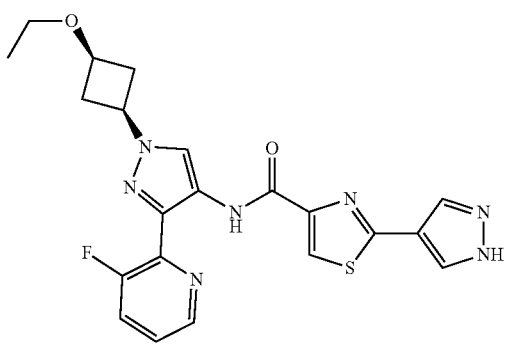
II-154
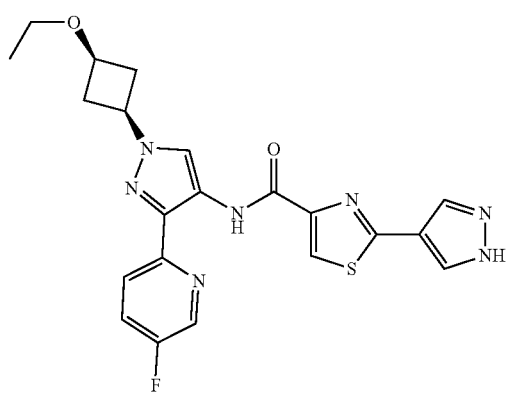
II-158 HCO2H
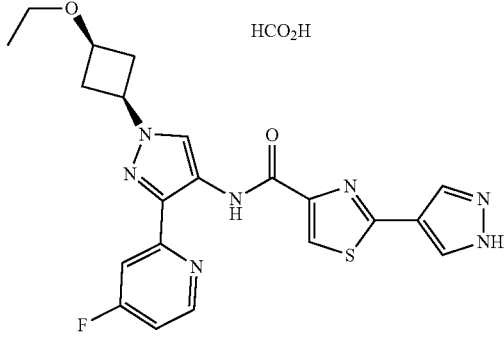
II-155 HCO2H
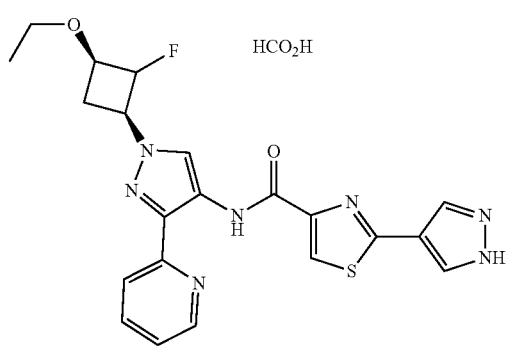
II-159
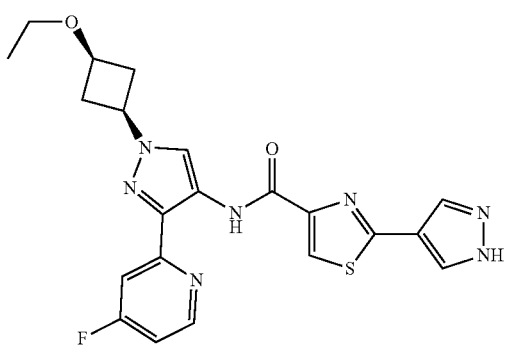

II-160
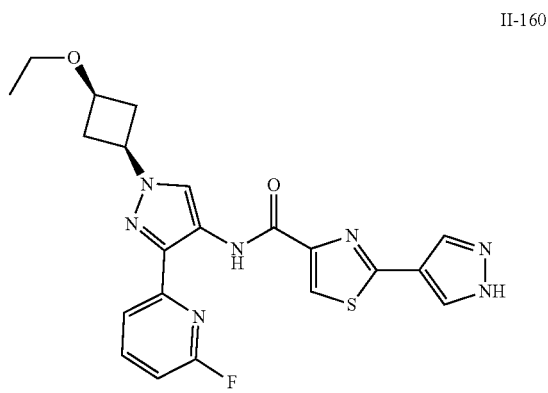
II-161
HCO₂H
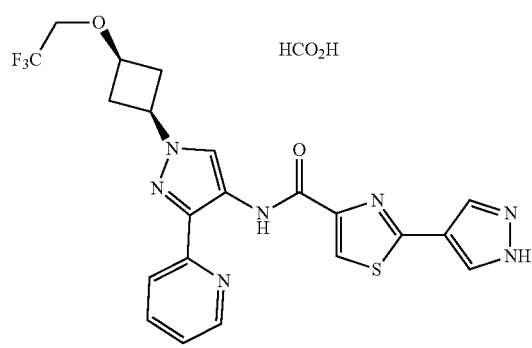
II-162
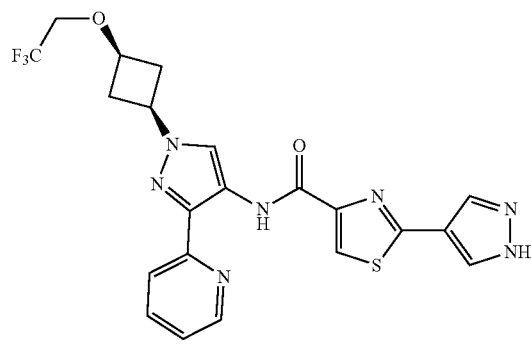
II-163
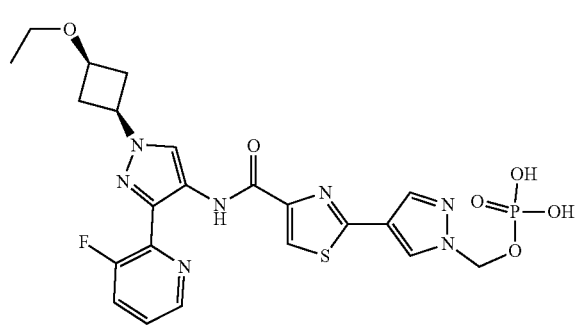
II-164
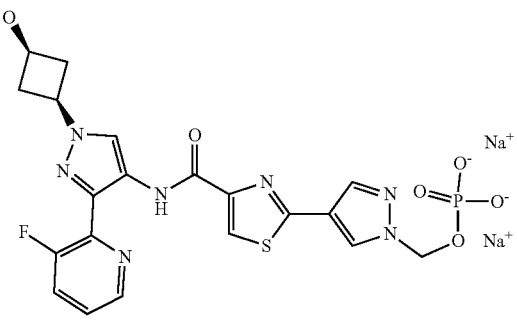
II-165
HCO₂H
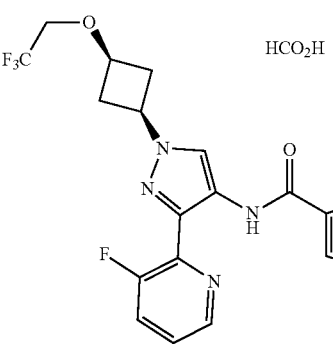
II-166
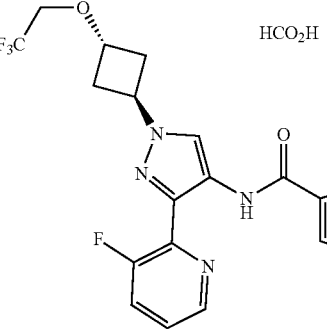
II-167
HCO₂H II-168
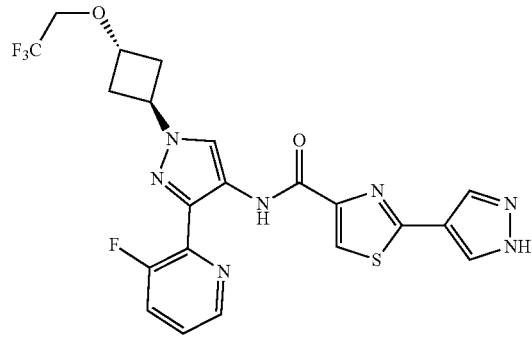
II-169
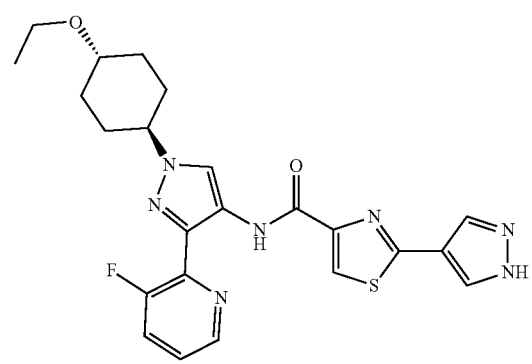
II-170
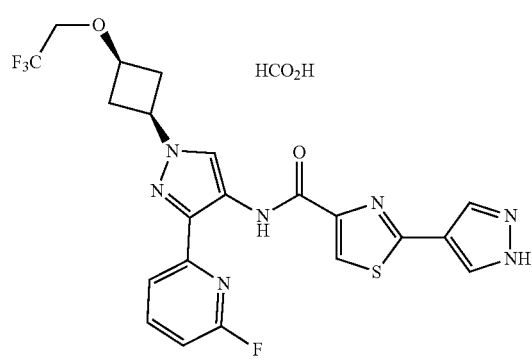
HCO2H
II-171
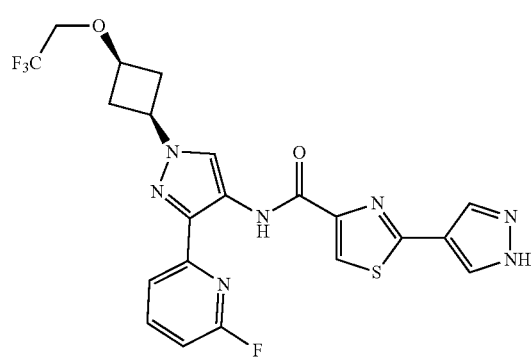
II-172
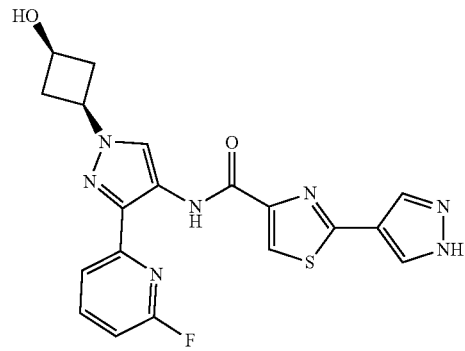
II-173
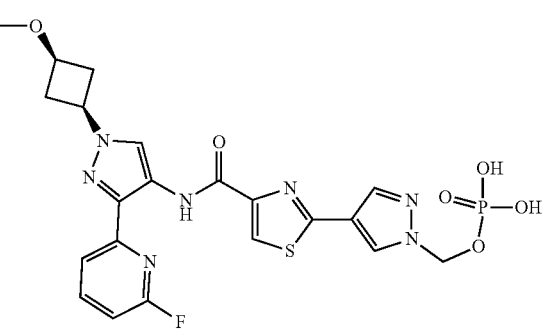
II-174
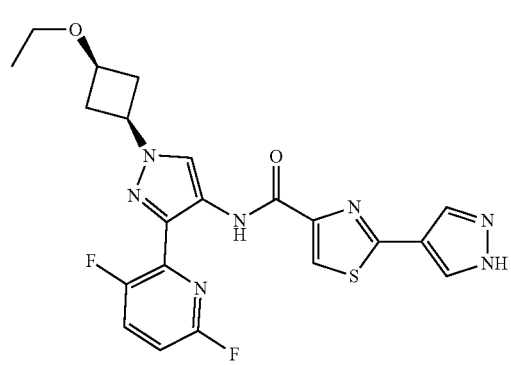
II-175
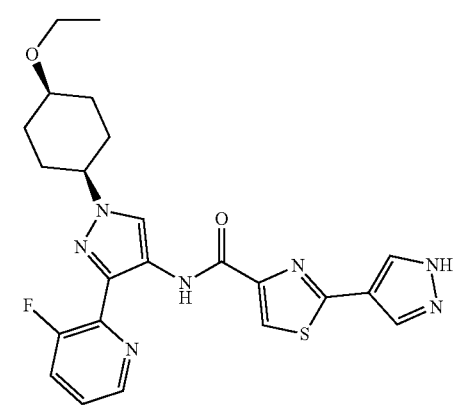

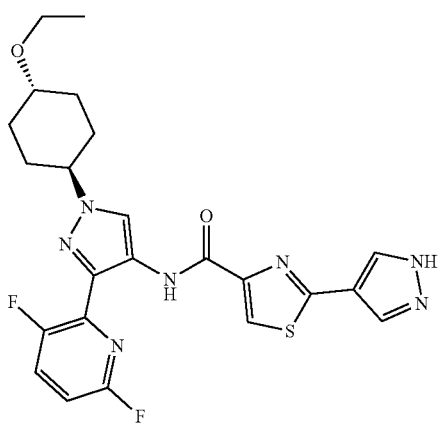
II-176
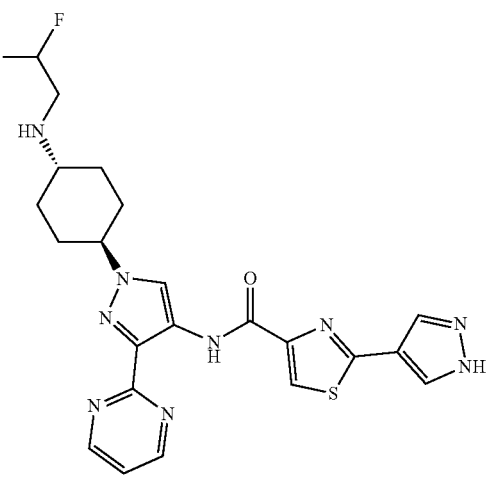
II-179
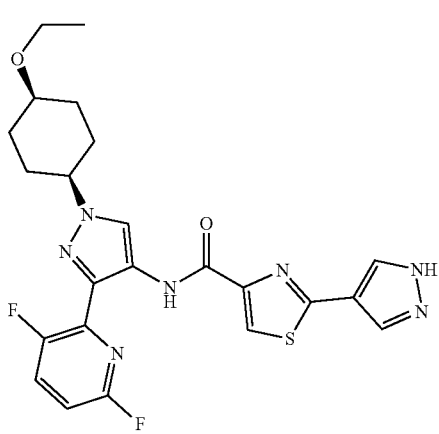
II-177
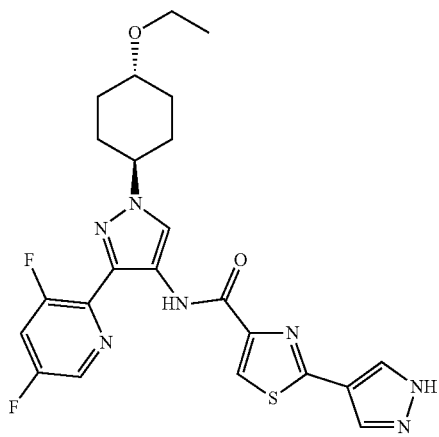
II-180
In other embodiments, the compound according to formula 1 is selected from
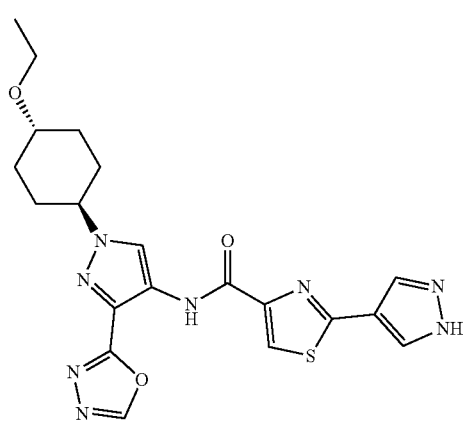
II-178
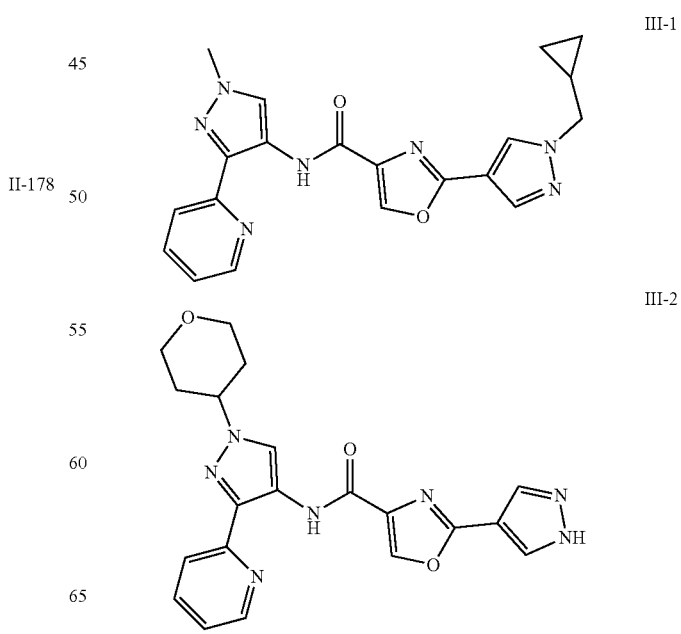
III-1
III-2

III-3
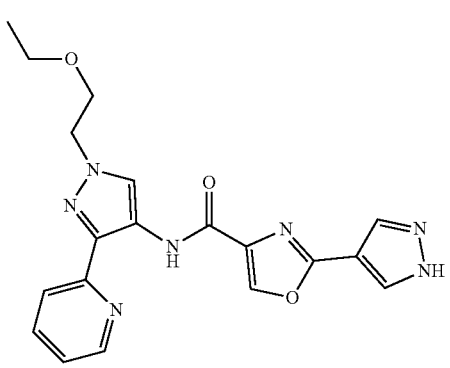

III-4
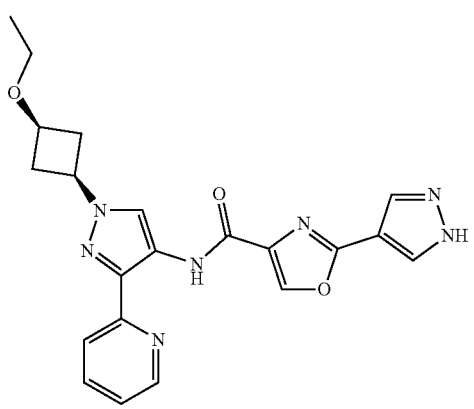

III-5
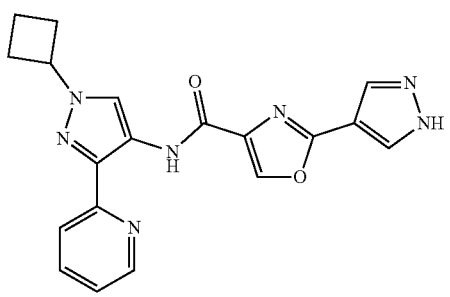

III-6
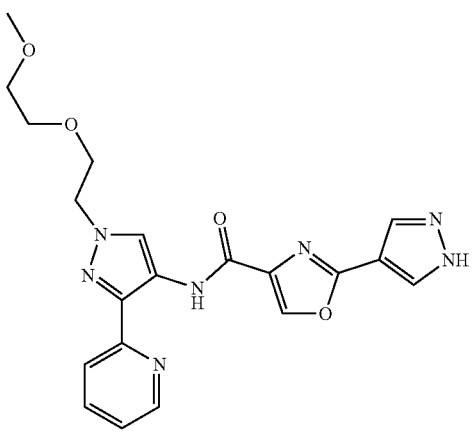

III-7
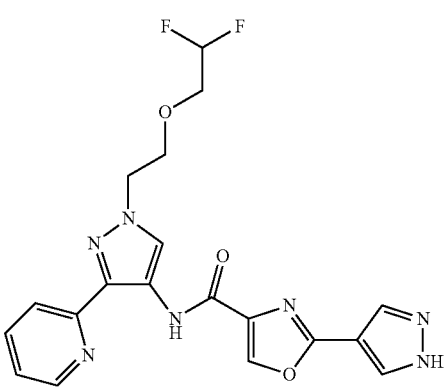

III-8
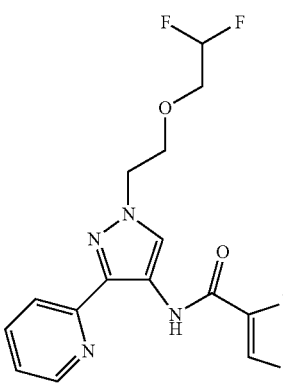

Exemplary compounds according to formula 1 include:
I-1: N-(1-(2-hydroxy-2-methylpropyl)-3-(pyridin-2-yl)-1H-pyrazol-4-yl)-5-(1-methyl-1H-pyrazol-4-yl)furan-2-carboxamide 2,2,2-trifluoroacetate;
I-2: N-(1-(2-hydroxy-2-methylpropyl)-3-(pyridin-2-yl)-1H-pyrazol-4-yl)-5-(1-methyl-1H-pyrazol-4-yl)furan-2-carboxamide;
I-3: N-(1-(2-hydroxy-2-methylpropyl)-3-(pyridin-2-yl)-1H-pyrazol-4-yl)-5-(1H-pyrazol-4-yl)furan-2-carboxamide;
I-4: tert-butyl 4-(5-((1-(2-ethoxyethyl)-3-(pyridin-2-yl)-1H-pyrazol-4-yl)carbamoyl)furan-2-yl)-1H-pyrazole-1-carboxylate;
I-5: N-(1-(2-methoxyethyl)-3-(pyridin-2-yl)-1H-pyrazol-4-yl)-5-(1H-pyrazol-4-yl)furan-2-carboxamide;
I-6: N-(1-(2-methoxyethyl)-3-(pyridin-2-yl)-1H-pyrazol-4-yl)-5-(3-methyl-1H-pyrazol-4-yl)furan-2-carboxamide formic acid;
I-7: N-(1-(2-methoxyethyl)-3-(pyrimidin-2-yl)-1H-pyrazol-4-yl)-5-(1H-pyrazol-4-yl)furan-2-carboxamide;
I-8: N-(1-(2-methoxyethyl)-3-(pyrimidin-2-yl)-1H-pyrazol-4-yl)-5-(3-methyl-1H-pyrazol-4-yl)furan-2-carboxamide;
I-9: N-(1-(2-methoxyethyl)-3-(pyridin-2-yl)-1H-pyrazol-4-yl)-5-(3-methyl-1H-pyrazol-4-yl)furan-2-carboxamide;
I-10: di-tert-butyl ((4-(5-((1-(2-methoxyethyl)-3-(pyridin-2-yl)-1H-pyrazol-4-yl)carbamoyl)furan-2-yl)-1H-pyrazol-1-yl)methyl) phosphate;
I-11: tert-butyl ((4-(5-((1-(2-methoxyethyl)-3-(pyridin-2-yl)-1H-pyrazol-4-yl)carbamoyl)furan-2-yl)-1H-pyrazol-1-yl)methyl) hydrogen phosphate;
I-12: (4-(5-((1-(2-methoxyethyl)-3-(pyridin-2-yl)-1H-pyrazol-4-yl)carbamoyl)furan-2-yl)-1H-pyrazol-1-yl)methyl dihydrogen phosphate;
I-13: N-(1-(2-methoxyethyl)-3-(pyridin-2-yl)-1H-pyrazol-4-yl)-5-(3-(trifluoromethyl)-1H-pyrazol-4-yl)furan-2-carboxamide;

I-14: sodium (4-(5-((1-(2-methoxyethyl)-3-(pyridin-2-yl)-1H-pyrazol-4-yl)carbamoyl)furan-2-yl)-1H-pyrazol-1-yl)methyl phosphate;

I-15: N-(1-(2-hydroxyethyl)-3-(pyrimidin-2-yl)-1H-pyrazol-4-yl)-5-(1H-pyrazol-4-yl)furan-2-carboxamide;

I-16: N-(1-(2-(2-methoxyethoxy)ethyl)-3-(pyridin-2-yl)-1H-pyrazol-4-yl)-5-(1H-pyrazol-4-yl)furan-2-carboxamide;

I-17: N-(1-(2-(2-methoxyethoxy)ethyl)-3-(pyridin-2-yl)-1H-pyrazol-4-yl)-5-(1H-pyrazol-4-yl)furan-2-carboxamide hydrochloride salt;

I-18: N-(1-(2-(2-methoxyethoxy)ethyl)-3-(pyridin-2-yl)-1H-pyrazol-4-yl)-5-(3-methyl-1H-pyrazol-4-yl)furan-2-carboxamide;

I-19: 1-(isobutyryloxy)ethyl 4-(5-((1-(2-methoxyethyl)-3-(pyridin-2-yl)-1H-pyrazol-4-yl)carbamoyl)furan-2-yl)-1H-pyrazole-1-carboxylate;

I-20: tert-butyl (S)-(1-(4-(5-((1-(2-methoxyethyl)-3-(pyridin-2-yl)-1H-pyrazol-4-yl)carbamoyl)furan-2-yl)-1H-pyrazol-1-yl)-3-methyl-1-oxobutan-2-yl)carbamate;

I-21: 1-methylcyclopropyl 4-(5-((1-(2-methoxyethyl)-3-(pyridin-2-yl)-1H-pyrazol-4-yl)carbamoyl)furan-2-yl)-1H-pyrazole-1-carboxylate;

I-22: 1-((4-methoxybenzyl)oxy)-2-methylpropan-2-yl 4-(5-((1-(2-methoxyethyl)-3-(pyridin-2-yl)-1H-pyrazol-4-yl)carbamoyl)furan-2-yl)-1H-pyrazole-1-carboxylate;

I-23: 5-(1H-pyrazol-4-yl)-N-(3-(pyridin-2-yl)-1-(tetrahydro-2H-pyran-4-yl)-1H-pyrazol-4-yl)furan-2-carboxamide;

I-24: 5-(5-nitro-1H-pyrrol-3-yl)-N-(1-(propoxymethyl)-3-(pyridin-2-yl)-1H-pyrazol-4-yl)furan-2-carboxamide;

I-25: N-(1-(oxetan-3-yl)-3-(pyridin-2-yl)-1H-pyrazol-4-yl)-5-(1H-pyrazol-4-yl)furan-2-carboxamide;

I-26: 5-(1-methyl-1H-pyrazol-4-yl)-N-(1-(oxetan-3-yl)-3-(pyridin-2-yl)-1H-pyrazol-4-yl)furan-2-carboxamide;

I-27: N-(1-((1,3-trans)-3-ethoxycyclobutyl)-3-(pyridin-2-yl)-1H-pyrazol-4-yl)-5-(1H-pyrazol-4-yl)furan-2-carboxamide;

I-28: N-(1-((1,3-cis)-3-ethoxycyclobutyl)-3-(pyridin-2-yl)-1H-pyrazol-4-yl)-5-(1H-pyrazol-4-yl)furan-2-carboxamide;

I-29: N-(1-((1,3-cis)-3-ethoxycyclobutyl)-3-(pyridin-2-yl)-1H-pyrazol-4-yl)-5-(3-methyl-1H-pyrazol-4-yl)furan-2-carboxamide;

I-30: 5-(3-methyl-1H-pyrazol-4-yl)-N-(1-(oxetan-3-yl)-3-(pyridin-2-yl)-1H-pyrazol-4-yl)furan-2-carboxamide;

I-31: N-(1-((1,3-cis)-3-ethoxycyclobutyl)-3-(pyridin-2-yl)-1H-pyrazol-4-yl)-5-(1-methyl-1H-pyrazol-4-yl)furan-2-carboxamide;

I-32: N-(1-((1,3-cis)-3-hydroxycyclobutyl)-3-(pyridin-2-yl)-1H-pyrazol-4-yl)-5-(1H-pyrazol-4-yl)furan-2-carboxamide;

I-33: N-(1-((1s,3s)-3-(dimethylamino)cyclobutyl)-3-(pyridin-2-yl)-1H-pyrazol-4-yl)-5-(1H-pyrazol-4-yl)furan-2-carboxamide;

I-34: N-(1-((1s,3s)-3-(dimethylamino)cyclobutyl)-3-(pyridin-2-yl)-1H-pyrazol-4-yl)-5-(1H-pyrazol-4-yl)furan-2-carboxamide formate;

I-35: (4-(5-((1-((1,3-cis)-3-ethoxycyclobutyl)-3-(pyridin-2-yl)-1H-pyrazol-4-yl)carbamoyl)furan-2-yl)-1H-pyrazol-1-yl)methyl phosphate bis-sodium salt;

I-36: (4-(5-((1-((1s,3s)-3-ethoxycyclobutyl)-3-(pyridin-2-yl)-1H-pyrazol-4-yl)carbamoyl)furan-2-yl)-1H-pyrazol-1-yl)methyl dihydrogen phosphate;

I-37: N-(1-(2-ethoxyethyl)-3-(pyridin-2-yl)-1H-pyrazol-4-yl)-5-(1H-pyrazol-4-yl)furan-2-carboxamide formate;

I-38: N-(1-(2-ethoxyethyl)-3-(pyridin-2-yl)-1H-pyrazol-4-yl)-5-(1H-pyrazol-4-yl)furan-2-carboxamide;

I-39: N-(1-(2-ethoxyethyl)-3-(pyridin-2-yl)-1H-pyrazol-4-yl)-5-(1-ethyl-1H-pyrazol-4-yl)furan-2-carboxamide formate;

I-40: N-(1-(2-ethoxyethyl)-3-(pyridin-2-yl)-1H-pyrazol-4-yl)-5-(1-ethyl-1H-pyrazol-4-yl)furan-2-carboxamide;

I-41: N-(1-(2-ethoxyethyl)-3-(pyridin-2-yl)-1H-pyrazol-4-yl)-5-(3-(trifluoromethyl)-1H-pyrazol-4-yl)furan-2-carboxamide formate;

I-42: N-(1-(2-ethoxyethyl)-3-(pyridin-2-yl)-1H-pyrazol-4-yl)-5-(3-(trifluoromethyl)-1H-pyrazol-4-yl)furan-2-carboxamide;

I-43: N-(1-(2-ethoxyethyl)-3-(pyridin-2-yl)-1H-pyrazol-4-yl)-5-(1-isopentyl-1H-pyrazol-4-yl)furan-2-carboxamide formate;

I-44: N-(1-(2-ethoxyethyl)-3-(pyridin-2-yl)-1H-pyrazol-4-yl)-5-(1-isopentyl-1H-pyrazol-4-yl)furan-2-carboxamide;

I-45: N-(1-(2-ethoxyethyl)-3-(pyridin-2-yl)-1H-pyrazol-4-yl)-5-(1-methyl-1H-pyrazol-4-yl)furan-2-carboxamide formate;

I-46: N-(1-(2-ethoxyethyl)-3-(pyridin-2-yl)-1H-pyrazol-4-yl)-5-(1-methyl-1H-pyrazol-4-yl)furan-2-carboxamide;

I-47: 5-(1H-pyrazol-4-yl)-N-(3-(pyridin-2-yl)-1H-pyrazol-4-yl)furan-2-carboxamide;

I-48: 5-(1-((3-methyloxetan-3-yl)methyl)-1H-pyrazol-4-yl)-N-(1-((3-methyloxetan-3-yl)methyl)-3-(pyridin-2-yl)-1H-pyrazol-4-yl)furan-2-carboxamide formate;

I-49: 5-(1-((3-methyloxetan-3-yl)methyl)-1H-pyrazol-4-yl)-N-(1-((3-methyloxetan-3-yl)methyl)-3-(pyridin-2-yl)-1H-pyrazol-4-yl)furan-2-carboxamide;

I-50: N-(2-(2-methoxyethoxy)ethyl)-5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide formate;

I-51: N-(2-(2-methoxyethoxy)ethyl)-5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide;

I-52: 5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide formate;

I-53: 5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide;

I-54: (4-(5-((1-(2-ethoxyethyl)-3-(pyridin-2-yl)-1H-pyrazol-4-yl)carbamoyl)furan-2-yl)-1H-pyrazol-1-yl)methyl dihydrogen phosphate;

I-55: sodium (4-(5-((1-(2-ethoxyethyl)-3-(pyridin-2-yl)-1H-pyrazol-4-yl)carbamoyl)furan-2-yl)-1H-pyrazol-1-yl)methyl phosphate;

I-56: N-(1-(2-ethoxyethyl)-3-(pyridin-2-yl)-1H-pyrazol-4-yl)-5-(3-methyl-1H-pyrazol-4-yl)furan-2-carboxamide formate;

I-57: N-(1-(2-ethoxyethyl)-3-(pyridin-2-yl)-1H-pyrazol-4-yl)-5-(3-methyl-1H-pyrazol-4-yl)furan-2-carboxamide;

I-58: 5-(3,5-dimethyl-1H-pyrazol-4-yl)-N-(1-(2-ethoxyethyl)-3-(pyridin-2-yl)-1H-pyrazol-4-yl)furan-2-carboxamide formate;

I-59: 5-(3,5-dimethyl-1H-pyrazol-4-yl)-N-(1-(2-ethoxyethyl)-3-(pyridin-2-yl)-1H-pyrazol-4-yl)furan-2-carboxamide;

I-60: 5-(1H-pyrazol-4-yl)-N-(1-(tetrahydro-2H-pyran-4-yl)-3-(thiazol-2-yl)-1H-pyrazol-4-yl)furan-2-carboxamide formate;

I-61: 5-(1H-pyrazol-4-yl)-N-(1-(tetrahydro-2H-pyran-4-yl)-3-(thiazol-2-yl)-1H-pyrazol-4-yl)furan-2-carboxamide;

I-62: N-(1-((1s,3s)-3-ethoxycyclobutyl)-3-(thiazol-2-yl)-1H-pyrazol-4-yl)-5-(1H-pyrazol-4-yl)furan-2-carboxamide formate;

I-63: N-(1-((1s,3s)-3-ethoxycyclobutyl)-3-(thiazol-2-yl)-1H-pyrazol-4-yl)-5-(1H-pyrazol-4-yl)furan-2-carboxamide;

I-64: N-(1-(2-(2-methoxyethoxy)ethyl)-3-(thiazol-2-yl)-1H-pyrazol-4-yl)-5-(1H-pyrazol-4-yl)furan-2-carboxamide;

I-65: 5-(1H-pyrazol-4-yl)-N-(1-(tetrahydro-2H-pyran-4-yl)-3-(thiazol-2-yl)-1H-pyrazol-4-yl)furan-2-carboxamide;

I-66: 5-(1H-pyrazol-4-yl)-N-(1-(tetrahydro-2H-pyran-4-yl)-3-(thiazol-2-yl)-1H-pyrazol-4-yl)furan-2-carboxamide;

I-67: N-{1-Methyl-3-(pyridine-2-yl)-1H-pyrazol-4-yl}-5-(1H-pyrazol-4-yl)furan-2-carboxamide, formate salt;

I-68: 5-(1-Methyl-1H-pyrazol-4-yl)-N-{1-methyl-3-(pyridine-2-yl)-1H-pyrazol-4-yl}furan-2-carboxamide;

I-69: 5-(1-Methyl-1H-pyrazol-4-yl)-N-{1-methyl-3-(pyridine-2-yl)-1H-pyrazol-4-yl}furan-2-carboxamide, formate salt;

I-70: tert-Butyl-3-[4-{5-(1H-pyrazole-4-yl)furan-2-carboxamido}-3-(pyridine-2-yl)-1H-pyrazol-1-yl]azetidine-1-carboxylate, formate salt;

I-71: N-{1-(3-Methoxycyclobutyl)-3-(pyridine-2-yl)-1H-pyrazol-4-yl}-5-(1H-pyrazol-4-yl)furan-2-carboxamide, formate salt, Cis isomer;

I-72: N-{1-(3-Methoxycyclobutyl)-3-(pyridine-2-yl)-1H-pyrazol-4-yl}-5-(1H-pyrazol-4-yl)furan-2-carboxamide, Cis isomer;

I-73: N-{1-(3-Benzyloxy)cyclobutyl)-3-(pyridine-2-yl)-1H-pyrazol-4-yl}-5-(1H-pyrazol-4-yl)furan-2-carboxamide, Trans isomer;

I-74: tert-Butyl-3-[4-{5-(1H-pyrazole-4-yl)furan-2-carboxamido}-3-(pyridine-2-yl)-1H-pyrazol-1-yl]azetidine-1-carboxylate;

I-75: N-(1-((1s,3s)-3-methoxycyclobutyl)-3-(pyridin-2-yl)-1H-pyrazol-4-yl)-5-(1H-pyrazol-4-yl)furan-2-carboxamide formate;

I-76: N-(1-((1s,3s)-3-methoxycyclobutyl)-3-(pyridin-2-yl)-1H-pyrazol-4-yl)-5-(1H-pyrazol-4-yl)furan-2-carboxamide;

I-77: N-{1-Methyl-3-(pyridine-2-yl)-1H-pyrazol-4-yl}-5-(1H-pyrazol-4-yl)furan-2-carboxamide, free base;

I-78: N-{1-(Azetidin-3-yl)-3-(pyridine-2-yl)-1H-pyrazol-4-yl}-5-(1H-pyrazol-4-yl)furan-2-carboxamide, TFA salt;

I-79: N-{1-(Azetidin-3-yl)-3-(pyridine-2-yl)-1H-pyrazol-4-yl}-5-(1H-pyrazol-4-yl)furan-2-carboxamide;

I-80: Di-tert-butyl-[[4-{4-(5-((1-methyl-3-(pyridine-2-yl)-1H-pyrazol-4-yl)carbamoyl)furan-2-yl)-1H-pyrazol-1-yl}methyl] phosphate;

I-81: [4-{5-((1-Methyl-3-(pyridine-2-yl)-1H-pyrazol-4-yl)carbamoyl)furan-2yl}-1H-pyrazol-1-yl]methyl dihydrogen phosphate;

I-82: Sodium [4-{5-((1-Methyl-3-(pyridine-2-yl)-1H-pyrazol-4-yl)carbamoyl)furan-2yl}-1H-pyrazol-1-yl]methyl phosphate;

I-83: N-{1-(1-Acetylazetidin-3-yl)-3-(pyridine-2-yl)-1H-pyrazol-4-yl}-5-(1H-pyrazol-4-yl)furan-2-carboxamide, free base;

I-84: 3-[4-{5-(1H-Pyrazol-4-yl)furan-2-carboxamido}-3-(pyridine-2-yl)-1H-pyrazol-1-yl]-N-(tert-butyl)azetidine-1-carboxamide, free base;

I-85: 3-[4-{5-(1H-Pyrazol-4-yl)furan-2-carboxamido}-3-(pyridine-2-yl)-1H-pyrazol-1-yl]-N-isopropylazetidine-1-carboxamide, free base;

I-86: 3-[4-{5-(1H-Pyrazol-4-yl)furan-2-carboxamido}-3-(pyridine-2-yl)-1H-pyrazol-1-yl]-N-propylazetidine-1-carboxamide, free base.

I-87: 3-[4-{5-(1H-Pyrazol-4-yl)furan-2-carboxamido}-3-(pyridine-2-yl)-1H-pyrazol-1-yl]-N-cyclopropylazetidine-1-carboxamide, formate salt;

I-88: 3-[4-{5-(1H-Pyrazol-4-yl)furan-2-carboxamido}-3-(pyridine-2-yl)-1H-pyrazol-1-yl]-N-cyclopropylazetidine-1-carboxamide;

I-89: N-[1-{1-(Cyclopropanecarbonyl)azetidin-3-yl}-3-(pyridine-2-yl)-1H-pyrazol-4-yl]-5-(1H-pyrazol-4-yl)furan-2-carboxamide, formate salt;

I-90: N-[1-{1-(Cyclopropanecarbonyl)azetidin-3-yl}-3-(pyridine-2-yl)-1H-pyrazol-4-yl]-5-(1H-pyrazol-4-yl)furan-2-carboxamide;

I-91: N-[1-{1-Pivaloylazetidin-3-yl}-3-(pyridine-2-yl)-1H-pyrazol-4-yl]-5-(1H-pyrazol-4-yl)furan-2-carboxamide, formate salt;

I-92: N-[1-{1-Pivaloylazetidin-3-yl}-3-(pyridine-2-yl)-1H-pyrazol-4-yl]-5-(1H-pyrazol-4-yl)furan-2-carboxamide;

I-93: 5-(1H-Pyrazol-4-yl)-N-{3-(pyridine-2-yl)-1-(pyrrolidine-1-carbonyl)azetidin-3-yl}-1H-pyrazol-4-yl)furan-2-carboxamide, formate salt;

I-94: 5-(1H-Pyrazol-4-yl)-N-{3-(pyridine-2-yl)-1-(pyrrolidine-1-carbonyl)azetidin-3-yl}-1H-pyrazol-4-yl)furan-2-carboxamide;

I-95: N-[1-{1-Isobutyrylazetidin-3-yl}-3-(pyridine-2-yl)-1H-pyrazol-4-yl]-5-(1H-pyrazol-4-yl)furan-2-carboxamide, formate salt;

I-96: N-[1-{1-Isobutyrylazetidin-3-yl}-3-(pyridine-2-yl)-1H-pyrazol-4-yl]-5-(1H-pyrazol-4-yl)furan-2-carboxamide;

I-97: N-(1H-Pyrazol-4-yl)-N-{3-(pyridine-2-yl)-1-{1-(2,2,2-trifluoroethyl)azetidin-3-yl}-1H-pyrazol-4-yl}furan-2-carboxamide, TFA salt;

I-98: N-(1H-Pyrazol-4-yl)-N-{3-(pyridine-2-yl)-1-{1-(2,2,2-trifluoroethyl)azetidin-3-yl}-1H-pyrazol-4-yl}furan-2-carboxamide;

I-99: N-[1-{1-Butyrylazetidin-3-yl}-3-(pyridine-2-yl)-1H-pyrazol-4-yl]-5-(1H-pyrazol-4-yl)furan-2-carboxamide, formate salt;

I-100: N-[1-{1-Butyrylazetidin-3-yl}-3-(pyridine-2-yl)-1H-pyrazol-4-yl]-5-(1H-pyrazol-4-yl)furan-2-carboxamide;

I-101: N-{1-(1-Methylazetidin-3-yl)-3-(pyridine-2-yl)-1H-pyrazol-4-yl}-5-(1H-pyrazol-4-yl)furan-2-carboxamide, formate salt;

I-102: N-{1-(1-Methylazetidin-3-yl)-3-(pyridine-2-yl)-1H-pyrazol-4-yl}-5-(1H-pyrazol-4-yl)furan-2-carboxamide;

I-103: N-[1-{1-(2,2-difluorocyclopropane-1-carbonyl)azetidin-3-yl}-3-(pyridine-2-yl)-1H-pyrazol-4-yl]-5-(1H-pyrazol-4-yl)furan-2-carboxamide, formate salt;

I-104: N-[1-{1-(2,2-difluorocyclopropane-1-carbonyl)azetidin-3-yl}-3-(pyridine-2-yl)-1H-pyrazol-4-yl]-5-(1H-pyrazol-4-yl)furan-2-carboxamide;

I-105: N-(1-methyl-3-(5-morpholinopyridin-2-yl)-1H-pyrazol-4-yl)-5-(1H-pyrazol-4-yl)furan-2-carboxamide;

I-106: N-(1-methyl-3-(5-(4-methylpiperazin-1-yl)pyridin-2-yl)-1H-pyrazol-4-yl)-5-(1H-pyrazol-4-yl)furan-2-carboxamide;

I-107: N-(3-(5-(2-hydroxy-2-methylpropoxy)pyridin-2-yl)-1-methyl-1H-pyrazol-4-yl)-5-(1H-pyrazol-4-yl)furan-2-carboxamide;

I-108: N-(1-methyl-3-(5-(oxetan-3-yloxy)pyridin-2-yl)-1H-pyrazol-4-yl)-5-(1H-pyrazol-4-yl)furan-2-carboxamide;

I-109: N-(3-(5-methoxypyridin-2-yl)-1-methyl-1H-pyrazol-4-yl)-5-(1H-pyrazol-4-yl)furan-2-carboxamide;

I-110: N-(1-isopropyl-3-(pyridin-2-yl)-1H-pyrazol-4-yl)-5-(1H-pyrazol-4-yl)furan-2-carboxamide;

I-111: N-(1-(2-morpholinoethyl)-3-(pyridin-2-yl)-1H-pyrazol-4-yl)-5-(1H-pyrazol-4-yl)furan-2-carboxamide;

I-112: N-(1-(2-(4-methylpiperazin-1-yl)ethyl)-3-(pyridin-2-yl)-1H-pyrazol-4-yl)-5-(1H-pyrazol-4-yl)furan-2-carboxamide;

I-113: 5-(1H-pyrazol-3-yl)-N-(3-(pyridin-2-yl)-1-(2-(2,2,2-trifluoroethoxy)ethyl)-1H-pyrazol-4-yl)furan-2-carboxamide;

I-114: N-(1-((1s,3s)-3-isopropoxycyclobutyl)-3-(pyridin-2-yl)-1H-pyrazol-4-yl)-5-(1H-pyrazol-4-yl)furan-2-carboxamide;

I-115: N-(1-(difluoromethyl)-3-(pyridin-2-yl)-1H-pyrazol-4-yl)-5-(1H-pyrazol-4-yl)furan-2-carboxamide;

I-116: N-(1-((1s,3s)-3-ethoxycyclobutyl)-3-(6-(trifluoromethyl)pyridin-2-yl)-1H-pyrazol-4-yl)-5-(1H-pyrazol-4-yl)furan-2-carboxamide;

I-117: 5-(1H-pyrazol-4-yl)-N-(3-(pyridin-2-yl)-1-(2,2,2-trifluoroethyl)-1H-pyrazol-4-yl)furan-2-carboxamide;

I-118: N-(1-(2-ethoxyethyl)-3-(thiazol-2-yl)-1H-pyrazol-4-yl)-5-(1H-pyrazol-4-yl)furan-2-carboxamide formate;

I-119: N-(1-(2-ethoxyethyl)-3-(thiazol-2-yl)-1H-pyrazol-4-yl)-5-(1H-pyrazol-4-yl)furan-2-carboxamide;

I-120: 5-(1H-pyrazol-4-yl)-N-(1-(tetrahydrofuran-3-yl)-3-(thiazol-2-yl)-1H-pyrazol-4-yl)furan-2-carboxamide formate;

I-121: 5-(1H-pyrazol-4-yl)-N-(1-(tetrahydrofuran-3-yl)-3-(thiazol-2-yl)-1H-pyrazol-4-yl)furan-2-carboxamide;

I-122: 5-(1-cyclobutyl-1H-pyrazol-4-yl)-N-(1-cyclobutyl-3-(pyridin-2-yl)-1H-pyrazol-4-yl)furan-2-carboxamide 2,2,2-trifluoroacetate;

I-123: 5-(1-cyclobutyl-1H-pyrazol-4-yl)-N-(1-cyclobutyl-3-(pyridin-2-yl)-1H-pyrazol-4-yl)furan-2-carboxamide;

I-124: N-(1-((1s,4s)-4-hydroxycyclohexyl)-3-(pyridin-2-yl)-1H-pyrazol-4-yl)-5-(1H-pyrazol-4-yl)furan-2-carboxamide formate;

I-125: N-(1-((1s,4s)-4-hydroxycyclohexyl)-3-(pyridin-2-yl)-1H-pyrazol-4-yl)-5-(1H-pyrazol-4-yl)furan-2-carboxamide;

I-126: N-(1-((1r,4r)-4-hydroxycyclohexyl)-3-(pyridin-2-yl)-1H-pyrazol-4-yl)-5-(1H-pyrazol-4-yl)furan-2-carboxamide formate;

I-127: N-(1-((1r,4r)-4-hydroxycyclohexyl)-3-(pyridin-2-yl)-1H-pyrazol-4-yl)-5-(1H-pyrazol-4-yl)furan-2-carboxamide;

I-128: 5-(1H-pyrazol-4-yl)-N-(3-(pyridin-2-yl)-1-(3-(2,2,2-trifluoroethoxy)cyclobutyl)-1H-pyrazol-4-yl)furan-2-carboxamide formate;

I-129: 5-(1H-pyrazol-4-yl)-N-(3-(pyridin-2-yl)-1-(3-(2,2,2-trifluoroethoxy)cyclobutyl)-1H-pyrazol-4-yl)furan-2-carboxamide;

I-130: N-(1-((1r,4r)-4-ethoxycyclohexyl)-3-(pyridin-2-yl)-1H-pyrazol-4-yl)-5-(1H-pyrazol-4-yl)furan-2-carboxamide formate;

I-131: N-(1-((1r,4r)-4-ethoxycyclohexyl)-3-(pyridin-2-yl)-1H-pyrazol-4-yl)-5-(1H-pyrazol-4-yl)furan-2-carboxamide;

I-132: N-(1-((1S,3R)-3-ethoxycyclopentyl)-3-(pyridin-2-yl)-1H-pyrazol-4-yl)-5-(1H-pyrazol-4-yl)furan-2-carboxamide formate;

I-133: N-(1-((1S,3R)-3-ethoxycyclopentyl)-3-(pyridin-2-yl)-1H-pyrazol-4-yl)-5-(1H-pyrazol-4-yl)furan-2-carboxamide;

I-134: N-(1-((1S,3R)-3-hydroxycyclopentyl)-3-(pyridin-2-yl)-1H-pyrazol-4-yl)-5-(1H-pyrazol-4-yl)furan-2-carboxamide formate;

I-135: N-(1-((1S,3R)-3-hydroxycyclopentyl)-3-(pyridin-2-yl)-1H-pyrazol-4-yl)-5-(1H-pyrazol-4-yl)furan-2-carboxamide;

I-136: N-(1-((1S,3S)-3-hydroxycyclopentyl)-3-(pyridin-2-yl)-1H-pyrazol-4-yl)-5-(1H-pyrazol-4-yl)furan-2-carboxamide formate;

I-137: N-(1-((1S,3S)-3-hydroxycyclopentyl)-3-(pyridin-2-yl)-1H-pyrazol-4-yl)-5-(1H-pyrazol-4-yl)furan-2-carboxamide;

I-138: N-(1-((1s,3s)-3-ethoxycyclobutyl)-3-(5-fluoropyridin-2-yl)-1H-pyrazol-4-yl)-5-(1H-pyrazol-4-yl)furan-2-carboxamide formate;

I-139: N-(1-((1s,3s)-3-ethoxycyclobutyl)-3-(5-fluoropyridin-2-yl)-1H-pyrazol-4-yl)-5-(1H-pyrazol-4-yl)furan-2-carboxamide;

I-140: N-(1-((1S,3R)-3-ethoxy-2-fluorocyclobutyl)-3-(pyridin-2-yl)-1H-pyrazol-4-yl)-5-(1H-pyrazol-4-yl)furan-2-carboxamide formate;

I-141: N-(1-((1S,3R)-3-ethoxy-2-fluorocyclobutyl)-3-(pyridin-2-yl)-1H-pyrazol-4-yl)-5-(1H-pyrazol-4-yl)furan-2-carboxamide;

I-142: N-(1-((1s,3s)-3-ethoxycyclobutyl)-3-(3-fluoropyridin-2-yl)-1H-pyrazol-4-yl)-5-(1H-pyrazol-4-yl)furan-2-carboxamide formate;

I-143: N-(1-((1s,3s)-3-ethoxycyclobutyl)-3-(3-fluoropyridin-2-yl)-1H-pyrazol-4-yl)-5-(1H-pyrazol-4-yl)furan-2-carboxamide;

I-144: N-(1-((1s,3s)-3-ethoxycyclobutyl)-3-(6-fluoropyridin-2-yl)-1H-pyrazol-4-yl)-5-(1H-pyrazol-4-yl)furan-2-carboxamide formate;

I-145: N-(1-((1s,3s)-3-ethoxycyclobutyl)-3-(6-fluoropyridin-2-yl)-1H-pyrazol-4-yl)-5-(1H-pyrazol-4-yl)furan-2-carboxamide;

I-146: 5-(1H-pyrazol-4-yl)-N-(3-(pyridin-2-yl)-1-((1s,3s)-3-(2,2,2-trifluoroethoxy)cyclobutyl)-1H-pyrazol-4-yl)furan-2-carboxamide formate;

I-147: 5-(1H-pyrazol-4-yl)-N-(3-(pyridin-2-yl)-1-((1s,3s)-3-(2,2,2-trifluoroethoxy)cyclobutyl)-1H-pyrazol-4-yl)furan-2-carboxamide;

I-148: N-(1-((1s,3s)-3-ethoxycyclobutyl)-3-(4-fluoropyridin-2-yl)-1H-pyrazol-4-yl)-5-(1H-pyrazol-4-yl)furan-2-carboxamide formate;

I-149: N-(1-((1s,3s)-3-ethoxycyclobutyl)-3-(4-fluoropyridin-2-yl)-1H-pyrazol-4-yl)-5-(1H-pyrazol-4-yl)furan-2-carboxamide;

I-150: N-(3-(6-fluoropyridin-2-yl)-1-((1s,3s)-3-(2,2,2-trifluoroethoxy)cyclobutyl)-1H-pyrazol-4-yl)-5-(1H-pyrazol-4-yl)furan-2-carboxamide formate;

I-151: N-(3-(6-fluoropyridin-2-yl)-1-((1s,3s)-3-(2,2,2-trifluoroethoxy)cyclobutyl)-1H-pyrazol-4-yl)-5-(1H-pyrazol-4-yl)furan-2-carboxamide;

I-152: N-(3-(3-fluoropyridin-2-yl)-1-((1s,3s)-3-(2,2,2-trifluoroethoxy)cyclobutyl)-1H-pyrazol-4-yl)-5-(1H-pyrazol-4-yl)furan-2-carboxamide formate;

I-153: N-(3-(3-fluoropyridin-2-yl)-1-((1s,3s)-3-(2,2,2-trifluoroethoxy)cyclobutyl)-1H-pyrazol-4-yl)-5-(1H-pyrazol-4-yl)furan-2-carboxamide;

I-154: N-(1-((1r,4r)-4-ethoxycyclohexyl)-3-(3-fluoropyridin-2-yl)-1H-pyrazol-4-yl)-5-(1H-pyrazol-4-yl)furan-2-carboxamide formate;

I-155: N-(1-((1r,4r)-4-ethoxycyclohexyl)-3-(3-fluoropyridin-2-yl)-1H-pyrazol-4-yl)-5-(1H-pyrazol-4-yl)furan-2-carboxamide; or I-156: N-(3-(3,6-difluoropyridin-2-yl)-1-((1s,3s)-3-ethoxycyclobutyl)-1H-pyrazol-4-yl)-5-(1H-pyrazol-4-yl)furan-2-carboxamide.

Exemplary embodiments of a compound according to formula 1 also include:

II-1: N-(1-(2-hydroxy-2-methylpropyl)-3-(pyridin-2-yl)-1H-pyrazol-4-yl)-2-(1H-pyrazol-4-yl)thiazole-4-carboxamide;

II-2: 1-(isobutyryloxy)ethyl 4-(4-((1-methyl-3-(pyridin-2-yl)-1H-pyrazol-4-yl)carbamoyl)thiazol-2-yl)-1H-pyrazole-1-carboxylate;

II-3: tert-butyl (R)-(3-methyl-1-(4-(4-((1-methyl-3-(pyridin-2-yl)-1H-pyrazol-4-yl)carbamoyl)thiazol-2-yl)-1H-pyrazol-1-yl)-1-oxobutan-2-yl)carbamate;

II-4: 2-(1-((5-methyl-2-oxo-1,3-dioxol-4-yl)methyl)-1H-pyrazol-4-yl)-N-(1-methyl-3-(pyridin-2-yl)-1H-pyrazol-4-yl)thiazole-4-carboxamide;

II-5: 1-methylcyclopropyl 4-(4-((1-methyl-3-(pyridin-2-yl)-1H-pyrazol-4-yl)carbamoyl)thiazol-2-yl)-1H-pyrazole-1-carboxylate;

II-6: 1-((4-methoxybenzyl)oxy)-2-methylpropan-2-yl 4-(4-((1-methyl-3-(pyridin-2-yl)-1H-pyrazol-4-yl)carbamoyl)thiazol-2-yl)-1H-pyrazole-1-carboxylate;

II-7: diethyl ((4-(4-((1-methyl-3-(pyridin-2-yl)-1H-pyrazol-4-yl)carbamoyl)thiazol-2-yl)-1H-pyrazol-1-yl)methyl)phosphonate;

II-8: sodium ((4-(4-((1-methyl-3-(pyridin-2-yl)-1H-pyrazol-4-yl)carbamoyl)thiazol-2-yl)-1H-pyrazol-1-yl)methyl)phosphonate;

II-9: ((4-(4-((1-methyl-3-(pyridin-2-yl)-1H-pyrazol-4-yl)carbamoyl)thiazol-2-yl)-1H-pyrazol-1-yl)methyl)phosphonic acid;

II-10: 2-(1H-pyrazol-4-yl)-N-(3-(pyridin-2-yl)-1-(tetrahydro-2H-pyran-4-yl)-1H-pyrazol-4-yl)thiazole-4-carboxamide;

II-11: N-(1-((1,3-cis)-3-ethoxycyclobutyl)-3-(pyridin-2-yl)-1H-pyrazol-4-yl)-2-(1H-pyrazol-4-yl)thiazole-4-carboxamide;

II-12: N-(1-((1,3-trans)-3-ethoxycyclobutyl)-3-(pyridin-2-yl)-1H-pyrazol-4-yl)-2-(1H-pyrazol-4-yl)thiazole-4-carboxamide;

II-13: N-(1-((1,3-cis)-3-ethoxycyclobutyl)-3-(pyridin-2-yl)-1H-pyrazol-4-yl)-2-(1-methyl-1H-pyrazol-4-yl)thiazole-4-carboxamide;

II-14: N-(1-((1,3-cis)-3-hydroxycyclobutyl)-3-(pyridin-2-yl)-1H-pyrazol-4-yl)-2-(1H-pyrazol-4-yl)thiazole-4-carboxamide;

II-15: N-(1-((1s,3s)-3-(dimethylamino)cyclobutyl)-3-(pyridin-2-yl)-1H-pyrazol-4-yl)-2-(1H-pyrazol-4-yl)thiazole-4-carboxamide;

II-16: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate bis-sodium salt;

II-17: (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl dihydrogen phosphate;

II-18: N-(1-(2-ethoxyethyl)-3-(pyridin-2-yl)-1H-pyrazol-4-yl)-2-(1H-pyrazol-4-yl)thiazole-4-carboxamide, formic acid salt;

II-19: N-(1-(2-ethoxyethyl)-3-(pyridin-2-yl)-1H-pyrazol-4-yl)-2-(5-(trifluoromethyl)-1H-pyrazol-4-yl)thiazole-4-carboxamide, formic acid salt;

II-20: N-(1-(2-ethoxyethyl)-3-(pyridin-2-yl)-1H-pyrazol-4-yl)-2-(5-(trifluoromethyl)-1H-pyrazol-4-yl)thiazole-4-carboxamide;

II-21: N-(1-(2-ethoxyethyl)-3-(pyridin-2-yl)-1H-pyrazol-4-yl)-2-(3-methyl-1H-pyrazol-4-yl)thiazole-4-carboxamide, formic acid salt;

II-22: N-(1-(2-ethoxyethyl)-3-(pyridin-2-yl)-1H-pyrazol-4-yl)-2-(3-methyl-1H-pyrazol-4-yl)thiazole-4-carboxamide;

II-23: 2-(3,5-dimethyl-1H-pyrazol-4-yl)-N-(1-(2-ethoxyethyl)-3-(pyridin-2-yl)-1H-pyrazol-4-yl)thiazole-4-carboxamide, formic acid salt;

II-24: 2-(3,5-dimethyl-1H-pyrazol-4-yl)-N-(1-(2-ethoxyethyl)-3-(pyridin-2-yl)-1H-pyrazol-4-yl)thiazole-4-carboxamide;

II-25: N-(1-(2-ethoxyethyl)-3-(pyridin-2-yl)-1H-pyrazol-4-yl)-2-(1H-pyrazol-4-yl)thiazole-4-carboxamide;

II-26: N-(1-methyl-3-(pyridin-2-yl)-1H-pyrazol-4-yl)-2-(1H-pyrazol-4-yl)thiazole-4-carboxamide;

II-27: 2-(3-methyl-1H-pyrazol-4-yl)-N-(1-methyl-3-(pyridin-2-yl)-1H-pyrazol-4-yl)thiazole-4-carboxamide;

II-28: N-(1-(2-methoxyethyl)-3-(pyridin-2-yl)-1H-pyrazol-4-yl)-2-(1H-pyrazol-4-yl)thiazole-4-carboxamide;

II-29: N-(1-(2-methoxyethyl)-3-(pyridin-2-yl)-1H-pyrazol-4-yl)-2-(3-methyl-1H-pyrazol-4-yl)thiazole-4-carboxamide, formic acid salt;

II-30: N-(1-(2-methoxyethyl)-3-(pyridin-2-yl)-1H-pyrazol-4-yl)-2-(3-methyl-1H-pyrazol-4-yl)thiazole-4-carboxamide;

II-31: N-(1-(2-ethoxyethyl)-3-(pyridin-2-yl)-1H-pyrazol-4-yl)-2-(3-methyl-1H-pyrazol-4-yl)thiazole-4-carboxamide;

II-32: 2-(1H-pyrazol-4-yl)-N-(3-(pyridin-2-yl)-1H-pyrazol-4-yl)thiazole-4-carboxamide formate;

II-33: 2-(1H-pyrazol-4-yl)-N-(3-(pyridin-2-yl)-1H-pyrazol-4-yl)thiazole-4-carboxamide;

II-34: N-(1-(oxetan-3-yl)-3-(pyridin-2-yl)-1H-pyrazol-4-yl)-2-(1H-pyrazol-4-yl)thiazole-4-carboxamide;

II-35: (4-(4-((1-methyl-3-(pyridin-2-yl)-1H-pyrazol-4-yl)carbamoyl)thiazol-2-yl)-1H-pyrazol-1-yl)methyl dihydrogen phosphate;

II-36: Sodium (4-(4-((1-methyl-3-(pyridin-2-yl)-1H-pyrazol-4-yl)carbamoyl)thiazol-2-yl)-1H-pyrazol-1-yl)methyl phosphate;

II-37: N-(1-(2-(2-methoxyethoxy)ethyl)-3-(pyridin-2-yl)-1H-pyrazol-4-yl)-2-(1H-pyrazol-4-yl)thiazole-4-carboxamide;

II-38: potassium (4-(4-((1-methyl-3-(pyridin-2-yl)-1H-pyrazol-4-yl)carbamoyl)thiazol-2-yl)-1H-pyrazol-1-yl)methyl phosphate;

II-39: N-(1-(2-(2-methoxyethoxy)ethyl)-3-(pyridin-2-yl)-1H-pyrazol-4-yl)-2-(3-methyl-1H-pyrazol-4-yl)thiazole-4-carboxamide formate;

II-40: N-(1-(2-(2-methoxyethoxy)ethyl)-3-(pyridin-2-yl)-1H-pyrazol-4-yl)-2-(3-methyl-1H-pyrazol-4-yl)thiazole-4-carboxamide;

II-41: 2-(3-methyl-1H-pyrazol-4-yl)-N-(1-(oxetan-3-yl)-3-(pyridin-2-yl)-1H-pyrazol-4-yl)thiazole-4-carboxamide, formic acid salt;

II-42: 2-(3-methyl-1H-pyrazol-4-yl)-N-(1-(oxetan-3-yl)-3-(pyridin-2-yl)-1H-pyrazol-4-yl)thiazole-4-carboxamide;

II-43: 2-(1H-pyrazol-4-yl)-N-(3-(pyridin-2-yl)-1-(tetrahydrofuran-3-yl)-1H-pyrazol-4-yl)thiazole-4-carboxamide formate;

II-44: 2-(1H-pyrazol-4-yl)-N-(3-(pyridin-2-yl)-1-(tetrahydrofuran-3-yl)-1H-pyrazol-4-yl)thiazole-4-carboxamide;

II-45: 2-(3-methyl-1H-pyrazol-4-yl)-N-(3-(pyridin-2-yl)-1-((tetrahydro-2H-pyran-4-yl)methyl)-1H-pyrazol-4-yl)thiazole-4-carboxamide formate;

II-46: 2-(3-methyl-1H-pyrazol-4-yl)-N-(3-(pyridin-2-yl)-1-((tetrahydro-2H-pyran-4-yl)methyl)-1H-pyrazol-4-yl)thiazole-4-carboxamide;

II-47: N-(1-((3-(hydroxymethyl)oxetan-3-yl)methyl)-3-(pyridin-2-yl)-1H-pyrazol-4-yl)-2-(3-methyl-1H-pyrazol-4-yl)thiazole-4-carboxamide formate;

II-48: N-(1-((3-(hydroxymethyl)oxetan-3-yl)methyl)-3-(pyridin-2-yl)-1H-pyrazol-4-yl)-2-(3-methyl-1H-pyrazol-4-yl)thiazole-4-carboxamide;

II-49: N-(1-(2-(diethylamino)ethyl)-3-(pyridin-2-yl)-1H-pyrazol-4-yl)-2-(1H-pyrazol-4-yl)thiazole-4-carboxamide, formic acid salt;

II-50: N-(1-(2-(diethylamino)ethyl)-3-(pyridin-2-yl)-1H-pyrazol-4-yl)-2-(1H-pyrazol-4-yl)thiazole-4-carboxamide;

II-51: 2-(1-(4-methoxybenzyl)-1H-pyrazol-4-yl)-N-(1-(3-methoxycyclobutyl)-3-(pyridin-2-yl)-1H-pyrazol-4-yl)thiazole-4-carboxamide;

II-52: N-(1-(2-fluoroethyl)-3-(pyridin-2-yl)-1H-pyrazol-4-yl)-2-(1-(4-methoxybenzyl)-1H-pyrazol-4-yl)thiazole-4-carboxamide;

II-53: 2-(1-(4-methoxybenzyl)-1H-pyrazol-4-yl)-N-(3-(pyridin-2-yl)-1H-pyrazol-4-yl)thiazole-4-carboxamide;

II-54: tert-Butyl-3-[4-{2-(1H-pyrazole-4-yl)thiazole-2-carboxamido}-3-(pyridine-2-yl)-1H-pyrazol-1-yl]azetidine-1-carboxylate, free base;

II-55: N-{1-(Azetidin-3-yl)-3-(pyridine-2-yl)-1H-pyrazol-4-yl}-2-(1H-pyrazol-4-yl)thiazole-4-carboxamide, TFA salt;

II-56: N-{1-(Azetidin-3-yl)-3-(pyridine-2-yl)-1H-pyrazol-4-yl}-2-(1H-pyrazol-4-yl)thiazole-4-carboxamide;

II-57: N-{1-(3-Methoxycyclobutyl)-3-(pyridine-2-yl)-1H-pyrazol-4-yl}-2-(1H-pyrazol-4-yl)thiazole-4-carboxamide, free base, Cis isomer;

II-58: N-(3-(5-methoxypyridin-2-yl)-1-methyl-1H-pyrazol-4-yl)-2-(1H-pyrazol-4-yl)thiazole-4-carboxamide;

II-59: N-(1-isopropyl-3-(pyridin-2-yl)-1H-pyrazol-4-yl)-2-(1H-pyrazol-4-yl)thiazole-4-carboxamide;

II-60: N-(1-(2-morpholinoethyl)-3-(pyridin-2-yl)-1H-pyrazol-4-yl)-2-(1H-pyrazol-4-yl)thiazole-4-carboxamide;

II-61: N-(1-(2-(4-methylpiperazin-1-yl)ethyl)-3-(pyridin-2-yl)-1H-pyrazol-4-yl)-2-(1H-pyrazol-4-yl)thiazole-4-carboxamide;

II-62: N-(1-((1s,3s)-3-ethoxycyclobutyl)-3-(trifluoromethyl)-1H-pyrazol-4-yl)-2-(1H-pyrazol-4-yl)thiazole-4-carboxamide;

II-63: N-(1-methyl-3-(trifluoromethyl)-1H-pyrazol-4-yl)-2-(1H-pyrazol-4-yl)thiazole-4-carboxamide 2,2,2-trifluoroacetate;

II-64: N-(1-methyl-3-(trifluoromethyl)-1H-pyrazol-4-yl)-2-(1H-pyrazol-4-yl)thiazole-4-carboxamide;

II-65: N-(3-(3-fluoropyridin-2-yl)-1-((1s,3s)-3-hydroxycyclobutyl)-1H-pyrazol-4-yl)-2-(1H-pyrazol-4-yl)thiazole-4-carboxamide;

II-66: 2-(1H-pyrazol-3-yl)-N-(3-(pyridin-2-yl)-1-(2-(2,2,2-trifluoroethoxy)ethyl)-1H-pyrazol-4-yl)thiazole-4-carboxamide;

II-67: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone;

II-68: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone 2,2,2-trifluoroacetate;

II-69: (2-(1H-pyrazol-4-yl)thiazol-4-yl)(1-(3-ethoxycyclobutyl)-1,5,6,7-tetrahydro-4H-pyrazolo[4,3-b]pyridin-4-yl)methanone 2,2,2-trifluoroacetate;

II-70: N-(3-carbamoyl-1-((1s,3s)-3-ethoxycyclobutyl)-1H-pyrazol-4-yl)-2-(1H-pyrazol-4-yl)thiazole-4-carboxamide;

II-71: N-(1-((1s,3s)-3-ethoxycyclobutyl)-3-(pyridin-2-yl)-1H-pyrazol-4-yl)-2-(5-fluoro-1-((2-(trimethylsilyl)ethoxy)methyl)-1H-pyrazol-4-yl)thiazole-4-carboxamide;

II-72: N-(1-((1s,3s)-3-ethoxycyclobutyl)-3-(pyridin-2-yl)-1H-pyrazol-4-yl)-2-(5-fluoro-1H-pyrazol-4-yl)thiazole-4-carboxamide;

II-73: N-(1-((1s,3s)-3-ethoxycyclobutyl)-3-(pyridin-2-yl)-1H-pyrazol-4-yl)-2-(5-fluoro-1H-pyrazol-4-yl)thiazole-4-carboxamide formate;

II-74: N-(1-((1s,3s)-3-ethoxycyclobutyl)-3-(1,3,4-oxadiazol-2-yl)-1H-pyrazol-4-yl)-2-(1H-pyrazol-4-yl)thiazole-4-carboxamide;

II-75: N-(3-(1,3,4-oxadiazol-2-yl)-1-(tetrahydro-2H-pyran-4-yl)-1H-pyrazol-4-yl)-2-(1H-pyrazol-4-yl)thiazole-4-carboxamide;

II-76: N-(1-((1s,3s)-3-isopropoxycyclobutyl)-3-(pyridin-2-yl)-1H-pyrazol-4-yl)-2-(1H-pyrazol-4-yl)thiazole-4-carboxamide;

II-77: potassium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-78: calcium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-79: N-(1-((1r,3r)-3-hydroxy-3-methylcyclobutyl)-3-(pyridin-2-yl)-1H-pyrazol-4-yl)-2-(1H-pyrazol-4-yl)thiazole-4-carboxamide;

II-80: ammonium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-81: 5-amino-5-carboxypentan-1-aminium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-82: 1-(4-amino-4-carboxybutyl)guanidinium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-83: (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl dihydrogen phosphate;

II-84: 1,3-dihydroxy-2-(hydroxymethyl)propan-2-aminium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl hydrogen phosphate;

II-85: triethylammonium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl hydrogen phosphate;

II-86: N-(1-((1s,3s)-3-ethoxycyclobutyl)-3-(5-(trifluoromethyl)pyridin-2-yl)-1H-pyrazol-4-yl)-2-(1H-pyrazol-4-yl)thiazole-4-carboxamide;

II-87: N-(1-(3-hydroxy-3-methylcyclobutyl)-3-(pyridin-2-yl)-1H-pyrazol-4-yl)-2-(1H-pyrazol-4-yl)thiazole-4-carboxamide;

II-88: N-(1-(difluoromethyl)-3-(pyridin-2-yl)-1H-pyrazol-4-yl)-2-(1H-pyrazol-4-yl)thiazole-4-carboxamide;

II-89: N-(1-((1s,3s)-3-ethoxycyclobutyl)-3-(3-(trifluoromethyl)pyridin-2-yl)-1H-pyrazol-4-yl)-2-(1H-pyrazol-4-yl)thiazole-4-carboxamide;

II-90: N-(1-((1s,3s)-3-ethoxycyclobutyl)-3-(6-(trifluoromethyl)pyridin-2-yl)-1H-pyrazol-4-yl)-2-(1H-pyrazol-4-yl)thiazole-4-carboxamide;

II-91: N-(1-((1s,3s)-3-ethoxycyclobutyl)-3-(pyridin-2-yl)-1H-pyrazol-4-yl)-2-(3-(trifluoromethyl)-1H-pyrazol-4-yl)thiazole-4-carboxamide;

II-92: N-(1-((1s,3s)-3-ethoxycyclobutyl)-3-(pyridin-2-yl)-1H-pyrazol-4-yl)-2-(3-methyl-1H-pyrazol-4-yl)thiazole-4-carboxamide;

II-93: 2-(3,5-dimethyl-1H-pyrazol-4-yl)-N-(1-((1s,3s)-3-ethoxycyclobutyl)-3-(pyridin-2-yl)-1H-pyrazol-4-yl)thiazole-4-carboxamide;

II-94: 2-(1H-pyrazol-4-yl)-N-(3-(pyridin-2-yl)-1-(2,2,2-trifluoroethyl)-1H-pyrazol-4-yl)thiazole-4-carboxamide;

II-95: N-(1-(difluoromethyl)-3-(pyridin-2-yl)-1H-pyrazol-4-yl)-2-(3-(trifluoromethyl)-1H-pyrazol-4-yl)thiazole-4-carboxamide;

II-96: N-(1-(difluoromethyl)-3-(pyridin-2-yl)-1H-pyrazol-4-yl)-2-(3-methyl-1H-pyrazol-4-yl)thiazole-4-carboxamide;

II-97: N-(1-(difluoromethyl)-3-(pyridin-2-yl)-1H-pyrazol-4-yl)-2-(1-(2,2,2-trifluoroethyl)-1H-pyrazol-4-yl)thiazole-4-carboxamide;

II-98: 2-(1-(difluoromethyl)-1H-pyrazol-4-yl)-N-(1-(difluoromethyl)-3-(pyridin-2-yl)-1H-pyrazol-4-yl)thiazole-4-carboxamide;

II-99: N-(1-((1s,3s)-3-ethoxycyclobutyl)-3-(6-(trifluoromethyl)pyridin-2-yl)-1H-pyrazol-4-yl)-2-(3-methyl-1H-pyrazol-4-yl)thiazole-4-carboxamide;

II-100: 2-(3-methyl-1H-pyrazol-4-yl)-N-(3-(pyridin-2-yl)-1-(2,2,2-trifluoroethyl)-1H-pyrazol-4-yl)thiazole-4-carboxamide;

II-101: N-(1-((1s,3s)-3-hydroxycyclobutyl)-3-(pyrazin-2-yl)-1H-pyrazol-4-yl)-2-(1H-pyrazol-4-yl)thiazole-4-carboxamide;

II-102: N-(1-((1s,3s)-3-ethoxycyclobutyl)-3-(pyrimidin-2-yl)-1H-pyrazol-4-yl)-2-(1H-pyrazol-4-yl)thiazole-4-carboxamide;

II-103: 2-(1-(4-methoxybenzyl)-1H-pyrazol-4-yl)-N-(3-(pyridin-2-yl)-1-(3,3,3-trifluoro-2-hydroxypropyl)-1H-pyrazol-4-yl)thiazole-4-carboxamide formate;

II-104: 2-(1-(4-methoxybenzyl)-1H-pyrazol-4-yl)-N-(3-(pyridin-2-yl)-1-(3,3,3-trifluoro-2-hydroxypropyl)-1H-pyrazol-4-yl)thiazole-4-carboxamide;

II-105: N-(1-(dimethylcarbamoyl)-3-(pyridin-2-yl)-1H-pyrazol-4-yl)-2-(1-(4-methoxybenzyl)-1H-pyrazol-4-yl)thiazole-4-carboxamide formate;

II-106: N-(1-(dimethylcarbamoyl)-3-(pyridin-2-yl)-1H-pyrazol-4-yl)-2-(1-(4-methoxybenzyl)-1H-pyrazol-4-yl)thiazole-4-carboxamide;

II-107: 2-(1-(4-methoxybenzyl)-1H-pyrazol-4-yl)-N-(3-(pyridin-2-yl)-1-(3,3,3-trifluoro-2-hydroxy-2-(trifluoromethyl)propyl)-1H-pyrazol-4-yl)thiazole-4-carboxamide formate;

II-108: 2-(1-(4-methoxybenzyl)-1H-pyrazol-4-yl)-N-(3-(pyridin-2-yl)-1-(3,3,3-trifluoro-2-hydroxy-2-(trifluoromethyl)propyl)-1H-pyrazol-4-yl)thiazole-4-carboxamide;

II-109: N-(1-(2-ethoxyethyl)-3-(thiazol-2-yl)-1H-pyrazol-4-yl)-2-(1H-pyrazol-4-yl)thiazole-4-carboxamide formate;

II-110: N-(1-(2-ethoxyethyl)-3-(thiazol-2-yl)-1H-pyrazol-4-yl)-2-(1H-pyrazol-4-yl)thiazole-4-carboxamide;

II-111: 2-(1H-pyrazol-4-yl)-N-(1-(tetrahydro-2H-pyran-4-yl)-3-(thiazol-2-yl)-1H-pyrazol-4-yl)thiazole-4-carboxamide formate;

II-112: 2-(1H-pyrazol-4-yl)-N-(1-(tetrahydro-2H-pyran-4-yl)-3-(thiazol-2-yl)-1H-pyrazol-4-yl)thiazole-4-carboxamide;

II-113: N-(1-(2-(2-methoxyethoxy)ethyl)-3-(thiazol-2-yl)-1H-pyrazol-4-yl)-2-(1H-pyrazol-4-yl)thiazole-4-carboxamide formate;

II-114: N-(1-(2-(2-methoxyethoxy)ethyl)-3-(thiazol-2-yl)-1H-pyrazol-4-yl)-2-(1H-pyrazol-4-yl)thiazole-4-carboxamide;

II-115: 2-(1H-pyrazol-4-yl)-N-(1-(tetrahydrofuran-3-yl)-3-(thiazol-2-yl)-1H-pyrazol-4-yl)thiazole-4-carboxamide formate;

II-116: 2-(1H-pyrazol-4-yl)-N-(1-(tetrahydrofuran-3-yl)-3-(thiazol-2-yl)-1H-pyrazol-4-yl)thiazole-4-carboxamide;

II-117: N-(1-(2-(diethylamino)ethyl)-3-(pyridin-2-yl)-1H-pyrazol-4-yl)-2-(1H-pyrazol-4-yl)thiazole-4-carboxamide;

II-118: N-(1-(2-(2-fluoroethoxy)ethyl)-3-(pyridin-2-yl)-1H-pyrazol-4-yl)-2-(1H-pyrazol-4-yl)thiazole-4-carboxamide formate;

II-119: N-(1-(2-(2-fluoroethoxy)ethyl)-3-(pyridin-2-yl)-1H-pyrazol-4-yl)-2-(1H-pyrazol-4-yl)thiazole-4-carboxamide;

II-120: N-(1-benzyl-3-(pyridin-2-yl)-1H-pyrazol-4-yl)-2-(1H-pyrazol-4-yl)thiazole-4-carboxamide;

II-121: N-(1-cyclobutyl-3-(pyridin-2-yl)-1H-pyrazol-4-yl)-2-(1H-pyrazol-4-yl)thiazole-4-carboxamide;

II-122: N-(1-(2-(2,2-difluoroethoxy)ethyl)-3-(pyridin-2-yl)-1H-pyrazol-4-yl)-2-(1H-pyrazol-4-yl)thiazole-4-carboxamide;

II-123: N-(1-(((1r,3r)-3-hydroxycyclobutyl)methyl)-3-(pyridin-2-yl)-1H-pyrazol-4-yl)-2-(1H-pyrazol-4-yl)thiazole-4-carboxamide formate;

II-124: N-(1-(((1r,3r)-3-hydroxycyclobutyl)methyl)-3-(pyridin-2-yl)-1H-pyrazol-4-yl)-2-(1H-pyrazol-4-yl)thiazole-4-carboxamide;

II-125: N-(1-(dimethylcarbamoyl)-3-(pyridin-2-yl)-1H-pyrazol-4-yl)-2-(1H-pyrazol-4-yl)thiazole-4-carboxamide formate;

II-126: N-(1-(dimethylcarbamoyl)-3-(pyridin-2-yl)-1H-pyrazol-4-yl)-2-(1H-pyrazol-4-yl)thiazole-4-carboxamide;

II-127: N-(1-((1s,3s)-3-(ethoxy-d5)cyclobutyl)-3-(pyridin-2-yl)-1H-pyrazol-4-yl)-2-(1H-pyrazol-4-yl)thiazole-4-carboxamide;

II-128: N-(1-(diethylcarbamoyl)-3-(pyridin-2-yl)-1H-pyrazol-4-yl)-2-(1H-pyrazol-4-yl)thiazole-4-carboxamide;

II-129: N-(1-(morpholine-4-carbonyl)-3-(pyridin-2-yl)-1H-pyrazol-4-yl)-2-(1H-pyrazol-4-yl)thiazole-4-carboxamide;

II-130: N-(1-((1s,3s)-3-(2-fluoroethoxy)cyclobutyl)-3-(pyridin-2-yl)-1H-pyrazol-4-yl)-2-(1H-pyrazol-4-yl)thiazole-4-carboxamide;

II-131: N-(1-(morpholine-4-carbonyl)-3-(pyridin-2-yl)-1H-pyrazol-4-yl)-2-(1H-pyrazol-4-yl)thiazole-4-carboxamide formate;

II-132: N-(1-(3-fluorocyclobut-2-en-1-yl)-3-(pyridin-2-yl)-1H-pyrazol-4-yl)-2-(1H-pyrazol-4-yl)thiazole-4-carboxamide;

II-133: N-(1-(3-fluorocyclobut-2-en-1-yl)-3-(pyridin-2-yl)-1H-pyrazol-4-yl)-2-(1H-pyrazol-4-yl)thiazole-4-carboxamide formate;

II-134: N-(1-(3,3-difluorocyclobutyl)-3-(pyridin-2-yl)-1H-pyrazol-4-yl)-2-(1H-pyrazol-4-yl)thiazole-4-carboxamide formate;

II-135: N-(1-(3,3-difluorocyclobutyl)-3-(pyridin-2-yl)-1H-pyrazol-4-yl)-2-(1H-pyrazol-4-yl)thiazole-4-carboxamide;

II-136: N-(3-cyano-1-((1s,3s)-3-hydroxycyclobutyl)-1H-pyrazol-4-yl)-2-(1H-pyrazol-4-yl)thiazole-4-carboxamide;

II-137: N-(3-cyano-1-methyl-1H-pyrazol-4-yl)-2-(1H-pyrazol-4-yl)thiazole-4-carboxamide;

II-138: N-(3-cyano-1-((1s,3s)-3-ethoxycyclobutyl)-1H-pyrazol-4-yl)-2-(1H-pyrazol-4-yl)thiazole-4-carboxamide;

II-139: N-(3-cyano-1-((1s,3s)-3-ethoxycyclobutyl)-1H-pyrazol-4-yl)-2-(1H-pyrazol-4-yl)thiazole-4-carboxamide formate;

II-140: N-(3-(3-fluoropyridin-2-yl)-1-(1,4-dioxaspiro[4.5]decan-8-yl)-1H-pyrazol-4-yl)-2-(1H-pyrazol-4-yl)thiazole-4-carboxamide;

II-141: 2-(1H-pyrazol-4-yl)-N-(3-(pyridin-2-yl)-1-((1r,3r)-3-(2,2,2-trifluoroethoxy)cyclobutyl)-1H-pyrazol-4-yl)thiazole-4-carboxamide formate;

II-142: 2-(1H-pyrazol-4-yl)-N-(3-(pyridin-2-yl)-1-((1r,3r)-3-(2,2,2-trifluoroethoxy)cyclobutyl)-1H-pyrazol-4-yl)thiazole-4-carboxamide;

II-143: N-(1-((1r,4r)-4-hydroxycyclohexyl)-3-(pyridin-2-yl)-1H-pyrazol-4-yl)-2-(1H-pyrazol-4-yl)thiazole-4-carboxamide formate;

II-144: N-(1-((1r,4r)-4-hydroxycyclohexyl)-3-(pyridin-2-yl)-1H-pyrazol-4-yl)-2-(1H-pyrazol-4-yl)thiazole-4-carboxamide;

II-145: N-(1-((1r,4r)-4-ethoxycyclohexyl)-3-(pyridin-2-yl)-1H-pyrazol-4-yl)-2-(1H-pyrazol-4-yl)thiazole-4-carboxamide formate;

II-146: N-(1-((1r,4r)-4-ethoxycyclohexyl)-3-(pyridin-2-yl)-1H-pyrazol-4-yl)-2-(1H-pyrazol-4-yl)thiazole-4-carboxamide;

II-147: N-(1-((1S,3R)-3-ethoxycyclopentyl)-3-(pyridin-2-yl)-1H-pyrazol-4-yl)-2-(1H-pyrazol-4-yl)thiazole-4-carboxamide formate;

II-148: N-(1-((1S,3R)-3-ethoxycyclopentyl)-3-(pyridin-2-yl)-1H-pyrazol-4-yl)-2-(1H-pyrazol-4-yl)thiazole-4-carboxamide;

II-149: N-(1-((1S,3R)-3-hydroxycyclopentyl)-3-(pyridin-2-yl)-1H-pyrazol-4-yl)-2-(1H-pyrazol-4-yl)thiazole-4-carboxamide formate;

II-150: N-(1-((1S,3R)-3-hydroxycyclopentyl)-3-(pyridin-2-yl)-1H-pyrazol-4-yl)-2-(1H-pyrazol-4-yl)thiazole-4-carboxamide;

II-151: N-(1-((1S,3S)-3-hydroxycyclopentyl)-3-(pyridin-2-yl)-1H-pyrazol-4-yl)-2-(1H-pyrazol-4-yl)thiazole-4-carboxamide formate;

II-152: N-(1-((1S,3S)-3-hydroxycyclopentyl)-3-(pyridin-2-yl)-1H-pyrazol-4-yl)-2-(1H-pyrazol-4-yl)thiazole-4-carboxamide;

II-153: N-(1-((1s,3s)-3-ethoxycyclobutyl)-3-(5-fluoropyridin-2-yl)-1H-pyrazol-4-yl)-2-(1H-pyrazol-4-yl)thiazole-4-carboxamide formate;

II-154: N-(1-((1s,3s)-3-ethoxycyclobutyl)-3-(5-fluoropyridin-2-yl)-1H-pyrazol-4-yl)-2-(1H-pyrazol-4-yl)thiazole-4-carboxamide;

II-155: N-(1-((1S,3R)-3-ethoxy-2-fluorocyclobutyl)-3-(pyridin-2-yl)-1H-pyrazol-4-yl)-2-(1H-pyrazol-4-yl)thiazole-4-carboxamide formate;

II-156: N-(1-((1S,3R)-3-ethoxy-2-fluorocyclobutyl)-3-(pyridin-2-yl)-1H-pyrazol-4-yl)-2-(1H-pyrazol-4-yl)thiazole-4-carboxamide;

II-157: N-(1-((1s,3s)-3-ethoxycyclobutyl)-3-(3-fluoropyridin-2-yl)-1H-pyrazol-4-yl)-2-(1H-pyrazol-4-yl)thiazole-4-carboxamide;

II-158: N-(1-((1s,3s)-3-ethoxycyclobutyl)-3-(4-fluoropyridin-2-yl)-1H-pyrazol-4-yl)-2-(1H-pyrazol-4-yl)thiazole-4-carboxamide formate;

II-159: N-(1-((1s,3s)-3-ethoxycyclobutyl)-3-(4-fluoropyridin-2-yl)-1H-pyrazol-4-yl)-2-(1H-pyrazol-4-yl)thiazole-4-carboxamide;

II-160: N-(1-((1s,3s)-3-ethoxycyclobutyl)-3-(6-fluoropyridin-2-yl)-1H-pyrazol-4-yl)-2-(1H-pyrazol-4-yl)thiazole-4-carboxamide;

II-161: 2-(1H-pyrazol-4-yl)-N-(3-(pyridin-2-yl)-1-((1s,3s)-3-(2,2,2-trifluoroethoxy)cyclobutyl)-1H-pyrazol-4-yl)thiazole-4-carboxamide formate;

II-162: 2-(1H-pyrazol-4-yl)-N-(3-(pyridin-2-yl)-1-((1s,3s)-3-(2,2,2-trifluoroethoxy)cyclobutyl)-1H-pyrazol-4-yl)thiazole-4-carboxamide;

II-163: (4-(4-((1-((1s,3s)-3-ethoxycyclobutyl)-3-(3-fluoropyridin-2-yl)-1H-pyrazol-4-yl)carbamoyl)thiazol-2-yl)-1H-pyrazol-1-yl)methyl dihydrogen phosphate; \

II-164: sodium (4-(4-((1-((1s,3s)-3-ethoxycyclobutyl)-3-(3-fluoropyridin-2-yl)-1H-pyrazol-4-yl)carbamoyl)thiazol-2-yl)-1H-pyrazol-1-yl)methyl phosphate;

II-165: N-(3-(3-fluoropyridin-2-yl)-1-((1s,3s)-3-(2,2,2-trifluoroethoxy)cyclobutyl)-1H-pyrazol-4-yl)-2-(1H-pyrazol-4-yl)thiazole-4-carboxamide formate;

II-166: N-(3-(3-fluoropyridin-2-yl)-1-((1s,3s)-3-(2,2,2-trifluoroethoxy)cyclobutyl)-1H-pyrazol-4-yl)-2-(1H-pyrazol-4-yl)thiazole-4-carboxamide;

II-167: N-(3-(3-fluoropyridin-2-yl)-1-((1r,3r)-3-(2,2,2-trifluoroethoxy)cyclobutyl)-1H-pyrazol-4-yl)-2-(1H-pyrazol-4-yl)thiazole-4-carboxamide formate;

II-168: N-(3-(3-fluoropyridin-2-yl)-1-((1r,3r)-3-(2,2,2-trifluoroethoxy)cyclobutyl)-1H-pyrazol-4-yl)-2-(1H-pyrazol-4-yl)thiazole-4-carboxamide;

II-169: N-(1-((1r,4r)-4-ethoxycyclohexyl)-3-(3-fluoropyridin-2-yl)-1H-pyrazol-4-yl)-2-(1H-pyrazol-4-yl)thiazole-4-carboxamide;

II-170: N-(3-(6-fluoropyridin-2-yl)-1-((1s,3s)-3-(2,2,2-trifluoroethoxy)cyclobutyl)-1H-pyrazol-4-yl)-2-(1H-pyrazol-4-yl)thiazole-4-carboxamide formate;

II-171: N-(3-(6-fluoropyridin-2-yl)-1-((1s,3s)-3-(2,2,2-trifluoroethoxy)cyclobutyl)-1H-pyrazol-4-yl)-2-(1H-pyrazol-4-yl)thiazole-4-carboxamide;

II-172: N-(3-(6-fluoropyridin-2-yl)-1-((1s,3s)-3-hydroxycyclobutyl)-1H-pyrazol-4-yl)-2-(1H-pyrazol-4-yl)thiazole-4-carboxamide;

II-173: (4-(4-((1-((1s,3s)-3-ethoxycyclobutyl)-3-(6-fluoropyridin-2-yl)-1H-pyrazol-4-yl)carbamoyl)thiazol-2-yl)-1H-pyrazol-1-yl)methyl dihydrogen phosphate;

II-174: N-(3-(3,6-difluoropyridin-2-yl)-1-((1s,3s)-3-ethoxycyclobutyl)-1H-pyrazol-4-yl)-2-(1H-pyrazol-4-yl)thiazole-4-carboxamide;

II-175: N-(1-((1s,4s)-4-ethoxycyclohexyl)-3-(3-fluoropyridin-2-yl)-1H-pyrazol-4-yl)-2-(1H-pyrazol-4-yl)thiazole-4-carboxamide;

II-176: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide;

II-177: N-(3-(3,6-difluoropyridin-2-yl)-1-((1s,4s)-4-ethoxycyclohexyl)-1H-pyrazol-4-yl)-2-(1H-pyrazol-4-yl)thiazole-4-carboxamide;

II-178: N-(1-((1r,4r)-4-ethoxycyclohexyl)-3-(1,3,4-oxadiazol-2-yl)-1H-pyrazol-4-yl)-2-(1H-pyrazol-4-yl)thiazole-4-carboxamide;

II-179: N-(1-((1r,4r)-4-((2,2-difluoroethyl)amino)cyclohexyl)-3-(pyrimidin-2-yl)-1H-pyrazol-4-yl)-2-(1H-pyrazol-4-yl)thiazole-4-carboxamide; or II-180: N-(3-(3,5-difluoropyridin-2-yl)-1-((1r,4r)-4-ethoxycyclohexyl)-1H-pyrazol-4-yl)-2-(1H-pyrazol-4-yl)thiazole-4-carboxamide.

In other embodiments, the compound according to formula 1 is

III-1: 2-(1-(cyclopropylmethyl)-1H-pyrazol-4-yl)-N-(1-methyl-3-(pyridin-2-yl)-1H-pyrazol-4-yl)oxazole-4-carboxamide;
III-2: 2-(1H-pyrazol-4-yl)-N-(3-(pyridin-2-yl)-1-(tetrahydro-2H-pyran-4-yl)-1H-pyrazol-4-yl)oxazole-4-carboxamide;
III-3: N-(1-(2-ethoxyethyl)-3-(pyridin-2-yl)-1H-pyrazol-4-yl)-2-(1H-pyrazol-4-yl)oxazole-4-carboxamide;
III-4: N-(1-((1s,3s)-3-ethoxycyclobutyl)-3-(pyridin-2-yl)-1H-pyrazol-4-yl)-2-(1H-pyrazol-4-yl)oxazole-4-carboxamide;
III-5: N-(1-cyclobutyl-3-(pyridin-2-yl)-1H-pyrazol-4-yl)-2-(1H-pyrazol-4-yl)oxazole-4-carboxamide;
III-6: N-(1-(2-(2-methoxyethoxy)ethyl)-3-(pyridin-2-yl)-1H-pyrazol-4-yl)-2-(1H-pyrazol-4-yl)oxazole-4-carboxamide;
III-7: N-(1-(2-(2,2-difluoroethoxy)ethyl)-3-(pyridin-2-yl)-1H-pyrazol-4-yl)-2-(1H-pyrazol-4-yl)oxazole-4-carboxamide; or
III-8: N-(1-(2-(2,2-difluoroethoxy)ethyl)-3-(pyridin-2-yl)-1H-pyrazol-4-yl)-2-(1H-pyrazol-4-yl)oxazole-4-carboxamide.

B. Synthesis

Disclosed pyrazole compounds can be prepared as exemplified below, and as will be understood by a person of ordinary skill in the art in organic synthesis. An exemplary synthesis may include the following 1$^{st}$ reaction step according to Scheme 1:

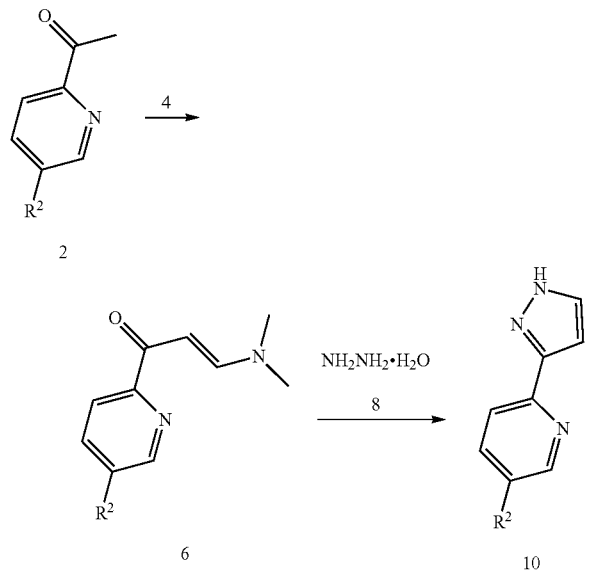

Acetyl compound 2 is reacted with dimethylformamide dimethylacetal 4 to form intermediate compound 6, at a temperature suitable to facilitate a reaction. A suitable temperature is typically from 85° C. to 130° C. Intermediate compound 6 is then reacted with hydrazine hydrate 8 to form the pyrazole compound 10. The reaction is performed in a suitable solvent, for example, an alcohol such as ethanol, methanol or isopropanol, and is typically heated, such as to reflux.

A 2$^{nd}$ reaction step in the exemplary synthesis is provided below according to Scheme 2:

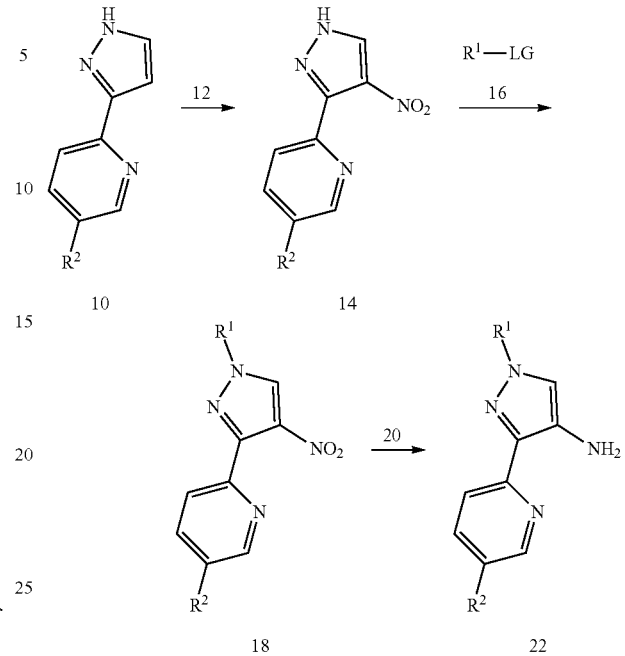

Compound 10 is nitrated using a suitable nitrating reagent or mixture of reagents 12 to form compound 14. Suitable nitrating conditions include reacting compound 10 with nitric acid, such as fuming nitric acid, optionally in the presence of sulfuric acid. Typically, compound 10 and the nitric acid are added slowly, one to the other. Cooling, such as by an ice bath, may be used to maintain the reaction temperature within a suitable range, such as from about 0° C. to less than 50° C., from 0° C. to 20° C., or from 0° C. to 10° C. After the addition is complete the reaction is allowed to proceed until the reaction is substantially complete, and may be allowed to warm to room temperature to facilitate the reaction. Optionally, additional nitrating reagent, or mixture of nitrating reagents, may be added to facilitate the reaction proceeding to completion. The reaction is then quenched, such as by addition to water and/or ice, and the product is separated or extracted from the aqueous and purified if required. Purification techniques suitable for purifying a product from any reaction disclosed herein include, but are not limited to, crystallization, distillation and/or chromatography.

With continued reference to Scheme 2, compound 14 is then reacted with compound 16 to form compound 18. Compound 16 comprises a desired R$^1$ moiety and a suitable leaving group, LG. Suitable leaving groups include any group that will act as a leaving group to facilitate the addition of the R$^1$ moiety to compound 14. Suitable leaving groups include, but are not limited to, halogens, typically bromo, chloro or iodo, and tosylate or mesylate groups. Compound 14 is reacted with compound 16 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may be heated, such as to 50° C., 100° C. or higher, as required, or the reaction may proceed at room temperature. Compound 18 is then isolated from the reaction mixture and purified if required.

Compound 18 is then reacted with a reducing agent 20 suitable to reduce the nitro moiety to an amine. Suitable reducing agents include, but are not limited to: hydrogen gas in the presence of a catalyst, such as a palladium catalyst; a borohydride, such as sodium borohydride, optionally in the presence of a catalyst, such as a nickel catalyst; zinc metal in acetic acid; or iron powder in water or water and acid. In certain embodiments, hydrogen gas is used, in the presence of a palladium on carbon catalyst, and in a suitable solvent, such as ethyl acetate or methanol. In some embodiments, a combination of reducing agents and/or techniques are used. For example, reduction may be initially performed using a first method comprising a first reducing agent and/or technique, but result in a mixture of products. The first method may be repeated, and/or a second method may be performed, comprising a second reducing agent and/or technique. Once the reaction is complete, as indicated by an analytical technique such as LC-MS, TLC or HPLC, the product compound 22 is isolated and purified if necessary.

A $3^{rd}$ step of the exemplary reaction sequence is provided below according to Scheme 3:

Scheme 3

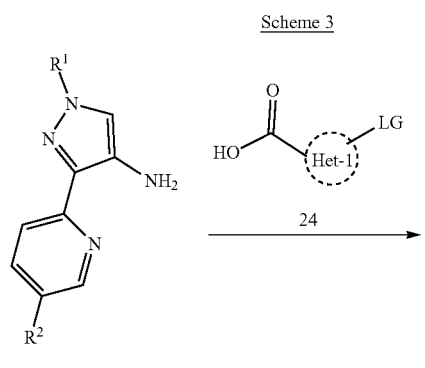

22

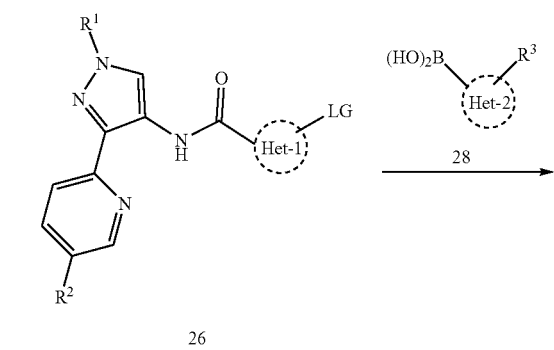

26

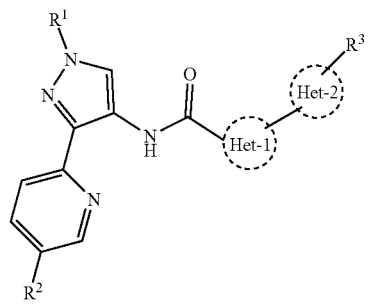

30

Compound 22 is reacted with a carboxylic acid 24 to form compound 26. The carboxylic acid 24 is activated by any suitable method and then reacted with the amine on compound 22. Suitable activation methods include, but are not limited to: forming the acid chloride by treatment with thionyl chloride; by treatment with 1-[Bis(dimethylamino) methylene]-1H-1,2,3-triazolo[4,5-b]pyridinium 3-oxid hexafluorophosphate (HATU) and a base such as diisopropylethylamine (DIPEA); by treatment with carbonyldiimidazole (CDI); or by treatment with a carbodiimide, such as dicyclohexylcarbodiimide (DCC) or 1-Ethyl-3-(3-dimethylaminopropyl)carbodiimide (EDC).

Compound 26 is then coupled with compound 28 to form compound 30 using any coupling reaction suitable to form a bond between two rings. In the example above, a boronic acid coupling is shown, where the leaving group LG on compound 26 is typically bromo or iodo. Other suitable coupling functional groups include trialkyl tin or boronic esters. The coupling reaction typically proceeds in the presence of a suitable catalyst. For a boronic acid coupling, the catalyst typically is a palladium catalyst, such as PdCl$_2$ (dppf)$_2$, Pd[P(Ph)$_3$]$_2$Cl$_2$, palladium acetate and triphenyl phosphine, or tetrakis(triphenylphosphine)palladium(0). The reaction is performed in the presence of a base, such as sodium, potassium or cesium carbonate, and is performed in a suitable solvent or solvent mixture, such as dioxane, dioxane/water or DME/ethanol/water. The reaction may be heated at a suitable temperature, such as from 50° C. to 125° C., typically about 100° C., and/or agitated for a suitable period of time, such as from 1 hour to 3 days, from 6 hours to 24 hours, or from 12 hours to 18 hours, to facilitate the reaction proceeding to completion. Compound 30 is then isolated from the reaction mixture and purified by a suitable technique.

An alternative exemplary synthesis may include the following $1^{st}$ reaction step according to Scheme 4:

Scheme 4

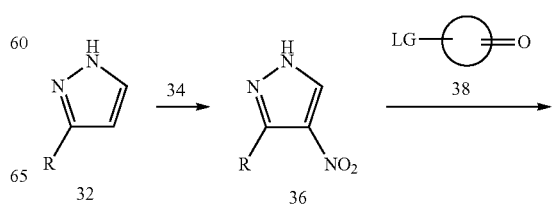

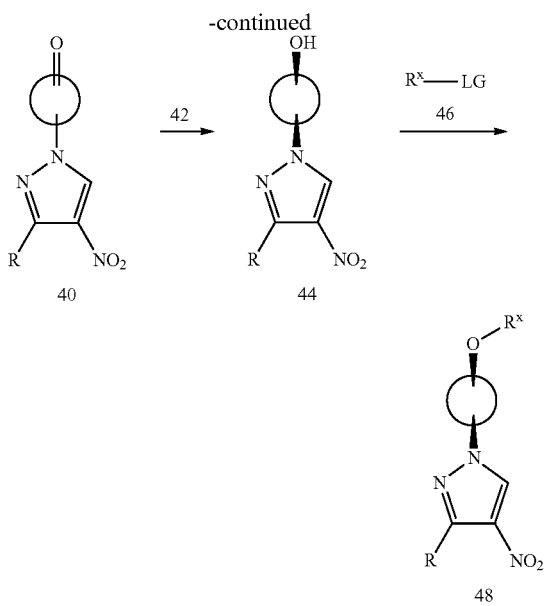

Compound 32 is nitrated using a suitable nitrating reagent or mixture of reagents 34 to form compound 36. Suitable nitrating conditions include reacting compound 32 with nitric acid, such as fuming nitric acid, optionally in the presence of sulfuric acid. Typically, compound 32 and the nitric acid are added slowly, one to the other. Cooling, such as by an ice bath, may be used to maintain the reaction temperature within a suitable range, such as from about 0° C. to less than 50° C., from 0° C. to 20° C., or from 0° C. to 10° C. After the addition is complete the reaction is allowed to proceed until the reaction is substantially complete, and may be allowed to warm to room temperature to facilitate the reaction. Optionally, additional nitrating reagent, or mixture of nitrating reagents, may be added to facilitate the reaction proceeding to completion. The reaction is then quenched, such as by addition to water and/or ice, and the product is separated or extracted from the aqueous and purified if required. Purification techniques suitable for purifying a product from any reaction disclosed herein include, but are not limited to, crystallization, distillation and/or chromatography.

With continued reference to Scheme 4, compound 36 is then reacted with compound 38 to form compound 40. Compound 38 comprises a desired ring, such as a cyclobutyl, cyclopentyl, or cyclohexyl ring, and a suitable leaving group, LG. Suitable leaving groups include any group that will act as a leaving group to facilitate the addition of the ring to compound 36. Suitable leaving groups include, but are not limited to, halogens, typically bromo, chloro or iodo, and tosylate or mesylate groups. Compound 36 is reacted with compound 38 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may be heated, such as to 50° C., 100° C. or higher, as required, or the reaction may proceed at room temperature. Compound 40 is then isolated from the reaction mixture and purified if required.

Compound 40 is then reacted with a reducing agent 42 suitable to reduce the carbonyl moiety to a hydroxyl. Suitable reducing agents include, but are not limited to, sodium borohydride, di-isobutyl aluminum hydride, or lithium aluminum hydride. The reaction is performed in a solvent suitable to facilitate the reaction, such as an alcohol, particularly methanol or ethanol; THF; or diethyl ether. The reaction may be heated, such as to 50° C., 100° C. or higher, as required, cooled, such as to below 20° C., below 10° C., below 0° C. or lower, or the reaction may proceed at room temperature. Once the reaction is complete, as indicated by an analytical technique such as LC-MS, TLC or HPLC, the product compound 44 is isolated and purified if necessary, by a suitable technique, such as column chromatography.

Optionally, compound 44 may be reacted with compound 46 to form compound 48. Compound 46 comprises a desired $R^x$ moiety and a suitable leaving group, LG. Suitable leaving groups include any group that will act as a leaving group to facilitate the addition of the $R^x$ moiety to compound 44. Suitable leaving groups include, but are not limited to, halogens, typically bromo, chloro or iodo, and tosylate or mesylate groups. Compound 44 is reacted with compound 46 in a suitable solvent and typically in the presence of a base or other reagent or reagents that facilitate the reaction. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases or reagents that facilitate the reaction include, but are not limited to, silver triflate, 2,6-di-t-butylpyridine, sodium hydride, or combinations thereof. Typically, compound 46 is slowly combined with the reaction. Cooling, such as by an ice bath, may be used to maintain the reaction temperature within a suitable range, such as from about 0° C. to less than 50° C., from 0° C. to 20° C., or from 0° C. to 10° C. After the addition is complete the reaction is allowed to proceed until the reaction is substantially complete, and may be allowed to warm to room temperature, or the reaction may be heated, such as to 50° C., 100° C. or higher, to facilitate the reaction. Once the reaction is complete, as indicated by an analytical technique such as LC-MS, TLC or HPLC, the product compound 48 is isolated and purified if necessary, by a suitable technique, such as column chromatography.

Alternatively, compound 40 may be prepared by an exemplary synthetic route according to Scheme 5:

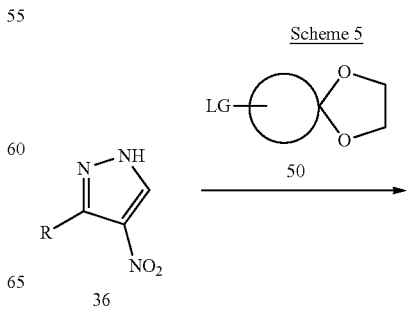

Scheme 6

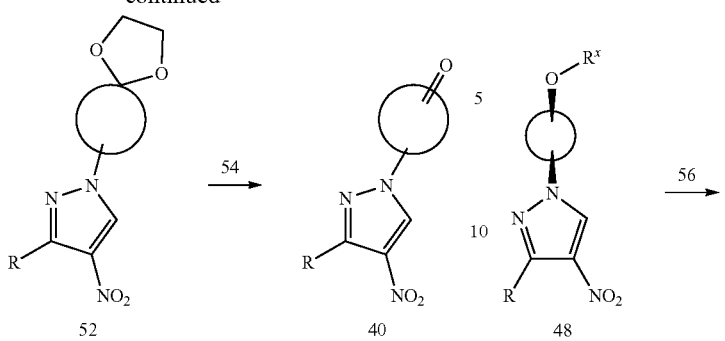

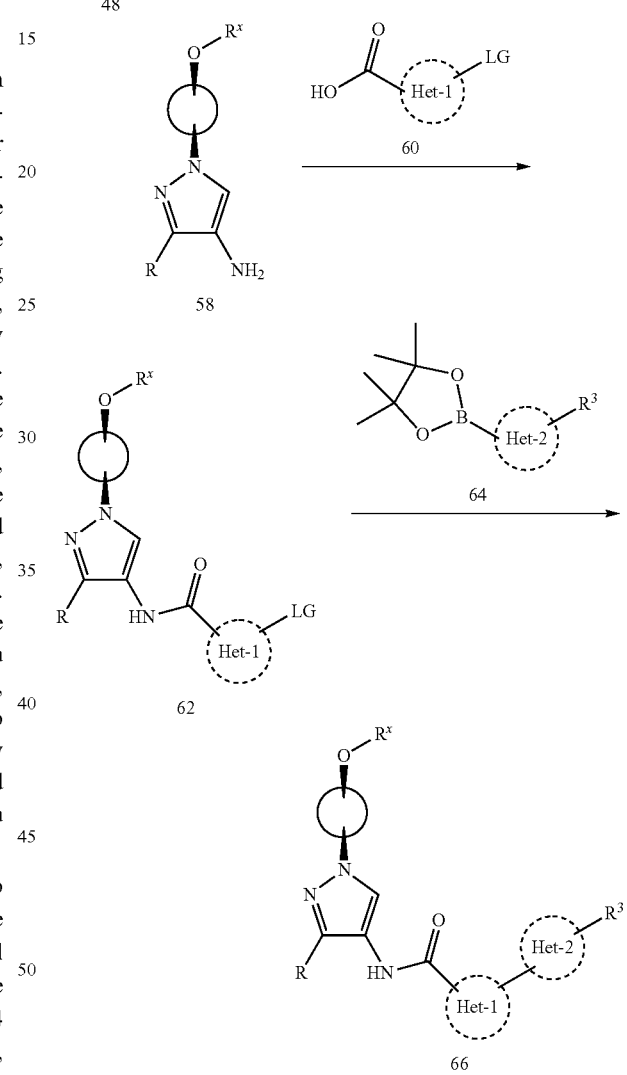

With respect to Scheme 5, compound 36 is reacted with compound 50 to form compound 52. Compound 50 comprises a desired ring, such as a cyclobutyl, cyclopentyl, or cyclohexyl ring, a suitable leaving group, LG, and a protected carbonyl moiety, such as an acetal or a ketal. In the example above a cyclic ketal moiety is shown. Suitable leaving groups include any group that will act as a leaving group to facilitate the addition of the ring to compound 36, and include, but are not limited to, halogens, typically bromo, chloro or iodo, and tosylate or mesylate groups. Compound 36 is reacted with compound 50 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may be heated, such as to 50° C., 100° C. or higher, as required, or the reaction may proceed at room temperature. Compound 52 is then isolated from the reaction mixture and purified if required by a suitable technique, such as column chromatography.

Compound 52 is then reacted with a suitable reagent 54 to form compound 40. Reagent 54 may be any reagent suitable to remove the protecting group and/or form the carbonyl moiety. In the exemplary synthesis shown in Scheme 5, the protecting group is a cyclic ketal, and suitable reagents 54 include, but are not limited to, pyridinium tosylate (PPTS), para-toluene sulfonic acid, hydrochloric acid, or acetic acid. The reaction is performed in a solvent or mixture of solvents suitable to facilitate the reaction, such as acetone, THF, acetic acid, water, or a combination thereof. The reaction may be heated, such as to 50° C., 100° C. or higher, or at reflux, as required, or the reaction may proceed at room temperature. Compound 40 is then isolated from the reaction mixture and purified if required by a suitable technique, such as column chromatography.

A $2^{nd}$ step of the exemplary reaction sequence is provided below according to Scheme 6:

Compound 48 is then reacted with a reducing agent 56 suitable to reduce the nitro moiety to an amine. In certain embodiments where the desired product compound comprises a hydroxyl moiety, compound 44 may be used in place of compound 48. Suitable reducing agents include, but are not limited to: hydrogen gas in the presence of a catalyst, such as a palladium catalyst; a borohydride, such as sodium borohydride, optionally in the presence of a catalyst, such as a nickel catalyst; zinc metal in acetic acid; or iron powder in water or water and acid. In certain embodiments, hydrogen gas is used, in the presence of a palladium on carbon catalyst, and in a suitable solvent, such as ethyl acetate or methanol. In some embodiments, a combination of reducing agents and/or techniques are used. For example, reduction may be initially performed using a first method comprising a first reducing agent and/or technique, but result in a mixture of products. The first method may be repeated, and/or a second method may be performed, comprising a second reducing agent and/or technique. Once the reaction is complete, as indicated by an analytical technique such as LC-MS, TLC or HPLC, the product compound 58 is isolated and purified if necessary.

Compound 58 is reacted with a carboxylic acid 60 to form compound 62. The carboxylic acid 60 is activated by any suitable method and then reacted with the amine on compound 58. Suitable activation methods include, but are not limited to: forming the acid chloride by treatment with thionyl chloride; by treatment with 1-[Bis(dimethylamino)methylene]-1H-1,2,3-triazolo[4,5-b]pyridinium 3-oxid hexafluorophosphate (HATU) and a base such as diisopropylethylamine (DIPEA); by treatment with carbonyldiimidazole (CDI); or by treatment with a carbodiimide, such as dicyclohexylcarbodiimide (DCC) or 1-Ethyl-3-(3-dimethylaminopropyl)carbodiimide (EDC).

Compound 62 is then coupled with compound 64 to form compound 66 using any coupling reaction suitable to form a bond between two rings. In the example above, a boronic ester coupling is shown, where the leaving group LG on compound 62 is typically bromo or iodo. Other suitable coupling functional groups include trialkyl tin or boronic acids. The coupling reaction typically proceeds in the presence of a suitable catalyst. For a boronic ester or boronic acid coupling, the catalyst typically is a palladium catalyst, such as $PdCl_2(dppf)_2$, $Pd[P(Ph)_3]_2Cl_2$, palladium acetate and triphenyl phosphine, or tetrakis(triphenylphosphine)palladium(0). The reaction is performed in the presence of a base, such as sodium, potassium or cesium carbonate, and is performed in a suitable solvent or solvent mixture, such as dioxane, dioxane/water or DME/ethanol/water. The reaction may be heated at a suitable temperature, such as from 50° C. to 125° C., typically about 100° C., and/or agitated for a suitable period of time, such as from 1 hour to 3 days, from 6 hours to 24 hours, or from 12 hours to 18 hours, to facilitate the reaction proceeding to completion. Compound 66 is then isolated from the reaction mixture and purified by a suitable technique.

Certain embodiments may comprise a phosphate moiety. Scheme 7 provides an exemplary synthesis of certain such embodiments:

Scheme 7

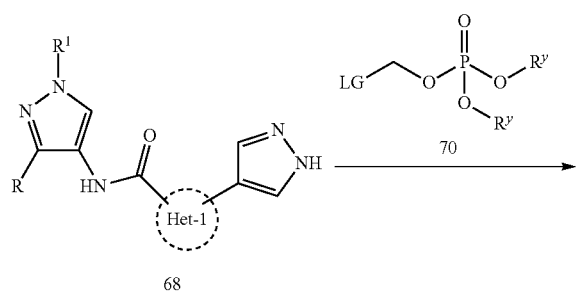

68

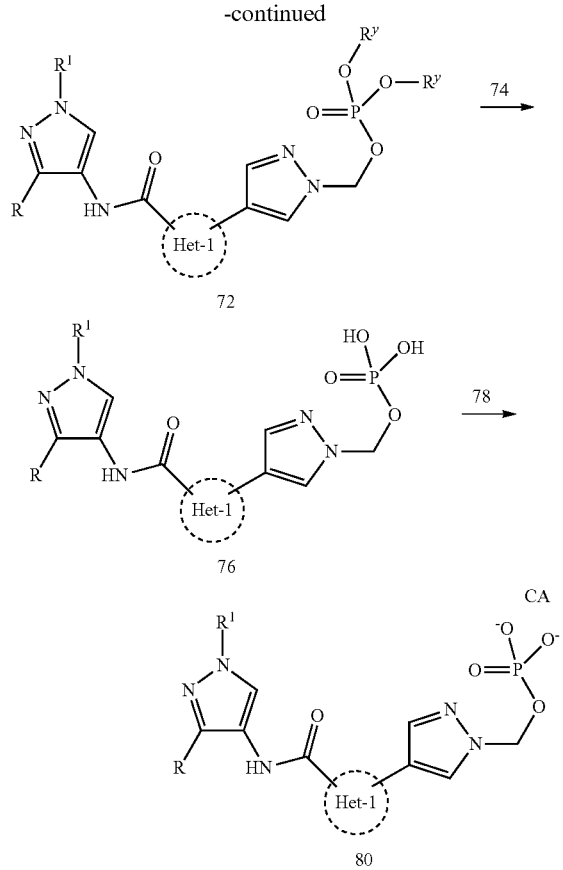

Compound 68 is reacted with compound 70 to form compound 72. Compound 70 comprises desired $R^y$ moieties and a suitable leaving group, LG. Typical $R^y$ moieties include, but are not limited to aliphatic, such as alkyl, typically methyl, ethyl, propyl, isopropyl or t-butyl; aryl; heteroaliphatic; or heterocyclic. The two $R^y$ moieties may be the same or different. Suitable leaving groups include, but are not limited to, halogens, typically bromo, chloro or iodo, and tosylate or mesylate groups. Compound 68 is reacted with compound 70 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may be heated, such as to 50° C., 100° C. or higher, as required, or the reaction may proceed at room temperature. Compound 72 is then isolated from the reaction mixture and purified if required.

Compound 72 is then reacted with compound 74 to form compound 76. Compound 74 may be any compound suitable to form the acid moieties in compound 76. Compound 74 may be an acidic reagent, such as trifluoroacetic acid, hydrochloride acid, or hydrobromic acid, or it may be a basic reagent, such as sodium hydroxide, lithium hydroxide or potassium hydroxide. Suitable solvents include, but are not limited to, chlorinated solvents such as dichloromethane and chloroform, alcohols such as methanol and ethanol, water, or combinations thereof. The reaction may be heated, such as to 50° C., 100° C. or higher, as required, cooled, such as to below 20° C., below 10° C., below 0° C. or lower, or the reaction may proceed at room temperature. Once the reaction is complete, as indicated by an analytical technique such as LC-MS, TLC or HPLC, the product compound 76 is isolated and purified if necessary, by a suitable technique, such as by agitating, such as by stirring or sonication, in a suitable solvent or solvent system. Suitable solvents or solvent systems include, but are not limited to, acetone/water, acetone, diethyl ether, or alcohol/water.

Compound 76 is then reacted with compound 78 to form the salt compound 80. Compound 78 can be any compound that will provide a suitable counterion CA for the salt compound 80, such as calcium hydroxide, sodium hydroxide, potassium hydroxide, lithium hydroxide, ammonia, trimethylamine, tris(hydroxymethyl)aminomethane, or an amino acid such as lysine or arginine. A person of ordinary skill in the art will appreciate that if counter ion CA has a single positive charge, as in $Na^+$, $K^+$, $Li^+$, or $NH_4^+$, then compound 80 will comprise two CA ions, whereas if counter ion CA has two positive charges, as in $CA^{2+}$ compound 80 will comprise one CA ion.

C. Combinations of Therapeutic Agents

The pyrazole compounds of the present invention may be used alone, in combination with one another, or as an adjunct to, or in combination with, other established therapies. In another aspect, the compounds of the present invention may be used in combination with other therapeutic agents useful for the disorder or condition being treated. These compounds may be administered simultaneously, sequentially in any order, by the same route of administration, or by a different route.

In some embodiments, the second therapeutic agent is an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with other anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an antineoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhibitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present pyrazole compounds include proteasome inhibitors, such as bortezomib, carfilzomib, marizomib and the like.

Examples of kinase inhibitors that are useful in combination with the presently disclosed compounds, particularly in treating malignancies include, Btk inhibitors, such as ibrutinib, CDK inhibitors, such as palbociclib, EGFR inhibitors, such as afatinib, erlotinib, gefitinib, lapatinib, osimertinib and vandetinib, Mek inhibitors, such as trametinib, Raf inhibitors, such as dabrafenib, sorafenib and vemurafenib, VEGFR inhibitors, such as axitinib, lenvatinib, nintedanib, pazopanib, BCR-Abl inhibitors, such as bosutinib, dasatinib, imatinib and nilotinib, Syk inhibitors, such as fostamatinib, and JAK inhibitors, such as ruxolitinib, In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides) e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, cleno liximab, clazakiumab, fezakinumab, fletikumab, mavrilimumab, ocrelizumab, sarilumab, secukinumab, toralizumab, zanolimumab;

anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents-steroids, e.g., budesonide, non-steroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues—for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

D. Compositions Comprising Pyrazole Compounds

The disclosed pyrazole compounds may be used alone, in any combination, and in combination with, or adjunctive to, at least one second therapeutic agent, and further the pyrazole compounds, and the at least one second therapeutic, may be used in combination with any suitable additive useful for forming compositions for administration to a subject. Additives can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. Typical additives include, by way of example and without limitation: pharmaceutically acceptable excipients; pharmaceutically acceptable carriers; and/or adjuvants, such as mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; antiadherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose), gelatin, synthetic polymers (such as polyvinylpyrrolidone, polyalkylene gylcols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

III. Methods of Use

A. Diseases/Disorders

The disclosed pyrazole compounds, as well as combinations and/or compositions thereof, may be used to ameliorate, treat or prevent a variety of diseases and/or disorders. In particular embodiments, the pyrazole compound, combinations of pyrazole compounds, or compositions thereof, may be used to treat or prevent auto-immune diseases, inflammatory disorders, cardiovascular diseases, nerve disorders, neurodegenerative disorders, allergic disorders, asthma, pancreatitis, multi-organ failure, kidney diseases, platelet aggregation, cancer, transplantation, sperm motility, erythrocyte deficiency, graft rejection, lung injuries, respiratory diseases, ischemic conditions, and bacterial and viral infections.

In some embodiments, the pyrazole compound, combinations of pyrazole compounds, or compositions thereof, may be used to treat or prevent allergic diseases, amyotrophic lateral sclerosis (ALS), systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy or asthma.

The pyrazole compound, combinations of pyrazole compounds, or compositions thereof, may also be useful for ameliorating, treating or preventing immune regulatory disorders related to bone marrow or organ transplant rejection or graft-versus-host disease. Examples of inflammatory and immune regulatory disorders that can be treated with the present compounds include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and postinfectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

In certain embodiments, the present compounds are useful for treating nerve pain, including neuropathic pain and inflammation induced pain.

In certain embodiments, the pyrazole compound, combinations of pyrazole compounds, or compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Cronh's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), Alzheimer's disease, Parkinson's disease.

Proliferative diseases that may be treated by the pyrazole compound, combinations of pyrazole compounds, or compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Examples of allergic disorders that may be treated using the pyrazole compound, combinations of pyrazole compounds, or compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, post-nasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The pyrazole compound, combinations of pyrazole compounds, or compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration

Pharmaceutical compositions comprising the active compounds of the invention (or prodrugs thereof) may be manufactured by means of conventional mixing, dissolving, granulating, dragee-making, levigating, emulsifying, encapsulating, entrapping or lyophilization processes. The compositions may be formulated in conventional manner using one or more physiologically acceptable excipients, diluents, carriers, adjuvants or auxiliaries to provide preparations which can be used pharmaceutically.

The active compound or prodrug may be formulated in the pharmaceutical compositions per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), hydrate, solvate, N-oxide or pharmaceutically acceptable salt or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), hydrate, solvate, N-oxide, pharmaceutically acceptable salt or prodrug(s) can be conveniently delivered in the form of an aerosol spray from pressurized packs or a nebulizer with the use of a suitable propellant, e.g.) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (1 15 mg/ml); phenylethanol (1 4 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL Compound or prodrug, 1% (v/v) Polysorbate 80 (TWEEN® 80), 50 mM citrate and/or 0.9% sodium chloride.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active compound(s) or prodrug(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s) or prodrug(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The pyrazole compound or combinations of pyrazole compounds will generally be used in an amount effective to achieve the intended result, for example, in an amount effective to treat or prevent a particular condition. The pyrazole compound(s), or compositions thereof, can be administered therapeutically to achieve therapeutic benefit or prophylactically to achieve prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of pyrazole compounds will also depend on various factors, including the age, weight, general health, and severity of the condition of the patient or subject being treated. Dosage may also need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, and respiratory infections. Dosage, and frequency of administration of the pyrazole compound(s) or compositions thereof, will also depend on whether the pyrazole compound(s) are formulated for treatment of acute episodes of a condition or for the prophylactic treatment of a disorder. A person or ordinary skill in the art will be able to determine the optimal dose for a particular individual.

For prophylactic administration, the pyrazole compound, combinations of pyrazole compounds, or compositions thereof, can be administered to a patient or subject at risk of developing one of the previously described conditions. For example, if it is unknown whether a patient or subject is allergic to a particular drug, the pyrazole compound, combinations of pyrazole compounds, or compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a pyrazole compound(s), or composition thereof, can be administered to an allergy sufferer prior to expected exposure to the allergen. A pyrazole compound, combinations of pyrazole compounds, or compositions thereof, can also be administered prophylactically to healthy individuals who are repeatedly exposed to agents known to one of the above-described maladies to prevent the onset of the disorder. For example, a pyrazole compound, combinations of pyrazole compounds, or compositions thereof, can be administered to a healthy individual who is repeatedly exposed to an allergen known to induce allergies, such as latex, in an effort to prevent the individual from developing an allergy. Alternatively, a pyrazole compound, combinations of pyrazole compounds, or compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 µM, such as from greater than 0 to 10 µM, from greater than 0 to 5 µM, from greater than 0 to 1 µM, from greater than 0 to 0.5 µM, or from greater than 0 to 0.1 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

Dosage amounts of disclosed pyrazole compounds will typically be in the range of from about greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the pyrazole compound, its bioavailability, the mode of administration, and various factors discussed above.

Dosage amount and dosage interval can be adjusted for individuals to provide plasma levels of the pyrazole compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Compositions comprising one or more of the disclosed pyrazole compounds typically comprise from greater than 0 up to 99% of the pyrazole compound, or compounds, and/or other therapeutic agent by total weight percent. More typically, compositions comprising one or more of the disclosed pyrazole compounds comprise from about 1 to about 20 total weight percent of the pyrazole compound and other therapeutic agent, and from about 80 to about 99 weight percent of a pharmaceutically acceptable additive.

Preferably, the pyrazole compound, combinations of pyrazole compounds, or compositions thereof, will provide therapeutic or prophylactic benefit without causing substantial toxicity. Toxicity of the pyrazole compound can be determined using standard pharmaceutical procedures. The dose ratio between toxic and therapeutic (or prophylactic) effect is the therapeutic index. Pyrazole compounds that exhibit high therapeutic indices are preferred.

IV. Examples

Example 1

Preparation of Amine 106

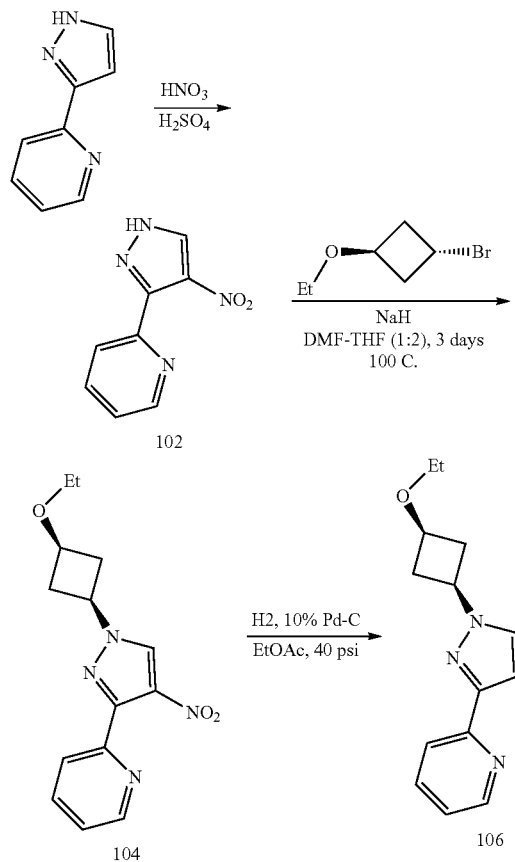

2-(1H-Pyrazol-3-yl)pyridine (10 g) was suspended in concentrated sulfonic acid (30 mL), then fuming nitric acid (6.5 mL, 2 eq.) was added to the solution dropwise while stirring. The reaction mixture was stirred overnight at room temperature. It was quenched by pouring into ice-water (500 mL). The aqueous solution was neutralized by adding solid sodium carbonate, until pH reached around 8. White precipitate was collected by filtration, washed with water and dried to give 2-(4-nitro-1H-pyrazol-3-yl)pyridine 102 (13 g, 99% yield).

2-(4-nitro-1H-pyrazol-3-yl)pyridine 102 (2 g), and 1-bromo-3-ethoxycyclobutane (90% trans isomer, 2 g) were suspended in THF (20 mL) and DMF (10 mL). Sodium hydride (60% in oil, 670 mg, 1.5 eq.) was added to the reaction. The reaction solution was heated at 100° C. for 3 days and then was evaporated. The residue was purified by combiflash chromatography (EtOAc in hexanes=10-100%) to give product 104.

Compound 104 was dissolved in EtOAc (100 mL) and charged with 10% Pd—C catalyst (200 mg). The reaction mixture was shaken under 40 psi hydrogen for 1 hour. LC-MS indicated fully reduction of nitro group. The catalyst was filtered off through celite and washed with EtOAc (5×20 mL). The filtrate was concentrated to give amine 106 (1.4 g, 52% yield in two steps).

Example 2

Exemplary Synthesis of I-28: N-(1-((1,3-cis)-3-ethoxycyclobutyl)-3-(pyridin-2-yl)-1H-pyrazol-4-yl)-5-(1H-pyrazol-4-yl)furan-2-carboxamide

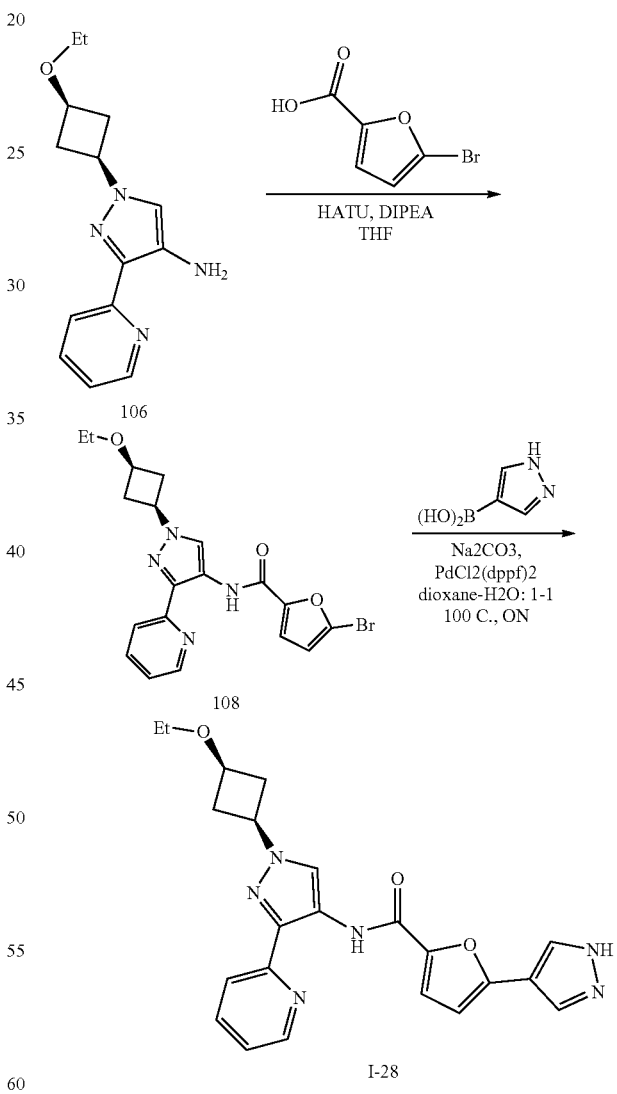

Compound 106 (700 mg), 5-bromo-2-furoic acid (622 mg, 1.2 eq.), and 1-[bis(dimethylamino)methylene]-1H-1,2,3-triazolo[4,5-b]pyridinium 3-oxid hexafluorophosphate (HATU) (1.54 g, 1.5 eq.) were dissolved in THF (30 mL) and diisopropylethylamine (DIPEA) (0.7 mL, 1.5 eq.) was added to the solution. The reaction mixture was stirred at room temperature overnight and evaporated. The residue was purified by combiflash chromatography (EtOAc in hexanes=10-100%) to give product 108 (1 g, 87% yield).

Compound 108 (1 g), pyrazole-4-boronic acid (780 mg, 3 eq.), Na$_2$CO$_3$ (2.45 g, 10 eq.) and PdCl$_2$ (dppf)$_2$ (250 mg) were stirred in dioxane (15 mL) and water (15 mL). The reaction mixture was heated at 100° C. overnight. LC-MS indicated fully conversion to the product. The reaction mixture was evaporated and purified by combiflash chromatography (2.0 M NH$_3$/MeOH in DCM=0-20%) to give desired product I-28 (750 mg, 77% yield). $^1$H NMR (300 MHz, DMSO) δ 13.25 (br, 1H), 11.63 (s, 1H), 8.72 (dd, J=6.0 Hz, 1H), 8.39 (s, 1H), 8.25 (s, 1H), 8.06 (d, J=6.9 Hz, 1H), 7.95 (m, 2H), 7.42 (m, 1H), 7.26 (d, J=3.9 Hz, 1H), 6.77 (d, J=3.3 Hz, 1H), 4.60 (p, J=7.8 Hz, 1H), 3.83 (p, J=7.5 Hz, 1H), 3.40 (q, J=6.9 Hz, 2H), 2.79 (m, 2H), 2.41 (m, 2H), 1.13 (t, J=6.9 Hz, 3H); LCMS: purity: 100%; MS (m/e): 419.60 (MH+).

Example 3

Preparation of 2-methyl-1-(4-nitro-3-(pyridin-2-yl)-1H-pyrazol-1-yl)propan-2-ol (110)

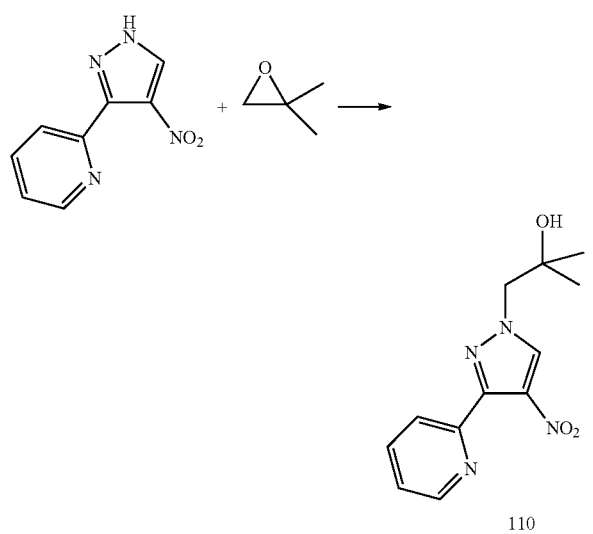

110

Sodium hydride (1.657 g, 41.4 mmol) was weighed out and added to a dry reaction tube with magnetic stir bar and cooled to 0° C. This was carefully suspended in 86 mL THF and the system was purged with nitrogen. 2-(4-Nitro-1H-pyrazol-3-yl)pyridine (3.928 g, 20.7 mmol) was added in 40 mL dimethylformamide followed by 7 mL dimethylformamide washings. This was stirred 30 minutes at 0° C. followed by 30 minutes at room temperature. It was then cooled back to 0° C. and isobutylene oxide (5.5 mL, 61.9 mmol) was added. The reaction was stirred warming to room temperature, heated 3 hours at 100° C. and stirred overnight at room temperature. The reaction was recharged with sodium hydride (0.445 g, 11.2 mmol) and isobutylene oxide (1.8 mL, 20.3 mmol) and heated 2 hours more at 100° C. The reaction was quenched with water and concentrated to dryness; the residue was partitioned between saturated aqueous sodium bicarbonate and ethyl acetate. The aqueous layer was extracted three times more with ethyl acetate and the combined organic layer was washed with brine and dried over sodium sulfate. Product solution was filtered, concentrated onto silica and purified by column chromatography. After drying, 1.92 g of the title compound 110 was obtained in two batches (35% yield).

$^1$H NMR (300 MHz, DMSO-d$_6$) δ8.73 (s, 1H), 8.72-8.45 (m, 1H), 7.95-7.88 (m, 1H), 7.71-7.65 (m, 1H), 7.51-7.43 (m, 1H), 4.89 (s, 1H), 4.14 (s, 2H), 1.14 (s, 6H). m/z=263 (M+H)$^+$.

Example 4

Preparation of 1-(4-amino-3-(pyridin-2-yl)-1H-pyrazol-1-yl)-2-methylpropan-2-ol 112

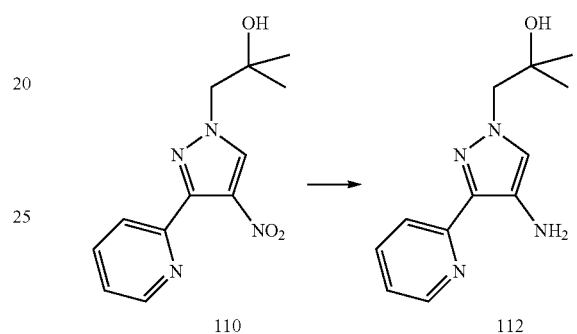

110          112

2-Methyl-1-(4-nitro-3-(pyridin-2-yl)-1H-pyrazol-1-yl)propan-2-ol 110 (0.994 g, 3.8 mmol) was added to a Parr reaction bottle in 100 mL ethyl acetate. This was put under nitrogen and charged with (wet) 10% Pd on carbon (0.404 g, 0.2 mmol). This was run at 60 psi hydrogen overnight on the Parr hydrogenator. The reaction was filtered through Celite with methanol washings, concentrated onto silica and purified by column chromatography. 0.723 g of the title compound 112 was obtained after drying on high vacuum (82% yield). $^1$H NMR (300 MHz, DMSO-d$_6$) δ 8.51 (ddt, J=5.0, 1.9, 0.9 Hz, 1H), 7.85-7.71 (m, 2H), 7.23-7.11 (m, 2H), 4.98 (s, 2H), 4.68 (s, 1H), 3.92 (s, 2H), 1.08 (s, 6H). m/z=233 (M+H)$^+$.

Example 5

Preparation of 5-bromo-N-(1-(2-hydroxy-2-methylpropyl)-3-(pyridin-2-yl)-1H-pyrazol-4-yl)furan-2-carboxamide 114

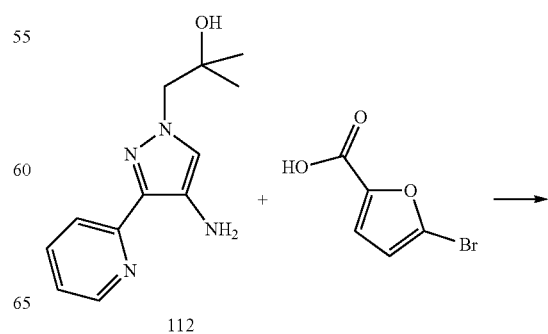

112

-continued

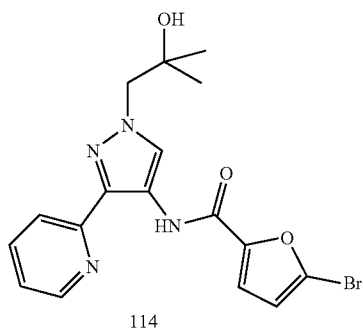

114

5-Bromofuran-2-carboxylic acid (0.148 g, 0.77 mmol) was weighed out and added to a flask with magnetic stir bar. This was dissolved in 33 mL dichloromethane and diisopropylethylamine (0.20 mL, 1.2 mmol) was added followed by HATU (0.381 g, 1.0 mmol). This is stirred 30 minutes at room temperature and 1-(4-amino-3-(pyridin-2-yl)-1H-pyrazol-1-yl)-2-methylpropan-2-ol 112 (0.214 g, 0.92 mmol) was added in 13 mL dichloromethane solution. The reaction was stirred overnight at room temperature. This was concentrated directly onto silica and purified by column chromatography. After drying, 0.358 g of the title compound 114 was obtained. (96% mass balance based on the aminopyrazole; hydroybutyl-related byproducts remained in the purified product. This was used directly) $^1$H NMR (300 MHz, DMSO-d$_6$) δ 11.82 (s, 1H), 8.65 (ddd, J=5.0, 1.8, 1.0 Hz, 1H), 8.34 (s, 1H), 8.02-7.90 (m, 2H), 7.41 (ddd, J=7.2, 5.0, 1.6 Hz, 1H), 7.27 (d, J=3.6 Hz, 1H), 6.88 (d, J=3.6 Hz, 1H), 4.77 (s, 1H), 4.11 (s, 2H), 1.12 (s, 6H). m/z=405/407 (M+H)$^+$ (bromine isotopes).

Example 6

Preparation of I-1: N-(1-(2-hydroxy-2-methylpropyl)-3-(pyridin-2-yl)-1H-pyrazol-4-yl)-5-(1-methyl-1H-pyrazol-4-yl)furan-2-carboxamide

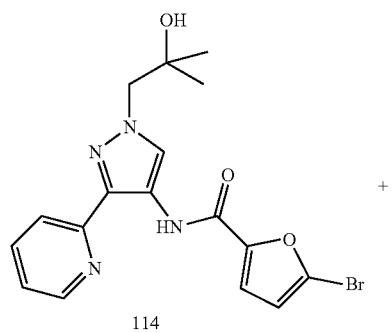

114

+

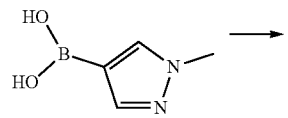

→

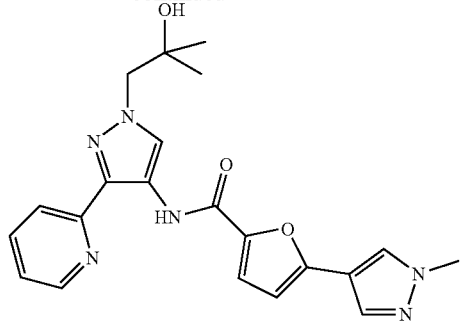

I-1

5-bromo-N-(1-(2-hydroxy-2-methylpropyl)-3-(pyridin-2-yl)-1H-pyrazol-4-yl)furan-2-carboxamide 114 (49 mg, 0.12 mmol) in 1.7 mL premixed 7/3 dimethoxyethane/ethanol solution was added to a microwave reaction vial with magnetic stir bar. (1-Methyl-1H-pyrazol-4-yl)boronic acid (99 mg, 0.78 mmol) was weighed out and added to the vial. 2M aqueous sodium carbonate solution (0.41 mL, 0.82 mmol) was added and the reaction was subjected to vigorous subsurface nitrogen sparge. Pd[P(Ph)$_3$]$_2$Cl$_2$ (16 mg, 0.02 mmol) was added, the tube was sealed under nitrogen and then heated 30 minutes in the microwave at 130° C. The reaction was worked up in the tube, first diluting with ethyl acetate. This was washed in succession with brine, 1M aqueous sodium hydroxide solution, and brine, pipetting the aqueous layer off the bottom of the tube. The aqueous was back-extracted twice with ethyl acetate and the combined organic layer was dried in a vial over sodium sulfate. The product solution was filtered into another vial, evaporated, and purified by preparative HPLC. After drying, 6 mg of the title compound I-1 was obtained as the TFA salt (10% yield; an additional 12 mg less pure product was recovered).

$^1$H NMR (300 MHz, DMSO-d$_6$) δ 11.65 (s, 1H), 8.75 (ddd, J=5.0, 1.8, 0.9 Hz, 1H), 8.38 (s, 1H), 8.19 (s, 1H), 8.02 (dt, J=8.2, 1.2 Hz, 1H), 7.99-7.92 (m, 1H), 7.90 (d, J=0.7 Hz, 1H), 7.43 (ddd, J=7.3, 4.9, 1.4 Hz, 1H), 7.27 (d, J=3.6 Hz, 1H), 6.76 (d, J=3.6 Hz, 1H), 4.78 (s, 1H), 4.11 (s, 2H), 3.95 (s, 3H), 1.12 (s, 6H). m/z=407 (M+H)$^+$.

Example 7

Preparation of I-3: N-(1-(2-hydroxy-2-methylpropyl)-3-(pyridin-2-yl)-1H-pyrazol-4-yl)-5-(1H-pyrazol-4-yl)furan-2-carboxamide

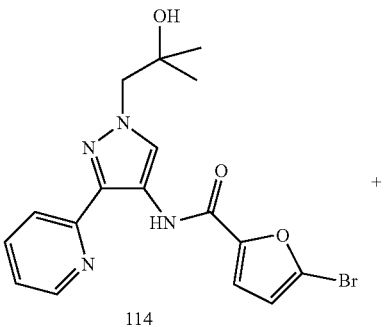

114

+

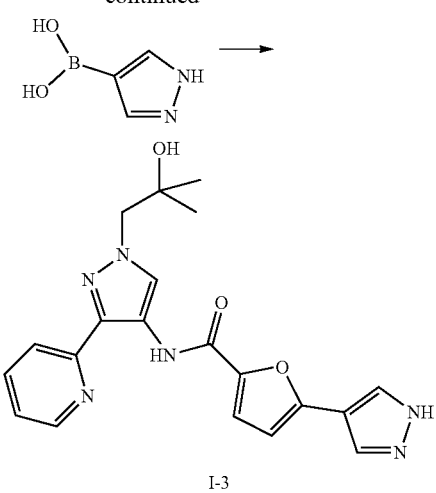

I-3

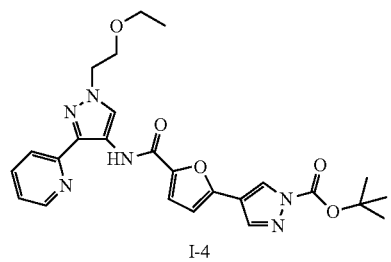

I-4

5-bromo-N-(1-(2-hydroxy-2-methylpropyl)-3-(pyridin-2-yl)-1H-pyrazol-4-yl)furan-2-carboxamide 114 (0.289 g, 0.71 mmol) was weighed out and added to a microwave reaction tube with magnetic stir bar. Pyrazole-4-boronic acid (0.511 g, 4.6 mmol) was added followed by 10 mL of a 7:3 dimethoxyethane/ethanol solution. Sodium carbonate (0.514 g, 4.8 mmol) was dissolved in 2.42 mL water and added to the reaction. This was subjected to vigorous sub-surface nitrogen sparge. Pd[P(Ph)$_3$]$_2$Cl$_2$ (60 mg, 0.09 mmol) was added, the tube was sealed under nitrogen and then heated 30 minutes in the microwave at 130° C.

The solution was diluted into ethyl acetate and washed first with brine, then 1M aqueous sodium hydroxide, and again with brine before drying over sodium sulfate. (The base wash was analyzed for desired product to monitor potential loss to the aqueous layer.) Product solution was filtered, concentrated onto silica and purified by column chromatography. 0.180 g of the title compound I-3 was obtained after drying (64% yield).

$^1$H NMR (300 MHz, DMSO-d$_6$) δ 13.27 (s, 1H), 11.67 (s, 1H), 8.74 (ddd, J=5.0, 1.8, 0.9 Hz, 1H), 8.38 (s, 1H), 8.26 (s, 1H), 8.10-7.80 (m, 3H), 7.43 (ddd, J=7.3, 5.0, 1.4 Hz, 1H), 7.27 (d, J=3.5 Hz, 1H), 6.78 (d, J=3.5 Hz, 1H), 4.78 (s, 1H), 4.11 (s, 2H), 1.13 (s, 6H). m/z=393 (M+H)$^+$.

Example 8

Preparation of I-4: tert-butyl 4-(5-((1-(2-ethoxyethyl)-3-(pyridin-2-yl)-1H-pyrazol-4-yl)carbamoyl)furan-2-yl)-1H-pyrazole-1-carboxylate

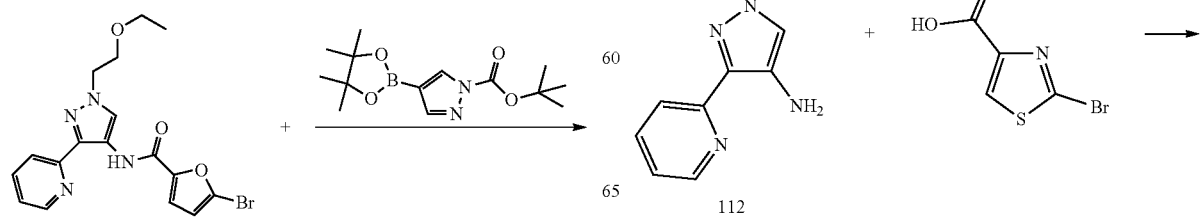

5-bromo-N-(1-(2-ethoxyethyl)-3-(pyridin-2-yl)-1H-pyrazol-4-yl)furan-2-carboxamide (2.435 g, 6.0 mmol) was weighed out and added to a reaction tube with magnetic stir bar. 1-Boc-pyrazole-4-boronic acid pinacol ester (3.535 g, 12.0 mmol) was added and these were dissolved in 60 mL dimethylformamide Cesium carbonate (3.916 g, 12.0 mmol) was weighed out and added and the reaction was subjected to vigorous sub-surface nitrogen sparge. Pd(dppf)Cl$_2$.CH$_2$Cl$_2$ (0.491 g, 0.60 mmol) was added followed by Ag$_2$O (1.391 g, 6.0 mmol). The tube was sealed under nitrogen and stirred overnight at room temperature. The reaction solution was then combined with a 0.64 mmol pilot reaction run under the same conditions and filtered through Celite with ethyl acetate washings. The filtrate was concentrated to dryness and partitioned between ethyl acetate and water. The aqueous layer is extracted three times more with ethyl acetate and the combined organic layer is washed with brine and dried over sodium sulfate. Product solution is filtered, concentrated onto silica and purified by column chromatography. Pure fractions are combined, concentrated and dried on high vacuum to give 2.2 g of the title compound I-4 (69% yield total).

$^1$H NMR (300 MHz, Chloroform-d) δ 11.83 (s, 1H), 8.69 (ddd, J=5.0, 1.9, 1.0 Hz, 1H), 8.60-8.33 (m, 2H), 8.29-7.91 (m, 2H), 7.79 (ddd, J=8.1, 7.5, 1.7 Hz, 1H), 7.28-7.21 (m, 2H), 6.62 (d, J=3.6 Hz, 1H), 4.35 (t, J=5.6 Hz, 2H), 3.86 (t, J=5.6 Hz, 2H), 3.51 (q, J=7.0 Hz, 2H), 1.72 (s, 9H), 1.19 (t, J=7.0 Hz, 3H). m/z=493 (M+H)$^+$.

Example 9

Preparation of 2-bromo-N-(1-(2-hydroxy-2-methylpropyl)-3-(pyridin-2-yl)-1H-pyrazol-4-yl)thiazole-4-carboxamide 116

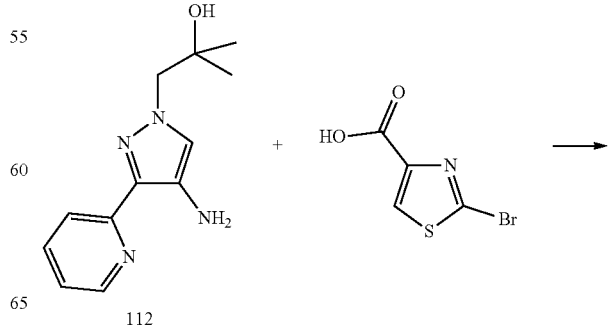

112

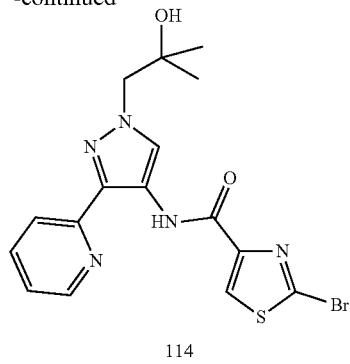

114

2-Bromothiazole-4-carboxylic acid (0.257 g, 1.2 mmol) was weighed out and added to a flask with a magnetic stir bar and taken up in 53 mL dichloromethane. Diisopropylethylamine (0.322 mL, 1.8 mmol) was added followed by HATU (0.611 g, 1.6 mmol) and the reaction was stirred at room temperature for 60 minutes. 1-(4-Amino-3-(pyridin-2-yl)-1H-pyrazol-1-yl)-2-methylpropan-2-ol 112 (0.344 g, 1.5 mmol) was added in 21 mL dichloromethane solution and the reaction was stirred overnight at room temperature. This was concentrated directly onto silica and purified by column chromatography. Product containing fractions were all found to contain hydroxyazabenzotriazole as a contaminant. These were concentrated and partitioned between ethyl acetate and saturated aqueous sodium bicarbonate. The aqueous layer was washed with ethyl acetate until product was completely extracted. The combined organic layer was washed with brine and dried over sodium sulfate. Filtration, concentration and drying on high vacuum afforded 0.429 g of the pure title compound 114 (82% yield).

$^1$H NMR (300 MHz, DMSO-$d_6$) δ 12.23 (s, 1H), 8.70-8.57 (m, 1H), 8.42 (d, J=5.7 Hz, 2H), 8.06-7.87 (m, 2H), 7.39 (ddd, J=7.3, 4.9, 1.5 Hz, 1H), 4.78 (s, 1H), 4.12 (s, 2H), 1.12 (s, 6H). m/z=422/424 (M+H)$^+$ (bromine isotopes).

Example 10

Preparation of II-1: N-(1-(2-hydroxy-2-methylpropyl)-3-(pyridin-2-yl)-1H-pyrazol-4-yl)-2-(1H-pyrazol-4-yl)thiazole-4-carboxamide

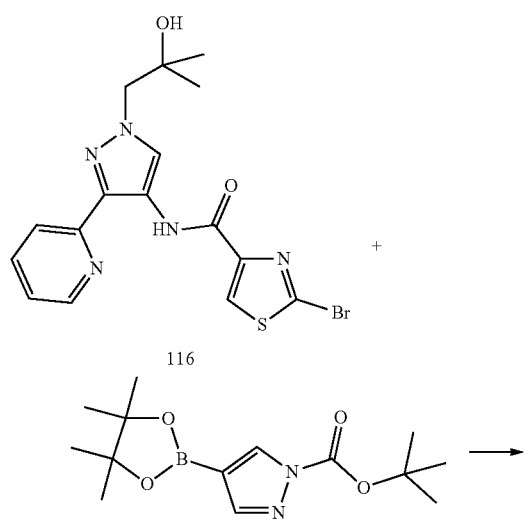

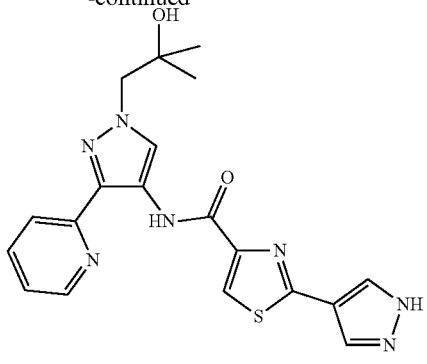

II-1

2-Bromo-N-(1-(2-hydroxy-2-methylpropyl)-3-(pyridin-2-yl)-1H-pyrazol-4-yl)thiazole-4-carboxamide 116 (0.212 g, 0.50 mmol) was weighed out and added to a microwave reaction vial with magnetic stir bar. 1-Boc-pyrazole-4-boronic acid pinacol ester (0.944 g, 3.2 mmol) was added followed by 4.9 mL dimethoxyethane and 2.1 mL ethanol. Sodium carbonate (0.362 g, 3.4 mmol) was dissolved in 1.7 mL water and added to the reaction. The solution was subjected to vigorous sub-surface nitrogen sparge and Pd[P(Ph)$_3$]$_2$Cl$_2$ (60 mg, 0.09 mmol) was added. The tube was sealed under nitrogen and heated 30 minutes in the microwave at 130° C. The solution was diluted into ethyl acetate and washed with saturated aqueous sodium bicarbonate and brine. The emulsified layer was back-extracted three times with ethyl acetate and the combined organic layer was dried over sodium sulfate. This was filtered, concentrated and purified by column chromatography to give 0.160 g of the title compound II-1 after drying (78% yield).

$^1$H NMR (300 MHz, DMSO-$d_6$) δ 13.42 (s, 1H), 12.21 (s, 1H), 8.77 (ddd, J=5.0, 1.8, 1.0 Hz, 1H), 8.45 (s, 1H), 8.44-8.05 (br s, 2H), 8.28 (s, 1H), 8.03-7.90 (m, 2H), 7.42 (ddd, J=7.4, 4.9, 1.4 Hz, 1H), 4.79 (s, 1H), 4.12 (s, 2H), 1.13 (s, 6H). m/z=410 (M+H)$^+$.

Example 11

Preparation of II-11: N-(1-((1,3-cis)-3-ethoxycyclobutyl)-3-(pyridin-2-yl)-1H-pyrazol-4-yl)-2-(1H-pyrazol-4-yl)thiazole-4-carboxamide

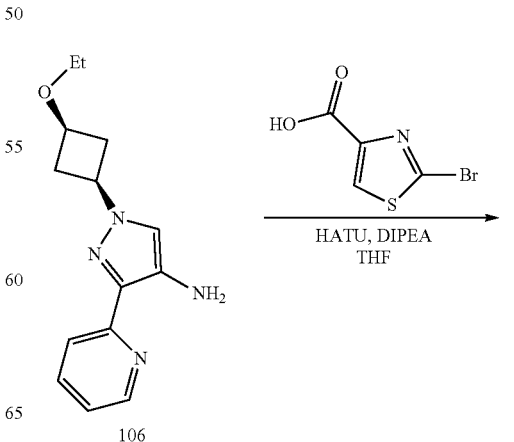

106

-continued

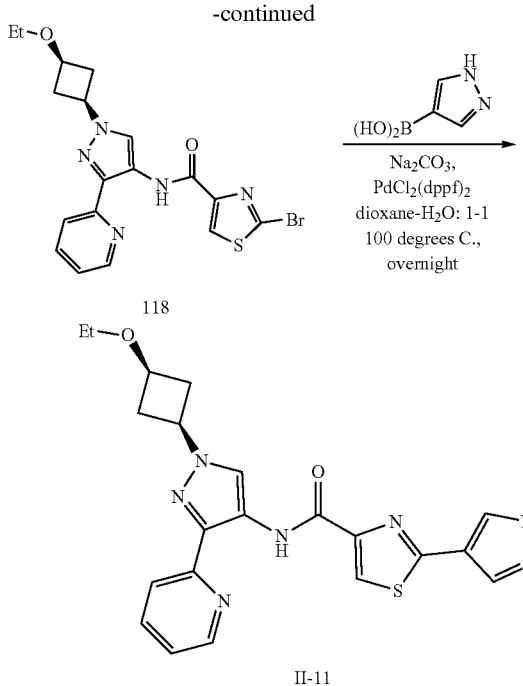

Compound 106 (680 mg), 2-bromothiazole-4-carboxylic acid (658 mg, 1.2 eq.), and HATU (1.5 g, 1.5 eq.) were dissolved in THF (30 mL) and DIPEA (0.7 mL, 1.5 eq.) was added to the solution. The reaction mixture was stirred at room temperature overnight and evaporated. The residue was purified by combiflash chromatography (EtOAc in hexanes=10-100%) to give product 118 (980 mg, 83% yield).

Compound 118 (1 g), pyrazole-4-boronic acid (750 mg, 3 eq.), $Na_2CO_3$ (2.37 g, 10 eq.) and $PdCl_2(dppf)_2$ (200 mg) were stirred in dioxane (15 mL) and water (15 mL). The reaction mixture was heated at 100° C. overnight. LC-MS indicated fully conversion to the product. The reaction mixture was evaporated and purified by combiflash chromatography (2.0 M NH3/MeOH in DCM=0-20%) to give desired product II-11 (700 mg, 72% yield). $^1$H NMR (300 MHz, DMSO) δ 13.41 (br, 1H), 12.18 (s, 1H), 8.75 (d, J=4.5 Hz, 1H), 8.46 (m, 2H), 8.27 (s, 1H), 8.06 (m, 2H), 7.93 (m, 1H), 7.42 (m, 1H), 4.61 (p, J=8.1 Hz, 1H), 3.84 (p, J=6.9 Hz, 1H), 3.41 (q, J=6.9 Hz, 2H), 2.80 (m, 2H), 2.44 (m, 2H), 1.13 (t, J=6.9 Hz, 3H); LCMS: purity: 100%; MS (m/e): 436.56 (MH+).

Example 12

Preparation of 4-nitro-3-(trifluoromethyl)-1H-pyrazole 120

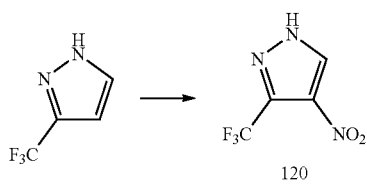 [SMILES: FC(F)(F)c1cc[nH]n1 ; O=[N+]([O-])c1c[nH]nc1C(F)(F)F]

72 mL concentrated sulfuric acid was added to a flask with magnetic stir bar and cooled to 0° C. 3-(trifluoromethyl)-pyrazole (12.070 g, 88.70 mmol) was weighed out and added gradually. An addition funnel was attached and charged with 90% fuming nitric acid (36 mL, 766 mmol). This was added in dropwise at 0° C., and the reaction was stirred warming to room temperature overnight. The reaction was then recharged with the same nitric acid described above (19 mL, 404 mmol) at room temperature and then stoppered. Stirring at room temperature continued overnight.

The reaction was poured over ice and neutralized by slow addition of 200 g sodium carbonate. The pH was adjusted to 6 with 1M hydrochloric acid and the solution was extracted six times with ethyl acetate. The combined organic layer was dried over sodium sulfate, filtered, and concentrated to an oil. This crystallized, and the solid was washed with minimal dichloromethane to give 3.250 g of the title compound 120 after drying. A second crop was isolated from the filtrate to give 1.752 g more product (31% yield). Additional product remained in the filtrate.

$^1$H NMR (300 MHz, DMSO-$d_6$) δ 9.16 (s, 1H). m/z=180 (M–H)$^-$.

Example 13

Preparation of 3-(4-nitro-3-(trifluoromethyl)-1H-pyrazol-1-yl)cyclobutan-1-one 122

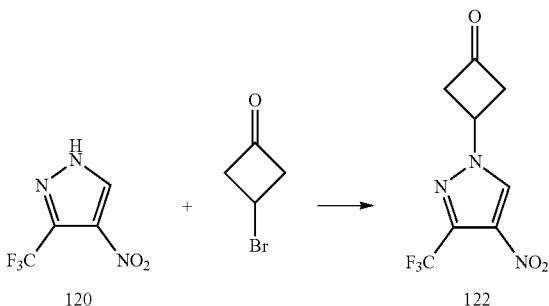 [SMILES: O=[N+]([O-])c1c[nH]nc1C(F)(F)F ; O=C1CC(Br)C1 ; O=C1CC(n2cc([N+](=O)[O-])c(C(F)(F)F)n2)C1]

Compound 120 (1.2356 g, 6.82 mmol) was dried in the tared reaction flask and weighed. This was taken up in 22 mL tetrahydrofuran, and a magnetic stir bar was added. 3-Bromocyclobutan-1-one (1.3837 g, 9.29 mmol) was weighed into a tared vial and added to the reaction in 11 mL tetrahydrofuran solution. Potassium carbonate (1.417 g, 10.25 mmol) was weighed out and added, and the reaction was stirred overnight at room temperature.

The reaction was next recharged with 3-bromocyclobutan-1-one (1.232 g, 8.27 mmol) in 5 mL tetrahydrofuran and stirred overnight at room temperature. The mixture was then concentrated to remove THF, and partitioned between ethyl acetate and water. The aqueous was extracted three times more with ethyl acetate and the combined organic layer was washed with brine and dried over sodium sulfate. This was filtered and concentrated and it spontaneously crystallized. The solid was collected, washed with a minimal volume of dichloromethane and dried on high vacuum to give 677.2 mg of the title compound 122. A second crop isolated after crystallizing from the filtrate gave 432.2 mg more product 122 (65% yield). A 1D NOE experiment confirmed the N1 assignment of the pyrazole alkylation. $^1$H NMR (300 MHz, DMSO-$d_6$) δ 9.44 (s, 1H), 5.34 (p, J=6.9 Hz, 1H), 3.67 (d, J=6.7 Hz, 4H). Parent ion not observed.

Example 14

Preparation of (1s,3s)-3-(4-nitro-3-(trifluoromethyl)-1H-pyrazol-1-yl)cyclobutan-1-ol 124

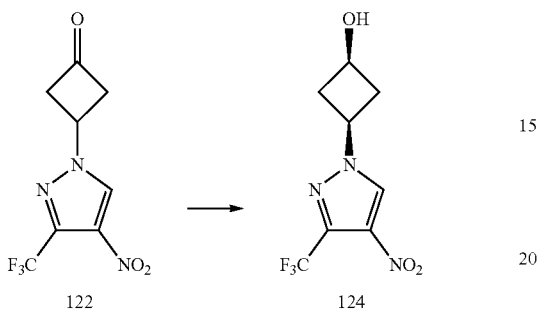

Compound 122 (601.0 mg, 2.41 mmol) was dried in the tared reaction flask and weighed. This was dissolved in 12 mL methanol, a magnetic stir bar was added, and the solution was cooled to 0° C. Sodium borohydride (137.9 mg, 3.64 mmol) was weighed out and added. The reaction was stirred 2 hours at room temperature. After HPLC showed completion, this was concentrated onto silica and purified by column chromatography. After drying, 536.2 mg was obtained of the title compound 124 (88% yield).

$^1$H NMR (300 MHz, DMSO-$d_6$) δ 9.23 (s, 1H), 5.38 (d, J=6.7 Hz, 1H), 4.63-4.46 (m, 1H), 4.06-3.89 (m, 1H), 2.83-2.70 (m, 2H), 2.42-2.29 (m, 2H). m/z=252 (M+H)$^+$.

Example 15

Preparation of 1-((1s,3s)-3-ethoxycyclobutyl)-4-nitro-3-(trifluoromethyl)-1H-pyrazole 126

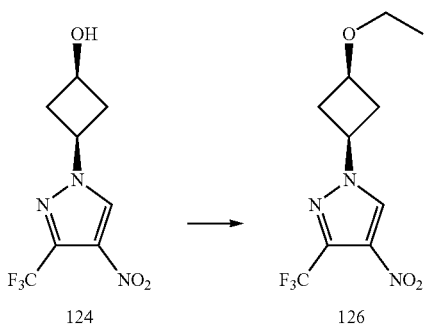 [SMILES: O=[N+]([O-])c1cn([C@H]2C[C@@H](O)C2)nc1C(F)(F)F ; CCO[C@H]1C[C@@H](n2cc([N+](=O)[O-])c(C(F)(F)F)n2)C1]

Compound 124 (189.6 mg, 0.76 mmol) was transferred to a reaction tube with magnetic stir bar in 5 mL dichloromethane. Silver triflate (586.2 mg, 2.28 mmol) was weighed out and added, and 2,6-di-t-butylpyridine was added (0.58 mL, 2.62 mmol). The reaction was cooled to 0° C. and ethyl iodide was added (0.20 mL, 2.50 mmol). The cooling bath was then removed, and it was stirred overnight at room temperature. This reaction was combined with another (46.0 mg, 0.18 mmol) run under the same conditions and filtered through Celite with dichloromethane washings. The filtrate was concentrated onto silica and purified by column chromatography. After drying, 172.8 mg was obtained of the pure title compound 126 (66% yield).

$^1$H NMR (300 MHz, Chloroform-d) δ 8.33 (s, 1H), 4.46 (tt, J=9.0, 7.5 Hz, 1H), 3.90 (tt, J=7.5, 6.4 Hz, 1H), 3.47 (q, J=7.0 Hz, 2H), 3.03-2.91 (m, 2H), 2.57-2.44 (m, 2H), 1.23 (t, J=7.0 Hz, 3H). m/z=280 (M+H)$^+$.

Example 16

Preparation of 1-((1s,3s)-3-ethoxycyclobutyl)-3-(trifluoromethyl)-1H-pyrazol-4-amine 128

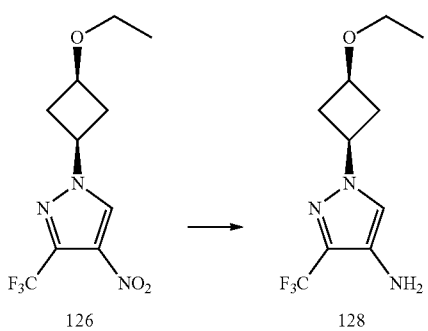 [SMILES: CCO[C@H]1C[C@@H](n2cc([N+](=O)[O-])c(C(F)(F)F)n2)C1 ; CCO[C@H]1C[C@@H](n2cc(N)c(C(F)(F)F)n2)C1]

Compound 126 (231.4 mg, 0.83 mmol) was added to a Parr reaction bottle in 30 mL ethyl acetate. This was put under nitrogen and charged with (wet) 10% Pd on carbon (90.1 mg, 0.04 mmol). This was run at 50 psi hydrogen for 5 hours on the Parr hydrogenator. The reaction was filtered through Celite with methanol washings and concentrated to dryness. HPLC showed a complex mixture. 110.6 mg of this residue was dissolved in 10 mL methanol. NiCl$_2$.x hydrate (400.1 mg, 1.68 mmol as the hexahydrate) was weighed out and added, and the mixture was cooled to 0° C. Sodium borohydride (127.4 mg, 3.4 mmol) was weighed out and added slowly, portionwise. The reaction was allowed to stir overnight, warming to room temperature. This was filtered through Celite with methanol washings, concentrated onto silica and purified by column chromatography. After drying, 76.2 mg was obtained of the title compound as an oil. (The remainder of the residue recovered from the hydrogenation was reduced using similar conditions and an additional 46.1 mg of the title compound 128 was obtained—59% yield).

$^1$H NMR (300 MHz, Chloroform-d) δ 7.17 (s, 1H), 4.31 (tt, J=9.1, 7.5 Hz, 1H), 3.82 (tt, J=7.6, 6.5 Hz, 1H), 3.44 (q, J=7.0 Hz, 2H), 2.93-2.80 (m, 2H), 2.45-2.32 (m, 2H), 1.22 (t, J=7.0 Hz, 3H). m/z=250 (M+H)$^+$.

Example 17

Preparation of 2-bromo-N-(1-((1s,3s)-3-ethoxycyclobutyl)-3-(trifluoromethyl)-1H-pyrazol-4-yl)thiazole-4-carboxamide 130

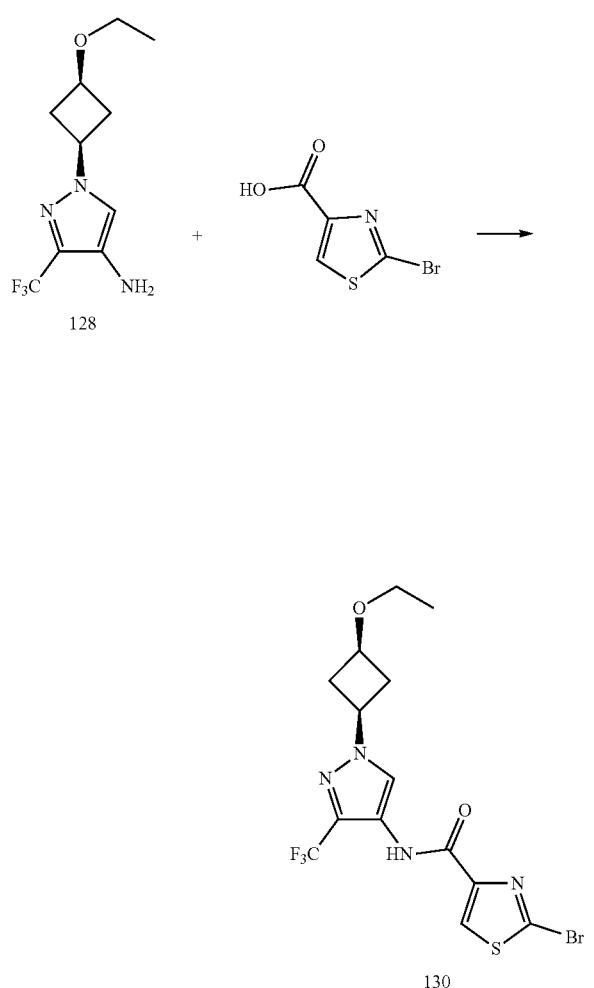

Example 18

Preparation of II-62: N-(1-((1s,3s)-3-ethoxycyclobutyl)-3-(trifluoromethyl)-1H-pyrazol-4-yl)-2-(1H-pyrazol-4-yl)thiazole-4-carboxamide

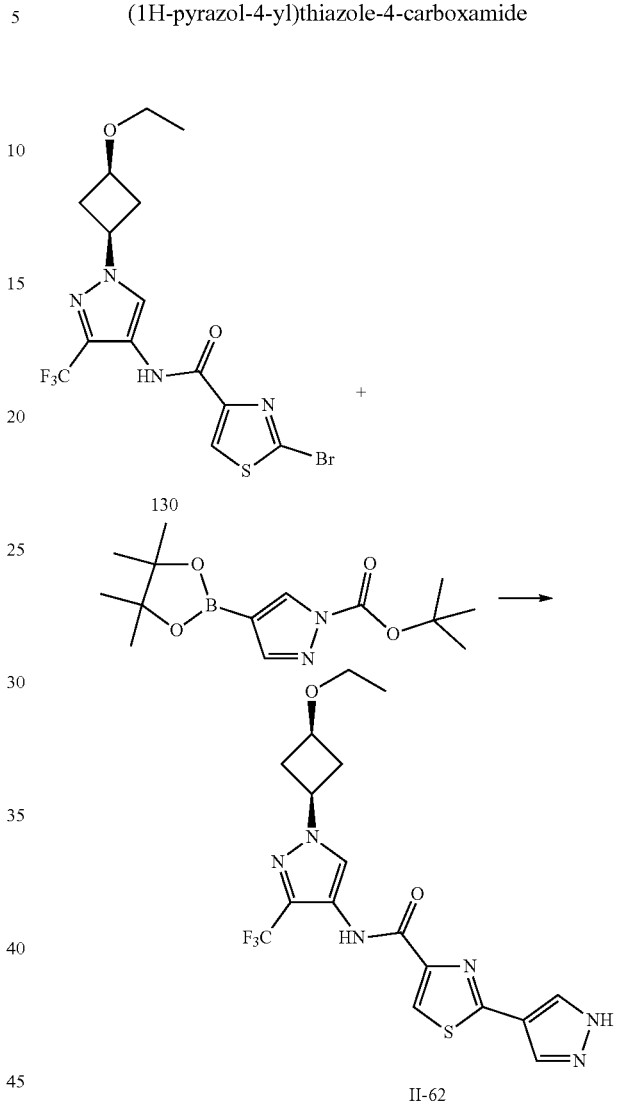

2-Bromothiazole-4-carboxylic acid (61.4 mg, 0.30 mmol) was weighed out and added to a flask with a magnetic stir bar and taken up in 12 mL dichloromethane. Diisopropylethylamine (0.077 mL, 0.44 mmol) was added followed by HATU (145.4 mg, 0.38 mmol) and the reaction was stirred at room temperature for 45 minutes. Compound 128 (73 mg, 0.29 mmol) was added in 5 mL dichloromethane solution and the reaction was stirred overnight at room temperature. This was concentrated directly onto silica and purified by column chromatography. Concentrating, then drying the pure fractions on high vacuum afforded 71.0 mg of the title compound 130 (55% yield).

$^1$H NMR (300 MHz, Chloroform-d) δ 9.12 (s, 1H), 8.40 (s, 1H), 8.13 (s, 1H), 4.52-4.32 (m, 1H), 3.86 (tt, J=7.6, 6.5 Hz, 1H), 3.46 (q, J=7.0 Hz, 2H), 2.91 (dddd, J=9.3, 7.5, 6.5, 2.9 Hz, 2H), 2.52 (qdd, J=9.9, 5.2, 2.6 Hz, 2H), 1.23 (t, J=7.0 Hz, 3H). m/z=439/441 (M+H)$^+$ (bromine isotopes).

Compound 130 (67.7 mg, 0.15 mmol) was transferred to a microwave reaction tube with magnetic stir bar in solution (4.2 mL dimethoxyethane and 3.0 mL ethanol). 1-Boc-pyrazole-4-boronic acid pinacol ester (290.6 mg, 1.0 mmol) was weighed out and added. Sodium carbonate (109.0 mg, 1.0 mmol) was weighed into a tared vial, dissolved in 1.0 mL water, and added to the reaction. The solution was subjected to vigorous sub-surface nitrogen sparge. Pd[P(Ph)$_3$]$_2$Cl$_2$ (18.4 mg, 0.03 mmol) was weighed out and added and the tube was sealed under nitrogen. This was heated 30 minutes at 100° C. in the microwave. The solution was partitioned between ethyl acetate and saturated aqueous sodium bicarbonate. The aqueous layer was extracted three more times with ethyl acetate and the combined organic layer was washed with brine and dried over sodium sulfate. This was filtered, concentrated and subjected to column chromatography. The purest fractions were concentrated to give a solid which was triturated with acetonitrile and dried on high vacuum to give 8.0 mg of the title compound II-62. (Additional less pure material was recovered.)

$^1$H NMR (300 MHz, Chloroform-d) δ 9.44 (s, 1H), 8.45 (s, 1H), 8.12 (s, 2H), 8.08 (s, 1H), 4.43 (ddd, J=16.6, 9.3, 7.5 Hz, 1H), 3.87 (tt, J=7.7, 6.4 Hz, 1H), 3.47 (q, J=7.0 Hz, 2H), 2.92 (dddd, J=9.3, 7.5, 6.5, 3.3 Hz, 2H), 2.54 (tdd, J=9.3, 7.7, 2.9 Hz, 2H), 1.23 (t, J=7.0 Hz, 3H). m/z=427 (M+H)$^+$.

Example 19

Preparation of 2-bromo-N-(1-methyl-3-(trifluoromethyl)-1H-pyrazol-4-yl)thiazole-4-carboxamide 132

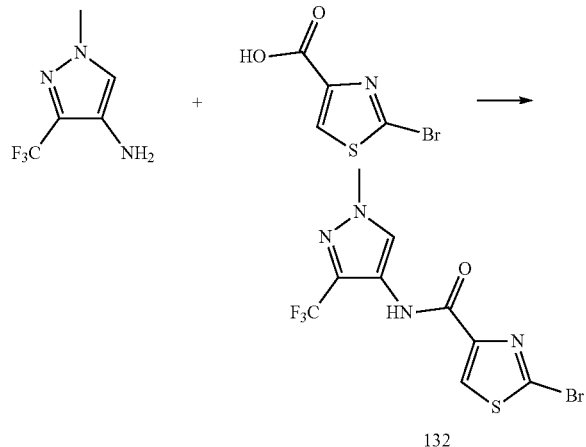

Bromothiazole-4-carboxylic acid (416.2 mg, 2.00 mmol) was weighed out and added to a flask with a magnetic stir bar and taken up in 40 mL dichloromethane. Diisopropylethylamine (0.52 mL, 3.0 mmol) was added followed by HATU (990.4 mg, 2.60 mmol) and the reaction was stirred at room temperature for 45 minutes. 1-methyl-3-(trifluoromethyl)-1H-pyrazol-4-amine (329.4 mg, 2.00 mmol) was added in 10 mL dichloromethane solution and the reaction was stirred overnight at room temperature. This was concentrated directly onto silica and purified by column chromatography. After drying, 471.6 mg was obtained of the title compound 132 (66% yield-additional less pure material was recovered).

$^1$H NMR (300 MHz, Chloroform-d) ι 9.12 (s, 1H), 8.29 (s, 1H), 8.13 (s, 1H), 3.96 (s, 3H). m/z=355/357 (M+H)$^+$ (bromine isotopes).

Example 20

Preparation of II-63: N-(1-methyl-3-(trifluoromethyl)-1H-pyrazol-4-yl)-2-(1H-pyrazol-4-yl)thiazole-4-carboxamide trifluoroacetate Salt

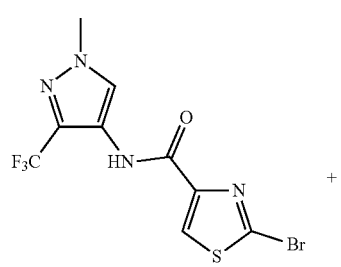

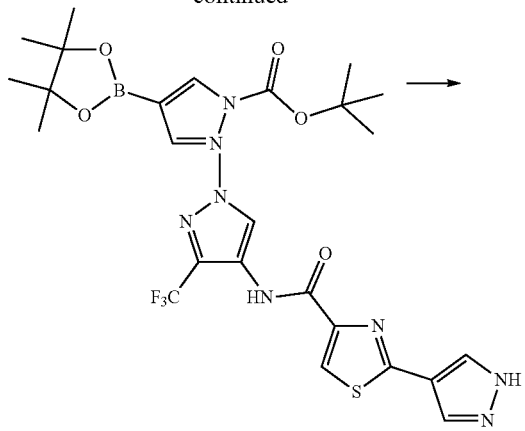

Compound 132 (100.0 mg, 0.28 mmol) and 1-Boc-pyrazole-4-boronic acid pinacol ester (531.4 mg, 1.80 mmol) were weighed out and added to a microwave reaction tube with magnetic stir bar. 7.7 mL dimethoxyethane and 5.5 mL ethanol were added. Sodium carbonate (200.2 mg, 1.89 mmol) was weighed into a tared vial, dissolved in 2.0 mL water, and added to the reaction. The solution was subjected to vigorous sub-surface nitrogen sparge. Pd[P(Ph)$_3$]$_2$Cl$_2$ (34.4 mg, 0.05 mmol) was weighed out and added and the tube was sealed under nitrogen. This was heated 30 minutes at 100° C. in the microwave. This was concentrated to remove dimethoxyethane and ethanol and extracted four times with ethyl acetate. The combined organic layer was washed with brine, dried over sodium sulfate, filtered and concentrated. This was purified by preparative HPLC to give compound II-64. After drying, 54.3 mg was obtained of the title compound II-63 as a trifluoroacetic acid salt.

$^1$H NMR (300 MHz, DMSO-d$_6$) δ 9.61 (s, 1H), 8.32 (s, 1H), 8.25 (s, 2H), 3.95 (s, 3H). m/z=343 (M+H)$^+$.

Example 21

Preparation of (1s,3s)-3-(4-amino-3-(3-fluoropyridin-2-yl)-1H-pyrazol-1-yl)cyclobutan-1-ol 134

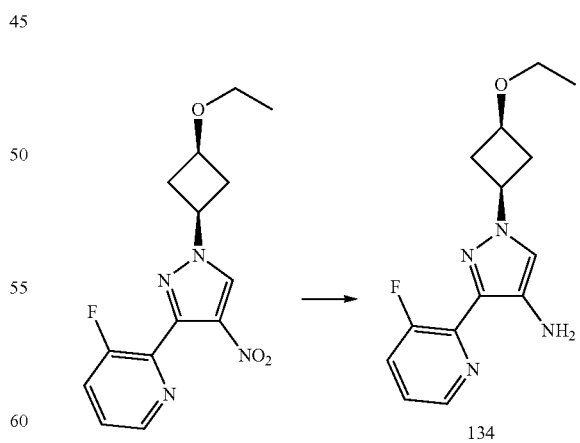

(1s,3s)-3-(3-(3-fluoropyridin-2-yl)-4-nitro-1H-pyrazol-1-yl)cyclobutan-1-ol (1.070 g, 3.85 mmol) was weighed out and added to a flask with magnetic stir bar, and dissolved in 98 mL ethyl acetate. This was put under nitrogen and charged with (wet) 10% Pd on carbon (117.8 mg, 0.014 mmol). After thoroughly purging with nitrogen, this was stirred for 3 hours under a balloon of hydrogen. The reaction was then filtered through Celite with excess ethyl acetate washings. The filtrate was concentrated and dried to give quantitative recovery of the title compound 134 as a foam. This was used in the next reaction without further purification.

$^1$H NMR (300 MHz, DMSO-d$_6$) δ 8.47-8.31 (m, 1H), 7.79-7.62 (m, 1H), 7.35-7.22 (m, 2H), 5.26 (d, J=6.6 Hz, 1H), 4.94 (s, 2H), 4.34-4.18 (m, 1H), 3.93 (td, J=7.4, 6.0 Hz, 1H), 2.71 (dtd, J=8.7, 7.1, 3.0 Hz, 2H), 2.27 (qd, J=8.7, 2.9 Hz, 2H). m/z=249 (M+H)$^+$.

Example 22

Preparation of 2-bromo-N-(3-(3-fluoropyridin-2-yl)-1-((1s,3s)-3-hydroxycyclobutyl)-1H-pyrazol-4-yl)thiazole-4-carboxamide 136

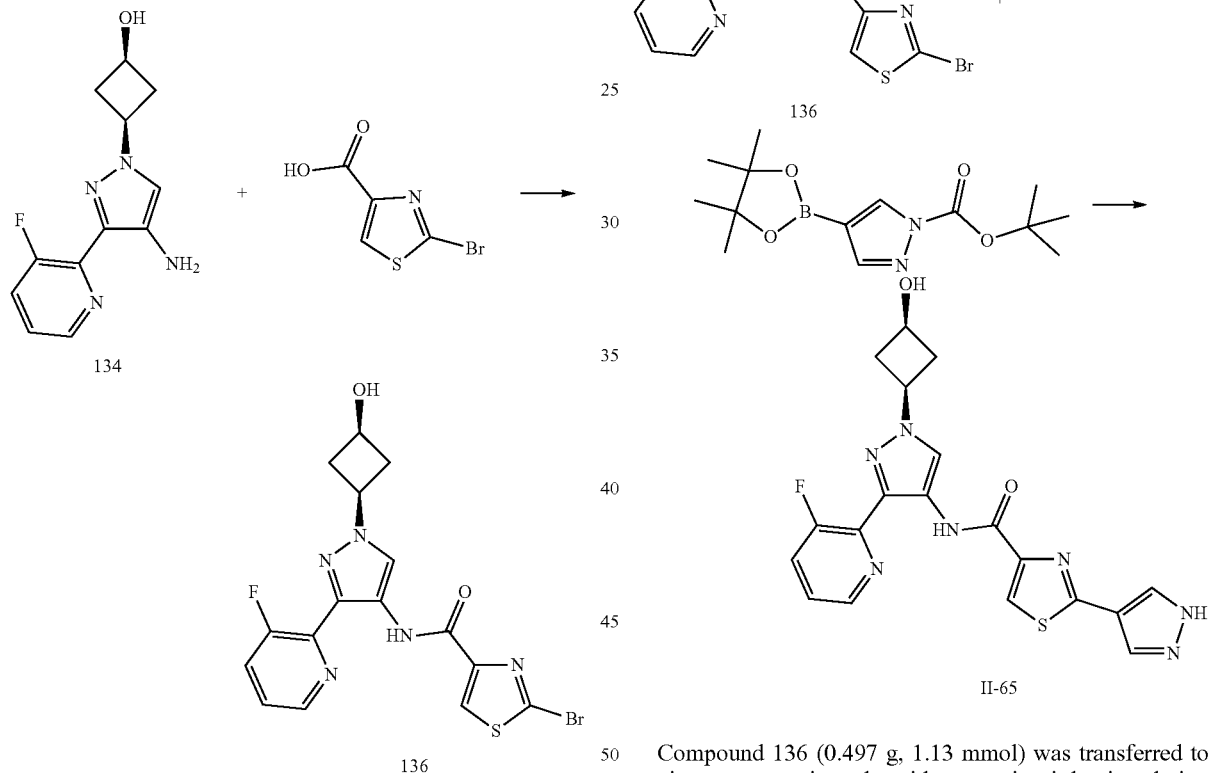

Compound 134 (0.96 g, 3.85 mmol) was dried in the tared reaction flask and weighed. This was dissolved in 30 mL dichloromethane, and 10 mL dimethylformamide was added along with a magnetic stir bar.

2-Bromothiazole-4-carboxylic acid (800.6 mg, 3.85 mmol) was weighed out and added. Diisopropylethylamine (1.0 mL, 5.7 mmol) was added followed by HATU (1.901 g, 5.00 mmol) and the reaction was stirred at room temperature overnight. This was concentrated directly onto silica and purified by column chromatography. Concentrating, then drying the pure fractions on high vacuum afforded 1.158 g of the title compound 136 (69% yield). $^1$H NMR (300 MHz, DMSO-d$_6$) δ 12.14 (s, 1H), 8.57-8.48 (m, 2H), 8.44 (s, 1H), 7.91 (ddd, J=11.5, 8.4, 1.3 Hz, 1H), 7.52 (ddd, J=8.4, 4.6, 3.8 Hz, 1H), 5.34 (d, J=6.9 Hz, 1H), 4.52 (tt, J=9.1, 7.3 Hz, 1H), 4.05-3.91 (m, 1H), 2.86-2.72 (m, 2H), 2.39 (qd, J=8.6, 2.8 Hz, 2H). m/z=438/440 (M+H)$^+$ (bromine isotopes).

Example 23

Preparation of II-65: N-(3-(3-fluoropyridin-2-yl)-1-((1s,3s)-3-hydroxycyclobutyl)-1H-pyrazol-4-yl)-2-(1H-pyrazol-4-yl)thiazole-4-carboxamide

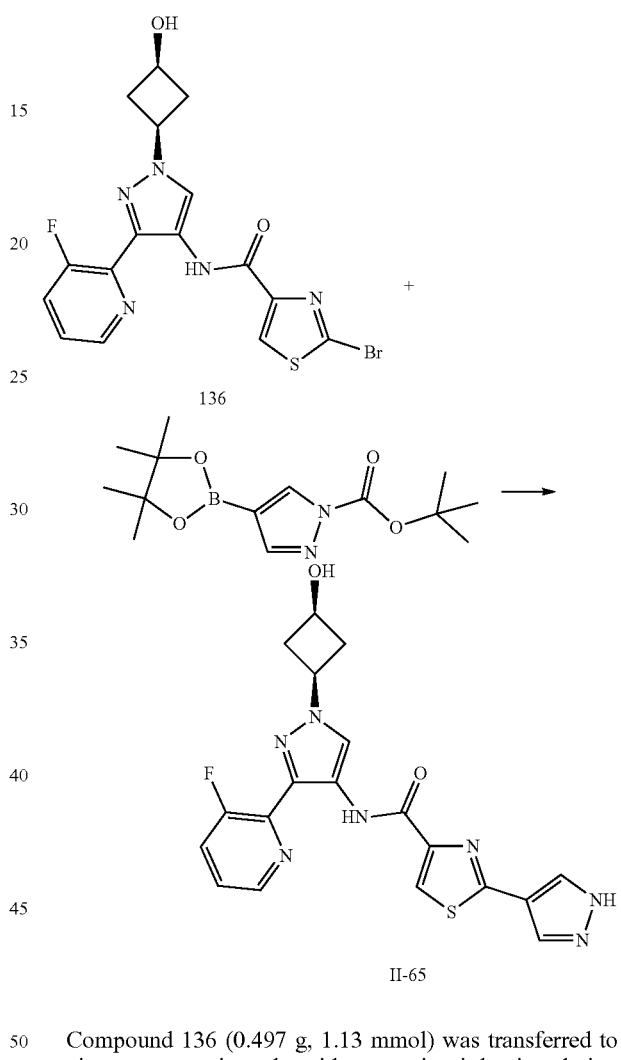

Compound 136 (0.497 g, 1.13 mmol) was transferred to a microwave reaction tube with magnetic stir bar in solution (13 mL dimethoxyethane and 5.5 mL ethanol). 1-Boc-pyrazole-4-boronic acid pinacol ester (1.334 g, 4.53 mmol) was weighed out and added. Sodium carbonate (0.480 g, 4.53 mmol) was weighed into a tared vial, dissolved in 4.5 mL water, and added to the reaction. The solution was subjected to vigorous sub-surface nitrogen sparge. Pd[P(Ph)$_3$]$_2$Cl$_2$ (79.6 mg, 0.11 mmol) was weighed out and added and the tube was sealed under nitrogen. This was heated 90 minutes at 100° C. in the microwave. This was concentrated to remove dimethoxyethane and ethanol and extracted four times with ethyl acetate. However, there was substantial undissolved solid. This was collected and washed repeatedly with methanol. After drying, this gave 174.0 mg of the title compound at 90% purity.

The combined organic layer from the extraction was washed with brine, dried over sodium sulfate, filtered, and combined with the methanol washings of the precipitated solid. The solution was concentrated onto silica and purified by column chromatography. Concentration of pure fractions gave a solid which was triturated with minimal dichloromethane. After drying, 169.2 mg was obtained of the pure title compound II-65. $^1$H NMR (300 MHz, DMSO-d$_6$) δ 13.43 (s, 1H), 12.09 (s, 1H), 8.66 (dt, J=4.6, 1.4 Hz, 1H), 8.57 (s, 1H), 8.50 (s, 1H), 8.30 (s, 1H), 8.11 (s, 1H), 7.91 (ddd, J=11.5, 8.4, 1.3 Hz, 1H), 7.54 (ddd, J=8.4, 4.6, 3.8 Hz, 1H), 5.34 (d, J=6.9 Hz, 1H), 4.61-4.42 (m, 1H), 3.98 (h, J=7.4 Hz, 1H), 2.80 (dtd, J=9.6, 6.9, 2.8 Hz, 2H), 2.47-2.33 (m, 2H). m/z=426 (M+H)$^+$.

Example 24

Preparation of 2-(4-nitro-1-(1,4-dioxaspiro[4.5]decan-8-yl)-1H-pyrazol-3-yl)pyridine 138

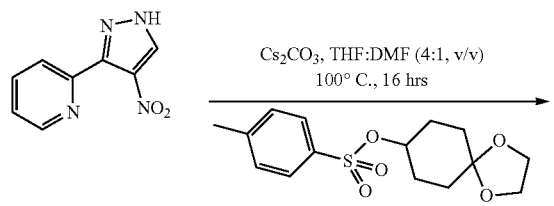

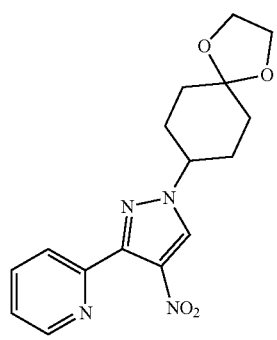

138

A stirring suspension of 2-(4-nitro-1H-pyrazol-3-yl)pyridine (950 mg, 5.00 mmol), 1,4-dioxaspiro[4.5]decan-8-yl 4-methylbenzenesulfonate (1.69 g, 5.41 mmol) and Cs$_2$CO$_3$ (2.44 g, 7.50 mmol) in anhydrous THF:DMF (15 mL, 4:1, v/v) was heated to 100° C. and stirred for 16 hours. The reaction mixture was diluted in water (50 mL), extracted with EtOAc (3×50 mL), the organic layer was washed with brine (50 mL), dried over MgSO$_4$, concentrated and column chromatography (0-100% EtOAc in hexane, gradient) gave compound 138 as a light brown semisolid (910 mg, 55.14%). MS (m/e): 330.34 (MH+).

Example 25

Preparation of 4-(4-nitro-3-(pyridin-2-yl)-1H-pyrazol-1-yl)cyclohexan-1-one 140

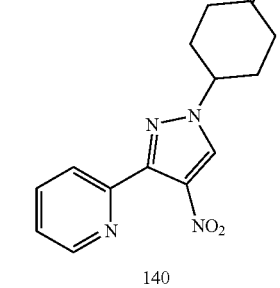

140

To a stirring solution of compound 138 (910 mg, 2.75 mmol) in acetone:H$_2$O (20 mL, 1:1, v/v) was added pyridinium p-tolulene sulfonate (1.38 g, 5.50 mmol) and the reaction mixture was heated to 80° C. and stirred for 16 hours. Acetone was evaporated in vacuo, the aqueous layer was quenched with NaOH to pH=8, extracted with EtOAc (3×50 mL), the organic layer was washed with brine (50 mL), dried over MgSO$_4$, concentrated and column chromatography (0-100% MeOH in DCM, gradient) gave compound 140 as a dark brown oil (600 mg, 76.08%). MS (m/e): 286.29 (MH+).

Example 26

Preparation of (trans)-4-(4-nitro-3-(pyridin-2-yl)-1H-pyrazol-1-yl)cyclohexan-1-ol 142

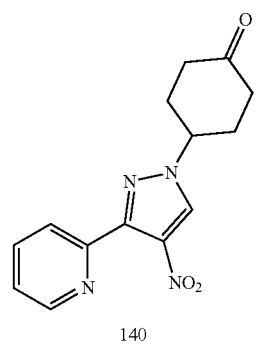

140

-continued

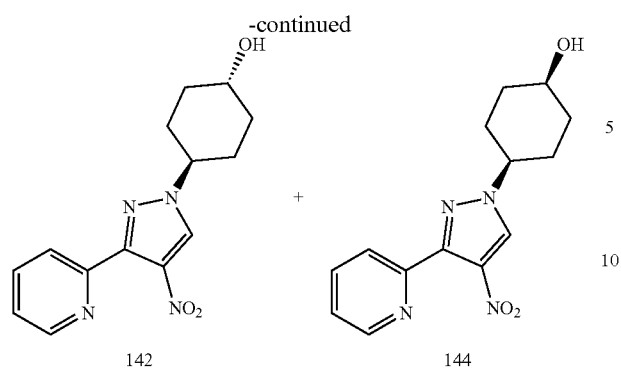

NaBH₄ (20 mg, 0.524 mmol) was added to a stirring solution of 2 (600 mg, 2.10 mmol) in MeOH (10 mL) at 0° C., stirred for 0.5 hours, concentrated and column chromatography (0-100% MeOH (1M NH₃ solution) in DCM, gradient) afforded the product 142 as a viscous oil (362 mg, 60%).

¹H NMR (300 MHz, Chloroform-d) δ 8.77 (d, J=4.8 Hz, 1H), 8.29 (s, 1H), 7.84 (m, 2H), 7.36 (m, 1H), 4.24 (m, 1H), 3.76 (m, 1H), 3.46 (s, 1H), 2.14 (m, 8H). LCMS: purity: 87.43%. MS (m/e): 288.31 (MH+).

Example 27

Preparation of 2-(1-((trans)-4-ethoxycyclohexyl)-4-nitro-1H-pyrazol-3-yl)pyridine 146

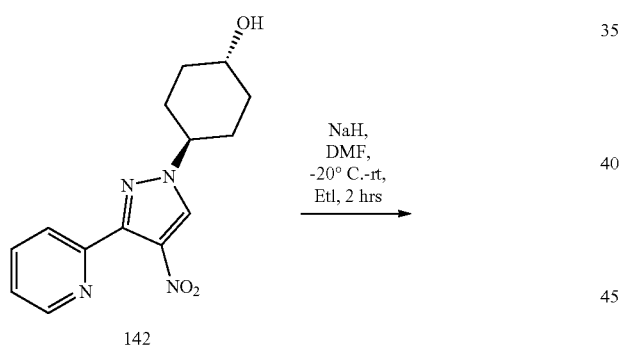

NaH (60% dispersion in mineral oil, 60 mg, 1.50 mmol) was added to a stirring solution of compound 142 (360 mg, 1.25 mmol) and iodoethane (200 µL, 2.50 mmol) in anhydrous DMF (8 mL) at −20° C. The reaction mixture was allowed to warm to room temperature for 2 hours. The reaction mixture was diluted in water (40 mL), extracted with EtOAc (3×50 mL), the organic layer was washed with brine (30 mL), dried over MgSO₄, concentrated, and column chromatography (0-100% EtOAc in hexane, gradient) afforded the product 146 as viscous oil (296 mg, 74.93%). MS (m/e): 316.36 (MH+).

Example 28

Preparation of 1-((trans)-4-ethoxycyclohexyl)-3-(pyridin-2-yl)-1H-pyrazol-4-amine 148

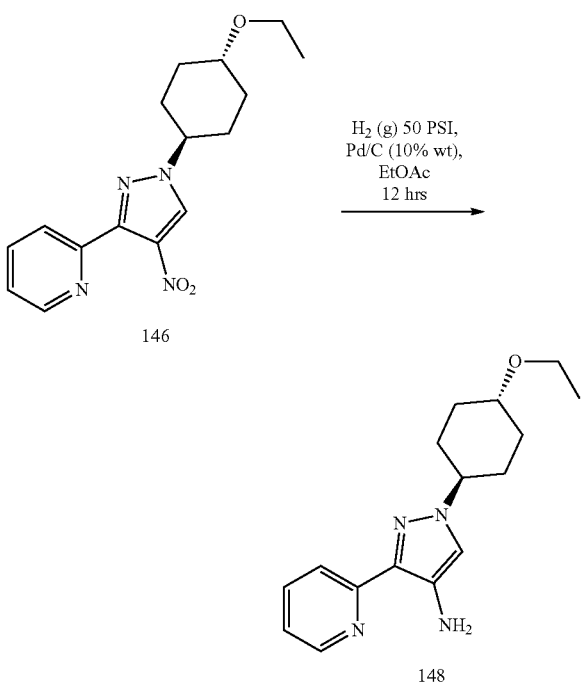

A solution of compound 146 (290 g, 0.917 mmol) in EtOAc (10 mL) with Pd/C (10% wt, 50 mg) was hydrogenated under 50 psi H₂ (g) for 12 hours, filtered through celite and concentrated to give compound 148 as a viscous oil (230 mg, 87.61%). MS (m/e): 286.38 (MH+).

Example 29

Preparation of 2-bromo-N-(1-((trans)-4-ethoxycyclohexyl)-3-(pyridin-2-yl)-1H-pyrazol-4-yl)thiazole-4-carboxamide 150

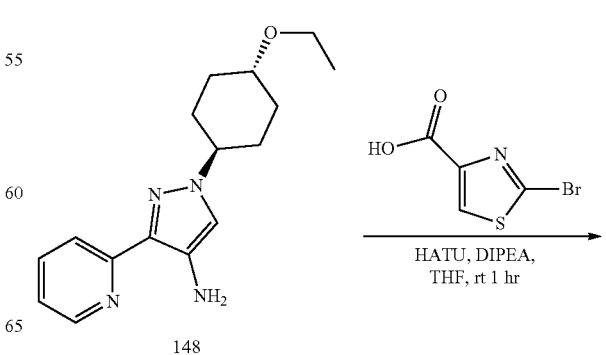

177
-continued

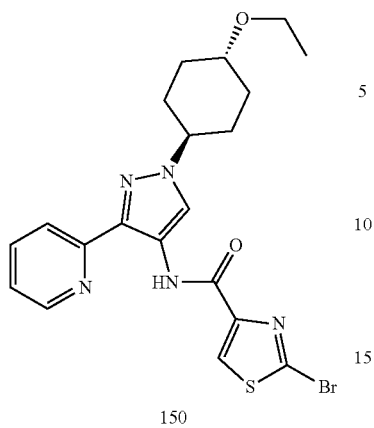

150

HATU (458 mg, 1.20 mmol) was added to a stirring solution of 2-bromothiazole-4-carboxylic acid (184 mg, 0.883 mmol) and DIPEA (280 μL, 1.61 mmol) in anhydrous THF (4 mL) at room temperature for 10 minutes, followed by addition of a solution of compound 148 (230 mg, 0.803 mmol) in anhydrous THF (4 mL). After 1 hour, the reaction mixture was diluted in water (10 mL), extracted with EtOAc (3×20 mL), the organic layer was washed with brine (20 mL), dried over MgSO$_4$, concentrated, and column chromatography (0-100% EtOAc in hexane, gradient) afforded the product 150 as a semisolid, which was used without further purification. Assumed quantitative yield. MS (m/e): 476.39 (MH+).

Example 30

Preparation of II-145: N-(1-(((trans)-4-ethoxycyclohexyl)-3-(pyridin-2-yl)-1H-pyrazol-4-yl)-2-(1H-pyrazol-4-yl)thiazole-4-carboxamide

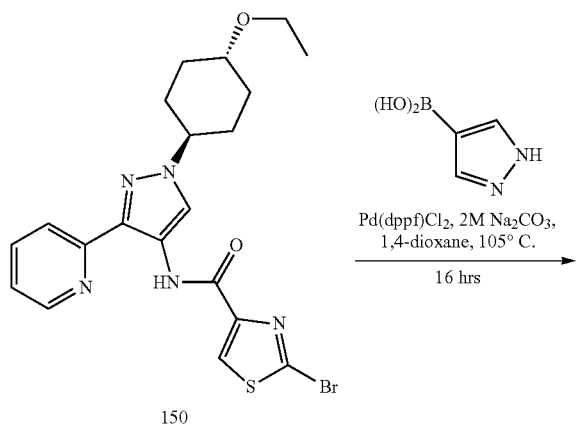

178
-continued

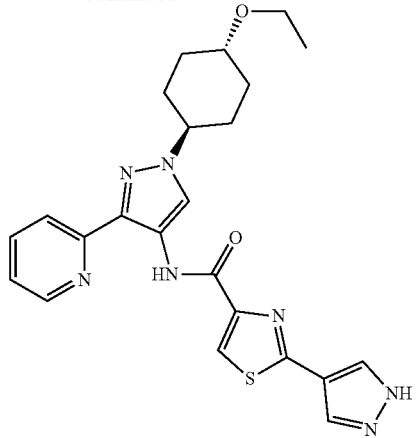

II-145

A mixture of crude compound 150 (0.803 mmol), 1H-pyrazole-4-boronic acid (180 mg, 1.61 mmol), Pd(dppf)Cl$_2$ (65.6 mg, 0.080 mmol), 2 M Na$_2$CO$_3$ (1.61 mL, 3.21 mmol) and anhydrous 1,4-dioxane (10 mL) was heated at 105° C. and stirred for 16 hours. The reaction mixture was cooled to room temperature, diluted in water (20 mL), extracted with EtOAc (3×30 mL), the organic layer was washed with brine (20 mL), dried over MgSO$_4$, concentrated, and column chromatography (0-100% EtOAc in hexane, gradient) gave a semisolid, which was submitted for analytical purification, followed by lyophilization to afford the title compound II-145 as a white fluffy solid (75 mg, 20.15%).

$^1$H NMR (300 MHz, DMSO-d$_6$) δ 13.40 (s, 1H), 12.18 (s, 1H), 8.74 (d, J=4.8 Hz, 1H), 8.49 (s, 1H), 8.35 (s, 1H), 8.27 (s, 1H), 8.10 (s, 1H), 7.97 (m, 2H), 7.39 (t, J=6.9 Hz, 1H), 4.29 (t, J=11.7 Hz, 1H), 3.47 (td, J=7.1, 5.8 Hz, 2H), 3.35 (t, J=11.7 Hz, 1H), 2.09 (d, J=11.6 Hz, 4H), 1.87 (q, J=11.8 Hz, 2H), 1.35 (q, J=11.2 Hz, 2H), 1.10 (t, J=6.9 Hz, 3H). LCMS: purity: 100%. MS (m/e): 463.56 (MH+).

The following exemplary compounds were prepared using the methods of Examples 1-23. Characterization data for these additional compounds are provided below.

I-5: N-(1-(2-methoxyethyl)-3-(pyridin-2-yl)-1H-pyrazol-4-yl)-5-(1H-pyrazol-4-yl)furan-2-carboxamide

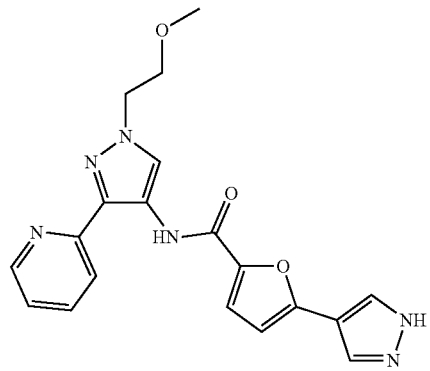 [SMILES: COCCn1cc(NC(=O)c2ccc(-c3cn[nH]c3)o2)c(-c2ccccn2)n1]

¹H NMR (DMSO d₆, 300 MHz): δ 11.66 (s, 1H), 8.75-8.73 (m, 1H), 8.38 (s, 1H), 8.12-7.92 (m, 4H), 7.45-7.41 (m, 1H), 7.29-7.27 (m, 1H), 6.79-6.78 (m, 1H), 4.37 (t, J=6.7 Hz, 2H), 3.75 (t, J=6.7 Hz, 2H), 3.27 (s, 3H); LCMS (m/z): 379.52 (MH⁺).

I-6: N-(1-(2-methoxyethyl)-3-(pyridin-2-yl)-1H-pyrazol-4-yl)-5-(3-methyl-1H-pyrazol-4-yl)furan-2-carboxamide Formic Acid

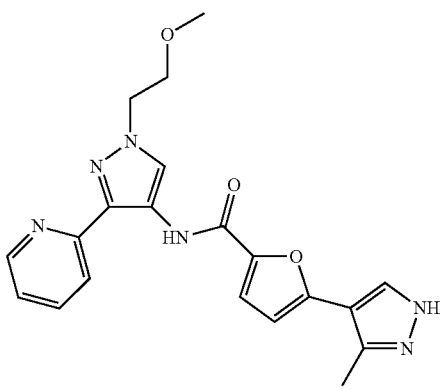 [SMILES: COCCn1cc(NC(=O)c2ccc(-c3c[nH]nc3C)o2)c(-c2ccccn2)n1]

LCMS (m/z): 393.49 (MH⁺).

I-7: N-(1-(2-methoxyethyl)-3-(pyrimidin-2-yl)-1H-pyrazol-4-yl)-5-(1H-pyrazol-4-yl)furan-2-carboxamide

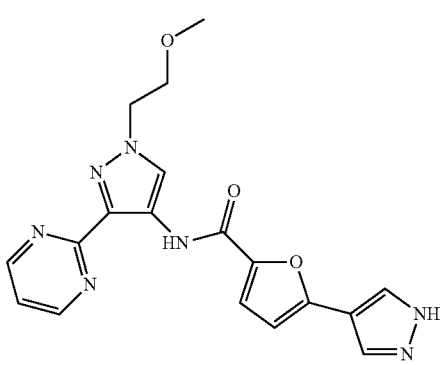 [SMILES: COCCn1cc(NC(=O)c2ccc(-c3cn[nH]c3)o2)c(-c2ncccn2)n1]

LCMS (m/z): 380.54 (MH⁺).

I-8: N-(1-(2-methoxyethyl)-3-(pyrimidin-2-yl)-1H-pyrazol-4-yl)-5-(3-methyl-1H-pyrazol-4-yl)furan-2-carboxamide

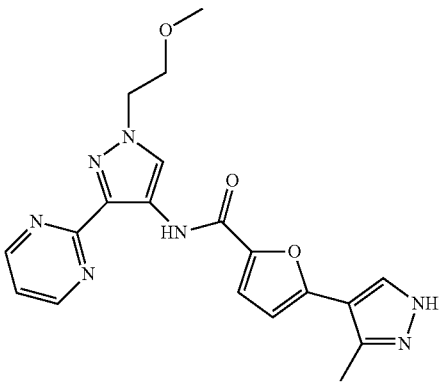 [SMILES: COCCn1cc(NC(=O)c2ccc(-c3c[nH]nc3C)o2)c(-c2ncccn2)n1]

¹H NMR (DMSO d₆, 300 MHz): δ 11.09 (s, 1H), 8.93 (d, J=3.3 Hz, 2H), 8.46 (s, 1H), 7.49 (t, J=6.7 Hz, 1H), 7.33 (d, J=3.3 Hz, 1H), 6.70 (d, J=3.3 Hz, 1H), 4.40 (t, J=6.7 Hz, 2H), 3.76 (t, J=6.7 Hz, 2H), 3.27 (s, 3H), 2.50 (s, 3H); LCMS (m/z): 394.45 (MH⁺).

I-9: N-(1-(2-methoxyethyl)-3-(pyridin-2-yl)-1H-pyrazol-4-yl)-5-(3-methyl-1H-pyrazol-4-yl)furan-2-carboxamide

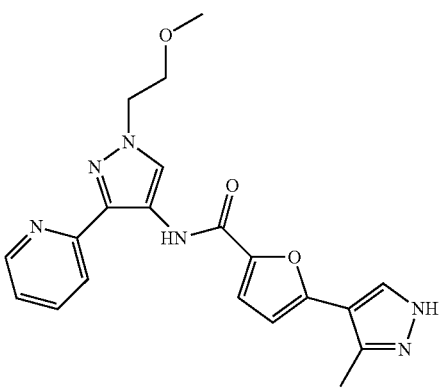 [SMILES: COCCn1cc(NC(=O)c2ccc(-c3c[nH]nc3C)o2)c(-c2ccccn2)n1]

¹H NMR (DMSO d₆, 300 MHz): δ 11.43 (s, 1H), 8.67-8.64 (m, 1H), 8.41 (s, 1H), 8.05-7.91 (m, 3H), 7.43-7.29 (m, 1H), 7.30 (d, J=3.3 Hz, 1H), 6.69 (d, J=3.3 Hz, 1H), 4.37 (t, J=6.7 Hz, 2H), 3.75 (t, J=6.7 Hz, 2H), 3.27 (s, 3H), 2.53 (s, 3H); LCMS (m/z): 393.53 (MH⁺).

I-10: di-tert-butyl ((4-(5-((1-(2-methoxyethyl)-3-(pyridin-2-yl)-1H-pyrazol-4-yl)carbamoyl)furan-2-yl)-1H-pyrazol-1-yl)methyl)phosphate

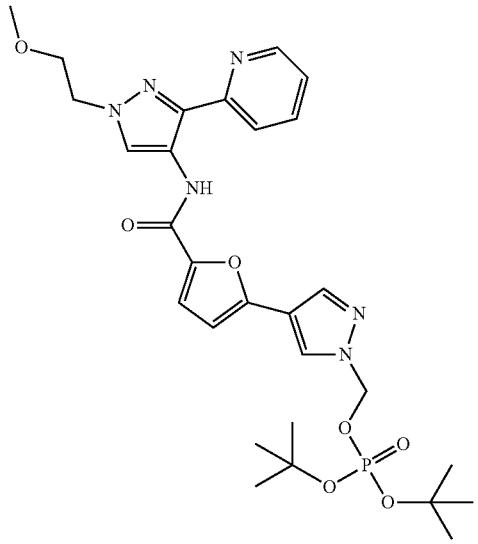 [SMILES: COCCn1cc(NC(=O)c2ccc(-c3cnn(COP(=O)(OC(C)(C)C)OC(C)(C)C)c3)o2)c(-c2ccccn2)n1]

¹H NMR (CDCl₃, 300 MHz): δ 11.86 (s, 1H), 8.77-8.75 (m, 1H), 8.41 (s, 1H), 8.12-8.07 (m, 2H), 7.98 (s, 1H), 7.80-7.74 (m, 1H), 7.23 (d, J=6.7 Hz, 1H), 6.52 (d, J=3.3 Hz, 1H), 5.94 (d, J=13.3 Hz, 2H), 4.34 (t, J=6.7 Hz, 2H), 3.83 (t, J=6.7 Hz, 2H), 3.37 (s, 3H), 1.44 (s, 18H); LCMS (m/z): 601.70 (MH⁺).

I-11: tert-butyl ((4-(5-((1-(2-methoxyethyl)-3-(pyridin-2-yl)-1H-pyrazol-4-yl)carbamoyl)furan-2-yl)-1H-pyrazol-1-yl)methyl) hydrogen phosphate

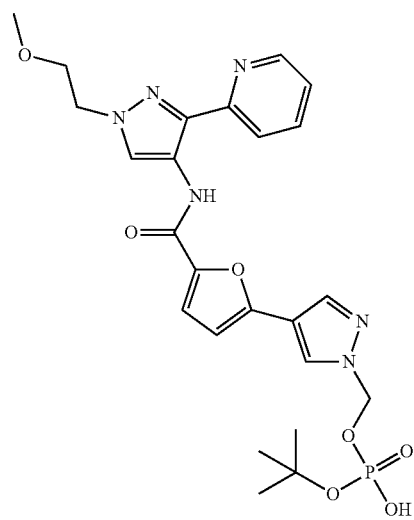 [SMILES: COCCn1cc(NC(=O)c2ccc(-c3cnn(COP(=O)(O)OC(C)(C)C)c3)o2)c(-c2ccccn2)n1]

¹H NMR (CDCl₃, 300 MHz): δ 11.61 (s, 1H), 8.51-8.49 (m, 1H), 8.26 (s, 1H), 8.00-7.93 (m, 2H), 7.77 (s, 1H), 7.66-7.58 (m, 2H), 7.14-7.10 (m, 1H), 7.03 (d, J=3.3 Hz, 1H), 6.37 (d, J=3.3 Hz, 1H), 5.79-5.70 (m, 2H), 4.26 (t, J=6.7 Hz, 2H), 3.78 (t, J=6.7 Hz, 2H), 3.34 (s, 3H), 1.27 (s, 9H); LCMS (m/z): 545.74 (MH⁺).

I-12: (4-(5-((1-(2-methoxyethyl)-3-(pyridin-2-yl)-1H-pyrazol-4-yl)carbamoyl)furan-2-yl)-1H-pyrazol-1-yl)methyl dihydrogen phosphate

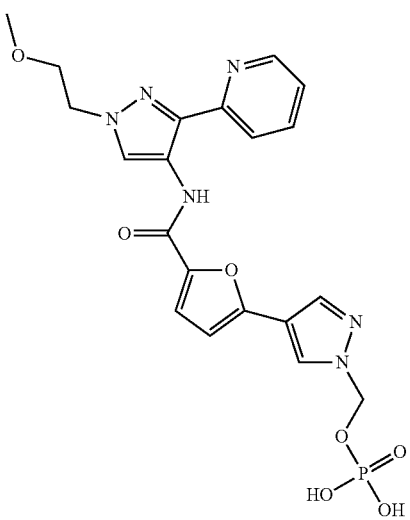 [SMILES: COCCn1cc(NC(=O)c2ccc(-c3cnn(COP(=O)(O)O)c3)o2)c(-c2ccccn2)n1]

¹H NMR (DMSO d₆, 300 MHz): δ 11.71 (s, 1H), 8.86-8.84 (m, 1H), 8.38-8.37 (m, 2H), 8.06-7.92 (m, 3H), 7.43-7.39 (m, 1H), 7.30 (d, J=3.3 Hz, 1H), 6.88 (d, J=3.3 Hz, 1H) 5.92 (d, J=10.0 Hz, 2H), 4.38 (t, J=6.7 Hz, 2H), 3.75 (t, J=6.7 Hz, 2H), 3.27 (s, 3H); LCMS (m/z): 489.51 (MH⁺).

I-13: N-(1-(2-methoxyethyl)-3-(pyridin-2-yl)-1H-pyrazol-4-yl)-5-(3-(trifluoromethyl)-1H-pyrazol-4-yl)furan-2-carboxamide

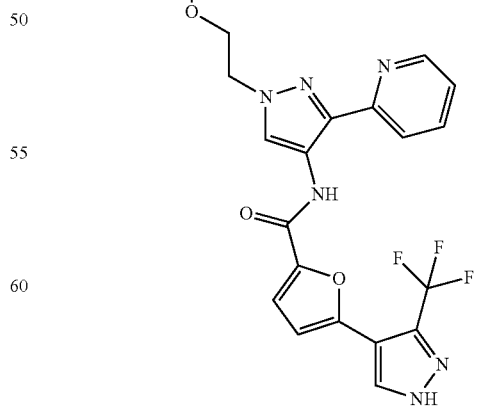

LCMS (m/z): 447.67 (MH⁺).

I-14: sodium (4-(5-((1-(2-methoxyethyl)-3-(pyridin-2-yl)-1H-pyrazol-4-yl)carbamoyl)furan-2-yl)-1H-pyrazol-1-yl)methyl phosphate

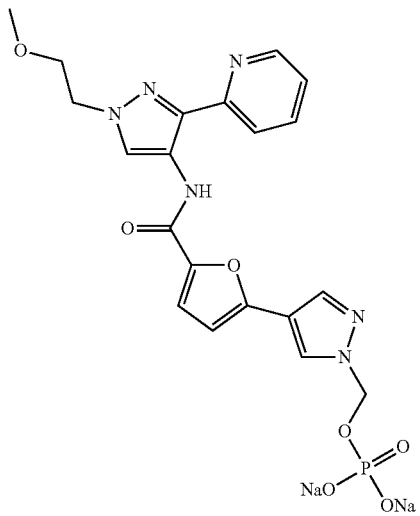

$^1$H NMR (D$_2$O, 300 MHz): δ 7.90-7.86 (m, 2H), 7.48 (s, 1H), 7.45 (t, J=10.0 Hz, 1H), 7.28-7.23 (m, 2H), 6.96-6.92 (m, 1H), 6.65 (d, J=3.3 Hz, 1H), 6.23 (d, J=3.3 Hz, 1H)), 5.64 (d, J=3.3 Hz, 2H), 4.02 (t, J=6.7 Hz, 2H), 3.75 (t, J=6.7 Hz, 2H), 3.35 (s, 3H); LCMS (m/z): 489.24 (MH$^+$).

I-15: N-(1-(2-hydroxyethyl)-3-(pyrimidin-2-yl)-1H-pyrazol-4-yl)-5-(1H-pyrazol-4-yl)furan-2-carboxamide

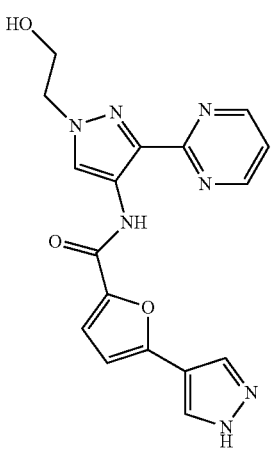 [SMILES: O=C(Nc1cn(CCO)nc1-c1ncccn1)c1ccc(-c2cn[nH]c2)o1]

$^1$H NMR (DMSO d$_6$, 300 MHz): δ 11.31 (s, 1H), 8.98 (d, J=3.3 Hz, 2H), 8.43 (s, 1H), 7.50 (t, J=6.7 Hz, 1H), 7.31 (d, J=3.3 Hz, 1H), 6.79 (d, J=6.7 Hz, 1H), 4.98 (t, J=6.7 Hz, 1H), 4.27 (t, J=6.7 Hz, 2H), 3.84-3.78 (m, 1H); LCMS (m/z): 366.55 (MH$^+$).

I-16: N-(1-(2-(2-methoxyethoxy)ethyl)-3-(pyridin-2-yl)-1H-pyrazol-4-yl)-5-(1H-pyrazol-4-yl)furan-2-carboxamide

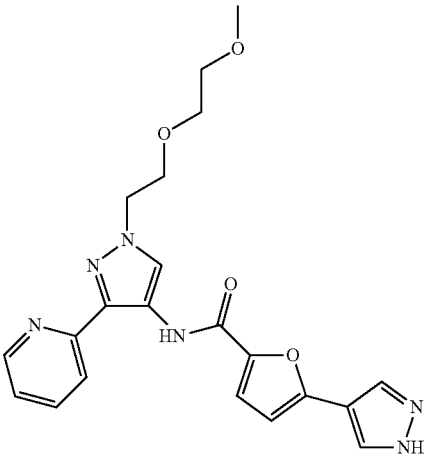 [SMILES: COCCOCCn1cc(NC(=O)c2ccc(-c3cn[nH]c3)o2)c(-c2ccccn2)n1]

LCMS (m/z): 423.60 (MH$^+$).

I-17: N-(1-(2-(2-methoxyethoxy)ethyl)-3-(pyridin-2-yl)-1H-pyrazol-4-yl)-5-(1H-pyrazol-4-yl)furan-2-carboxamide hydrochloride Salt

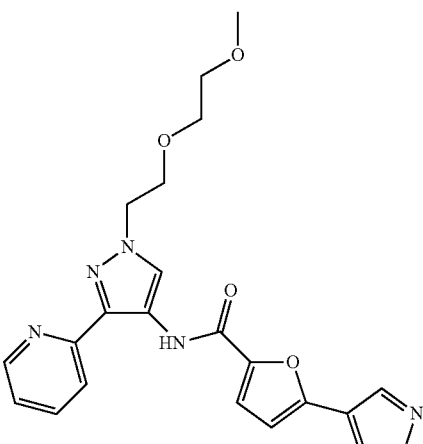

$^1$H NMR (DMSO d$_6$, 300 MHz): δ 11.65 (s, 1H), 8.75-8.73 (m, 1H), 8.40 (s, 1H), 8.12 (s, 2H), 8.04-7.93 (m, 2H), 7.29 (d, J=3.3 Hz, 1H), 6.79 (d, J=6.7 Hz, 1H), 4.37 (t, J=6.7 Hz, 1H), 3.84 (t, J=6.7 Hz, 2H), 3.56-3.53 (m, 2H), 3.44-3.41 (m, 2H), 3.22 (s, 3H); LCMS (m/z): 423.62 (MH$^+$).

I-18: N-(1-(2-(2-methoxyethoxy)ethyl)-3-(pyridin-2-yl)-1H-pyrazol-4-yl)-5-(3-methyl-1H-pyrazol-4-yl)furan-2-carboxamide I-20: tert-butyl (S)-(1-(4-(5-((1-(2-methoxyethyl)-3-(pyridin-2-yl)-1H-pyrazol-4-yl)carbamoyl)furan-2-yl)-1H-pyrazol-1-yl)-3-methyl-1-oxobutan-2-yl)carbamate

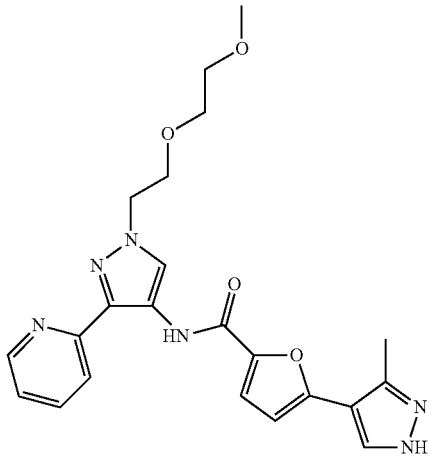 [SMILES: COCCOCCn1cc(NC(=O)c2ccc(-c3c[nH]nc3C)o2)c(-c2ccccn2)n1]

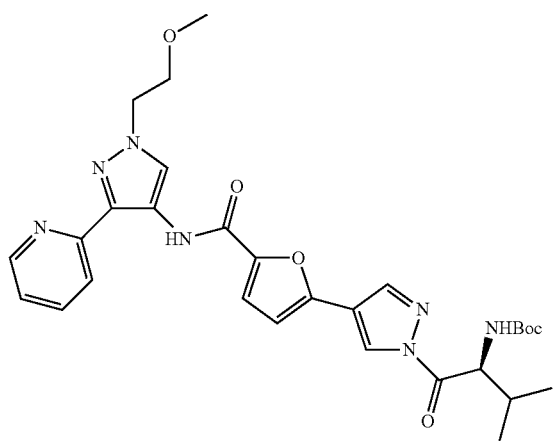

¹H NMR (DMSO d₆, 300 MHz): δ 11.40 (s, 1H), 8.63-8.61 (m, 1H), 8.40 (s, 1H), 8.02-7.89 (m, 3H), 7.40-7.36 (m, 1H), 7.27 (d, J=3.3 Hz, 1H), 6.66 (d, J=3.3 Hz, 1H), 4.34 (t, J=6.7 Hz, 1H), 3.81 (t, J=6.7 Hz, 2H), 3.53-3.50 (m, 2H), 3.41-3.37 (m, 2H), 3.18 (s, 3H), 2.47 (s, 3H); LCMS (m/z): 437.66 (MH⁺).

¹H NMR (DMSO d₆, 300 MHz): δ 11.71 (s, 1H), 8.92 (s, 1H), 8.76-8.74 (m, 1H), 8.40 (s, 2H), 8.05-7.93 (m, 2H), 7.50-7.41 (m, 2H), 7.36 (d, J=3.3 Hz, 1H), 7.12 (d, J=3.3 Hz, 1H), 5.25-5.20 (m, 1H), 4.38 (t, J=6.7 Hz, 1H), 3.76 (t, J=6.7 Hz, 2H), 3.27 (s, 3H), 1.84 (s, 1H), 1.39 (s, 9H), 0.93 (s, J=6.7 Hz, 6H); LCMS (m/z): 578.76 (MH⁺).

I-19: 1-(isobutyryloxy)ethyl 4-(5-((1-(2-methoxy-ethyl)-3-(pyridin-2-yl)-1H-pyrazol-4-yl)carbamoyl)furan-2-yl)-1H-pyrazole-1-carboxylate I-21: 1-methylcyclopropyl 4-(5-((1-(2-methoxy-ethyl)-3-(pyridin-2-yl)-1H-pyrazol-4-yl)carbamoyl)furan-2-yl)-1H-pyrazole-1-carboxylate

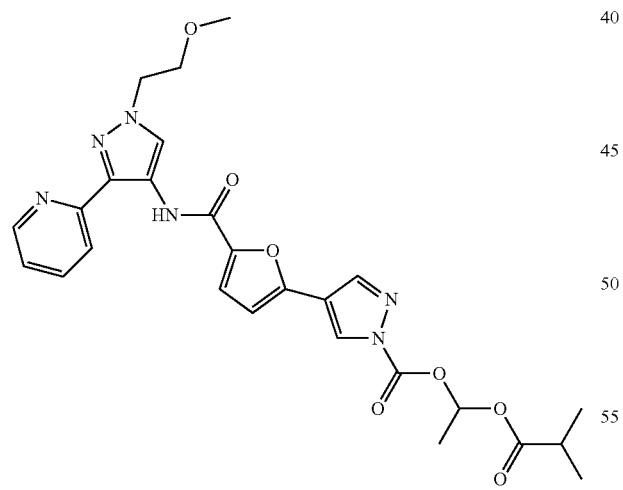

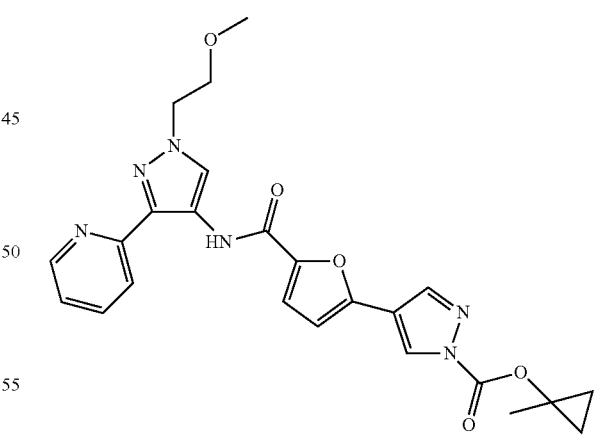

¹H NMR (DMSO d₆, 300 MHz): δ 11.72 (s, 1H), 8.80 (s, 1H), 8.75-8.73 (m, 1H), 8.38 (d, J=3.3 Hz, 2H), 8.05-7.94 (m, 2H), 7.44-7.40 (m, 1H), 7.34 (d, J=3.3 Hz, 1H), 7.10 (d, J=3.3 Hz, 1H), 7.05-7.00 (m, 1H), 4.38 (t, J=6.7 Hz, 1H), 3.76 (t, J=6.7 Hz, 2H), 3.27 (s, 3H), 2.63 (s, J=3.3 Hz, 1H), 1.66 (d, J=6.7 Hz, 3H), 1.11 (d, J=6.7 Hz, 6H); LCMS (m/z): 537.68 (MH⁺).

¹H NMR (DMSO d₆, 300 MHz): δ 11.71 (s, 1H), 8.75-8.72 (m, 2H), 8.39 (s, 1H), 8.31 (s, 1H), 8.05-7.94 (m, 2H), 7.45-7.41 (m, 1H), 7.33 (d, J=3.3 Hz, 1H), 7.06 (d, J=6.7 Hz, 1H), 4.38 (t, J=6.7 Hz, 1H), 3.76 (t, J=6.7 Hz, 2H), 3.27 (s, 3H), 1.69 (s, 3H), 1.16 (t, J=6.7 Hz, 1H), 0.86 (t, J=6.7 Hz, 2H); LCMS (m/z): 477.66 (MH⁺).

I-22: 1-((4-methoxybenzyl)oxy)-2-methylpropan-2-yl 4-(5-((1-(2-methoxyethyl)-3-(pyridin-2-yl)-1H-pyrazol-4-yl)carbamoyl)furan-2-yl)-1H-pyrazole-1-carboxylate

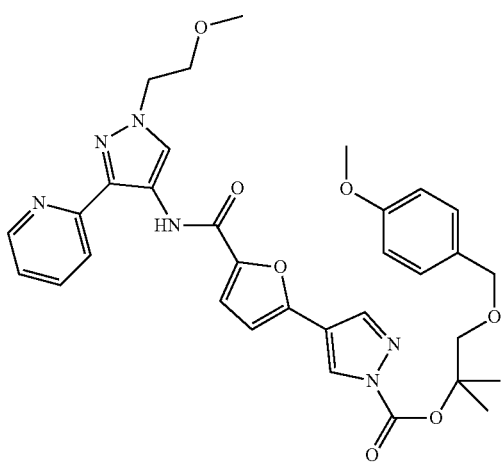 [SMILES: COCCn1cc(NC(=O)c2ccc(-c3cnn(C(=O)OC(C)(C)COCc4ccc(OC)cc4)c3)o2)c(-c2ccccn2)n1]

¹H NMR (DMSO d₆, 300 MHz): δ 11.73 (s, 1H), 8.71-8.70 (m, 1H), 8.64 (s, 1H), 8.39 (s, 1H), 8.30 (s, 1H), 8.04-7.92 (m, 2H), 7.40-7.33 (m, 1H), 7.21 (d, J=6.7 Hz, 1H), 7.07 (d, J=3.3 Hz, 1H), 6.83 (d, J=6.7 Hz, 1H), 4.47 (s, 2H), 4.38 (t, J=6.7 Hz, 1H), 3.75 (t, J=6.7 Hz, 2H), 3.67 (s, 3H), 3.27 (s, 3H), 1.61 (s, 6H); LCMS (m/z): 615.79 (MH⁺).

I-23: 5-(1H-pyrazol-4-yl)-N-(3-(pyridin-2-yl)-1-(tetrahydro-2H-pyran-4-yl)-1H-pyrazol-4-yl)furan-2-carboxamide

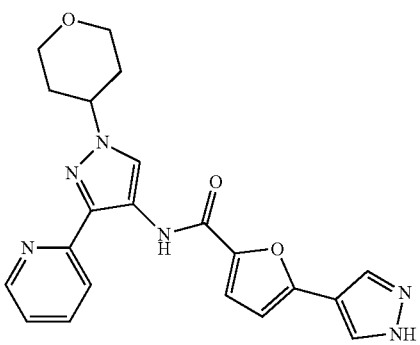 [SMILES: O=C(Nc1cn(C2CCOCC2)nc1-c1ccccn1)c1ccc(-c2cn[nH]c2)o1]

¹H NMR (DMSO d₆, 300 MHz): δ 13.27 (s, 1H), 11.67 (s, 1H), 8.75-8.73 (m, 1H), 8.42 (s, 1H), 8.26 (s, 1H), 8.06-7.95 (m, 3H), 7.45-7.43 (m, 1H), 7.28 (d, J=3.3 Hz, 1H), 6.79 (d, J=3.3 Hz, 1H), 4.53 (s, br, 1H), 4.02-3.98 (m, 2H), 3.53-3.45 (m, 2H), 2.04 (s, br, 4H); LCMS (m/z): 405.56 (MH⁺).

I-24: 5-(5-nitro-1H-pyrrol-3-yl)-N-(1-(propoxymethyl)-3-(pyridin-2-yl)-1H-pyrazol-4-yl)furan-2-carboxamide

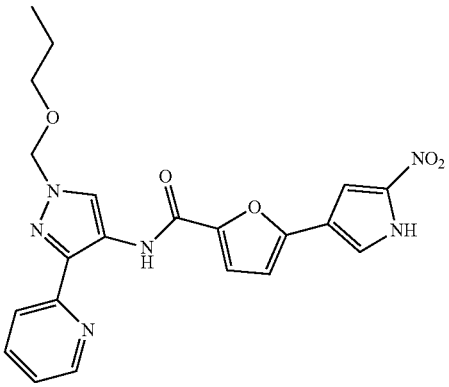 [SMILES: CCCOCn1cc(NC(=O)c2ccc(-c3c[nH]c([N+](=O)[O-])c3)o2)c(-c2ccccn2)n1]

LCMS (m/z): 437.54 (MH⁺).

I-25: N-(1-(oxetan-3-yl)-3-(pyridin-2-yl)-1H-pyrazol-4-yl)-5-(1H-pyrazol-4-yl)furan-2-carboxamide

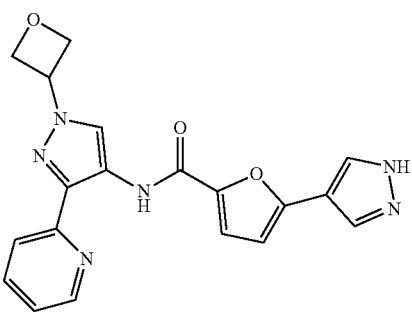 [SMILES: O=C(Nc1cn(C2COC2)nc1-c1ccccn1)c1ccc(-c2cn[nH]c2)o1]

1H NMR (300 MHz, DMSO-d6) δ 13.20 (br, 1H), 11.61 (s, 1H), 8.70 (d, J=6.6 Hz, 1H), 8.44 (s, 1H), 8.20 (s, 1H), 8.8.07 (d, J=9.0 Hz, 1H), 7.96-7.90 (m, 2H), 7.42-7.38 (m, 1H), 7.23 (d, J=3.6 Hz, 1H), 6.72 (d, J=3.6 Hz, 1H), 5.66 (p, J=6.6 Hz, 1H), 4.94-4.87 (m, 4H); LCMS: purity: 100%; MS (m/e): 377.47 (MH+).

I-26: 5-(1-methyl-1H-pyrazol-4-yl)-N-(1-(oxetan-3-yl)-3-(pyridin-2-yl)-1H-pyrazol-4-yl)furan-2-carboxamide

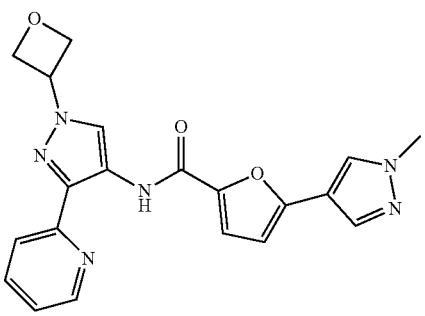 [SMILES: Cn1cc(-c2ccc(C(=O)Nc3cn(C4COC4)nc3-c3ccccn3)o2)cn1]

1H NMR (300 MHz, DMSO-d6) δ 11.64 (s, 1H), 8.76 (d, J=7.8 Hz, 1H), 8.48 (s, 1H), 8.18 (s, 1H), 8.11 (d, J=10.2 Hz, 1H), 7.97 (dt, J=7.5, 1.8 Hz, 1H), 7.89 (s, 1H), 7.45 (ddd, J=7.5, 4.8, 1.2 Hz, 1H), 7.28 (d, J=3.6 Hz, 1H), 6.75 (d, J=3.6 Hz, 1H), 5.71 (p, J=6.9 Hz, 1H), 4.97-4.94 (m, 4H), 3.94 (s, 3H); LCMS: purity: 100%; MS (m/e): 391.48 (MH+).

I-27: N-(1-((1,3-trans)-3-ethoxycyclobutyl)-3-(pyridin-2-yl)-1H-pyrazol-4-yl)-5-(1H-pyrazol-4-yl)furan-2-carboxamide

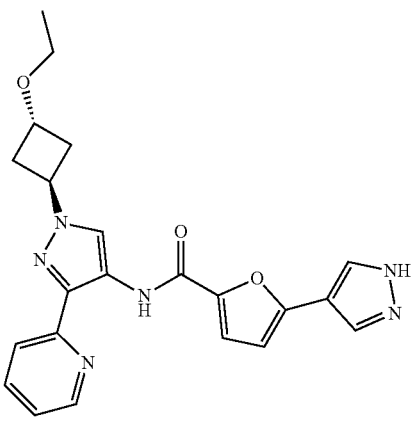 [SMILES: CCO[C@H]1C[C@H](n2cc(NC(=O)c3ccc(-c4cn[nH]c4)o3)c(-c3ccccn3)n2)C1]

1H NMR (300 MHz, DMSO-d6) δ 13.25 (s, 1H), 11.64 (s, 1H), 8.73 (d, J=4.8 Hz, 1H), 8.40 (s, 1H), 8.25 (s, 1H), 8.06 (d, J=7.8 Hz, 1H), 7.98-7.92 (m, 2H), 7.42 (m, 1H), 7.26 (d, J=3.6 Hz, 1H), 6.77 (d, J=3.9 Hz, 1H), 5.06 (p, J=6.0 Hz, 1H), 4.28 (m, 1H), 3.40 (q, J=6.9 Hz, 2H), 2.74-2.66 (m, 2H), 1.14 (t, J=6.9 Hz, 3H); LCMS: purity: 91.98%; MS (m/e): 419.60 (MH+).

I-29: N-(1-((1,3-cis)-3-ethoxycyclobutyl)-3-(pyridin-2-yl)-1H-pyrazol-4-yl)-5-(3-methyl-1H-pyrazol-4-yl)furan-2-carboxamide

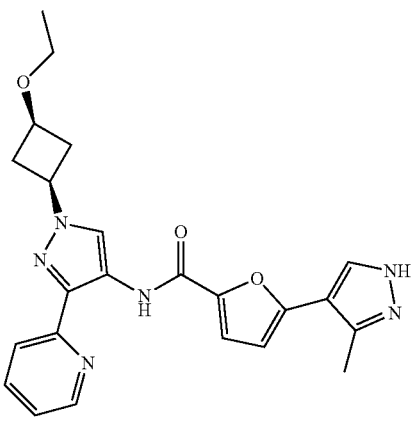 [SMILES: CCO[C@H]1C[C@@H](n2cc(NC(=O)c3ccc(-c4c[nH]nc4C)o3)c(-c3ccccn3)n2)C1]

1H NMR (300 MHz, DMSO-d6) δ 11.40 (s, 1H), 8.64 (d, J=4.8 Hz, 1H), 8.41 (s, 1H), 8.07 (d, J=7.8 Hz, 1H), 7.93 (m, 1H), 7.39 (m, 1H), 7.28 (d, J=3.6 Hz, 1H), 6.67 (d, J=3.6 Hz, 1H), 4.60 (p, J=6.9 Hz, 1H), 3.83 (p, J=7.5 Hz, 1H), 3.40 (q, J=6.9 Hz, 2H), 2.79 (m, 2H), 2.41 (m, 2H), 1.13 (t, J=7.2 Hz, 3H); LCMS: purity: 91.56%; MS (m/e): 433.52 (MH+).

I-30: 5-(3-methyl-1H-pyrazol-4-yl)-N-(1-(oxetan-3-yl)-3-(pyridin-2-yl)-1H-pyrazol-4-yl)furan-2-carboxamide

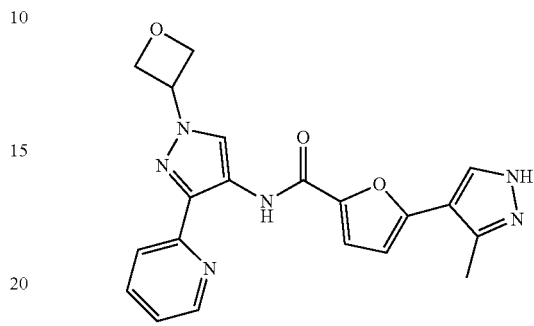

1H NMR (300 MHz, DMSO-d6) δ 12.99 (br, 1H), 11.43 (s, 1H), 8.67 (d, 1H), 8.51 (s, 1H), 8.12 (d, J=7.8 Hz, 1H), 7.97 (t, J=8.4 Hz, 1H), 7.85 (s, 1H), 7.43 (d, J=5.7 Hz, 1H), 7.30 (d, J=3.6 Hz, 1H), 6.67 (d, J=3.9 Hz, 1H), 5.70 (p, J=6.9 Hz, 1H), 4.96-4.92 (m, 4H), 2.54 (s, 3H); LCMS: purity: 88.90%; MS (m/e): 391.51 (MH+).

I-31: N-(1-((1,3-cis)-3-ethoxycyclobutyl)-3-(pyridin-2-yl)-1H-pyrazol-4-yl)-5-(1-methyl-1H-pyrazol-4-yl)furan-2-carboxamide

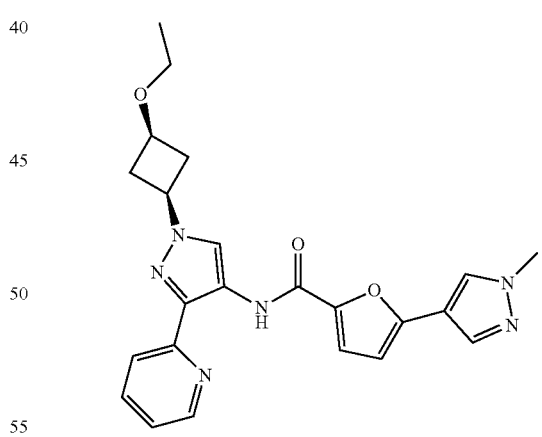

1H NMR (300 MHz, DMSO-d6) δ 11.62 (s, 1H), 8.74 (d, J=5.4 Hz, 1H), 8.39 (s, 1H), 8.18 (s, 1H), 8.06 (d, J=8.1 Hz, 1H), 7.94 (td, J=7.8, 1.8 Hz, 1H), 7.88 (s, 1H), 7.43 (ddd, J=7.5, 5.0, 1.3 Hz, 1H), 7.26 (d, J=3.6 Hz, 1H), 6.75 (d, J=3.6 Hz, 1H), 4.60 (p, J=8.4 Hz, 1H), 3.94 (s, 3H), 3.83 (p, J=6.6 Hz, 1H), 3.40 (q, J=6.9 Hz, 2H), 2.84-2.75 (m, 2H), 2.46-2.36 (m, 2H), 1.13 (t, J=6.9 Hz, 3H); LCMS: purity: 91.65%; MS (m/e): 433.57 (MH+).

I-32: N-(1-((1,3-cis)-3-hydroxycyclobutyl)-3-(pyridin-2-yl)-1H-pyrazol-4-yl)-5-(1H-pyrazol-4-yl)furan-2-carboxamide

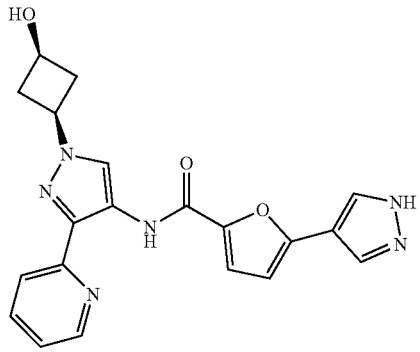 [SMILES: O=C(Nc1cn([C@H]2C[C@@H](O)C2)nc1-c1ccccn1)c1ccc(-c2cn[nH]c2)o1]

1H NMR (300 MHz, DMSO-d6) δ 13.23 (br, 1H), 11.64 (s, 1H), 8.72 (d, J=5.1 Hz, 1H), 8.41 (s, 1H), 8.25 (br, 1H), 8.04 (d, J=8.4 Hz, 1H), 7.98-7.92 (m, 2H), 7.40 (m, 1H), 7.27 (d, J=3.6 Hz, 1H), 6.77 (d, J=3.3 Hz, 1H), 5.31 (d, J=6.6 Hz, 1H), 4.42 (m, 1H), 3.96 (q, J=7.2 Hz, 1H), 2.79 (m, 2H), 2.40 (m, 2H); LCMS: purity: 92.77%; MS (m/e): 391.56 (MH+).

I-34: N-(1-((1,3-cis)-3-(dimethylamino)cyclobutyl)-3-(pyridin-2-yl)-1H-pyrazol-4-yl)-5-(1H-pyrazol-4-yl)furan-2-carboxamide

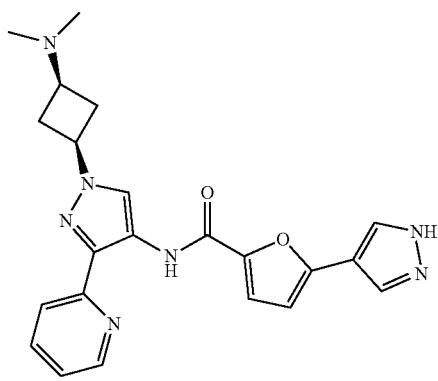 [SMILES: CN(C)[C@H]1C[C@@H](n2cc(NC(=O)c3ccc(-c4cn[nH]c4)o3)c(-c3ccccn3)n2)C1]

LCMS: purity: 94.57%; MS (m/e): 418.59 (MH+).

I-35: (4-(5-((1-((1,3-cis)-3-ethoxycyclobutyl)-3-(pyridin-2-yl)-1H-pyrazol-4-yl)carbamoyl)furan-2-yl)-1H-pyrazol-1-yl)methyl phosphate bis-sodium Salt

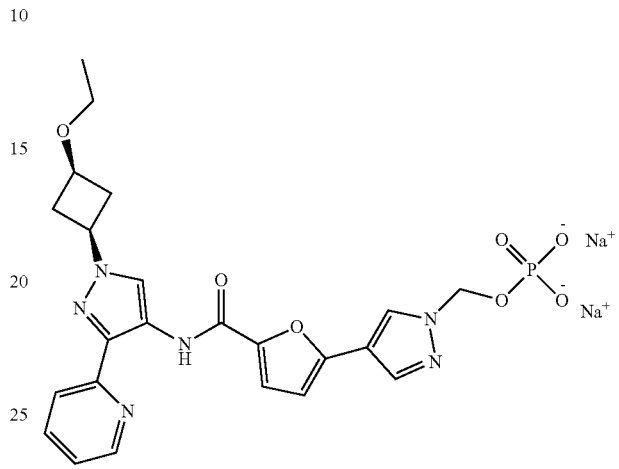

1H NMR (300 MHz, Deuterium Oxide) δ 7.77 (d, 1H), 7.50 (m, 3H), 7.16 (m, 2H), 6.94 (m, 1H), 6.50 (d, 1H), 6.03 (d, J=3.3 Hz, 1H), 5.50 (d, J=9.9 Hz, 2H), 4.07 (t, J=8.1 Hz, 1H), 3.86 (t, J=6.9 Hz, 1H), 3.44 (q, J=6.9 Hz, 2H), 2.73 (m, 2H), 2.10 (q, J=9.3 Hz, 2H), 1.10 (t, J=7.2 Hz, 3H); LCMS: purity: 98.27%; MS (m/e): 529.62 (MH+).

I-37: N-(1-(2-ethoxyethyl)-3-(pyridin-2-yl)-1H-pyrazol-4-yl)-5-(1H-pyrazol-4-yl)furan-2-carboxamide Formic Acid Salt

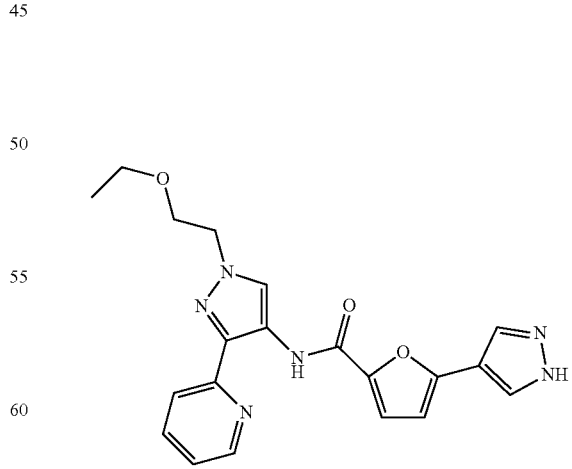

MS (ESI) (m/z): 393 [M+H]+

I-38: N-(1-(2-ethoxyethyl)-3-(pyridin-2-yl)-1H-pyrazol-4-yl)-5-(1H-pyrazol-4-yl)furan-2-carboxamide

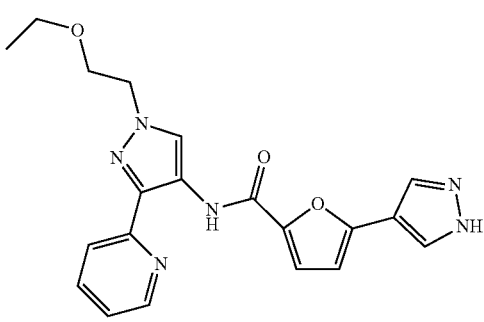 [SMILES: CCOCCn1cc(NC(=O)c2ccc(-c3cn[nH]c3)o2)c(-c2ccccn2)n1]

¹H NMR (300 MHz, DMSO-d₆) δ 11.65 (s, 1H), 8.74 (d, J=4.9 Hz, 1H), 8.39 (s, 1H), 8.11 (s, 2H), 8.02 (d, J=7.9 Hz, 1H), 7.94 (td, J=7.8, 1.8 Hz, 1H), 7.42 (t, J=6.1 Hz, 1H), 7.28 (d, J=3.6 Hz, 1H), 6.76 (d, J=3.6 Hz, 1H), 4.36 (t, J=5.3 Hz, 2H), 3.79 (t, J=5.3 Hz, 2H), 3.45 (q, J=7.1 Hz, 3H), 1.08 (t, J=7.0 Hz, 3H); MS (ESI) (m/z): 393 [M+H]⁺.

I-39: N-(1-(2-ethoxyethyl)-3-(pyridin-2-yl)-1H-pyrazol-4-yl)-5-(1H-pyrazol-4-yl)furan-2-carboxamide, Formic Acid Salt

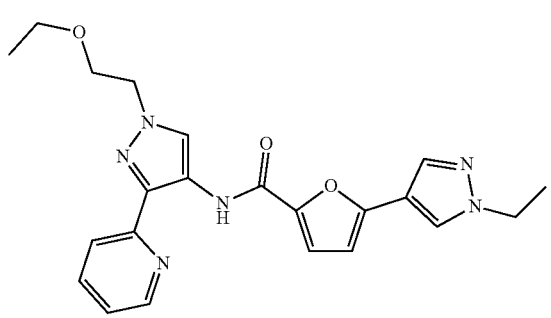 [SMILES: CCOCCn1cc(NC(=O)c2ccc(-c3cnn(CC)c3)o2)c(-c2ccccn2)n1]

¹H NMR (300 MHz, DMSO-d₆) δ 11.64 (s, 1H), 8.77-8.71 (m, 1H), 8.39 (s, 1H), 8.24 (d, J=0.7 Hz, 1H), 8.02 (dt, J=8.1, 1.2 Hz, 1H), 7.98-7.91 (m, 1H), 7.91 (d, J=0.8 Hz, 1H), 7.42 (ddd, J=7.3, 5.0, 1.4 Hz, 1H), 7.27 (d, J=3.6 Hz, 1H), 6.76 (d, J=3.5 Hz, 1H), 4.36 (t, J=5.3 Hz, 2H), 4.24 (q, J=7.3 Hz, 2H), 3.79 (t, J=5.3 Hz, 2H), 3.45 (q, J=7.0 Hz, 2H), 1.45 (t, J=7.3 Hz, 3H), 1.08 (t, J=7.0 Hz, 3H); MS (ESI) (m/z): 421 [M+H]⁺.

I-41: N-(1-(2-ethoxyethyl)-3-(pyridin-2-yl)-1H-pyrazol-4-yl)-5-(3-(trifluoromethyl)-1H-pyrazol-4-yl)furan-2-carboxamide, Formic Acid Salt

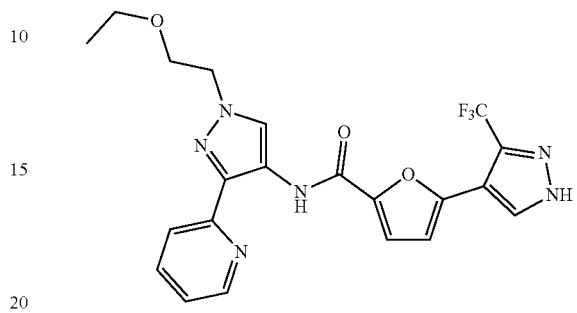

¹H NMR (300 MHz, DMSO-d₆) δ 11.47 (s, 1H), 8.63 (ddd, J=5.1, 1.8, 1.0 Hz, 1H), 8.50 (d, J=1.2 Hz, 1H), 8.43 (s, 1H), 8.01 (dt, J=8.0, 1.1 Hz, 1H), 7.92 (td, J=7.7, 1.7 Hz, 1H), 7.38 (ddd, J=7.3, 5.0, 1.4 Hz, 1H), 7.34 (dd, J=3.6, 0.6 Hz, 1H), 6.80 (d, J=3.6 Hz, 1H), 4.36 (t, J=5.3 Hz, 2H), 3.79 (t, J=5.3 Hz, 2H), 3.45 (q, J=7.0 Hz, 2H), 1.08 (t, J=7.0 Hz, 3H); MS (ESI) (m/z): 461 [M+H]⁺.

I-43: N-(1-(2-ethoxyethyl)-3-(pyridin-2-yl)-1H-pyrazol-4-yl)-5-(1-isopentyl-1H-pyrazol-4-yl)furan-2-carboxamide, Formic Acid Salt

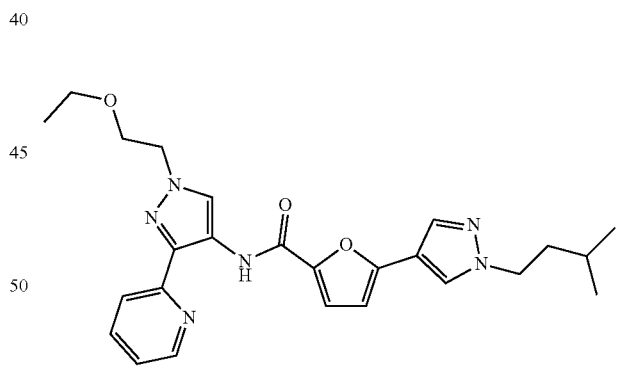

¹H NMR (300 MHz, DMSO-d₆) ι 11.64 (s, 1H), 8.73 (ddd, J=5.0, 1.7, 1.0 Hz, 1H), 8.39 (s, 1H), 8.25 (d, J=0.7 Hz, 1H), 8.02 (dt, J=8.0, 1.2 Hz, 1H), 7.98-7.93 (m, 1H), 7.93-7.89 (m, 1H), 7.40 (ddd, J=7.3, 5.0, 1.4 Hz, 1H), 7.27 (d, J=3.6 Hz, 1H), 6.75 (d, J=3.5 Hz, 1H), 4.35 (t, J=5.3 Hz, 2H), 4.23 (t, J=7.2 Hz, 2H), 3.78 (t, J=5.3 Hz, 2H), 3.45 (q, J=7.0 Hz, 2H), 1.74 (q, J=6.9 Hz, 2H), 1.51 (dp, J=13.4, 6.7 Hz, 1H), 1.08 (t, J=7.0 Hz, 3H), 0.93 (d, J=6.6 Hz, 6H); MS (ESI) (m/z): 463 [M+H]⁺.

I-45: N-(1-(2-ethoxyethyl)-3-(pyridin-2-yl)-1H-pyrazol-4-yl)-5-(1-methyl-1H-pyrazol-4-yl)furan-2-carboxamide, Formic Acid Salt

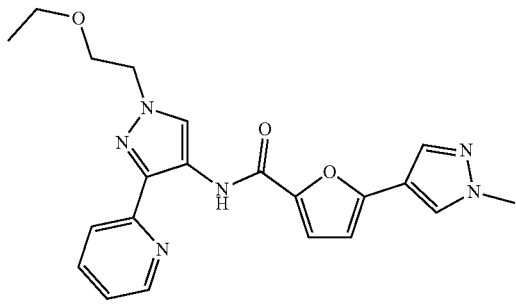 [SMILES: CCOCCn1cc(NC(=O)c2ccc(-c3cnn(C)c3)o2)c(-c2ccccn2)n1]

$^1$H NMR (300 MHz, DMSO-d$_6$) δ 11.64 (s, 1H), 8.39 (s, 1H), 8.19 (d, J=0.7 Hz, 1H), 8.02 (dt, J=8.1, 1.2 Hz, 1H), 7.94 (ddd, J=8.0, 7.3, 1.7 Hz, 1H), 7.90 (s, 1H), 7.70-7.47 (m, 1H), 7.43 (ddd, J=7.3, 4.9, 1.4 Hz, 1H), 7.28 (dd, J=3.6, 0.5 Hz, 1H), 6.83-6.70 (m, 1H), 4.36 (t, J=5.3 Hz, 2H), 3.95 (s, 3H), 3.79 (t, J=5.3 Hz, 2H), 3.45 (q, J=7.0 Hz, 2H), 1.08 (t, J=7.0 Hz, 3H); MS (ESI) (m/z): 407 [M+H]$^+$.

I-47: 5-(1H-pyrazol-4-yl)-N-(3-(pyridin-2-yl)-1H-pyrazol-4-yl)furan-2-carboxamide

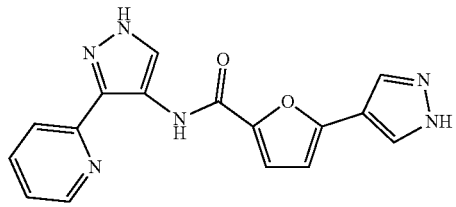 [SMILES: O=C(Nc1c[nH]nc1-c1ccccn1)c1ccc(-c2cn[nH]c2)o1]

$^1$H NMR (300 MHz, DMSO-d$_6$) ι 13.40-12.84 (m, 1H), 11.67 (s, 1H), 8.75 (dt, J=5.0, 1.3 Hz, 1H), 8.34 (s, 1H), 8.26 (s, 1H), 8.16-7.81 (m, 3H), 7.42 (ddd, J=7.5, 5.0, 1.3 Hz, 1H), 7.27 (d, J=3.6 Hz, 1H), 6.78 (d, J=3.5 Hz, 1H); MS (ESI) (m/z): 321 [M+H]$^+$.

I-48: 5-(1-((3-methyloxetan-3-yl)methyl)-1H-pyrazol-4-yl)-N-(1-((3-methyloxetan-3-yl)methyl)-3-(pyridin-2-yl)-1H-pyrazol-4-yl)furan-2-carboxamide Formic Acid Salt

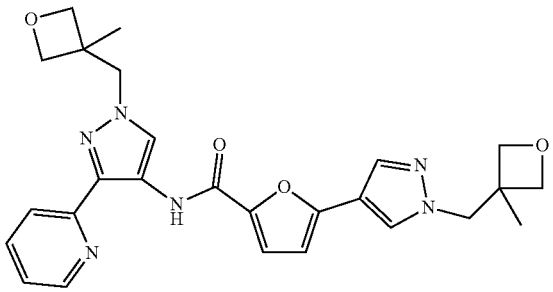 [SMILES: CC1(Cn2cc(-c3ccc(C(=O)Nc4cn(CC5(C)COC5)nc4-c4ccccn4)o3)cn2)COC1]

MS (ESI) (m/z): 489 [M+H]$^+$.

I-50: N-(2-(2-methoxyethoxy)ethyl)-5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide Formic Acid Salt

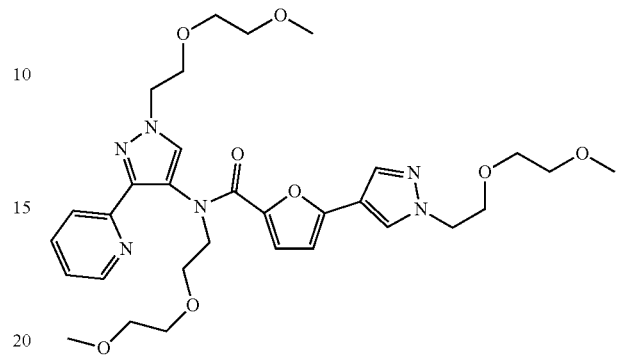

MS (ESI) (m/z): 627 [M+H]$^+$.

I-52: 5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide Formic Acid Salt

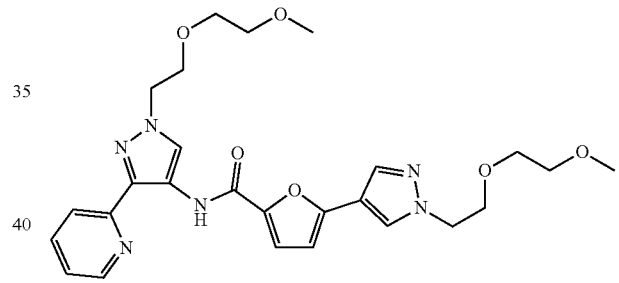

MS (ESI) (m/z): 525 [M+H]$^+$.

I-54: (4-(5-((1-(2-ethoxyethyl)-3-(pyridin-2-yl)-1H-pyrazol-4-yl)carbamoyl)furan-2-yl)-1H-pyrazol-1-yl)methyl dihydrogen phosphate

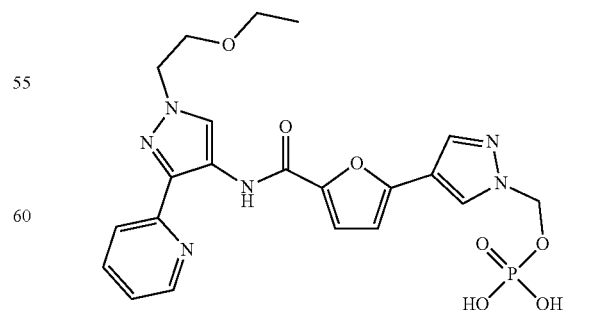

$^1$H NMR (300 MHz, DMSO-d$_6$) δ 11.70 (s, 1H), 8.83 (dt, J=5.0, 1.3 Hz, 1H), 8.36 (d, J=8.6 Hz, 2H), 8.09-7.86 (m,

3H), 7.49-7.33 (m, 1H), 7.28 (d, J=3.6 Hz, 1H), 6.86 (d, J=3.6 Hz, 1H), 5.88 (d, J=10.9 Hz, 2H), 4.35 (t, J=5.3 Hz, 2H), 3.78 (t, J=5.3 Hz, 2H), 3.45 (dd, J=14.0, 7.0 Hz, 2H), 1.08 (t, J=7.0 Hz, 3H); MS (ESI) (m/z): 503 [M+H]$^+$.

I-56: N-(1-(2-ethoxyethyl)-3-(pyridin-2-yl)-1H-pyrazol-4-yl)-5-(3-methyl-1H-pyrazol-4-yl)furan-2-carboxamide

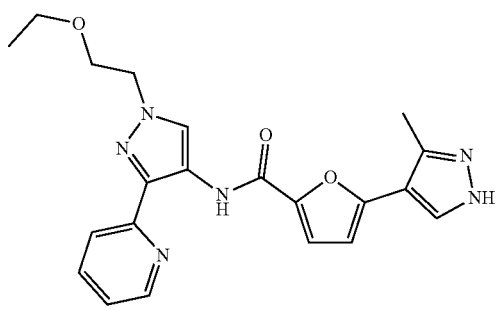 [SMILES: CCOCCn1cc(NC(=O)c2ccc(-c3c[nH]nc3C)o2)c(-c2ccccn2)n1]

MS (ESI) (m/z): 407 [M+H]$^+$.

I-58: 5-(3,5-dimethyl-1H-pyrazol-4-yl)-N-(1-(2-ethoxyethyl)-3-(pyridin-2-yl)-1H-pyrazol-4-yl)furan-2-carboxamide

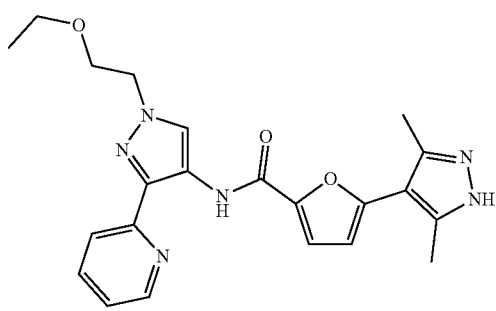 [SMILES: CCOCCn1cc(NC(=O)c2ccc(-c3c(C)n[nH]c3C)o2)c(-c2ccccn2)n1]

MS (ESI) (m/z): 421 [M+H]$^+$.

I-60: 5-(1H-pyrazol-4-yl)-N-(1-(tetrahydro-2H-pyran-4-yl)-3-(thiazol-2-yl)-1H-pyrazol-4-yl)furan-2-carboxamide Formic Acid Salt

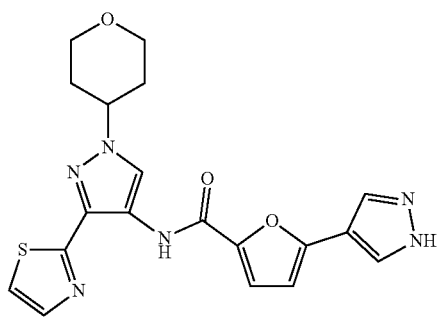 [SMILES: O=C(Nc1cn(C2CCOCC2)nc1-c1nccs1)c1ccc(-c2cn[nH]c2)o1]

MS (ESI) (m/z): 411 [M+H]$^+$.

I-62: N-(1-((1s,3s)-3-ethoxycyclobutyl)-3-(thiazol-2-yl)-1H-pyrazol-4-yl)-5-(1H-pyrazol-4-yl)furan-2-carboxamide, Formic Acid Salt

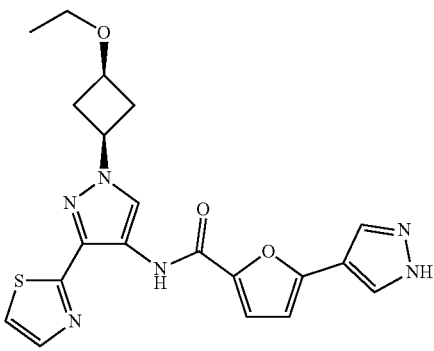 [SMILES: CCO[C@H]1C[C@@H](n2cc(NC(=O)c3ccc(-c4cn[nH]c4)o3)c(-c3nccs3)n2)C1]

$^1$H NMR (300 MHz, DMSO-d$_6$) δ 10.83 (s, 1H), 8.38 (s, 1H), 8.11 (s, 1H), 8.09 (d, J=3.3 Hz, 1H), 7.82 (d, J=3.3 Hz, 1H), 7.29 (d, J=3.6 Hz, 1H), 6.78 (d, J=3.6 Hz, 1H), 4.61 (tt, J=8.9, 7.3 Hz, 1H), 3.82 (qd, J=7.6, 6.4 Hz, 1H), 3.40 (q, J=7.0 Hz, 2H), 2.80 (dddd, J=11.5, 7.1, 5.9, 2.6 Hz, 2H), 2.46-2.31 (m, 2H), 1.14 (t, J=7.1 Hz, 3H)

MS (ESI) (m/z): 425 [M+H]$^+$.

I-64: N-(1-(2-(2-methoxyethoxy)ethyl)-3-(thiazol-2-yl)-1H-pyrazol-4-yl)-5-(1H-pyrazol-4-yl)furan-2-carboxamide

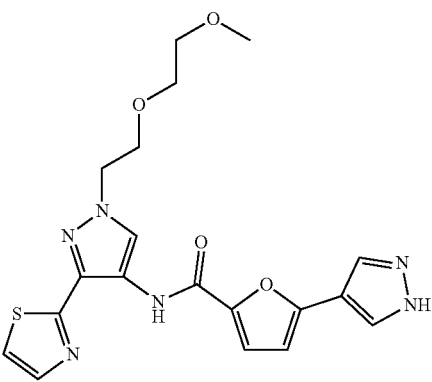 [SMILES: COCCOCCn1cc(NC(=O)c2ccc(-c3cn[nH]c3)o2)c(-c2nccs2)n1]

$^1$H NMR (300 MHz, DMSO-d$_6$) δ 13.25 (s, 1H), 10.82 (s, 1H), 8.38 (s, 1H), 8.26 (s, 1H), 8.09 (d, J=3.3 Hz, 1H), 7.98 (s, 1H), 7.80 (d, J=3.3 Hz, 1H), 7.30 (dd, J=3.6, 0.5 Hz, 1H), 6.79 (d, J=3.5 Hz, 1H), 4.37 (t, J=5.2 Hz, 2H), 3.82 (t, J=5.2 Hz, 2H), 3.58-3.50 (m, 2H), 3.45-3.38 (m, 2H), 3.21 (d, J=0.5 Hz, 3H); MS (ESI) (m/z): 429 [M+H]$^+$.

I-65: 5-(1H-pyrazol-4-yl)-N-(1-(tetrahydro-2H-pyran-4-yl)-3-(thiazol-2-yl)-1H-pyrazol-4-yl)furan-2-carboxamide

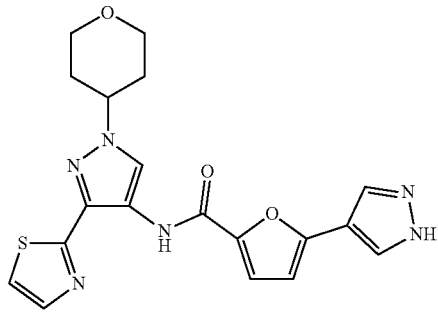 [SMILES: O=C(Nc1cn(C2CCOCC2)nc1-c1nccs1)c1ccc(-c2cn[nH]c2)o1]

$^1$H NMR (300 MHz, DMSO-d$_6$) δ 10.83 (s, 1H), 8.40 (d, J=1.0 Hz, 1H), 8.09 (dd, J=3.4, 1.0 Hz, 2H), 7.81 (dd, J=3.2, 1.2 Hz, 1H), 7.70-7.50 (m, 3H), 7.30 (dd, J=3.6, 1.2 Hz, 1H), 6.79 (dd, J=3.6, 1.1 Hz, 1H), 4.56 (tt, J=10.6, 6.0 Hz, 1H), 3.99 (dt, J=11.5, 3.3 Hz, 2H), 3.48 (td, J=11.2, 4.1 Hz, 2H), 2.09-1.95 (m, 4H); MS (ESI) (m/z): 411 [M+H]$^+$.

I-67: N-{1-Methyl-3-(pyridine-2-yl)-1H-pyrazol-4-yl}-5-(1H-pyrazol-4-yl)furan-2-carboxamide, Formate Salt

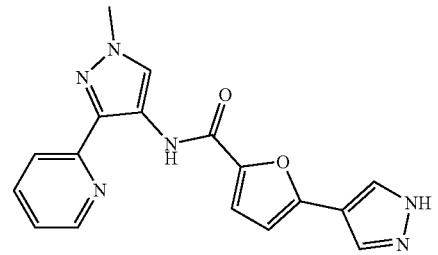 [SMILES: Cn1cc(NC(=O)c2ccc(-c3cn[nH]c3)o2)c(-c2ccccn2)n1]

$^1$H NMR (300 MHz, DMSO-d$_6$) δ 8.72 (d, J=4.8 Hz, 1H), 8.34 (s, 1H), 8.25 (bs, 1H), 8.01-7.9 (m, 3H), 7.43-7.38 (m, 1H), 7.26 (d, J=3.3 Hz, 1H), 6.76 (d, J=3.3 Hz, 1H), 3.93 (s, 3H); MS (m/e) 335.16 MH$^+$.

I-69: 5-(1-Methyl-1H-pyrazol-4-yl)-N-{1-methyl-3-(pyridine-2-yl)-1H-pyrazol-4-yl}furan-2-carboxamide, Formate Salt

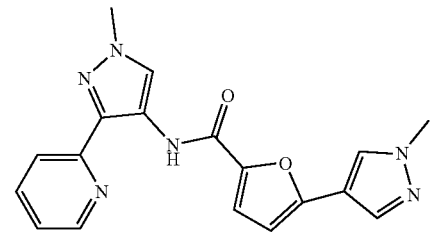 [SMILES: Cn1cc(-c2ccc(C(=O)Nc3cn(C)nc3-c3ccccn3)o2)cn1]

$^1$H NMR (300 MHz, DMSO-d$_6$) δ 8.73 (d, J=4.8 Hz, 1H), 8.34 (s, 1H), 8.17 (s, 1H), 8.00-7.9 (m, 3H), 7.43-7.39 (m, 1H), 7.26 (d, J=3.3 Hz, 1H), 6.74 (d, J=3.6 Hz, 1H), 3.9 (s, 3H); MS (m/e) 349.12 MH$^+$.

I-70: tert-Butyl-3-[4-{5-(1H-pyrazole-4-yl)furan-2-carboxamido}-3-(pyridine-2-yl)-1H-pyrazol-1-yl]azetidine-1-carboxylate, Formate Salt

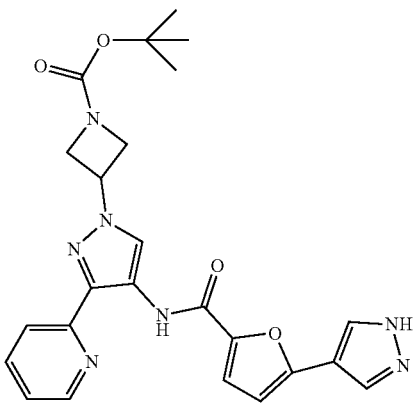 [SMILES: CC(C)(C)OC(=O)N1CC(n2cc(NC(=O)c3ccc(-c4cn[nH]c4)o3)c(-c3ccccn3)n2)C1]

MS (m/e) 476.51 MH$^+$

I-71: N-{1-(3-Methoxycyclobutyl)-3-(pyridine-2-yl)-1H-pyrazol-4-yl}-5-(1H-pyrazol-4-yl)furan-2-carboxamide, Formate Salt, Cis Isomer

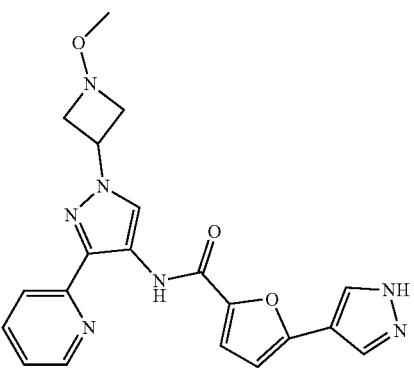

$^1$H NMR (300 MHz, DMSO-d$_6$) δ 8.73 (d, J=4.2 Hz, 1H), 8.39 (s, 1H), 8.25 (bs, 1H), 8.07-8.05 (m, 1H), 7.98-7.92 (m, 2H), 7.45-7.4 (m, 1H), 7.27 (d, J=3.6 Hz, 1H), 6.77 (d, J=3.9 Hz, 1H), 4.64-4.58 (m, 1H), 3.78-3.73 (m, 1H), 3.2 (s, 3H), 2.84-2.78 (m, 2H), 2.45-2.39 (m, 2H); MS (m/e) 405.4 MH$^+$.

I-72: N-{1-(3-Methoxycyclobutyl)-3-(pyridine-2-yl)-1H-pyrazol-4-yl}-5-(1H-pyrazol-4-yl)furan-2-carboxamide, Cis Isomer

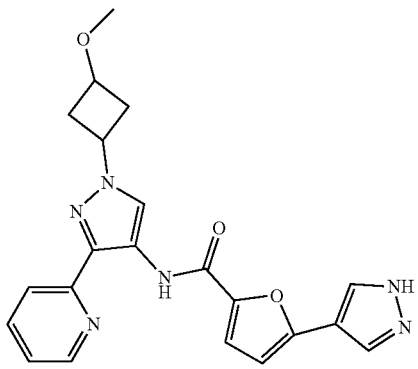 [SMILES: CON1CC(n2cc(NC(=O)c3ccc(-c4cn[nH]c4)o3)c(-c3ccccn3)n2)C1]

¹H NMR (300 MHz, DMSO-d₆) δ 8.73 (d, J=4.2 Hz, 1H), 8.39 (s, 1H), 8.25 (bs, 1H), 8.07-8.04 (m, 1H), 7.97-7.92 (m, 2H), 7.44-7.4 (m, 1H), 7.27 (d, J=3.6 Hz, 1H), 6.77 (d, J=3.9 Hz, 1H), 4.64-4.58 (m, 1H), 3.78-3.73 (m, 1H), 3.2 (s, 3H), 2.84-2.78 (m, 2H), 2.45-2.39 (m, 2H); MS (m/e) 405.5 MH⁺.

I-73: N-{1-(3-Benzyloxy)cyclobutyl)-3-(pyridine-2-yl)-1H-pyrazol-4-yl}-5-(1H-pyrazol-4-yl)furan-2-carboxamide, Trans Isomer

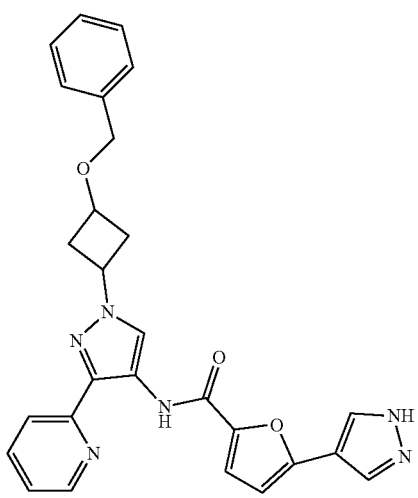 [SMILES: O=C(Nc1cn(C2CC(OCc3ccccc3)C2)nc1-c1ccccn1)c1ccc(-c2cn[nH]c2)o1]

¹H NMR (300 MHz, DMSO-d₆) δ 8.73 (d, J=5.7 Hz, 1H), 8.41 (s, 1H), 8.25 (bs, 1H), 8.07-8.04 (m, 1H), 7.98-7.92 (m, 2H), 7.44-7.4 (m, 1H), 7.37-7.36 (m, 4H), 7.33-7.28 (m, 1H), 7.26 (d, J=3.3 Hz, 1H), 6.76 (d, J=3.6 Hz, 1H), 5.15-5.1 (m, 1H), 4.45 (s, 2H), 4.43-4.38 (m, 1H), 2.77-2.59 (m, 2H), 2.58-2.52 (m, 2H); MS (m/e) 481.53 MH⁺.

I-74: tert-Butyl-3-[4-{5-(1H-pyrazole-4-yl)furan-2-carboxamido}-3-(pyridine-2-yl)-1H-pyrazol-1-yl]azetidine-1-carboxylate

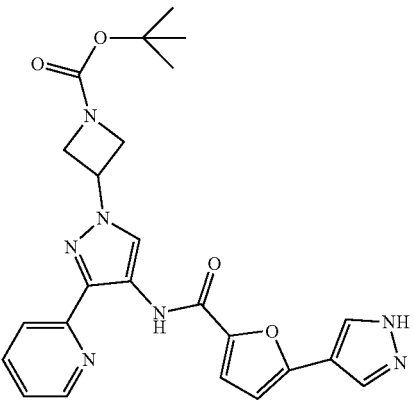 [SMILES: CC(C)(C)OC(=O)N1CC(n2cc(NC(=O)c3ccc(-c4cn[nH]c4)o3)c(-c3ccccn3)n2)C1]

¹H NMR (300 MHz, DMSO-d₆) δ 8.75 (d, J=4.2 Hz, 1H), 8.45 (s, 1H), 8.24 (m, 1H), 8.09-8.06 (m, 1H), 7.99-7.95 (m, 1H), 7.46-7.42 (m, 1H), 6.77 (d, J=3.6 Hz, 1H), 5.34-5.32 (m, 1H), 4.32 (t, J=8.4 Hz, 2H), 4.2 (m, 2H), 1.42 (s, 9H); MS (m/e) 476.78 MH⁺.

I-75: N-{1-(3-Methoxycyclobutyl)-3-(pyridine-2-yl)-1H-pyrazol-4-yl}-5-(1H-pyrazol-4-yl)furan-2-carboxamide, Trans Isomer

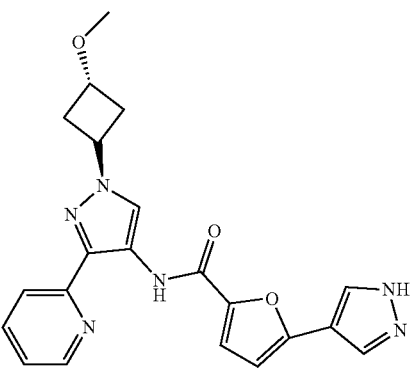

¹H NMR (300 MHz, DMSO-d₆) δ 8.73 (d, J=4.2 Hz, 1H), 8.4 (s, 1H), 8.25 (bs, 1H), 8.07-8.05 (m, 1H), 7.98-7.92 (m, 2H), 7.44-7.4 (m, 1H), 7.27 (d, J=3.6 Hz, 1H), 6.77 (d, J=3.9 Hz, 1H), 5.08-5.03 (m, 1H), 4.21-4.17 (m, 1H), 3.2 (s, 3H), 2.73-2.64 (m, 2H); MS (m/e) 405.51 MH⁺.

I-77: N-{1-Methyl-3-(pyridine-2-yl)-1H-pyrazol-4-yl}-5-(1H-pyrazol-4-yl)furan-2-carboxamide, Free Base

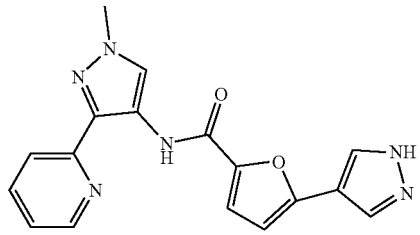 [SMILES: Cn1cc(NC(=O)c2ccc(-c3cn[nH]c3)o2)c(-c2ccccn2)n1]

¹H NMR (300 MHz, DMSO-d₆) δ 8.72 (d, J=4.8 Hz, 1H), 8.34 (s, 1H), 8.25 (bs, 1H), 8.01-7.9 (m, 3H), 7.43-7.38 (m, 1H), 7.26 (d, J=3.3 Hz, 1H), 6.76 (d, J=3.3 Hz, 1H), 3.93 (s, 3H); MS (m/e) 335.16 MH⁺.

I-78: N-{1-(Azetidin-3-yl)-3-(pyridine-2-yl)-1H-pyrazol-4-yl}-5-(1H-pyrazol-4-yl)furan-2-carboxamide, TFA Salt

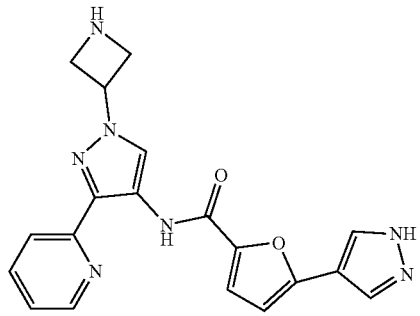 [SMILES: O=C(Nc1cn(C2CNC2)nc1-c1ccccn1)c1ccc(-c2cn[nH]c2)o1]

¹H NMR (300 MHz, DMSO-d₆) δ 8.78-8.76 (m, 1H), 8.58 (s, 1H), 8.15-7.99 (m, 4H), 7.51-7.46 (m, 1H), 7.29 (d, J=3.3 Hz, 1H), 6.78 (d, J=3.3 Hz, 1H), 5.56-5.51 (m, 1H), 4.46-4.39 (m, 4H); MS (m/e) 376.45 MH⁺.

I-80: Di-tert-butyl-[[4-{4-(4-((1-methyl-3-(pyridine-2-yl)-1H-pyrazol-4-yl)carbamoyl)furan-2-yl)-1H-pyrazol-1-yl}methyl]phosphate

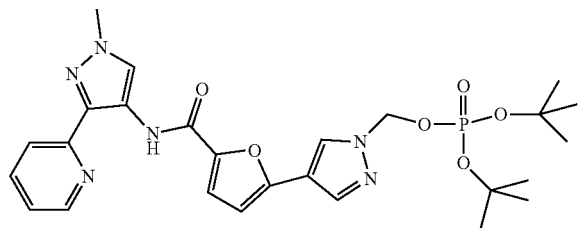 [SMILES: Cn1cc(NC(=O)c2ccc(-c3cnn(COP(=O)(OC(C)(C)C)OC(C)(C)C)c3)o2)c(-c2ccccn2)n1]

¹H NMR (300 MHz, DMSO-d₆) δ 8.84 (d, J=5.1 Hz, 1H), 8.37 (s, 1H), 8.35 (s, 1H), 8.08 (bs, 1H), 8.01-7.9 (m, 2H), 7.39-7.35 (m, 1H), 7.29 (d, J=3.3 Hz, 1H), 6.87 (d, J=3.6 Hz, 1H), 5.97 (s, 1H), 5.93 (s, 1H), 3.93 (s, 3H), 1.37 (s, 18H); MS (m/e) 557.69 MH⁺.

I-81: [4-{5-((1-Methyl-3-(pyridine-2-yl)-1H-pyrazol-4-yl)carbamoyl)furan-2yl}-1H-pyrazol-1-yl]methyl dihydrogen phosphate

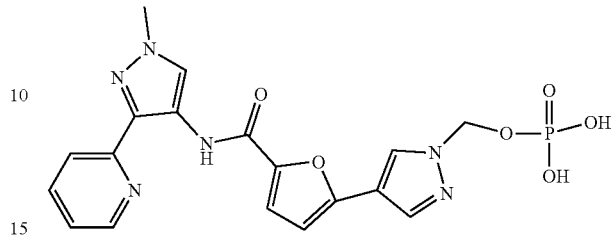

¹H NMR (300 MHz, DMSO-d₆) δ 8.82 (d, J=4.8 Hz, 1H), 8.35 (s, 1H), 8.34 (bs, 1H), 8.04 (s, 1H), 7.99-7.92 (m, 2H), 7.41-7.37 (m, 1H), 7.28 (d, J=3.6 Hz, 1H), 6.86 (d, J=3.6 Hz, 1H), 5.88 (d, J=10.8 Hz, 2H), 3.93 (s, 3H); MS (m/e) 445.53 MH⁺.

I-82: Sodium [4-{5-((1-Methyl-3-(pyridine-2-yl)-1H-pyrazol-4-yl)carbamoyl)furan-2-yl}-1H-pyrazol-1-yl]methyl phosphate

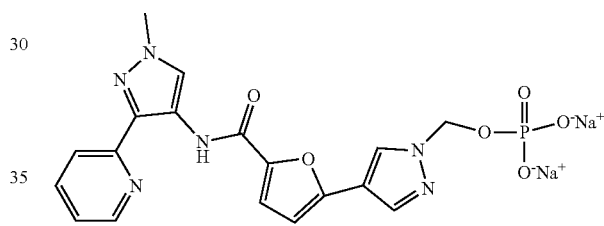

¹H NMR (300 MHz, D₂O) δ 8.11 (bs, 1H), 7.95 (s, 1H), 7.71 (s, 1H), 7.56 (t, J=8.4 Hz, 1H), 7.49 (s, 1H), 7.37-7.34 (m, 1H), 7.07 (t, J=7.5 Hz, 1H), 6.78 (d, J=3.9 Hz, 1H), 6.36 (d, J=3.6 Hz, 1H), 5.6 (d, J=6.6 Hz, 2H), 3.6 (s, 3H); MS (m/e) 445.53 MH⁺.

I-83: N-{1-(1-Acetylazetidin-3-yl)-3-(pyridine-2-yl)-1H-pyrazol-4-yl}-5-(1H-pyrazol-4-yl)furan-2-carboxamide, Free Base

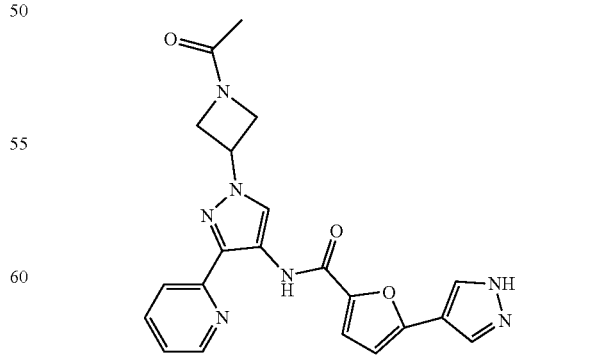

¹H NMR (300 MHz, DMSO-d₆) δ 8.75 (d, J=4.2 Hz, 1H), 8.53 (s, 1H), 8.1-8.08 (m, 1H), 7.99-7.94 (m, 1H), 7.47-7.43 (m, 1H), 7.28 (d, J=3.3 Hz, 1H), 6.77 (d, J=3.6 Hz, 1H), 5.43-5.34 (m, 1H), 4.58 (t, J=8.7 Hz, 1H), 4.5-4.46 (m, 1H), 4.31 (t, J=9.6 Hz, 1H), 4.2-4.16 (m, 1H), 1.84 (s, 3H); MS (m/e) 418.61 MH⁺.

I-84: 3-[4-{5-(1H-Pyrazol-4-yl)furan-2-carboxamido}-3-(pyridine-2-yl)-1H-pyrazol-1-yl]-N-(tert-butyl)azetidine-1-carboxamide, Free Base

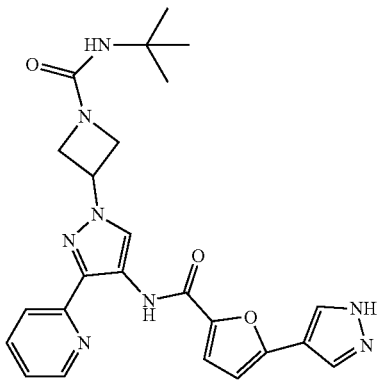 [SMILES: CC(C)(C)NC(=O)N1CC(n2cc(NC(=O)c3ccc(-c4cn[nH]c4)o3)c(-c3ccccn3)n2)C1]

$^1$H NMR (300 MHz, DMSO-d$_6$) δ 8.75 (d, J=4.8 Hz, 1H), 8.47 (s, 1H), 8.07-8.05 (m, 1H), 7.99-7.93 (m, 1H), 7.47-7.42 (m, 1H), 7.28 (d, J=3.3 Hz, 1H), 6.77 (d, J=3.3 Hz, 1H), 5.87 (s, 1H), 5.3-5.25 (m, 1H), 4.24 (t, J=8.4 Hz, 2H), 4.14-4.09 (m, 2H), 1.26 (s, 9H); MS (m/e) 475.65 MH⁺.

I-85: 3-[4-{5-(1H-Pyrazol-4-yl)furan-2-carboxamido}-3-(pyridine-2-yl)-1H-pyrazol-1-yl]-N-isopropylazetidine-1-carboxamide, Free Base

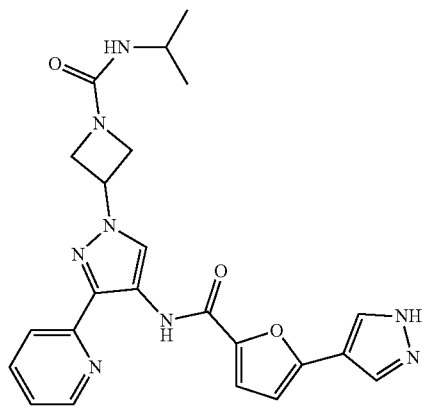 [SMILES: CC(C)NC(=O)N1CC(n2cc(NC(=O)c3ccc(-c4cn[nH]c4)o3)c(-c3ccccn3)n2)C1]

$^1$H NMR (300 MHz, DMSO-d$_6$) δ 8.73 (m, 1H), 8.47 (s, 1H), 8.25 (bs, 1H), 8.08-8.05 (m, 1H), 7.99-7.96 (m, 2H), 7.47-7.42 (m, 1H), 7.29-7.28 (m, 1H), 6.78-6.76 (m, 1H), 6.25 (d, J=8.1 Hz, 1H), 5.31 (m, 1H), 4.24 (t, J=8.4 Hz, 2H), 4.14-4.09 (m, 2H), 3.76-3.69 (m, 1H), 1.07 (s, 3H), 1.05 (s, 3H); MS (m/e) 461.58 MH⁺.

I-86: 3-[4-{5-(1H-Pyrazol-4-yl)furan-2-carboxamido}-3-(pyridine-2-yl)-1H-pyrazol-1-yl]-N-propylazetidine-1-carboxamide, Free Base

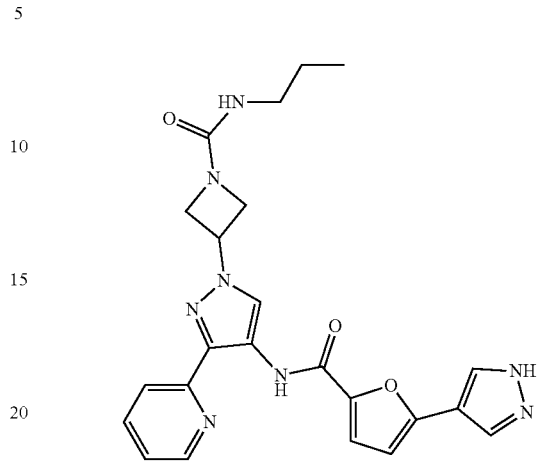

$^1$H NMR (300 MHz, DMSO-d$_6$) δ 8.75-8.74 (m, 1H), 8.47 (s, 1H), 8.25 (bs, 1H), 8.08-8.05 (m, 1H), 7.99-7.93 (m, 2H), 7.47-7.42 (d, J=3.3 Hz, 1H), 7.29-7.28 (d, J=3.6 Hz, 1H), 6.49 (m, 1H), 6.25 (d, J=8.1 Hz, 1H), 5.32 (m, 1H), 4.25 (t, J=8.4 Hz, 2H), 4.16-4.12 (m, 2H), 3.0-2.94 (m, 2H), 1.45-1.38 (m, 2H), 0.84 (t, J=7.5 Hz, 3H); MS (m/e) 461.58 MH⁺.

I-87: 3-[4-{5-(1H-Pyrazol-4-yl)furan-2-carboxamido}-3-(pyridine-2-yl)-1H-pyrazol-1-yl]-N-cyclopropylazetidine-1-carboxamide, Formate Salt

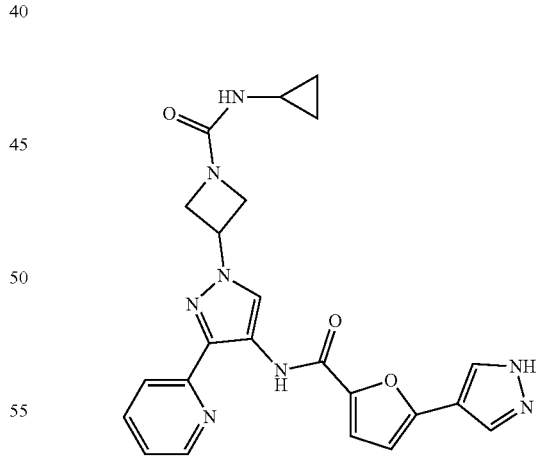

$^1$H NMR (300 MHz, DMSO-d$_6$) δ 8.75 (bs, 1H), 8.47 (bs, 1H), 8.14-8.04 (bs, 2H), 8.08-7.94 (m, 1H), 7.47-7.42 (m, 1H), 7.29-7.27 (m, 1H), 6.76 (m, 1H), 5.31 (m, 1H), 4.24-4.21 (m, 2H), 4.18-4.12 (m, 2H), 0.55 (m, 2H), 0.4 (m, 2H); MS (m/e) 459.57 MH⁺.

I-89: N-[1-{1-(Cyclopropanecarbonyl)azetidin-3-yl}-3-(pyridine-2-yl)-1H-pyrazol-4-yl]-5-(1H-pyrazol-4-yl)furan-2-carboxamide, Formate Salt

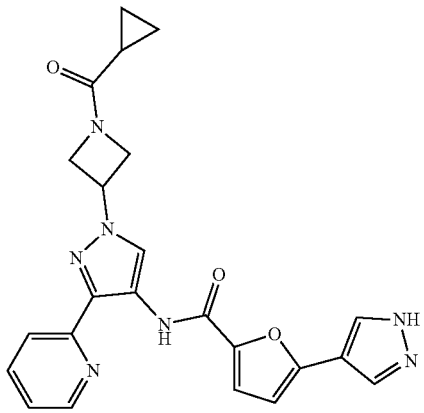 [SMILES: O=C(Nc1cn(C2CN(C(=O)C3CC3)C2)nc1-c1ccccn1)c1ccc(-c2cn[nH]c2)o1]

$^1$H NMR (300 MHz, DMSO-d$_6$) δ 8.75 (d, J=5.1 Hz, 1H), 8.52 (s, 1H), 8.5 (s, 1H), 8.1-8.08 (m, 1H), 7.99-7.94 (m, 1H), 7.47-7.43 (m, 1H), 7.28 (d, J=3.3 Hz, 1H), 6.77 (d, J=3.9 Hz, 1H), 5.47-5.43 (m, 1H), 4.73 (t, J=8.4 Hz, 1H), 4.6 (m 1H), 4.37-4.3 (m, 1H), 4.2-4.16 (m, 1H), 1.66-1.59 (m, 1H), 0.76 (s, 2H), 0.74 (s, 2H); MS (m/e) 444.61 MH$^+$.

I-91: N-[1-{1-Pivaloylazetidin-3-yl}-3-(pyridine-2-yl)-1H-pyrazol-4-yl]-5-(1H-pyrazol-4-yl)furan-2-carboxamide, Formate Salt

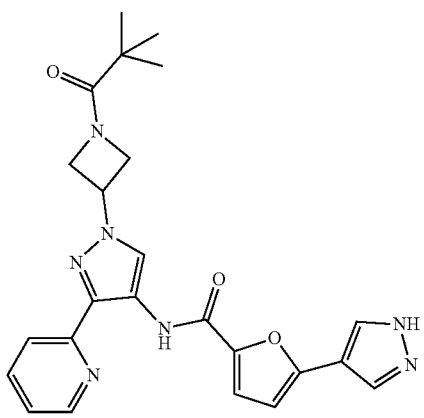 [SMILES: CC(C)(C)C(=O)N1CC(n2cc(NC(=O)c3ccc(-c4cn[nH]c4)o3)c(-c3ccccn3)n2)C1]

$^1$H NMR (300 MHz, DMSO-d$_6$) δ 8.75 (d, J=4.5 Hz, 1H), 8.51 (s, 1H), 8.3-8.2 (ms, 1H), 8.08-8.05 (m, 1H), 7.99-7.94 (m, 2H), 7.47-7.43 (m, 1H), 7.29-7.27 (m, 1H), 6.78-6.76 (m, 1H), 5.37 (m, 1H), 1.16 (s, 9H); MS (m/e) 460.61 MH$^+$.

I-93: 5-(1H-Pyrazol-4-yl)-N-{3-(pyridine-2-yl)-1-(pyrrolidine-1-carbonyl)azetidin-3-yl}-1H-pyrazol-4-yl)furan-2-carboxamide, Formate Salt

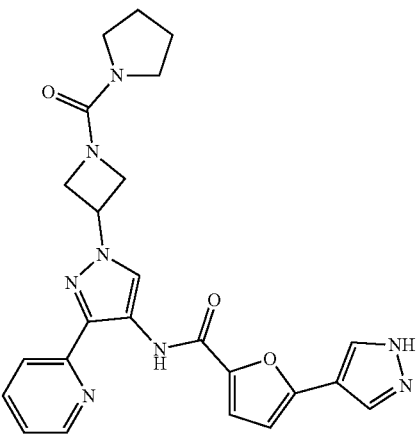 [SMILES: O=C(Nc1cn(C2CN(C(=O)N3CCCC3)C2)nc1-c1ccccn1)c1ccc(-c2cn[nH]c2)o1]

$^1$H NMR (300 MHz, DMSO-d$_6$) δ 8.74 (m, 1H), 8.49 b (s, 1H), 8.25-8.2 (bs, 1H), 8.06 (m, 1H), 7.96 (m, 2H), 7.44 (m, 1H), 7.28 (m, 1H), 6.77 (m, 1H), 5.34 (m, 1H), 4.32-4.25 (m, 4H), 1.77 (bs, 4H); MS (m/e) 473.6 MH$^+$.

I-95: N-[1-{1-Isobutyrylazetidin-3-yl}-3-(pyridine-2-yl)-1H-pyrazol-4-yl]-5-(1H-pyrazol-4-yl)furan-2-carboxamide, Formate Salt

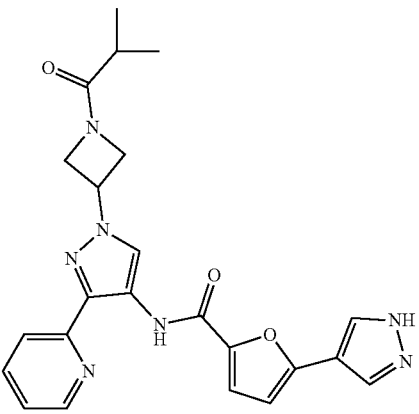 [SMILES: CC(C)C(=O)N1CC(n2cc(NC(=O)c3ccc(-c4cn[nH]c4)o3)c(-c3ccccn3)n2)C1]

MS (m/e) 446.55 MH$^+$.

I-97: N-(1H-Pyrazol-4-yl)-N-{3-(pyridine-2-yl)-1-{1-(2,2,2-trifluoroethyl)azetidin-3-yl}-1H-pyrazol-4-yl}furan-2-carboxamide, TFA Salt

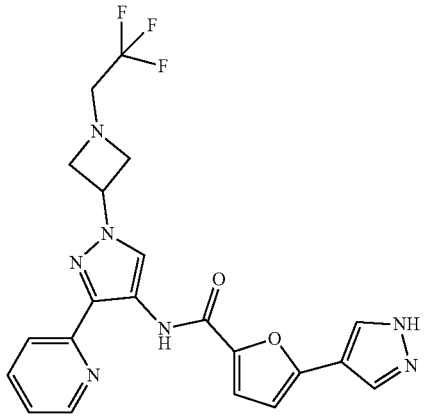 [SMILES: O=C(Nc1cn(C2CN(CC(F)(F)F)C2)nc1-c1ccccn1)c1ccc(-c2cn[nH]c2)o1]

¹H NMR (300 MHz, DMSO-d₆) δ 8.74 (d, J=4.5 Hz, 1H), 8.54 (s, 1H), 8.09-8.07 (m, 1H), 7.99-7.94 (m, 1H), 7.46-7.42 (m, 1H), 7.28 (d, J=3.6 Hz, 1H), 6.77 (d, J=3.3 Hz, 1H), 5.21-5.16 (m, 1H), 3.89 (t, J=7.8 Hz, 2H), 3.74 (t, J=7.2 Hz, 2H), 3.38 (q, J=9.9 Hz, 2H); MS (m/e) 458.55 MH⁺.

I-75: N-[1-{1-Butyrylazetidin-3-yl}-3-(pyridine-2-yl)-1H-pyrazol-4-yl]-5-(1H-pyrazol-4-yl)furan-2-carboxamide, Formate Salt

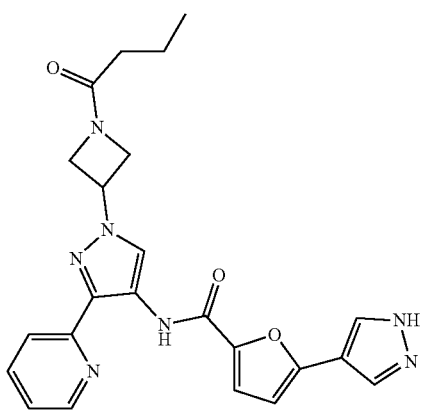 [SMILES: CCCC(=O)N1CC(n2cc(NC(=O)c3ccc(-c4cn[nH]c4)o3)c(-c3ccccn3)n2)C1]

¹H NMR (300 MHz, DMSO-d₆) δ 8.75-8.74 (m, 1H), 8.52 (s, 1H), 8.09-8.06 (m, 1H), 7.99-7.94 (m, 2H), 7.47-7.43 (m, 1H), 7.29-7.27 (m, 1H), 6.78-6.77 (m, 1H), 5.39 (m, 1H), 4.59 (t, J=8.7 Hz, 1H), 4.5-4.45 (m, 1H), 4.32 (t, J=9.9 Hz, 1H), 4.2-4.16 (m, 1H), 2.1 (t, J=7.5 Hz, 2H), 1.53 (q, J=7.5 Hz, 2H), 0.9 (t, J=7.2 Hz, 9H); MS (m/e) 446.58 MH⁺.

I-101: N-{1-(1-Methylazetidin-3-yl)-3-(pyridine-2-yl)-1H-pyrazol-4-yl}-5-(1H-pyrazol-4-yl)furan-2-carboxamide, Formate Salt

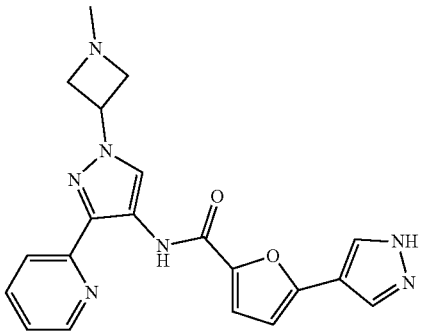 [SMILES: CN1CC(n2cc(NC(=O)c3ccc(-c4cn[nH]c4)o3)c(-c3ccccn3)n2)C1]

¹H NMR (300 MHz, DMSO-d₆) δ 8.29 (d, J=5.7 Hz, 1H), 8.07 (s, 1H), 7.8 (s, 1H), 7.63-7.61 (m, 1H), 7.55-7.49 (m, 1H), 7.01-6.97 (m, 1H), 6.83 (d, J=3.6 Hz, 1H), 6.33 (d, J=3.6 Hz, 1H), 4.64-4.59 (m, 1H), 3.26 (t, J=8.1 Hz, 2H), m (t, 2H); MS (m/e) 390.55 MH⁺.

I-103: N-[1-{1-(2,2-difluorocyclopropane-1-carbonyl)azetidin-3-yl}-3-(pyridine-2-yl)-1H-pyrazol-4-yl]-5-(1H-pyrazol-4-yl)furan-2-carboxamide, Formate Salt

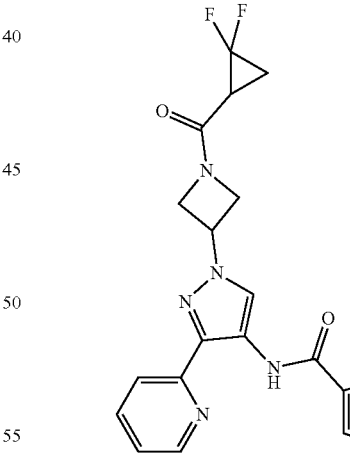

¹H NMR (300 MHz, DMSO-d₆) δ 8.76 (m, 1H), 8.55 (s, 1H), 8.53 (s, 1H), 8.25 (m, 1H), 8.11-8.08 (m, 1H), 7.99-7.94 (m, 2H), 7.47-7.43 (m, 1H), 7.29 (d, J=3.6 Hz, 1H), 6.77 (d, J=3.3 Hz, 1H), 5.46 (m, 1H), 4.8 (m, 1H), 4.69 (m, 1H), 4.57 (m, 1H), 4.4 (m, 1H), 4.3 (m, 1H), 2.79 (m, 1H), 1.9 (m, 2H); MS (m/e) 480.49 MH⁺.

I-105: N-(1-methyl-3-(5-morpholinopyridin-2-yl)-1H-pyrazol-4-yl)-5-(1H-pyrazol-4-yl)furan-2-carboxamide

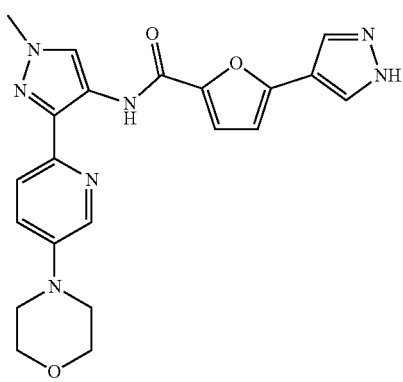 [SMILES: Cn1cc(NC(=O)c2ccc(-c3cn[nH]c3)o2)c(-c2ccc(N3CCOCC3)cn2)n1]

$^1$H NMR (300 MHz, DMSO-d$_6$) δ 11.66 (s, 1H), 8.38 (d, J=2.9 Hz, 1H), 8.28 (s, 1H), 8.10 (s, 2H), 7.85 (d, J=8.9 Hz, 1H), 7.56 (dd, J=8.9, 2.9 Hz, 1H), 7.25 (d, J=3.6 Hz, 1H), 6.74 (d, J=3.6 Hz, 1H), 3.91 (s, 3H), 3.80 (t, J=4.9 Hz, 4H), 3.27 (t, J=4.9 Hz, 4H). LCMS (m/z): 420.55 (MH$^+$).

I-106: N-(1-methyl-3-(5-(4-methylpiperazin-1-yl)pyridin-2-yl)-1H-pyrazol-4-yl)-5-(1H-pyrazol-4-yl)furan-2-carboxamide

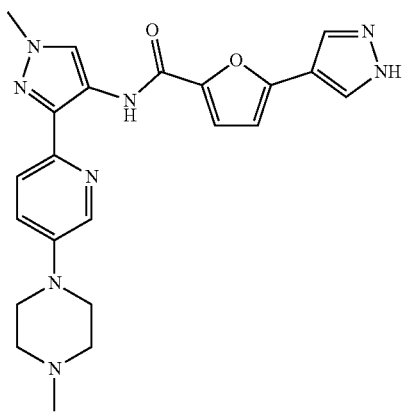 [SMILES: CN1CCN(c2ccc(-c3nn(C)cc3NC(=O)c3ccc(-c4cn[nH]c4)o3)nc2)CC1]

$^1$H NMR (300 MHz, DMSO-d$_6$) δ 13.31 (s, 1H), 11.69 (s, 1H), 8.37 (d, J=2.9 Hz, 1H), 8.27 (m, 8.27-8.23, 2H), 7.98 (s, 1H), 7.83 (d, J=8.9 Hz, 1H), 7.55 (dd, J=8.9, 2.9 Hz, 1H), 7.26 (d, J=3.6 Hz, 1H), 6.77 (d, J=3.6 Hz, 1H), 3.90 (s, 3H), 3.32 (t, J=6.4 Hz, 4H), 2.51 (t, J=6.4 Hz, 4H), 2.26 (s, 3H). LCMS (m/z): 433.72 (MH$^+$).

I-107: N-(3-(5-(2-hydroxy-2-methylpropoxy)pyridin-2-yl)-1-methyl-1H-pyrazol-4-yl)-5-(1H-pyrazol-4-yl)furan-2-carboxamide

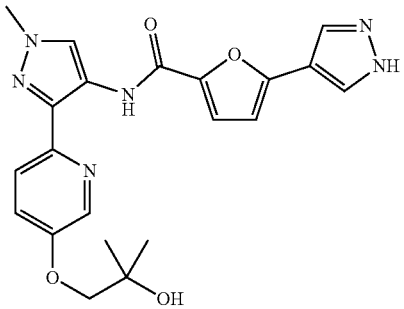 [SMILES: Cn1cc(NC(=O)c2ccc(-c3cn[nH]c3)o2)c(-c2ccc(OCC(C)(C)O)cn2)n1]

$^1$H NMR (300 MHz, DMSO-d$_6$) δ 13.30 (s, 1H), 11.46 (s, 1H), 8.43 (s, 1H), 8.32 (s, 1H), 8.27 (s, 1H), 8.01-7.91 (m, 2H), 7.60 (dd, J=8.9, 2.9 Hz, 1H), 7.28 (d, J=3.6 Hz, 1H), 6.78 (d, J=3.6 Hz, 1H), 4.72 (s, 1H), 3.92 (s, 3H), 3.90 (s, 3H), 1.25 (s, 6H).

LCMS (m/z): 423.60 (MH$^+$).

I-108: N-(1-methyl-3-(5-(oxetan-3-yloxy)pyridin-2-yl)-1H-pyrazol-4-yl)-5-(1H-pyrazol-4-yl)furan-2-carboxamide

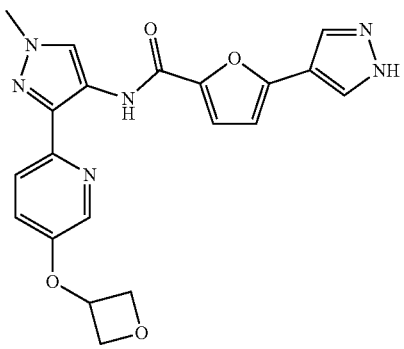 [SMILES: Cn1cc(NC(=O)c2ccc(-c3cn[nH]c3)o2)c(-c2ccc(OC3COC3)cn2)n1]

$^1$H NMR (300 MHz, DMSO-d$_6$) δ 13.34 (s, 1H), 11.45 (s, 1H), 8.32 (s, 1H), 8.25 (d, J=2.6 Hz, 1H), 7.94 (d, J=9.2 Hz, 1H), 7.45 (dd, J=8.9, 2.9 Hz, 1H), 7.28 (d, J=3.6 Hz, 1H), 6.78 (d, J=3.6 Hz, 1H), 6.62 (s, 1H), 5.48 (p, J=5.4, 5.0 Hz, 1H), 5.00 (t, J=6.9 Hz, 2H), 4.70-4.63 (m, 2H), 3.92 (s, 3H).

LCMS (m/z): 407.35 (MH$^+$).

I-109: N-(3-(5-methoxypyridin-2-yl)-1-methyl-1H-pyrazol-4-yl)-5-(1H-pyrazol-4-yl)furan-2-carboxamide

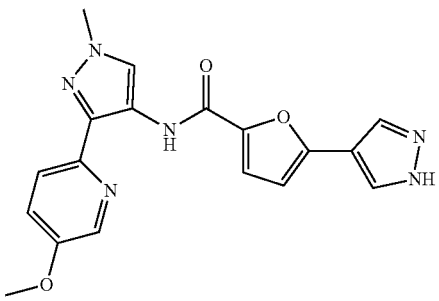 [SMILES: COc1ccc(-c2nn(C)cc2NC(=O)c2ccc(-c3cn[nH]c3)o2)nc1]

$^1$H NMR (300 MHz, DMSO-d$_6$) δ 13.33 (s, 1H), 11.55 (s, 1H), 8.44 (d, J=2.9 Hz, 1H), 8.35 (s, 1H), 8.30 (s, 1H), 8.00-7.97 (m, 2H), 7.62 (dd, J=8.9, 3.0 Hz, 1H), 7.31 (d, J=3.5 Hz, 1H), 6.81 (d, J=3.5 Hz, 1H), 3.96 (s, 3H), 3.96 (s, 3H); LRMS (M+H) m/z 365.57.

I-110: N-(1-isopropyl-3-(pyridin-2-yl)-1H-pyrazol-4-yl)-5-(1H-pyrazol-4-yl)furan-2-carboxamide

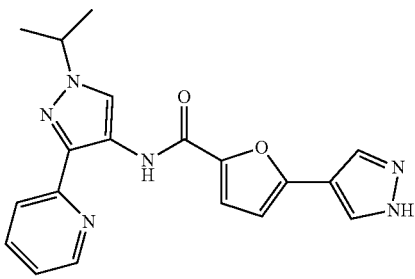 [SMILES: CC(C)n1cc(NC(=O)c2ccc(-c3cn[nH]c3)o2)c(-c2ccccn2)n1]

$^1$H NMR (300 MHz, DMSO-d$_6$) δ 13.31 (s, 1H), 11.70 (s, 1H), 8.78 (ddd, J=5.0, 1.6, 1.0 Hz, 1H), 8.42 (s, 1H), 8.31-8.30 (m, 1H), 8.08 (ddd, J=8.1, 1.1, 1.1 Hz, 1H), 8.02-7.96 (m, 2H), 7.46 (ddd, J=7.3, 5.0, 1.3 Hz, 1H), 7.31 (d, J=3.5 Hz, 1H), 6.82 (d, J=3.5 Hz, 1H), 4.67 (hept, J=6.7 Hz, 1H), 1.53 (d, J=6.7 Hz, 6H); LRMS (M+H) m/z 363.67.

I-111: N-(1-(2-morpholinoethyl)-3-(pyridin-2-yl)-1H-pyrazol-4-yl)-5-(1H-pyrazol-4-yl)furan-2-carboxamide

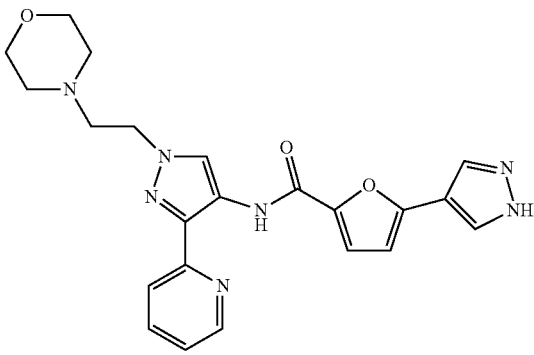 [SMILES: O=C(Nc1cn(CCN2CCOCC2)nc1-c1ccccn1)c1ccc(-c2cn[nH]c2)o1]

$^1$H NMR (300 MHz, Chloroform-d) δ 11.82 (s, 1H), 10.31 (v br s, 1H), 8.67 (ddd, J=5.0, 1.7, 1.0 Hz, 1H), 8.41 (s, 1H), 8.09 (ddd, J=8.1, 1.1, 1.1 Hz, 1H), 7.99 (s, 2H), 7.78 (ddd, J=8.0, 7.6, 1.8 Hz, 1H), 7.26-7.21 (m, 2H, partially overlapped with CHCl$_3$), 6.53 (d, J=3.5 Hz, 1H), 4.30 (t, J=6.7 Hz, 2H), 3.73-3.70 (m, 4H), 2.90 (t, J=6.7 Hz, 2H), 2.54-2.51 (m, 4H); LRMS (M+H) m/z 434.84.

I-112: N-(1-(2-(4-methylpiperazin-1-yl)ethyl)-3-(pyridin-2-yl)-1H-pyrazol-4-yl)-5-(1H-pyrazol-4-yl)furan-2-carboxamide

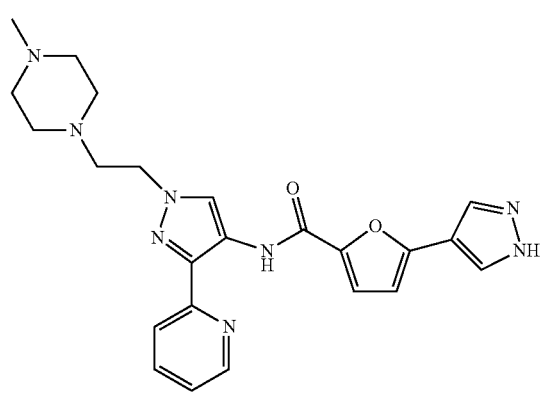 [SMILES: CN1CCN(CCn2cc(NC(=O)c3ccc(-c4cn[nH]c4)o3)c(-c3ccccn3)n2)CC1]

$^1$H NMR (300 MHz, DMSO-d$_6$) δ 13.33 (br s, 1H), 11.69 (s, 1H), 8.77 (ddd, J=5.0, 1.6, 1.0 Hz, 1H), 8.46 (s, 1H), 8.15 (br s, 2H), 8.06 (ddd, J=8.1, 1.2, 1.0 Hz, 1H), 7.98 (ddd, J=7.7, 7.7, 1.7 Hz, 1H), 7.46 (ddd, J=7.3, 5.0, 1.4 Hz, 1H), 7.32 (d, J=3.6 Hz, 1H), 6.82 (d, J=3.6 Hz, 1H), 4.35 (t, J=6.5 Hz, 2H), 3.41 (br s, 2H), 2.80 (t, J=6.5 Hz, 3H), 2.50 (br s, partially overlapped with DMSO, 2H), 2.34 (br s, 4H), 2.17 (s, 3H); LRMS (M+H) m/z 447.76.

I-113: 5-(1H-pyrazol-3-yl)-N-(3-(pyridin-2-yl)-1-(2-(2,2,2-trifluoroethoxy)ethyl)-1H-pyrazol-4-yl)furan-2-carboxamide

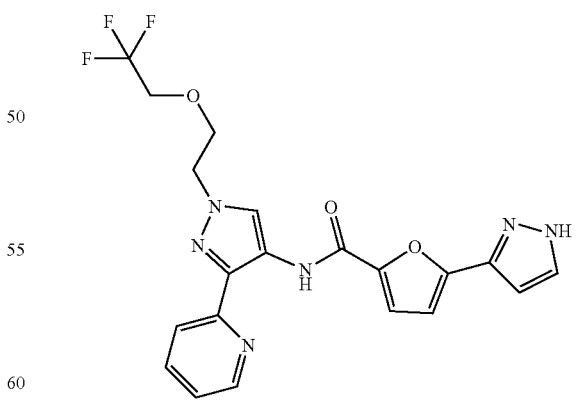

$^1$HNMR (300 MHz, DMSO-d6) δ 11.66 (s, 1H), 8.74 (d, J=6.7 Hz, 1H), 8.42 (s, 1H), 8.27 (s, 1H), 8.05-7.93 (m, 3H), 7.46-7.42 (m, 1H), 7.28 (d, J=3.3 Hz, 1H), 6.79 (d, J=3.3 Hz, 1H), 4.43 (t, J=6.7 Hz, 2H), 4.16-4.01 (m, 4H); LCMS (m/z): 447.13 (MH$^+$).

I-114: N-(1-((1,3-cis)-3-isopropoxycyclobutyl)-3-(pyridin-2-yl)-1H-pyrazol-4-yl)-5-(1H-pyrazol-4-yl)furan-2-carboxamide

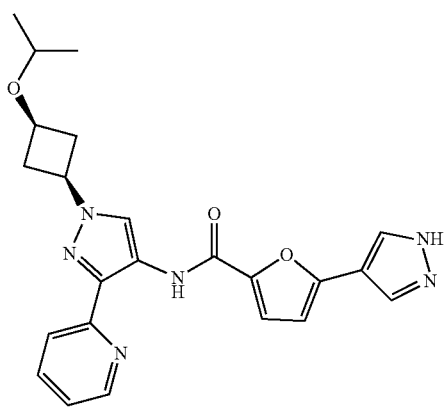 [SMILES: CC(C)O[C@H]1C[C@@H](n2cc(NC(=O)c3ccc(-c4cn[nH]c4)o3)c(-c3ccccn3)n2)C1]

1H NMR (300 MHz, DMSO-d6) δ 11.63 (s, 1H), 8.73 (d, J=4.8 Hz, 1H), 8.38 (s, 1H), 8.06 (d, J=7.8 Hz, 1H), 7.97 (t, J=7.8 Hz, 1H), 7.42 (t, d=6.3 Hz, 1H), 7.26 (d, J=3.6 Hz, 1H), 6.77 (d, J=3.6 Hz, 1H), 4.58 (m, 1H), 3.89 (p, J=6.6 Hz, 1H), 3.62 (p, J=6.3 Hz, 1H), 2.78 (m, 2H), 2.41 (m, 2H), 1.10 (d, J=6.3 Hz, 6H); LCMS: purity: 91.77%; MS (m/e): 433.22 (MH+).

I-115: N-(1-(difluoromethyl)-3-(pyridin-2-yl)-1H-pyrazol-4-yl)-5-(1H-pyrazol-4-yl)furan-2-carboxamide

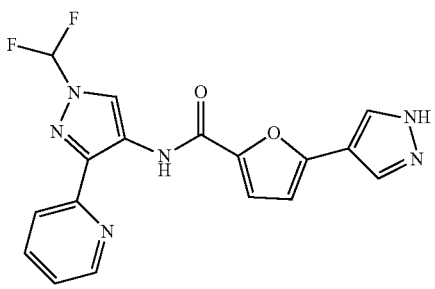 [SMILES: O=C(Nc1cn(C(F)F)nc1-c1ccccn1)c1ccc(-c2cn[nH]c2)o1]

1H NMR (300 MHz, DMSO-d6) δ 13.27 (s, 1H), 11.69 (s, 1H), 8.81 (d, J=7.5 Hz, 1H), 8.76 (s, 1H), 8.27 (s, 1H), 8.13 (d, J=8.4 Hz, 1H), 8.03 (t, J=8.1 Hz, 1H), 7.96 (s, 1H), 7.92 (t, J=58.5 Hz, 1H), 7.55 (dd, J=7.4, 5.0 Hz, 1H), 7.34 (d, J=3.6 Hz, 1H), 6.79 (d, J=3.6 Hz, 1H); LCMS: purity: 100%; MS (m/e): 371.18 (MH+).

I-116: N-(1-((1,3-cis)-3-ethoxycyclobutyl)-3-(6-(trifluoromethyl)pyridin-2-yl)-1H-pyrazol-4-yl)-5-(1H-pyrazol-4-yl)furan-2-carboxamide

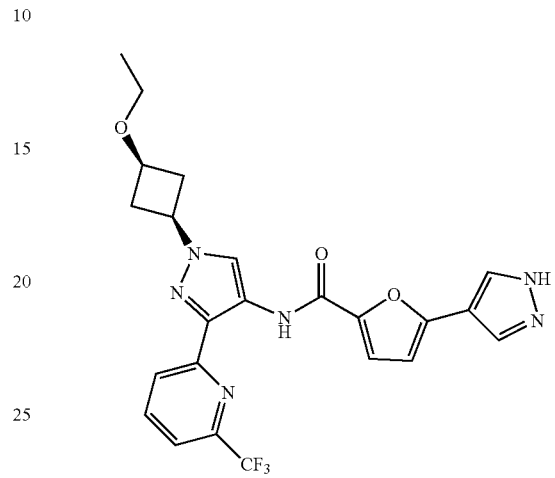

1H NMR (300 MHz, DMSO-d6) δ 13.22 (s, 1H), 10.43 (s, 1H), 8.50 (s, 1H), 8.33 (d, J=8.1 Hz, 1H), 8.20 (t, J=8.1 Hz, 1H), 8.15 (s, 1H), 7.88 (d, J=8.4 Hz, 2H), 7.25 (d, J=3.6 Hz, 1H), 6.78 (d, J=3.6 Hz, 1H), 4.64 (p, J=7.9 Hz, 1H), 3.84 (p, J=6.9 Hz, 1H), 3.41 (q, J=6.9 Hz, 2H), 2.85-2.77 (m, 2H), 2.44-2.37 (m, 2H), 1.13 (t, J=7.0 Hz, 3H); LCMS: purity: 100%; MS (m/e): 487.25 (MH+).

I-117: 5-(1H-pyrazol-4-yl)-N-(3-(pyridin-2-yl)-1-(2,2,2-trifluoroethyl)-1H-pyrazol-4-yl)furan-2-carboxamide

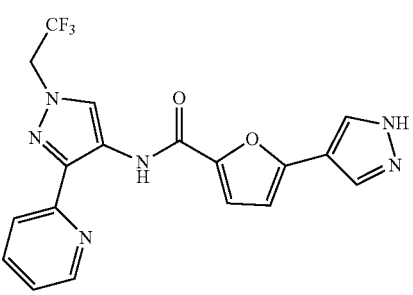 [SMILES: O=C(Nc1cn(CC(F)(F)F)nc1-c1ccccn1)c1ccc(-c2cn[nH]c2)o1]

1H NMR (300 MHz, DMSO-d6) δ 13.26 (s, 1H), 11.67 (s, 1H), 8.76 (d, J=5.1 Hz, 1H), 8.54 (s, 1H), 8.26 (s, 1H), 8.05-7.95 (m, 3H), 7.47 (t, J=5.1 Hz, 1H), 7.29 (d, J=3.6 Hz, 1H), 6.78 (d, J=3.3 Hz, 1H), 5.28 (q, J=9.1 Hz, 2H); LCMS: purity: 100%; MS (m/e): 403.18 (MH+); LCMS: purity: 100%; MS (m/e): 403.18 (MH+).

217

I-119: N-(1-(2-ethoxyethyl)-3-(thiazol-2-yl)-1H-pyrazol-4-yl)-5-(1H-pyrazol-4-yl)furan-2-carboxamide

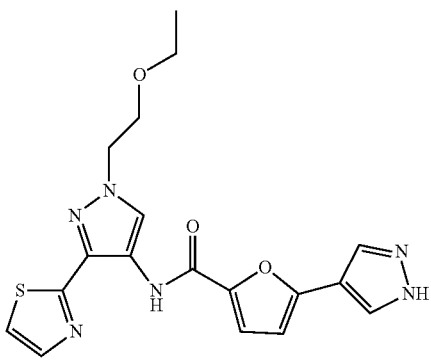 [SMILES: CCOCCn1cc(NC(=O)c2ccc(-c3cn[nH]c3)o2)c(-c2nccs2)n1]

¹H NMR (400 MHz, DMSO-d₆) δ 8.36 (s, 1H), 8.11 (s, 2H), 8.07 (d, J=3.3 Hz, 1H), 7.78 (d, J=3.2 Hz, 1H), 7.28 (d, J=3.6 Hz, 1H), 6.77 (d, J=3.5 Hz, 1H), 4.34 (t, J=5.3 Hz, 2H), 3.81-3.71 (m, 2H), 3.43 (q, J=7.0 Hz, 2H), 1.06 (t, J=7.0 Hz, 3H).

MS (ESI) (m/z): 399 [M+H]⁺

I-120: 5-(1H-pyrazol-4-yl)-N-(1-(tetrahydrofuran-3-yl)-3-(thiazol-2-yl)-1H-pyrazol-4-yl)furan-2-carboxamide

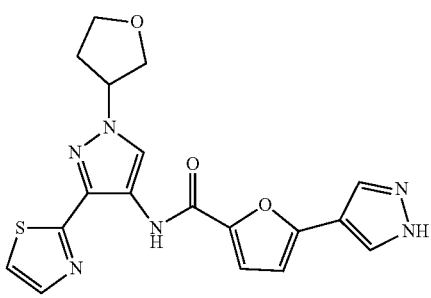 [SMILES: O=C(Nc1cn(C2CCOC2)nc1-c1nccs1)c1ccc(-c2cn[nH]c2)o1]

¹H NMR (300 MHz, DMSO-d₆) ι 13.20 (s, 1H), 10.78 (s, 1H), 8.32 (s, 1H), 8.20 (s, 1H), 8.03 (d, J=3.3 Hz, 1H), 7.91 (s, 1H), 7.76 (d, J=3.3 Hz, 1H), 7.24 (d, J=3.6 Hz, 1H), 6.73 (d, J=3.6 Hz, 1H), 5.11 (dq, J=8.5, 4.1 Hz, 1H), 4.03-3.88 (m, 3H), 3.76 (td, J=8.3, 5.8 Hz, 1H), 2.42-2.31 (m, 1H), 2.30-2.17 (m, 1H).

MS (ESI) (m/z): 397 [M+H]⁺

218

I-122: 5-(1-cyclobutyl-1H-pyrazol-4-yl)-N-(1-cyclobutyl-3-(pyridin-2-yl)-1H-pyrazol-4-yl)furan-2-carboxamide

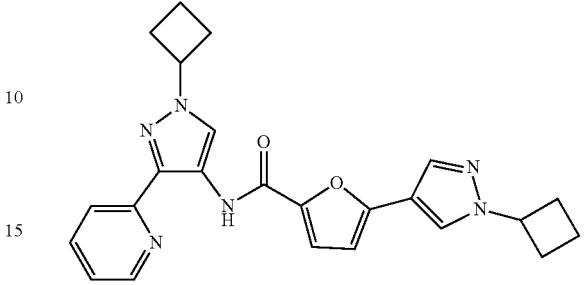

MS (ESI) (m/z): 429 [M+H]⁺

I-124: N-(1-((cis)-4-hydroxycyclohexyl)-3-(pyridin-2-yl)-1H-pyrazol-4-yl)-5-(1H-pyrazol-4-yl)furan-2-carboxamide

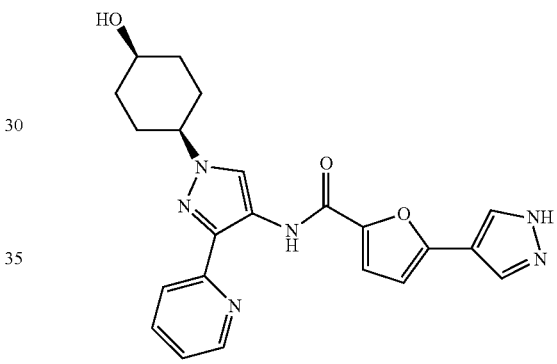

¹H NMR (300 MHz, DMSO-d₆) δ 13.23 (s, 1H), 11.64 (s, 1H), 8.72 (d, J=3.0 Hz, 1H), 8.34 (s, 1H), 7.98 (m, 3H), 7.39 (m, 1H), 7.26 (d, J=3.6 Hz, 1H), 6.77 (d, J=3.6 Hz, 1H), 6.49 (s, 1H), 4.58 (m, 1H), 4.27 (m, 1H), 3.85 (m, 1H), 2.21 (m, 2H), 1.88 (m, 4H), 1.58 (m, 2H). LCMS: purity: 81.36%. MS (m/e): 418.46 (MH⁺).

I-126: N-(1-((trans)-4-hydroxycyclohexyl)-3-(pyridin-2-yl)-1H-pyrazol-4-yl)-5-(1H-pyrazol-4-yl)furan-2-carboxamide

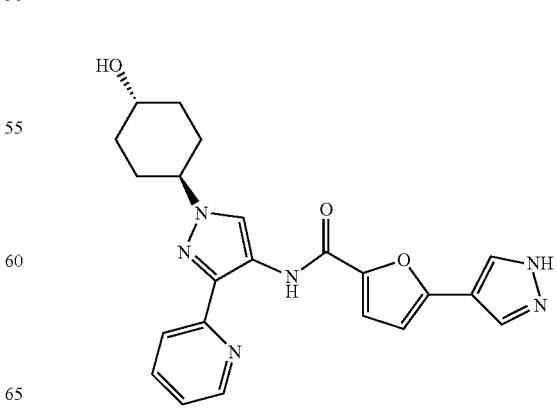

¹H NMR (300 MHz, DMSO-d₆) δ 13.26 (s, 1H), 11.64 (s, 1H), 8.71 (d, J=5.1 Hz, 1H), 8.35 (s, 1H), 8.24 (m, 1H), 7.95 (m, 3H), 7.40 (t, J=6.9 Hz, 1H), 7.25 (d, J=3.6 Hz, 1H), 6.77 (d, J=3.6 Hz, 1H), 4.66 (m, 1H), 4.25 (m, 1H), 4.27 (m, 1H), 3.52 (m, 1H), 1.95 (m, 6H), 1.38 (m, 2H). LCMS: purity: 89.15%. MS (m/e): 418.46 (MH⁺).

I-128: 5-(1H-pyrazol-4-yl)-N-(3-(pyridin-2-yl)-1-((trans)-3-(2,2,2-trifluoroethoxy)cyclobutyl)-1H-pyrazol-4-yl)furan-2-carboxamide

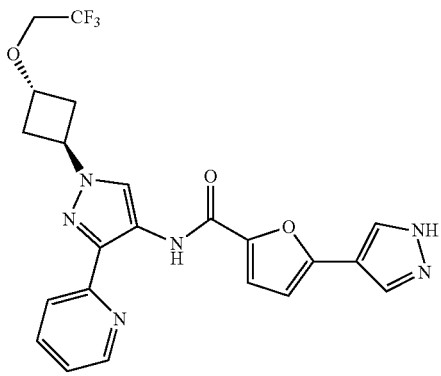 [SMILES: O=C(Nc1cn([C@H]2C[C@H](OCC(F)(F)F)C2)nc1-c1ccccn1)c1ccc(-c2cn[nH]c2)o1]

¹H NMR (300 MHz, DMSO-d₆) δ 13.25 (s, 1H), 11.64 (s, 1H), 8.73 (d, J=4.8 Hz, 1H), 8.42 (s, 1H), 8.25 (s, 1H), 8.07 (d, J=7.8 Hz, 1H), 7.96 (t, J=7.8 Hz, 1H), 7.43 (t, J=6.0 Hz, 1H), 7.26 (d, J=3.6 Hz, 1H), 6.77 (d, J=3.6 Hz, 1H), 5.08 (m, 1H), 4.54 (m, 1H), 4.06 (m, 2H), 2.74 (m, 2H), 2.58 (m, 2H). LCMS: purity: 92.43%. MS (m/e): 472.43 (MH⁺).

I-130: N-(1-((trans)-4-ethoxycyclohexyl)-3-(pyridin-2-yl)-1H-pyrazol-4-yl)-5-(1H-pyrazol-4-yl)furan-2-carboxamide

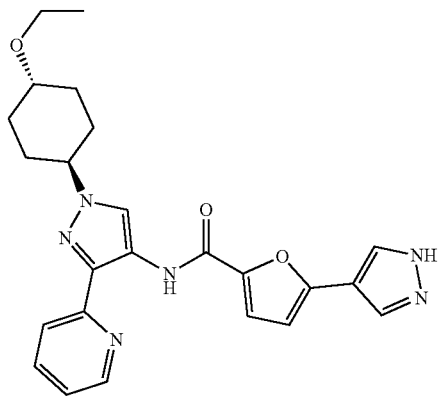 [SMILES: CCO[C@H]1CC[C@H](n2cc(NC(=O)c3ccc(-c4cn[nH]c4)o3)c(-c3ccccn3)n2)CC1]

¹H NMR (300 MHz, DMSO-d₆) δ 13.20 (s, 1H), 11.59 (s, 1H), 8.67 (d, J=4.2 Hz, 1H), 8.30 (s, 1H), 8.19 (s, 1H), 7.92 (m, 2H), 7.35 (m, 2H), 7.21 (d, J=3.3 Hz, 1H), 4.77 (m, 1H), 3.93 (m, 1H), 3.40 (m, 2H), 2.04 (m, 4H), 1.81 (m, 2H), 1.73 (t, J=6.9 Hz, 3H). LCMS: purity: 93.93%. MS (m/e): 446.51 (MH⁺).

I-132: N-(1-((cis)-3-ethoxycyclopentyl)-3-(pyridin-2-yl)-1H-pyrazol-4-yl)-5-(1H-pyrazol-4-yl)furan-2-carboxamide

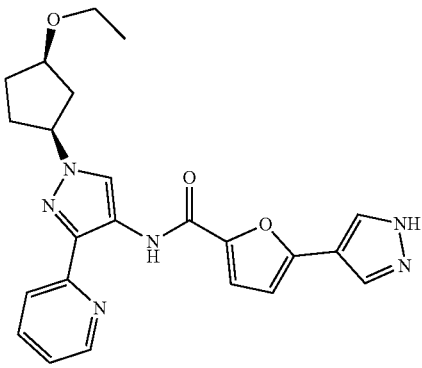 [SMILES: CCO[C@@H]1CC[C@H](n2cc(NC(=O)c3ccc(-c4cn[nH]c4)o3)c(-c3ccccn3)n2)C1]

¹H NMR (300 MHz, DMSO-d₆) δ 13.20 (s, 1H), 11.59 (s, 1H), 8.67 (d, J=4.8 Hz, 1H), 8.38 (s, 1H), 8.20 (s, 1H), 7.92 (m, 2H), 7.35 (m, 1H), 7.21 (d, J=3.3 Hz, 1H), 6.71 (d, J=3.6 Hz, 1H), 4.24 (m, 1H), 3.44 (m, 2H), 2.01 (m, 4H), 1.81 (m, 2H), 1.32 (m, 2H), 1.05 (t, J=6.9 Hz, 3H). LCMS: purity: 98.04%. MS (m/e): 432.48 (MH⁺).

I-134: N-(1-((cis)-3-hydroxycyclopentyl)-3-(pyridin-2-yl)-1H-pyrazol-4-yl)-5-(1H-pyrazol-4-yl)furan-2-carboxamide

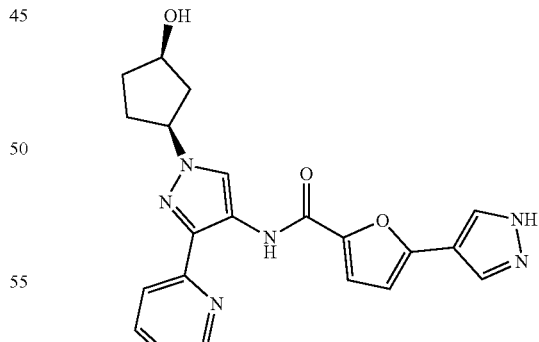

¹H NMR (300 MHz, DMSO-d₆) δ 11.64 (s, 1H), 8.72 (d, J=4.8 Hz, 1H), 8.43 (d, J=14.7 Hz, 1H), 8.10 (s, 1H), 7.94 (m, 2H), 7.41 (m, 1H), 7.27 (m, 1H), 6.77 (d, J=3.6 Hz, 1H), 4.79 (m, 1H), 4.20 (m, 1H), 2.39 (m, 2H), 2.06 (m, 2H), 1.80 (m, 2H). LCMS: purity: 93.14%. MS (m/e): 404.43 (MH⁺).

I-136: N-(1-((trans)-3-hydroxycyclopentyl)-3-(pyridin-2-yl)-1H-pyrazol-4-yl)-5-(1H-pyrazol-4-yl)furan-2-carboxamide I-140: N-(1-((cis)-3-ethoxy-2-fluorocyclobutyl)-3-(pyridin-2-yl)-1H-pyrazol-4-yl)-5-(1H-pyrazol-4-yl)furan-2-carboxamide

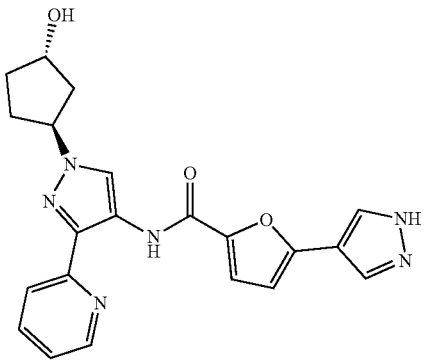 [SMILES: O=C(Nc1cn([C@H]2CC[C@H](O)C2)nc1-c1ccccn1)c1ccc(-c2cn[nH]c2)o1]

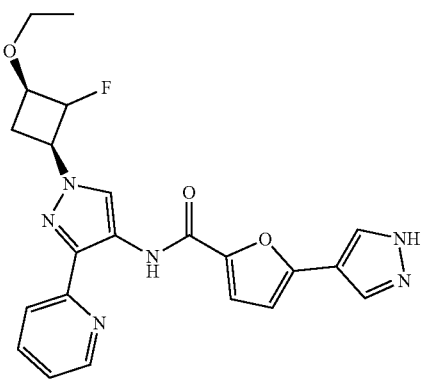

¹H NMR (300 MHz, DMSO-d₆) δ 11.63 (s, 1H), 8.71 (d, J=3.9 Hz, 1H), 8.43 (d, J=6.3 Hz, 1H), 8.37 (s, 1H), 8.09 (m, 1H), 7.93 (m, 3H), 7.40 (m, 1H), 7.27 (m, 1H), 7.76 (d, J=3.6 Hz, 1H), 4.97 (m, 1H), 4.37 (m, 1H), 2.33 (m, 2H), 2.07 (m, 2H), 1.93 (m, 2H). LCMS: purity: 90.43%. MS (m/e): 404.43 (MH⁺).

I-138: N-(1-((cis)-3-ethoxycyclobutyl)-3-(5-fluoropyridin-2-yl)-1H-pyrazol-4-yl)-5-(1H-pyrazol-4-yl)furan-2-carboxamide ¹H NMR (300 MHz, CDCl₃) δ 11.81 (s, 1H), 8.66 (d, J=3.3 Hz, 1H), 8.42 (s, 1H), 8.14 (m, 1H), 7.79 (m, 1H), 7.48 (m, 2H), 7.25 (m, 2H), 6.53 (m, 1H), 5.29 (m, 1H), 4.42 (m, 1H), 3.97 (m, 1H), 3.64 (m, 1H), 2.75 (m, 1H), 2.17 (m, 1H), 1.59 (m, 1H), 1.29 (t, J=7.5 Hz, 3H). LCMS: purity: 94.28%. MS (m/e): 436.45 (MH⁺).

I-142: N-(1-((cis)-3-ethoxycyclobutyl)-3-(3-fluoropyridin-2-yl)-1H-pyrazol-4-yl)-5-(1H-pyrazol-4-yl)furan-2-carboxamide

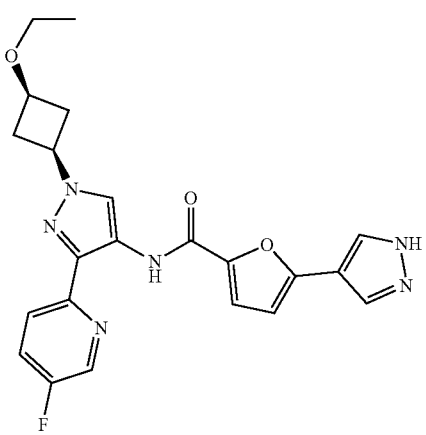 [SMILES: CCO[C@H]1C[C@@H](n2cc(NC(=O)c3ccc(-c4cn[nH]c4)o3)c(-c3ccc(F)cn3)n2)C1]

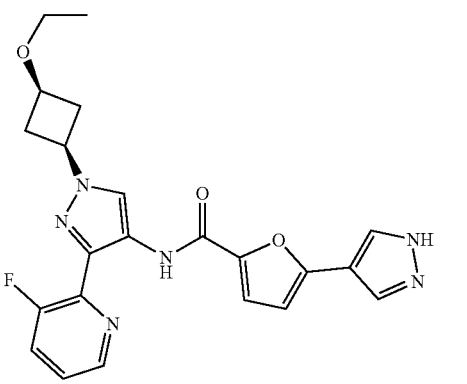 [SMILES: CCO[C@H]1C[C@@H](n2cc(NC(=O)c3ccc(-c4cn[nH]c4)o3)c(-c3ncccc3F)n2)C1]

¹H NMR (300 MHz, DMSO-d₆) δ 13.24 (s, 1H), 11.20 (s, 1H0, 8.71 (d, J=3.0 Hz, 1H), 8.40 (s, 1H), 8.26 (s, 1H), 8.12 (m, 1H), 7.88 (m, 2H), 7.27 (m, 1H), 6.76 (m, 1H), 4.60 (m, 1H), 3.82 (m, 1H), 3.36 (m, 2H), 2.77 (m, 2H), 2.42 (m, 2H), 1.21 (t, J=7.2 Hz, 3H). LCMS: purity: 100%. MS (m/e): 436.45 (MH⁺).

¹H NMR (300 MHz, DMSO-d₆) δ 13.25 (s, 1H), 11.44 (s, 1H), 8.62 (m, 1H), 8.45 (s, 1H), 8.09 (s, 2H), 7.91 (m, 1H), 7.54 (m, 1H), 7.27 (m, 1H), 6.76 (d, J=3.6 Hz, 1H), 4.62 (m, 1H), 3.81 (m, 1H), 3.39 (m, 2H), 2.79 (m, 2H), 2.41 (m, 2H), 1.13 (t, J=7.2 Hz, 3H). LCMS: purity: 100%. MS (m/e): 436.45 (MH⁺).

I-144: N-(1-((cis)-3-ethoxycyclobutyl)-3-(6-fluoro-pyridin-2-yl)-1H-pyrazol-4-yl)-5-(1H-pyrazol-4-yl)furan-2-carboxamide

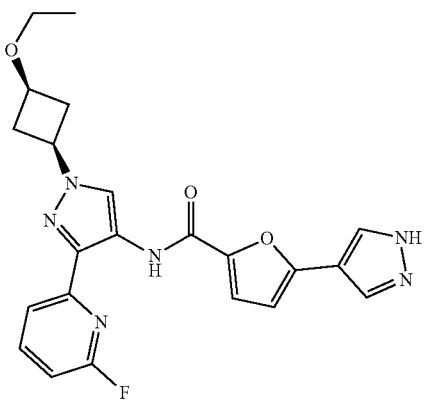 [SMILES: CCO[C@H]1C[C@@H](n2cc(NC(=O)c3ccc(-c4cn[nH]c4)o3)c(-c3cccc(F)n3)n2)C1]

$^{1}$H NMR (300 MHz, DMSO-d$_{6}$) δ 13.28 (s, 1H), 10.90 (s, 1H), 8.44 (s, 1H), 8.23 (s, 1H), 8.12 (m, 1H), 7.98 (m, 1H), 7.50 (m, 2H), 7.27 (m, 1H), 6.78 (d, J=3.6 Hz, 1H), 4.62 (m, 1H), 3.83 (m, 1H), 3.37 (m, 2H), 2.80 (m, 2H), 2.48 (m, 2H, 1.15 (t, J=6.9 Hz, 3H). LCMS: purity: 100%. MS (m/e): 436.45 (MH$^{+}$).

I-146: 5-(1H-pyrazol-4-yl)-N-(3-(pyridin-2-yl)-1-((cis)-3-(2,2,2-trifluoroethoxy)cyclobutyl)-1H-pyrazol-4-yl)furan-2-carboxamide

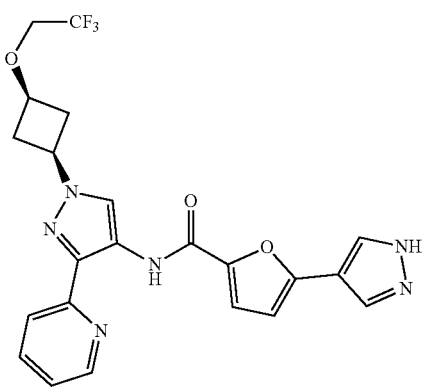 [SMILES: O=C(Nc1cn([C@H]2C[C@@H](OCC(F)(F)F)C2)nc1-c1ccccn1)c1ccc(-c2cn[nH]c2)o1]

$^{1}$H NMR (300 MHz, DMSO-d$_{6}$) δ 11.63 (s, 1H), 8.74 (t, J=4.8 Hz, 1H), 8.42 (s, 1H), 8.09 (s, 1H), 8.05 (s, 1H), 7.93 (m, 2H), 7.42 (m, 1H), 7.26 (d, J=3.9 Hz, 1H), 6.76 (d, J=3.6 Hz, 1H), 5.08 (m, 1H), 4.54 (m, 1H), 4.06 (m, 2H), 2.75 (m, 2H), 2.54 (m, 2H). LCMS: purity: 95.52%. MS (m/e): 472.43 (MH$^{+}$).

I-148: N-(1-((cis)-3-ethoxycyclobutyl)-3-(4-fluoro-pyridin-2-yl)-1H-pyrazol-4-yl)-5-(1H-pyrazol-4-yl)furan-2-carboxamide

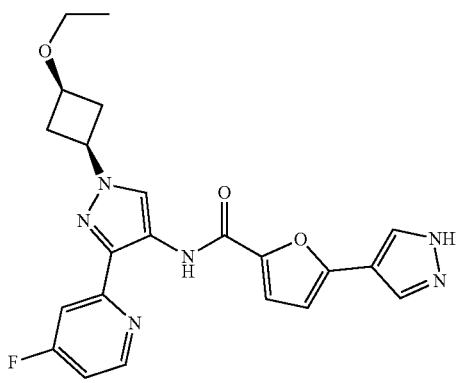 [SMILES: CCO[C@H]1C[C@@H](n2cc(NC(=O)c3ccc(-c4cn[nH]c4)o3)c(-c3cc(F)ccn3)n2)C1]

$^{1}$H NMR (300 MHz, DMSO-d$_{6}$) δ 13.41 (s, 1H), 12.02 (s, 1H), 8.81 (m, 1H), 8.50 (m, 2H), 8.29 (s, 1H), 7.80 (s, 1H), 7.76 (m, 1H), 7.34 (m, 2H), 4.56 (m, 1H), 3.84 (m, 1H), 3.43 (m, 2H), 2.80 (m, 2H), 2.42 (m, 2H), 1.16 (t, J=6.9 Hz, 3H). LCMS: purity: 100%. MS (m/e): 436.45 (MH$^{+}$).

I-150: N-(3-(6-fluoropyridin-2-yl)-1-((cis)-3-(2,2,2-trifluoroethoxy)cyclobutyl)-1H-pyrazol-4-yl)-5-(1H-pyrazol-4-yl)furan-2-carboxamide

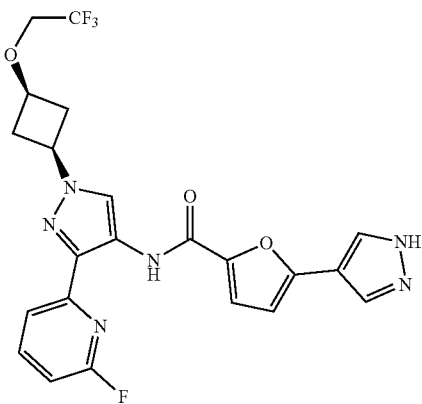 [SMILES: O=C(Nc1cn([C@H]2C[C@@H](OCC(F)(F)F)C2)nc1-c1cccc(F)n1)c1ccc(-c2cn[nH]c2)o1]

$^{1}$H NMR (300 MHz, DMSO-d$_{6}$) δ 13.24 (s, 1H), 11.45 (s, 1H), 8.62 (d, J=4.5 Hz, 1H), 8.48 (s, 1H), 8.25 (s, 1H), 7.91 (m, 2H), 7.52 (m, 1H), 7.27 (d, J=3.3 Hz, 1H), 6.76 (d, J=3.6 Hz, 1H), 5.10 (m, 1H), 4.51 (m, 1H), 4.03 (m, 2H), 2.72 (m, 2H), 2.54 (m, 2H). LCMS: purity: 97.7%. MS (m/e): 490.42 (MH$^{+}$).

I-152: N-(3-(3-fluoropyridin-2-yl)-1-((cis)-3-(2,2,2-trifluoroethoxy)cyclobutyl)-1H-pyrazol-4-yl)-5-(1H-pyrazol-4-yl)furan-2-carboxamide

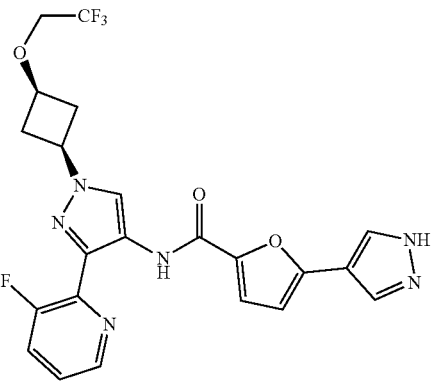 [SMILES: O=C(Nc1cn([C@H]2C[C@@H](OCC(F)(F)F)C2)nc1-c1ncccc1F)c1ccc(-c2cn[nH]c2)o1]

¹H NMR (300 MHz, DMSO-d₆) δ 13.24 (s, 1H), 11.44 (s, 1H), 8.62 (d, J=4.5 Hz, 1H), 8.46 (s, 1H), 8.24 (s, 1H), 7.91 (m, 2H), 7.54 (m, 1H), 7.27 (d, J=3.3 Hz, 1H), 6.76 (d, J=3.6 Hz, 1H), 4.64 (m, 1H), 4.06 (m, 2H), 3.58 (m, 1H), 2.83 (m, 2H), 2.54 (m, 2H). LCMS: purity: 94.59%. MS (m/e): 490.42 (MH⁺).

I-154: N-(1-((trans)-4-ethoxycyclohexyl)-3-(3-fluoropyridin-2-yl)-1H-pyrazol-4-yl)-5-(1H-pyrazol-4-yl)furan-2-carboxamide

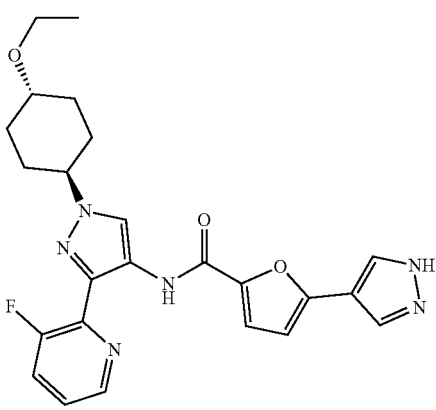 [SMILES: CCO[C@H]1CC[C@H](n2cc(NC(=O)c3ccc(-c4cn[nH]c4)o3)c(-c3ncccc3F)n2)CC1]

¹H NMR (300 MHz, DMSO-d₆) δ 13.26 (s, 1H), 11.47 (s, 1H), 8.62 (d, J=4.2 Hz, 1H), 8.50 (s, 2H), 8.41 (s, 1H), 7.90 (m, 2H), 7.50 (m, 1H), 7.26 (d, J=3.6 Hz, 1H), 6.76 (d, J=3.6 Hz, 1H), 4.31 (m, 1H), 3.46 (m, 2H), 3.36 (m, 1H), 2.05 (m, 4H), 1.82 (m, 2H), 1.35 (m, 2H), 1.12 (t, J=7.2 Hz, 3H). LCMS: purity: 100%. MS (m/e): 464.50 (MH⁺).

I-156: N-(3-(3,6-difluoropyridin-2-yl)-1-((cis)-3-ethoxycyclobutyl)-1H-pyrazol-4-yl)-5-(1H-pyrazol-4-yl)furan-2-carboxamide

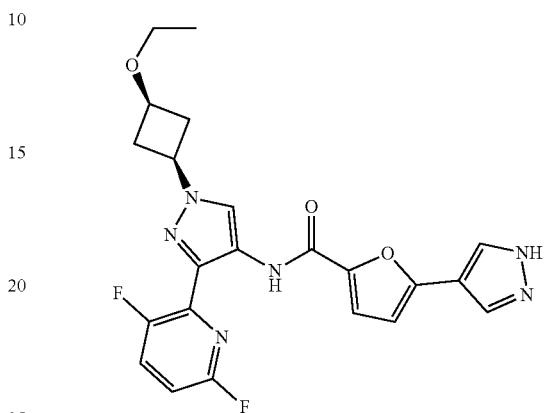

¹H NMR (300 MHz, DMSO-d₆) δ 13.26 (s, 1H), 10.75 (s, 1H), 8.48 (s, 1H), 8.21 (s, 1H), 8.13 (m, 1H), 7.98 (s, 1H), 7.29 (m, 2H), 6.78 (d, J=3.6 Hz, 1H), 4.63 (m, 1H), 3.83 (m, 1H), 3.42 (m, 2H), 2.78 (m, 2H), 2.41 (m, 2H), 1.13 (t, J=7.2 Hz, 3H). LCMS: purity: 100%. MS (m/e): 454.44 (MH⁺).

II-2: 1-(isobutyryloxy)ethyl 4-(4-((1-methyl-3-(pyridin-2-yl)-1H-pyrazol-4-yl)carbamoyl)thiazol-2-yl)-1H-pyrazole-1-carboxylate

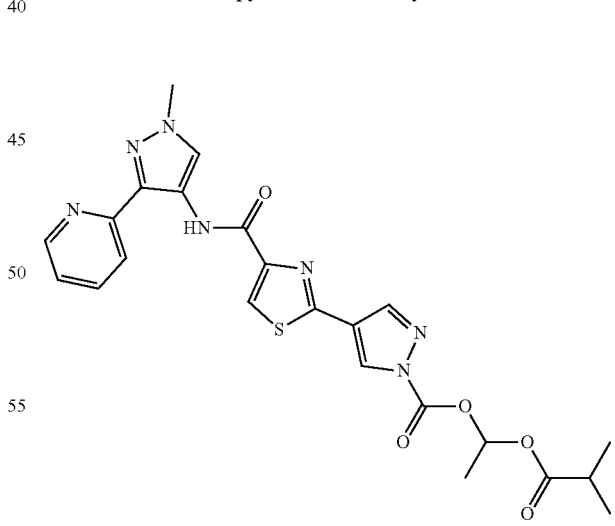

¹H NMR (DMSO d₆, 300 MHz): δ 12.23 (s, 1H), 9.12 (s, 1H), 8.75-8.73 (m, 1H), 8.48-8.43 (m, 3H), 8.02-7.91 (m, 2H), 7.42-7.38 (m, 1H), 7.05-7.00 (m, 1H), 3.96 (s, 3H), 2.63 (septet, J=6.7 Hz, 1H), 1.66 (d, J=6.7 Hz, 3H), 1.14-1.11 (m, 6H);

LCMS (m/z): 422.60 (MH⁺).

II-3: tert-butyl (S)-(3-methyl-1-(4-(4-((1-methyl-3-(pyridin-2-yl)-1H-pyrazol-4-yl)carbamoyl)thiazol-2-yl)-1H-pyrazol-1-yl)-1-oxobutan-2-yl)carbamate

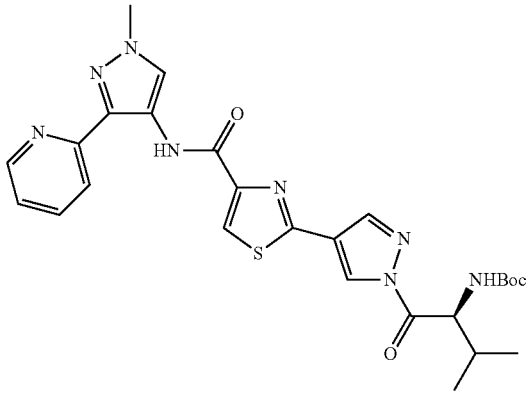 [SMILES: CC(C)[C@H](NC(=O)OC(C)(C)C)C(=O)n1cc(-c2nc(C(=O)Nc3cn(C)nc3-c3ccccn3)cs2)cn1]

¹H NMR (DMSO d₆, 300 MHz): δ 12.22 (s, 1H), 9.21 (s, 1H), 8.79-8.76 (m, IH), 8.51-8.44 (m, 3H), 8.02-7.91 (m, 2H), 7.53-7.40 (m, 2H), 5.26-5.24 (m, IH), 3.96 (s, 3H), 1.40 (s, 9H), 1.23-1.18 (m, 1H), 0.95 (d, J=6.7 Hz, 6H), 0.86-0.80 (m, 1H);

LCMS (m/z): 551.72 (MH⁺).

II-4: 2-(1-((5-methyl-2-oxo-1,3-dioxol-4-yl)methyl)-1H-pyrazol-4-yl)-N-(1-methyl-3-(pyridin-2-yl)-1H-pyrazol-4-yl)thiazole-4-carboxamide

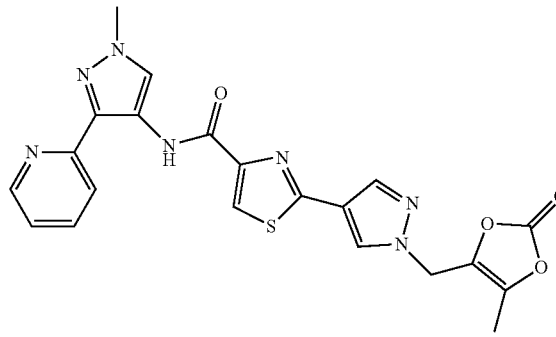

¹H NMR (300 MHz, DMSO-d₆) δ 12.23 (s, 1H), 8.95 (s, 1H), 8.77 (d, J=6.2 Hz, 1H), 8.44 (s, 1H), 8.40 (s, 1H), 8.34 (s, 1H), 8.05-7.87 (m, 2H), 7.42 (t, J=6.6 Hz, 1H), 3.96 (s, 3H), 2.45 (s, 3H);

LCMS (m/z): 464.61 (MH⁺).

II-5: 1-methylcyclopropyl 4-(4-((1-methyl-3-(pyridin-2-yl)-1H-pyrazol-4-yl)carbamoyl)thiazol-2-yl)-1H-pyrazole-1-carboxylate

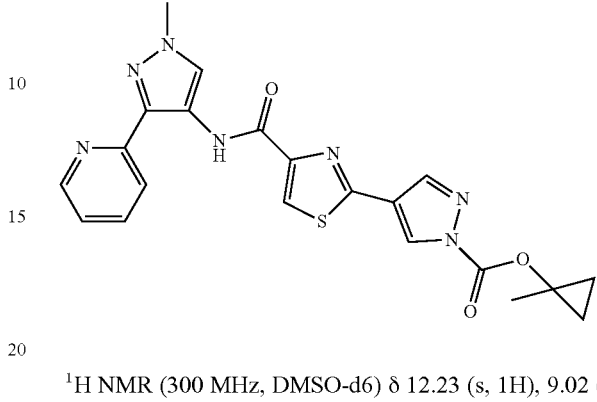

¹H NMR (300 MHz, DMSO-d6) δ 12.23 (s, 1H), 9.02 (t, J=0.6 Hz, 1H), 8.73 (ddd, J=5.0, 1.7, 0.9 Hz, 1H), 8.58-8.27 (m, 3H), 8.15-7.77 (m, 3H), 7.41 (ddd, J=7.1, 4.9, 1.5 Hz, 1H), 3.96 (d, J=0.6 Hz, 3H), 1.69 (s, 3H), 1.33-1.04 (m, 2H), 1.03-0.70 (m, 2H);

LCMS (m/z): 450.60 (MH⁺).

II-6: 1-((4-methoxybenzyl)oxy)-2-methylpropan-2-yl 4-(4-((1-methyl-3-(pyridin-2-yl)-1H-pyrazol-4-yl)carbamoyl)thiazol-2-yl)-1H-pyrazole-1-carboxylate

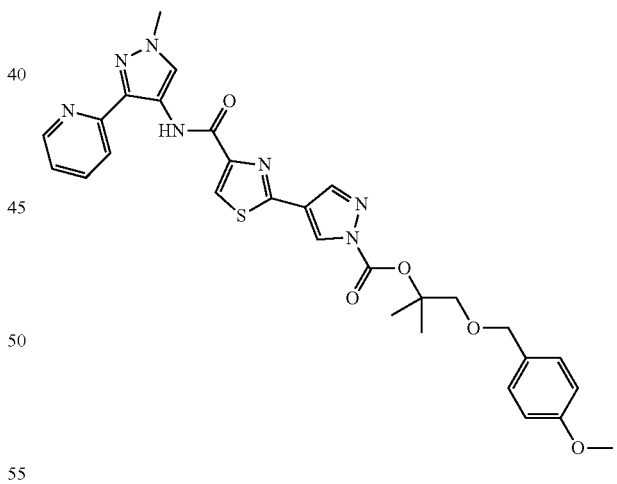

¹H NMR (300 MHz, DMSO-d6) δ 12.34-12.12 (m, 1H), 9.07-8.85 (m, 1H), 8.83-8.61 (m, 1H), 8.54-8.34 (m, 2H), 7.96 (dtd, J=16.9, 8.0, 1.4 Hz, 2H), 7.38 (ddd, J=7.3, 4.8, 1.3 Hz, 1H), 7.34-7.11 (m, 2H), 6.94-6.70 (m, 2H), 4.49 (s, 2H), 3.96 (d, J=1.1 Hz, 3H), 3.81-3.60 (m, 5H), 1.80-1.47 (m, 6H);

LCMS (m/z): 588.74 (MH⁺).

II-7: diethyl ((4-(4-((1-methyl-3-(pyridin-2-yl)-1H-pyrazol-4-yl)carbamoyl)thiazol-2-yl)-1H-pyrazol-1-yl)methyl)phosphonate

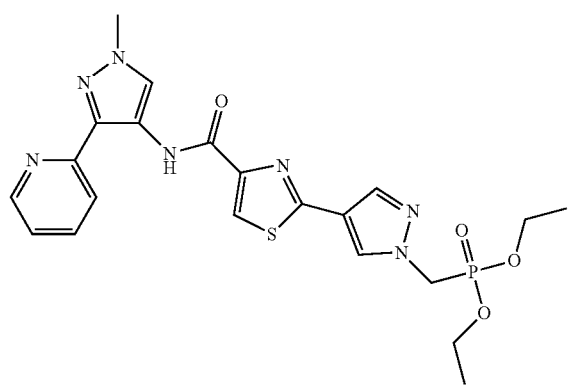 [SMILES: CCOP(=O)(Cn1cc(-c2nc(C(=O)Nc3cn(C)nc3-c3ccccn3)cs2)cn1)OCC]

LCMS (m/z): 502.52 (MH⁺).

II-8: sodium ((4-(4-((1-methyl-3-(pyridin-2-yl)-1H-pyrazol-4-yl)carbamoyl)thiazol-2-yl)-1H-pyrazol-1-yl)methyl)phosphonate

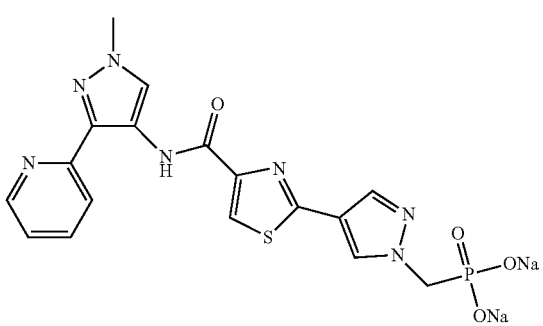

$^1$H NMR (300 MHz, Deuterium Oxide) δ 8.14 (t, J=6.0 Hz, 2H), 7.94-7.69 (m, 1H), 7.71-7.45 (m, 3H), 7.31 (t, J=9.7 Hz, 1H), 7.25-7.01 (m, 1H), 4.29 (d, J=13.3 Hz, 2H), 3.67 (s, 3H);
LCMS (m/z): 446.50 (MH⁺).

II-10: 2-(1H-pyrazol-4-yl)-N-(3-(pyridin-2-yl)-1-(tetrahydro-2H-pyran-4-yl)-1H-pyrazol-4-yl)thiazole-4-carboxamide

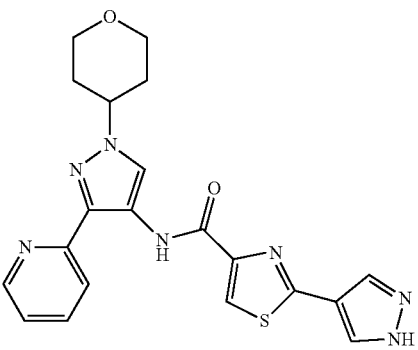 [SMILES: O=C(Nc1cn(C2CCOCC2)nc1-c1ccccn1)c1csc(-c2cn[nH]c2)n1]

$^1$H NMR (300 MHz, DMSO-d6) δ 13.42 (s, 1H), 12.21 (s, 1H), 8.96-8.67 (m, 1H), 8.48 (d, J=2.8 Hz, 2H), 8.42-8.22 (m, 1H), 8.25-7.80 (m, 3H), 7.59-7.19 (m, 1H), 4.56 (s, 1H), 4.00 (dd, J=10.8, 3.7 Hz, 2H), 3.73-3.39 (m, 2H), 2.19-1.82 (m, 4H);
LCMS (m/z): 422.52 (MH⁺).

II-12: N-(1-(((1,3-trans)-3-ethoxycyclobutyl)-3-(pyridin-2-yl)-1H-pyrazol-4-yl)-2-(1H-pyrazol-4-yl)thiazole-4-carboxamide

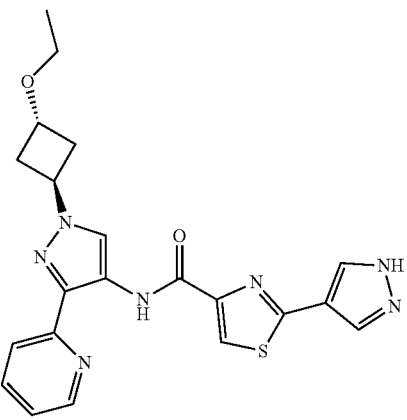 [SMILES: CCO[C@H]1C[C@H](n2cc(NC(=O)c3csc(-c4cn[nH]c4)n3)c(-c3ccccn3)n2)C1]

1H NMR (300 MHz, DMSO-d6) δ 13.41 (s, 1H), 12.18 (s, 1H), 8.75 (d, J=4.2 Hz, 1H), 8.47 (m, 2H), 8.27 (s, 1H), 8.09 (s, 1H), 8.04 (d, J=8.1 Hz, 1H), 7.93 (t, J=7.2 Hz, 1H), 7.42 (dd, J=5.1 Hz, 1H), 5.06 (p, J=6.9 Hz, 1H), 4.28 (p, J=6.6 Hz, 1H), 3.40 (q, J=6.9 Hz, 2H), 2.71 (m, 2H), 1.14 (t, J=6.9 Hz, 3H); LCMS: purity: 86.42%; MS (m/e): 436.50 (MH+).

II-13: N-(1-((1,3-cis)-3-ethoxycyclobutyl)-3-(pyridin-2-yl)-1H-pyrazol-4-yl)-2-(1-methyl-1H-pyrazol-4-yl)thiazole-4-carboxamide

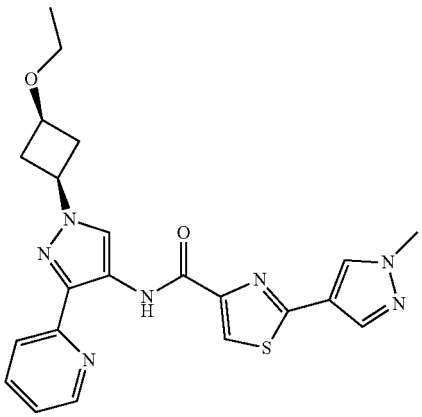 [SMILES: CCO[C@H]1C[C@@H](n2cc(NC(=O)c3csc(-c4cnn(C)c4)n3)c(-c3ccccn3)n2)C1]

1H NMR (300 MHz, DMSO-d6) δ 12.15 (s, 1H), 8.77 (d, J=4.5 Hz, 1H), 8.46 (s, 1H), 8.43 (s, 1H), 8.27 (s, 1H), 8.04 (m, 2H), 7.93 (t, J=8.7 Hz, 1H), 7.42 (dd, J=6.0 Hz, 1H), 4.61 (p, J=7.5 Hz, 1H), 3.95 (s, 3H), 3.83 (p, J=6.6 Hz, 1H), 3.41 (q, J=6.9 Hz, 2H), 2.80 (m, 2H), 2.41 (m, 2H), 1.14 (t, J=6.9 Hz, 3H); LCMS: purity: 96.61%; MS (m/e): 450.77 (MH+).

II-14: N-(1-((1,3-cis)-3-hydroxycyclobutyl)-3-(pyridin-2-yl)-1H-pyrazol-4-yl)-2-(1H-pyrazol-4-yl)thiazole-4-carboxamide

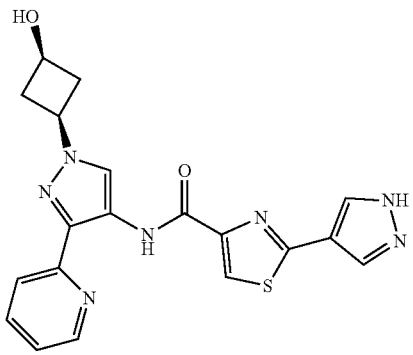 [SMILES: O=C(Nc1cn([C@H]2C[C@@H](O)C2)nc1-c1ccccn1)c1csc(-c2cn[nH]c2)n1]

1H NMR (300 MHz, DMSO-d6) δ 13.41 (s, 1H), 12.19 (s, 1H), 8.75 (d, J=4.5 Hz, 1H), 8.48 (s, 2H), 8.28 (s, 1H), 8.10 (s, 1H), 8.03 (d, J=7.8 Hz, 1H), 7.93 (t, J=8.4 Hz, 1H), 7.41 (ddd, J=7.4, 4.9, 1.3 Hz, 1H), 5.32 (d, J=6.6 Hz, 1H), 4.48 (p, J=6.6 Hz, 1H), 3.96 (q, J=6.6 Hz, 1H), 2.82-2.74 (m, 2H), 2.41-2.34 (m, 2H); LCMS: purity: 97.58%; MS (m/e): 408.53 (MH+).

II-15: N-(1-((1s,3s)-3-(dimethylamino)cyclobutyl)-3-(pyridin-2-yl)-1H-pyrazol-4-yl)-2-(1H-pyrazol-4-yl)thiazole-4-carboxamide

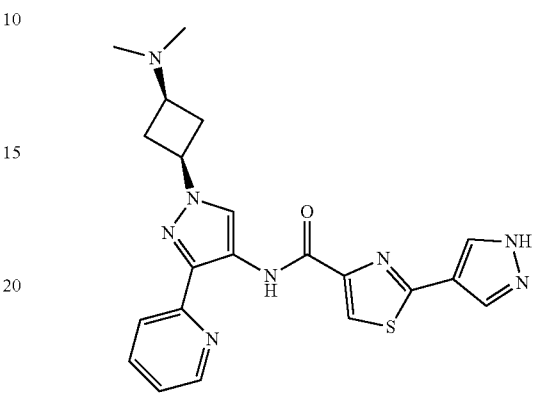

1H NMR (300 MHz, DMSO-d6) δ 13.40 (br, 1H), 12.19 (s, 1H), 8.76 (d, J=4.5 Hz, 1H), 8.52 (d, J=8.7 Hz, 2H), 8.28 (s, 1H), 8.12 (s, 1H), 8.04 (d, J=7.8 Hz, 1H), 7.94 (td, J=7.8, 1.8 Hz, 1H), 7.42 (dd, J=6.6 Hz, 1H), 4.73 (p, J=8.1 Hz, 1H), 2.71 (m, 2H), 2.40 (s, 6H); LCMS: purity: 100%; MS (m/e): 435.57 (MH+).

II-16: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate bis-sodium Salt

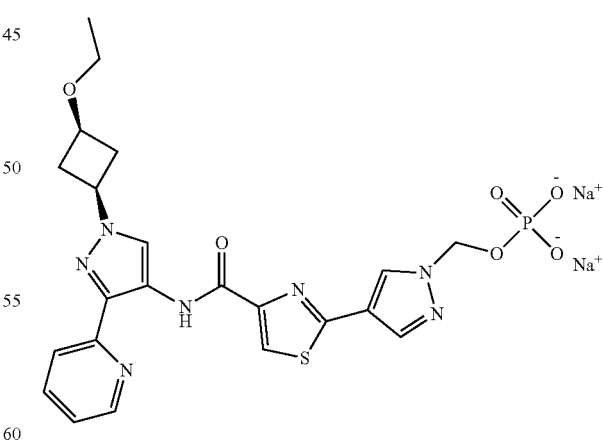

1H NMR (300 MHz, Deuterium Oxide) δ 7.77 (s, 1H), 7.67 (s, 1H), 7.50 (s, 1H), 7.45 (s, 1H), 7.31 (s, 1H), 7.08 (m, 2H), 6.95 (s, 1H), 5.50 (d, J=9.3 Hz, 2H), 4.10 (t, J=7.5 Hz, 1H), 3.87 (t, J=7.5 Hz, 2H), 3.46 (q, J=6.9 Hz, 2H), 2.78 (m, 2H), 2.14 (m, 2H), 1.12 (t, J=6.9 Hz, 3H); LCMS: purity: 100%; MS (m/e): 546.57 (MH+).

II-18: N-(1-(2-ethoxyethyl)-3-(pyridin-2-yl)-1H-pyrazol-4-yl)-2-(1H-pyrazol-4-yl)thiazole-4-carboxamide, Formic Acid Salt

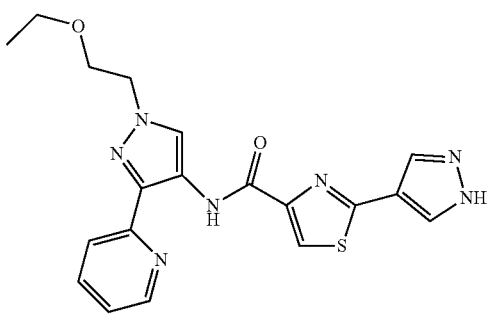 [SMILES: CCOCCn1cc(NC(=O)c2csc(-c3cn[nH]c3)n2)c(-c2ccccn2)n1]

¹H NMR (300 MHz, DMSO-d₆) δ 12.20 (s, 1H), 8.76 (ddd, J=4.9, 1.7, 1.0 Hz, 1H), 8.46 (s, 1H), 8.29 (d, J=0.5 Hz, 1H), 8.06-7.87 (m, 2H), 7.42 (ddd, J=7.3, 4.9, 1.4 Hz, 1H), 4.36 (t, J=5.3 Hz, 2H), 3.80 (t, J=5.3 Hz, 2H), 3.50-3.42 (m, 2H), 1.17-1.00 (m, 3H); MS (ESI) (m/z): 410 [M+H]⁺.

II-19: N-(1-(2-ethoxyethyl)-3-(pyridin-2-yl)-1H-pyrazol-4-yl)-2-(5-(trifluoromethyl)-1H-pyrazol-4-yl)thiazole-4-carboxamide, Formic Acid Salt

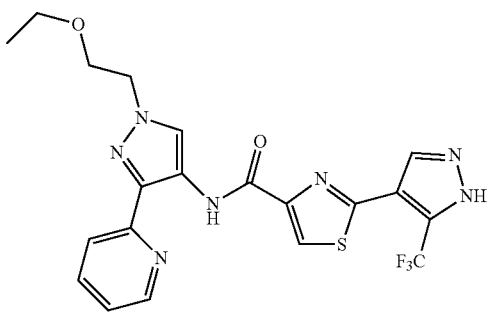 [SMILES: CCOCCn1cc(NC(=O)c2csc(-c3cn[nH]c3C(F)(F)F)n2)c(-c2ccccn2)n1]

¹H NMR (300 MHz, DMSO-d₆) δ 11.82 (s, 1H), 8.70 (d, J=1.1 Hz, 1H), 8.60 (dt, J=5.0, 1.4 Hz, 1H), 8.51 (s, 1H), 8.48 (s, 1H), 8.00 (dt, J=8.1, 1.2 Hz, 1H), 7.90 (td, J=7.7, 1.8 Hz, 1H), 7.36 (ddd, J=7.4, 5.0, 1.3 Hz, 1H), 4.36 (t, J=5.3 Hz, 2H), 3.79 (t, J=5.3 Hz, 2H), 3.46 (dd, J=14.0, 7.0 Hz, 2H), 1.09 (t, J=7.0 Hz, 3H); MS (ESI) (m/z): 478 [M+H]⁺.

II-21: N-(1-(2-ethoxyethyl)-3-(pyridin-2-yl)-1H-pyrazol-4-yl)-2-(3-methyl-1H-pyrazol-4-yl)thiazole-4-carboxamide, Formic Acid Salt

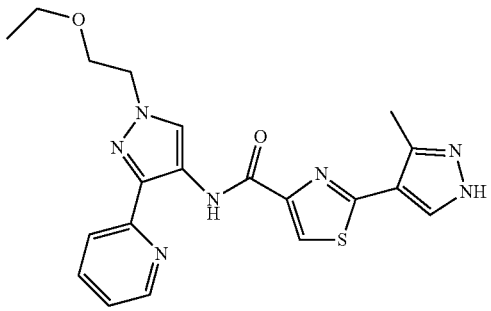 [SMILES: CCOCCn1cc(NC(=O)c2csc(-c3c[nH]nc3C)n2)c(-c2ccccn2)n1]

¹H NMR (300 MHz, DMSO-d₆) δ 8.64 (ddd, J=5.0, 1.7, 0.9 Hz, 1H), 8.51 (s, 1H), 8.31 (d, J=0.6 Hz, 1H), 8.05-7.98 (m, 1H), 7.92 (td, J=7.7, 1.8 Hz, 1H), 7.67-7.50 (m, 3H), 7.44-7.35 (m, 1H), 4.36 (t, J=5.3 Hz, 2H), 3.84-3.75 (m, 2H), 3.46 (q, J=6.9 Hz, 2H), 2.70 (s, 3H), 1.15-1.02 (m, 3H); MS (ESI) (m/z): 424 [M+H]⁺.

II-23: 2-(3,5-dimethyl-1H-pyrazol-4-yl)-N-(1-(2-ethoxyethyl)-3-(pyridin-2-yl)-1H-pyrazol-4-yl)thiazole-4-carboxamide, Formic Acid Salt

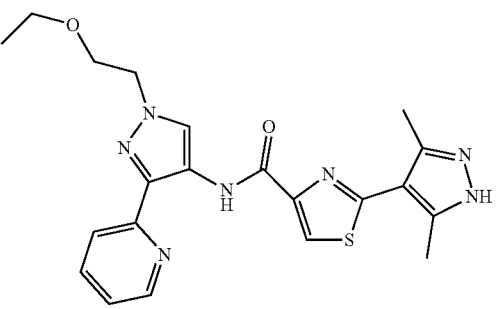 [SMILES: CCOCCn1cc(NC(=O)c2csc(-c3c(C)n[nH]c3C)n2)c(-c2ccccn2)n1]

¹H NMR (300 MHz, DMSO-d₆) δ 11.64 (s, 1H), 8.58 (dd, J=3.9, 2.7 Hz, 1H), 8.53 (s, 1H), 8.35 (d, J=0.3 Hz, 1H), 8.07-7.97 (m, 1H), 7.91 (td, J=7.7, 1.8 Hz, 1H), 7.38 (ddd, J=7.5, 5.0, 1.3 Hz, 1H), 4.36 (t, J=5.3 Hz, 2H), 3.84-3.74 (m, 2H), 3.50-3.41 (m, 2H), 2.63 (s, 3H), 2.57 (s, 3H), 1.09 (t, J=7.0 Hz, 3H); MS (ESI) (m/z): 438 [M+H]⁺.

II-26: N-(1-methyl-3-(pyridin-2-yl)-1H-pyrazol-4-yl)-2-(1H-pyrazol-4-yl)thiazole-4-carboxamide

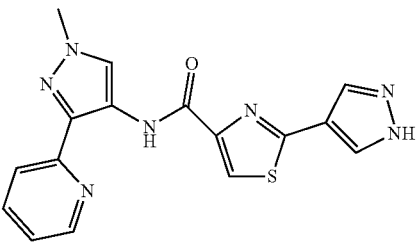

¹H NMR (300 MHz, DMSO-d₆) ι 12.20 (s, 1H), 8.76 (d, J=4.8 Hz, 0H), 8.59-8.45 (s br, 1H), 8.43 (s, 1H), 8.30 (d, J=0.4 Hz, 1H), 8.13 (s br, 1H), 8.02-7.89 (m, 2H), 7.41 (ddd, J=7.2, 4.9, 1.5 Hz, 1H), 3.96 (s, 3H); MS (ESI) (m/z): 352 [M+H]⁺.

II-27: 2-(3-methyl-1H-pyrazol-4-yl)-N-(1-methyl-3-(pyridin-2-yl)-1H-pyrazol-4-yl)thiazole-4-carboxamide

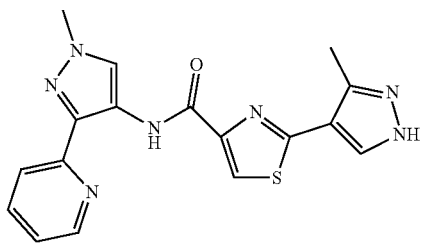 [SMILES: Cc1n[nH]cc1-c1nc(C(=O)Nc2cn(C)nc2-c2ccccn2)cs1]

¹H NMR (300 MHz, DMSO-d₆) δ 11.82 (s, 1H), 8.62 (ddd, J=5.1, 1.7, 0.9 Hz, 1H), 8.45 (s, 1H), 8.27 (s, 1H), 8.05-7.95 (m, 1H), 7.89 (td, J=7.8, 1.8 Hz, 1H), 7.83-7.65 (m, 1H), 7.36 (ddd, J=7.4, 5.0, 1.3 Hz, 1H), 3.94 (s, 3H), 2.68 (s, 3H); MS (ESI) (m/z): 366 [M+H]⁺.

II-28: N-(1-(2-methoxyethyl)-3-(pyridin-2-yl)-1H-pyrazol-4-yl)-2-(1H-pyrazol-4-yl)thiazole-4-carboxamide

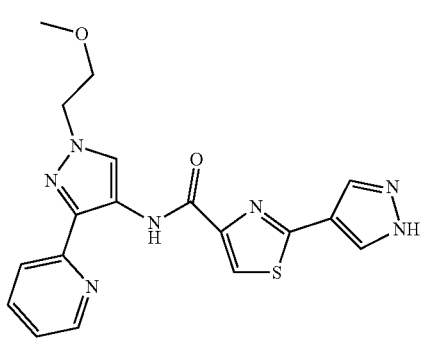 [SMILES: COCCn1cc(NC(=O)c2csc(-c3cn[nH]c3)n2)c(-c2ccccn2)n1]

¹H NMR (300 MHz, DMSO-d₆) δ 12.21 (s, 1H), 8.82-8.73 (m, 1H), 8.46 (d, J=0.8 Hz, 1H), 8.36-8.27 (m, 3H), 8.06-7.87 (m, 2H), 7.46-7.37 (m, 1H), 4.38 (t, J=5.4 Hz, 2H), 3.81-3.72 (m, 2H), 3.27 (s, 3H); MS (ESI) (m/z): 395 [M+H]⁺.

II-29: N-(1-(2-methoxyethyl)-3-(pyridin-2-yl)-1H-pyrazol-4-yl)-2-(3-methyl-1H-pyrazol-4-yl)thiazole-4-carboxamide, Formic Acid Salt

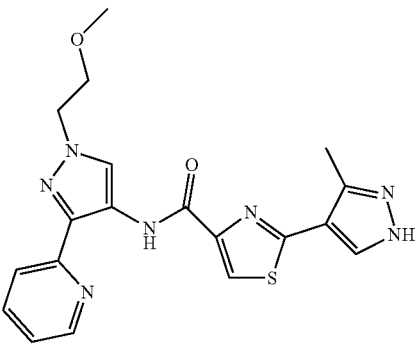 [SMILES: COCCn1cc(NC(=O)c2csc(-c3c[nH]nc3C)n2)c(-c2ccccn2)n1]

¹H NMR (300 MHz, DMSO-d₆) δ 11.85 (s, 1H), 8.67-8.61 (m, 1H), 8.49 (s, 1H), 8.30 (s, 1H), 8.15 (s, 1H), 8.05-7.99 (m, 1H), 7.92 (td, J=7.7, 1.8 Hz, 1H), 7.39 (ddd, J=7.4, 5.0, 1.3 Hz, 2H), 4.38 (t, J=5.2 Hz, 2H), 3.76 (t, J=5.2 Hz, 2H), 3.27 (s, 3H), 2.69 (s, 3H); MS (ESI) (m/z): 410 [M+H]⁺.

II-31: N-(1-(2-ethoxyethyl)-3-(pyridin-2-yl)-1H-pyrazol-4-yl)-2-(3-methyl-1H-pyrazol-4-yl)thiazole-4-carboxamide

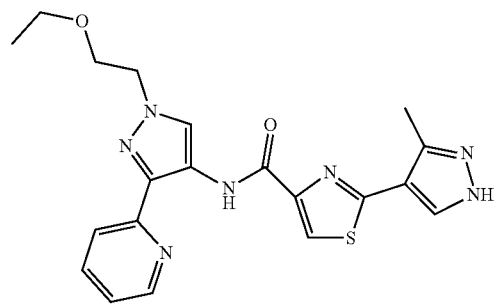 [SMILES: CCOCCn1cc(NC(=O)c2csc(-c3c[nH]nc3C)n2)c(-c2ccccn2)n1]

MS (ESI) (m/z): 424 [M+H]⁺.

II-32: 2-(1H-pyrazol-4-yl)-N-(3-(pyridin-2-yl)-1H-pyrazol-4-yl)thiazole-4-carboxamide Formic Acid Salt

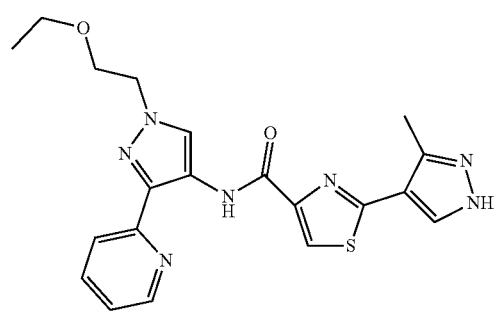 [SMILES: CCOCCn1cc(NC(=O)c2csc(-c3c[nH]nc3C)n2)c(-c2ccccn2)n1]

MS (ESI) (m/z): 338 [M+H]⁺.

II-34: N-(1-(oxetan-3-yl)-3-(pyridin-2-yl)-1H-pyrazol-4-yl)-2-(1H-pyrazol-4-yl)thiazole-4-carboxamide II-37: N-(1-(2-(2-methoxyethoxy)ethyl)-3-(pyridin-2-yl)-1H-pyrazol-4-yl)-2-(1H-pyrazol-4-yl)thiazole-4-carboxamide

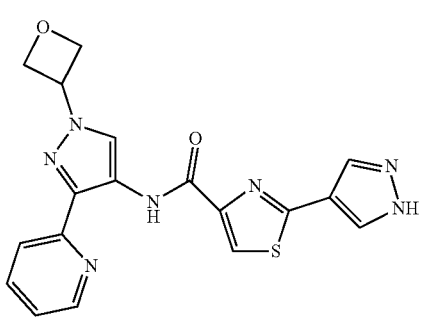 [SMILES: O=C(Nc1cn(C2COC2)nc1-c1ccccn1)c1csc(-c2cn[nH]c2)n1]

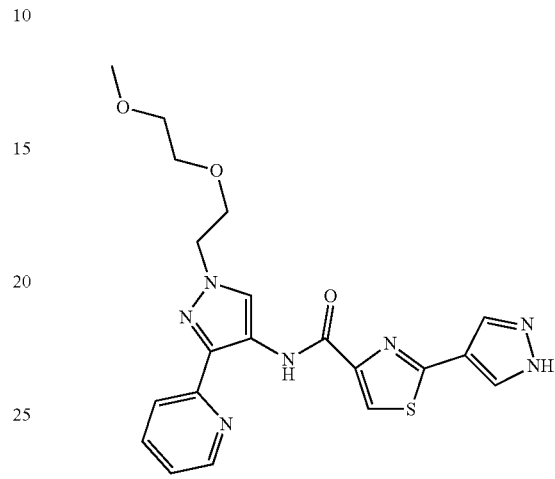

$^1$H NMR (300 MHz, DMSO-d$_6$) δ 13.43 (s, 1H), 12.22 (s, 1H), 8.78 (ddd, J=5.0, 1.8, 0.9 Hz, 1H), 8.56 (s, 1H), 8.50 (d, J=3.5 Hz, 0H), 8.29 (s, 1H), 8.10 (dt, J=8.0, 1.1 Hz, 1H), 7.96 (td, J=7.8, 1.8 Hz, 1H), 7.45 (ddd, J=7.5, 4.9, 1.3 Hz, 1H), 5.72 (tt, J=7.4, 6.5 Hz, 1H), 4.98 (dd, J=6.9, 2.0 Hz, 4H); MS (ESI) (m/z): 394 [M+H]$^+$.

II-36: Sodium (4-(4-((1-methyl-3-(pyridin-2-yl)-1H-pyrazol-4-yl)carbamoyl)thiazol-2-yl)-1H-pyrazol-1-yl)methyl phosphate $^1$H NMR (300 MHz, Acetone-d$_6$) δ 11.75 (d, J=2.6 Hz, 1H), 8.31 (dt, J=3.0, 1.4 Hz, 1H), 8.09-7.94 (m, 1H), 7.95-7.78 (m, 2H), 7.63-7.41 (m, 2H), 6.96 (dddd, J=7.4, 4.9, 2.3, 1.2 Hz, 1H), 3.98-3.85 (m, 2H), 3.45-3.34 (m, 2H), 3.16-3.05 (m, 2H), 2.97 (dt, J=3.0, 1.8 Hz, 2H), 2.76 (s, 3H); MS (ESI) (m/z): 440 [M+H]$^+$.

II-38: Potassium (4-(4-((1-methyl-3-(pyridin-2-yl)-1H-pyrazol-4-yl)carbamoyl)thiazol-2-yl)-1H-pyrazol-1-yl)methyl phosphate

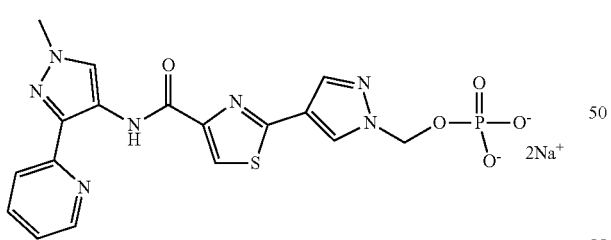

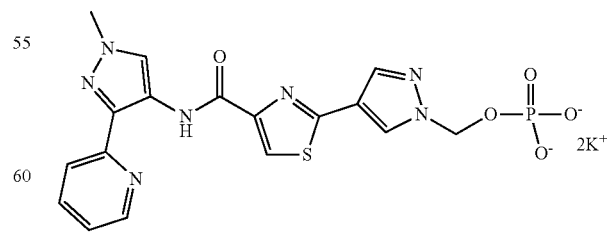

$^1$H NMR (300 MHz, DMSO-d$_6$) δ 12.21 (s, 1H), 8.86 (dt, J=4.8, 1.3 Hz, 1H), 4.68-4.35 (m, 2H), 8.63 (d, J=0.8 Hz, 1H), 8.38 (s, 1H), 8.23 (s, 1H), 8.02 (d, J=0.8 Hz, 1H), 7.96-7.81 (m, 2H), 7.42 (ddd, J=6.9, 4.9, 1.5 Hz, 1H), 5.72 (d, J=10.9 Hz, 2H), 3.94 (s, 3H); MS (ESI) (m/z): 462 [M+H]$^+$.

MS (ESI) (m/z): 462 [M+H]$^+$.

239

II-39: N-(1-(2-(2-methoxyethoxy)ethyl)-3-(pyridin-2-yl)-1H-pyrazol-4-yl)-2-(3-methyl-1H-pyrazol-4-yl)thiazole-4-carboxamide

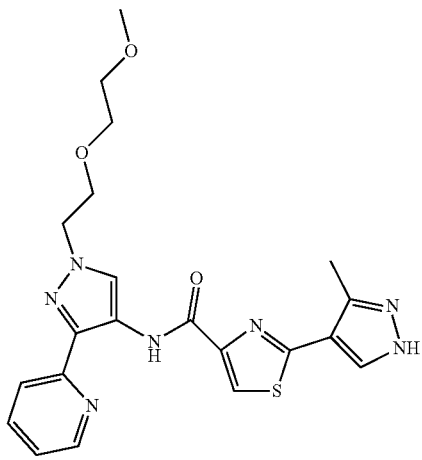 [SMILES: COCCOCCn1cc(NC(=O)c2csc(-c3c[nH]nc3C)n2)c(-c2ccccn2)n1]

MS (ESI) (m/z): 454 [M+H]⁺.

II-41: 2-(3-methyl-1H-pyrazol-4-yl)-N-(1-(oxetan-3-yl)-3-(pyridin-2-yl)-1H-pyrazol-4-yl)thiazole-4-carboxamide, Formic Acid Salt

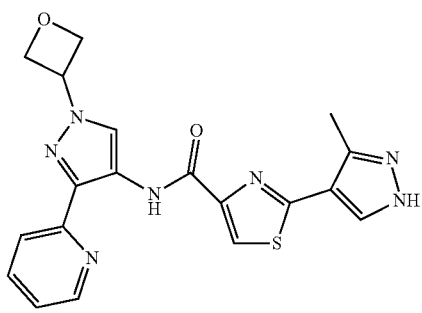 [SMILES: Cc1n[nH]cc1-c1nc(C(=O)Nc2cn(C3COC3)nc2-c2ccccn2)cs1]

$^1$H NMR (300 MHz, DMSO-$d_6$) ι 11.87 (s, 1H), 8.67 (ddd, J=5.0, 1.8, 1.0 Hz, 1H), 8.62 (s, 1H), 8.52 (s, 1H), 8.32 (s, 1H), 8.17-8.09 (m, 1H), 7.96 (td, J=7.8, 1.8 Hz, 1H), 7.44 (ddd, J=7.6, 5.0, 1.3 Hz, 1H), 5.80-5.66 (m, 1H), 4.98 (dd, J=6.9, 1.7 Hz, 4H), 2.69 (s, 3H); MS (ESI) (m/z): 408 [M+H]⁺.

240

II-43: 2-(1H-pyrazol-4-yl)-N-(3-(pyridin-2-yl)-1-(tetrahydrofuran-3-yl)-1H-pyrazol-4-yl)thiazole-4-carboxamide Formic Acid Salt

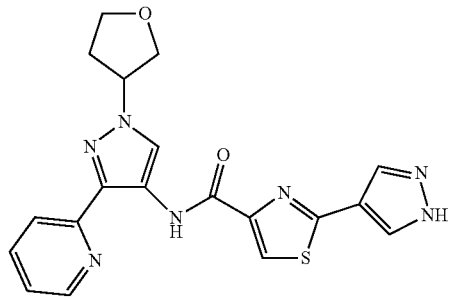 [SMILES: O=C(Nc1cn(C2CCOC2)nc1-c1ccccn1)c1csc(-c2cn[nH]c2)n1]

MS (ESI) (m/z): 408 [M+H]⁺.

II-45: 2-(1H-pyrazol-4-yl)-N-(3-(pyridin-2-yl)-1-((tetrahydro-2H-pyran-4-yl)methyl)-1H-pyrazol-4-yl)thiazole-4-carboxamide Formic Acid Salt

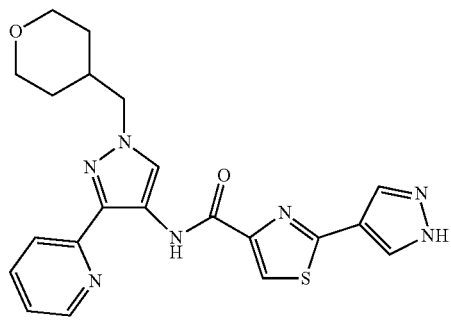 [SMILES: O=C(Nc1cn(CC2CCOCC2)nc1-c1ccccn1)c1csc(-c2cn[nH]c2)n1]

MS (ESI) (m/z): 436 [M+H]⁺.

II-47: N-(1-((3-(hydroxymethyl)oxetan-3-yl)methyl)-3-(pyridin-2-yl)-1H-pyrazol-4-yl)-2-(1H-pyrazol-4-yl)thiazole-4-carboxamide Formic Acid Salt

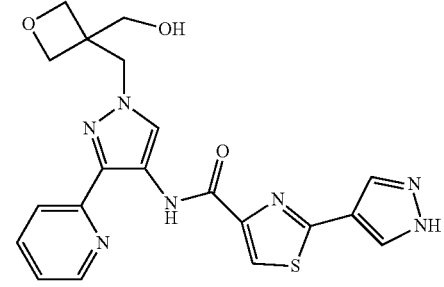 [SMILES: O=C(Nc1cn(CC2(CO)COC2)nc1-c1ccccn1)c1csc(-c2cn[nH]c2)n1]

MS (ESI) (m/z): 438 [M+H]⁺.

II-49: N-(1-(2-(diethylamino)ethyl)-3-(pyridin-2-yl)-1H-pyrazol-4-yl)-2-(1H-pyrazol-4-yl)thiazole-4-carboxamide, Formic Acid Salt

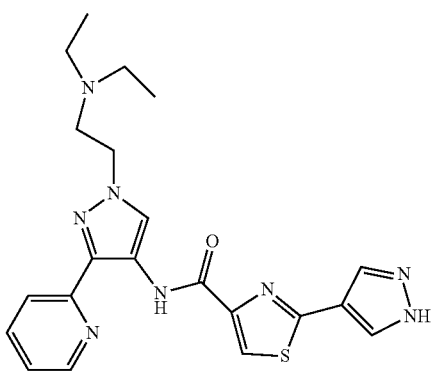 [SMILES: CCN(CC)CCn1cc(NC(=O)c2csc(-c3cn[nH]c3)n2)c(-c2ccccn2)n1]

¹H NMR (300 MHz, DMSO-d₆) δ 12.19 (s, 1H), 8.76 (dt, J=4.9, 1.4 Hz, 1H), 8.48 (s, 1H), 8.37-8.30 (m, 2H), 8.29 (s, 1H), 8.04-7.98 (m, 1H), 7.93 (td, J=7.7, 1.8 Hz, 1H), 7.41 (ddd, J=7.3, 4.9, 1.4 Hz, 1H), 4.25 (t, J=6.4 Hz, 2H), 3.60-3.44 (m, 4H), 2.85 (t, J=6.4 Hz, 2H), 0.93 (t, J=7.1 Hz, 6H); MS (ESI) (m/z): 437 [M+H]⁺.

II-54: tert-Butyl-3-[4-{2-(1H-pyrazole-4-yl)thiazole-2-carboxamido}-3-(pyridine-2-yl)-1H-pyrazol-1-yl]azetidine-1-carboxylate, Free Base

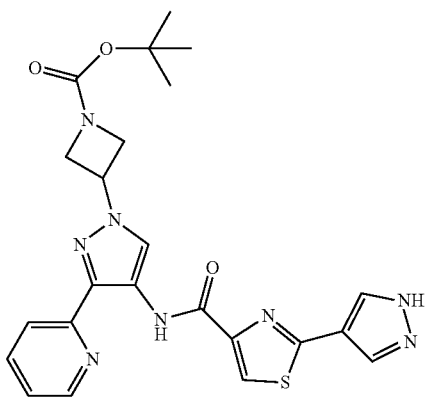 [SMILES: CC(C)(C)OC(=O)N1CC(n2cc(NC(=O)c3csc(-c4cn[nH]c4)n3)c(-c3ccccn3)n2)C1]

¹H NMR (300 MHz, DMSO-d₆) δ 8.76 (d, J=5.1 Hz, 1H), 8.55 (s, 1H), 8.5 (bs, 1H), 8.29 (s, 1H), 8.11-8.05 (m, 2H), 7.98-7.92 (m, 1H), 7.46-7.42 (m, 1H), 5.38-5.33 (m, 1H), 4.33 (t, J=8.7 Hz, 2H), 4.23-3.36 (m, 2H), 1.42 (s, 9H); MS (m/e) 493.62 MH⁺.

II-55: N-{1-(Azetidin-3-yl)-3-(pyridine-2-yl)-1H-pyrazol-4-yl}-2-(1H-pyrazol-4-yl)thiazole-4-carboxamide, TFA Salt

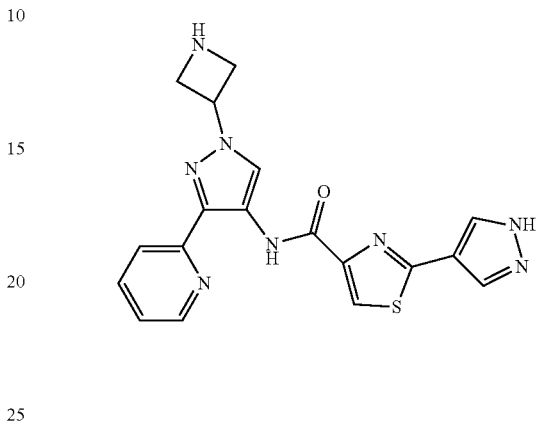

¹H NMR (300 MHz, DMSO-d₆) δ 8.8 (d, J=5.1 Hz, 1H), 8.66 (s, 1H), 8.3 (s, 2H), 8.13-8.1 (m, 1H), 8.03-7.98 (m, 1H), 7.5-7.46 (m, 1H), 5.57-5.52 (m, 1H), 4.45-4.41 (m, 4H); MS (m/e) 393.54 MH⁺.

II-57: N-{1-(3-Methoxycyclobutyl)-3-(pyridine-2-yl)-1H-pyrazol-4-yl}-2-(1H-pyrazol-4-yl)thiazole-4-carboxamide, Free Base, Cis Isomer

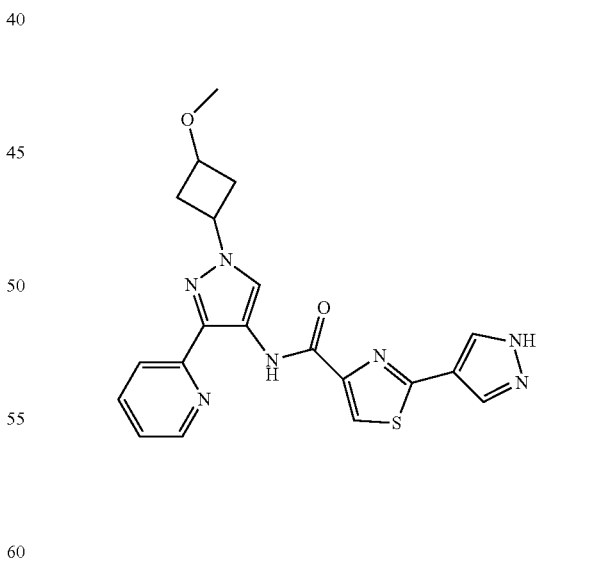

¹H NMR (300 MHz, DMSO-d₆) δ 8.75 (d, J=4.8 Hz, 1H), 8.49 (bs, 1H), 8.46 (s, 1H), 8.26 (bs, 1H), 8.1 (bs, 1H), 8.05-8.03 (m, 1H), 7.96-7.91 (m, 1H), 4.64-4.59 (m, 1H), 3.78-3.74 (m, 1H), 2.83-2.78 (m, 2H), 2.43-2.39 (m, 2H); MS (m/e) 422.58 MH⁺.

II-58: N-(3-(5-methoxypyridin-2-yl)-1-methyl-1H-pyrazol-4-yl)-2-(1H-pyrazol-4-yl)thiazole-4-carboxamide

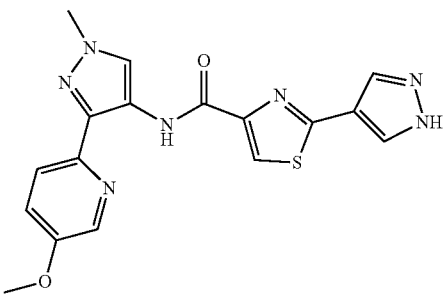 [SMILES: COc1ccc(-c2nn(C)cc2NC(=O)c2csc(-c3cn[nH]c3)n2)nc1]

$^1$H NMR (300 MHz, DMSO-d$_6$) δ 13.48 (s, 1H), 12.11 (s, 1H), 8.55 (s, 1H), 8.45 (dd, J=3.0, 0.6 Hz, 1H), 8.42 (s, 1H), 8.32 (s, 1H), 8.16 (br s, 1H), 7.99 (dd, J=8.9, 0.6 Hz, 1H), 7.62 (dd, J=8.9, 3.0 Hz, 1H), 3.97 (s, 6H); LRMS (M+H) m/z 382.66.

II-59: N-(1-isopropyl-3-(pyridin-2-yl)-1H-pyrazol-4-yl)-2-(1H-pyrazol-4-yl)thiazole-4-carboxamide

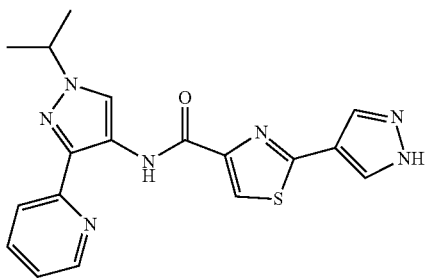 [SMILES: CC(C)n1cc(NC(=O)c2csc(-c3cn[nH]c3)n2)c(-c2ccccn2)n1]

$^1$H NMR (300 MHz, DMSO-d$_6$) δ 13.47 (s, 1H), 12.25 (s, 1H), 8.80 (ddd, J=4.9, 1.7, 1.0 Hz, 1H), 8.55-8.54 (m, 1H), 8.49 (s, 1H), 8.32 (s, 1H), 8.16 (d, J=1.5 Hz, 1H), 8.06 (ddd, J=8.1, 1.2, 1.2 Hz, 1H), 7.97 (ddd, J=7.7, 7.7, 1.8 Hz, 1H), 7.45 (ddd, J=7.4, 4.9, 1.3 Hz, 1H), 4.67 (hept, J=6.7 Hz, 1H), 1.54 (d, J=6.7 Hz, 6H); LRMS (M+H) m/z 380.65.

II-60: N-(1-(2-morpholinoethyl)-3-(pyridin-2-yl)-1H-pyrazol-4-yl)-2-(1H-pyrazol-4-yl)thiazole-4-carboxamide

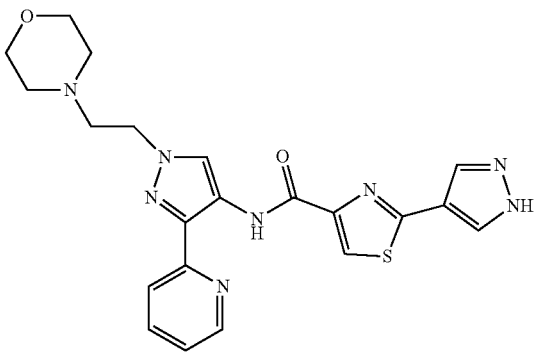 [SMILES: O=C(Nc1cn(CCN2CCOCC2)nc1-c1ccccn1)c1csc(-c2cn[nH]c2)n1]

$^1$H NMR (300 MHz, Chloroform-d) δ 12.40 (s, 1H), 10.38 (br s, 1H), 8.72 (ddd, J=4.9, 1.8, 1.0 Hz, 1H), 8.46 (s, 1H), 8.17 (s, 2H), 8.09-8.06 (m, 2H), 7.77 (ddd, J=8.0, 7.5, 1.8 Hz, 1H), 7.26-7.21 (m, 1H, partially overlapped with CHCl$_3$), 4.31 (t, J=6.7 Hz, 2H), 3.74-3.70 (m, 4H), 2.91 (t, J=6.7 Hz, 2H), 2.55-2.52 (m, 4H); LRMS (M+H) m/z 451.75

II-61: N-(1-(2-(4-methylpiperazin-1-yl)ethyl)-3-(pyridin-2-yl)-1H-pyrazol-4-yl)-2-(1H-pyrazol-4-yl)thiazole-4-carboxamide

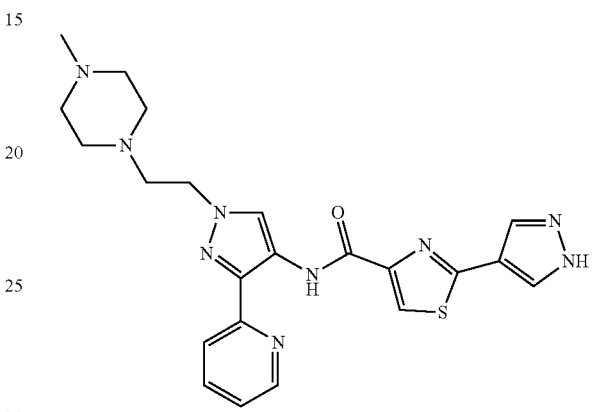

$^1$H NMR (300 MHz, DMSO-d$_6$) δ 13.49 (br s, 1H), 12.24 (s, 1H), 8.80 (br d, J=4.9 Hz, 1H), 8.53 (s, 1H), 8.35 (v br s, 2H), 8.34 (s, 1H), 8.04 (d, J=8.0 Hz, 1H), 7.97 (ddd, J=7.5, 7.5, 1.7 Hz, 1H), 7.45 (ddd, J=7.2, 5.0, 1.4 Hz, 1H), 4.36 (t, J=6.5 Hz, 2H), 3.40 (br s, 2H), 2.81 (t, J=6.5 Hz, 2H), 2.51 (s, partially overlapped with DMSO, 2H), 2.35 (br s, 4H), 2.18 (s, 3H); LRMS (M+H) m/z 464.74.

II-66: 2-(1H-pyrazol-3-yl)-N-(3-(pyridin-2-yl)-1-(2-(2,2,2-trifluoroethoxy)ethyl)-1H-pyrazol-4-yl)thiazole-4-carboxamide

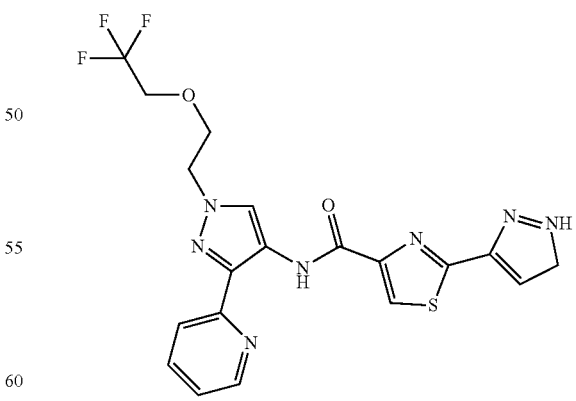

$^1$HNMR (300 MHz, DMSO-d6) δ 13.41 (s, 1H), 12.21 (s, 1H), 8.78-8.76 (m, 1H), 8.49 (s, 2H), 8.30 (s, 1H), 8.12 (s, br, 1H), 8.03-7.92 (m, 2H), 7.46-7.41 (m, 1H), 4.44 (t, J=6.7 Hz, 2H), 4.13 (q, J=10.8 Hz, 2H), 4.04 (t, J=6.7 Hz, 2H); LCMS (m/z): 464.11 (MH$^+$).

II-67: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone

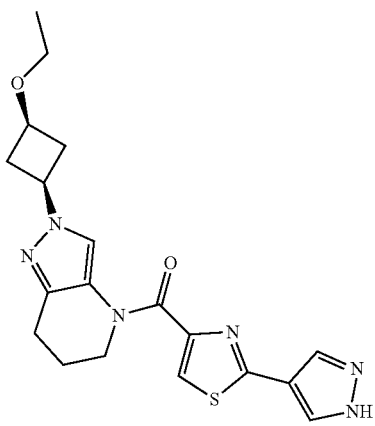 [SMILES: CCO[C@H]1C[C@@H](n2cc3c(n2)CCCN3C(=O)c2csc(-c3cn[nH]c3)n2)C1]

¹HNMR (300 MHz, MeOD-d4) δ 8.28 (s, 1H), 8.17 (s, 1H), 7.92 (m, 1H), 4.48-4.37 (m, 1H), 4.06-4.02 (m, 2H), 3.95-3.87 (m, 1H), 2.87-2.78 (m, 4H), 2.48-2.39 (m, 2H), 2.10-2.04 (m, 2H), 1.21 (t, J=6.7 Hz, 3H); LCMS (m/z): 399.21 (MH⁺).

II-68: R927583 (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone as TFA Salt

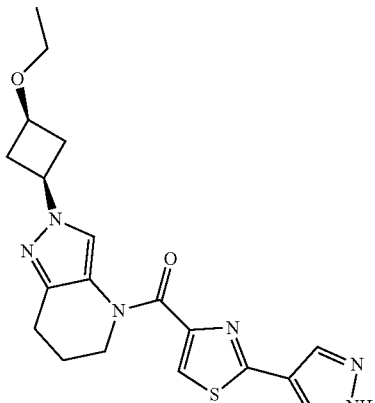

¹HNMR (300 MHz, MeOD-d4) ι 8.17 (s, br, 3H), 7.92 (s, 1H), 4.44-4.37 (m, 1H), 4.02-3.89 (m, 4H), 3.49 (q, J=6.7 Hz, 2H), 2.83-2.53 (m, 6H), 2.07 (s, br, 2H), 1.21 (t, J=6.7 Hz, 3H), 4.13 (q, J=10.8 Hz, 2H).

II-69: R927597: (2-(1H-pyrazol-4-yl)thiazol-4-yl)(1-(3-ethoxycyclobutyl)-1,5,6,7-tetrahydro-4H-pyrazolo[4,3-b]pyridin-4-yl)methanone as TFA Salt

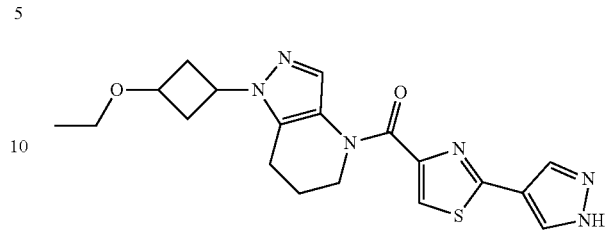

63:37 mixture of regioisomers with R927583 (II-68, above).

II-70: N-(3-carbamoyl-1-((1s,3s)-3-ethoxycyclobutyl)-1H-pyrazol-4-yl)-2-(1H-pyrazol-4-yl)thiazole-4-carboxamide

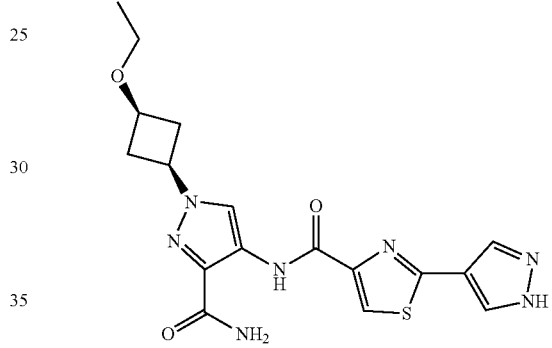

¹HNMR (300 MHz, DMSO-d6) δ 13.41 (s, 1H), 11.25 (s, 1H), 8.40 (s, 1H), 8.39 (s, 1H), 8.29 (s, 1H), 8.00 (s, 1H), 7.73 (s, 1H), 7.55 (s, 1H), 4.65-4.54 (m, 1H), 3.87-3.78 (m, 1H), 3.40 (q, J=6.7 Hz, 2H), 2.83-2.74 (m, 2H), 2.47-2.37 (m, 2H), 1.13 (t, J=6.7 Hz, 2H); LCMS (m/z): 402.20 (MH⁺).

II-71: N-(1-((1s,3s)-3-ethoxycyclobutyl)-3-(pyridin-2-yl)-1H-pyrazol-4-yl)-2-(5-fluoro-1-((2-(trimethylsilyl)ethoxy)methyl)-1H-pyrazol-4-yl)thiazole-4-carboxamide

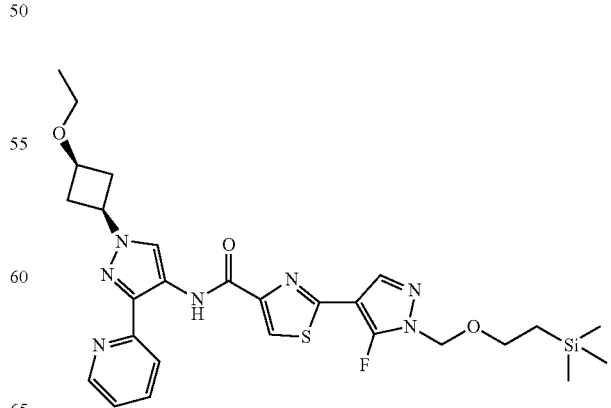

LCMS (m/z): 584.33 (MH⁺).

II-72: N-(1-((1s,3s)-3-ethoxycyclobutyl)-3-(pyridin-2-yl)-1H-pyrazol-4-yl)-2-(5-fluoro-1H-pyrazol-4-yl)thiazole-4-carboxamide

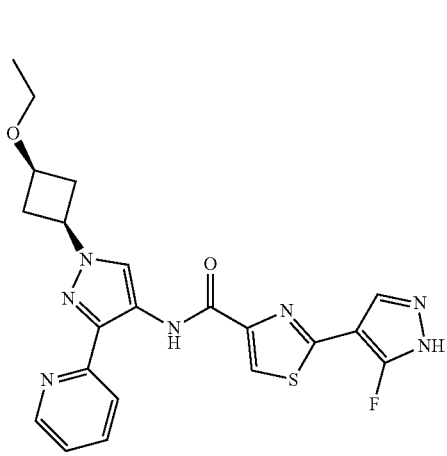 [SMILES: CCO[C@H]1C[C@@H](n2cc(NC(=O)c3csc(-c4cn[nH]c4F)n3)c(-c3ccccn3)n2)C1]

¹HNMR (300 MHz, DMSO-d6) δ 12.17 (s, 1H), 8.75-8.73 (m, 1H), 8.49-8.46 (m, 2H), 8.36 (s, 1H), 8.07-8.04 (m, 1H), 7.97-7.91 (m, 1H), 7.44-7.39 (m, 1H), 4.68-4.57 (m, 1H), 3.90-3.80 (m, 1H), 3.42 (q, J=6.7 Hz, 2H), 2.85-2.73 (m, 2H), 2.45-2.42 (m, 2H), 1.15 (t, J=6.7 Hz, 2H); LCMS (m/z): 454.22 (MH⁺).

II-73: N-(1-((1s,3s)-3-ethoxycyclobutyl)-3-(pyridin-2-yl)-1H-pyrazol-4-yl)-2-(5-fluoro-1H-pyrazol-4-yl)thiazole-4-carboxamide as Formate Salt

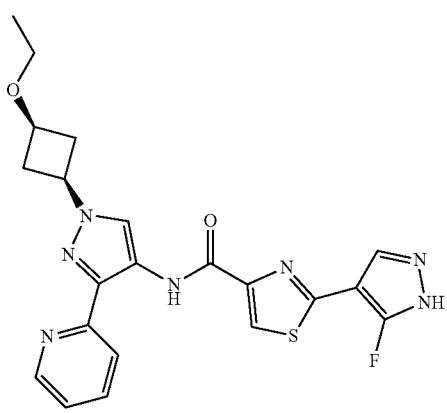 [SMILES: CCO[C@H]1C[C@@H](n2cc(NC(=O)c3csc(-c4cn[nH]c4F)n3)c(-c3ccccn3)n2)C1]

LCMS (m/z): 454.15 (MH⁺).

II-74: N-(1-((1s,3s)-3-ethoxycyclobutyl)-3-(1,3,4-oxadiazol-2-yl)-1H-pyrazol-4-yl)-2-(1H-pyrazol-4-yl)thiazole-4-carboxamide

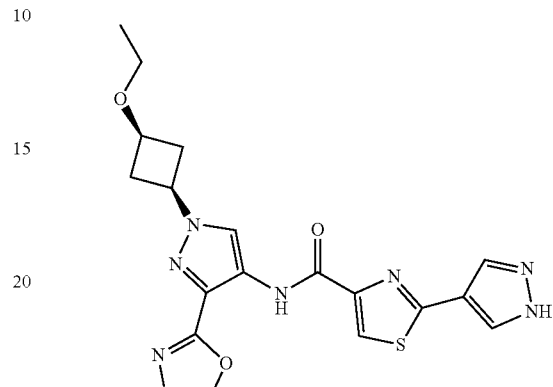

¹HNMR (300 MHz, DMSO-d6) ι 10.88 (s, 1H), 9.43 (s, 1H), 8.55 (s, 1H), 8.36 (s, 1H), 8.29 (s, 1H), 4.77-4.66 (m, 1H), 3.91-3.81 (m, 1H), 3.42 (q, J=6.7 Hz, 2H), 2.88-2.79 (m, 2H), 2.47-2.37 (m, 2H), 1.15 (t, J=6.7 Hz, 2H); LCMS (m/z): 427.24 (MH⁺).

II-75: N-(3-(1,3,4-oxadiazol-2-yl)-1-(tetrahydro-2H-pyran-4-yl)-1H-pyrazol-4-yl)-2-(1H-pyrazol-4-yl)thiazole-4-carboxamide

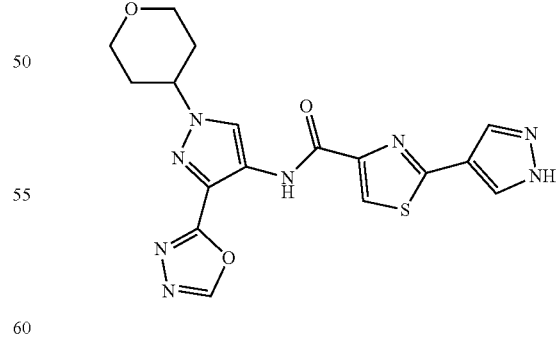

¹HNMR (300 MHz, DMSO-d6) ι 10.89 (s, 1H), 9.41 (s, 1H), 8.56 (s, 1H), 8.36 (s, 1H), 4.71-4.59 (m, 1H), 4.02-3.92 (m, 2H), 3.53-3.44 (m, 2H), 2.07-2.03 (m, 4H); LCMS (m/z): 413.13 (MH⁺).

II-76: N-(1-((1,3-cis)-3-isopropoxycyclobutyl)-3-(pyridin-2-yl)-1H-pyrazol-4-yl)-2-(1H-pyrazol-4-yl)thiazole-4-carboxamide

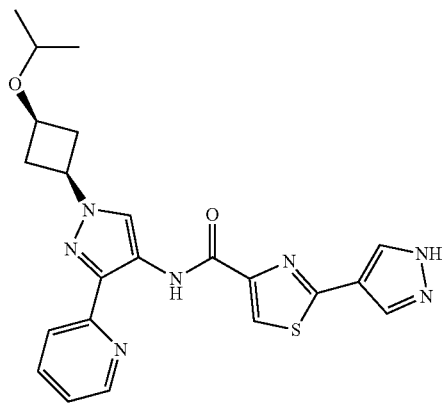 [SMILES: CC(C)O[C@H]1C[C@@H](n2cc(NC(=O)c3csc(-c4cn[nH]c4)n3)c(-c3ccccn3)n2)C1]

1H NMR (300 MHz, DMSO-d6) δ 13.41 (s, 1H), 12.18 (s, 1H), 8.75 (d, J=5.1 Hz, 1H), 8.49 (s, 1H), 8.45 (s, 1H), 8.28 (s, 1H), 8.10 (s, 1H), 8.04 (d, J=8.1 Hz, 1H), 7.93 (t, J=8.7 Hz, 1H), 7.42 (t, J=6.6 Hz, 1H), 4.58 (p, J=7.8 Hz, 1H), 3.89 (p, J=7.5 Hz, 1H), 3.63 (p, J=6.0 Hz, 1H), 2.85-2.76 (m, 2H), 2.43-2.36 (m, 2H), 1.10 (d, J=6.0 Hz, 6H); LCMS: purity: 100%; MS (m/e): 450.19 (MH+).

II-77: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate bis-potassium Salt

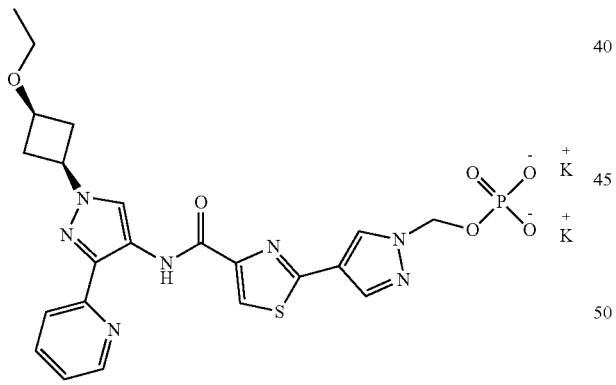

To a mixture of (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate (300 mg) in acetonitrile (2 mL) and water (1 mL), was added 1.0 N potassium hydroxide aqueous solution (1.1 mL, 2 eq.) After sonicating for five minutes, the solution was lyophilized for 24 hours. The resulting powder was suspended in water (1 mL) and isopropanol (5 mL). The mixture was stirred at 70° C. for five minutes until a clear solution formed. The solution was cooled to room temperature. The resulting precipitate was collected through filtration, washed with isopropanol (3×1 mL) and dried under high vacuum at room temperature for 24 hours to give potassium salt as a white solid (280 mg).

$^1$H NMR (300 MHz, Deuterium Oxide) δ 7.83 (d, 1H), 7.80 (s, 1H), 7.64 (s, 1H), 7.42 (s, 1H), 7.41 (m, 1H), 7.29 (s, 1H), 7.17 (d, J=7.2 Hz, 1H), 6.89 (m, 1H), 5.57 (d, J=8.1 Hz, 2H), 4.13 (m, 1H), 3.91 (t, J=7.8 Hz, 1H), 3.49 (q, J=7.2 Hz, 2H), 2.83 (m, 2H), 2.19 (m, 2H), 1.14 (t, J=7.2 Hz, 3H); LCMS: purity: 100%; MS (m/e): 546.23 (MH+).

II-78: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate Calcium Salt

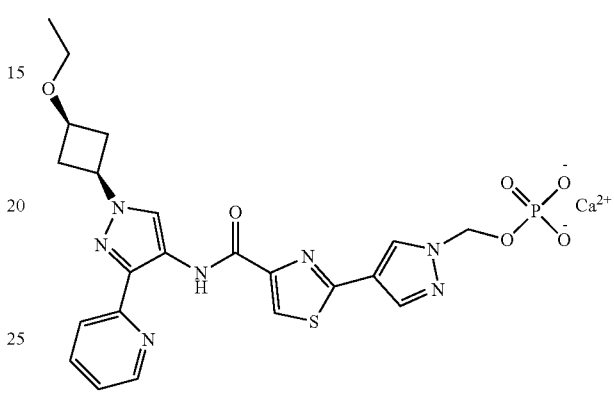

To a mixture of (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate (309 mg) in acetonitrile (2 mL) and water (1 mL), was added calcium hydroxide (42 mg, 1 eq.). After sonicating for five minutes, the reaction mixture was lyophilized for 24 hours. The resulting powder was suspended in water (1 mL) and isopropanol (5 mL). The mixture was stirred at 70° C. for five minutes and then cooled to room temperature. The resulting precipitate was collected through filtration, washed with isopropanol (3×1 mL) and dried under high vacuum at room temperature for 24 hours to give calcium salt as a white solid (300 mg).

LCMS: purity: 95.41%; MS (m/e): 546.22 (MH+).

II-79: N-(1-((1r, 3r)-3-hydroxy-3-methylcyclobutyl)-3-(pyridin-2-yl)-1H-pyrazol-4-yl)-2-(1H-pyrazol-4-yl)thiazole-4-carboxamide

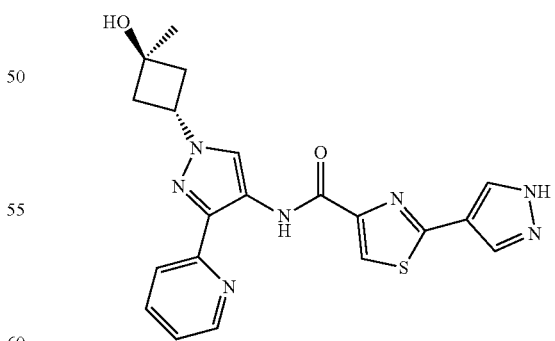

1H NMR (300 MHz, DMSO-d6) ι 13.41 (s, 1H), 12.17 (s, 1H), 8.74 (d, J=5.1 Hz, 1H), 8.49 (s, 1H), 8.46 (s, 1H), 8.27 (s, 1H), 8.10 (s, 1H), 8.03 (d, J=7.8 Hz, 1H), 7.93 (t, J=8.4 Hz, 1H), 7.40 (t, J=6.6 Hz, 1H), 5.06 (s, 1H), 5.04 (p, J=7.8 Hz, 1H), 1.37 (s, 3H); LCMS: purity: 100%; MS (m/e): 422.22 (MH+).

II-80: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate bis-ammonium Salt

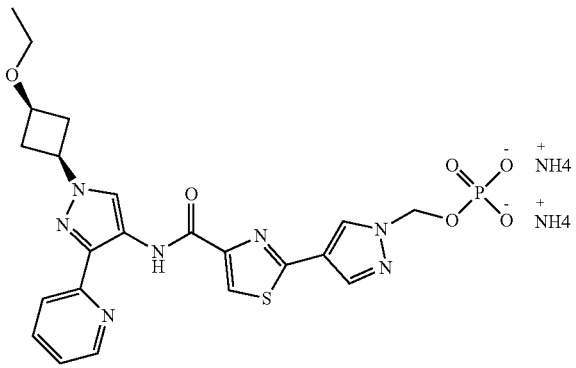

To a mixture of (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate (200 mg) in acetonitrile (1 mL) and water (1 mL), was added 2.0 N ammonia in methanol solution (0.37 mL, 2 eq.). After sonicating for five minutes, the solution was lyophilized for 24 hours. The resulting powder was suspended in water (0.5 mL) and isopropanol (3 mL). The resulting precipitate was collected through filtration, washed with isopropanol (3×1 mL) and dried under high vacuum at room temperature for 24 hours to give ammonium salt (180 mg) as a white solid.

$^1$H NMR (300 MHz, Deuterium Oxide) δ 7.71 (s, 2H), 7.56 (s, 1H), 7.33 (m, 2H), 7.19 (s, 1H), 7.08 (d, J=8.1 Hz, 1H), 6.82 (t, J=5.7 Hz, 1H), 5.53 (d, J=7.8 Hz, 2H), 4.08 (p, J=7.8 Hz, 1H), 3.89 (m, 1H), 3.48 (q, J=7.2 Hz, 2H), 2.79 (m, 2H), 2.13 (m, 2H), 1.13 (t, J=7.2 Hz, 3H); LCMS: purity: 100%; MS (m/e): 546.15 (MH+).

II-81: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate bis-lysine Salt

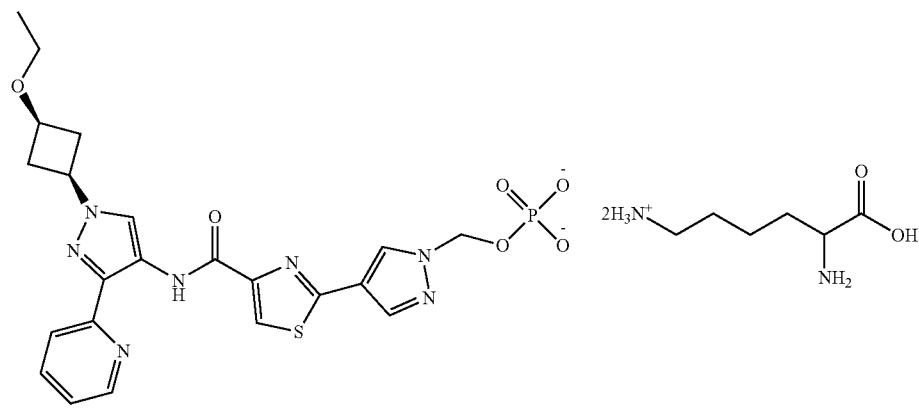

To a mixture of (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate (200 mg) in acetonitrile (1 mL) and water (1 mL), was added L-lysine (107 mg, 2 eq.). After sonicating for five minutes, the solution was lyophilized for 24 hours. The resulting powder was suspended in water (0.5 mL) and isopropanol (3 mL). The resulting precipitate was collected through filtration, washed with isopropanol (3×1 mL) and dried under high vacuum at room temperature for 24 hours to give bis-lysine salt (200 mg) as a white solid.

$^1$H NMR (300 MHz, Deuterium Oxide) δ 7.82 (m, 1H), 7.79 (s, 1H), 7.63 (s, 1H), 7.41 (s, 1H), 7.39 (m, 1H), 7.28 (s, 1H), 7.16 (d, J=9.0 Hz, 1H), 6.88 (m, 1H), 5.56 (d, J=8.1 Hz, 2H), 4.12 (m, 1H), 3.90 (t, J=7.8 Hz, 1H), 3.61 (t, J=5.7 Hz, 1H), 3.48 (q, J=6.9 Hz, 2H), 2.88 (t, J=7.5 Hz, 4H), 2.82 (m, 2H), 2.16 (m, 2H), 1.80-1.72 (m, 4H), 1.63-1.53 (m, 4H), 1.42-1.29 (m, 4H), 1.13 (t, J=7.2 Hz, 3H); LCMS: purity: 100%; MS (m/e): 546.15 (MH+).

II-82: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate bis-arginine Salt

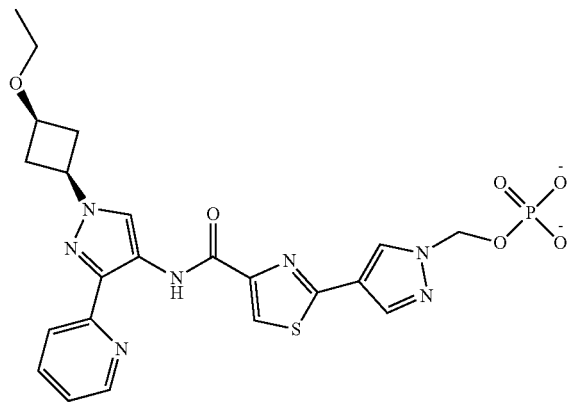
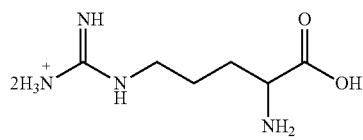

To a mixture of (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate (200 mg) in acetonitrile (1 mL) and water (1 mL), was added L-arginine (128 mg, 2 eq.). After sonicating for five minutes, the solution was lyophilized for 24 hours. The resulting powder was suspended in water (0.5 mL) and isopropanol (3 mL). The resulting precipitate was collected through filtration, washed with isopropanol (3×1 mL) and dried under high vacuum at room temperature for 24 hours to give bis-arginine salt (200 mg) as a white solid. The salt was re-dissolved in water (0.5 mL) and acetone (8 mL). After heating at 50° C. for 10 minutes, the solution was cooled to room temperature. The resulting precipitate was collected through filtration, washed with acetone and dried under high vacuum at room temperature for 24 hours to give bis-arginine salt (120 mg) as a white solid.

$^1$H NMR (300 MHz, Deuterium Oxide) δ 7.88 (d, J=5.4 Hz, 1H), 7.84 (s, 1H), 7.68 (s, 1H), 7.46 (s, 1H), 7.41 (d, J=6.3 Hz, 1H), 7.33 (s, 1H), 7.20 (d, J=8.1 Hz, 1H), 6.92 (m, 1H), 5.57 (d, J=8.7 Hz, 2H), 4.15 (t, J=8.7 Hz, 1H), 3.91 (t, J=6.6 Hz, 1H), 3.62 (t, J=6.0 Hz, 2H), 3.49 (q, J=7.2 Hz, 2H), 3.08 (t, J=6.9 Hz, 4H), 2.82 (m, 2H), 2.11 (m, 2H), 1.80-1.72 (m, 4H), 1.63-1.44 (m, 4H), 1.14 (t, J=7.2 Hz, 3H); LCMS: purity: 100%; MS (m/e): 546.15 (MH+).

II-83: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl dihydrogen phosphate

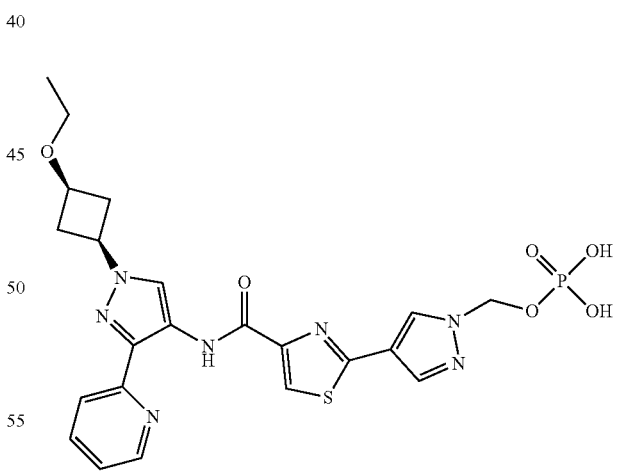

N-(1-((1,3-Cis)-3-ethoxycyclobutyl)-3-(pyridin-2-yl)-1H-pyrazol-4-yl)-2-(1H-pyrazol-4-yl)thiazole-4-carboxamide (59 g) and cesium carbonate (88 g, 2eq.) were suspended in dimethylformamide (500 mL), di-tert-butyl (chloromethyl) phosphate (53 g, 1.5 eq.) was added to the reaction and the mixture allowed to stir at room temperature for 16-20 hours. The reaction mixture was diluted with water (1 L) and extracted with ethyl acetate (2×800 mL). The combined organic layers were evaporated at room temperature and purified using the Torrent Combiflash®Rf column chromatography (ethyl acetate in hexanes, 20 to 100%) to give the prodrug ester as a colorless oil (85 g, 95% yield). LCMS: purity: 100%; MS (m/e): 658.38 (MH+).

Di-tert-butyl((4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl) phosphate (85 g) was dissolved in anhydrous dichloromethane (700 mL), the resulting solution was cooled to 0° C. and trifluoroacetic acid (150 mL) was added drop-wise. The reaction mixture was stirred at 0° C. for 6 hours, when LC-MS analysis showed full conversion to the acid, the solution was evaporated on a rotary evaporator at room temperature. The residue was dried further under high vacuum at room temperature for 24 hours to give a light yellow semi-solid as the acid and used subsequently to form salts.

(4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl dihydrogen phosphate (100 mg) was stirred overnight at 50° C. in acetone (10 mL) and water (0.5 mL). The cloudy solution was cooled to room temperature. The white precipitate was collected by filtration, washed with acetone and dried under high vacuum at room temperature for 24 hours (90 mg).

$^1$H NMR (300 MHz, DMSO-d6) δ 12.20 (s, 1H), 8.83 (d, J=4.8 Hz, 1H), 8.61 (s, 1H), 8.46 (s, 1H), 8.32 (s, 1H), 8.18 (s, 1H), 8.04 (d, J=8.1 Hz, 1H), 7.93 (t, J=6.9 Hz, 1H), 7.40 (t, J=6.0 Hz, 1H), 5.90 (d, J=11.1 Hz, 2H), 4.60 (t, J=8.4 Hz, 1H), 3.83 (t, J=6.6 Hz, 1H), 3.41 (q, J=6.9 Hz, 2H), 2.80 (m, 2H), 2.42 (m, 2H), 1.13 (t, J=6.9 Hz, 3H); LCMS: purity: 100%; MS (m/e): 546.15 (MH+).

II-84: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate Tris Salt

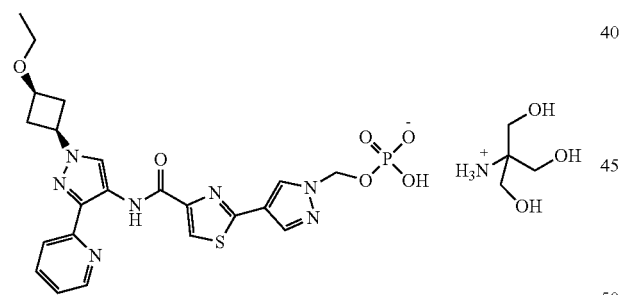

To a mixture of (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate (118 mg) in acetonitrile (1 mL) and water (1 mL), was added Tris(hydroxymethyl)aminomethane (52 mg, 2 eq.). After sonicating for five minutes, the solution was lyophilized for 24 hours. The resulting powder was suspended in water (0.5 mL) and acetone (5 mL). The solution was stirred at 50° C. for 30 minutes and cooled to room temperature. After one week at room temperature, the resulting precipitate was collected through filtration, washed with acetone (3×1 mL) and dried under high vacuum at room temperature for 24 hours to give mono-Tris salt (120 mg) as a white solid.

$^1$H NMR (300 MHz, Deuterium Oxide) δ 7.83 (m, 2H), 7.65 (s, 1H), 7.43 (s, 1H), 7.40 (d, J=7.5 Hz, 1H), 7.30 (s, 1H), 7.17 (d, J=8.1 Hz, 1H), 6.90 (t, J=6.0 Hz, 1H), 5.57 (d, J=8.1 Hz, 2H), 4.13 (t, J=7.5 Hz, 1H), 3.91 (t, J=6.9 Hz, 1H), 3.60 (s, 6H), 3.49 (q, J=6.9 Hz, 2H), 2.82 (m, 2H), 2.18 (m, 2H), 1.14 (t, J=6.9 Hz, 3H); LCMS: purity: 100%; MS (m/e): 546.16 (MH+).

II-85: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate triethylamine Salt

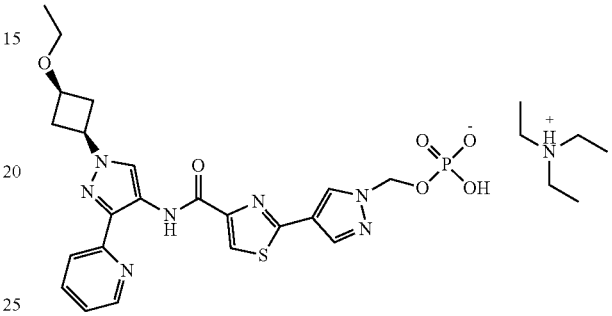

$^1$H NMR (300 MHz, Deuterium Oxide) δ 7.81 (d, 1H), 7.77 (s, 1H), 7.61 (s, 1H), 7.39 (s, 2H), 7.26 (s, 1H), 7.14 (d, J=7.8 Hz, 1H), 6.87 (t, J=6.6 Hz, 1H), 5.55 (d, J=9.0 Hz, 2H), 4.11 (p, J=8.4 Hz, 1H), 3.90 (p, J=7.1 Hz, 1H), 3.48 (q, J=7.1 Hz, 2H), 3.05 (q, J=7.4 Hz, 6H), 2.80 (m, 2H), 2.15 (m, 2H), 1.13 (t, J=7.3 Hz, 12H); LCMS: purity: 100%; MS (m/e): 546.15 (MH+).

II-86: N-(1-((1,3-cis)-3-ethoxycyclobutyl)-3-(5-(trifluoromethyl)pyridin-2-yl)-1H-pyrazol-4-yl)-2-(1H-pyrazol-4-yl)thiazole-4-carboxamide

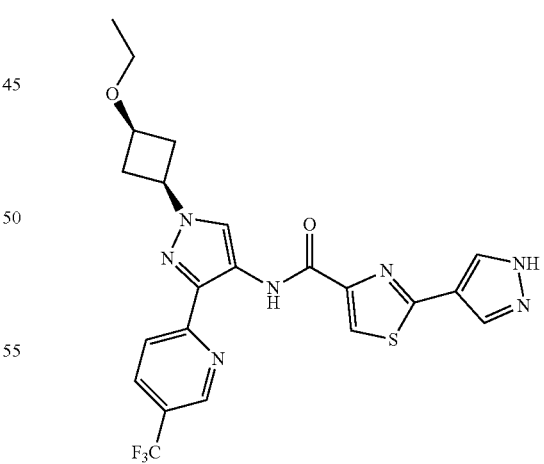

$^1$H NMR (300 MHz, DMSO-d6) δ 13.45 (s, 1H), 11.84 (s, 1H), 9.04 (s, 1H), 8.53 (s, 2H), 8.32-8.30 (m, 2H), 8.23 (d, J=8.1 Hz, 1H), 8.12 (s, 1H), 4.65 (p, J=7.5 Hz, 1H), 3.84 (p, J=6.6 Hz, 1H), 3.41 (q, J=7.0 Hz, 2H), 2.82 (m, 2H), 2.42 (m, 2H), 1.13 (t, J=7.0 Hz, 3H); LCMS: purity: 94.79%; MS (m/e): 502.27 (MH+).

II-87: N-(1-(3-hydroxy-3-methylcyclobutyl)-3-(pyridin-2-yl)-1H-pyrazol-4-yl)-2-(1H-pyrazol-4-yl)thiazole-4-carboxamide

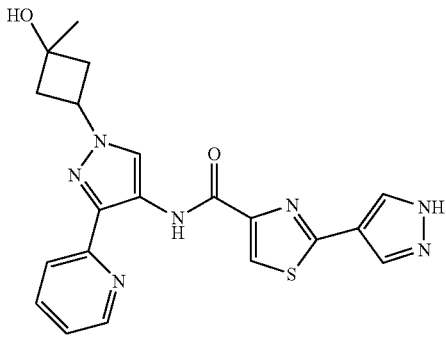 [SMILES: CC1(O)CC(n2cc(NC(=O)c3csc(-c4cn[nH]c4)n3)c(-c3ccccn3)n2)C1]

LCMS: purity: 91.70%; MS (m/e): 422.16 (MH+).

II-88: N-(1-(difluoromethyl)-3-(pyridin-2-yl)-1H-pyrazol-4-yl)-2-(1H-pyrazol-4-yl)thiazole-4-carboxamide

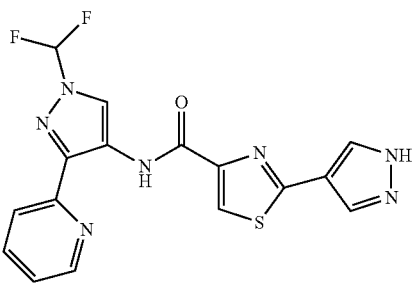 [SMILES: O=C(Nc1cn(C(F)F)nc1-c1ccccn1)c1csc(-c2cn[nH]c2)n1]

¹H NMR (300 MHz, DMSO-d6) δ 13.42 (s, 1H), 12.26 (s, 1H), 8.85-8.82 (m, 2H), 8.51 (s, 1H), 8.35 (s, 1H), 8.13-8.10 (m, 2H), 8.02 (t, J=8.7 Hz, 1H), 7.93 (t, J=59.1 Hz, 1H), 7.55 (dd, J=7.5, 4.9 Hz, 1H); LCMS: purity: 100%; MS (m/e): 388.10 (MH+).

II-89: N-(1-((1,3-cis)-3-ethoxycyclobutyl)-3-(3-(trifluoromethyl)pyridin-2-yl)-1H-pyrazol-4-yl)-2-(1H-pyrazol-4-yl)thiazole-4-carboxamide

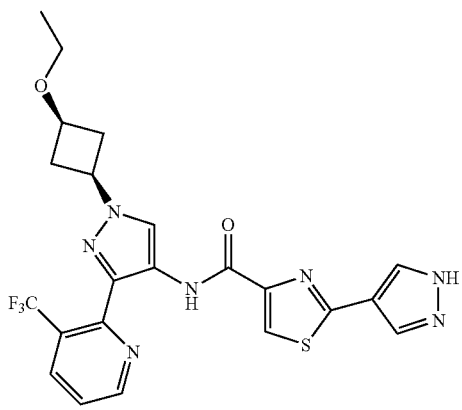 [SMILES: CCO[C@H]1C[C@@H](n2cc(NC(=O)c3csc(-c4cn[nH]c4)n3)c(-c3ncccc3C(F)(F)F)n2)C1]

¹H NMR (300 MHz, DMSO-d6) δ 13.43 (s, 1H), 11.68 (s, 1H), 9.05 (d, J=4.8 Hz, 1H), 8.48 (m, 1H), 8.38 (d, J=7.9 Hz, 1H), 8.28 (s, 3H), 7.66 (dd, J=8.1, 4.9 Hz, 1H), 4.62 (p, J=8.1 Hz, 1H), 3.83 (p, J=7.2 Hz, 1H), 3.40 (q, J=7.0 Hz, 2H), 2.82-2.73 (m, 2H), 2.45-2.38 (m, 2H), 1.12 (t, J=7.0 Hz, 3H); LCMS: purity: 92.15%; MS (m/e): 504.22 (MH+).

II-90: N-(1-((1,3-cis)-3-ethoxycyclobutyl)-3-(6-(trifluoromethyl)pyridin-2-yl)-1H-pyrazol-4-yl)-2-(1H-pyrazol-4-yl)thiazole-4-carboxamide

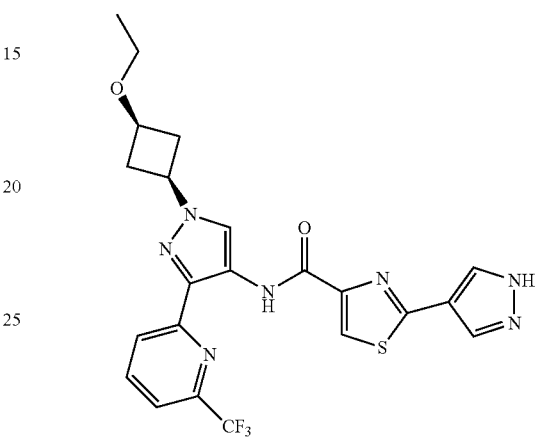

1H NMR (300 MHz, DMSO-d6) δ 13.40 (s, 1H), 10.93 (s, 1H), 8.60 (s, 1H), 8.38-8.33 (m, 3H), 8.19 (t, J=7.9 Hz, 1H), 8.05 (s, 1H), 7.87 (d, J=7.6 Hz, 1H), 4.64 (p, J=8.4 Hz, 1H), 3.84 (p, J=7.1 Hz, 1H), 3.41 (q, J=7.0 Hz, 2H), 2.86-2.77 (m, 2H), 2.42-2.38 (m, 2H), 1.13 (t, J=7.0 Hz, 3H); LCMS: purity: 100%; MS (m/e): 504.22 (MH+).

II-91: N-(1-((1,3-cis)-3-ethoxycyclobutyl)-3-(pyridin-2-yl)-1H-pyrazol-4-yl)-2-(3-(trifluoromethyl)-1H-pyrazol-4-yl)thiazole-4-carboxamide

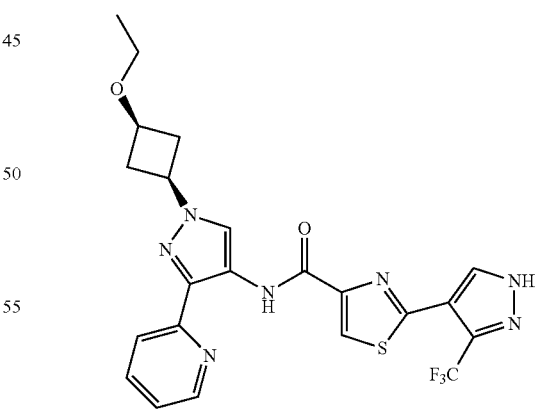

1H NMR (300 MHz, DMSO-d6) δ 11.80 (s, 1H), 8.67 (s, 1H), 8.59 (d, J=5.0 Hz, 1H), 8.51 (s, 1H), 8.44 (s, 1H), 8.04 (d, J=8.0 Hz, 1H), 7.90 (td, J=7.8, 1.8 Hz, 1H), 7.36 (dd, J=4.8, 1.2 Hz, 1H), 4.61 (p, J=7.5 Hz, 1H), 3.83 (p, J=6.9 Hz, 1H), 3.41 (q, J=7.0 Hz, 2H), 2.82-2.76 (m, 2H), 2.43-2.40 (m, 2H), 1.13 (t, J=7.0 Hz, 3H); LCMS: purity: 100%; MS (m/e): 504.22 (MH+).

II-92: N-(1-((1,3-cis)-3-ethoxycyclobutyl)-3-(pyridin-2-yl)-1H-pyrazol-4-yl)-2-(3-methyl-1H-pyrazol-4-yl)thiazole-4-carboxamide

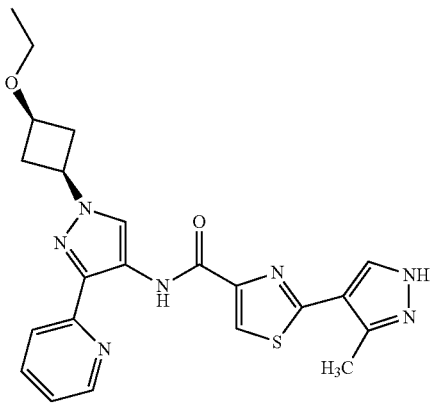 [SMILES: CCO[C@H]1C[C@@H](n2cc(NC(=O)c3csc(-c4c[nH]nc4C)n3)c(-c3ccccn3)n2)C1]

1H NMR (300 MHz, DMSO-d6) δ 13.19 (s, 1H), 11.83 (s, 1H), 8.63 (d, J=5.1 Hz, 1H), 8.50 (s, 1H), 8.29 (s, 1H), 8.06 (d, J=7.8 Hz, 1H), 7.99 (m, 1H), 7.92 (td, J=7.5, 1.2 Hz, 1H), 7.39 (t, J=6.0 Hz, 1H), 4.61 (p, J=8.1 Hz, 1H), 3.83 (p, J=6.9 Hz, 1H), 3.41 (q, J=7.1 Hz, 2H), 2.85-2.76 (m, 2H), 2.68 (s, 3H), 2.43-2.37 (m, 2H), 1.13 (t, J=6.9 Hz, 3H); LCMS: purity: 100%; MS (m/e): 450.25 (MH+).

II-93: 2-(3,5-dimethyl-1H-pyrazol-4-yl)-N-(1-((1,3-cis)-3-ethoxycyclobutyl)-3-(pyridin-2-yl)-1H-pyrazol-4-yl)thiazole-4-carboxamide

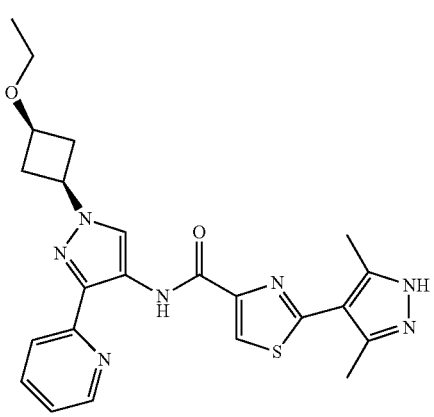 [SMILES: CCO[C@H]1C[C@@H](n2cc(NC(=O)c3csc(-c4c(C)n[nH]c4C)n3)c(-c3ccccn3)n2)C1]

1H NMR (300 MHz, DMSO-d6) δ 12.79 (s, 1H), 11.61 (s, 1H), 8.57 (d, J=4.8 Hz, 1H), 8.53 (s, 1H), 8.33 (s, 1H), 8.07 (d, J=8.0 Hz, 1H), 7.91 (td, J=7.7, 1.8 Hz, 1H), 7.37 (dd, J=7.5, 1.2 Hz, 1H), 4.61 (p, J=7.5 Hz, 1H), 3.83 (p, J=6.9 Hz, 1H), 3.41 (q, J=7.0 Hz, 2H), 2.85-2.76 (m, 2H), 2.56 (br, 6H), 2.43-2.37 (m, 2H), 1.13 (t, J=7.0 Hz, 3H); LCMS: purity: 100%; MS (m/e): 464.23 (MH+).

II-94: 2-(1H-pyrazol-4-yl)-N-(3-(pyridin-2-yl)-1-(2,2,2-trifluoroethyl)-1H-pyrazol-4-yl)thiazole-4-carboxamide

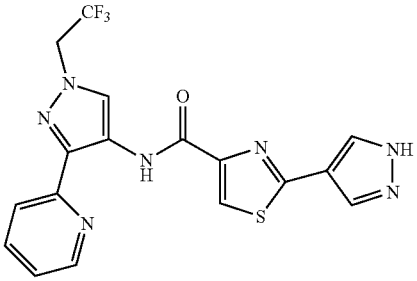 [SMILES: O=C(Nc1cn(CC(F)(F)F)nc1-c1ccccn1)c1csc(-c2cn[nH]c2)n1]

1H NMR (300 MHz, DMSO-d6) δ 13.41 (s, 1H), 12.22 (s, 1H), 8.79 (dd, J=4.9, 1.5 Hz, 1H), 8.61 (s, 1H), 8.50 (s, 1H), 8.31 (s, 1H), 8.11 (s, 1H), 8.02 (d, J=6.6 Hz, 1H), 7.96 (td, J=8.1, 1.8 Hz, 1H), 7.47 (dd, J=8.7, 1.5 Hz, 1H), 5.29 (q, J=9.0 Hz, 2H); LCMS: purity: 100%; MS (m/e): 420.15 (MH+).

II-95: N-(1-(difluoromethyl)-3-(pyridin-2-yl)-1H-pyrazol-4-yl)-2-(3-(trifluoromethyl)-1H-pyrazol-4-yl)thiazole-4-carboxamide

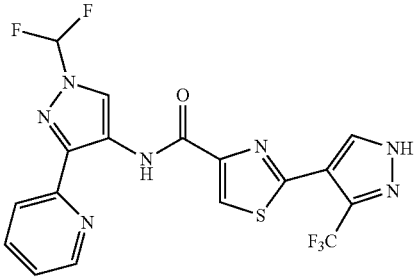

1H NMR (300 MHz, DMSO-d6) δ 11.88 (s, 1H), 8.89 (s, 1H), 8.72 (s, 1H), 8.66 (d, J=4.2 Hz, 1H), 8.54 (s, 1H), 8.14-8.10 (m, 2H), 7.99 (t, J=8.1 Hz, 1H), 7.94 (t, J=58.8 Hz, 1H), 7.50 (dd, J=6.0, 1.2 Hz, 1H); LCMS: purity: 100%; MS (m/e): 456.10 (MH+).

II-96: N-(1-(difluoromethyl)-3-(pyridin-2-yl)-1H-pyrazol-4-yl)-2-(3-methyl-1H-pyrazol-4-yl)thiazole-4-carboxamide

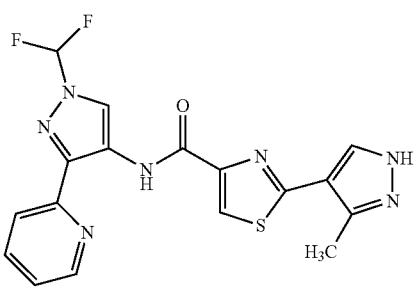 [SMILES: O=C(Nc1cn(C(F)F)nc1-c1ccccn1)c1csc(-c2c[nH]nc2C(F)(F)F)n1]

1H NMR (300 MHz, DMSO-d6) δ 13.20 (s, 1H), 11.93 (s, 1H), 8.88 (s, 1H), 8.72 (d, J=5.4 Hz, 1H), 8.37 (s, 1H), 8.13 (d, J=8.1 Hz, 1H), 8.01 (t, J=7.5 Hz, 2H), 7.94 (t, J=58.8 Hz, 1H), 7.54 (t, J=6.3 Hz, 1H), 2.69 (s, 3H); LCMS: purity: 100%; MS (m/e): 402.14 (MH+).

II-97: N-(1-(difluoromethyl)-3-(pyridin-2-yl)-1H-pyrazol-4-yl)-2-(1-(2,2,2-trifluoroethyl)-1H-pyrazol-4-yl)thiazole-4-carboxamide

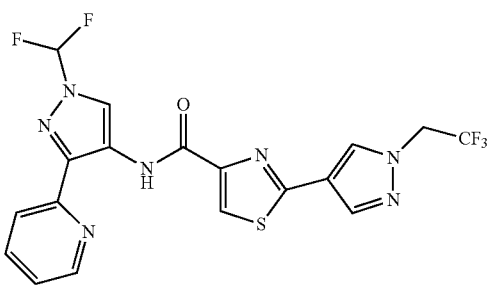 [SMILES: O=C(Nc1cn(C(F)F)nc1-c1ccccn1)c1csc(-c2cnn(CC(F)(F)F)c2)n1]

1H NMR (300 MHz, DMSO-d6) δ 12.26 (s, 1H), 8.84 (d, J=3.7 Hz, 2H), 8.61 (s, 1H), 8.42 (s, 1H), 8.23 (s, 1H), 8.12 (d, J=8.1 Hz, 1H), 8.01 (t, J=8.1 Hz, 1H), 7.94 (t, J=59.1 Hz, 1H), 7.54 (ddd, J=7.5, 4.9, 1.3 Hz, 1H), 5.31 (q, J=9.0 Hz, 2H); LCMS: purity: 100%; MS (m/e): 470.15 (MH+).

II-98: 2-(1-(difluoromethyl)-1H-pyrazol-4-yl)-N-(1-(difluoromethyl)-3-(pyridin-2-yl)-1H-pyrazol-4-yl)thiazole-4-carboxamide

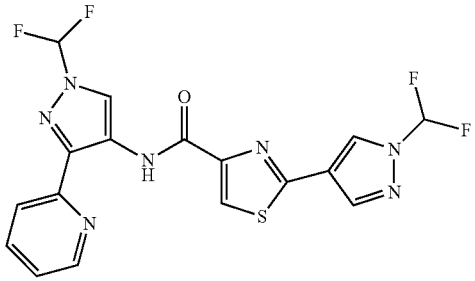 [SMILES: O=C(Nc1cn(C(F)F)nc1-c1ccccn1)c1csc(-c2cnn(C(F)F)c2)n1]

1H NMR (300 MHz, DMSO-d6) δ 12.27 (s, 1H), 9.02 (s, 1H), 8.84 (m, 2H), 8.48 (s, 1H), 8.41 (s, 1H), 8.12 (d, J=9.0 Hz, 1H), 8.02 (t, J=8.1 Hz, 1H), 7.94 (t, J=58.5 Hz, 2H), 7.55 (ddd, J=7.5, 4.9, 1.3 Hz, 1H); LCMS: purity: 100%; MS (m/e): 438.09 (MH+).

II-99: N-(1-((1,3-cis)-3-ethoxycyclobutyl)-3-(6-(trifluoromethyl)pyridin-2-yl)-1H-pyrazol-4-yl)-2-(3-methyl-1H-pyrazol-4-yl)thiazole-4-carboxamide

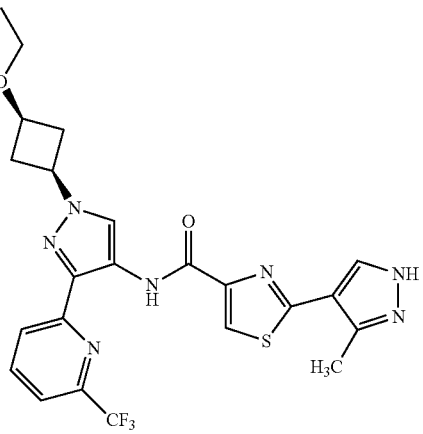

1H NMR (300 MHz, DMSO-d6) δ 10.87 (s, 1H), 8.59 (s, 1H), 8.36-8.32 (m, 2H), 8.18 (t, J=7.9 Hz, 1H), 7.97 (s, 1H), 7.85 (d, J=7.6 Hz, 1H), 4.65 (p, J=8.1 Hz, 1H), 3.85 (p, J=6.5 Hz, 1H), 3.41 (q, J=7.0 Hz, 2H), 2.82 (m, 2H), 2.42 (m, 2H), 1.14 (t, J=7.2 Hz, 3H); LCMS: purity: 94.50%; MS (m/e): 518.33 (MH+).

II-100: 2-(3-methyl-1H-pyrazol-4-yl)-N-(3-(pyridin-2-yl)-1-(2,2,2-trifluoroethyl)-1H-pyrazol-4-yl)thiazole-4-carboxamide

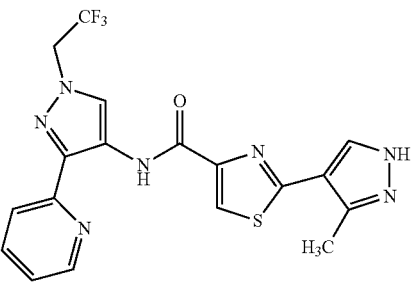 [SMILES: Cc1n[nH]cc1-c1nc(C(=O)Nc2cn(CC(F)(F)F)nc2-c2ccccn2)cs1]

1H NMR (300 MHz, DMSO-d6) δ 13.18 (s, 1H), 11.88 (s, 1H), 8.68-8.65 (m, 2H), 8.32 (s, 1H), 8.05-7.92 (m, 3H), 7.44 (t, J=5.8 Hz, 1H), 5.29 (q, J=9.1 Hz, 2H), 2.68 (s, 3H); LCMS: purity: 100%; MS (m/e): 434.26 (MH+).

II-101: N-(1-((1,3-cis)-3-hydroxycyclobutyl)-3-(pyrazin-2-yl)-1H-pyrazol-4-yl)-2-(1H-pyrazol-4-yl)thiazole-4-carboxamide

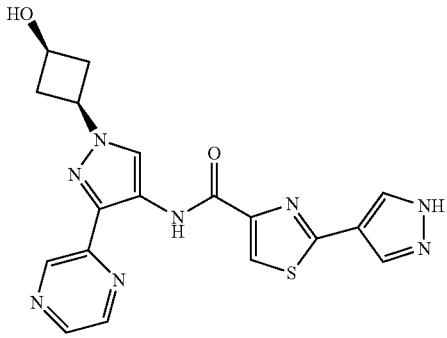 [SMILES: O=C(Nc1cn([C@H]2C[C@@H](O)C2)nc1-c1cnccn1)c1csc(-c2cn[nH]c2)n1]

1H NMR (300 MHz, DMSO-d6) δ 13.41 (s, 1H), 11.68 (s, 1H), 9.24 (d, J=1.5 Hz, 1H), 8.80 (dd, J=2.6, 1.6 Hz, 1H), 8.63 (d, J=2.6 Hz, 1H), 8.54 (s, 1H), 8.51 (s, 1H), 8.30 (s, 1H), 8.11 (d, J=1.7 Hz, 1H), 5.33 (d, J=7.0 Hz, 1H), 4.52 (p, J=7.2 Hz, 1H), 3.97 (h, J=6.6 Hz, 1H), 2.84-2.75 (m, 2H), 2.43-2.39 (m, 2H); LCMS: purity: 96.50%; MS (m/e): 409.16 (MH+).

II-102: N-(1-((1,3-cis)-3-ethoxycyclobutyl)-3-(pyrimidin-2-yl)-1H-pyrazol-4-yl)-2-(1H-pyrazol-4-yl)thiazole-4-carboxamide

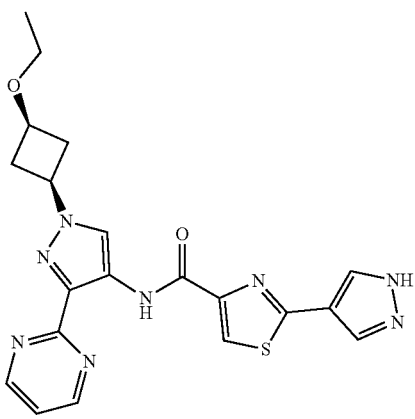 [SMILES: CCO[C@H]1C[C@@H](n2cc(NC(=O)c3csc(-c4cn[nH]c4)n3)c(-c3ncccn3)n2)C1]

1H NMR (300 MHz, DMSO-d6) δ 13.40 (s, 1H), 11.91 (s, 1H), 8.98 (d, J=4.9 Hz, 2H), 8.51 (s, 2H), 8.30 (s, 1H), 8.10 (s, 1H), 7.49 (t, J=4.9 Hz, 1H), 4.65 (p, J=8.5 Hz, 1H), 3.85 (p, J=7.3 Hz, 1H), 3.41 (q, J=7.0 Hz, 2H), 2.85-2.76 (m, 2H), 2.43 (m, 2H), 1.14 (t, J=7.0 Hz, 3H); LCMS: purity: 100%; MS (m/e): 437.19 (MH+).

II-103: 2-(1-(4-methoxybenzyl)-1H-pyrazol-4-yl)-N-(3-(pyridin-2-yl)-1-(3,3,3-trifluoro-2-hydroxypropyl)-1H-pyrazol-4-yl)thiazole-4-carboxamide

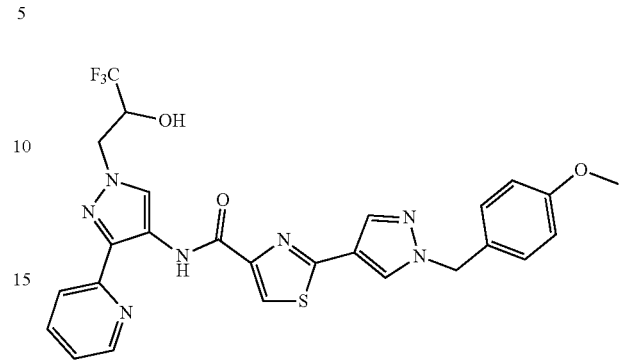

MS (ESI) (m/z): 570 [M+H]+

II-105: N-(1-(dimethylcarbamoyl)-3-(pyridin-2-yl)-1H-pyrazol-4-yl)-2-(1-(4-methoxybenzyl)-1H-pyrazol-4-yl)thiazole-4-carboxamide

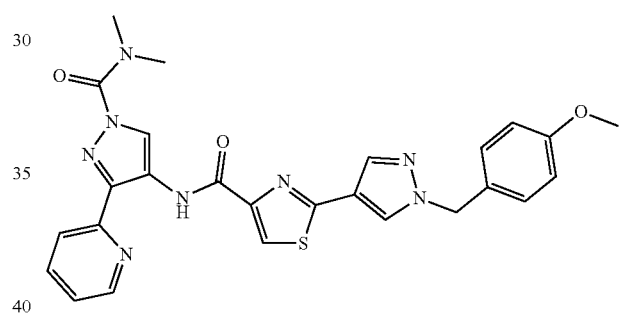

MS (ESI) (m/z): 529 [M+H]+

II-107: 2-(1-(4-methoxybenzyl)-1H-pyrazol-4-yl)-N-(3-(pyridin-2-yl)-1-(3,3,3-trifluoro-2-hydroxy-2-(trifluoromethyl)propyl)-1H-pyrazol-4-yl)thiazole-4-carboxamide

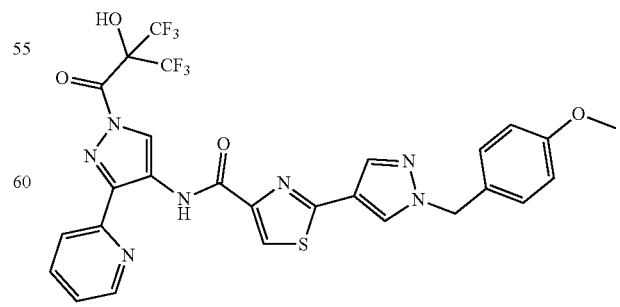

MS (ESI) (m/z): 638 [M+H]+

II-109: 6 N-(1-(2-ethoxyethyl)-3-(thiazol-2-yl)-1H-pyrazol-4-yl)-2-(1H-pyrazol-4-yl)thiazole-4-carboxamide

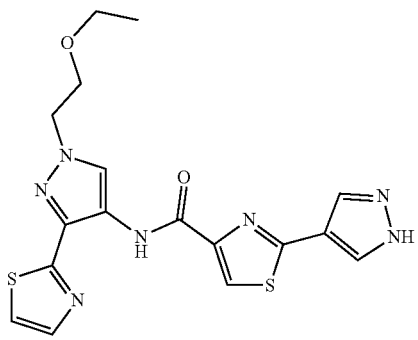 [SMILES: CCOCCn1cc(NC(=O)c2csc(-c3cn[nH]c3)n2)c(-c2nccs2)n1]

¹H NMR (400 MHz, DMSO-d₆) δ 13.40 (s, 1H), 11.43 (s, 1H), 8.48 (s, 1H), 8.45 (s, 1H), 8.31 (s, 1H), 8.11 (d, J=3.3 Hz, 1H), 7.78 (d, J=3.3 Hz, 1H), 7.65-7.48 (m, 2H), 4.36 (t, J=5.2 Hz, 2H), 3.77 (dd, J=5.7, 4.9 Hz, 2H), 3.45 (q, J=7.0 Hz, 2H), 1.07 (t, J=7.0 Hz, 3H).
MS (ESI) (m/z): 416 [M+H]⁺

II-111: 2-(1H-pyrazol-4-yl)-N-(1-(tetrahydro-2H-pyran-4-yl)-3-(thiazol-2-yl)-1H-pyrazol-4-yl)thiazole-4-carboxamide

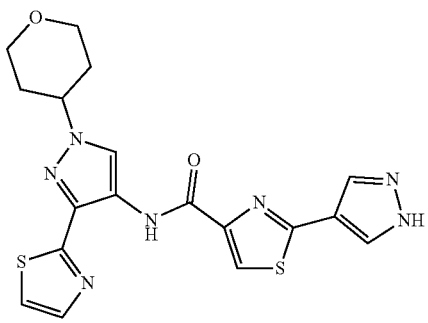 [SMILES: O=C(Nc1cn(C2CCOCC2)nc1-c1nccs1)c1csc(-c2cn[nH]c2)n1]

MS (ESI) (m/z): 428 [M+H]⁺

II-113: N-(1-(2-(2-methoxyethoxy)ethyl)-3-(thiazol-2-yl)-1H-pyrazol-4-yl)-2-(1H-pyrazol-4-yl)thiazole-4-carboxamide

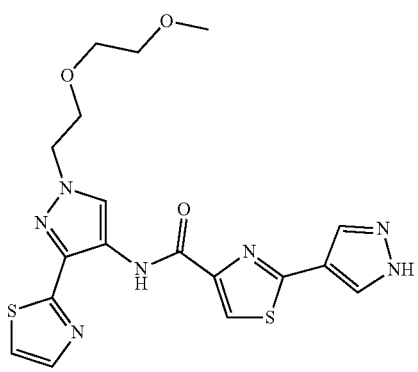 [SMILES: COCCOCCn1cc(NC(=O)c2csc(-c3cn[nH]c3)n2)c(-c2nccs2)n1]

¹H NMR (400 MHz, DMSO-d₆) δ 11.43 (s, 1H), 8.45 (s, 1H), 8.31 (s, 1H), 8.11 (d, J=3.3 Hz, 1H), 7.78 (d, J=3.3 Hz, 1H), 4.36 (t, J=5.3 Hz, 2H), 3.82 (dd, J=5.7, 4.9 Hz, 2H), 3.56-3.52 (m, 2H), 3.43-3.39 (m, 2H), 3.20 (s, 3H).
MS (ESI) (m/z): 446 [M+H]⁺

II-115: 2-(1H-pyrazol-4-yl)-N-(1-(tetrahydrofuran-3-yl)-3-(thiazol-2-yl)-1H-pyrazol-4-yl)thiazole-4-carboxamide

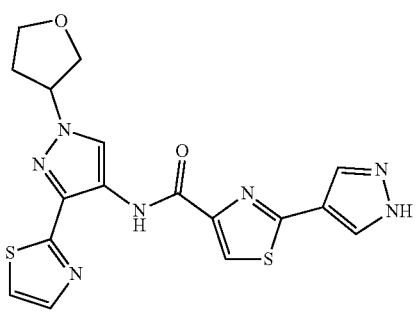 [SMILES: O=C(Nc1cn(C2CCOC2)nc1-c1nccs1)c1csc(-c2cn[nH]c2)n1]

¹H NMR (400 MHz, DMSO-d₆) δ 13.48 (s, 1H), 11.45 (s, 1H), 8.46 (s, 1H), 8.30 (s, 1H), 8.12 (d, J=3.3 Hz, 1H), 7.79 (d, J=3.3 Hz, 1H), 5.16 (dq, J=8.5, 4.5 Hz, 1H), 4.08-3.99 (m, 1H), 3.98 (d, J=4.9 Hz, 2H), 3.82 (td, J=8.3, 5.8 Hz, 1H), 2.47-2.39 (m, 1H), 2.30 (dddd, J=13.3, 7.7, 5.8, 3.7 Hz, 1H).
MS (ESI) (m/z): 414 [M+H]⁺

II-117: N-(1-(2-(diethylamino)ethyl)-3-(pyridin-2-yl)-1H-pyrazol-4-yl)-2-(1H-pyrazol-4-yl)thiazole-4-carboxamide

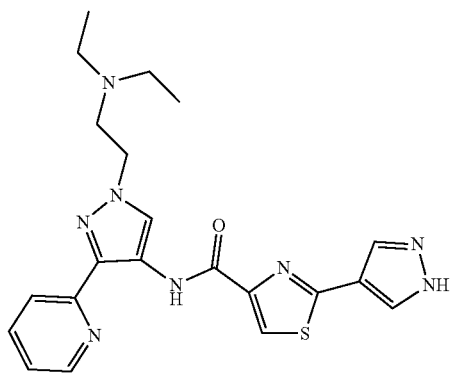 [SMILES: CCN(CC)CCn1cc(NC(=O)c2csc(-c3cn[nH]c3)n2)c(-c2ccccn2)n1]

¹H NMR (400 MHz, DMSO-d₆) δ 13.45 (s, 1H), 12.18 (s, 1H), 8.74 (ddd, J=4.9, 1.8, 1.0 Hz, 1H), 8.46 (s, 1H), 8.30 (s, 2H), 8.27 (s, 1H), 7.99 (dt, J=8.0, 1.2 Hz, 1H), 7.91 (ddd, J=8.0, 7.4, 1.8 Hz, 1H), 7.39 (ddd, J=7.4, 4.9, 1.3 Hz, 1H), 4.22 (t, J=6.4 Hz, 2H), 2.83 (t, J=6.4 Hz, 2H), 2.52-2.44 (m, 4H), 0.90 (t, J=7.1 Hz, 6H).
MS (ESI) (m/z): 437 [M+H]⁺

II-118: N-(1-(2-(2-fluoroethoxy)ethyl)-3-(pyridin-2-yl)-1H-pyrazol-4-yl)-2-(1H-pyrazol-4-yl)thiazole-4-carboxamide

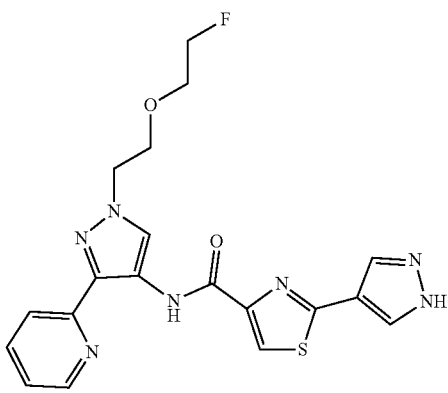 [SMILES: O=C(Nc1cn(CCOCCF)nc1-c1ccccn1)c1csc(-c2cn[nH]c2)n1]

¹H NMR (400 MHz, DMSO-d₆) δ 12.19 (s, 1H), 8.75 (ddd, J=4.9, 1.8, 1.0 Hz, 1H), 8.47 (s, 1H), 8.30 (s, 2H), 8.28 (s, 1H), 7.99 (dt, J=8.0, 1.2 Hz, 1H), 7.91 (ddd, J=8.0, 7.4, 1.8 Hz, 1H), 7.40 (ddd, J=7.4, 5.0, 1.3 Hz, 1H), 4.58-4.54 (m, 1H), 4.45-4.42 (m, 1H), 4.38 (t, J=5.3 Hz, 2H), 3.88 (t, J=5.3 Hz, 2H), 3.73-3.68 (m, 1H), 3.65-3.60 (m, 1H).

MS (ESI) (m/z): 428 [M+H]⁺

II-120: N-(1-benzyl-3-(pyridin-2-yl)-1H-pyrazol-4-yl)-2-(1H-pyrazol-4-yl)thiazole-4-carboxamide

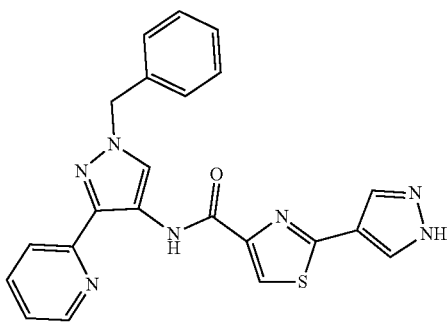 [SMILES: O=C(Nc1cn(Cc2ccccc2)nc1-c1ccccn1)c1csc(-c2cn[nH]c2)n1]

¹H NMR (400 MHz, DMSO-d₆) δ 13.41 (s, 1H), 12.21 (s, 1H), 8.75 (ddd, J=5.0, 1.8, 1.0 Hz, 1H), 8.52 (s, 1H), 8.49 (s, 1H), 8.26 (s, 1H), 8.10 (s, 1H), 7.99 (dt, J=8.0, 1.1 Hz, 1H), 7.91 (ddd, J=8.1, 7.5, 1.8 Hz, 1H), 7.47-7.25 (m, 6H), 5.44 (s, 2H).

MS (ESI) (m/z): 428 [M+H]⁺

II-121: N-(1-cyclobutyl-3-(pyridin-2-yl)-1H-pyrazol-4-yl)-2-(1H-pyrazol-4-yl)thiazole-4-carboxamide

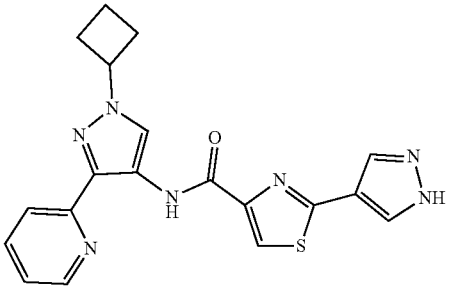 [SMILES: O=C(Nc1cn(C2CCC2)nc1-c1ccccn1)c1csc(-c2cn[nH]c2)n1]

¹H NMR (300 MHz, DMSO-d₆) δ 13.40 (s, 1H), 12.18 (s, 1H), 8.75 (ddt, J=4.9, 1.7, 0.9 Hz, 1H), 8.47 (d, J=0.7 Hz, 1H), 8.27 (d, J=0.9 Hz, 1H), 8.04 (dd, J=8.0, 1.0 Hz, 1H), 7.97-7.88 (m, 1H), 7.45-7.37 (m, 1H), 5.08-4.77 (m, 1H), 2.63-2.35 (m, 4H), 1.82 (dtd, J=10.5, 7.2, 2.2 Hz, 2H).

MS (ESI) (m/z): 392 [M+H]⁺

II-122: N-(1-(2-(2,2-difluoroethoxy)ethyl)-3-(pyridin-2-yl)-1H-pyrazol-4-yl)-2-(1H-pyrazol-4-yl)thiazole-4-carboxamide

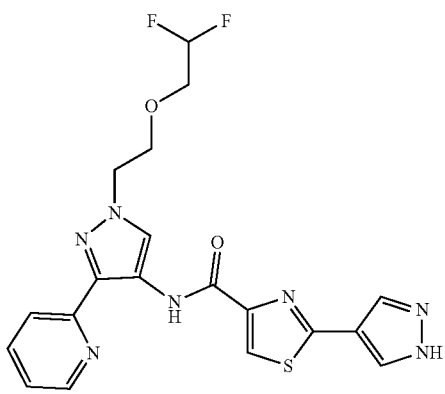 [SMILES: O=C(Nc1cn(CCOCC(F)F)nc1-c1ccccn1)c1csc(-c2cn[nH]c2)n1]

¹H NMR (400 MHz, DMSO-d₆) δ 13.43 (s, 1H), 12.21 (s, 1H), 8.75 (ddd, J=4.9, 1.8, 1.0 Hz, 1H), 8.48 (s, 2H), 8.27 (s, 1H), 8.13 (s, 1H), 7.99 (dt, J=8.1, 1.1 Hz, 1H), 7.95-7.84 (m, 1H), 7.38 (ddd, J=7.5, 4.9, 1.2 Hz, 1H), 6.11 (tt, J=54.9, 3.7 Hz, 1H), 4.40 (t, J=5.2 Hz, 2H), 3.96 (t, J=5.3 Hz, 2H), 3.72 (td, J=15.1, 3.8 Hz, 2H).

MS (ESI) (m/z): 446 [M+H]⁺

II-123: N-(1-(((1r,3r)-3-hydroxycyclobutyl)methyl)-3-(pyridin-2-yl)-1H-pyrazol-4-yl)-2-(1H-pyrazol-4-yl)thiazole-4-carboxamide

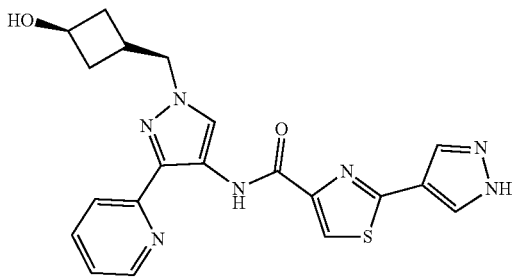

MS (ESI) (m/z): 422 [M+H]+

II-125: N-(1-(dimethylcarbamoyl)-3-(pyridin-2-yl)-1H-pyrazol-4-yl)-2-(1H-pyrazol-4-yl)thiazole-4-carboxamide

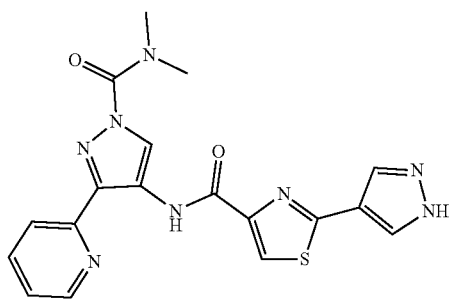 [SMILES: CN(C)C(=O)n1cc(NC(=O)c2csc(-c3cn[nH]c3)n2)c(-c2ccccn2)n1]

MS (ESI) (m/z): 409 [M+H]+

II-127: N-(1-((1s,3s)-3-(ethoxy-d5)cyclobutyl)-3-(pyridin-2-yl)-1H-pyrazol-4-yl)-2-(1H-pyrazol-4-yl)thiazole-4-carboxamide

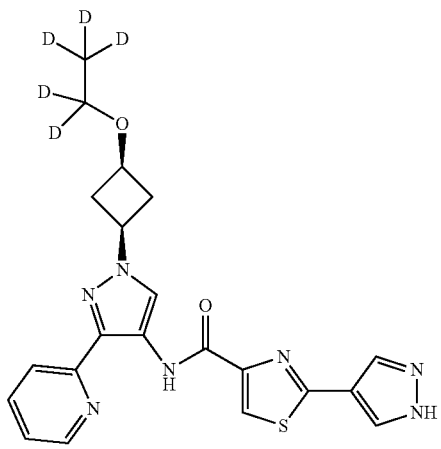 [SMILES: [2H]C([2H])([2H])C([2H])([2H])O[C@H]1C[C@@H](n2cc(NC(=O)c3csc(-c4cn[nH]c4)n3)c(-c3ccccn3)n2)C1]

¹H NMR (400 MHz, DMSO-d₆) δ 13.42 (s, 1H), 12.19 (s, 1H), 8.75 (ddd, J=5.0, 1.8, 1.0 Hz, 1H), 8.49 (s, 1H), 8.45 (s, 1H), 8.27 (s, 1H), 8.11 (s, 1H), 8.03 (dt, J=8.1, 1.1 Hz, 1H), 7.91 (ddd, J=8.0, 7.5, 1.8 Hz, 1H), 7.39 (ddd, J=7.5, 4.9, 1.2 Hz, 1H), 4.57 (tt, J=9.0, 7.4 Hz, 1H), 3.79 (tt, J=7.7, 6.6 Hz, 1H), 2.78 (dddd, J=9.9, 9.0, 4.8, 2.7 Hz, 2H), 2.41 (dddd, J=10.6, 9.0, 6.7, 2.8 Hz, 2H).

MS (ESI) (m/z): 441 [M+H]+

II-128: N-(1-(diethylcarbamoyl)-3-(pyridin-2-yl)-1H-pyrazol-4-yl)-2-(1H-pyrazol-4-yl)thiazole-4-carboxamide

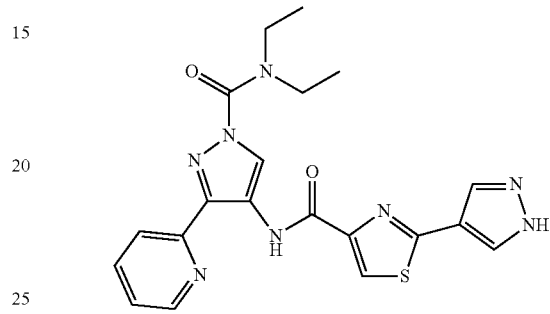

¹H NMR (400 MHz, DMSO-d₆) δ 13.42 (s, 1H), 12.20 (s, 1H), 8.81 (ddd, J=5.0, 1.7, 1.0 Hz, 1H), 8.76 (s, 1H), 8.34 (s, 1H), 8.32-8.16 (m, 2H), 8.11-7.97 (m, 2H), 7.52 (ddd, J=7.3, 4.9, 1.4 Hz, 1H), 3.55 (d, J=8.8 Hz, 4H), 1.27 (t, J=6.9 Hz, 6H).

MS (ESI) (m/z): 437 [M+H]+

II-129: N-(1-(morpholine-4-carbonyl)-3-(pyridin-2-yl)-1H-pyrazol-4-yl)-2-(1H-pyrazol-4-yl)thiazole-4-carboxamide

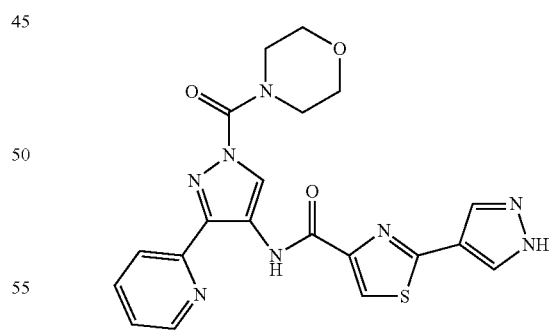

¹H NMR (400 MHz, DMSO-d₆) δ 12.21 (s, 1H), 8.83 (ddd, J=5.0, 1.8, 1.0 Hz, 1H), 8.77 (s, 1H), 8.35 (s, 1H), 8.33-8.23 (m, 2H), 8.11 (dt, J=8.0, 1.1 Hz, 1H), 8.02 (td, J=7.8, 1.8 Hz, 1H), 7.54 (ddd, J=7.5, 4.9, 1.3 Hz, 1H), 3.81 (s, 4H), 3.72 (dd, J=5.6, 3.6 Hz, 4H).

MS (ESI) (m/z): 451 [M+H]+

II-130: N-(1-((1s,3s)-3-(2-fluoroethoxy)cyclobutyl)-3-(pyridin-2-yl)-1H-pyrazol-4-yl)-2-(1H-pyrazol-4-yl)thiazole-4-carboxamide

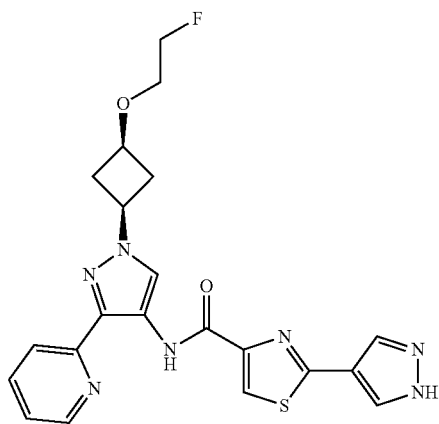 [SMILES: O=C(Nc1cn([C@H]2C[C@@H](OCCF)C2)nc1-c1ccccn1)c1csc(-c2cn[nH]c2)n1]

¹H NMR (400 MHz, DMSO-d$_6$) δ 13.42 (s, 1H), 12.18 (s, 1H), 8.75 (ddd, J=5.0, 1.8, 1.0 Hz, 1H), 8.53-8.47 (m, 1H), 8.46 (s, 1H), 8.27 (s, 1H), 8.11 (s, 1H), 8.04 (dt, J=8.0, 1.1 Hz, 1H), 7.92 (ddd, J=8.1, 7.5, 1.8 Hz, 1H), 7.41 (ddd, J=7.5, 4.9, 1.2 Hz, 1H), 4.68-4.54 (m, 2H), 4.52-4.45 (m, 1H), 3.90 (tt, J=7.7, 6.5 Hz, 1H), 3.68-3.63 (m, 1H), 3.60-3.54 (m, 1H), 2.82 (dddd, J=11.6, 7.3, 6.0, 2.7 Hz, 2H), 2.53-2.39 (m, 2H).

MS (ESI) (m/z): 454 [M+H]⁺

II-132: N-(1-(3-fluorocyclobut-2-en-1-yl)-3-(pyridin-2-yl)-1H-pyrazol-4-yl)-2-(1H-pyrazol-4-yl)thiazole-4-carboxamide

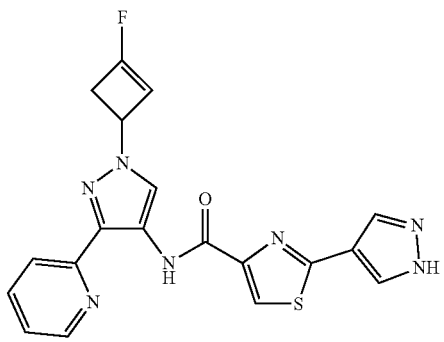 [SMILES: O=C(Nc1cn(C2C=C(F)C2)nc1-c1ccccn1)c1csc(-c2cn[nH]c2)n1]

MS (ESI) (m/z): 408 [M+H]⁺

II-134: N-(1-(3,3-difluorocyclobutyl)-3-(pyridin-2-yl)-1H-pyrazol-4-yl)-2-(1H-pyrazol-4-yl)thiazole-4-carboxamide

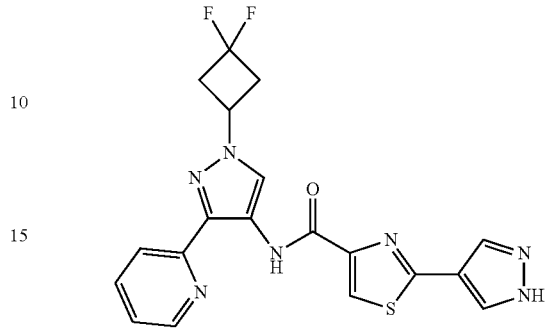

¹H NMR (400 MHz, DMSO-d$_6$) δ 12.19 (s, 1H), 8.77 (ddd, J=5.0, 1.8, 1.0 Hz, 1H), 8.56 (s, 1H), 8.29 (s, 1H), 8.06 (dt, J=8.0, 1.1 Hz, 1H), 7.95 (td, J=7.7, 1.8 Hz, 1H), 7.44 (ddd, J=7.5, 4.9, 1.3 Hz, 1H), 5.07 (qd, J=8.4, 6.5 Hz, 1H), 3.28-3.14 (m, 4H).

MS (ESI) (m/z): 428 [M+H]⁺

II-136: N-(3-cyano-1-((1s,3s)-3-hydroxycyclobutyl)-1H-pyrazol-4-yl)-2-(1H-pyrazol-4-yl)thiazole-4-carboxamide

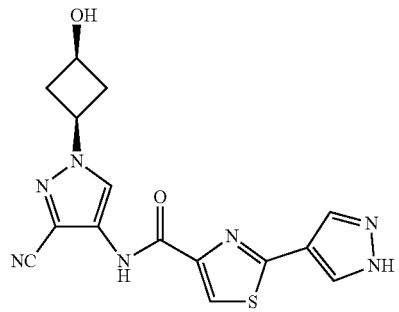 [SMILES: N#Cc1nn([C@H]2C[C@@H](O)C2)cc1NC(=O)c1csc(-c2cn[nH]c2)n1]

¹H NMR (400 MHz, DMSO-d$_6$) δ 13.37 (s, 1H), 10.30 (s, 1H), 8.32 (s, 1H), 8.23 (s, 1H), 5.34 (d, J=7.0 Hz, 1H), 4.50 (tt, J=9.1, 7.3 Hz, 1H), 3.95 (q, J=7.0 Hz, 1H), 2.83-2.69 (m, 2H), 2.33 (dddd, J=10.9, 9.1, 6.7, 2.7 Hz, 2H).

MS (ESI) (m/z): 356 [M+H]⁺

II-137: N-(3-cyano-1-methyl-1H-pyrazol-4-yl)-2-(1H-pyrazol-4-yl)thiazole-4-carboxamide

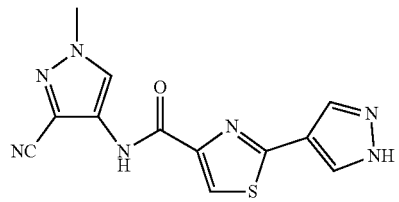 [SMILES: Cn1cc(NC(=O)c2csc(-c3cn[nH]c3)n2)c(C#N)n1]

¹H NMR (400 MHz, DMSO-d$_6$) δ 8.32 (s, 1H), 8.25 (s, 2H), 8.15 (s, 1H), 3.94 (s, 3H).

MS (ESI) (m/z): 300 [M+H]⁺

II-138: N-(3-cyano-1-((1s,3s)-3-ethoxycyclobutyl)-1H-pyrazol-4-yl)-2-(1H-pyrazol-4-yl)thiazole-4-carboxamide II-141: 2-(1H-pyrazol-4-yl)-N-(3-(pyridin-2-yl)-1-((trans)-3-(2,2,2-trifluoroethoxy)cyclobutyl)-1H-pyrazol-4-yl)thiazole-4-carboxamide

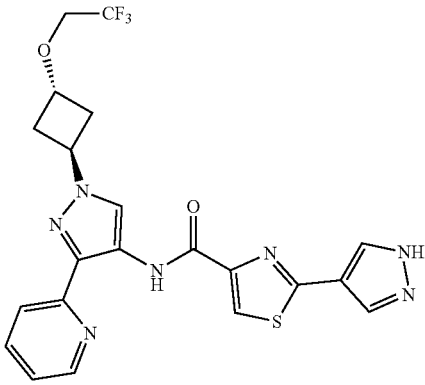

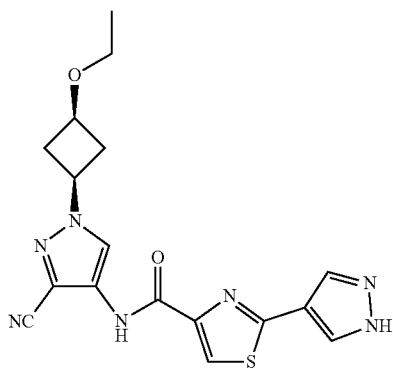 [SMILES: CCO[C@H]1C[C@@H](n2cc(NC(=O)c3csc(-c4cn[nH]c4)n3)c(C#N)n2)C1]

$^1$H NMR (300 MHz, DMSO-d$_6$) δ 13.41 (s, 1H), 12.18 (s, 1H), 8.76 (d, J=4.8 Hz, 1H), 8.49 (s, 2H), 8.28 (s, 1H), 8.10 (m, 2H), 7.94 (m, 1H), 7.42 (t, J=6.6 Hz, 1H), 5.09 (m, 1H), 4.54 (m, 1H), 4.05 (m, 2H), 2.71 (m, 2H), 2.60 (m, 2H). LCMS: purity: 88.96%. MS (m/e): 489.48 (MH$^+$).

II-143: N-(1-((trans)-4-hydroxycyclohexyl)-3-(pyridin-2-yl)-1H-pyrazol-4-yl)-2-(1H-pyrazol-4-yl)thiazole-4-carboxamide $^1$H NMR (300 MHz, DMSO-d$_6$) δ 13.29 (s, 1H), 8.22 (s, 2H), 8.06 (s, 1H), 8.05-7.54 (m, 2H), 4.54-4.28 (m, 1H), 3.92 (q, J=6.9 Hz, 1H), 3.84-3.68 (m, 2H), 2.67 (q, J=8.6, 7.9 Hz, 2H), 2.34-2.17 (m, 2H), 1.15 (t, J=7.1 Hz, 3H). MS (ESI) (m/z): 384 [M+H]$^+$ II-140: N-(3-(3-fluoropyridin-2-yl)-1-(1,4-dioxaspiro[4.5]decan-8-yl)-1H-pyrazol-4-yl)-2-(1H-pyrazol-4-yl)thiazole-4-carboxamide

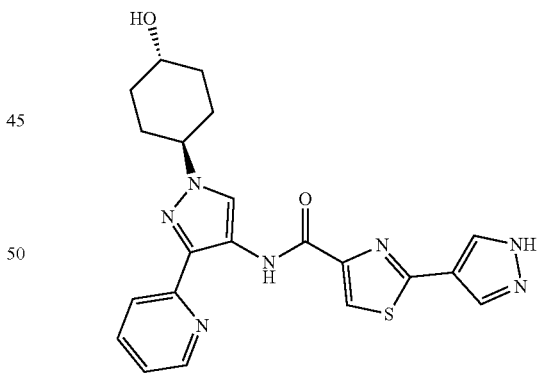

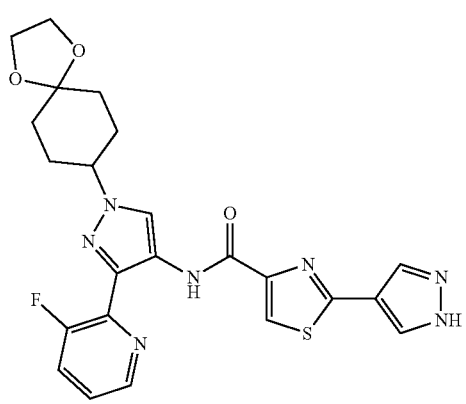 [SMILES: O=C(Nc1cn(C2CCC3(CC2)OCCO3)nc1-c1ncccc1F)c1csc(-c2cn[nH]c2)n1]

$^1$H NMR (300 MHz, DMSO-d$_6$) δ 13.41 (s, 1H), 12.18 (s, 1H), 8.74 (d, J=4.8 Hz, 1H), 8.49 (s, 1H), 8.42 (s, 1H), 8.27 (s, 1H), 8.10 (s, 1H), 7.98 (m, 1H), 7.91 (t, J=7.8 Hz, 1H), 7.39 (t, J=6.0 Hz, 1H), 4.66 (d, J=4.2 Hz, 1H), 4.25 (t, J=11.1 Hz, 1H), 3.53 (m, 1H), 2.02 (m, 2H), 1.90 (m, 4H), 1.37 (m, 2H). LCMS: purity: 94.52%. MS (m/e): 435.51 (MH$^+$).

MS (ESI) (m/z): 496 [M+H]$^+$

II-147: N-(1-((cis)-3-ethoxycyclopentyl)-3-(pyridin-2-yl)-1H-pyrazol-4-yl)-2-(1H-pyrazol-4-yl)thiazole-4-carboxamide

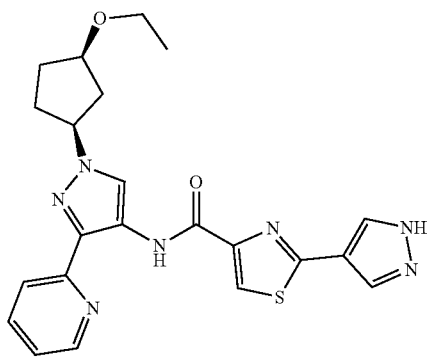 [SMILES: CCO[C@@H]1CC[C@H](n2cc(NC(=O)c3csc(-c4cn[nH]c4)n3)c(-c3ccccn3)n2)C1]

¹H NMR (300 MHz, DMSO-d₆) δ 13.36 (s, 1H), 12.14 (s, 1H), 8.69 (d, J=4.8 Hz, 1H), 8.45 (s, 1H), 8.22 (s, 1H), 8.05 (s, 1H), 7.89 (m, 2H), 7.45 (m, 2H), 7.35 (m, 1H), 4.77 (m, 1H), 3.93 (m, 2H), 3.41 (m, 2H), 2.12 (m, 2H), 1.98 (m, 2H), 1.80 (m, 2H), 1.50 (t, J=8.4 Hz, 3H). LCMS: purity: 96.91%. MS (m/e): 449.53 (MH⁺).

II-149: N-(1-((cis)-3-hydroxycyclopentyl)-3-(pyridin-2-yl)-1H-pyrazol-4-yl)-2-(1H-pyrazol-4-yl)thiazole-4-carboxamide

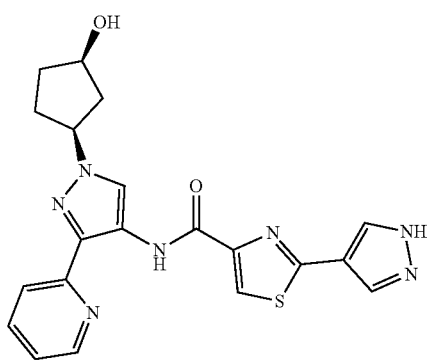 [SMILES: O=C(Nc1cn([C@H]2CC[C@@H](O)C2)nc1-c1ccccn1)c1csc(-c2cn[nH]c2)n1]

¹H NMR (300 MHz, DMSO-d₆) δ 12.18 (s, 1H), 8.75 (t, J=0.9 Hz, 1H), 8.50 (d, J=15.6 Hz, 1H), 8.27 (m, 3H), 7.95 (m, 2H), 7.38 (m, 1H), 4.80 (m, 1H), 4.21 (m, 1H), 3.60 (m, 1H), 2.19 (m, 2H), 2.12 (m, 2H), 1.81 (m, 2H). LCMS: purity: 95.63%. MS (m/e): 421.48 (MH⁺).

II-151: N-(1-((trans)-3-hydroxycyclopentyl)-3-(pyridin-2-yl)-1H-pyrazol-4-yl)-2-(1H-pyrazol-4-yl)thiazole-4-carboxamide

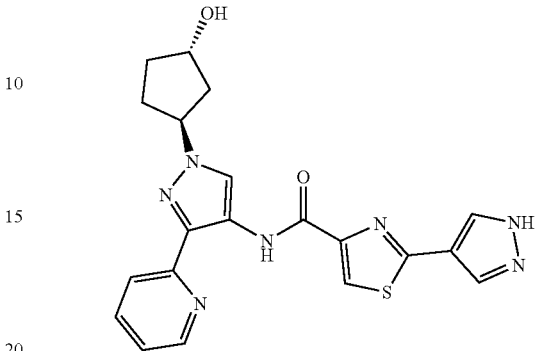

¹H NMR (300 MHz, DMSO-d₆) δ 12.17 (s, 1H), 8.73 (t, J=1.8 Hz, 1H), 8.44 (s, 1H), 8.27 (m, 3H), 7.92 (m, 2H), 7.40 (m, 1H), 4.98 (m, 1H), 4.38 (m, 1H), 3.44 (m, 1H), 2.24 (m, 2H), 2.07 (m, 3H), 1.72 (m, 1H). LCMS: purity: 100%. MS (m/e): 421.48 (MH⁺).

II-153: N-(1-((cis)-3-ethoxycyclobutyl)-3-(5-fluoropyridin-2-yl)-1H-pyrazol-4-yl)-2-(1H-pyrazol-4-yl)thiazole-4-carboxamide

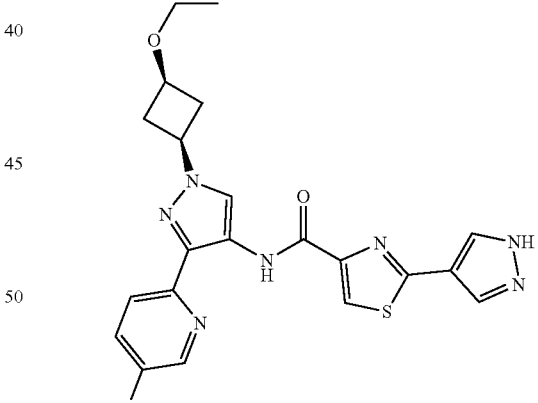

¹H NMR (300 MHz, DMSO-d₆) δ 13.36 (s, 1H), 11.76 (s, 1H), 8.68 (d, J=3.0 Hz, 1H), 8.47 (s, 1H), 8.42 (s, 1H), 8.23 (s, 1H), 8.06 (s, 1H), 7.85 (m, 1H), 7.50 (m, 1H), 4.54 (m, 1H), 3.75 (m, 1H), 3.40 (m, 2H), 2.74 (m, 2H), 2.42 (m, 2H), 1.08 (t, J=7.2 Hz, 3H). LCMS: purity: 96.80%. MS (m/e): 453.50 (MH⁺).

II-155: N-(1-((cis)-3-ethoxy-2-fluorocyclobutyl)-3-(pyridin-2-yl)-1H-pyrazol-4-yl)-2-(1H-pyrazol-4-yl)thiazole-4-carboxamide

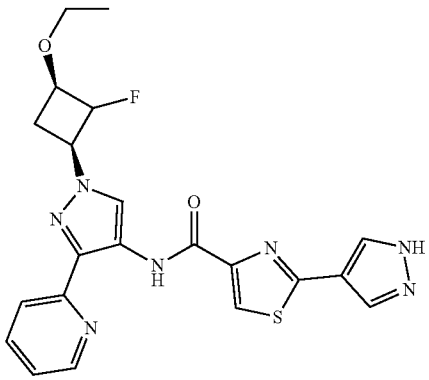 [SMILES: CCO[C@@H]1C[C@H](n2cc(NC(=O)c3csc(-c4cn[nH]c4)n3)c(-c3ccccn3)n2)C1F]

$^1$H NMR (300 MHz, CDCl$_3$) δ 12.39 (s, 1H), 8.71 (d, J=3.9 Hz, 1H), 8.47 (s, 1H), 8.13 (d, J=8.1 Hz, 1H), 8.07 (s, 1H), 7.78 (t, J=7.8 Hz, 1H), 7.56 (m, 2H), 7.25 (t, J=3.9 Hz, 1H), 5.17 (m, 1H), 4.36 (m, 1H), 3.93 (m, 1H), 3.64 (m, 1H), 2.76 (t, J=8.7 Hz, 1H), 2.18 (q, J=18.6 Hz, 1H), 1.55 (s, 1H), 1.29 (t, J=6.9 Hz, 3H). LCMS: purity: 96.40%. MS (m/e): 453.50 (MH$^+$).

II-157: N-(1-((cis)-3-ethoxycyclobutyl)-3-(3-fluoro-pyridin-2-yl)-1H-pyrazol-4-yl)-2-(1H-pyrazol-4-yl)thiazole-4-carboxamide

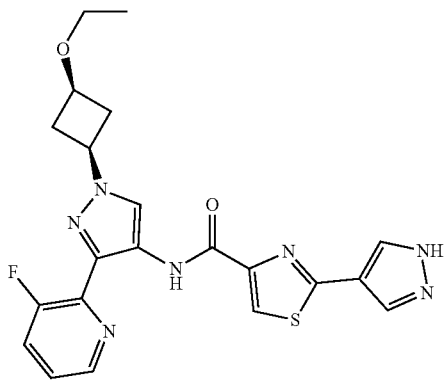 [SMILES: CCO[C@H]1C[C@@H](n2cc(NC(=O)c3csc(-c4cn[nH]c4)n3)c(-c3ncccc3F)n2)C1]

$^1$H NMR (300 MHz, DMSO-d$_6$) δ 613.41 (s, 1H), 12.05 (s, 1H), 8.56 (m, 1H), 8.52 (s, 1H), 8.49 (s, 1H), 8.28 (s, 1H), 8.09 (s, 1H), 7.90 (t, J=9.9 Hz, 1H), 7.53 (m, 1H), 4.61 (m, 1H), 3.83 (m, 1H), 3.42 (m, 2H), 2.81 (m, 2H), 2.42 (m, 2H), 1.14 (t, J=7.2 Hz, 3H). LCMS: purity: 100%. MS (m/e): 453.50 (MH$^+$).

II-158: N-(1-((cis)-3-ethoxycyclobutyl)-3-(4-fluoro-pyridin-2-yl)-1H-pyrazol-4-yl)-2-(1H-pyrazol-4-yl)thiazole-4-carboxamide

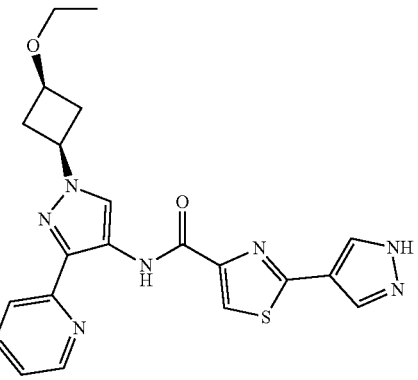

$^1$H NMR (300 MHz, DMSO-d$_6$) δ 13.25 (s, 1H), 11.43 (s, 1H), 8.78 (m, 1H), 8.45 (s, 1H), 8.26 (s, 1H), 7.95 (s, 1H), 7.79 (m, 1H), 7.36 (m, 1H), 7.28 (d, J=3.6 Hz, 1H), 4.61 (m, 1H), 3.83 (m, 1H), 3.41 (m, 2H), 2.80 (m, 2H), 2.41 (m, 2H), (t, J=6.9 Hz, 3H). LCMS: purity: 100%. MS (m/e): 453.50 (MH$^+$).

II-160: N-(1-((cis)-3-ethoxycyclobutyl)-3-(6-fluoro-pyridin-2-yl)-1H-pyrazol-4-yl)-2-(1H-pyrazol-4-yl)thiazole-4-carboxamide

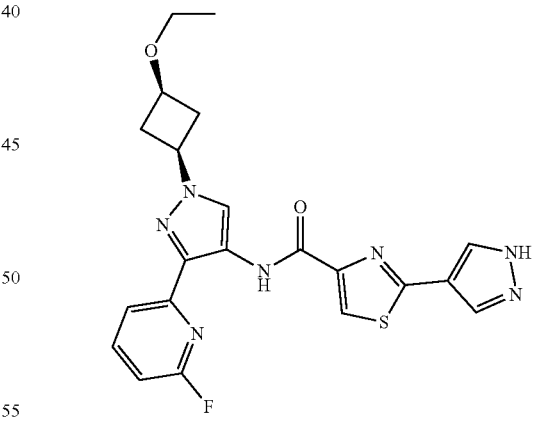

$^1$H NMR (300 MHz, DMSO-d$_6$) δ 13.42 (s, 1H), 11.58 (s, 1H), 8.50 (s, 1H), 8.46 (s, 1H), 8.29 (s, 1H), 8.16 (s, 1H), 8.13 (m, 1H), 7.96 (d, J=2.4 Hz, 1H), 7.20 (d, J=7.8 Hz, 1H), 4.63 (m, 1H), 3.83 (m, 1H), 3.40 (m, 2H), 2.80 (m, 2H), 2.45 (m, 2H), 1.14 (t, J=6.9 Hz, 3H). LCMS: purity: 100%. MS (m/e): 453.50 (MH$^+$).

II-161: 2-(1H-pyrazol-4-yl)-N-(3-(pyridin-2-yl)-1-((cis)-3-(2,2,2-trifluoroethoxy)cyclobutyl)-1H-pyrazol-4-yl)thiazole-4-carboxamide

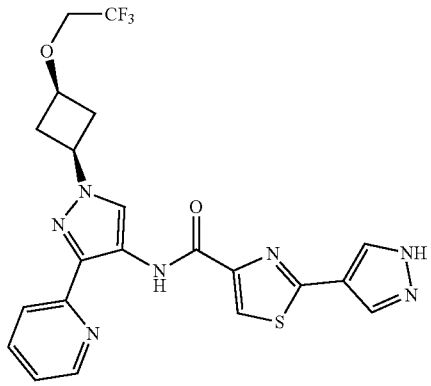 [SMILES: O=C(Nc1cn([C@H]2C[C@@H](OCC(F)(F)F)C2)nc1-c1ccccn1)c1csc(-c2cn[nH]c2)n1]

¹H NMR (300 MHz, DMSO-d₆) δ 13.43 (s, 1H), 12.18 (s, 1H), 8.76 (t, J=4.2 Hz, 1H), 8.48 (t, J=3.0 Hz, 2H), 8.13 (s, 1H), 8.04 (d, J=6.9 Hz, 1H), 7.96 (m, 2H), 7.43 (m, 1H), 5.07 (m, 1H), 4.54 (m, 1H), 4.08 (m, 2H), 2.74 (m, 2H), 2.61 (m, 2H). LCMS: purity: 97.81%. MS (m/e): 489.48 (MH⁺).

II-163: (4-(4-((1-((cis)-3-ethoxycyclobutyl)-3-(3-fluoropyridin-2-yl)-1H-pyrazol-4-yl)carbamoyl)thiazol-2-yl)-1H-pyrazol-1-yl)methyl dihydrogen phosphate

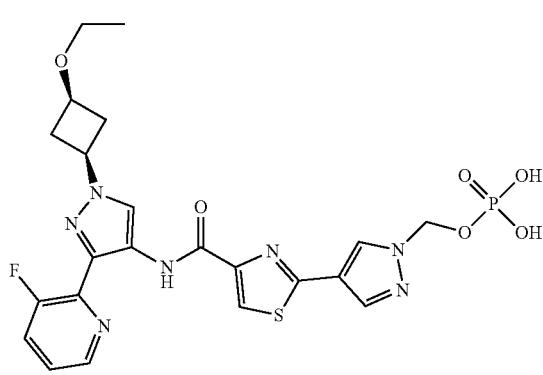 [SMILES: CCO[C@H]1C[C@@H](n2cc(NC(=O)c3csc(-c4cnn(COP(=O)(O)O)c4)n3)c(-c3ncccc3F)n2)C1]

¹H NMR (300 MHz, DMSO-d₆) δ 12.10 (s, 1H), 8.72 (m, 1H), 8.60 (s, 1H), 8.52 (s, 1H), 8.34 (s, 1H), 8.17 (s, 1H), 7.89 (m, 1H), 7.50 (m, 1H), 5.92 (s, 1H), 5.88 (s, 1H), 4.63 (m, 1H), 3.83 (m, 1H), 3.40 (m, 2H), 2.82 (m, 2H), 2.44 (m, 2H), 1.13 (t, J=6.9 Hz, 3H). LCMS: purity: 95.89%. MS (m/e): 563.50 (MH⁺).

II-164: (4-(4-((1-((cis)-3-ethoxycyclobutyl)-3-(3-fluoropyridin-2-yl)-1H-pyrazol-4-yl)carbamoyl)thiazol-2-yl)-1H-pyrazol-1-yl)methyl disodium phosphate

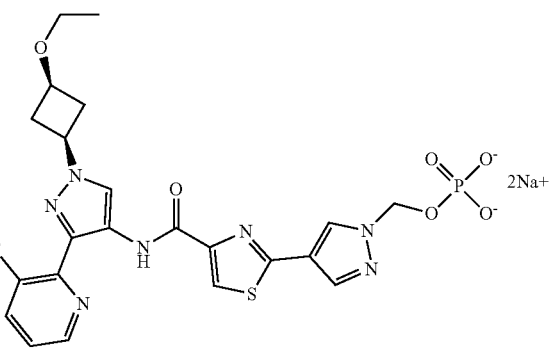

¹H NMR (300 MHz, Deuterium Oxide) δ 8.11 (s, 1H), 8.04 (d, J=4.2 Hz, 1H), 8.00 (s, 1H), 7.68 (s, 1H), 7.56 (s, 1H), 7.41 (t, J=8.1 Hz, 1H), 7.16 (m, 1H), 5.62 (s, 1H), 5.59 (s, 1H), 4.30 (m, 1H), 3.93 (m, 1H), 3.50 (m, 2H), 2.85 (m, 2H), 2.26 (m, 2H), 1.12 (t, J=6.9 Hz, 3H). LCMS: purity: 95.89%. MS (m/e): 563.50 (MH⁺).

II-165: N-(3-(3-fluoropyridin-2-yl)-1-((cis)-3-(2,2,2-trifluoroethoxy)cyclobutyl)-1H-pyrazol-4-yl)-2-(1H-pyrazol-4-yl)thiazole-4-carboxamide

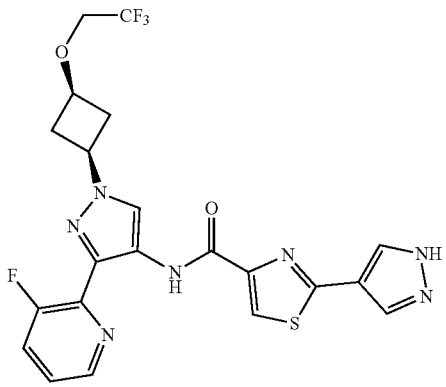 [SMILES: O=C(Nc1cn([C@H]2C[C@@H](OCC(F)(F)F)C2)nc1-c1ncccc1F)c1csc(-c2cn[nH]c2)n1]

¹H NMR (300 MHz, DMSO-d₆) δ 13.37 (s, 1H), 12.00 (s, 1H), 8.60 (d, J=4.8 Hz, 1H), 8.48 (s, 1H), 8.40 (s, 1H), 8.24 (s, 1H), 8.18 (s, 1H), 7.83 (m, 1H), 7.46 (m, 1H), 4.58 (m, 1H), 3.98 (m, 2H), 3.54 (m, 1H), 2.78 (m, 2H), 2.44 (m, 2H). LCMS: purity: 96.48%. MS (m/e): 507.47 (MH⁺).

II-167: N-(3-(3-fluoropyridin-2-yl)-1-((trans)-3-(2,2,2-trifluoroethoxy)cyclobutyl)-1H-pyrazol-4-yl)-2-(1H-pyrazol-4-yl)thiazole-4-carboxamide

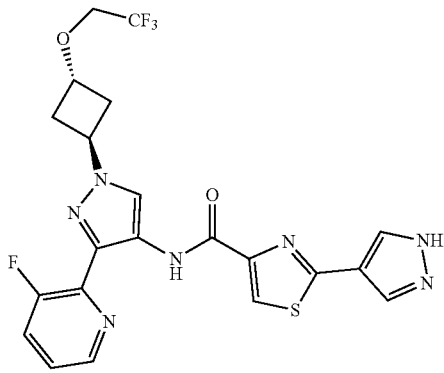 [SMILES: O=C(Nc1cn([C@H]2C[C@H](OCC(F)(F)F)C2)nc1-c1ncccc1F)c1csc(-c2cn[nH]c2)n1]

¹H NMR (300 MHz, DMSO-d₆) δ 13.41 (s, 1H), 12.06 (s, 1H), 8.66 (d, J=4.5 Hz, 1H), 8.55 (s, 1H), 8.28 (m, 3H), 7.91 (m, 1H), 7.55 (m, 1H), 5.11 (m, 1H), 4.52 (m, 1H), 4.05 (m, 2H), 2.71 (m, 2H), 2.48 (m, 2H). LCMS: purity: 95.89%. MS (m/e): 507.47 (MH⁺).

II-169: N-(1-((trans)-4-ethoxycyclohexyl)-3-(3-fluoropyridin-2-yl)-1H-pyrazol-4-yl)-2-(1H-pyrazol-4-yl)thiazole-4-carboxamide

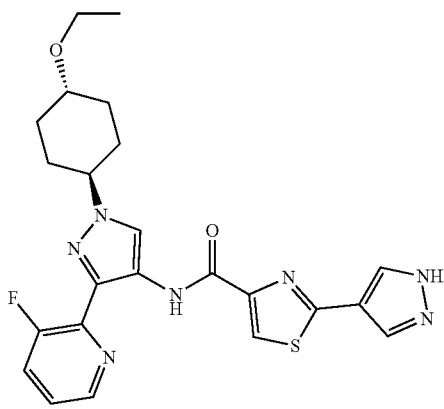 [SMILES: CCO[C@H]1CC[C@H](n2cc(NC(=O)c3csc(-c4cn[nH]c4)n3)c(-c3ncccc3F)n2)CC1]

¹H NMR (300 MHz, DMSO-d₆) δ 13.42 (s, 1H), 12.07 (s, 1H), 8.64 (d, J=3.3 Hz, 1H), 8.48 (s, 2H), 8.28 (s, 1H), 8.09 (s, 1H), 7.87 (m, 1H), 7.53 (m, 1H), 4.32 (m, 1H), 3.44 (m, 2H), 3.35 (m, 1H), 2.06 (m, 4H), 1.92 (m, 2H), 1.38 (m, 2H), 1.10 (t, J=6.9 Hz, 3H). LCMS: purity: 97.81%. MS (m/e): 481.55 (MH⁺).

II-170: N-(3-(6-fluoropyridin-2-yl)-1-((cis)-3-(2,2,2-trifluoroethoxy)cyclobutyl)-1H-pyrazol-4-yl)-2-(1H-pyrazol-4-yl)thiazole-4-carboxamide

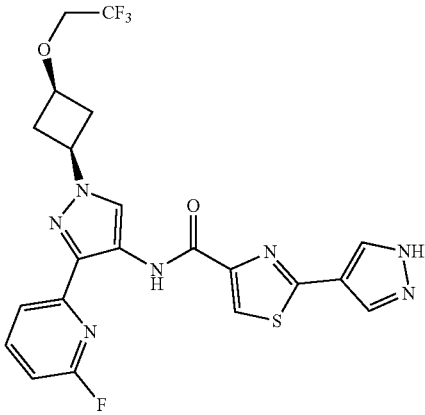 [SMILES: O=C(Nc1cn([C@H]2C[C@@H](OCC(F)(F)F)C2)nc1-c1cccc(F)n1)c1csc(-c2cn[nH]c2)n1]

¹H NMR (300 MHz, DMSO-d₆) δ 13.37 (s, 1H), 11.53 (s, 1H), 8.49 (d, J=6.9 Hz, 1H), 8.24 (m, 4H), 8.08 (m, 1H), 7.93 (m, 1H), 7.16 (d, J=7.5 Hz, 1H), 4.60 (m, 1H), 4.00 (m, 3H), 2.78 (m, 2H), 2.46 (m, 2H). LCMS: purity: 100%. MS (m/e): 507.47 (MH⁺).

II-172: N-(3-(6-fluoropyridin-2-yl)-1-((cis)-3-hydroxycyclobutyl)-1H-pyrazol-4-yl)-2-(1H-pyrazol-4-yl)thiazole-4-carboxamide

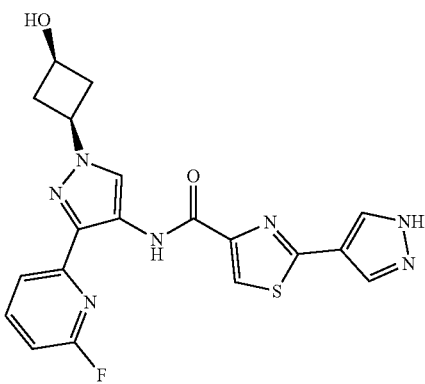 [SMILES: O=C(Nc1cn([C@H]2C[C@@H](O)C2)nc1-c1cccc(F)n1)c1csc(-c2cn[nH]c2)n1]

¹H NMR (300 MHz, DMSO-d₆) δ 13.44 (s, 1H), 11.58 (s, 1H), 8.53 (s, 1H), 8.50 (s, 1H), 8.41 (s, 1H), 8.28 (s, 1H), 8.10 (m, 1H), 7.95 (d, J=7.5 Hz, 1H), 7.20 (d, J=7.8 Hz, 1H), 5.32 (m, 1H), 4.50 (m, 1H), 3.96 (m, 1H), 2.79 (m, 2H), 2.40 (m, 2H). LCMS: purity: 100%. MS (m/e): 425.45 (MH⁺).

II-173: (4-(4-((1-((cis)-3-ethoxycyclobutyl)-3-(6-fluoropyridin-2-yl)-1H-pyrazol-4-yl)carbamoyl)thiazol-2-yl)-1H-pyrazol-1-yl)methyl dihydrogen phosphate

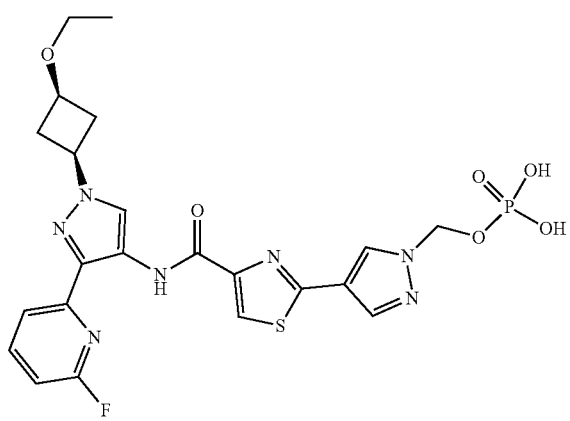 [SMILES: CCO[C@H]1C[C@@H](n2cc(NC(=O)c3csc(-c4cnn(COP(=O)(O)O)c4)n3)c(-c3cccc(F)n3)n2)C1]

¹H NMR (300 MHz, DMSO-d₆) δ 11.59 (s, 1H), 8.61 (s, 1H), 8.51 (s, 1H), 8.35 (s, 1H), 8.22 (s, 1H), 8.10 (m, 1H), 7.96 (m, 1H), 7.21 (d, J=6.6 Hz, 1H), 5.86 (s, 1H), 5.82 (s, 1H), 4.63 (m, 1H), 3.84 (m, 1H), 3.40 (m, 2H), 2.81 (m, 2H), 2.43 (m, 2H), 1.14 (t, J=7.2 Hz, 3H). LCMS: purity: 100%. MS (m/e): 563.51 (MH⁺).

II-174: N-(3-(3,6-difluoropyridin-2-yl)-1-((cis)-3-ethoxycyclobutyl)-1H-pyrazol-4-yl)-2-(1H-pyrazol-4-yl)thiazole-4-carboxamide

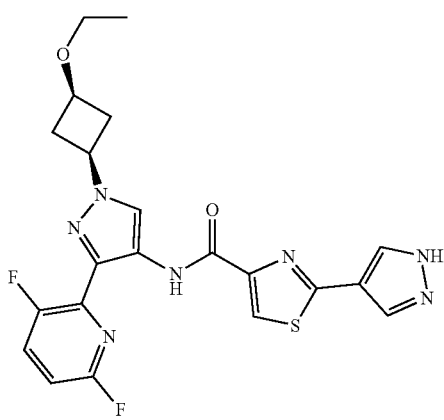 [SMILES: CCO[C@H]1C[C@@H](n2cc(NC(=O)c3csc(-c4cn[nH]c4)n3)c(-c3nc(F)ccc3F)n2)C1]

¹H NMR (300 MHz, DMSO-d₆) δ 13.41 (s, 1H), 11.46 (s, 1H), 8.56 (s, 1H), 8.44 (s, 1H), 8.30 (s, 1H), 8.14 (m, 2H), 7.32 (m, 1H), 4.62 (m, 1H), 3.83 (m, 1H), 3.39 (m, 2H), 2.80 (m, 2H), 2.40 (m, 2H), 1.15 (t, J=7.5 Hz, 3H). LCMS: purity: 100%. MS (m/e): 471.49 (MH⁺).

II-175: N-(1-((cis)-4-ethoxycyclohexyl)-3-(3-fluoropyridin-2-yl)-1H-pyrazol-4-yl)-2-(1H-pyrazol-4-yl)thiazole-4-carboxamide

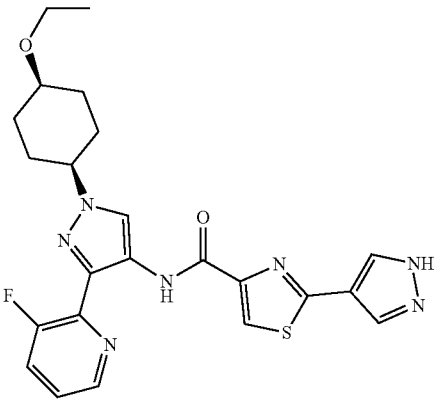 [SMILES: CCO[C@H]1CC[C@@H](n2cc(NC(=O)c3csc(-c4cn[nH]c4)n3)c(-c3ncccc3F)n2)CC1]

¹H NMR (300 MHz, DMSO-d₆) δ 13.41 (s, 1H), 12.07 (s, 1H), 8.65 (d, J=4.2 Hz, 1H), 8.49 (s, 1H), 8.45 (s, 1H), 8.28 (s, 1H), 8.08 (s, 1H), 7.85 (m, 1H), 7.50 (m, 1H), 4.33 (m, 1H), 3.55 (m, 1H), 3.43 (m, 2H), 2.05 (m, 2H), 1.91 (m, 4H), 1.59 (m, 2H), 1.14 (t, J=6.6 Hz, 3H). LCMS: purity: 100%. MS (m/e): 481.55 (MH⁺).

II-176: N-(3-(3,6-difluoropyridin-2-yl)-1-((trans)-4-ethoxycyclohexyl)-1H-pyrazol-4-yl)-2-(1H-pyrazol-4-yl)thiazole-4-carboxamide

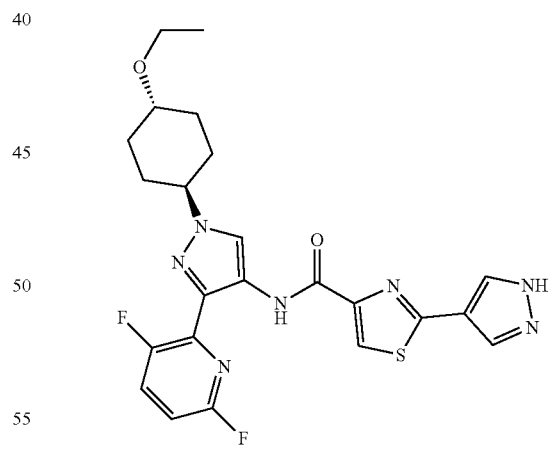

¹H NMR (300 MHz, DMSO-d₆) δ 13.41 (s, 1H), 11.47 (s, 1H), 8.53 (s, 1H), 8.49 (s, 1H), 8.44 (s, 1H), 8.30 (s, 1H), 8.09 (s, 1H), 7.28 (m, 1H), 4.33 (m, 1H), 3.46 (m, 1H), 3.35 (m, 2H), 2.10 (m, 2H), 1.86 (m, 4H), 1.33 (m, 2H), 1.11 (t, J=7.2 Hz, 3H). LCMS: purity: 97.57%. MS (m/e): 499.54 (MH⁺).

II-177: N-(3-(3,6-difluoropyridin-2-yl)-1-((cis)-4-ethoxycyclohexyl)-1H-pyrazol-4-yl)-2-(1H-pyrazol-4-yl)thiazole-4-carboxamide II-179: N-(1-((1r,4r)-4-((2,2-difluoroethyl)amino)cyclohexyl)-3-(pyrimidin-2-yl)-1H-pyrazol-4-yl)-2-(1H-pyrazol-4-yl)thiazole-4-carboxamide

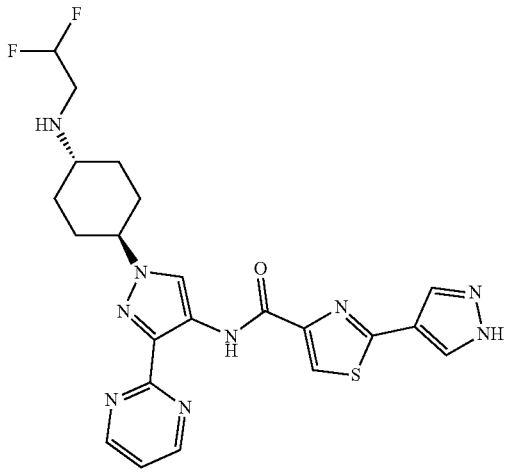

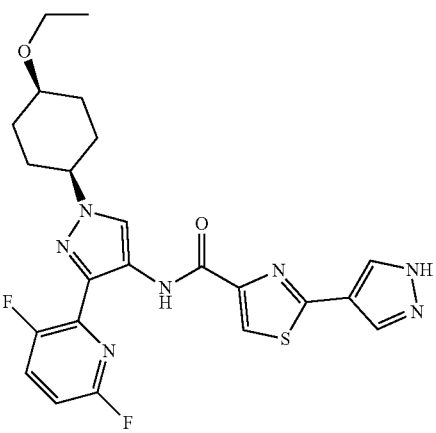 [SMILES: CCO[C@H]1CC[C@@H](n2cc(NC(=O)c3csc(-c4cn[nH]c4)n3)c(-c3nc(F)ccc3F)n2)CC1]

$^1$H NMR (DMSO d$_6$, 300 MHz): δ 13.42 (s, 1H), 11.93 (s, 1H), 8.98 (d, J=6.7 Hz, 2H), 8.50 (s, br, 2H), 8.31 (s, IH), 8.12 (s, 1H), 0 7.50-7.47 (m, 1H), 6.16-5.78 (m, 1H), 4.35-4.27 (m, 1H), 3.00-2.88 (m, 2H), 2.12-1.82 (m, 6H), 1.29-1.17 (m, 2H); LCMS (m/z): 500.18 (MH$^+$).

II-180: N-(3-(3,5-difluoropyridin-2-yl)-1-((1r,4r)-4-ethoxycyclohexyl)-1H-pyrazol-4-yl)-2-(1H-pyrazol-4-yl)thiazole-4-carboxamide $^1$H NMR (300 MHz, DMSO-d$_6$) δ 13.41 (s, 1H), 11.47 (s, 1H), 8.53 (s, 1H), 8.49 (s, 1H), 8.44 (s, 1H), 8.29 (s, 1H), 8.09 (s, 1H), 7.28 (m, 1H), 4.36 (m, 1H), 3.55 (m, 1H), 3.43 (m, 2H), 2.05 (m, 2H), 1.90 (m, 4H), 1.59 (m, 2H), 1.14 (t, J=7.2 Hz, 3H). LCMS: purity: 100%. MS (m/e): 499.54 (MH$^+$).

II-178: N-(1-((1r,4r)-4-ethoxycyclohexyl)-3-(1,3,4-oxadiazol-2-yl)-1H-pyrazol-4-yl)-2-(1H-pyrazol-4-yl)thiazole-4-carboxamide

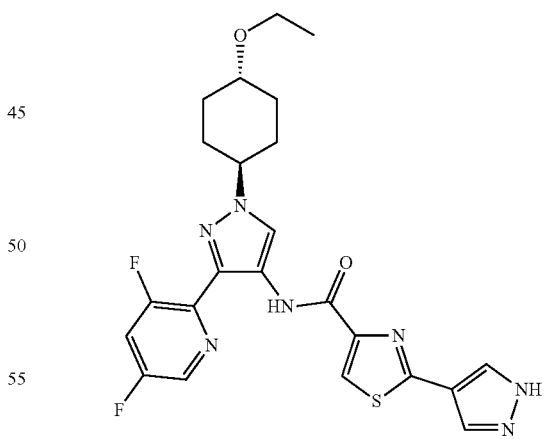

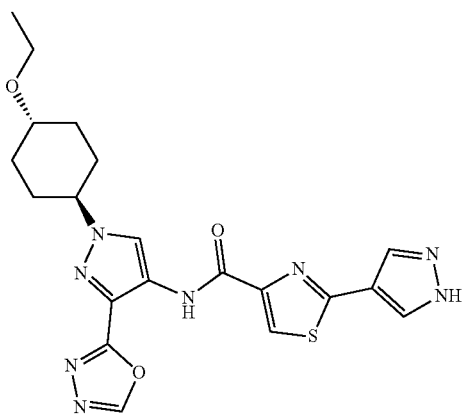 [SMILES: CCO[C@H]1CC[C@H](n2cc(NC(=O)c3csc(-c4cn[nH]c4)n3)c(-c3nnco3)n2)CC1]

LCMS (m/z): 455.28 (MH$^+$).

$^1$H NMR (300 MHz, DMSO-d$_6$) δ 11.67 (s, 1H), 8.68 (d, J=2.4 Hz, 1H), 8.49 (s, 0H), 8.28 (s, 1H), 8.11 (ddd, J=11.3, 9.1, 2.4 Hz, 1H), 4.31 (t, J=11.6 Hz, 1H), 3.47 (q, J=7.0 Hz, 2H), 2.08 (d, J=11.5 Hz, 4H), 1.85 (q, J=12.3, 11.9 Hz, 2H), 1.35 (q, J=10.7 Hz, 2H), 1.10 (t, J=7.0 Hz, 3H). LCMS (m/z): 500.44 (MH$^+$).

287

III-1: 2-(1-(cyclopropylmethyl)-1H-pyrazol-4-yl)-N-(1-methyl-3-(pyridin-2-yl)-1H-pyrazol-4-yl)oxazole-4-carboxamide

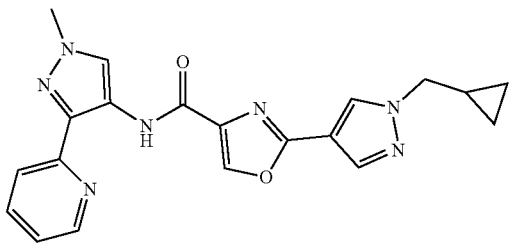 [SMILES: Cn1cc(NC(=O)c2coc(-c3cnn(CC4CC4)c3)n2)c(-c2ccccn2)n1]

1H NMR (300 MHz, DMSO-d6) δ 11.99 (s, 1H), 8.82 (d, J=4.8 Hz, 1H), 8.72 (s, 1H), 8.52 (s, 1H), 8.38 (s, 1H), 8.08 (s, 1H), 7.98-7.88 (m, 2H), 7.40-7.36 (m, 1H), 4.09 (d, J=6.9 Hz, 2H), 3.93 (s, 3H), 1.32 (m, 1H), 0.59-0.53 (m, 2H), 0.45-0.40 (m, 2H); LCMS: purity: 100%; MS (m/e): 390.59 (MH+).

III-2: 2-(1H-pyrazol-4-yl)-N-(3-(pyridin-2-yl)-1-(tetrahydro-2H-pyran-4-yl)-1H-pyrazol-4-yl)oxazole-4-carboxamide

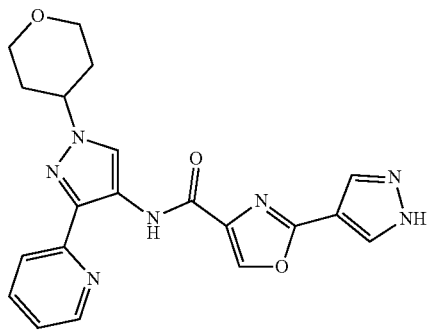 [SMILES: O=C(Nc1cn(C2CCOCC2)nc1-c1ccccn1)c1coc(-c2cn[nH]c2)n1]

¹H NMR (300 MHz, DMSO-d₆) δ 13.54 (s, 1H), 12.04 (s, 1H), 8.86 (ddd, J=5.0, 1.7, 0.9 Hz, 1H), 8.74 (s, 1H), 8.61-8.49 (m, 1H), 8.46 (s, 1H), 8.26-8.08 (m, 1H), 8.04-7.98 (m, 1H), 7.93 (td, J=7.7, 1.8 Hz, 1H), 7.44-7.34 (m, 1H), 4.67-4.42 (m, 1H), 4.06-3.95 (m, 2H), 3.55-3.42 (m, 2H), 2.04 (h, J=5.0, 4.3 Hz, 4H); MS (ESI) (m/z): 406 [M+H]⁺.

288

III-3: N-(1-(2-ethoxyethyl)-3-(pyridin-2-yl)-1H-pyrazol-4-yl)-2-(1H-pyrazol-4-yl)oxazole-4-carboxamide

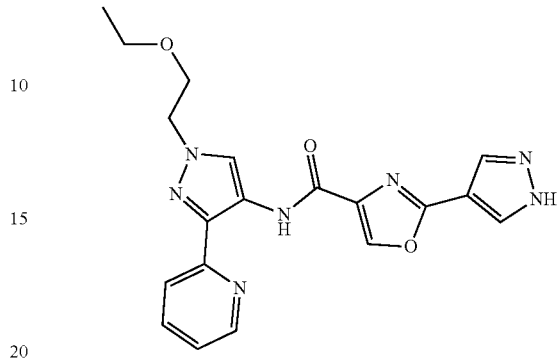

¹HNMR (300 MHz, DMSO-d6) δ 12.02 (s, 1H), 8.86 (d, J=6.7 Hz, 2H), 8.74 (s, 1H), 8.44 (s, 1H), 8.34 (s, 1H), 8.01-7.90 (m, 2H), 7.42-7.38 (m, 1H), 4.37 (t, J=6.7 Hz, 2H), 3.79 (t, J=6.7 Hz, 2H), 3.46 (q, J=6.7 Hz, 2H), 1.09 (t, J=6.7 Hz, 3H); LCMS (m/z): 394.21 (MH⁺).

III-4: N-(1-((1s,3s)-3-ethoxycyclobutyl)-3-(pyridin-2-yl)-1H-pyrazol-4-yl)-2-(1H-pyrazol-4-yl)oxazole-4-carboxamide

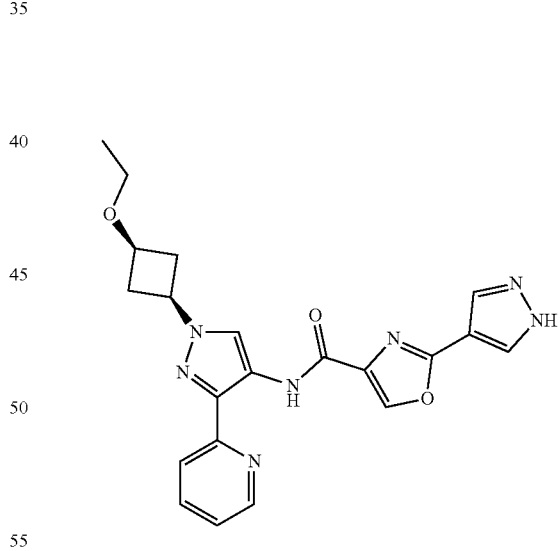

¹HNMR (300 MHz, DMSO-d6) δ 12.01 (s, 1H), 8.86 (d, J=6.7 Hz, 1H), 8.74 (s, 1H), 8.45 (s, 1H), 8.33 (s, 1H), 8.06-8.03 (m, 1H), 7.97-7.92 (m, 1H), 7.43-7.39 (m, 1H), 4.65-4.59 (m, 1H), 3.87-3.82 (m, 1H), 3.42 (q, J=6.7 Hz, 2H), 2.86-2.77 (m, 2H), 2.45-2.41 (m, 1H), 1.15 (t, J=6.7 Hz, 3H); LCMS (m/z): 420.21 (MH⁺).

III-5: N-(1-cyclobutyl-3-(pyridin-2-yl)-1H-pyrazol-4-yl)-2-(1H-pyrazol-4-yl)oxazole-4-carboxamide as Formate Salt

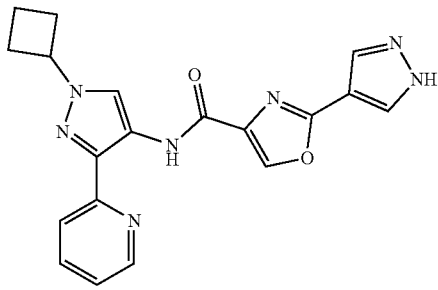 [SMILES: O=C(Nc1cn(C2CCC2)nc1-c1ccccn1)c1coc(-c2cn[nH]c2)n1]

LCMS (m/z): 376.20 (MH+).

III-6: N-(1-(2-(2-methoxyethoxy)ethyl)-3-(pyridin-2-yl)-1H-pyrazol-4-yl)-2-(1H-pyrazol-3-yl)oxazole-4-carboxamide

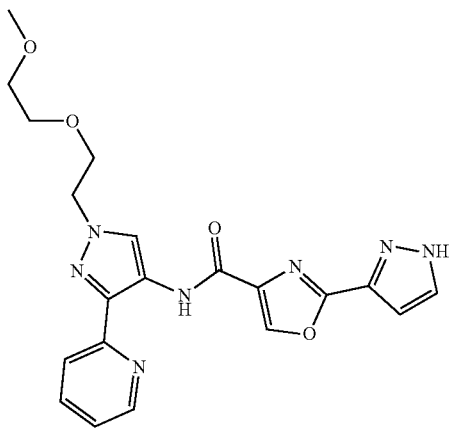 [SMILES: COCCOCCn1cc(NC(=O)c2coc(-c3cc[nH]n3)n2)c(-c2ccccn2)n1]

¹HNMR (300 MHz, DMSO-d6) δ 12.02 (s, 1H), 8.86 (d, J=6.7 Hz, 1H), 8.74 (s, 1H), 8.44 (s, 1H), 8.34 (s, 1H), 8.01-7.90 (m, 2H), 7.42-7.38 (m, 1H), 4.37 (t, J=6.7 Hz, 2H), 3.84 (t, J=6.7 Hz, 2H), 3.56-3.53 (m, 2H); 3.44-3.41 (m, 2H); 3.22 (s, 3H); LCMS (m/z): 424.24 (MH+).

III-7: 2-(1H-pyrazol-3-yl)-N-(3-(pyridin-2-yl)-1-(2-(2,2,2-trifluoroethoxy)ethyl)-1H-pyrazol-4-yl)oxazole-4-carboxamide

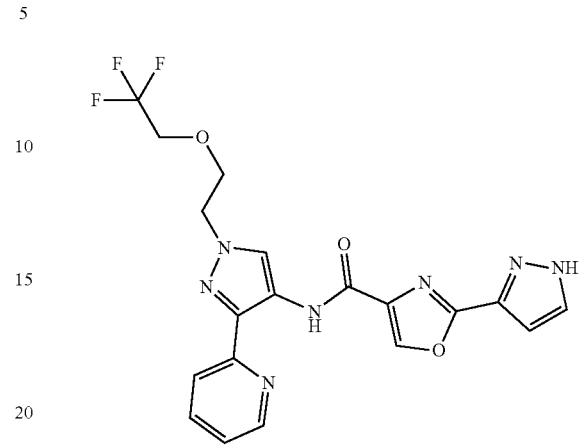

¹HNMR (300 MHz, DMSO-d6) δ 12.03 (s, 1H), 8.87 (d, J=6.7 Hz, 1H), 8.74 (s, 1H), 8.46 (s, 1H), 8.01-7.94 (m, 2H), 7.43-7.39 (m, 1H), 4.44 (t, J=6.7 Hz, 2H), 4.13-4.01 (m, 4H); LCMS (m/z): 448.17 (MH+).

III-8: N-(1-(2-(2,2-difluoroethoxy)ethyl)-3-(pyridin-2-yl)-1H-pyrazol-4-yl)-2-(1H-pyrazol-4-yl)oxazole-4-carboxamide

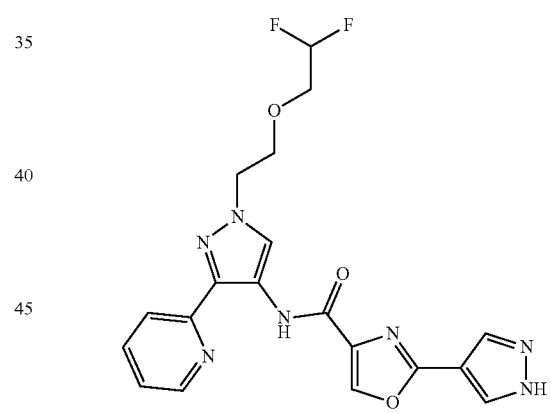

¹H NMR (400 MHz, DMSO-d₆) δ 13.53 (s, 1H), 12.04 (s, 1H), 8.84 (ddd, J=5.0, 1.8, 1.0 Hz, 1H), 8.71 (s, 1H), 8.46 (s, 1H), 7.98 (dt, J=8.0, 1.1 Hz, 1H), 7.89 (ddd, J=8.1, 7.4, 1.8 Hz, 1H), 7.36 (ddd, J=7.4, 4.9, 1.3 Hz, 1H), 6.11 (tt, J=54.9, 3.7 Hz, 1H), 4.40 (t, J=5.2 Hz, 2H), 3.96 (t, J=5.3 Hz, 2H), 3.72 (td, J=15.2, 3.7 Hz, 2H).
MS (ESI) (m/z): 430 [M+H]+

Example 24

LPS Induced IL23p19 in THP-1 Cells (with IFNγ Primed) Assay

Materials and Equipment

THP-1 Cells (ATCC, Cat #TIB-202), Dimethyl Sulfoxide (DMSO) (Sigma-Aldrich, Cat #D2650), RPMI 1640 (Cellgro, Cat #10-040-CM), Fetal Bovine Serum (Sigma, Cat

F4135), Albumin From Bovine Serum (BSA) (Sigma-Aldrich, Cat #A7906), LPS (Serotype K-235, Sigma, Product Number L 2143), IFNγ (Peprotech, Cat #300-02) Capture antibody: Human IL-23p19 ELISA (e-Bioscience, Cat. #14-7238-85), Detection antibody: Primary Mouse Biotinylated anti-human IL-12(p40/p70) (e-Bioscience, Cat. #13-7129-85), Secondary HRP-conjugated Streptavidin (R&D Systems, Cat #DY998), 1× PBST Washing Buffer (PBS-Tween tablet) (VWR International, Cat #80058-558), ELISA Blocking Buffer (PBS with 1% BSA), ELISA Dilution Buffer (PBS with 1% BSA), 384 Well Flat-Bottom, MaxiSorp Black Immuno Plates (Thermo Scientific, Cat #12-565-346), 384 Well Flat-Bottom, White Tissue Culture Plates (Thermo Scientific, Cat #12-565-343), Super Signal ELISA Pico Chemiluminescent Substrate (Thermo Scientific, Cat #37070), Cell Titer Glo reagent (Promega, Cat #G7573), Positive control, IKK2VI inhibitor (Calbiochem, Cat #401483), AquaMax 4000 plate washer (Molecular Devices), Luminometer, Wallac Victor2 1420 Multilabel Counter.

Method

THP-1 Cells Stimulation:

On day 1, 50K/well THP-1 cells were seeded and primed with IFNγ (50 ng/mL) in 384-well plates for about 18 hours in RPMI media with 10% FBS. On day 2, the compound was serially diluted in DMSO from 5 mM in 3-fold dilutions, and then diluted 1:125 in RPMI media with 10% FBS. 50 µL/well 2× compound was added to 50 µL/well THP-1 cells (with IFNy primed) in duplicate in 384 well tissue culture plates. The cells were pre-incubated with compound for 1 hour at 37° C., 5% $CO_2$ before addition of 10 µL/well 11× LPS to give a final concentration of 1 ug/mL LPS. Day 3, after stimulation for 18 hours at 37° C., 5% $CO_2$, the assay plate was centrifuged and 70 µL/well supernatant was harvested. IL-23p19 protein in 70 µL/well of supernatant was measured by sandwich ELISA, and 25 µl/well Cell Titer Glo reagent was added to the remaining cells to measure compound toxicity.

Human IL-23p19 Sandwich ELISA:

Maxisorp immuno ELISA plates were pre-coated with 25 µL/well of anti-IL-23p19 capture antibody (2.5 ug/mL) in PBS overnight at room temperature. After washing with 1× PBST, the plates were blocked using 100 µL/well of 1% BSA in PBS for 2 hours at room temperature. The plates were washed three times with 1× PBST and 70 µL/well supernatant were added. The plates were incubated at room temperature for 2 hours with shaking and washed three times with 1× PBST. 25 µL/well of biotin labeled anti-IL-12(p40/p70) detection antibody (100 ng/mL) in PBS with 1% BSA was added and the plates were incubated at room temperature for 2 hours with shaking. After washing three times with 1× PBST, 25 µL/well of streptavidin-HRP (1:200) in PBS with 1% BSA was added and the plates were incubated at room temperature for 20 minutes with shaking. The plates were washed three times with 1× PBST and 25 µL/well of Super Signal ELISA Pico Chemiluminescent Substrate were added. The plates were read with a luminometer, and the chemiluminescence values were entered into Athena (Rigel) for curve fitting, $EC_{50}$ calculation, and database storage. The results are shown in Table 1.

Example 25

Compound Screening Using DC Cells

Materials

Human PBMC cells (All Cells, Cat No. PB002)
RPMI growth media containing 10% FBS
IFNγ (Peprotech, Cat No. 300-02)
GMCSF (Peprotech, Cat No. 300-03) and IL4 (Peprotech Cat No. 200-04)
White clear bottom 96 well plates (Fisher, Cat No. 07-200-587, Corning #3903)
LPS (Make 2.5 mg/ml Stock in PBS) from Sigma Aldrich (Cat No. L2018-5MG)
Cell Titer Glo reagent (Promega, Cat No. G7573)
Positive controls, IKK2VI inhibitor (Calbiochem, Cat No. 401483)

Protocol

I. Differentiation of PBMC's to DC Cells:

Human PBMC cells (400 million) obtained from the vendor were transferred into a T-175 flask containing 15 ml RPMI media (10% FBS) and incubate for 2 hours at 37° C. After 2 hours, the media including floating cells was aspirated out carefully and 12 ml of fresh RPMI media (10% FBS) containing GMCSF (100 ng/ml) and IL4 (20 ng/ml) was added, and the flask was kept in a 37° C. incubator for 7 days.

After 3 days, fresh GMCSF (100 ng/ml) and IL4 (20 ng/ml) were added to the flask and the incubation continued. After 7 days, the fully differentiated cells were harvested by spinning down (1200 rpm/5 min) and aspirating the media. The cells were suspended in fresh RPMI media (10% FBS) containing 50 ng/ml IFNγ (1000 U/ml) and then plated (50K/well in 100 µl) onto a white clear bottom 96 well plate and left in a 37° C. incubator for 24 hours.

II. Addition of Compounds:

After 24 hours incubation, 100 µl of RPMI media was added containing 2× concentrated test compound per well to the above cell-culture media (final concentration becomes 1×) and the plates were pre-incubated for 1 hour at 37° C. before stimulating with LPS.

After 1 hour compound pre-incubation, 10 µl per well of 20× concentrated LPS solution in RPMI media was added to give a final concentration of 1 µg/ml. The mixture was shaken and incubated the plates at 37° C. for an additional 18 hours.

155 µl of the supernatant was harvested from each well carefully (without the tip touching the bottom of the well) and to the remaining 50 µl/well of the cell culture plate was added 50 µl of Cell Titer Glo reagent. The mixture was incubated for 1-2 minutes on a shaker and the plate was read for luminescence intensity to determine the compound cytotoxicity. The cell culture supernatant collected above was used to carry out IL23 ELISA (65 µl —Supernatant) and IL10 ELISA (90 µl—Supernatant) as described below.

Example 26

Human IL-23 (p19/p40) ELISA Protocol
(e-Biosciences)

Materials:
96-well high binding opaque white plates (from Pierce, Cat No. 15042);
1× PBS; 1× TBST washing buffer;
Blocking Solution: 0.5% Casein in PBS (from BDH, Cat No. 440203H);

Dilution Solution: 1% BSA in PBS (10% BSA from Fisher, Cat No. 37525);
Capture antibody: Rat anti-human IL-23 (p19) (e-Biosciences, Cat. No. 14-7238-85);
Detection antibody: Primary Mouse Biotinylated anti-human IL-12 (p40/p70) (e-biosciences, Cat No. 13-7129-85);
Secondary HRP-conjugated Streptavidin (R&D Systems, Cat No. DY998);
rHuman-IL-23 (e-biosciences, Cat No. 34-8239) (Suggested starting concentration=5 ng/ml in RPMI cell culture media);
Cell Culture Supernatant (65 µl from THP-1 cells primed with IFNγ (50 ng/ml-1000 U/ml) and stimulated with 0.01% SAC);
SuperSignal ELISA Pico Chemiluminescent substrate [Pierce, Cat No. 37069].

Coating Plates:

To 10.5 ml PBS add 50 µl of anti-IL23 (p19) was added capture antibody (2.5 µg/ml). The mixture was mixed well and 100 µl of the coating solution was added to each well of the 96 well white plates from Pierce. The wells were covered and incubated overnight at 4° C.

Blocking the Plates:

The anti-IL23 (p19)-antibody-coated plates were washed 2× using TBST (use plate washer) and blocked using 200 µl of 0.5% Casein for 1.5-2 hours at room temperature with shaking.

Addition of Supernatant and Detection:

The plates were washed 2× using TBST and the supernatant was transferred (65 µl/well) to the above pre-blocked/IL23(p19)-antibody-coated 96 well plate, and incubated at room temperature for 1.5 hours with shaking.

The plates were washed 4× using TBST (plate washer) and 100 µl/well detection antibody solution prepared from 2 µl of biotin labeled anti-IL-12 (p40/p70) antibody in 11 ml 1% BSA/PBS solution (1-5000 dilution) was added. The plates were incubated for 1 hour with shaking at Room temperature.

Again, the plates were washed 4× with TBST and 100 µl of HRP labeled Streptavidin (R&D Systems) solution (10 µl/10 ml 1% BSA solution) was added, and the plates were incubated at room temperature for another 45 minutes with shaking.

After 45 minutes, the plates were washed with TBST 4× and 100 ul/well Super Signal ELISA Pico Chemiluminescent Substrate from Pierce (3.5 ml A+3.5 ml B+3.5 ml MQ water) was added. The plates were shaken for 1-2 minutes then read on a plate reader.

The $EC_{50}$ results from the assays described in Examples 24 and 26 are shown in Tables 1-3.

TABLE 1

| Compound | IL23-p19 ELISA, Dendritic, LPS, 10 pt $EC_{50}$ (µM) | IL23-p19 ELISA, THP1-IFNy, LPS, 10 pt $EC_{50}$ (µM) |
|---|---|---|
| I-1 | 3.731 | 5.662 |
| I-3 | 0.3619 | 0.4237 |
| I-4 | 0.6189 | 0.7126 |
| I-5 | 0.136 | 0.0826 |
| I-6 | 0.9932 | 0.2635 |
| I-7 | 0.3991 | 0.4334 |
| I-8 | 0.4294 | 0.88 |
| I-9 | 0.3092 | 0.281 |
| I-10 | 3.271 | 21.94 |
| I-11 | 5.192 | 4.845 |
| I-12 | 1.05 | 0.5925 |

TABLE 1-continued

| Compound | IL23-p19 ELISA, Dendritic, LPS, 10 pt $EC_{50}$ (µM) | IL23-p19 ELISA, THP1-IFNy, LPS, 10 pt $EC_{50}$ (µM) |
|---|---|---|
| I-13 | 11.01 | 136.5 |
| I-14 | 0.5714 | 1.246 |
| I-15 | 2.2 | 2.232 |
| I-16 | 0.4029 | 0.1249 |
| I-17 | 0.4244 | 0.285 |
| I-18 | 1.197 | 0.5139 |
| I-19 | 0.3368 | 0.3 |
| I-20 | 0.1945 | 0.1666 |
| I-21 | 0.4582 | 0.2013 |
| I-22 | 1.552 | 0.2036 |
| I-23 | 0.0372 | 0.0217 |
| I-24 | 7777 | 4.218 |
| I-25 | 0.0441 | 0.0571 |
| I-26 | 0.2755 | 1.323 |
| I-27 | 0.0158 | 0.1594 |
| I-28 | 0.0218 | 0.0497 |
| I-29 | 0.0972 | 0.2064 |
| I-30 | 0.0589 | 0.038 |
| I-31 | 1.253 | 6.289 |
| I-32 | 0.083 | 0.0288 |
| I-34 | 0.0144 | 0.0138 |
| I-35 | 0.5201 | 0.0633 |
| I-37 | 0.0174 | 0.1439 |
| I-38 | 0.0582 | 0.1721 |
| I-39 | 4.317 | 1.953 |
| I-41 | 3.945 | 2.568 |
| I-43 | 9999 | 4464 |
| I-45 | 5.449 | 1.084 |
| I-47 | 0.3271 | 0.3924 |
| I-48 | 7.505 | 5.518 |
| I-50 | 3.506 | 14.24 |
| I-52 | 9999 | 1.378 |
| I-54 | 1.575 | 0.617 |
| I-55 | 0.8006 | 1.204 |
| I-56 | 7.718 | 0.1562 |
| I-58 | 27.53 | 2.812 |
| I-60 | 0.0338 | 0.1745 |
| I-62 | 0.1148 | 0.0481 |
| I-64 | 0.3663 | 0.0777 |
| I-65 | 0.1993 | 0.0543 |
| I-67 | 0.0041 | 0.0723 |
| I-69 | 0.3249 | 1.249 |
| I-70 | 0.0283 | 0.3662 |
| I-71 | 0.0225 | 0.0265 |
| I-72 | 0.005 | 0.0568 |
| I-73 | 0.4102 | 0.697 |
| I-74 | 0.1311 | 0.1514 |
| I-75 | 0.0195 | 0.1024 |
| I-77 | 0.041 | 0.0504 |
| I-78 | 0.1051 | 0.0784 |
| I-80 | 2.06 | 2.223 |
| I-81 | 0.9595 | 0.1529 |
| I-82 | 0.7802 | 0.2052 |
| I-83 | 0.0932 | 0.0348 |
| I-84 | 0.0977 | 0.0423 |
| I-85 | 0.0196 | 0.0767 |
| I-86 | 0.0637 | 0.0614 |
| I-87 | 0.1051 | 0.0433 |
| I-89 | 0.0231 | 0.0166 |
| I-91 | 0.0106 | 0.0122 |
| I-93 | 0.008 | 0.0108 |
| I-95 | 0.0338 | 0.0678 |
| I-97 | 0.0329 | 0.0362 |
| I-99 | 0.0156 | 0.018 |
| I-101 | 0.0501 | 0.0143 |
| I-103 | 0.0554 | 0.031 |
| I-105 | 0.0265 | 8888 |
| I-106 | 1.221 | 18.89 |
| I-107 | 0.3054 | 0.8602 |
| I-108 | 0.7298 | 0.4911 |
| I-109 | 0.0221 | 0.1041 |
| I-110 | 0.3881 | 0.2792 |
| I-111 | 0.0268 | 0.0291 |
| I-112 | 0.0407 | 0.0428 |
| I-133 | 0.3865 | 0.0806 |
| I-114 | 0.0616 | 0.0493 |

TABLE 1-continued

| Compound | IL23-p19 ELISA, Dendritic, LPS, 10 pt EC$_{50}$ (µM) | IL23-p19 ELISA, THP1-IFNy, LPS, 10 pt EC$_{50}$ (µM) |
| --- | --- | --- |
| I-115 | 0.3649 | 0.0913 |
| I-116 | 0.2182 | 0.2265 |
| I-117 | 0.0257 | 0.2837 |
| I-118 | 0.1607 | 0.0681 |
| I-119 | 0.4303 | 0.1535 |
| I-120 | 0.0948 | 0.0528 |
| I-122 | 9999 | 3.764 |
| I-124 | 0.1012 | 0.0534 |
| I-126 | 0.0215 | 0.0819 |
| I-128 | 0.0604 | 0.1339 |
| I-130 | 0.023 | 0.0483 |
| I-132 | 0.1028 | 0.0812 |
| I-134 | 0.091 | 0.0296 |
| I-136 | 0.0878 | 0.0448 |
| I-138 | 0.6863 | 0.9263 |
| I-140 | 0.224 | 0.7994 |
| I-142 | 0.0262 | 0.0689 |
| I-144 | 0.0343 | 0.078 |
| I-146 | 0.3704 | 0.1494 |
| I-148 | 0.11 | 0.1732 |
| I-150 | 0.2258 | 0.0648 |
| I-152 | 0.0716 | 0.0319 |
| I-154 | 1.392 | 0.0575 |
| I-156 | 0.1052 | 0.0595 |

TABLE 2

| Compound | IL23-p19 ELISA, Dendritic, LPS, 10 pt EC$_{50}$ (µM) | IL23-p19 ELISA, THP1-IFNy, LPS, 10 pt EC$_{50}$ (µM) |
| --- | --- | --- |
| II-1 | 0.7791 | 0.1288 |
| II-2 | 0.2981 | 0.1962 |
| II-3 | 0.3707 | 0.1976 |
| II-4 | 0.3066 | 0.0861 |
| II-5 | 0.157 | 0.0902 |
| II-6 | 6.888 | 0.0874 |
| II-7 | 9999 | 6.087 |
| II-8 | 9999 | 9999 |
| II-10 | 0.0105 | 0.0226 |
| II-11 | 0.0623 | 0.05 |
| II-12 | 0.0616 | 0.1353 |
| II-13 | 10.39 | 4.799 |
| II-14 | 0.0057 | 0.0434 |
| II-15 | 0.0096 | 0.0064 |
| II-16 | 0.5254 | 0.121 |
| II-18 | 0.0314 | 0.3009 |
| II-19 | 3.508 | 4.006 |
| II-21 | 0.5689 | 0.3147 |
| II-23 | 16.29 | 4.761 |
| II-25 | 0.1704 | 0.1465 |
| II-26 | 0.1125 | 0.0771 |
| II-27 | 0.3314 | 0.0741 |
| II-28 | 0.063 | 0.2757 |
| II-29 | 0.2482 | 0.1349 |
| II-31 | 0.7993 | 0.1701 |
| II-32 | 0.191 | 0.3608 |
| II-34 | 0.0557 | 0.0861 |
| II-35 | 0.2922 | 0.2064 |
| II-36 | 0.2412 | 0.1649 |
| II-37 | 0.1927 | 0.1293 |
| II-38 | 0.7712 | 0.5055 |
| II-39 | 0.1778 | 0.1672 |
| II-41 | 0.0188 | 0.0413 |
| II-43 | 0.0502 | 0.0278 |
| II-45 | 0.1292 | 0.1287 |
| II-47 | 3.207 | 1.166 |
| II-49 | 0.0812 | 0.238 |
| II-51 | 26.62 | 3.609 |
| II-52 | 7777 | 6.158 |
| II-53 | 7777 | 24.07 |
| II-54 | 0.1887 | 0.1706 |
| II-55 | 0.0435 | 0.0749 |

TABLE 2-continued

| Compound | IL23-p19 ELISA, Dendritic, LPS, 10 pt EC$_{50}$ (µM) | IL23-p19 ELISA, THP1-IFNy, LPS, 10 pt EC$_{50}$ (µM) |
| --- | --- | --- |
| II-57 | 0.0854 | 0.0418 |
| II-58 | 0.112 | 0.1303 |
| II-59 | 0.2156 | 0.4225 |
| II-60 | 0.0533 | 0.0473 |
| II-61 | 0.0504 | 0.0225 |
| II-62 | Not tested | 6.477 |
| II-63 | 5.447 | 20.76 |
| II-65 | 0.0489 | 0.0373 |
| II-66 | 0.2438 | 0.1057 |
| II-67 | 9999 | 26.22 |
| II-68 | 9999 | 5011 |
| II-69 | 9999 | 5014 |
| II-70 | 1.016 | 1.865 |
| II-71 | 10.39 | 49.57 |
| II-72 | 0.1399 | 1.139 |
| II-73 | 0.3429 | 0.3691 |
| II-74 | 0.4046 | 0.4006 |
| II-75 | 0.5369 | 2.493 |
| II-76 | 0.0475 | 0.0524 |
| II-77 | 0.1457 | 0.1471 |
| II-78 | 0.0799 | 0.1651 |
| II-79 | 0.0152 | 0.0758 |
| II-80 | 0.2467 | 0.0495 |
| II-81 | 0.1707 | 0.019 |
| II-82 | 0.176 | 0.0387 |
| II-83 | 0.2411 | 0.0863 |
| II-84 | 0.3039 | 0.085 |
| II-85 | 0.2866 | 0.0499 |
| II-86 | 5.782 | 0.1372 |
| II-87 | Not tested | 0.6147 |
| II-88 | 0.3898 | 0.0965 |
| II-89 | 1.127 | 0.5891 |
| II-90 | 0.2176 | 0.176 |
| II-91 | 9999 | Not tested |
| II-92 | 0.2583 | Not tested |
| II-93 | 9999 | 0.1087 |
| II-94 | 0.0333 | 0.3106 |
| II-95 | 6.225 | 2.25 |
| II-96 | 0.4566 | 0.0837 |
| II-97 | 9999 | 4183028 |
| II-98 | 9999 | 24.64 |
| II-99 | 0.9888 | 0.4203 |
| II-100 | 0.2259 | 0.0561 |
| II-101 | 0.0355 | 0.023 |
| II-102 | 0.0554 | 0.0619 |
| II-103 | 9999 | 8.08 |
| II-105 | 7777 | 5.546 |
| II-107 | 2.309 | 1.503 |
| II-109 | 0.3273 | 0.1399 |
| II-111 | 0.0343 | 0.0651 |
| II-113 | 0.2881 | 0.0844 |
| II-115 | 0.1593 | 0.0438 |
| II-117 | 0.1065 | 0.0566 |
| II-118 | 0.2115 | 0.1086 |
| II-120 | 1.17 | 0.6641 |
| II-121 | 0.0444 | 0.0986 |
| II-122 | 0.3037 | 0.2131 |
| II-123 | 0.1489 | 0.0271 |
| II-125 | 27.27 | 1.241 |
| II-127 | 0.081 | 0.0487 |
| II-128 | 2.475 | 1.152 |
| II-129 | 9999 | 0.377 |
| II-130 | 0.0898 | 0.056 |
| II-131 | 9.359 | 0.3602 |
| II-132 | 0.9242 | 0.2242 |
| II-133 | 1.521 | 0.313 |
| II-134 | 0.225 | 0.1021 |
| II-136 | 10.67 | 1.216 |
| II-137 | 9999 | 0.206 |
| II-138 | 9999 | 9999 |
| II-139 | 9999 | 9999 |
| II-140 | 0.0323 | 0.0308 |
| II-141 | 0.0517 | 0.2509 |
| II-143 | 0.0164 | 0.0308 |
| II-145 | 0.0784 | 0.066 |
| II-147 | 0.0987 | 0.0574 |

TABLE 2-continued

| Compound | IL23-p19 ELISA, Dendritic, LPS, 10 pt, EC$_{50}$ (µM) | IL23-p19 ELISA, THP1-IFNy, LPS, 10 pt EC$_{50}$ (µM) |
|---|---|---|
| II-149 | 0.0568 | 0.0343 |
| II-151 | 0.0622 | 0.0649 |
| II-153 | 0.1411 | 0.7485 |
| II-155 | 0.0612 | 0.3993 |
| II-157 | 0.5641 | 0.0615 |
| II-158 | 0.0921 | 0.1445 |
| II-160 | 0.0385 | 0.0267 |
| II-161 | 0.4821 | 0.1124 |
| II-163 | 0.3477 | 0.1087 |
| II-164 | 0.9118 | 0.1106 |
| II-165 | 0.0454 | 0.0444 |
| II-167 | 0.0962 | 0.0949 |
| II-169 | 0.4098 | 0.042 |
| II-170 | 0.0904 | 0.0491 |
| II-172 | 0.0242 | 0.013 |
| II-173 | 0.3137 | 0.0414 |
| II-174 | 0.0708 | 0.0821 |
| II-178 | 0.0373 | 0.1193 |
| II-179 | 0.0748 | 0.0125 |
| II-180 | 0.2629 | 0.0802 |

TABLE 3

| Compound | IL23-p19 ELISA, Dendritic, LPS, 10 pt, EC$_{50}$ (µM) | IL23-p19 ELISA, THP1-IFNy, LPS, 10 pt EC$_{50}$ (µM) |
|---|---|---|
| III-1 | Not tested | 20.34 |
| III-2 | 0.1347 | 0.0399 |
| III-3 | 0.1704 | 0.2433 |
| III-4 | 0.0369 | 0.0434 |
| III-5 | 0.071 | 0.2702 |
| III-6 | 0.2171 | 0.2377 |
| III-7 | 0.4512 | 0.0853 |
| III-8 | 0.161 | 0.4003 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a disease or condition for which an IRAK inhibitor is indicated, comprising administering to a subject in need thereof an amount of a compound effective to treat the disease or condition, wherein the compound has a formula

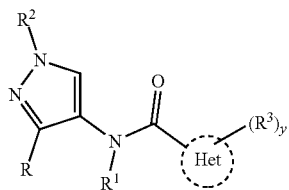

or salt thereof, wherein:
R is monocyclic heteroaryl;
R$^1$ is H, aliphatic or heteroaliphatic;
R$^2$ is H, aliphatic, heteroaliphatic, heterocycloaliphatic, aryl, amide, heterocyclyl or araliphatic;
each R$^3$ independently is H, aliphatic, halogen, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl, haloalkyl, alkylphosphate, or alkylphosphonate, wherein R$^3$ is not pyridinyl;
y is from 1 to 6; and
Het-1 is furanyl or thiazolyl, and is substituted with pyrazolyl; or
the compound is
II-62: N-(1-((1s,3s)-3-ethoxycyclobutyl)-3-(trifluoromethyl)-1H-pyrazol-4-yl)-2-(1H-pyrazol-4-yl)thiazole-4-carboxamide;
II-63: N-(1-methyl-3-(trifluoromethyl)-1H-pyrazol-4-yl)-2-(1H-pyrazol-4-yl)thiazole-4-carboxamide 2,2,2-trifluoroacetate;
II-64: N-(1-methyl-3-(trifluoromethyl)-1H-pyrazol-4-yl)-2-(1H-pyrazol-4-yl)thiazole-4-carboxamide;
II-67: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone;
II-68: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone 2,2,2-trifluoroacetate;
II-69: (2-(1H-pyrazol-4-yl)thiazol-4-yl)(1-(3-ethoxycyclobutyl)-1,5,6,7-tetrahydro-4H-pyrazolo[4,3-b]pyridin-4-yl)methanone 2,2,2-trifluoroacetate;
II-70: N-(3-carbamoyl-1-((1s,3s)-3-ethoxycyclobutyl)-1H-pyrazol-4-yl)-2-(1H-pyrazol-4-yl)thiazole-4-carboxamide;
II-136: N-(3-cyano-1-((1s,3s)-3-hydroxycyclobutyl)-1H-pyrazol-4-yl)-2-(1H-pyrazol-4-yl)thiazole-4-carboxamide;
II-137: N-(3-cyano-1-methyl-1H-pyrazol-4-yl)-2-(1H-pyrazol-4-yl)thiazole-4-carboxamide;
II-138: N-(3-cyano-1-((1s,3s)-3-ethoxycyclobutyl)-1H-pyrazol-4-yl)-2-(1H-pyrazol-4-yl)thiazole-4-carboxamide; or
II-139: N-(3-cyano-1-((1s,3s)-3-ethoxycyclobutyl)-1H-pyrazol-4-yl)-2-(1H-pyrazol-4-yl)thiazole-4-carboxamide formate.

2. A method for inhibiting an IRAK protein, comprising contacting the IRAK protein with an effective amount of a compound wherein the compound has a formula

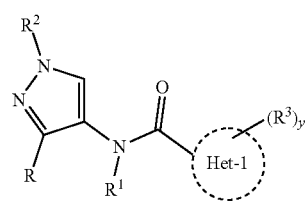

or salt thereof, wherein:
R is monocyclic heteroaryl;
R$^1$ is H, aliphatic or heteroaliphatic;
R$^2$ is H, aliphatic, heteroaliphatic, heterocycloaliphatic, aryl, amide, heterocyclyl or araliphatic;
each R$^3$ independently is H, aliphatic, halogen, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl, haloalkyl, alkylphosphate, or alkylphosphonate, wherein $R^3$ is not pyridinyl;

y is from 1 to 6; and

Het-1 is furanyl or thiazolyl, and is substituted with pyrazolyl; or wherein the compound is II-62: N-(1-((1s,3s)-3-ethoxycyclobutyl)-3-(trifluoromethyl)-1H-pyrazol-4-yl)-2-(1H-pyrazol-4-yl)thiazole-4-carboxamide;

II-63: N-(1-methyl-3-(trifluoromethyl)-1H-pyrazol-4-yl)-2-(1H-pyrazol-4-yl)thiazole-4-carboxamide 2,2,2-trifluoroacetate;

II-64: N-(1-methyl-3-(trifluoromethyl)-1H-pyrazol-4-yl)-2-(1H-pyrazol-4-yl)thiazole-4-carboxamide;

II-67: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone;

II-68: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone 2,2,2-trifluoroacetate;

II-69: (2-(1H-pyrazol-4-yl)thiazol-4-yl)(1-(3-ethoxycyclobutyl)-1,5,6,7-tetrahydro-4H-pyrazolo[4,3-b]pyridin-4-yl)methanone 2,2,2-trifluoroacetate;

II-70: N-(3-carbamoyl-1-((1s,3s)-3-ethoxycyclobutyl)-1H-pyrazol-4-yl)-2-(1H-pyrazol-4-yl)thiazole-4-carboxamide;

II-136: N-(3-cyano-1-((1s,3s)-3-hydroxycyclobutyl)-1H-pyrazol-4-yl)-2-(1H-pyrazol-4-yl)thiazole-4-carboxamide;

II-137: N-(3-cyano-1-methyl-1H-pyrazol-4-yl)-2-(1H-pyrazol-4-yl)thiazole-4-carboxamide;

II-138: N-(3-cyano-1-((1s,3s)-3-ethoxycyclobutyl)-1H-pyrazol-4-yl)-2-(1H-pyrazol-4-yl)thiazole-4-carboxamide; or II-139: N-(3-cyano-1-((1s,3s)-3-ethoxycyclobutyl)-1H-pyrazol-4-yl)-2-(1H-pyrazol-4-yl)thiazole-4-carboxamide formate.

3. The method of claim 2, wherein the compound has a formula

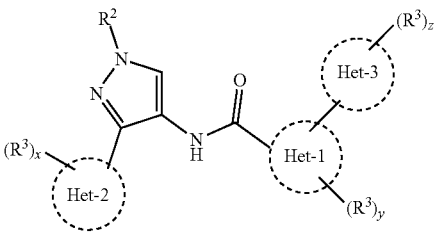

or salt thereof, wherein:

$R^2$ is H, aliphatic, heteroaliphatic, heterocycloaliphatic, aryl, amide, heterocyclyl or aralphatic;

each $R^3$ independently is H, aliphatic, halogen, heteroaliphatic, —O-aliphatic, heterocyclyl, aryl, aralphatic, —O-heterocyclyl, hydroxyl, nitro, cyano, carboxyl, carboxyl ester, acyl, amide, amino, sulfonyl, sulfonamide, sulfanyl, sulfinyl, haloalkyl, alkylphosphate, or alkylphosphonate, providing $R^3$ is not pyridinyl;

x is from 1 to 6;
y is from 1 to 6;
z is from 1 to 6;

Het-1 is furanyl or thiazolyl;
Het-2 is monocyclic heteroaryl; and
Het-3 is pyrazolyl.

4. The method of claim 3, wherein Het-2 is pyridinyl, pyrimidinyl, pyrazinyl, oxadiazolyl or thiazolyl.

5. The method of claim 4, wherein the compound has a formula

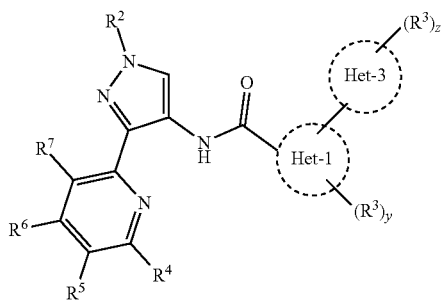

wherein $R^4$, $R^5$, $R^6$ and $R^7$ are each independently H, aliphatic, heteroaliphatic, alkoxy, heterocyclyl, aryl, aralphatic, —O-heterocyclyl, hydroxyl, haloalkyl, halogen, nitro, cyano, carboxyl, carboxyl ester, acyl, amide, amino, sulfonyl, sulfonamide, sulfanyl or sulfinyl.

6. The method of claim 5, wherein each of $R^4$, $R^6$, and $R^7$ independently is H, F or $CF_3$, and $R^5$ is H, F, $CF_3$, methoxy, morpholin-4-yl, 1-methylpiperidin-4-yl, —O—$CH_2C(CH_3)_2OH$, or —O-(oxetan-3-yl).

7. The method of claim 5, wherein the compound has a formula

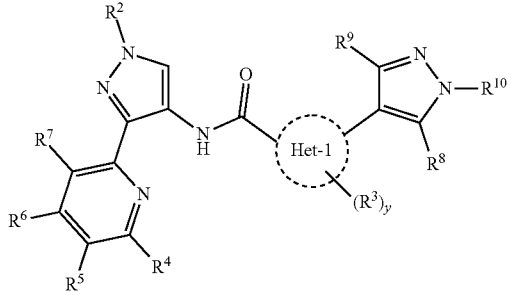

wherein:

$R^8$ and $R^9$ are each independently H, aliphatic, heteroaliphatic, aryl, heterocyclyl, sulfonyl, nitro, halogen, haloalkyl, carboxyl ester, cyano or amino; and $R^{10}$ is H, aliphatic, alkoxy, heteroaliphatic, carboxyl ester, aralphatic, $NO_2$, CN, OH, haloalkyl, acyl, alkyl phosphate or alkylphosphonate.

8. The method of claim 7, wherein $R^8$ and $R^9$ are each independently H, halogen, haloalkyl, or alkyl.

9. The method of claim 7, wherein $R^{10}$ is H, alkyl, carboxyl ester, acyl, alkyl phosphate, alkyl phosphonate or aralkyl.

10. The method of claim 2, wherein the compound is selected from

I-1: N-(1-(2-hydroxy-2-methylpropyl)-3-(pyridin-2-yl)-1H-pyrazol-4-yl)-5-(1-methyl-1H-pyrazol-4-yl)furan-2-carboxamide 2,2,2-trifluoroacetate;

I-2: N-(1-(2-hydroxy-2-methylpropyl)-3-(pyridin-2-yl)-1H-pyrazol-4-yl)-5-(1-methyl-1H-pyrazol-4-yl)furan-2-carboxamide;

I-3: N-(1-(2-hydroxy-2-methylpropyl)-3-(pyridin-2-yl)-1H-pyrazol-4-yl)-5-(1H-pyrazol-4-yl)furan-2-carboxamide;

I-4: tert-butyl 4-(5-((1-(2-ethoxyethyl)-3-(pyridin-2-yl)-1H-pyrazol-4-yl)carbamoyl)furan-2-yl)-1H-pyrazole-1-carboxylate;

I-5: N-(1-(2-methoxyethyl)-3-(pyridin-2-yl)-1H-pyrazol-4-yl)-5-(1H-pyrazol-4-yl)furan-2-carboxamide;

I-6: N-(1-(2-methoxyethyl)-3-(pyridin-2-yl)-1H-pyrazol-4-yl)-5-(3-methyl-1H-pyrazol-4-yl)furan-2-carboxamide formic acid;

I-7: N-(1-(2-methoxyethyl)-3-(pyrimidin-2-yl)-1H-pyrazol-4-yl)-5-(1H-pyrazol-4-yl)furan-2-carboxamide;

I-8: N-(1-(2-methoxyethyl)-3-(pyrimidin-2-yl)-1H-pyrazol-4-yl)-5-(3-methyl-1H-pyrazol-4-yl)furan-2-carboxamide;

I-9: N-(1-(2-methoxyethyl)-3-(pyridin-2-yl)-1H-pyrazol-4-yl)-5-(3-methyl-1H-pyrazol-4-yl)furan-2-carboxamide;

I-10: di-tert-butyl ((4-(5-((1-(2-methoxyethyl)-3-(pyridin-2-yl)-1H-pyrazol-4-yl)carbamoyl)furan-2-yl)-1H-pyrazol-1-yl)methyl) phosphate;

I-11: tert-butyl ((4-(5-((1-(2-methoxyethyl)-3-(pyridin-2-yl)-1H-pyrazol-4-yl)carbamoyl)furan-2-yl)-1H-pyrazol-1-yl)methyl) hydrogen phosphate;

I-12: (4-(5-((1-(2-methoxyethyl)-3-(pyridin-2-yl)-1H-pyrazol-4-yl)carbamoyl)furan-2-yl)-1H-pyrazol-1-yl)methyl dihydrogen phosphate;

I-13: N-(1-(2-methoxyethyl)-3-(pyridin-2-yl)-1H-pyrazol-4-yl)-5-(3-(trifluoromethyl)-1H-pyrazol-4-yl)furan-2-carboxamide;

I-14: sodium (4-(5-((1-(2-methoxyethyl)-3-(pyridin-2-yl)-1H-pyrazol-4-yl)carbamoyl)furan-2-yl)-1H-pyrazol-1-yl)methyl phosphate;

I-15: N-(1-(2-hydroxyethyl)-3-(pyrimidin-2-yl)-1H-pyrazol-4-yl)-5-(1H-pyrazol-4-yl)furan-2-carboxamide;

I-16: N-(1-(2-(2-methoxyethoxy)ethyl)-3-(pyridin-2-yl)-1H-pyrazol-4-yl)-5-(1H-pyrazol-4-yl)furan-2-carboxamide;

I-17: N-(1-(2-(2-methoxyethoxy)ethyl)-3-(pyridin-2-yl)-1H-pyrazol-4-yl)-5-(1H-pyrazol-4-yl)furan-2-carboxamide hydrochloride salt;

I-18: N-(1-(2-(2-methoxyethoxy)ethyl)-3-(pyridin-2-yl)-1H-pyrazol-4-yl)-5-(3-methyl-1H-pyrazol-4-yl)furan-2-carboxamide;

I-19: 1-(isobutyryloxy)ethyl 4-(5-((1-(2-methoxyethyl)-3-(pyridin-2-yl)-1H-pyrazol-4-yl)carbamoyl)furan-2-yl)-1H-pyrazole-1-carboxylate;

I-20: tert-butyl (S)-(1-(4-(5-((1-(2-methoxyethyl)-3-(pyridin-2-yl)-1H-pyrazol-4-yl)carbamoyl)furan-2-yl)-1H-pyrazol-1-yl)-3-methyl-1-oxobutan-2-yl)carbamate;

I-21: 1-methylcyclopropyl 4-(5-((1-(2-methoxyethyl)-3-(pyridin-2-yl)-1H-pyrazol-4-yl)carbamoyl)furan-2-yl)-1H-pyrazole-1-carboxylate;

I-22: 1-((4-methoxybenzyl)oxy)-2-methylpropan-2-yl 4-(5-((1-(2-methoxyethyl)-3-(pyridin-2-yl)-1H-pyrazol-4-yl)carbamoyl)furan-2-yl)-1H-pyrazole-1-carboxylate;

I-23: 5-(1H-pyrazol-4-yl)-N-(3-(pyridin-2-yl)-1-(tetrahydro-2H-pyran-4-yl)-1H-pyrazol-4-yl)furan-2-carboxamide;

I-24: 5-(5-nitro-1H-pyrrol-3-yl)-N-(1-(propoxymethyl)-3-(pyridin-2-yl)-1H-pyrazol-4-yl)furan-2-carboxamide;

I-25: N-(1-(oxetan-3-yl)-3-(pyridin-2-yl)-1H-pyrazol-4-yl)-5-(1H-pyrazol-4-yl)furan-2-carboxamide;

I-26: 5-(1-methyl-1H-pyrazol-4-yl)-N-(1-(oxetan-3-yl)-3-(pyridin-2-yl)-1H-pyrazol-4-yl)furan-2-carboxamide;

I-27: N-(1-((1,3-trans)-3-ethoxycyclobutyl)-3-(pyridin-2-yl)-1H-pyrazol-4-yl)-5-(1H-pyrazol-4-yl)furan-2-carboxamide;

I-28: N-(1-((1,3-cis)-3-ethoxycyclobutyl)-3-(pyridin-2-yl)-1H-pyrazol-4-yl)-5-(1H-pyrazol-4-yl)furan-2-carboxamide;

I-29: N-(1-((1,3-cis)-3-ethoxycyclobutyl)-3-(pyridin-2-yl)-1H-pyrazol-4-yl)-5-(3-methyl-1H-pyrazol-4-yl)furan-2-carboxamide;

I-30: 5-(3-methyl-1H-pyrazol-4-yl)-N-(1-(oxetan-3-yl)-3-(pyridin-2-yl)-1H-pyrazol-4-yl)furan-2-carboxamide;

I-31: N-(1-((1,3-cis)-3-ethoxycyclobutyl)-3-(pyridin-2-yl)-1H-pyrazol-4-yl)-5-(1-methyl-1H-pyrazol-4-yl)furan-2-carboxamide;

I-32: N-(1-((1,3-cis)-3-hydroxycyclobutyl)-3-(pyridin-2-yl)-1H-pyrazol-4-yl)-5-(1H-pyrazol-4-yl)furan-2-carboxamide;

I-33: N-(1-((1s,3s)-3-(dimethylamino)cyclobutyl)-3-(pyridin-2-yl)-1H-pyrazol-4-yl)-5-(1H-pyrazol-4-yl)furan-2-carboxamide;

I-34: N-(1-((1s,3s)-3-(dimethylamino)cyclobutyl)-3-(pyridin-2-yl)-1H-pyrazol-4-yl)-5-(1H-pyrazol-4-yl)furan-2-carboxamide formate;

I-35: (4-(5-((1-((1,3-cis)-3-ethoxycyclobutyl)-3-(pyridin-2-yl)-1H-pyrazol-4-yl)carbamoyl)furan-2-yl)-1H-pyrazol-1-yl)methyl phosphate bis-sodium salt;

I-36: (4-(5-((1-((1s,3s)-3-ethoxycyclobutyl)-3-(pyridin-2-yl)-1H-pyrazol-4-yl)carbamoyl)furan-2-yl)-1H-pyrazol-1-yl)methyl dihydrogen phosphate;

I-37: N-(1-(2-ethoxyethyl)-3-(pyridin-2-yl)-1H-pyrazol-4-yl)-5-(1H-pyrazol-4-yl)furan-2-carboxamide formate;

I-38: N-(1-(2-ethoxyethyl)-3-(pyridin-2-yl)-1H-pyrazol-4-yl)-5-(1H-pyrazol-4-yl)furan-2-carboxamide;

I-39: N-(1-(2-ethoxyethyl)-3-(pyridin-2-yl)-1H-pyrazol-4-yl)-5-(1-ethyl-1H-pyrazol-4-yl)furan-2-carboxamide formate;

I-40: N-(1-(2-ethoxyethyl)-3-(pyridin-2-yl)-1H-pyrazol-4-yl)-5-(1-ethyl-1H-pyrazol-4-yl)furan-2-carboxamide;

I-41: N-(1-(2-ethoxyethyl)-3-(pyridin-2-yl)-1H-pyrazol-4-yl)-5-(3-(trifluoromethyl)-1H-pyrazol-4-yl)furan-2-carboxamide formate;

I-42: N-(1-(2-ethoxyethyl)-3-(pyridin-2-yl)-1H-pyrazol-4-yl)-5-(3-(trifluoromethyl)-1H-pyrazol-4-yl)furan-2-carboxamide;

I-43: N-(1-(2-ethoxyethyl)-3-(pyridin-2-yl)-1H-pyrazol-4-yl)-5-(1-isopentyl-1H-pyrazol-4-yl)furan-2-carboxamide formate;

I-44: N-(1-(2-ethoxyethyl)-3-(pyridin-2-yl)-1H-pyrazol-4-yl)-5-(1-isopentyl-1H-pyrazol-4-yl)furan-2-carboxamide;

I-45: N-(1-(2-ethoxyethyl)-3-(pyridin-2-yl)-1H-pyrazol-4-yl)-5-(1-methyl-1H-pyrazol-4-yl)furan-2-carboxamide formate;

I-46: N-(1-(2-ethoxyethyl)-3-(pyridin-2-yl)-1H-pyrazol-4-yl)-5-(1-methyl-1H-pyrazol-4-yl)furan-2-carboxamide;

I-47: 5-(1H-pyrazol-4-yl)-N-(3-(pyridin-2-yl)-1H-pyrazol-4-yl)furan-2-carboxamide;

I-48: 5-(1-((3-methyloxetan-3-yl)methyl)-1H-pyrazol-4-yl)-N-(1-((3-methyloxetan-3-yl)methyl)-3-(pyridin-2-yl)-1H-pyrazol-4-yl)furan-2-carboxamide formate;

I-49: 5-(1-((3-methyloxetan-3-yl)methyl)-1H-pyrazol-4-yl)-N-(1-((3-methyloxetan-3-yl)methyl)-3-(pyridin-2-yl)-1H-pyrazol-4-yl)furan-2-carboxamide;

I-50: N-(2-(2-methoxyethoxy)ethyl)-5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide formate;

I-51: N-(2-(2-methoxyethoxy)ethyl)-5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide;

I-52: 5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide formate;

I-53: 5-(1-(2-(2-methoxyethoxy)ethyl)-1H-pyrazol-4-yl)-N-(1-(2-(2-methoxyethoxy)ethyl)-3-(pyridin-2-yl)-1H-pyrazol-4-yl)furan-2-carboxamide;

I-54: (4-(5-((1-(2-ethoxyethyl)-3-(pyridin-2-yl)-1H-pyrazol-4-yl)carbamoyl)furan-2-yl)-1H-pyrazol-1-yl)methyl dihydrogen phosphate;

I-55: sodium (4-(5-((1-(2-ethoxyethyl)-3-(pyridin-2-yl)-1H-pyrazol-4-yl)carbamoyl)furan-2-yl)-1H-pyrazol-1-yl)methyl phosphate;

I-56: N-(1-(2-ethoxyethyl)-3-(pyridin-2-yl)-1H-pyrazol-4-yl)-5-(3-methyl-1H-pyrazol-4-yl)furan-2-carboxamide formate;

I-57: N-(1-(2-ethoxyethyl)-3-(pyridin-2-yl)-1H-pyrazol-4-yl)-5-(3-methyl-1H-pyrazol-4-yl)furan-2-carboxamide;

I-58: 5-(3,5-dimethyl-1H-pyrazol-4-yl)-N-(1-(2-ethoxyethyl)-3-(pyridin-2-yl)-1H-pyrazol-4-yl)furan-2-carboxamide formate;

I-59: 5-(3,5-dimethyl-1H-pyrazol-4-yl)-N-(1-(2-ethoxyethyl)-3-(pyridin-2-yl)-1H-pyrazol-4-yl)furan-2-carboxamide;

I-60: 5-(1H-pyrazol-4-yl)-N-(1-(tetrahydro-2H-pyran-4-yl)-3-(thiazol-2-yl)-1H-pyrazol-4-yl)furan-2-carboxamide formate;

I-61: 5-(1H-pyrazol-4-yl)-N-(1-(tetrahydro-2H-pyran-4-yl)-3-(thiazol-2-yl)-1H-pyrazol-4-yl)furan-2-carboxamide;

I-62: N-(1-((1s,3s)-3-ethoxycyclobutyl)-3-(thiazol-2-yl)-1H-pyrazol-4-yl)-5-(1H-pyrazol-4-yl)furan-2-carboxamide formate;

I-63: N-(1-((1s,3s)-3-ethoxycyclobutyl)-3-(thiazol-2-yl)-1H-pyrazol-4-yl)-5-(1H-pyrazol-4-yl)furan-2-carboxamide;

I-64: N-(1-(2-(2-methoxyethoxy)ethyl)-3-(thiazol-2-yl)-1H-pyrazol-4-yl)-5-(1H-pyrazol-4-yl)furan-2-carboxamide;

I-65: 5-(1H-pyrazol-4-yl)-N-(1-(tetrahydro-2H-pyran-4-yl)-3-(thiazol-2-yl)-1H-pyrazol-4-yl)furan-2-carboxamide;

I-66: 5-(1H-pyrazol-4-yl)-N-(1-(tetrahydro-2H-pyran-4-yl)-3-(thiazol-2-yl)-1H-pyrazol-4-yl)furan-2-carboxamide;

I-67: N-{1-Methyl-3-(pyridine-2-yl)-1H-pyrazol-4-yl}-5-(1H-pyrazol-4-yl)furan-2-carboxamide, formate salt;

I-68: 5-(1-Methyl-1H-pyrazol-4-yl)-N-{1-methyl-3-(pyridine-2-yl)-1H-pyrazol-4-yl}furan-2-carboxamide;

I-69: 5-(1-Methyl-1H-pyrazol-4-yl)-N-{1-methyl-3-(pyridine-2-yl)-1H-pyrazol-4-yl}furan-2-carboxamide, formate salt;

I-70: tert-Butyl-3-[4-{5-(1H-pyrazole-4-yl)furan-2-carboxamido}-3-(pyridine-2-yl)-1H-pyrazol-1-yl]azetidine-1-carboxylate, formate salt;

I-71: N-{1-(3-Methoxycyclobutyl)-3-(pyridine-2-yl)-1H-pyrazol-4-yl}-5-(1H-pyrazol-4-yl)furan-2-carboxamide, formate salt, Cis isomer;

I-72: N-{1-(3-Methoxycyclobutyl)-3-(pyridine-2-yl)-1H-pyrazol-4-yl}-5-(1H-pyrazol-4-yl)furan-2-carboxamide, Cis isomer;

I-73: N-{1-(3-Benzyloxy)cyclobutyl)-3-(pyridine-2-yl)-1H-pyrazol-4-yl}-5-(1H-pyrazol-4-yl)furan-2-carboxamide, Trans isomer;

I-74: tert-Butyl-3-[4-{5-(1H-pyrazole-4-yl)furan-2-carboxamido}-3-(pyridine-2-yl)-1H-pyrazol-1-yl]azetidine-1-carboxylate;

I-75: N-(1-((1s,3s)-3-methoxycyclobutyl)-3-(pyridin-2-yl)-1H-pyrazol-4-yl)-5-(1H-pyrazol-4-yl)furan-2-carboxamide formate;

I-76: N-(1-((1s,3s)-3-methoxycyclobutyl)-3-(pyridin-2-yl)-1H-pyrazol-4-yl)-5-(1H-pyrazol-4-yl)furan-2-carboxamide;

I-77: N-{1-Methyl-3-(pyridine-2-yl)-1H-pyrazol-4-yl}-5-(1H-pyrazol-4-yl)furan-2-carboxamide, free base;

I-78: N-{1-(Azetidin-3-yl)-3-(pyridine-2-yl)-1H-pyrazol-4-yl}-5-(1H-pyrazol-4-yl)furan-2-carboxamide, TFA salt;

I-79: N-{1-(Azetidin-3-yl)-3-(pyridine-2-yl)-1H-pyrazol-4-yl}-5-(1H-pyrazol-4-yl)furan-2-carboxamide;

I-80: Di-tert-butyl-[[4-{4-(5-((1-methyl-3-(pyridine-2-yl)-1H-pyrazol-4-yl)carbamoyl)furan-2-yl)-1H-pyrazol-1-yl}methyl] phosphate;

I-81: [4-{5-((1-Methyl-3-(pyridine-2-yl)-1H-pyrazol-4-yl)carbamoyl)furan-2yl}-1H-pyrazol-1-yl]methyl dihydrogen phosphate;

I-82: Sodium [4-{5-((1-Methyl-3-(pyridine-2-yl)-1H-pyrazol-4-yl)carbamoyl)furan-2-yl}-1H-pyrazol-1-yl]methyl phosphate;

I-83: N-{1-(1-Acetylazetidin-3-yl)-3-(pyridine-2-yl)-1H-pyrazol-4-yl}-5-(1H-pyrazol-4-yl)furan-2-carboxamide, free base;

I-84: 3-[4-{5-(1H-Pyrazol-4-yl)furan-2-carboxamido}-3-(pyridine-2-yl)-1H-pyrazol-1-yl]-N-(tert-butyl)azetidine-1-carboxamide, free base;

I-85: 3-[4-{5-(1H-Pyrazol-4-yl)furan-2-carboxamido}-3-(pyridine-2-yl)-1H-pyrazol-1-yl]-N-isopropylazetidine-1-carboxamide, free base;

I-86: 3-[4-{5-(1H-Pyrazol-4-yl)furan-2-carboxamido}-3-(pyridine-2-yl)-1H-pyrazol-1-yl]-N-propylazetidine-1-carboxamide, free base;

I-87: 3-[4-{5-(1H-Pyrazol-4-yl)furan-2-carboxamido}-3-(pyridine-2-yl)-1H-pyrazol-1-yl]-N-cyclopropylazetidine-1-carboxamide, formate salt;

I-88: 3-[4-{5-(1H-Pyrazol-4-yl)furan-2-carboxamido}-3-(pyridine-2-yl)-1H-pyrazol-1-yl]-N-cyclopropylazetidine-1-carboxamide;

I-89: N-[1-{1-(Cyclopropanecarbonyl)azetidin-3-yl}-3-(pyridine-2-yl)-1H-pyrazol-4-yl]-5-(1H-pyrazol-4-yl)furan-2-carboxamide, formate salt;

I-90: N-[1-{1-(Cyclopropanecarbonyl)azetidin-3-yl}-3-(pyridine-2-yl)-1H-pyrazol-4-yl]-5-(1H-pyrazol-4-yl)furan-2-carboxamide;

I-91: N-[1-{1-Pivaloylazetidin-3-yl}-3-(pyridine-2-yl)-1H-pyrazol-4-yl]-5-(1H-pyrazol-4-yl)furan-2-carboxamide, formate salt;

I-92: N-[1-{1-Pivaloylazetidin-3-yl}-3-(pyridine-2-yl)-1H-pyrazol-4-yl]-5-(1H-pyrazol-4-yl)furan-2-carboxamide;

I-93: 5-(1H-Pyrazol-4-yl)-N-{3-(pyridine-2-yl)-1-(pyrrolidine-1-carbonyl)azetidin-3-yl}-1H-pyrazol-4-yl)furan-2-carboxamide, formate salt;

I-94: 5-(1H-Pyrazol-4-yl)-N-{3-(pyridine-2-yl)-1-(pyrrolidine-1-carbonyl)azetidin-3-yl}-1H-pyrazol-4-yl)furan-2-carboxamide;

I-95: N-[1-{1-Isobutyrylazetidin-3-yl}-3-(pyridine-2-yl)-1H-pyrazol-4-yl]-5-(1H-pyrazol-4-yl)furan-2-carboxamide, formate salt;

I-96: N-[1-{1-Isobutyrylazetidin-3-yl}-3-(pyridine-2-yl)-1H-pyrazol-4-yl]-5-(1H-pyrazol-4-yl)furan-2-carboxamide;

I-97: N-(1H-Pyrazol-4-yl)-N-{3-(pyridine-2-yl)-1-{1-(2,2,2-trifluoroethyl)azetidin-3-yl}-1H-pyrazol-4-yl}furan-2-carboxamide, TFA salt;

I-98: N-(1H-Pyrazol-4-yl)-N-{3-(pyridine-2-yl)-1-{1-(2,2,2-trifluoroethyl)azetidin-3-yl}-1H-pyrazol-4-yl}furan-2-carboxamide;

I-99: N-[1-{1-Butyrylazetidin-3-yl}-3-(pyridine-2-yl)-1H-pyrazol-4-yl]-5-(1H-pyrazol-4-yl)furan-2-carboxamide, formate salt;

I-100: N-[1-{1-Butyrylazetidin-3-yl}-3-(pyridine-2-yl)-1H-pyrazol-4-yl]-5-(1H-pyrazol-4-yl)furan-2-carboxamide;

I-101: N-{1-(1-Methylazetidin-3-yl)-3-(pyridine-2-yl)-1H-pyrazol-4-yl}-5-(1H-pyrazol-4-yl)furan-2-carboxamide, formate salt;

I-102: N-{1-(1-Methylazetidin-3-yl)-3-(pyridine-2-yl)-1H-pyrazol-4-yl}-5-(1H-pyrazol-4-yl)furan-2-carboxamide;

I-103: N-[1-{1-(2,2-difluorocyclopropane-1-carbonyl)azetidin-3-yl}-3-(pyridine-2-yl)-1H-pyrazol-4-yl]-5-(1H-pyrazol-4-yl)furan-2-carboxamide, formate salt;

I-104: N-[1-{1-(2,2-difluorocyclopropane-1-carbonyl)azetidin-3-yl}-3-(pyridine-2-yl)-1H-pyrazol-4-yl]-5-(1H-pyrazol-4-yl)furan-2-carboxamide;

I-105: N-(1-methyl-3-(5-morpholinopyridin-2-yl)-1H-pyrazol-4-yl)-5-(1H-pyrazol-4-yl)furan-2-carboxamide;

I-106: N-(1-methyl-3-(5-(4-methylpiperazin-1-yl)pyridin-2-yl)-1H-pyrazol-4-yl)-5-(1H-pyrazol-4-yl)furan-2-carboxamide;

I-107: N-(3-(5-(2-hydroxy-2-methylpropoxy)pyridin-2-yl)-1-methyl-1H-pyrazol-4-yl)-5-(1H-pyrazol-4-yl)furan-2-carboxamide;

I-108: N-(1-methyl-3-(5-(oxetan-3-yloxy)pyridin-2-yl)-1H-pyrazol-4-yl)-5-(1H-pyrazol-4-yl)furan-2-carboxamide;

I-109: N-(3-(5-methoxypyridin-2-yl)-1-methyl-1H-pyrazol-4-yl)-5-(1H-pyrazol-4-yl)furan-2-carboxamide;

I-110: N-(1-isopropyl-3-(pyridin-2-yl)-1H-pyrazol-4-yl)-5-(1H-pyrazol-4-yl)furan-2-carboxamide;

I-111: N-(1-(2-morpholinoethyl)-3-(pyridin-2-yl)-1H-pyrazol-4-yl)-5-(1H-pyrazol-4-yl)furan-2-carboxamide;

I-112: N-(1-(2-(4-methylpiperazin-1-yl)ethyl)-3-(pyridin-2-yl)-1H-pyrazol-4-yl)-5-(1H-pyrazol-4-yl)furan-2-carboxamide;

I-113: 5-(1H-pyrazol-3-yl)-N-(3-(pyridin-2-yl)-1-(2-(2,2,2-trifluoroethoxy)ethyl)-1H-pyrazol-4-yl)furan-2-carboxamide;

I-114: N-(1-((1s,3s)-3-isopropoxycyclobutyl)-3-(pyridin-2-yl)-1H-pyrazol-4-yl)-5-(1H-pyrazol-4-yl)furan-2-carboxamide;

I-115: N-(1-(difluoromethyl)-3-(pyridin-2-yl)-1H-pyrazol-4-yl)-5-(1H-pyrazol-4-yl)furan-2-carboxamide;

I-116: N-(1-((1s,3s)-3-ethoxycyclobutyl)-3-(6-(trifluoromethyl)pyridin-2-yl)-1H-pyrazol-4-yl)-5-(1H-pyrazol-4-yl)furan-2-carboxamide;

I-117: 5-(1H-pyrazol-4-yl)-N-(3-(pyridin-2-yl)-1-(2,2,2-trifluoroethyl)-1H-pyrazol-4-yl)furan-2-carboxamide;

I-118: N-(1-(2-ethoxyethyl)-3-(thiazol-2-yl)-1H-pyrazol-4-yl)-5-(1H-pyrazol-4-yl)furan-2-carboxamide formate;

I-119: N-(1-(2-ethoxyethyl)-3-(thiazol-2-yl)-1H-pyrazol-4-yl)-5-(1H-pyrazol-4-yl)furan-2-carboxamide;

I-120: 5-(1H-pyrazol-4-yl)-N-(1-(tetrahydrofuran-3-yl)-3-(thiazol-2-yl)-1H-pyrazol-4-yl)furan-2-carboxamide formate;

I-121: 5-(1H-pyrazol-4-yl)-N-(1-(tetrahydrofuran-3-yl)-3-(thiazol-2-yl)-1H-pyrazol-4-yl)furan-2-carboxamide;

I-122: 5-(1-cyclobutyl-1H-pyrazol-4-yl)-N-(1-cyclobutyl-3-(pyridin-2-yl)-1H-pyrazol-4-yl)furan-2-carboxamide 2,2,2-trifluoroacetate;

I-123: 5-(1-cyclobutyl-1H-pyrazol-4-yl)-N-(1-cyclobutyl-3-(pyridin-2-yl)-1H-pyrazol-4-yl)furan-2-carboxamide;

I-124: N-(1-((1s,4s)-4-hydroxycyclohexyl)-3-(pyridin-2-yl)-1H-pyrazol-4-yl)-5-(1H-pyrazol-4-yl)furan-2-carboxamide formate;

I-125: N-(1-((1s,4s)-4-hydroxycyclohexyl)-3-(pyridin-2-yl)-1H-pyrazol-4-yl)-5-(1H-pyrazol-4-yl)furan-2-carboxamide;

I-126: N-(1-((1r,4r)-4-hydroxycyclohexyl)-3-(pyridin-2-yl)-1H-pyrazol-4-yl)-5-(1H-pyrazol-4-yl)furan-2-carboxamide formate;

I-127: N-(1-((1r,4r)-4-hydroxycyclohexyl)-3-(pyridin-2-yl)-1H-pyrazol-4-yl)-5-(1H-pyrazol-4-yl)furan-2-carboxamide;

I-128: 5-(1H-pyrazol-4-yl)-N-(3-(pyridin-2-yl)-1-(3-(2,2,2-trifluoroethoxy)cyclobutyl)-1H-pyrazol-4-yl)furan-2-carboxamide formate;

I-129: 5-(1H-pyrazol-4-yl)-N-(3-(pyridin-2-yl)-1-(3-(2,2,2-trifluoroethoxy)cyclobutyl)-1H-pyrazol-4-yl)furan-2-carboxamide;

I-130: N-(1-((1r,4r)-4-ethoxycyclohexyl)-3-(pyridin-2-yl)-1H-pyrazol-4-yl)-5-(1H-pyrazol-4-yl)furan-2-carboxamide formate;

I-131: N-(1-((1r,4r)-4-ethoxycyclohexyl)-3-(pyridin-2-yl)-1H-pyrazol-4-yl)-5-(1H-pyrazol-4-yl)furan-2-carboxamide;

I-132: N-(1-((1S,3R)-3-ethoxycyclopentyl)-3-(pyridin-2-yl)-1H-pyrazol-4-yl)-5-(1H-pyrazol-4-yl)furan-2-carboxamide formate;

I-133: N-(1-((1S,3R)-3-ethoxycyclopentyl)-3-(pyridin-2-yl)-1H-pyrazol-4-yl)-5-(1H-pyrazol-4-yl)furan-2-carboxamide;

I-134: N-(1-((1S,3R)-3-hydroxycyclopentyl)-3-(pyridin-2-yl)-1H-pyrazol-4-yl)-5-(1H-pyrazol-4-yl)furan-2-carboxamide formate;

I-135: N-(1-((1S,3R)-3-hydroxycyclopentyl)-3-(pyridin-2-yl)-1H-pyrazol-4-yl)-5-(1H-pyrazol-4-yl)furan-2-carboxamide;

I-136: N-(1-((1S,3S)-3-hydroxycyclopentyl)-3-(pyridin-2-yl)-1H-pyrazol-4-yl)-5-(1H-pyrazol-4-yl)furan-2-carboxamide formate;

I-137: N-(1-((1S,3S)-3-hydroxycyclopentyl)-3-(pyridin-2-yl)-1H-pyrazol-4-yl)-5-(1H-pyrazol-4-yl)furan-2-carboxamide;

I-138: N-(1-((1s,3s)-3-ethoxycyclobutyl)-3-(5-fluoropyridin-2-yl)-1H-pyrazol-4-yl)-5-(1H-pyrazol-4-yl)furan-2-carboxamide formate;

I-139: N-(1-((1s,3s)-3-ethoxycyclobutyl)-3-(5-fluoropyridin-2-yl)-1H-pyrazol-4-yl)-5-(1H-pyrazol-4-yl)furan-2-carboxamide;

I-140: N-(1-((1S,3R)-3-ethoxy-2-fluorocyclobutyl)-3-(pyridin-2-yl)-1H-pyrazol-4-yl)-5-(1H-pyrazol-4-yl)furan-2-carboxamide formate;

I-141: N-(1-((1S,3R)-3-ethoxy-2-fluorocyclobutyl)-3-(pyridin-2-yl)-1H-pyrazol-4-yl)-5-(1H-pyrazol-4-yl)furan-2-carboxamide;

I-142: N-(1-((1s,3s)-3-ethoxycyclobutyl)-3-(3-fluoropyridin-2-yl)-1H-pyrazol-4-yl)-5-(1H-pyrazol-4-yl)furan-2-carboxamide formate;

I-143: N-(1-((1s,3s)-3-ethoxycyclobutyl)-3-(3-fluoropyridin-2-yl)-1H-pyrazol-4-yl)-5-(1H-pyrazol-4-yl)furan-2-carboxamide;

I-144: N-(1-((1s,3s)-3-ethoxycyclobutyl)-3-(6-fluoropyridin-2-yl)-1H-pyrazol-4-yl)-5-(1H-pyrazol-4-yl)furan-2-carboxamide formate;

I-145: N-(1-((1s,3s)-3-ethoxycyclobutyl)-3-(6-fluoropyridin-2-yl)-1H-pyrazol-4-yl)-5-(1H-pyrazol-4-yl)furan-2-carboxamide;

I-146: 5-(1H-pyrazol-4-yl)-N-(3-(pyridin-2-yl)-1-((1s,3s)-3-(2,2,2-trifluoroethoxy)cyclobutyl)-1H-pyrazol-4-yl)furan-2-carboxamide formate;

I-147: 5-(1H-pyrazol-4-yl)-N-(3-(pyridin-2-yl)-1-((1s,3s)-3-(2,2,2-trifluoroethoxy)cyclobutyl)-1H-pyrazol-4-yl)furan-2-carboxamide;

I-148: N-(1-((1s,3s)-3-ethoxycyclobutyl)-3-(4-fluoropyridin-2-yl)-1H-pyrazol-4-yl)-5-(1H-pyrazol-4-yl)furan-2-carboxamide formate;

I-149: N-(1-((1s,3s)-3-ethoxycyclobutyl)-3-(4-fluoropyridin-2-yl)-1H-pyrazol-4-yl)-5-(1H-pyrazol-4-yl)furan-2-carboxamide;

I-150: N-(3-(6-fluoropyridin-2-yl)-1-((1s,3s)-3-(2,2,2-trifluoroethoxy)cyclobutyl)-1H-pyrazol-4-yl)-5-(1H-pyrazol-4-yl)furan-2-carboxamide formate;

I-151: N-(3-(6-fluoropyridin-2-yl)-1-((1s,3s)-3-(2,2,2-trifluoroethoxy)cyclobutyl)-1H-pyrazol-4-yl)-5-(1H-pyrazol-4-yl)furan-2-carboxamide;

I-152: N-(3-(3-fluoropyridin-2-yl)-1-((1s,3s)-3-(2,2,2-trifluoroethoxy)cyclobutyl)-1H-pyrazol-4-yl)-5-(1H-pyrazol-4-yl)furan-2-carboxamide formate;

I-153: N-(3-(3-fluoropyridin-2-yl)-1-((1s,3s)-3-(2,2,2-trifluoroethoxy)cyclobutyl)-1H-pyrazol-4-yl)-5-(1H-pyrazol-4-yl)furan-2-carboxamide;

I-154: N-(1-((1r,4r)-4-ethoxycyclohexyl)-3-(3-fluoropyridin-2-yl)-1H-pyrazol-4-yl)-5-(1H-pyrazol-4-yl)furan-2-carboxamide formate;

I-155: N-(1-((1r,4r)-4-ethoxycyclohexyl)-3-(3-fluoropyridin-2-yl)-1H-pyrazol-4-yl)-5-(1H-pyrazol-4-yl)furan-2-carboxamide;

I-156: N-(3-(3,6-difluoropyridin-2-yl)-1-((1s,3s)-3-ethoxycyclobutyl)-1H-pyrazol-4-yl)-5-(1H-pyrazol-4-yl)furan-2-carboxamide;

II-1: N-(1-(2-hydroxy-2-methylpropyl)-3-(pyridin-2-yl)-1H-pyrazol-4-yl)-2-(1H-pyrazol-4-yl)thiazole-4-carboxamide;

II-2: 1-(isobutyryloxy)ethyl 4-(4-((1-methyl-3-(pyridin-2-yl)-1H-pyrazol-4-yl)carbamoyl)thiazol-2-yl)-1H-pyrazole-1-carboxylate;

II-3: tert-butyl (R)-(3-methyl-1-(4-(4-((1-methyl-3-(pyridin-2-yl)-1H-pyrazol-4-yl)carbamoyl)thiazol-2-yl)-1H-pyrazol-1-yl)-1-oxobutan-2-yl)carbamate;

II-4: 2-(1-((5-methyl-2-oxo-1,3-dioxol-4-yl)methyl)-1H-pyrazol-4-yl)-N-(1-methyl-3-(pyridin-2-yl)-1H-pyrazol-4-yl)thiazole-4-carboxamide;

II-5: 1-methylcyclopropyl 4-(4-((1-methyl-3-(pyridin-2-yl)-1H-pyrazol-4-yl)carbamoyl)thiazol-2-yl)-1H-pyrazole-1-carboxylate;

II-6: 1-((4-methoxybenzyl)oxy)-2-methylpropan-2-yl 4-(4-((1-methyl-3-(pyridin-2-yl)-1H-pyrazol-4-yl)carbamoyl)thiazol-2-yl)-1H-pyrazole-1-carboxylate;

II-7: diethyl ((4-(4-((1-methyl-3-(pyridin-2-yl)-1H-pyrazol-4-yl)carbamoyl)thiazol-2-yl)-1H-pyrazol-1-yl)methyl)phosphonate;

II-8: sodium ((4-(4-((1-methyl-3-(pyridin-2-yl)-1H-pyrazol-4-yl)carbamoyl)thiazol-2-yl)-1H-pyrazol-1-yl)methyl)phosphonate;

II-9: ((4-(4-((1-methyl-3-(pyridin-2-yl)-1H-pyrazol-4-yl)carbamoyl)thiazol-2-yl)-1H-pyrazol-1-yl)methyl)phosphonic acid;

II-10: 2-(1H-pyrazol-4-yl)-N-(3-(pyridin-2-yl)-1-(tetrahydro-2H-pyran-4-yl)-1H-pyrazol-4-yl)thiazole-4-carboxamide;

II-11: N-(1-((1,3-cis)-3-ethoxycyclobutyl)-3-(pyridin-2-yl)-1H-pyrazol-4-yl)-2-(1H-pyrazol-4-yl)thiazole-4-carboxamide;

II-12: N-(1-((1,3-trans)-3-ethoxycyclobutyl)-3-(pyridin-2-yl)-1H-pyrazol-4-yl)-2-(1H-pyrazol-4-yl)thiazole-4-carboxamide;

II-13: N-(1-((1,3-cis)-3-ethoxycyclobutyl)-3-(pyridin-2-yl)-1H-pyrazol-4-yl)-2-(1-methyl-1H-pyrazol-4-yl)thiazole-4-carboxamide;

II-14: N-(1-((1,3-cis)-3-hydroxycyclobutyl)-3-(pyridin-2-yl)-1H-pyrazol-4-yl)-2-(1H-pyrazol-4-yl)thiazole-4-carboxamide;

II-15: N-(1-((1s,3s)-3-(dimethylamino)cyclobutyl)-3-(pyridin-2-yl)-1H-pyrazol-4-yl)-2-(1H-pyrazol-4-yl)thiazole-4-carboxamide;

II-16: (4-(4-((1-((1,3-cis)-3-ethoxycyclobutyl)-3-(pyridin-2-yl)-1H-pyrazol-4-yl)carbamoyl)thiazol-2-yl)-1H-pyrazol-1-yl)methyl phosphate bis-sodium salt;

II-17: (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl dihydrogen phosphate;

II-18: N-(1-(2-ethoxyethyl)-3-(pyridin-2-yl)-1H-pyrazol-4-yl)-2-(1H-pyrazol-4-yl)thiazole-4-carboxamide, formic acid salt;

II-19: N-(1-(2-ethoxyethyl)-3-(pyridin-2-yl)-1H-pyrazol-4-yl)-2-(5-(trifluoromethyl)-1H-pyrazol-4-yl)thiazole-4-carboxamide, formic acid salt;

II-20: N-(1-(2-ethoxyethyl)-3-(pyridin-2-yl)-1H-pyrazol-4-yl)-2-(5-(trifluoromethyl)-1H-pyrazol-4-yl)thiazole-4-carboxamide;

II-21: N-(1-(2-ethoxyethyl)-3-(pyridin-2-yl)-1H-pyrazol-4-yl)-2-(3-methyl-1H-pyrazol-4-yl)thiazole-4-carboxamide, formic acid salt;

II-22: N-(1-(2-ethoxyethyl)-3-(pyridin-2-yl)-1H-pyrazol-4-yl)-2-(3-methyl-1H-pyrazol-4-yl)thiazole-4-carboxamide;

II-23: 2-(3,5-dimethyl-1H-pyrazol-4-yl)-N-(1-(2-ethoxyethyl)-3-(pyridin-2-yl)-1H-pyrazol-4-yl)thiazole-4-carboxamide, formic acid salt;

II-24: 2-(3,5-dimethyl-1H-pyrazol-4-yl)-N-(1-(2-ethoxyethyl)-3-(pyridin-2-yl)-1H-pyrazol-4-yl)thiazole-4-carboxamide;

II-25: N-(1-(2-ethoxyethyl)-3-(pyridin-2-yl)-1H-pyrazol-4-yl)-2-(1H-pyrazol-4-yl)thiazole-4-carboxamide;

II-26: N-(1-methyl-3-(pyridin-2-yl)-1H-pyrazol-4-yl)-2-(1H-pyrazol-4-yl)thiazole-4-carboxamide;

II-27: 2-(3-methyl-1H-pyrazol-4-yl)-N-(1-methyl-3-(pyridin-2-yl)-1H-pyrazol-4-yl)thiazole-4-carboxamide;

II-28: N-(1-(2-methoxyethyl)-3-(pyridin-2-yl)-1H-pyrazol-4-yl)-2-(1H-pyrazol-4-yl)thiazole-4-carboxamide;

II-29: N-(1-(2-methoxyethyl)-3-(pyridin-2-yl)-1H-pyrazol-4-yl)-2-(3-methyl-1H-pyrazol-4-yl)thiazole-4-carboxamide, formic acid salt;

II-30: N-(1-(2-methoxyethyl)-3-(pyridin-2-yl)-1H-pyrazol-4-yl)-2-(3-methyl-1H-pyrazol-4-yl)thiazole-4-carboxamide;

II-31: N-(1-(2-ethoxyethyl)-3-(pyridin-2-yl)-1H-pyrazol-4-yl)-2-(3-methyl-1H-pyrazol-4-yl)thiazole-4-carboxamide;

II-32: 2-(1H-pyrazol-4-yl)-N-(3-(pyridin-2-yl)-1H-pyrazol-4-yl)thiazole-4-carboxamide formate;

II-33: 2-(1H-pyrazol-4-yl)-N-(3-(pyridin-2-yl)-1H-pyrazol-4-yl)thiazole-4-carboxamide;

II-34: N-(1-(oxetan-3-yl)-3-(pyridin-2-yl)-1H-pyrazol-4-yl)-2-(1H-pyrazol-4-yl)thiazole-4-carboxamide;

II-35: (4-(4-((1-methyl-3-(pyridin-2-yl)-1H-pyrazol-4-yl)carbamoyl)thiazol-2-yl)-1H-pyrazol-1-yl)methyl dihydrogen phosphate;

II-36: Sodium (4-(4-((1-methyl-3-(pyridin-2-yl)-1H-pyrazol-4-yl)carbamoyl)thiazol-2-yl)-1H-pyrazol-1-yl)methyl phosphate;

II-37: N-(1-(2-(2-methoxyethoxy)ethyl)-3-(pyridin-2-yl)-1H-pyrazol-4-yl)-2-(1H-pyrazol-4-yl)thiazole-4-carboxamide;

II-38: potassium (4-(4-((1-methyl-3-(pyridin-2-yl)-1H-pyrazol-4-yl)carbamoyl)thiazol-2-yl)-1H-pyrazol-1-yl)methyl phosphate;

II-39: N-(1-(2-(2-methoxyethoxy)ethyl)-3-(pyridin-2-yl)-1H-pyrazol-4-yl)-2-(3-methyl-1H-pyrazol-4-yl)thiazole-4-carboxamide formate;

II-40: N-(1-(2-(2-methoxyethoxy)ethyl)-3-(pyridin-2-yl)-1H-pyrazol-4-yl)-2-(3-methyl-1H-pyrazol-4-yl)thiazole-4-carboxamide;

II-41: 2-(3-methyl-1H-pyrazol-4-yl)-N-(1-(oxetan-3-yl)-3-(pyridin-2-yl)-1H-pyrazol-4-yl)thiazole-4-carboxamide, formic acid salt;

II-42: 2-(3-methyl-1H-pyrazol-4-yl)-N-(1-(oxetan-3-yl)-3-(pyridin-2-yl)-1H-pyrazol-4-yl)thiazole-4-carboxamide;

II-43: 2-(1H-pyrazol-4-yl)-N-(3-(pyridin-2-yl)-1-(tetrahydrofuran-3-yl)-1H-pyrazol-4-yl)thiazole-4-carboxamide formate;

II-44: 2-(1H-pyrazol-4-yl)-N-(3-(pyridin-2-yl)-1-(tetrahydrofuran-3-yl)-1H-pyrazol-4-yl)thiazole-4-carboxamide;

II-45: 2-(3-methyl-1H-pyrazol-4-yl)-N-(3-(pyridin-2-yl)-1-((tetrahydro-2H-pyran-4-yl)methyl)-1H-pyrazol-4-yl)thiazole-4-carboxamide formate;

II-46: 2-(3-methyl-1H-pyrazol-4-yl)-N-(3-(pyridin-2-yl)-1-((tetrahydro-2H-pyran-4-yl)methyl)-1H-pyrazol-4-yl)thiazole-4-carboxamide;

II-47: N-(1-((3-(hydroxymethyl)oxetan-3-yl)methyl)-3-(pyridin-2-yl)-1H-pyrazol-4-yl)-2-(3-methyl-1H-pyrazol-4-yl)thiazole-4-carboxamide formate;

II-48: N-(1-((3-(hydroxymethyl)oxetan-3-yl)methyl)-3-(pyridin-2-yl)-1H-pyrazol-4-yl)-2-(3-methyl-1H-pyrazol-4-yl)thiazole-4-carboxamide;

II-49: N-(1-(2-(diethylamino)ethyl)-3-(pyridin-2-yl)-1H-pyrazol-4-yl)-2-(1H-pyrazol-4-yl)thiazole-4-carboxamide, formic acid salt;

II-50: N-(1-(2-(diethylamino)ethyl)-3-(pyridin-2-yl)-1H-pyrazol-4-yl)-2-(1H-pyrazol-4-yl)thiazole-4-carboxamide;

II-51: 2-(1-(4-methoxybenzyl)-1H-pyrazol-4-yl)-N-(1-(3-methoxycyclobutyl)-3-(pyridin-2-yl)-1H-pyrazol-4-yl)thiazole-4-carboxamide;

II-52: N-(1-(2-fluoroethyl)-3-(pyridin-2-yl)-1H-pyrazol-4-yl)-2-(1-(4-methoxybenzyl)-1H-pyrazol-4-yl)thiazole-4-carboxamide;

II-53: 2-(1-(4-methoxybenzyl)-1H-pyrazol-4-yl)-N-(3-(pyridin-2-yl)-1H-pyrazol-4-yl)thiazole-4-carboxamide;

II-54: tert-Butyl-3-[4-{2-(1H-pyrazole-4-yl)thiazole-2-carboxamido}-3-(pyridine-2-yl)-1H-pyrazol-1-yl]azetidine-1-carboxylate, free base;

II-55: N-{1-(Azetidin-3-yl)-3-(pyridine-2-yl)-1H-pyrazol-4-yl}-2-(1H-pyrazol-4-yl)thiazole-4-carboxamide, TFA salt;

II-56: N-{1-(Azetidin-3-yl)-3-(pyridin-2-yl)-1H-pyrazol-4-yl}-2-(1H-pyrazol-4-yl)thiazole-4-carboxamide;

II-57: N-{1-(3-Methoxycyclobutyl)-3-(pyridine-2-yl)-1H-pyrazol-4-yl}-2-(1H-pyrazol-4-yl)thiazole-4-carboxamide, free base, Cis isomer;

II-58: N-(3-(5-methoxypyridin-2-yl)-1-methyl-1H-pyrazol-4-yl)-2-(1H-pyrazol-4-yl)thiazole-4-carboxamide;

II-59: N-(1-isopropyl-3-(pyridin-2-yl)-1H-pyrazol-4-yl)-2-(1H-pyrazol-4-yl)thiazole-4-carboxamide;

II-60: N-(1-(2-morpholinoethyl)-3-(pyridin-2-yl)-1H-pyrazol-4-yl)-2-(1H-pyrazol-4-yl)thiazole-4-carboxamide;

II-61: N-(1-(2-(4-methylpiperazin-1-yl)ethyl)-3-(pyridin-2-yl)-1H-pyrazol-4-yl)-2-(1H-pyrazol-4-yl)thiazole-4-carboxamide;

II-62: N-(1-((1s,3s)-3-ethoxycyclobutyl)-3-(trifluoromethyl)-1H-pyrazol-4-yl)-2-(1H-pyrazol-4-yl)thiazole-4-carboxamide;

II-63: N-(1-methyl-3-(trifluoromethyl)-1H-pyrazol-4-yl)-2-(1H-pyrazol-4-yl)thiazole-4-carboxamide 2,2,2-trifluoroacetate;

II-64: N-(1-methyl-3-(trifluoromethyl)-1H-pyrazol-4-yl)-2-(1H-pyrazol-4-yl)thiazole-4-carboxamide;

II-65: N-(3-(3-fluoropyridin-2-yl)-1-((1s,3s)-3-hydroxycyclobutyl)-1H-pyrazol-4-yl)-2-(1H-pyrazol-4-yl)thiazole-4-carboxamide;

II-66: 2-(1H-pyrazol-3-yl)-N-(3-(pyridin-2-yl)-1-(2-(2,2,2-trifluoroethoxy)ethyl)-1H-pyrazol-4-yl)thiazole-4-carboxamide;

II-67: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone;

II-68: (2-(1H-pyrazol-4-yl)thiazol-4-yl)(2-((1s,3s)-3-ethoxycyclobutyl)-2,5,6,7-tetrahydro-4H-pyrazolo[4,3-b]pyridin-4-yl)methanone 2,2,2-trifluoroacetate;

II-69: (2-(1H-pyrazol-4-yl)thiazol-4-yl)(1-(3-ethoxycyclobutyl)-1,5,6,7-tetrahydro-4H-pyrazolo[4,3-b]pyridin-4-yl)methanone 2,2,2-trifluoroacetate;

II-70: N-(3-carbamoyl-1-((1s,3s)-3-ethoxycyclobutyl)-1H-pyrazol-4-yl)-2-(1H-pyrazol-4-yl)thiazole-4-carboxamide;

II-71: N-(1-((1s,3s)-3-ethoxycyclobutyl)-3-(pyridin-2-yl)-1H-pyrazol-4-yl)-2-(5-fluoro-1-((2-(trimethylsilyl)ethoxy)methyl)-1H-pyrazol-4-yl)thiazole-4-carboxamide;

II-72: N-(1-((1s,3s)-3-ethoxycyclobutyl)-3-(pyridin-2-yl)-1H-pyrazol-4-yl)-2-(5-fluoro-1H-pyrazol-4-yl)thiazole-4-carboxamide;

II-73: N-(1-((1s,3s)-3-ethoxycyclobutyl)-3-(pyridin-2-yl)-1H-pyrazol-4-yl)-2-(5-fluoro-1H-pyrazol-4-yl)thiazole-4-carboxamide formate;

II-74: N-(1-((1s,3s)-3-ethoxycyclobutyl)-3-(1,3,4-oxadiazol-2-yl)-1H-pyrazol-4-yl)-2-(1H-pyrazol-4-yl)thiazole-4-carboxamide;

II-75: N-(3-(1,3,4-oxadiazol-2-yl)-1-(tetrahydro-2H-pyran-4-yl)-1H-pyrazol-4-yl)-2-(1H-pyrazol-4-yl)thiazole-4-carboxamide;

II-76: N-(1-((1s,3s)-3-isopropoxycyclobutyl)-3-(pyridin-2-yl)-1H-pyrazol-4-yl)-2-(1H-pyrazol-4-yl)thiazole-4-carboxamide;

II-77: potassium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-78: calcium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-79: N-(1-((1r,3r)-3-hydroxy-3-methylcyclobutyl)-3-(pyridin-2-yl)-1H-pyrazol-4-yl)-2-(1H-pyrazol-4-yl)thiazole-4-carboxamide;

II-80: ammonium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-81: 5-amino-5-carboxypentan-1-aminium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-82: 1-(4-amino-4-carboxybutyl)guanidinium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl phosphate;

II-83: (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl dihydrogen phosphate;

II-84: 1,3-dihydroxy-2-(hydroxymethyl)propan-2-aminium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl hydrogen phosphate;

II-85: triethylammonium (4-(4-((1-((1s,3s)-3-ethoxycyclobutyl)-3-(pyridin-2-yl)-1H-pyrazol-4-yl)carbamoyl)thiazol-2-yl)-1H-pyrazol-1-yl)methyl hydrogen phosphate;

II-86: N-(1-((1s,3s)-3-ethoxycyclobutyl)-3-(5-(trifluoromethyl)pyridin-2-yl)-1H-pyrazol-4-yl)-2-(1H-pyrazol-4-yl)thiazole-4-carboxamide;

II-87: N-(1-(3-hydroxy-3-methylcyclobutyl)-3-(pyridin-2-yl)-1H-pyrazol-4-yl)-2-(1H-pyrazol-4-yl)thiazole-4-carboxamide;

II-88: N-(1-(difluoromethyl)-3-(pyridin-2-yl)-1H-pyrazol-4-yl)-2-(1H-pyrazol-4-yl)thiazole-4-carboxamide;

II-89: N-(1-((1s,3s)-3-ethoxycyclobutyl)-3-(3-(trifluoromethyl)pyridin-2-yl)-1H-pyrazol-4-yl)-2-(1H-pyrazol-4-yl)thiazole-4-carboxamide;

II-90: N-(1-((1s,3s)-3-ethoxycyclobutyl)-3-(6-(trifluoromethyl)pyridin-2-yl)-1H-pyrazol-4-yl)-2-(1H-pyrazol-4-yl)thiazole-4-carboxamide;

II-91: N-(1-((1s,3s)-3-ethoxycyclobutyl)-3-(pyridin-2-yl)-1H-pyrazol-4-yl)-2-(3-(trifluoromethyl)-1H-pyrazol-4-yl)thiazole-4-carboxamide;

II-92: N-(1-((1s,3s)-3-ethoxycyclobutyl)-3-(pyridin-2-yl)-1H-pyrazol-4-yl)-2-(3-methyl-1H-pyrazol-4-yl)thiazole-4-carboxamide;

II-93: 2-(3,5-dimethyl-1H-pyrazol-4-yl)-N-(1-((1s,3s)-3-ethoxycyclobutyl)-3-(pyridin-2-yl)-1H-pyrazol-4-yl)thiazole-4-carboxamide;

II-94: 2-(1H-pyrazol-4-yl)-N-(3-(pyridin-2-yl)-1-(2,2,2-trifluoroethyl)-1H-pyrazol-4-yl)thiazole-4-carboxamide;

II-95: N-(1-(difluoromethyl)-3-(pyridin-2-yl)-1H-pyrazol-4-yl)-2-(3-(trifluoromethyl)-1H-pyrazol-4-yl)thiazole-4-carboxamide;

II-96: N-(1-(difluoromethyl)-3-(pyridin-2-yl)-1H-pyrazol-4-yl)-2-(3-methyl-1H-pyrazol-4-yl)thiazole-4-carboxamide;

II-97: N-(1-(difluoromethyl)-3-(pyridin-2-yl)-1H-pyrazol-4-yl)-2-(1-(2,2,2-trifluoroethyl)-1H-pyrazol-4-yl)thiazole-4-carboxamide;

II-98: 2-(1-(difluoromethyl)-1H-pyrazol-4-yl)-N-(1-(difluoromethyl)-3-(pyridin-2-yl)-1H-pyrazol-4-yl)thiazole-4-carboxamide;

II-99: N-(1-((1s,3s)-3-ethoxycyclobutyl)-3-(6-(trifluoromethyl)pyridin-2-yl)-1H-pyrazol-4-yl)-2-(3-methyl-1H-pyrazol-4-yl)thiazole-4-carboxamide;

II-100: 2-(3-methyl-1H-pyrazol-4-yl)-N-(3-(pyridin-2-yl)-1-(2,2,2-trifluoroethyl)-1H-pyrazol-4-yl)thiazole-4-carboxamide;

II-101: N-(1-((1s,3s)-3-hydroxycyclobutyl)-3-(pyrazin-2-yl)-1H-pyrazol-4-yl)-2-(1H-pyrazol-4-yl)thiazole-4-carboxamide;

II-102: N-(1-((1s,3s)-3-ethoxycyclobutyl)-3-(pyrimidin-2-yl)-1H-pyrazol-4-yl)-2-(1H-pyrazol-4-yl)thiazole-4-carboxamide;

II-103: 2-(1-(4-methoxybenzyl)-1H-pyrazol-4-yl)-N-(3-(pyridin-2-yl)-1-(3,3,3-trifluoro-2-hydroxypropyl)-1H-pyrazol-4-yl)thiazole-4-carboxamide formate;

II-104: 2-(1-(4-methoxybenzyl)-1H-pyrazol-4-yl)-N-(3-(pyridin-2-yl)-1-(3,3,3-trifluoro-2-hydroxypropyl)-1H-pyrazol-4-yl)thiazole-4-carboxamide;

II-105: N-(1-(dimethylcarbamoyl)-3-(pyridin-2-yl)-1H-pyrazol-4-yl)-2-(1-(4-methoxybenzyl)-1H-pyrazol-4-yl)thiazole-4-carboxamide formate;

II-106: N-(1-(dimethylcarbamoyl)-3-(pyridin-2-yl)-1H-pyrazol-4-yl)-2-(1-(4-methoxybenzyl)-1H-pyrazol-4-yl)thiazole-4-carboxamide;

II-107: 2-(1-(4-methoxybenzyl)-1H-pyrazol-4-yl)-N-(3-(pyridin-2-yl)-1-(3,3,3-trifluoro-2-hydroxy-2-(trifluoromethyl)propyl)-1H-pyrazol-4-yl)thiazole-4-carboxamide formate;

II-108: 2-(1-(4-methoxybenzyl)-1H-pyrazol-4-yl)-N-(3-(pyridin-2-yl)-1-(3,3,3-trifluoro-2-hydroxy-2-(trifluoromethyl)propyl)-1H-pyrazol-4-yl)thiazole-4-carboxamide;

II-109: N-(1-(2-ethoxyethyl)-3-(thiazol-2-yl)-1H-pyrazol-4-yl)-2-(1H-pyrazol-4-yl)thiazole-4-carboxamide formate;

II-110: N-(1-(2-ethoxyethyl)-3-(thiazol-2-yl)-1H-pyrazol-4-yl)-2-(1H-pyrazol-4-yl)thiazole-4-carboxamide;

II-111: 2-(1H-pyrazol-4-yl)-N-(1-(tetrahydro-2H-pyran-4-yl)-3-(thiazol-2-yl)-1H-pyrazol-4-yl)thiazole-4-carboxamide formate;

II-112: 2-(1H-pyrazol-4-yl)-N-(1-(tetrahydro-2H-pyran-4-yl)-3-(thiazol-2-yl)-1H-pyrazol-4-yl)thiazole-4-carboxamide;

II-113: N-(1-(2-(2-methoxyethoxy)ethyl)-3-(thiazol-2-yl)-1H-pyrazol-4-yl)-2-(1H-pyrazol-4-yl)thiazole-4-carboxamide formate;

II-114: N-(1-(2-(2-methoxyethoxy)ethyl)-3-(thiazol-2-yl)-1H-pyrazol-4-yl)-2-(1H-pyrazol-4-yl)thiazole-4-carboxamide;

II-115: 2-(1H-pyrazol-4-yl)-N-(1-(tetrahydrofuran-3-yl)-3-(thiazol-2-yl)-1H-pyrazol-4-yl)thiazole-4-carboxamide formate;

II-116: 2-(1H-pyrazol-4-yl)-N-(1-(tetrahydrofuran-3-yl)-3-(thiazol-2-yl)-1H-pyrazol-4-yl)thiazole-4-carboxamide;

II-117: N-(1-(2-(diethylamino)ethyl)-3-(pyridin-2-yl)-1H-pyrazol-4-yl)-2-(1H-pyrazol-4-yl)thiazole-4-carboxamide;

II-118: N-(1-(2-(2-fluoroethoxy)ethyl)-3-(pyridin-2-yl)-1H-pyrazol-4-yl)-2-(1H-pyrazol-4-yl)thiazole-4-carboxamide formate;

II-119: N-(1-(2-(2-fluoroethoxy)ethyl)-3-(pyridin-2-yl)-1H-pyrazol-4-yl)-2-(1H-pyrazol-4-yl)thiazole-4-carboxamide;

II-120: N-(1-benzyl-3-(pyridin-2-yl)-1H-pyrazol-4-yl)-2-(1H-pyrazol-4-yl)thiazole-4-carboxamide;

II-121: N-(1-cyclobutyl-3-(pyridin-2-yl)-1H-pyrazol-4-yl)-2-(1H-pyrazol-4-yl)thiazole-4-carboxamide;

II-122: N-(1-(2-(2,2-difluoroethoxy)ethyl)-3-(pyridin-2-yl)-1H-pyrazol-4-yl)-2-(1H-pyrazol-4-yl)thiazole-4-carboxamide;

II-123: N-(1-(((1r,3r)-3-hydroxycyclobutyl)methyl)-3-(pyridin-2-yl)-1H-pyrazol-4-yl)-2-(1H-pyrazol-4-yl)thiazole-4-carboxamide formate;

II-124: N-(1-(((1r,3r)-3-hydroxycyclobutyl)methyl)-3-(pyridin-2-yl)-1H-pyrazol-4-yl)-2-(1H-pyrazol-4-yl)thiazole-4-carboxamide;

II-125: N-(1-(dimethylcarbamoyl)-3-(pyridin-2-yl)-1H-pyrazol-4-yl)-2-(1H-pyrazol-4-yl)thiazole-4-carboxamide formate;

II-126: N-(1-(dimethylcarbamoyl)-3-(pyridin-2-yl)-1H-pyrazol-4-yl)-2-(1H-pyrazol-4-yl)thiazole-4-carboxamide;

II-127: N-(1-((1s,3s)-3-(ethoxy-d5)cyclobutyl)-3-(pyridin-2-yl)-1H-pyrazol-4-yl)-2-(1H-pyrazol-4-yl)thiazole-4-carboxamide;

II-128: N-(1-(diethylcarbamoyl)-3-(pyridin-2-yl)-1H-pyrazol-4-yl)-2-(1H-pyrazol-4-yl)thiazole-4-carboxamide;

II-129: N-(1-(morpholine-4-carbonyl)-3-(pyridin-2-yl)-1H-pyrazol-4-yl)-2-(1H-pyrazol-4-yl)thiazole-4-carboxamide;

II-130: N-(1-((1s,3s)-3-(2-fluoroethoxy)cyclobutyl)-3-(pyridin-2-yl)-1H-pyrazol-4-yl)-2-(1H-pyrazol-4-yl)thiazole-4-carboxamide;

II-131: N-(1-(morpholine-4-carbonyl)-3-(pyridin-2-yl)-1H-pyrazol-4-yl)-2-(1H-pyrazol-4-yl)thiazole-4-carboxamide formate;

II-132: N-(1-(3-fluorocyclobut-2-en-1-yl)-3-(pyridin-2-yl)-1H-pyrazol-4-yl)-2-(1H-pyrazol-4-yl)thiazole-4-carboxamide;

II-133: N-(1-(3-fluorocyclobut-2-en-1-yl)-3-(pyridin-2-yl)-1H-pyrazol-4-yl)-2-(1H-pyrazol-4-yl)thiazole-4-carboxamide formate;

II-134: N-(1-(3,3-difluorocyclobutyl)-3-(pyridin-2-yl)-1H-pyrazol-4-yl)-2-(1H-pyrazol-4-yl)thiazole-4-carboxamide formate;

II-135: N-(1-(3,3-difluorocyclobutyl)-3-(pyridin-2-yl)-1H-pyrazol-4-yl)-2-(1H-pyrazol-4-yl)thiazole-4-carboxamide;

II-136: N-(3-cyano-1-((1s,3s)-3-hydroxycyclobutyl)-1H-pyrazol-4-yl)-2-(1H-pyrazol-4-yl)thiazole-4-carboxamide;

II-137: N-(3-cyano-1-methyl-1H-pyrazol-4-yl)-2-(1H-pyrazol-4-yl)thiazole-4-carboxamide;

II-138: N-(3-cyano-1-((1s,3s)-3-ethoxycyclobutyl)-1H-pyrazol-4-yl)-2-(1H-pyrazol-4-yl)thiazole-4-carboxamide;

II-139: N-(3-cyano-1-((1s,3s)-3-ethoxycyclobutyl)-1H-pyrazol-4-yl)-2-(1H-pyrazol-4-yl)thiazole-4-carboxamide formate;

II-140: N-(3-(3-fluoropyridin-2-yl)-1-(1,4-dioxaspiro[4.5]decan-8-yl)-1H-pyrazol-4-yl)-2-(1H-pyrazol-4-yl)thiazole-4-carboxamide;

II-141: 2-(1H-pyrazol-4-yl)-N-(3-(pyridin-2-yl)-1-((1r,3r)-3-(2,2,2-trifluoroethoxy)cyclobutyl)-1H-pyrazol-4-yl)thiazole-4-carboxamide formate;

II-142: 2-(1H-pyrazol-4-yl)-N-(3-(pyridin-2-yl)-1-((1r,3r)-3-(2,2,2-trifluoroethoxy)cyclobutyl)-1H-pyrazol-4-yl)thiazole-4-carboxamide;

II-143: N-(1-((1r,4r)-4-hydroxycyclohexyl)-3-(pyridin-2-yl)-1H-pyrazol-4-yl)-2-(1H-pyrazol-4-yl)thiazole-4-carboxamide formate;

II-144: N-(1-((1r,4r)-4-hydroxycyclohexyl)-3-(pyridin-2-yl)-1H-pyrazol-4-yl)-2-(1H-pyrazol-4-yl)thiazole-4-carboxamide;

II-145: N-(1-((1r,4r)-4-ethoxycyclohexyl)-3-(pyridin-2-yl)-1H-pyrazol-4-yl)-2-(1H-pyrazol-4-yl)thiazole-4-carboxamide formate;

II-146: N-(1-((1r,4r)-4-ethoxycyclohexyl)-3-(pyridin-2-yl)-1H-pyrazol-4-yl)-2-(1H-pyrazol-4-yl)thiazole-4-carboxamide;

II-147: N-(1-((1S,3R)-3-ethoxycyclopentyl)-3-(pyridin-2-yl)-1H-pyrazol-4-yl)-2-(1H-pyrazol-4-yl)thiazole-4-carboxamide formate;

II-148: N-(1-((1S,3R)-3-ethoxycyclopentyl)-3-(pyridin-2-yl)-1H-pyrazol-4-yl)-2-(1H-pyrazol-4-yl)thiazole-4-carboxamide;

II-149: N-(1-((1S,3R)-3-hydroxycyclopentyl)-3-(pyridin-2-yl)-1H-pyrazol-4-yl)-2-(1H-pyrazol-4-yl)thiazole-4-carboxamide formate;

II-150: N-(1-((1S,3R)-3-hydroxycyclopentyl)-3-(pyridin-2-yl)-1H-pyrazol-4-yl)-2-(1H-pyrazol-4-yl)thiazole-4-carboxamide;

II-151: N-(1-((1S,3S)-3-hydroxycyclopentyl)-3-(pyridin-2-yl)-1H-pyrazol-4-yl)-2-(1H-pyrazol-4-yl)thiazole-4-carboxamide formate;

II-152: N-(1-((1S,3S)-3-hydroxycyclopentyl)-3-(pyridin-2-yl)-1H-pyrazol-4-yl)-2-(1H-pyrazol-4-yl)thiazole-4-carboxamide;

II-153: N-(1-((1s,3s)-3-ethoxycyclobutyl)-3-(5-fluoropyridin-2-yl)-1H-pyrazol-4-yl)-2-(1H-pyrazol-4-yl)thiazole-4-carboxamide formate;

II-154: N-(1-((1s,3s)-3-ethoxycyclobutyl)-3-(5-fluoropyridin-2-yl)-1H-pyrazol-4-yl)-2-(1H-pyrazol-4-yl)thiazole-4-carboxamide;

II-155: N-(1-((1S,3R)-3-ethoxy-2-fluorocyclobutyl)-3-(pyridin-2-yl)-1H-pyrazol-4-yl)-2-(1H-pyrazol-4-yl)thiazole-4-carboxamide formate;

II-156: N-(1-((1S,3R)-3-ethoxy-2-fluorocyclobutyl)-3-(pyridin-2-yl)-1H-pyrazol-4-yl)-2-(1H-pyrazol-4-yl)thiazole-4-carboxamide;

II-157: N-(1-((1s,3s)-3-ethoxycyclobutyl)-3-(3-fluoropyridin-2-yl)-1H-pyrazol-4-yl)-2-(1H-pyrazol-4-yl)thiazole-4-carboxamide;

II-158: N-(1-((1s,3s)-3-ethoxycyclobutyl)-3-(4-fluoropyridin-2-yl)-1H-pyrazol-4-yl)-2-(1H-pyrazol-4-yl)thiazole-4-carboxamide formate;

II-159: N-(1-((1s,3s)-3-ethoxycyclobutyl)-3-(4-fluoropyridin-2-yl)-1H-pyrazol-4-yl)-2-(1H-pyrazol-4-yl)thiazole-4-carboxamide;

II-160: N-(1-((1s,3s)-3-ethoxycyclobutyl)-3-(6-fluoropyridin-2-yl)-1H-pyrazol-4-yl)-2-(1H-pyrazol-4-yl)thiazole-4-carboxamide;

II-161: 2-(1H-pyrazol-4-yl)-N-(3-(pyridin-2-yl)-1-((1s,3s)-3-(2,2,2-trifluoroethoxy)cyclobutyl)-1H-pyrazol-4-yl)thiazole-4-carboxamide formate;

II-162: 2-(1H-pyrazol-4-yl)-N-(3-(pyridin-2-yl)-1-((1s,3s)-3-(2,2,2-trifluoroethoxy)cyclobutyl)-1H-pyrazol-4-yl)thiazole-4-carboxamide;

II-163: (4-(4-((1-((1s,3s)-3-ethoxycyclobutyl)-3-(3-fluoropyridin-2-yl)-1H-pyrazol-4-yl)carbamoyl)thiazol-2-yl)-1H-pyrazol-1-yl)methyl dihydrogen phosphate;

II-164: sodium (4-(4-((1-((1s,3s)-3-ethoxycyclobutyl)-3-(3-fluoropyridin-2-yl)-1H-pyrazol-4-yl)carbamoyl)thiazol-2-yl)-1H-pyrazol-1-yl)methyl phosphate;

II-165: N-(3-(3-fluoropyridin-2-yl)-1-((1s,3s)-3-(2,2,2-trifluoroethoxy)cyclobutyl)-1H-pyrazol-4-yl)-2-(1H-pyrazol-4-yl)thiazole-4-carboxamide formate;

II-166: N-(3-(3-fluoropyridin-2-yl)-1-((1s,3s)-3-(2,2,2-trifluoroethoxy)cyclobutyl)-1H-pyrazol-4-yl)-2-(1H-pyrazol-4-yl)thiazole-4-carboxamide;

II-167: N-(3-(3-fluoropyridin-2-yl)-1-((1r,3r)-3-(2,2,2-trifluoroethoxy)cyclobutyl)-1H-pyrazol-4-yl)-2-(1H-pyrazol-4-yl)thiazole-4-carboxamide formate;

II-168: N-(3-(3-fluoropyridin-2-yl)-1-((1r,3r)-3-(2,2,2-trifluoroethoxy)cyclobutyl)-1H-pyrazol-4-yl)-2-(1H-pyrazol-4-yl)thiazole-4-carboxamide;

II-169: N-(1-((1r,4r)-4-ethoxycyclohexyl)-3-(3-fluoropyridin-2-yl)-1H-pyrazol-4-yl)-2-(1H-pyrazol-4-yl)thiazole-4-carboxamide;

II-170: N-(3-(6-fluoropyridin-2-yl)-1-((1s,3s)-3-(2,2,2-trifluoroethoxy)cyclobutyl)-1H-pyrazol-4-yl)-2-(1H-pyrazol-4-yl)thiazole-4-carboxamide formate;

II-171: N-(3-(6-fluoropyridin-2-yl)-1-((1s,3s)-3-(2,2,2-trifluoroethoxy)cyclobutyl)-1H-pyrazol-4-yl)-2-(1H-pyrazol-4-yl)thiazole-4-carboxamide;

II-172: N-(3-(6-fluoropyridin-2-yl)-1-((1s,3s)-3-hydroxycyclobutyl)-1H-pyrazol-4-yl)-2-(1H-pyrazol-4-yl)thiazole-4-carboxamide;

II-173: (4-(4-((1-((1s,3s)-3-ethoxycyclobutyl)-3-(6-fluoropyridin-2-yl)-1H-pyrazol-4-yl)carbamoyl)thiazol-2-yl)-1H-pyrazol-1-yl)methyl dihydrogen phosphate;

II-174: N-(3-(3,6-difluoropyridin-2-yl)-1-((1s,3s)-3-ethoxycyclobutyl)-1H-pyrazol-4-yl)-2-(1H-pyrazol-4-yl)thiazole-4-carboxamide;

II-175: N-(1-((1s,4s)-4-ethoxycyclohexyl)-3-(3-fluoropyridin-2-yl)-1H-pyrazol-4-yl)-2-(1H-pyrazol-4-yl)thiazole-4-carboxamide;

II-176: N-(3-(3,6-difluoropyridin-2-yl)-1-((1r,4r)-4-ethoxycyclohexyl)-1H-pyrazol-4-yl)-2-(1H-pyrazol-4-yl)thiazole-4-carboxamide;

II-177: N-(3-(3,6-difluoropyridin-2-yl)-1-((1s,4s)-4-ethoxycyclohexyl)-1H-pyrazol-4-yl)-2-(1H-pyrazol-4-yl)thiazole-4-carboxamide;

II-178: N-(1-((1r,4r)-4-ethoxycyclohexyl)-3-(1,3,4-oxadiazol-2-yl)-1H-pyrazol-4-yl)-2-(1H-pyrazol-4-yl)thiazole-4-carboxamide;

II-179: N-(1-((1r,4r)-4-((2,2-difluoroethyl)amino)cyclohexyl)-3-(pyrimidin-2-yl)-1H-pyrazol-4-yl)-2-(1H-pyrazol-4-yl)thiazole-4-carboxamide; or II-180: N-(3-(3,5-difluoropyridin-2-yl)-1-((1r,4r)-4-ethoxycyclohexyl)-1H-pyrazol-4-yl)-2-(1H-pyrazol-4-yl)thiazole-4-carboxamide.

11. The method of claim 2, comprising inhibiting an IRAK protein in vivo.

12. The method of claim 11, wherein the IRAK protein is in a subject.

13. The method of claim 12, wherein the method is a method for treating a disease or condition for which an IRAK inhibitor is indicated.

14. The method of claim 13, wherein the disease is an auto-immune disease, inflammatory disorder, cardiovascular disease, neurodegenerative disorder, allergic disorder, multi-organ failure, kidney disease, platelet aggregation, cancer, transplantation, sperm motility, erythrocyte deficiency, graft rejection, lung injury, respiratory disease, ischemic condition, bacterial infection, viral infection, immune regulatory disorder or a combination thereof.

15. The method of claim 14, wherein the disease or condition is an auto-immune disease, inflammatory disorder, cardiovascular disease, cancer, ischemic condition, immune regulatory disorder or a combination thereof.

16. The method of claim 14, wherein the disease or condition is an auto-immune disease or inflammatory disorder.

17. The method of claim 14, wherein the cancer is breast cancer, lung cancer, melanoma, leukemia, large B-cell lymphoma, Waldenström's macroglobulinemia, myelodysplastic syndromes, Kaposi's sarcoma, or a combination thereof.

* * * * *